(12) United States Patent
Tanaka et al.

(10) Patent No.: US 8,946,144 B2
(45) Date of Patent: Feb. 3, 2015

(54) PHOSPHONATED GLYCOPEPTIDE AND LIPOGLYCOPEPTIDE ANTIBIOTICS AND USES THEREOF FOR THE PREVENTION AND TREATMENT OF BONE AND JOINT INFECTIONS

(75) Inventors: Kelly Tanaka, Toronto (CA); Stephane Ciblat, Montréal (CA); Adel Rafai Far, Ville Mont-Royal (CA); Evelyne Dietrich, Laval (CA)

(73) Assignee: The Medicines Company, Parsippany, NJ (US)

( * ) Notice: Subject to any disclaimer, the term of this patent is extended or adjusted under 35 U.S.C. 154(b) by 1093 days.

(21) Appl. No.: 12/520,364

(22) PCT Filed: Dec. 21, 2007

(86) PCT No.: PCT/CA2007/002288
§ 371 (c)(1),
(2), (4) Date: Jul. 27, 2009

(87) PCT Pub. No.: WO2008/077241
PCT Pub. Date: Jul. 3, 2008

(65) Prior Publication Data
US 2010/0113333 A1 May 6, 2010

Related U.S. Application Data

(60) Provisional application No. 60/876,511, filed on Dec. 22, 2006.

(51) Int. Cl.
*A61K 38/00* (2006.01)
*C07K 9/00* (2006.01)
*C07F 9/6561* (2006.01)

(52) U.S. Cl.
CPC ................ *C07K 9/008* (2013.01); *A61K 38/00* (2013.01); *C07F 9/6561* (2013.01)
USPC .............................. 514/2.9; 530/317; 530/322

(58) Field of Classification Search
None
See application file for complete search history.

(56) References Cited

U.S. PATENT DOCUMENTS 5,840,684 A * 11/1998 Cooper et al. ................. 514/2.4
2001/0041689 A1 * 11/2001 Padioukova et al. ............ 514/79

FOREIGN PATENT DOCUMENTS

| EP | 0 145 484 A2 | 6/1985 |
| WO | 9640190 A1 | 12/1996 |
| WO | WO 96/40156 | * 12/1996 |
| WO | WO 96/40156 A1 | 12/1996 |
| WO | WO 98/15560 | * 4/1998 |
| WO | WO 98/15560 A1 | 4/1998 |
| WO | 2007138381 | 12/2007 |
| WO | 2008097364 | 8/2008 |

OTHER PUBLICATIONS

Bhavnani, S M et al., Pharmacokinetics, safety, and tolerability of ascending single intravenous doses of oritavancin administered to healthy human subjects, Diagnostic Microbiology and infectious Diseases, vol. 50, No. 2, Oct. 1, 2004, pp. 95-102.
Herczegh P et al., Osteoadsorptive Bisphosphonate Derivatives of Fluoroquinone Antibacterials, Journal of Medicinal Chemistry, vol. 45, Jan. 1, 2002, pp. 2338-2341.
Supplementary European Search Report, Appln. No. 07 85 5570, dated Jul. 14, 2010.
International Search Report for PCT/CA2007/002288, dated Apr. 8, 2008.

* cited by examiner

*Primary Examiner* — Karlheinz R Skowronek
*Assistant Examiner* — Roy Teller
(74) *Attorney, Agent, or Firm* — Roylance, Abrams, Berdo & Goodman, L.L.P.

(57) ABSTRACT

The present invention is directed to antimicrobial compounds which have an affinity for binding bones. More particularly, the invention is directed to phosphonated derivatives of glycopeptide or lipoglycopeptide antibiotics. These compounds are useful as antibiotics for the prevention or treatment of bone and joint infections, especially for the prevention and treatment of osteomyelitis.

17 Claims, No Drawings

PHOSPHONATED GLYCOPEPTIDE AND LIPOGLYCOPEPTIDE ANTIBIOTICS AND USES THEREOF FOR THE PREVENTION AND TREATMENT OF BONE AND JOINT INFECTIONS

BACKGROUND OF THE INVENTION a) Field of the Invention

The invention relates to phosphonated derivatives of glycopeptide and lipoglycopeptide antibiotics. These compounds are useful as antibiotics for prevention and/or the treatment of bone and joint infections, especially for the prophylaxis and/or treatment of osteomyelitis.

b) Brief Description of the Prior Art

Osteomyelitis is an inflammation of bone caused by a variety of microorganisms, mainly *Staphylococcus aureus* (Carek et al., American Family Physician (2001), Vol 12, 12:2413-2420). This painful and debilitating disease occurs more commonly in children. Within the adult population, diabetics and kidney dialysis patients are also vulnerable. The acute form of the disease is treatable with antibiotics, but requires a lengthy period of daily therapy. It can, however, revert to a recurrent or chronic form requiring repeated hospital stays and heavy treatment regimens.

Glycopeptide and lipoglycopeptide antibiotics are a class of biologically produced or semi-synthetic antimicrobial agents which affect the bacterial cell wall and/or membrane integrity (Williams, D. H et al, Angewandte Chemie International Edition in English (1999), 1999, 38; 1172-1193. Nicolaou, K. C. et al, Angewandte Chemie International Edition in English (1999), 38; 2097-2152. Kahne, D. et al Chemical Reviews (2005), 105; 425-448; Pace, J. L. et al, Biochemical Pharmacology (2006), 71; 968-980). Best known glycopeptide and lipoglycopeptide antibiotics are certainly vancomycin, teicoplanin, oritavancin (U.S. Pat. No. 5,840,684), dalbavancin (U.S. Pat. No. 5,750,509) and telavancin (U.S. Pat. No. 6,635,618). The two first drugs were proven clinically and microbiologically to have potent activity against gram-positive organisms and the latter three drugs are in clinical trials. Oritavancin, dalbavancin and telavancin possess extremely attractive pharmacological profiles with potent activity against gram-positive organisms, including methicillin-resistant *Staphylococcus aureus*, intermediate and fully vancomycin-resistant *Staphylococcus aureus*, vancomycin-resistant *Enterococcus* spp., and *Streptococcus* spp. Although the use of highly active systemic anti-staphylococcal agents for the treatment of bone and joint infections is becoming attractive, results obtained in animal models using vancomycin or teicoplanin for the treatment of osteomyelitis have not been convincing (Luu, Q. N. et al, European Journal of Clinical Microbiology and Infectious Diseases (1989); 8; 562-563. Mader, J. T. et al Antimicrobial Agents and Chemotherapy (1989); 33; 689-692). The problem may be that although the drug are highly active, the actual intra-bone concentration of the drug is but a fraction of the systemic dose and therefore glycopeptide and lipoglycopeptide antibiotics could prove to be more effective if the proportion of the drug reaching the bone could be increased.

Bisphosphonates are well-characterized bone-seeking agents. These compounds are known to have a high affinity to the bones due to their ability to bind the $Ca^{2+}$ ions found in the hydroxyapatite forming the bone tissues (Hirabayashi and Fujisaki, Clin. Pharmacokinet. (2003) 42(15): 1319-1330). Therefore, many different types of bisphosphonate-conjugated compounds have been made for targeting drugs selectively to the bone, including proteins (Uludag et al., Biotechnol Prog. (2000) 16:1115-1118), vitamins (U.S. Pat. No. 6,214,812 and WO 02/083150), tyrosine kinase inhibitors (WO 01/44258 and WO 01/44259), hormones (U.S. Pat. No. 5,183,815) and bone scanning agents (U.S. Pat. No. 4,810,486). These and other bisphosphonate derivatives have been used as therapeutic agents for bone diseases such as arthritis (U.S. Pat. No. 4,746,654), osteoporosis (U.S. Pat. No. 5,428,181 and U.S. Pat. No. 6,420,384), hypercalcemia (U.S. Pat. No. 4,973,576), and bone cancers (U.S. Pat. No. 6,548,042). Although some have suggested that bisphosphonate-antibiotics could also be made, only few of such compounds have actually being synthesized, including macrolides (U.S. Pat. No. 5,359,060), fluoroquinolones and β-lactams (U.S. Pat. No. 5,854,227; U.S. Pat. No. 5,880,111; DE 195 32 235; Pieper and Keppler, Phosphorus, Sulfur and Silicon (2001) 170:5-14; and Herczegh et al. J. Med. Chem (2002) 45:2338-41). Furthermore, prior to the present invention, no one has ever made or suggested to make phosphonated derivatives of glycopeptide or lipoglycopeptide antibiotics, nor suggested the use of such derivatives for the prevention or treatment of osteomyelitis.

In view of the above, there is a need for highly active antibiotics for the prevention and treatment of bone and joint infections. More particularly, there is a need for glycopeptide or lipoglycopeptide antibiotics with a higher affinity for bone, and a need for treatment methods wherein the intra-bone concentration of glycopeptide or lipoglycopeptide antibiotics is increased, for an extended period of time, above the minimal effective inhibitory concentrations which are required for killing bacteria.

The present invention fulfills these needs and also other needs as will be apparent to those skilled in the art upon reading the following specification.

SUMMARY OF THE INVENTION

The present invention is directed to antimicrobial compounds which have an affinity for binding bones. More particularly, the invention is directed to phosphonated derivatives of glycopeptide or lipoglycopeptide antibiotics. These compounds are useful as antibiotics for the prevention or treatment of bone and joint infections, especially for the prevention and treatment of osteomyelitis.

In one embodiment, the compounds of the invention are represented by the general Formula (I) as illustrated below:

as well as pharmaceutically acceptable salts, esters and prodrugs thereof, wherein:

B is a phosphonated group, preferably having a high affinity to osseous tissues;

L is a bond or a linker for coupling B to A;

A is a glycopeptide or lipoglycopeptide antimicrobial molecule; and

α is 1, 2, 3, 4, 5, 6 or 7, preferably 1, 2 or 3.

In a preferred embodiment, B is a bisphosphonate. More preferably, B is a bisphosphonate selected from the group consisting of:

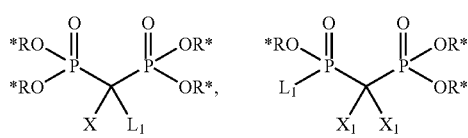

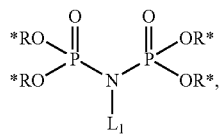

wherein:
each R* is independently selected from the group consisting of H, lower alkyl, cycloalkyl, aryl and heteroaryl, with the proviso that at least two R* are H;

X is H, OH, NH$_2$, or a halo group;

X$_1$ are both H, or each is independently selected from the group consisting of H, OH, NH$_2$, and a halo group; and L$_1$ is the point of attachment to L.

In another preferred embodiment, L is a cleavable linker for covalently and/or reversibly coupling B to A. In a further preferred embodiment, L is a hydrolysable linker.

In another preferred embodiment, the substructure represented by B-L- is represented by the following formula BL$_1$:

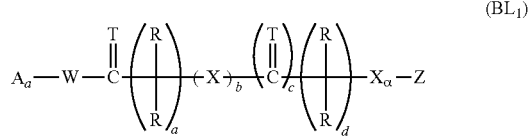

wherein:

A$_a$ indicates the point of attachment to the glycopeptide or lipoglycopeptide antimicrobial molecule A;

W is a covalent bond or is selected from the group of

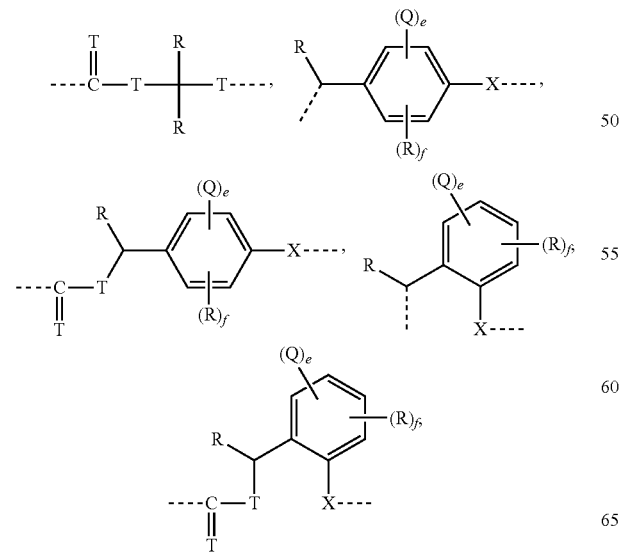

-continued

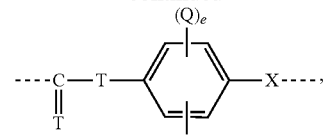

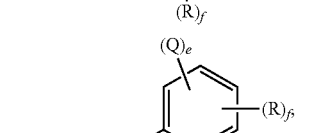

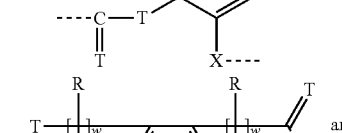

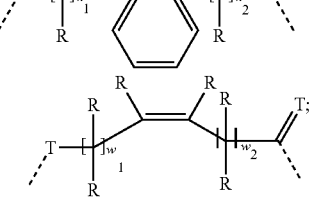

T is oxygen or sulfur;

each R is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, amino, substituted amino, hydroxyl, alkoxy, substituted alkoxy, aryloxy, substituted aryloxy, and —R$^a$—Y—R$^b$—Y—R$^b$—B;

each R$^a$ is independently selected from the group consisting of a covalent bond, alkylene, substituted alkylene, alkenylene, substituted alkenylene, alkynylene, substituted alkynylene, arylene, substituted arylene, —(CO)-alkylene-, substituted —(CO)-alkylene-, —(CO)-alkenylene-, substituted —(CO)-alkenylene-, —(CO)-alkynylene-, substituted —(CO)-alkynylene-, —(CO)-arylene- and substituted —(CO)-arylene-;

each R$^b$ is independently selected from the group consisting of a covalent bond, alkylene, substituted alkylene, alkenylene, substituted alkenylene, alkynylene, substituted alkynylene, arylene and substituted arylene;

each Y is independently selected from the group consisting of a covalent bond, —CH$_2$—, —O—, —S—, —S—S—, —NR$^c$—, —S(O)—, —SO$_2$—, —NR$^c$C(O)—, —OSO$_2$—, —OC(O)—, —N(R$^c$)SO$_2$—, —C(O)NR$^c$—, —C(O)O—, —SO$_2$NR$^c$—, —SO$_2$O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^c$C(O)O—, —NR$^c$C(O)NR$^c$—, —OC(O)NR$^c$—, —C(O)—, and —N(R$^c$)SO$_2$NR$^c$—;

each R$^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^d$—;

each R$^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

B is a phosphonated group;

each Q is independently selected from the group consisting of nitro, chloro, bromo, iodo and fluoro;

each X is independently selected from the group consisting of —O—, —S—, and —N(R)—;

Z is selected from the group consisting of hydrogen, acyl, substituted acyl, aroyl, substituted aroyl, alkoxycarbonyl, substituted alkoxycarbonyl, aryloxycarbonyl, substituted aryloxycarbonyl,

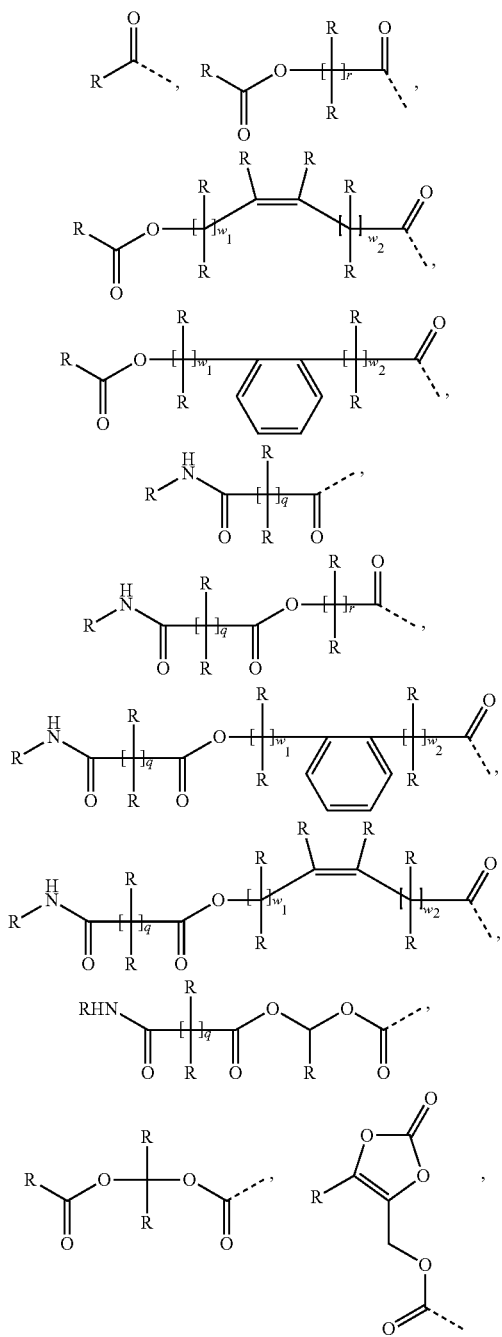

-continued

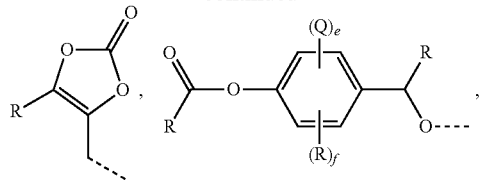

q is 2 or 3;

r is 1, 2, 3, 4 or 5;

$w_1$ and $w_2$ are each integers $\geq 0$ such that their sum $(w_1+w_2)$ is 1, 2 or 3;

a, b, c, d are integers $\geq 0$ such that $a+b+c+d \geq 7$ or null;

e and f are integers $\geq 0$ such that $e+f=4$;

α is 0 or 1.

In preferred embodiments of formula (I), L couples B to A through one or more hydroxyl groups on A, through one or more nitrogen atoms on A, through one or more carboxylic carbonyl groups on A, or through more than one of a combination of hydroxyl groups, nitrogen atoms and carboxylic carbonyl groups on A. When L couples B to A through a hydroxyl group on A, preferably L is one or more of the following linkers:

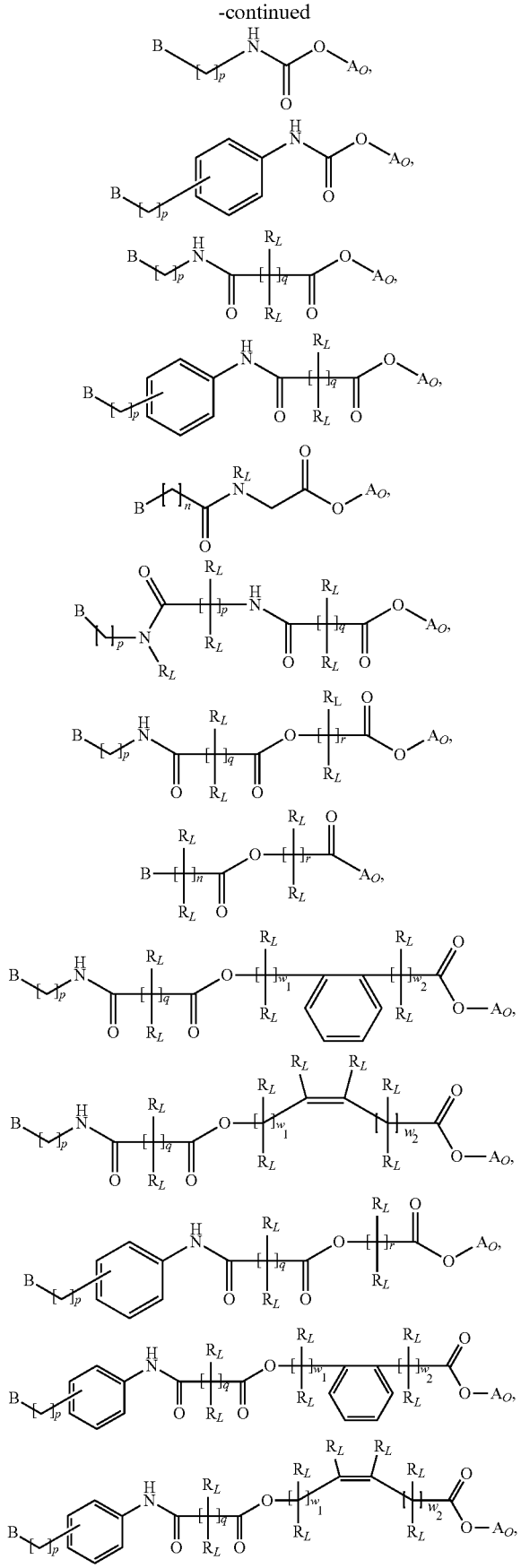

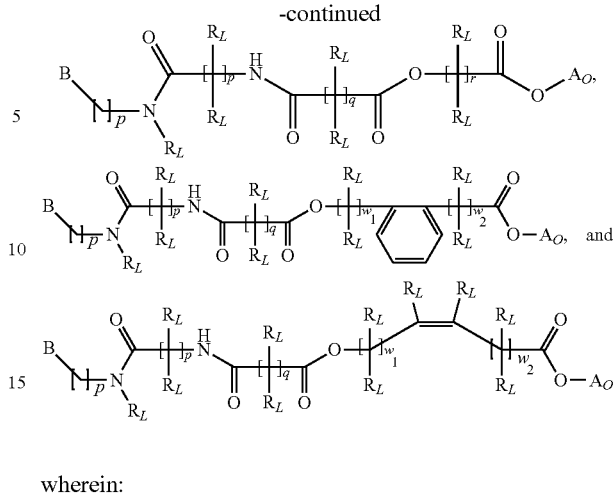

wherein:
n is an integer ≤10, preferably 1, 2, 3 or 4, more preferably 1 or 2;
each p is independently 0 or an integer ≤10, preferably 0, 1, 2, 3 or 4, more preferably 0 or 1;
q is 2 or 3
r is 1, 2, 3, 4 or 5
$w_1$ and $w_2$ are integers ≥0 such that their sum ($w_1+w_2$) is 1, 2 or 3
each $R_L$ is independently selected from the group consisting of H, ethyl and methyl, preferably H;
B represents the phosphonated group; and
the substructure

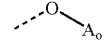

of the linker represents the hydroxyl moiety of A.
When L couples B to A through a nitrogen atom on A, preferably L is one or more of the following linkers:

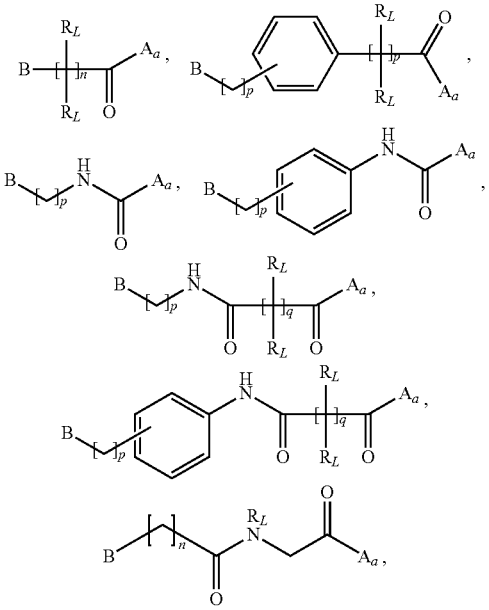

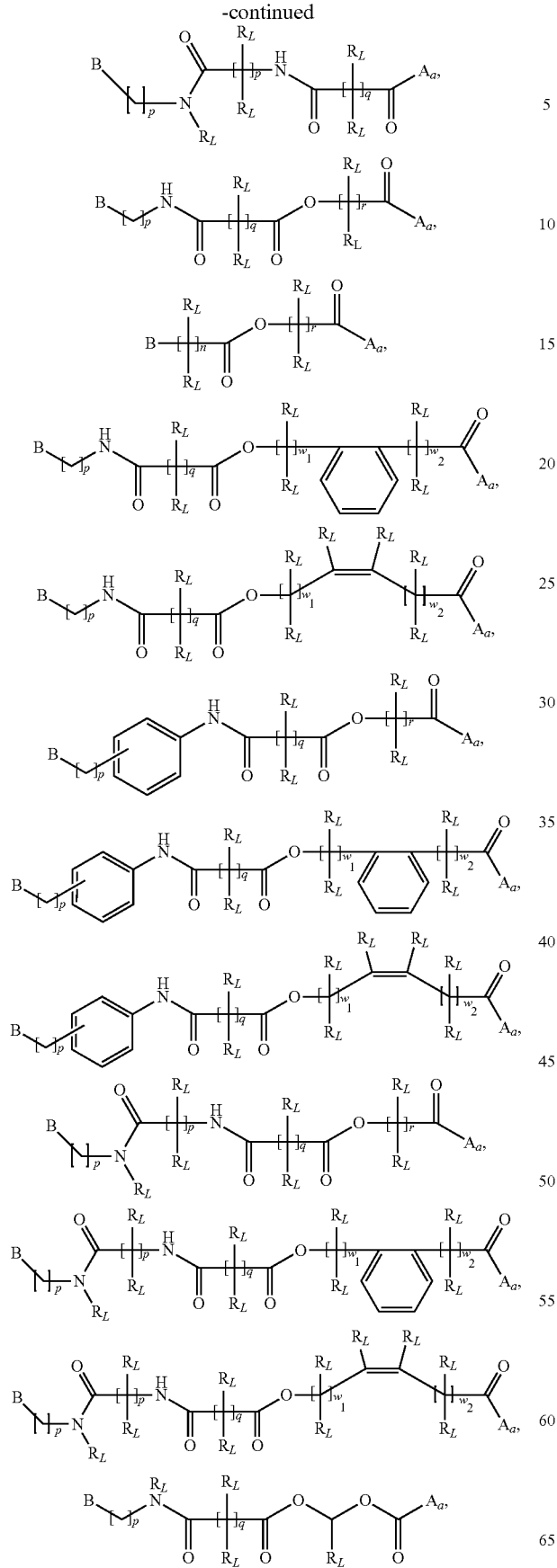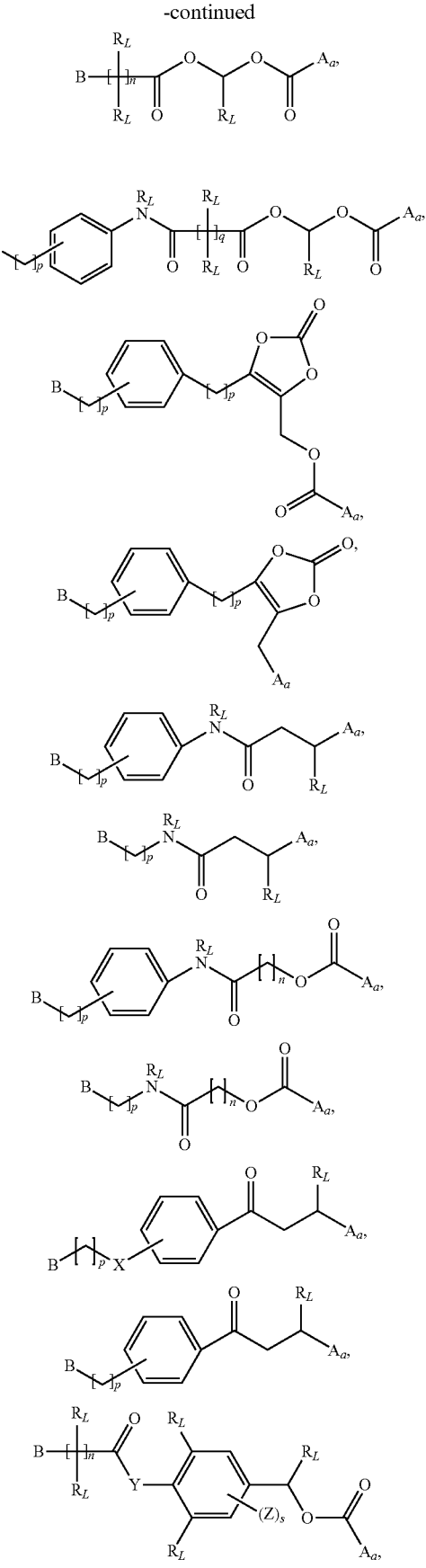

-continued

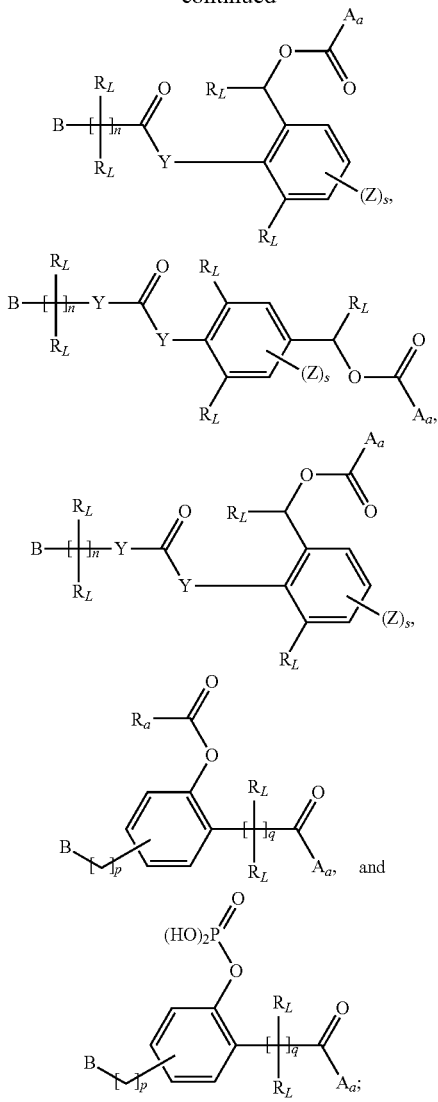

wherein:
B represents said phosphonated group;
n is an integer ≤10;
each p is independently 0 or an integer ≤10;
each $R_L$ is independently selected from the group consisting of H, ethyl and methyl;
q is 2 or 3;
r is 1, 2, 3, 4 or 5;
$w_1$ and $w_2$ are each integers ≥0 such that their sum ($w_1+w_2$) is 1, 2 or 3.
X is —$CH_2$—, —$CONR_L$—, —CO—O—$CH_2$—, or —CO—O—;
each Y is independently selected from the group consisting of —O—, —S— and —$NR_L$—;
each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro, wherein s is 1, 2, 3, or 4; and
$R_a$ is $C_xH_y$, where x is an integer of 0 to 20 and y is an integer of 1 to 2x+1.
B represents said phosphonated group; and
$A_a$ represents the nitrogen atom on A.

When L couples B to A through the carbonyl of a carboxylate group on A, preferably L is one or more of the following linkers:

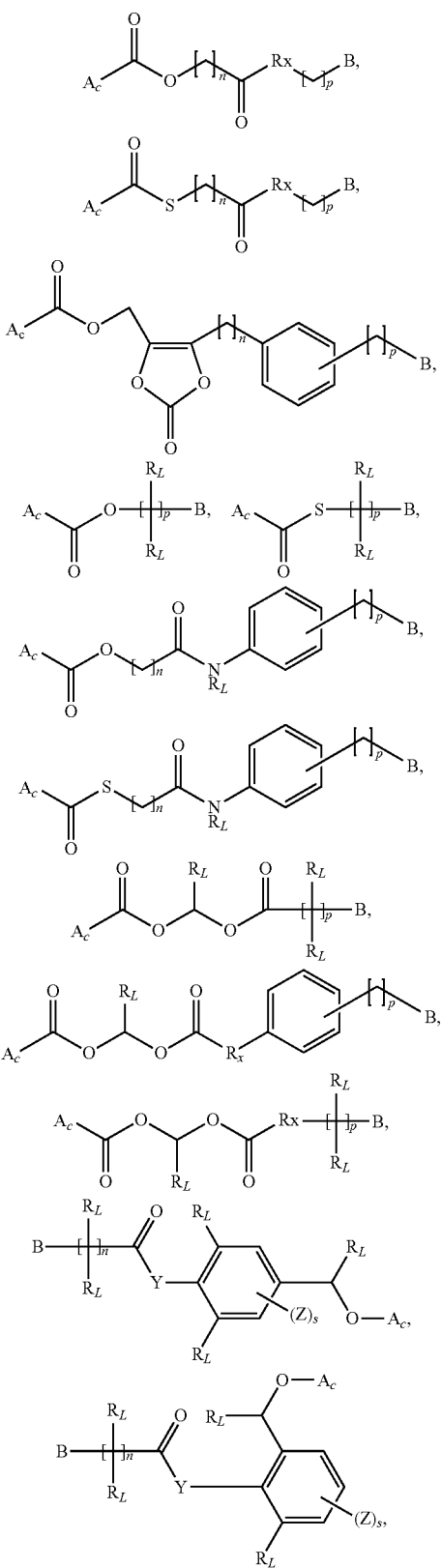

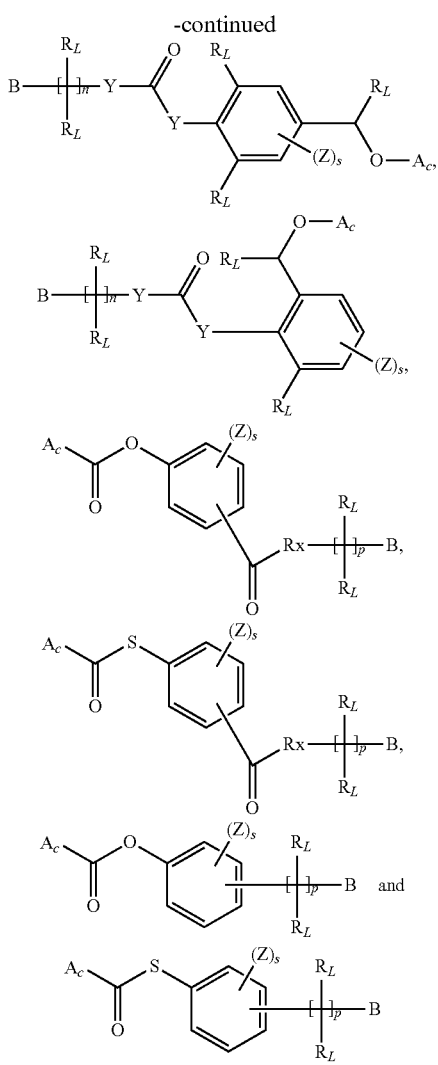

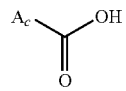

of A.

In further preferred embodiment, at least one of B-L- is coupled to a hydroxyl functionality on the glycopeptide or lipoglycopeptide antimicrobial molecule A. Preferably, when B-L- is coupled to a hydroxyl functionality B-L- is one or more of the following:

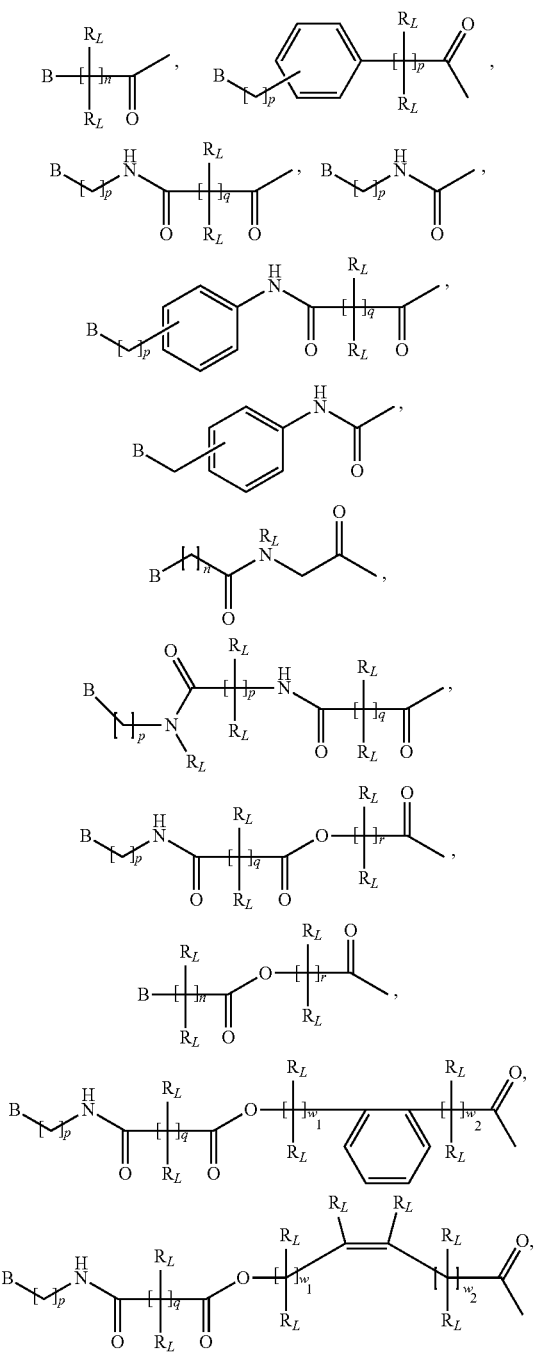

wherein:
- n is an integer ≤10, preferably 1, 2, 3 or 4, more preferably 1 or 2;
- p is 0 or an integer ≤10, preferably 0, 1, 2, 3 or 4, more preferably 0 or 1;
- $R_L$ is H, ethyl or methyl, preferably H;
- $R_x$ is —S—, —C($R_L$)$_2$—, —N$R_L$— or —O—; preferably —N$R_L$—, more preferably —NH—;
- each Y is independently selected from the group consisting of —O—, —S—, and —N$R_L$—;
- each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro; wherein s is 1, 2, 3 or 4;
- B represents the phosphonated group; and
- the substructure

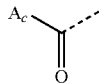

of the linker represents the carbonyl of a carboxylate group

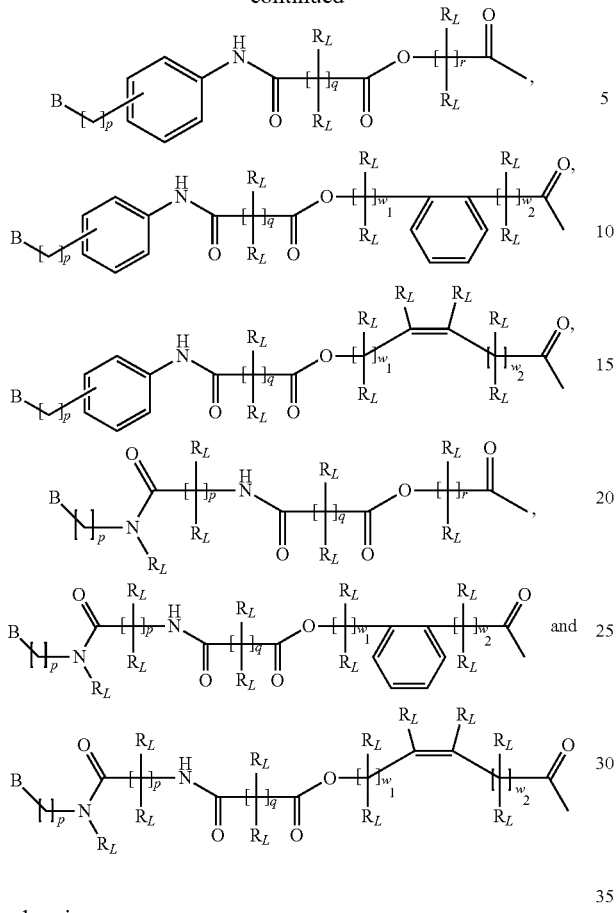

wherein:
- B represents said phosphonated group;
- each p is independently 0 or an integer ≤10, preferably 0, 1, 2, 3 or 4, more preferably 0 or 1;
- each $R_L$ is independently selected from the group consisting of H, ethyl and methyl;
- q is 2 or 3;
- n is an integer ≤10, preferably 1, 2, 3 or 4, more preferably 1 or 2;
- r is 1, 2, 3, 4 or 5; and
- $w_1$ and $w_2$ are each integers ≤0 such that their sum ($w_1+w_2$) is 1, 2 or 3.

In further preferred embodiment, at least one of B-L- is coupled to a nitrogen atom on the glycopeptide or lipoglycopeptide antimicrobial molecule A. Preferably, when B-L- is coupled to a nitrogen atom B-L- is one or more of the following:

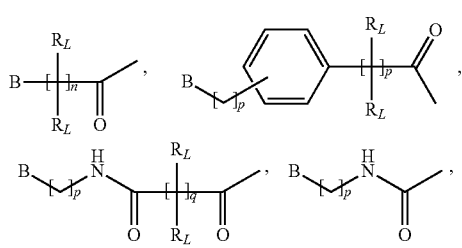

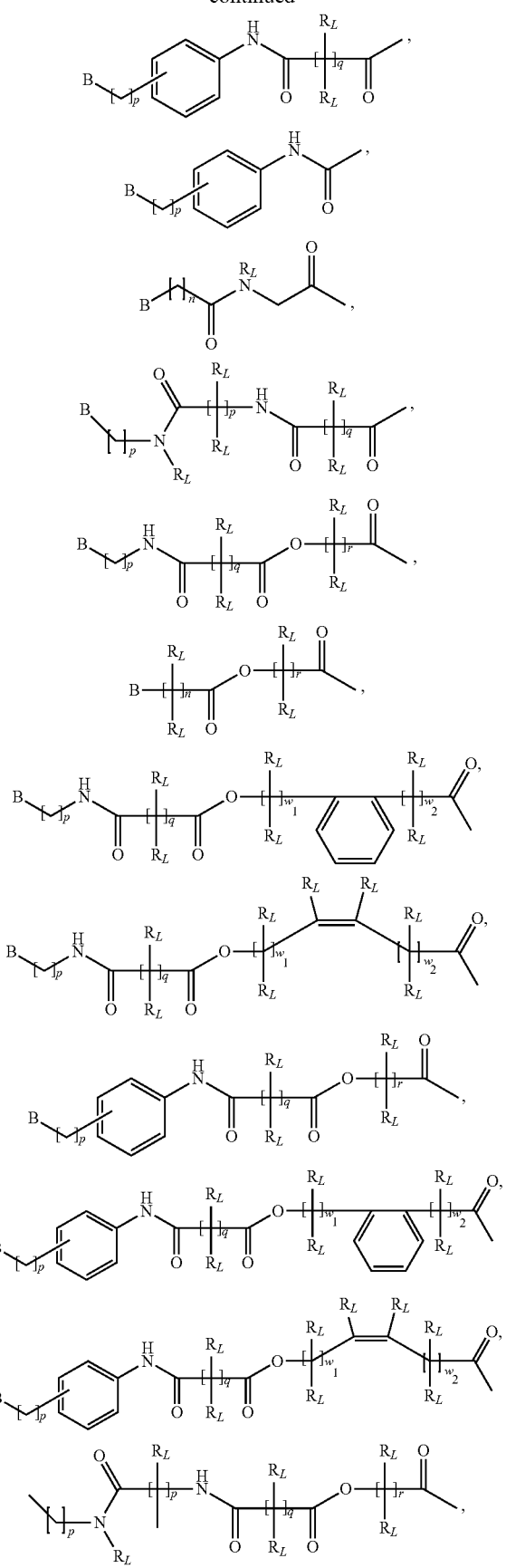

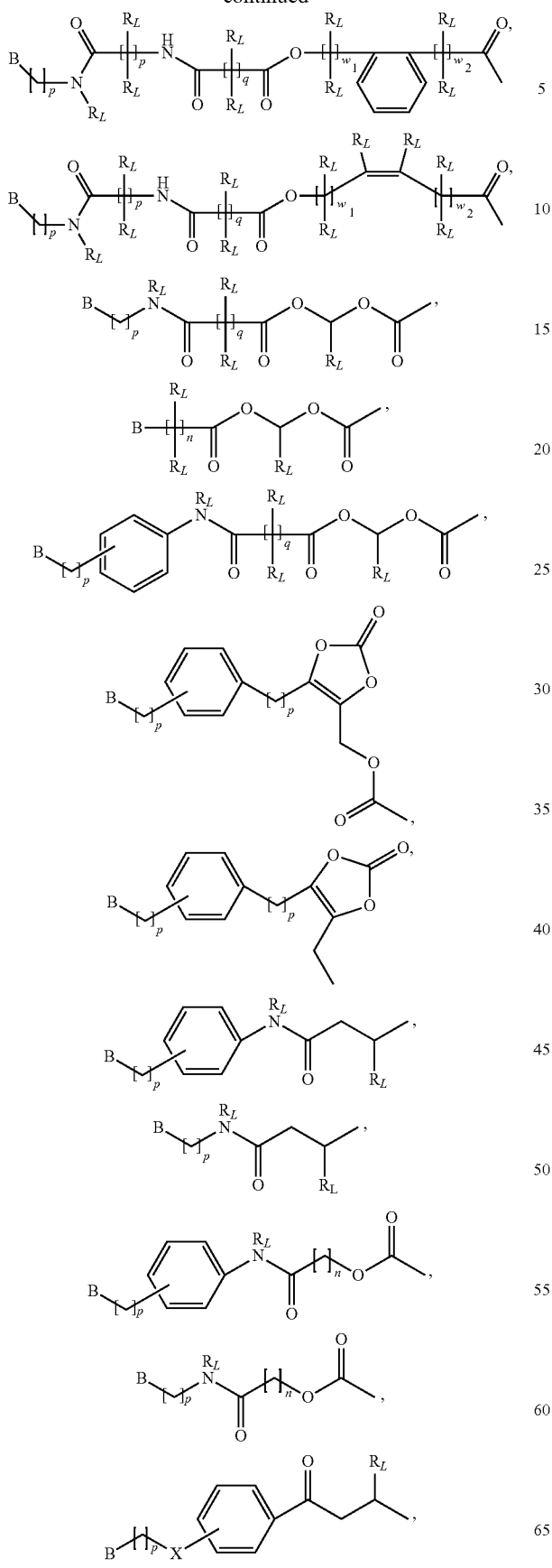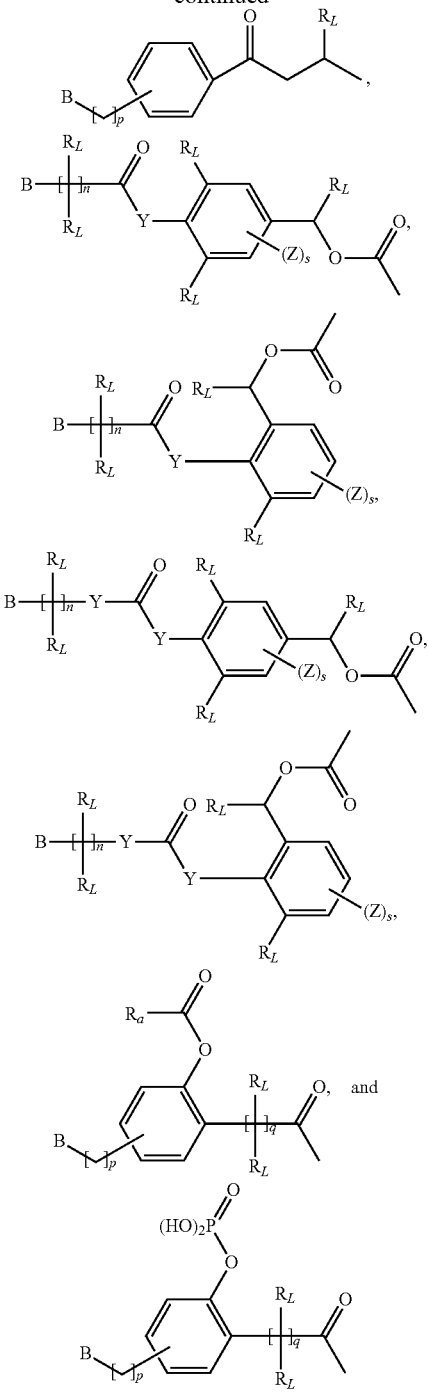
wherein:
B represents said phosphonated group;
n is an integer ≤10;
each p is independently 0 or an integer ≤10;
each $R_L$ is independently selected from the group consisting of H, ethyl and methyl;
q is 2 or 3;
r is 1, 2, 3, 4 or 5;
$w_1$ and $w_2$ are each integers ≥0 such that their sum ($w_1+w_2$) is 1, 2 or 3.
X is —$CH_2$—, —$CONR_L$—, —CO—O—$CH_2$—, or —CO—O—; and each Y is independently selected from the group consisting of —O—, —S— and —NR$_L$—;

each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro, wherein s is 1, 2, 3 or 4; and R$_a$ is C$_x$H$_y$, where x is an integer of 0 to 20 and y is an integer of 1 to 2x+1.

B represents said phosphonated group;

In further preferred embodiment of formula (I), at least one of B-L- is coupled to the carbonyl of a carboxylate group on the glycopeptide or lipoglycopeptide antimicrobial molecule A. Preferably, when B-L- is coupled to the carbonyl of a carboxylate group on A, B-L- is one or more of the following:

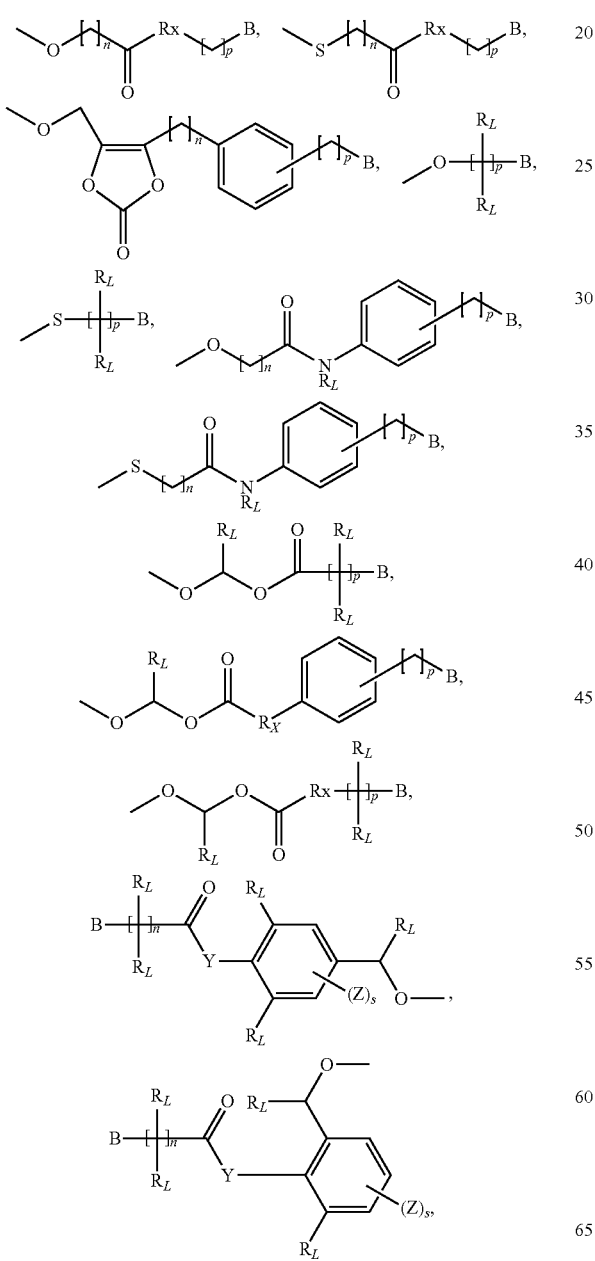

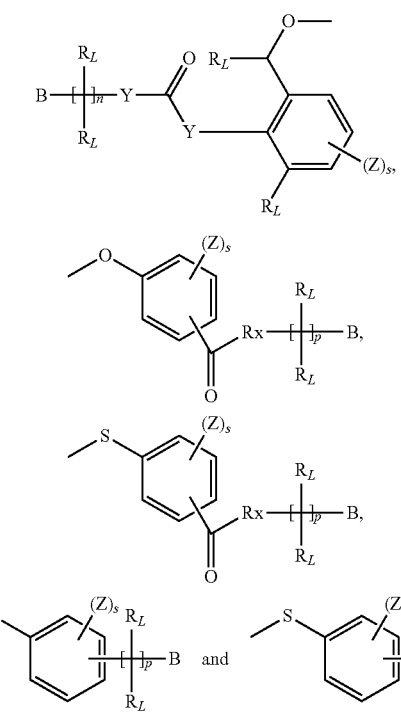

wherein:

n is an integer ≤10, preferably 1, 2, 3 or 4, more preferably 1 or 2;

p is 0 or an integer ≤10, preferably 0, 1, 2, 3 or 4, more preferably 0 or 1;

R$_L$ is H, ethyl or methyl, preferably H;

R$_x$ is —S—, —NR$_L$— or —O—; preferably —NR$_L$—, more preferably —NH—;

each Y is independently selected from the group consisting of —O—, —S—, and —NR$_L$—;

each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro; wherein s is 1, 2, 3 or 4; and B represents the phosphonated group.

In an additional preferred embodiment of formula (I), α is an integer of 2 to 3, B-L- is coupled to a combination of at least two of a hydroxyl functionality on the glycopeptide or lipoglycopeptide antimicrobial molecule A, a nitrogen atom on the glycopeptide or lipoglycopeptide antimicrobial molecule A or the carbonyl of a carboxylate group on the glycopeptide or lipoglycopeptide antimicrobial molecule A. Preferably, when B-L- is coupled to a hydroxyl functionality B-L- is one or more of the following:

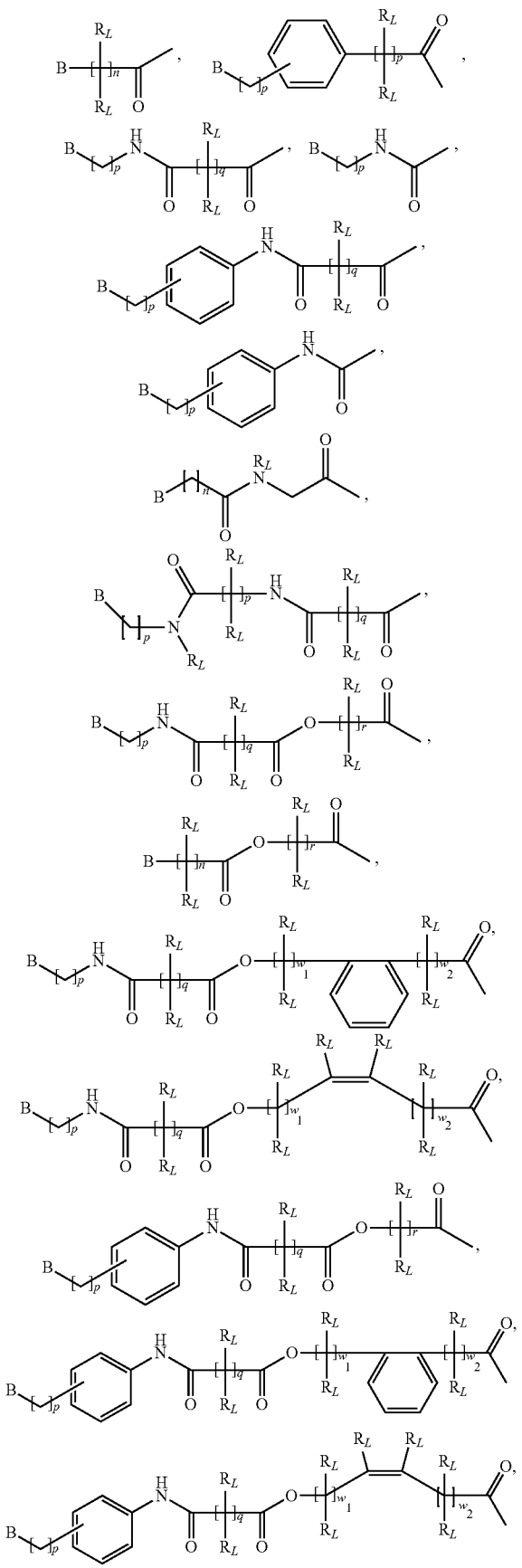

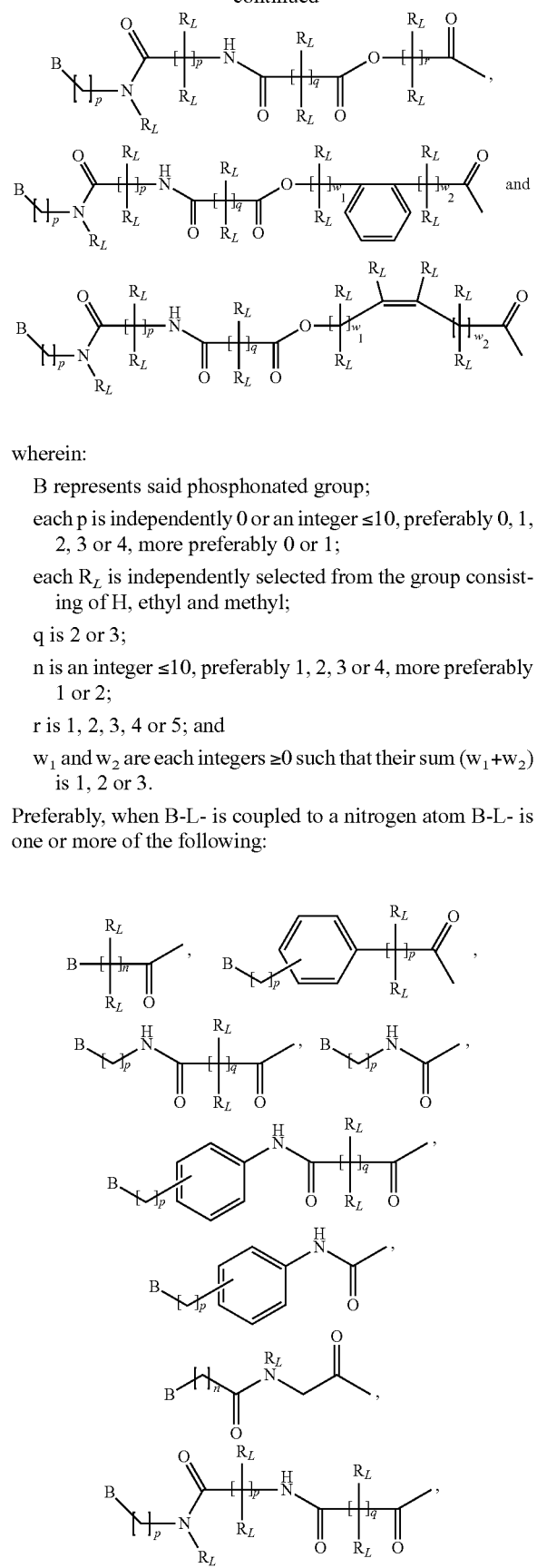

wherein:
B represents said phosphonated group;
each p is independently 0 or an integer ≤10, preferably 0, 1, 2, 3 or 4, more preferably 0 or 1;
each $R_L$ is independently selected from the group consisting of H, ethyl and methyl;
q is 2 or 3;
n is an integer ≤10, preferably 1, 2, 3 or 4, more preferably 1 or 2;
r is 1, 2, 3, 4 or 5; and
$w_1$ and $w_2$ are each integers ≥0 such that their sum ($w_1+w_2$) is 1, 2 or 3.

Preferably, when B-L- is coupled to a nitrogen atom B-L- is one or more of the following:

-continued
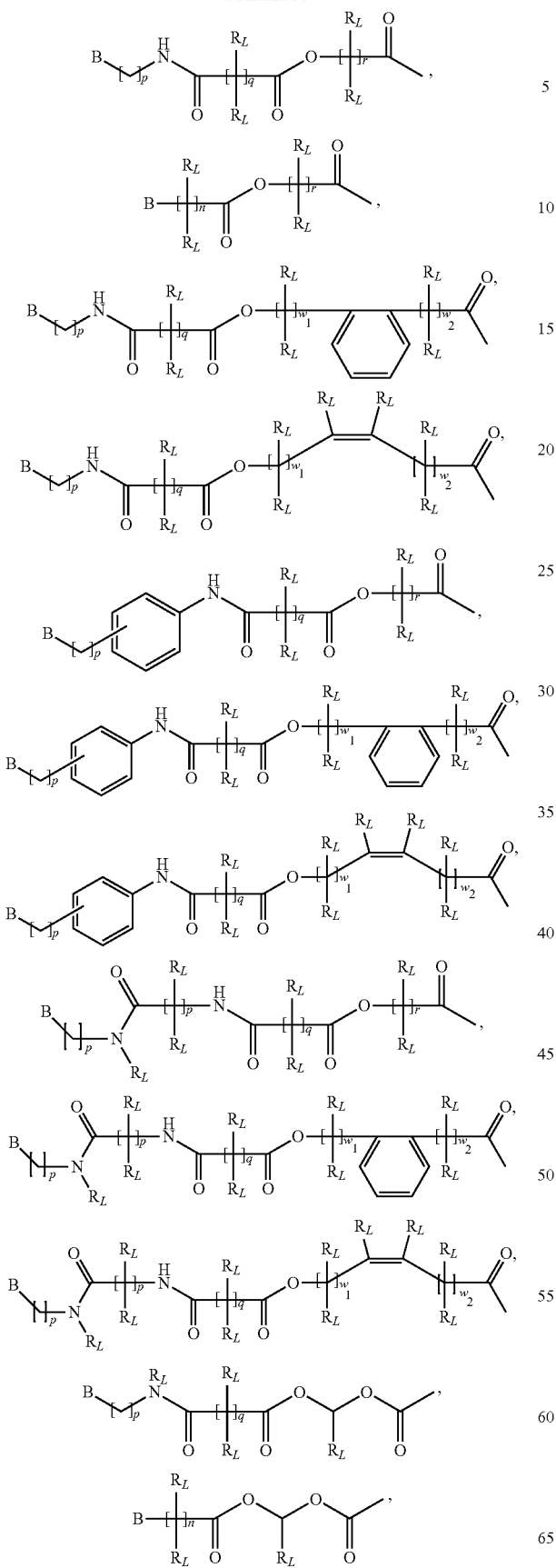
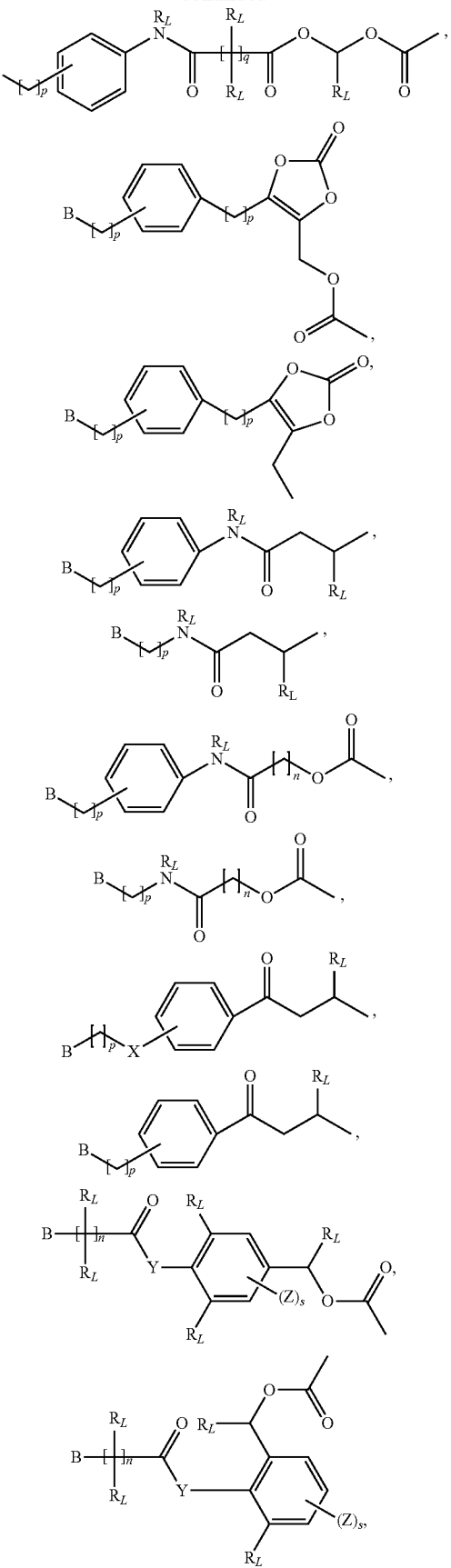

-continued

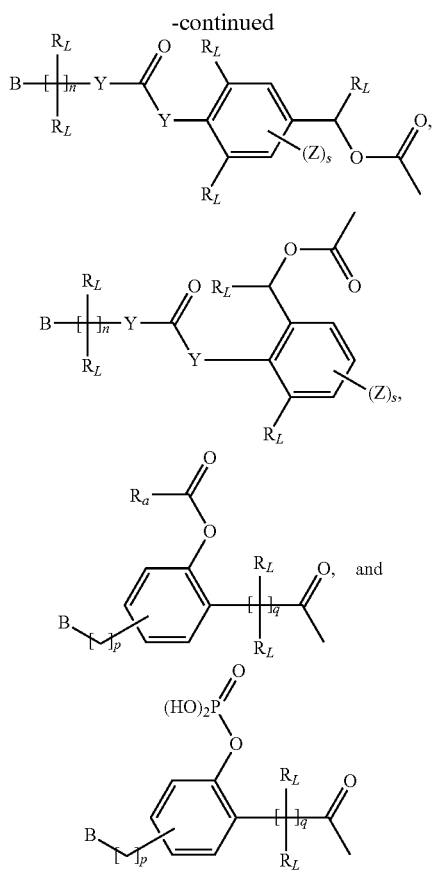
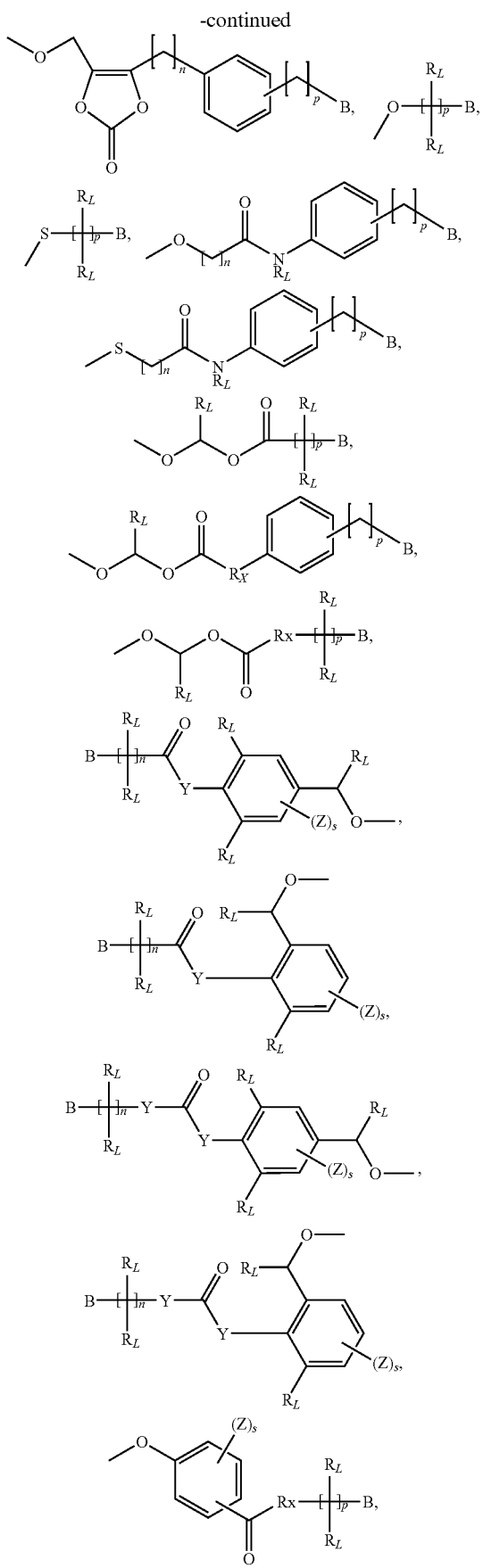

wherein:
- B represents said phosphonated group;
- n is an integer ≤10;
- each p is independently 0 or an integer ≤10;
- each $R_L$ is independently selected from the group consisting of H, ethyl and methyl;
- q is 2 or 3;
- r is 1, 2, 3, 4 or 5;
- $w_1$ and $w_2$ are each integers ≥0 such that their sum ($w_1+w_2$) is 1, 2 or 3.
- X is —$CH_2$—, —$CONR_L$—, —CO—O—$CH_2$—, or —CO—O—; and
- each Y is independently selected from the group consisting of —O—, —S— and —$NR_L$—;
- each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro, wherein s is 1, 2, 3 or 4; and
- $R_a$ is $C_xH_y$, where x is an integer of 0 to 20 and y is an integer of 1 to 2x+1.

Preferably, when B-L- is coupled to the carbonyl of a carboxylate group B-L- is one or more of the following:

-continued

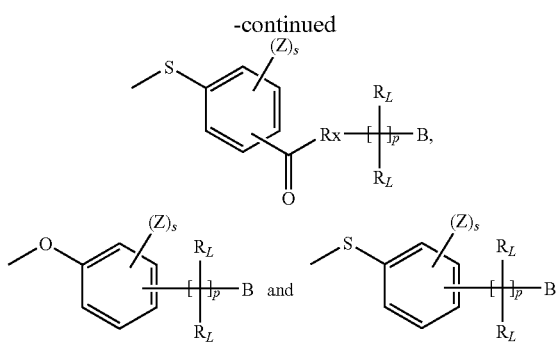

wherein:
n is an integer ≤10, preferably 1, 2, 3 or 4, more preferably 1 or 2;
p is 0 or an integer ≤10, preferably 0, 1, 2, 3 or 4, more preferably 0 or 1;
$R_L$ is H, ethyl or methyl, preferably H;
$R_x$ is —S—, —C($R_L$)$_2$—, —$NR_L$— or —O—; preferably —$NR_L$—, more preferably —NH—;
each Y is independently selected from the group consisting of —O—, —S—, and —$NR_L$—;
each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro; wherein s is 1, 2, 3 or 4; and
B represents the phosphonated group.

In a further preferred embodiment, α is 1, 2 or 3.

Preferably, the glycopeptide or lipoglycopeptide antimicrobial molecule A has a structure represented by the following Formula ($A_1$):

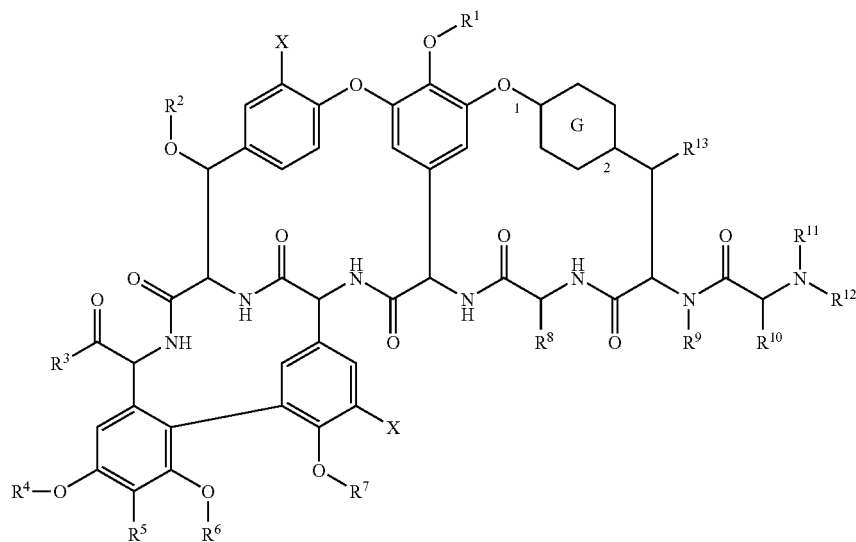

(A$_1$)

as well as pharmaceutically acceptable salts, stereoisomers, esters and prodrugs thereof, where:

$R^1$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$R^a$—Y—$R^b$—(Z)$_x$; or $R^1$ is a saccharide group optionally substituted with —$R^a$—Y—$R^b$—(Z)$_x$, —$R^f$, —C(O)$R_f$, or —C(O)—$R^a$—Y—$R^b$—(Z)$_x$;

$R^2$ is hydrogen or a saccharide group optionally substituted with $R^a$—Y—$R^b$—(Z)$_x$, —$R^f$, —C(O)$R^f$, or —C(O)—$R^a$—Y—$R^b$—(Z)$_x$;

$R^3$ is —OR$^c$, —NR$^c$R$^c$, —O—$R^a$—Y—$R^b$—(Z)$_x$, —NR$^c$—$R^a$—Y—$R^b$—(Z)$_x$, —NR$^c$R$^e$, or —O—R$^e$;

$R^4$ is selected from the group consisting of hydrogen, alkyl, substituted alkyl, alkenyl, substituted alkenyl, alkynyl, substituted alkynyl, —$R^a$—Y—$R^b$—(Z)$_x$, —C(O)R$^d$ and a saccharide group optionally substituted with —$R^a$—Y—$R^b$—(Z)$_x$, —$R^f$, or —C(O)—$R^a$—Y—$R^b$—(Z)$_x$, or $R^4$ and $R^5$ can be joined, together with the atoms to which they are attached, to form a heterocyclic ring optionally substituted with —NR$^c$—$R^a$—Y—$R^b$—(Z)$_x$;

$R^5$ is selected from the group consisting of hydrogen, halo, —CH(R$^c$)—NR$^c$R$^c$, —CH(R$^c$)—NR$^c$R$^e$, —CH(R$^c$)—NR$^c$—$R^a$—Y—$R^b$—(Z)$_x$, —CH(R$^c$)—R$^x$, and —CH(R$^c$)—NR$^c$—$R^a$C(O)—R$^x$;

$R^6$ is selected from the group consisting of hydrogen, alkyl, substituted alkyl, alkenyl, substituted alkenyl, alkynyl, substituted alkynyl, —$R^a$—Y—$R^b$—(Z)$_x$, —C(O)R$^d$ and a saccharide group optionally substituted with —$R^a$—Y—$R^b$—(Z)$_x$, —$R^f$, —C(O)R$^f$, or —C(O)—$R^a$—Y—$R^b$—(Z)$_x$, or $R^5$ and $R^6$ can be joined, together with the atoms to which they are attached, to form a heterocyclic ring optionally substituted with —NR$^c$—$R^a$—Y—$R^b$—(Z)$_x$;

$R^7$ is selected from the group consisting of hydrogen, alkyl, substituted alkyl, alkenyl, substituted alkenyl, alkynyl, substituted alkynyl, —$R^a$—Y—$R^b$—(Z)$_x$, and —C(O)R$^d$;

$R^8$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$R^a$—Y—$R^b$—(Z)$_x$;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^{10}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or $R^8$ and $R^{10}$ are joined to form —$Ar^1$—O—$Ar^2$—, where $Ar^1$ and $Ar^2$ are independently arylene or heteroarylene;

$R^{11}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic, or $R^{10}$ and $R^{11}$ are joined, together with the carbon and nitrogen atoms to which they are attached, to form a heterocyclic ring;

$R^{12}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —C(O)$R^d$, —C(NH)$R^d$, —C(O)N$R^cR^c$, —C(O)O$R^d$, —C(NH)N$R^cR^c$, —$R^a$—Y—$R^b$—(Z)$_x$, and —C(O)—$R^b$—Y—$R^b$—(Z)$_x$, or $R^{11}$ and $R^{12}$ are joined, together with the nitrogen atom to which they are attached, to form a heterocyclic ring;

$R^{13}$ is hydrogen or —O$R^{14}$;

$R^{14}$ is hydrogen, —C(O)$R^d$ or a saccharide group;

$R^a$ is each independently selected from the group consisting of alkylene, substituted alkylene, alkenylene, substituted alkenylene, alkynylene and substituted alkynylene;

$R^b$ is each independently selected from the group consisting of a covalent bond, alkylene, substituted alkylene, alkenylene, substituted alkenylene, alkynylene and substituted alkynylene;

$R^c$ is each independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

$R^d$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^e$ is each a saccharide group;

$R^f$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, and heterocyclic;

$R^x$ is an N-linked amino saccharide or an N-linked heterocycle;

X is each independently selected from the group consisting of hydrogen, fluoro, chloro, bromo and iodo;

Y is each independently selected from the group consisting of, —$CH_2$—, —O—, —S—, —S—S—, —$NR^c$—, —S(O)—, —$SO_2$—, —$NR^cC(O)$—, —$OSO_2$—, —OC(O)—, —N($R^c$)$SO_2$—, —C(O)$NR^c$—, —C(O)O—, —$SO_2NR^c$—, —$SO_2$O—, —P(O)(O$R^c$)O—, —P(O)(O$R^c$)$NR^c$—, —OP(O)(O$R^c$)O—, —OP(O)(O$R^c$)$NR^c$—, —OC(O)O—, —$NR^cC(O)$O—, —$NR^cC(O)NR^c$—, —OC(O)$NR^c$—, —C(O)—, and —N($R^c$)$SO_2NR^c$—;

Z is each independently selected from the group consisting of hydrogen, aryl, cycloalkyl, cycloalkenyl, heteroaryl, heterocyclic; and a saccharide;

x is 1 or 2; and

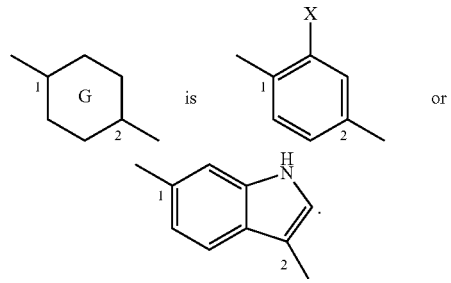

More preferably, the glycopeptide or lipoglycopeptide antimicrobial molecule A is vancomycin, teicoplanin, oritavancin, dalbavancin, telavancin, compound A35512 A, compound A35512 C, compound A35512 E, compound A35512 F, compound A35512 G, compound A35512 H, compound A40926 A, compound A40926 B, compound A40926 PB, parvodicin B2, parvodicin C1, parvodicin C3, compound A41030, compound A42867, compound A477, compound A47934, compound A51568A, N-demethylvancomycin, compound A80407, compound A83850, compound A84575, compound AB65, compound AM374, actaplanin, compound A4696, actinoidin, ardacin, aricidin, compound AAD216, avoparcin, compound LL-AV290, azureomycin, balhimycin, balhimycin V, chloroorienticin, compound A82846B, compound LY264826, chloroeremomycin, chloropeptin, chloropolysporin, complestatin, decaplanin, dechlorobalhimycin, dechlorobalhimycin V, chlorobalhimycin, chlorobromobalhimycin, fluorobalhimycin, deglucobalhimycin, N-demethylbalhimycin, N-demethylvancomycin, devancosamine-vancomycin, eremomycin, galacardin, helvecardin, izupeptin, kibdelin, kistamicin, mannopeptin, methylbalhimycin, compound MM47761, compound MM47766, compound MM47767, compound MM49721, compound MM49727, compound MM55256, compound MM55260, compound MM55266, compound MM55268, compound MM55270, compound MM55272, compound MM56597, compound MM56598, nogabecin F, compound OA7653, orienticin, dechloroeremomycin, compound PA42867, compound PA45052, chloroorienticin, parvodicin, rhamnosyl-balhimycin, ristocetin, ristomycin, spontin, symnonicin, teichomycin, Targocid, ureido-balhimycin or [Ψ[$CH_2NH$]Tpg$^4$]Vancomycin.

In another embodiment, the compounds of the invention are represented by Formula (II):

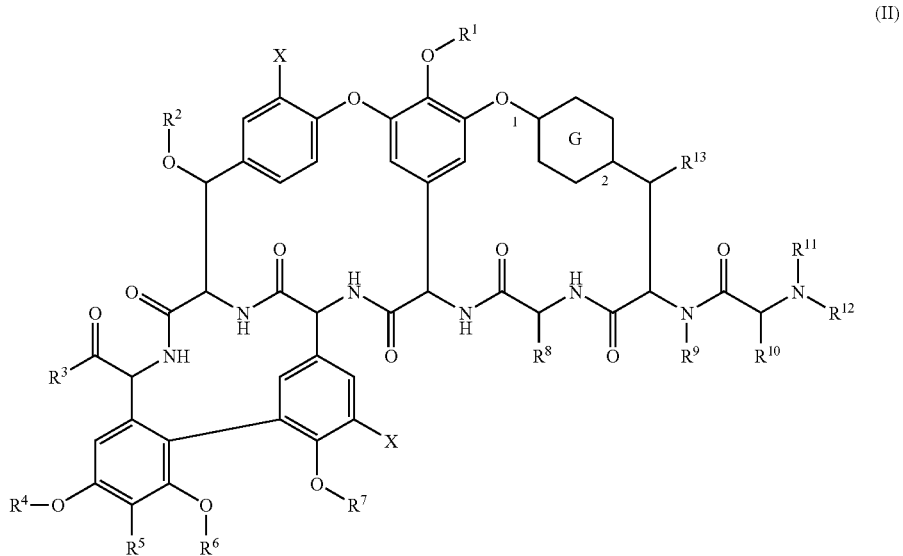

as well as pharmaceutically acceptable salts, esters and prodrugs thereof, where:

R¹ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —Rᵃ—Y—Rᵇ—(Z)ₓ and -L¹; or R¹ is a saccharide group optionally substituted with —Rᵃ—Y—Rᵇ—(Z)ₓ, —Rᶠ, —C(O)Rᶠ, —C(O)—Rᵃ—Y—Rᵇ—(Z)ₓ, —C(NL²)Rᶠ, or —C(NL³)-Rᵃ—Y—Rᵇ—(Z)ₓ;

R² is hydrogen, -L⁴ or a saccharide group optionally substituted with —Rᵃ—Y—Rᵇ—(Z)ₓ, —Rᶠ, —C(O)Rᶠ, —C(O)—Rᵃ—Y—Rᵇ—(Z)ₓ, —C(NL⁵)Rᶠ, or —C(NL⁶)—Rᵃ—Y—Rᵇ—(Z)ₓ;

R³ is selected from the group consisting of —ORᶜ, —NRᶜRᶜ, —O—Rᵃ—Y—Rᵇ—(Z)ₓ, —NRᶜ—Rᵃ—Y—Rᵇ—(Z)ₓ, —NRᶜRᵉ, —O—Rᵉ, —OL⁷, —NL⁸Rᶜ, and —NL⁹Rᵉ;

R⁴ is selected from the group consisting of hydrogen, alkyl, substituted alkyl, alkenyl, substituted alkenyl, alkynyl, substituted alkynyl, -L¹⁰, —Rᵃ—Y—Rᵇ—(Z)ₓ, —C(O)Rᵈ, —C(NL¹¹)Rᵈ and a saccharide group optionally substituted with —Rᵃ—Y—Rᵇ—(Z)ₓ, —Rᶠ, —C(O)—Rᵃ—Y—Rᵇ—(Z)ₓ, or —C(NL¹²)—Rᵃ—Y—Rᵇ—(Z)ₓ, or R⁴ and R⁵ can be joined, together with the atoms to which they are attached, to form a heterocyclic ring optionally substituted with —NRᶜ—Rᵃ—Y—Rᵇ—(Z)ₓ or —NL¹³-Rᵃ—Y—Rᵇ—(Z)ₓ;

R⁵ is selected from the group consisting of hydrogen, halo, —CH(Rᶜ)—NRᶜRᶜ, —CH(Rᶜ)—NRᶜRᵉ, —CH(Rᶜ)—NRᶜ—Rᵃ—Y—Rᵇ—(Z)ₓ, —CH(Rᶜ)—Rˣ, —CH(Rᶜ)—NRᶜ—Rᵃ—C(O)—Rˣ; —CH(Rᶜ)—NL¹⁴Rᶜ, —CH(Rᶜ)—NL¹⁵Rᵉ, —CH(Rᶜ)—NL¹⁶-Rᵃ—Y—Rᵇ—(Z)ₓ, —CH(Rᶜ)—NL¹⁷-Rᵃ—C(O)—Rˣ and —CH(Rᶜ)—NRᶜ—RᵃC(NL¹⁸)—Rˣ, R⁶ is selected from the group consisting of hydrogen, alkyl, substituted alkyl, alkenyl, substituted alkenyl, alkynyl, substituted alkynyl, -L¹⁹, —Rᵃ—Y—Rᵇ—(Z)ₓ, —C(O)Rᵈ, —C(NL²⁰)Rᵈ and a saccharide group optionally substituted with —Rᵃ—Y—Rᵇ—(Z)ₓ, —Rᶠ, —C(O)Rᶠ, —C(O)—Rᵃ—Y—Rᵇ—(Z)ₓ, —C(NL²¹)Rᶠ, or —C(NL²²)—Rᵃ—Y—Rᵇ—(Z)ₓ; or R⁵ and R⁶ can be joined, together with the atoms to which they are attached, to form a heterocyclic ring optionally substituted with —NRᶜ—Rᵃ—Y—Rᵇ—(Z)ₓ or —NL²³-Rᵃ—Y—Rᵇ—(Z)ₓ;

R⁷ is selected from the group consisting of hydrogen, alkyl, substituted alkyl, alkenyl, substituted alkenyl, alkynyl, substituted alkynyl, -L²⁴, —Rᵃ—Y—Rᵇ—(Z)ₓ, —C(O)Rᵈ, and —C(NL²⁵)Rᵈ;

R⁸ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —Rᵃ—Y—Rᵇ—(Z)ₓ;

R⁹ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic; and -L²⁶;

R¹⁰ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or R⁸ and R¹⁰ are joined to form —Ar¹—O—Ar²—, where Ar¹ and Ar² are independently arylene or heteroarylene which may optionally be substituted with —OL²⁷;

R¹¹ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, and -L²⁸; or R¹⁰ and R¹¹ are joined, together with the carbon and nitrogen atoms to which they are attached, to form a heterocyclic ring which may optionally be substituted with —OL²⁹, —CO₂L³⁰ or —NL³¹Rᶜ;

R¹² is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, -$L^{32}$, —C(O)$R^d$, —C(NH)$R^d$, —C(O)NR$^c$R$^c$, —C(O)OR$^d$, —C(NH)NR$^c$R$^c$, —R$^a$—Y—R$^b$—(Z)$_x$, and —C(O)—R$^b$—Y—R$^b$—(Z)$_x$, —C(N$L^{33}$)R$^d$, —C(O)N$L^{34}$R$^c$, —C(O)O$L^{35}$, —C(NH)N$L^{36}$R$^c$, —C(N$L^{37}$)NR$^c$R$^c$, and —C(N$L^{38}$)—R$^b$—Y—R$^b$—(Z)$_x$; or $R^{11}$ and $R^{12}$ are joined, together with the nitrogen atom to which they are attached, to form a heterocyclic ring which may optionally be substituted with —O$L^{39}$, —CO$_2$$L^{40}$ or —N$L^{41}$R$^c$;

$R^{13}$ is hydrogen or —O$R^{14}$;

$R^{14}$ is selected from the group consisting of hydrogen, -$L^{42}$, —C(O)$R^d$, —C(N$L^{43}$)$R^d$ and a saccharide group optionally substituted with —R$^a$—Y—R$^b$—(Z)$_x$, —R$^f$, —C(O)R$^f$, —C(O)—R$^a$—Y—R$^b$—(Z)$_x$, —C(N$L^{44}$)R$^f$, or —C(N$L^{45}$)—R$^a$—Y—R$^b$—(Z)$_x$;

R$^a$ is each independently selected from the group consisting of alkylene, substituted alkylene, alkenylene, substituted alkenylene, alkynylene and substituted alkynylene;

R$^b$ is each independently selected from the group consisting of a covalent bond, alkylene, substituted alkylene, alkenylene, substituted alkenylene, alkynylene and substituted alkynylene;

R$^c$ is each independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^d$;

R$^d$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

R$^e$ is each a saccharide group optionally substituted with —R$^a$—Y—R$^b$—(Z)$_x$, —R$^f$, —C(O)R$^f$, —C(O)—R$^a$—Y—R$^b$—(Z)$_x$, —C(N$L^{46}$)R$^f$, or —C(N$L^{47}$)—R$^a$—Y—R$^b$—(Z)$_x$;

R$^f$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, and heterocyclic;

R$^x$ is an N-linked amino saccharide or an N-linked heterocycle, either of which may be optionally substituted with —R$^a$—Y—R$^b$—(Z)$_x$, —R$^f$, —C(O)R$_f$, —C(O)—R$^a$—Y—R$^b$—(Z)$_x$, —C(N$L^{48}$)R$_f$, or —C(N$L^{49}$)—R$^a$—Y—R$^b$—(Z)$_x$;

X is each independently selected from the group consisting of hydrogen, fluoro, chloro, bromo and iodo;

Y is each independently selected from the group consisting of —CH$_2$—, —O—, —S—, —S—S—, —NR$^c$—, —S(O)—, —SO$_2$—, —NR$^c$C(O)—, —OSO$_2$—, —OC(O)—, —N(R$^c$)SO$_2$—, —C(O)NR$^c$—, —C(O)O—, —SO$_2$NR$^c$—, —SO$_2$O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^c$C(O)O—, —NR$^c$C(O)NR$^c$—, —OC(O)NR$^c$, —C(O)—, —N(R$^c$)SO$_2$NR$^c$—, —N$L^{50}$-, —N$L^{51}$C(O)—, —OSO$_2$—, —OC(O)—, —N($L^{52}$)SO$_2$—, —C(O)N$L^{53}$—, —SO$_2$N$L^{54}$-, —P(O)(O$L^{55}$)O—, —P(O)(O$L^{56}$)NR$^c$—, —P(O)(OR$^c$)N$L^{57}$-, —OP(O)(O$L^{58}$)O—, —OP(O)(O$L^{59}$)NR$^c$—, —OP(O)(OR$^c$)N$L^{60}$-, —N$L^{61}$C(O)O—, —N$L^{62}$C(O)NR$^c$—, —NR$^c$C(O)N$L^{63}$-, —OC(O)N$L^{64}$-, —N($L^{65}$)SO$_2$NR$^c$— and —N(R$^c$)SO$_2$N$L^{66}$-;

Z is each independently selected from the group consisting of hydrogen, aryl, cycloalkyl, cycloalkenyl, heteroaryl, heterocyclic, a saccharide, -$L^{67}$, -$L^{68}$ and -$L^{69}$;

x is 1 or 2; and

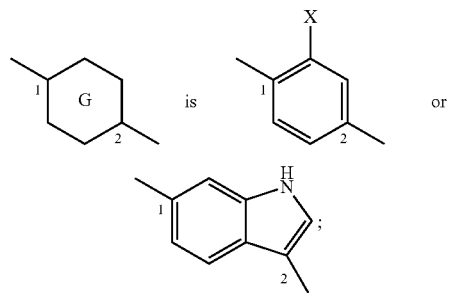

each $L^1$, $L^4$, $L^{10}$, $L^{19}$, $L^{24}$, $L^{27}$, $L^{29}$, $L^{39}$, $L^{42}$, and $L^{67}$ is a linker independently selected from the group consisting of

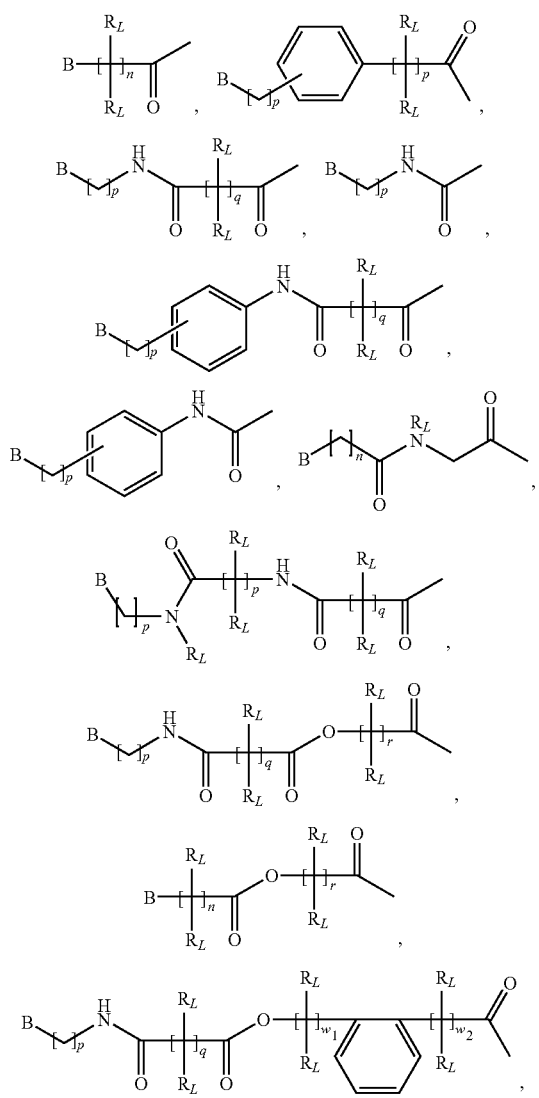

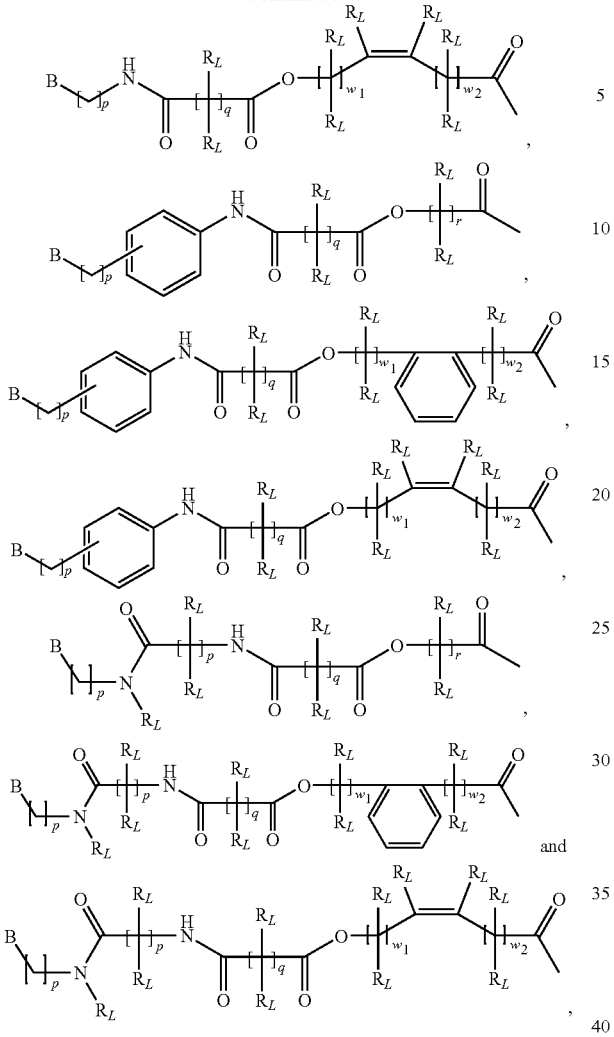
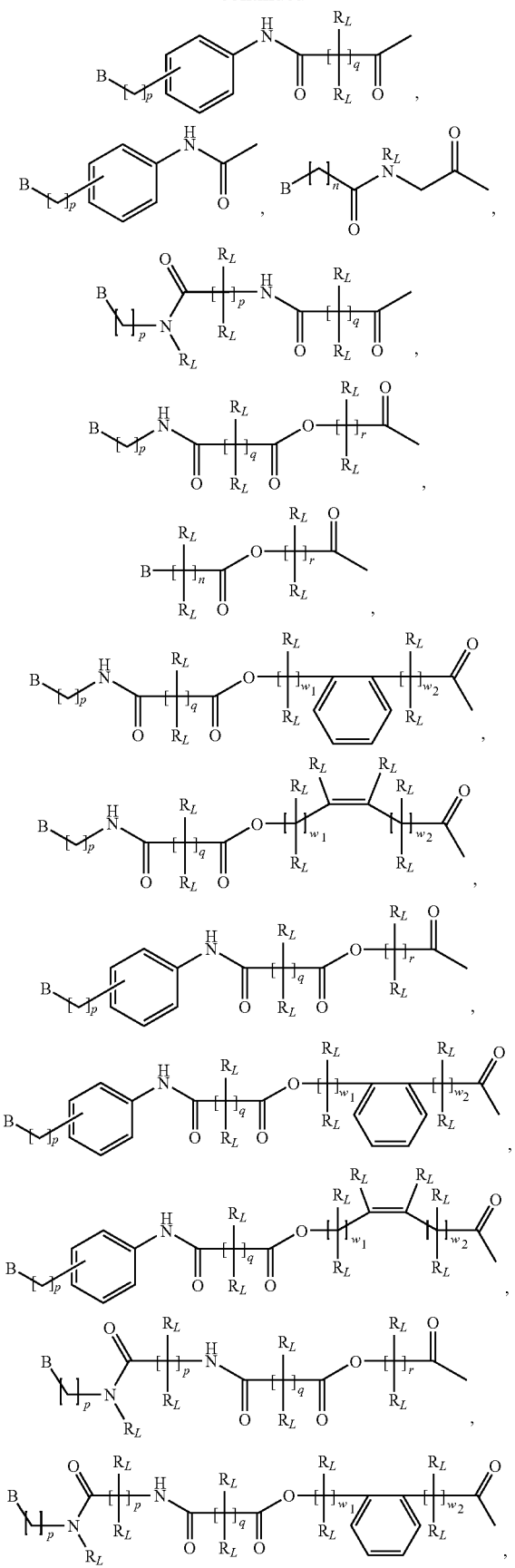

wherein:
B represents said phosphonated group;
each p is independently 0 or an integer ≤10;
each $R_L$ is independently selected from the group consisting of H, ethyl and methyl;
q is 2 or 3;
n is an integer ≤10;
r is 1, 2, 3, 4 or 5; and
$w_1$ and $w_2$ are each integers ≥0 such that their sum ($w_1+w_2$) is 1, 2 or 3;
each $L^8$, $L^9$, $L^{13}$, $L^{14}$, $L^{15}$, $L^{16}$, $L^{17}$, $L^{23}$, $L^{26}$, $L^{28}$, $L^{31}$, $L^{32}$, $L^{34}$, $L^{36}$, $L^{37}$, $L^{41}$, $L^{50}$, $L^{51}$, $L^{52}$, $L^{53}$, $L^{54}$, $L^{57}$, $L^{60}$, $L^{61}$, $L^{62}$, $L^{63}$, $L^{64}$, $L^{65}$, $L^{66}$ and $L^{68}$ is a linker independently selected from the group consisting of

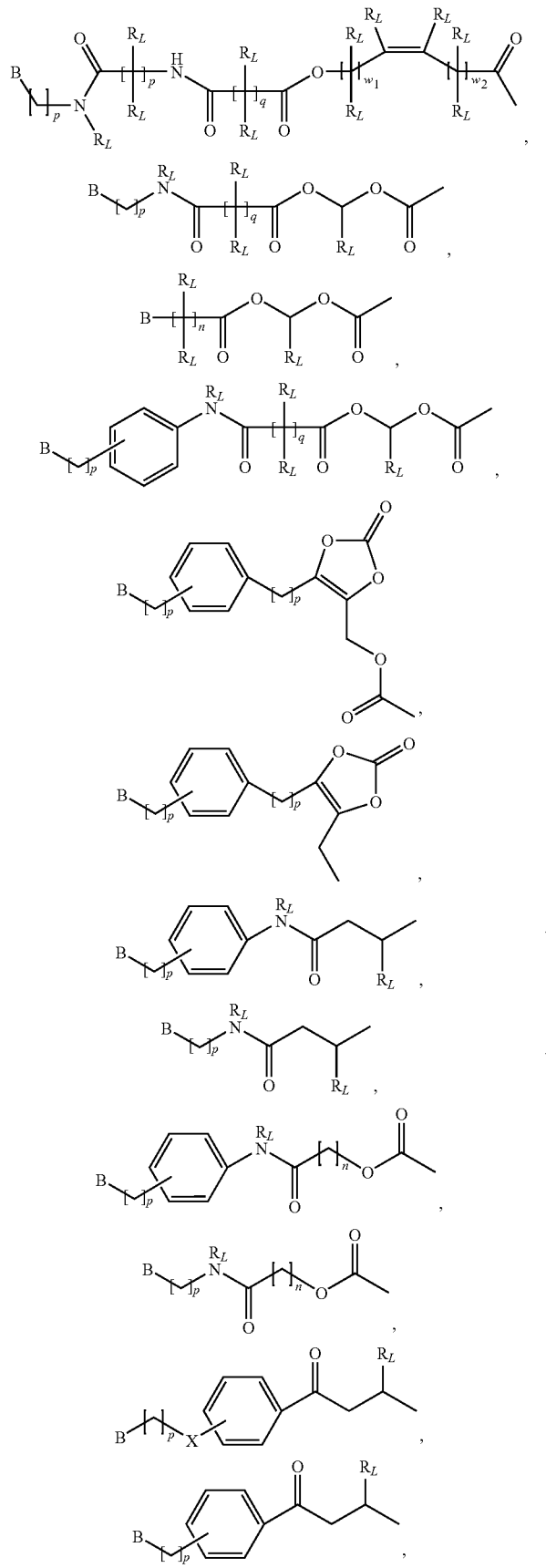

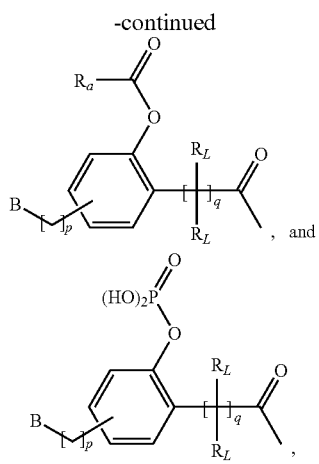

wherein:
B represents said phosphonated group;
n is an integer ≤10;
each p is independently 0 or an integer ≤10;
each $R_L$ is independently selected from the group consisting of H, ethyl and methyl;
q is 2 or 3;
r is 1, 2, 3, 4 or 5;
$w_1$ and $w_2$ are each integers ≥0 such that their sum ($w_1+w_2$) is 1, 2 or 3;
X is —$CH_2$—, —$CONR_L$—, —CO—O—$CH_2$—, or —CO—O—; and
$R_a$ is $C_xH_y$ where x is an integer of 0 to 20 and y is an integer of 1 to 2x+1;
each $L^7$, $L^{30}$, $L^{35}$, $L^{40}$, $L^{55}$, $L^{56}$, $L^{58}$, $L^{59}$ and $L^{69}$ is a linker independently selected from the group consisting of

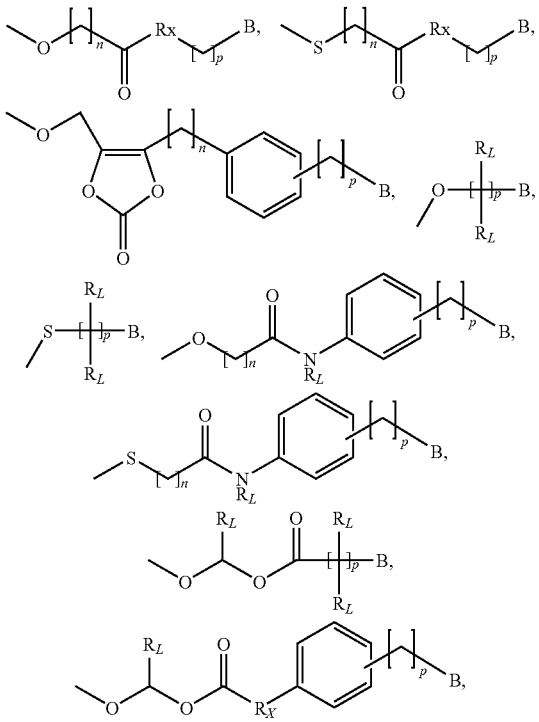

-continued

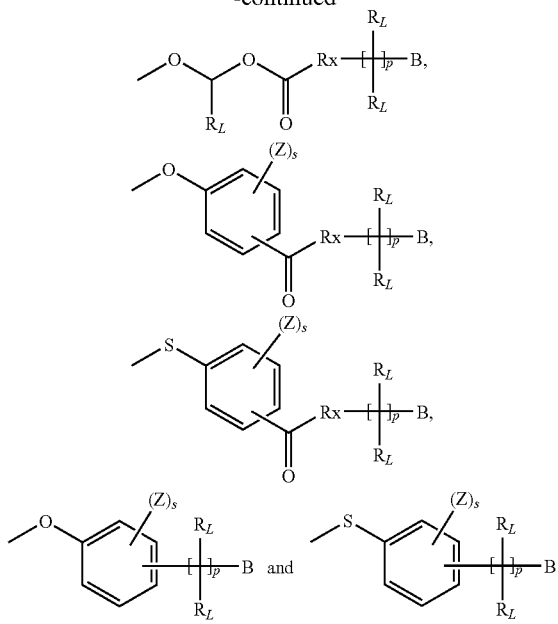

wherein:
n is an integer ≤10, preferably 1, 2, 3 or 4, more preferably 1 or 2;
p is 0 or an integer 10, preferably 0, 1, 2, 3 or 4, more preferably 0 or 1;
$R_L$ is H, ethyl or methyl, preferably H;
$R_x$ is —S—, —C($R_L$)$_2$—, —NR$_L$— or —O—; preferably —NR$_L$—, more preferably —NH—;
each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro, wherein s is 1, 2, 3 or 4; and
B represents the phosphonated group;
each $L^2$, $L^3$, $L^5$, $L^6$, $L^{11}$, $L^{12}$, $L^{18}$, $L^{20}$, $L^{21}$, $L^{22}$, $L^{25}$, $L^{33}$, $L^{38}$, $L^{43}$, $L^{44}$, $L^{45}$, $L^{46}$, $L^{47}$, $L^{48}$ and $L^{49}$ is a linker independently

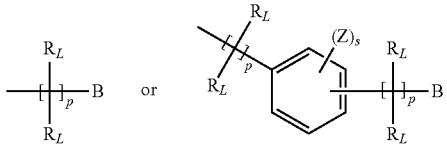

wherein:
p is 0 or an integer ≤10, preferably 0, 1, 2, 3 or 4, more preferably 0 or 1;
$R_L$ is H, ethyl or methyl, preferably H;
each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro, wherein s is 1, 2, 3 or 4; and
B represents the phosphonated group;

with the proviso that at least one of $L^1$, $L^2$, $L^3$, $L^4$, $L^5$, $L^6$, $L^7$, $L^8$, $L^9$, $L^{10}$, $L^{11}$, $L^{12}$, $L^{13}$, $L^{14}$, $L^{15}$, $L^{16}$, $L^{17}$, $L^{18}$, $L^{19}$, $L^{20}$, $L^{21}$, $L^{22}$, $L^{23}$, $L^{24}$, $L^{25}$, $L^{26}$, $L^{27}$, $L^{28}$, $L^{29}$, $L^{30}$, $L^{31}$, $L^{32}$, $L^{33}$, $L^{34}$, $L^{35}$, $L^{36}$, $L^{37}$, $L^{38}$, $L^{39}$, $L^{40}$, $L^{41}$, $L^{42}$, $L^{43}$, $L^{44}$, $L^{45}$, $L^{46}$, $L^{47}$, $L^{48}$, $L^{49}$, $L^{50}$, $L^{51}$, $L^{52}$, $L^{53}$, $L^{54}$, $L^{55}$, $L^{56}$, $L^{57}$, $L^{58}$, $L^{59}$, $L^{60}$, $L^{61}$, $L^{62}$, $L^{63}$, $L^{64}$, $L^{65}$, $L^{66}$, $L^{67}$, $L^{68}$ and $L^{69}$ is present.

In a preferred embodiment of formula (II), B is a phosphonated group selected from the group consisting of:

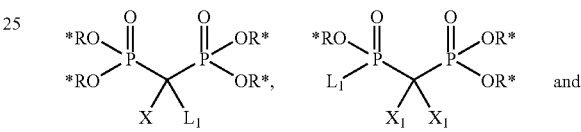

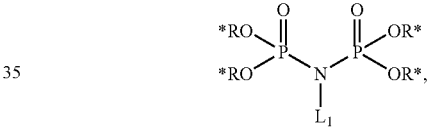

wherein:
each R* is independently selected from the group consisting of H, lower alkyl, cycloalkyl, aryl and heteroaryl, with the proviso that at least two R* are H;
X is H, OH, NH$_2$, or a halo group;
$X_1$ are both H, or each is independently selected from the group consisting of H, OH, NH$_2$, and a halo group; and
$L_1$ is the point of attachment to L.

In further preferred embodiments, the compounds of the invention have a structure selected among the structures illustrated below, as well as pharmaceutically acceptable salts, esters, stereoisomers, and prodrugs thereof:

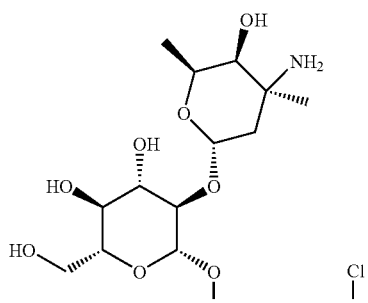

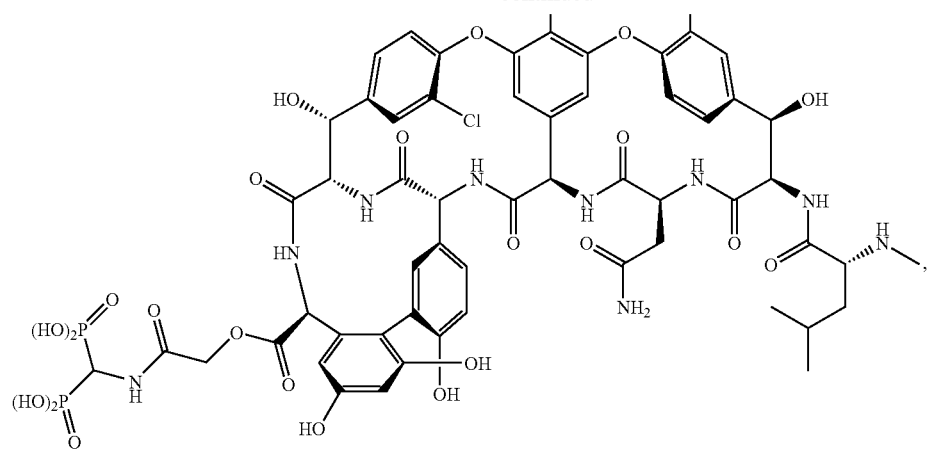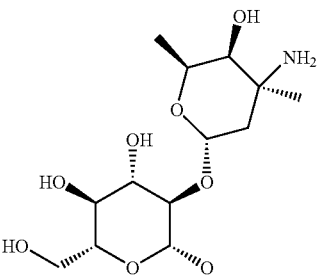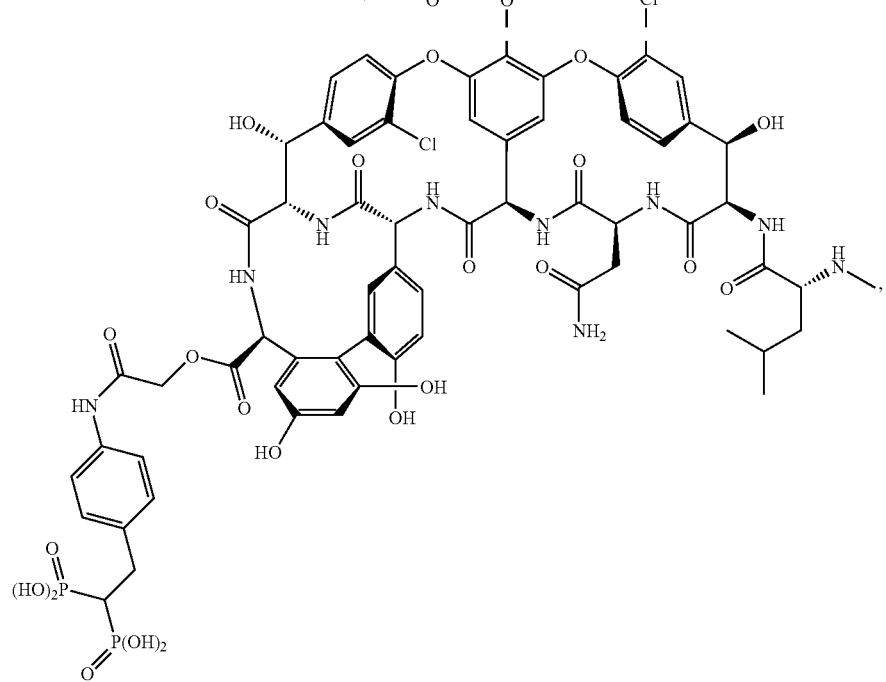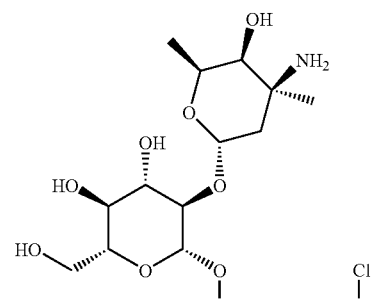

-continued
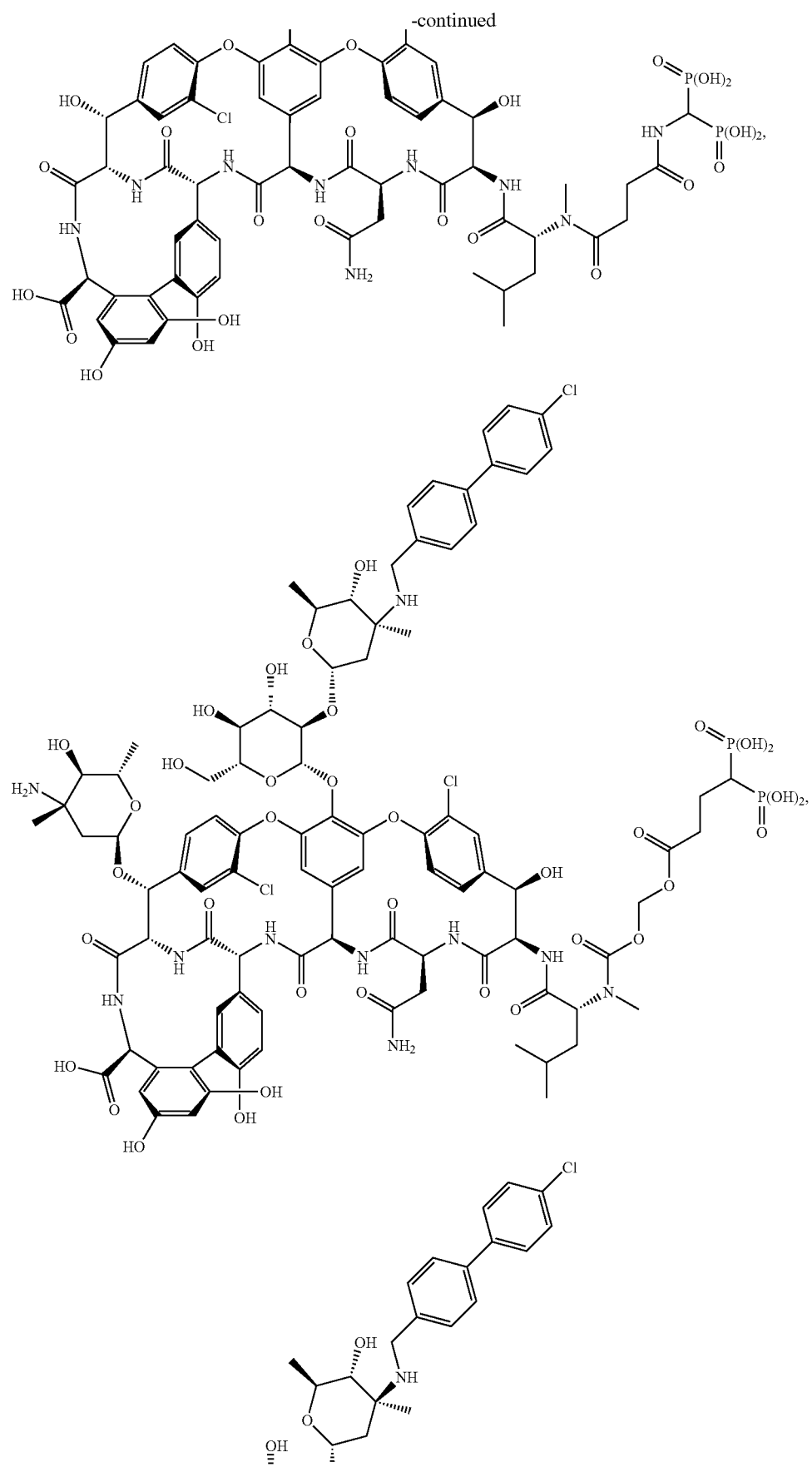

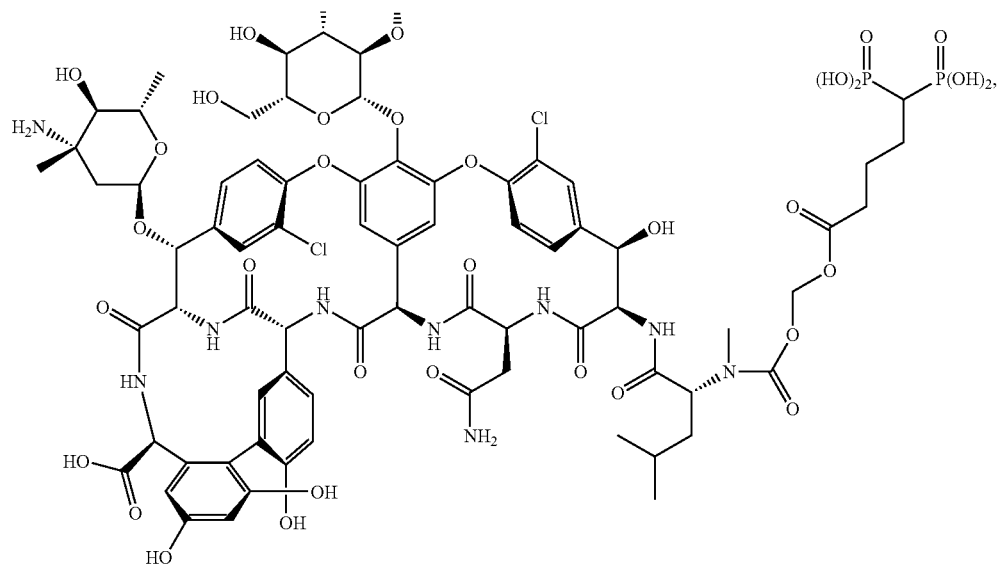
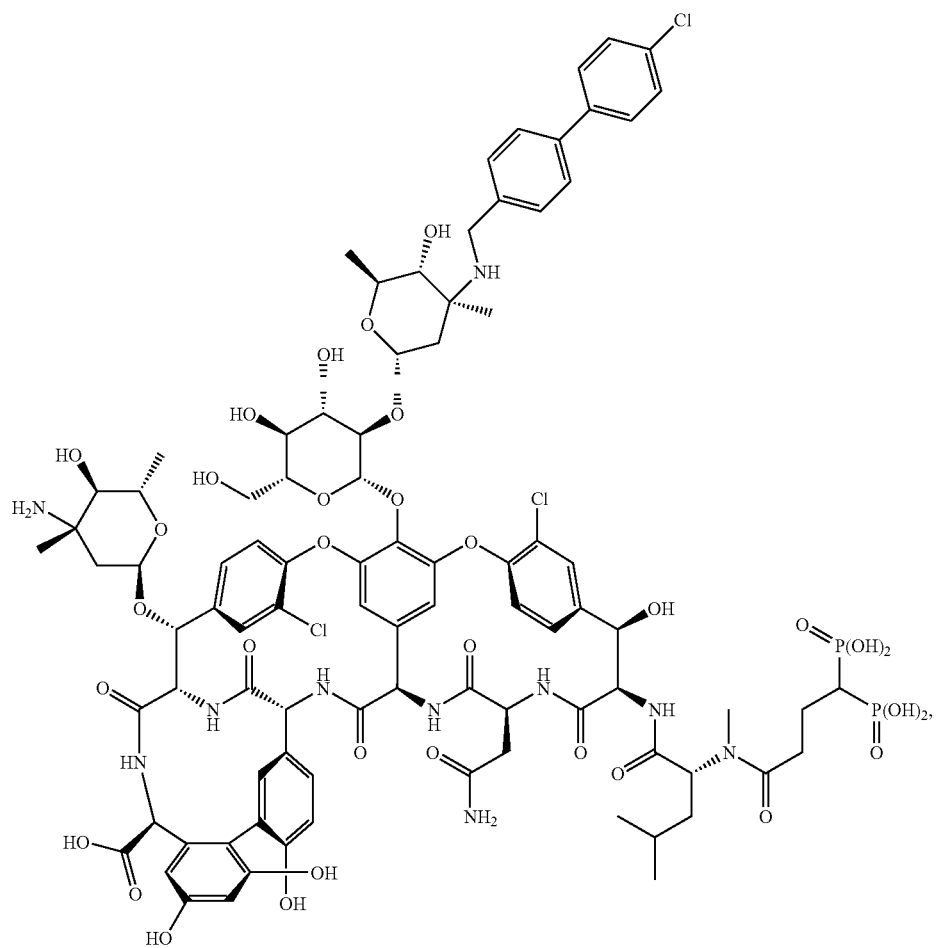

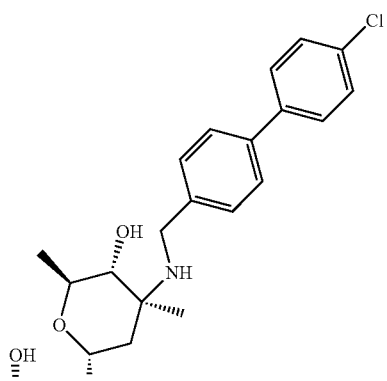
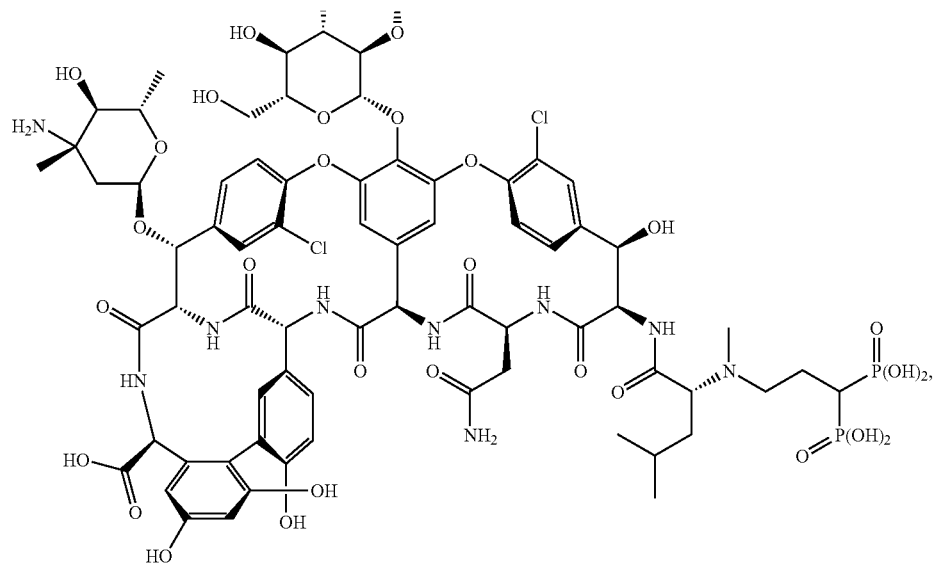
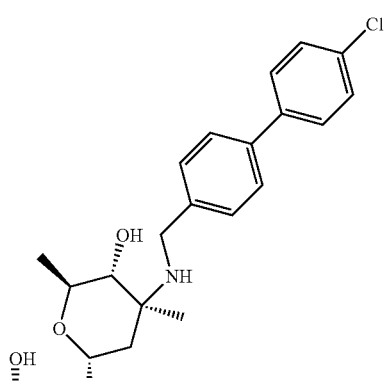

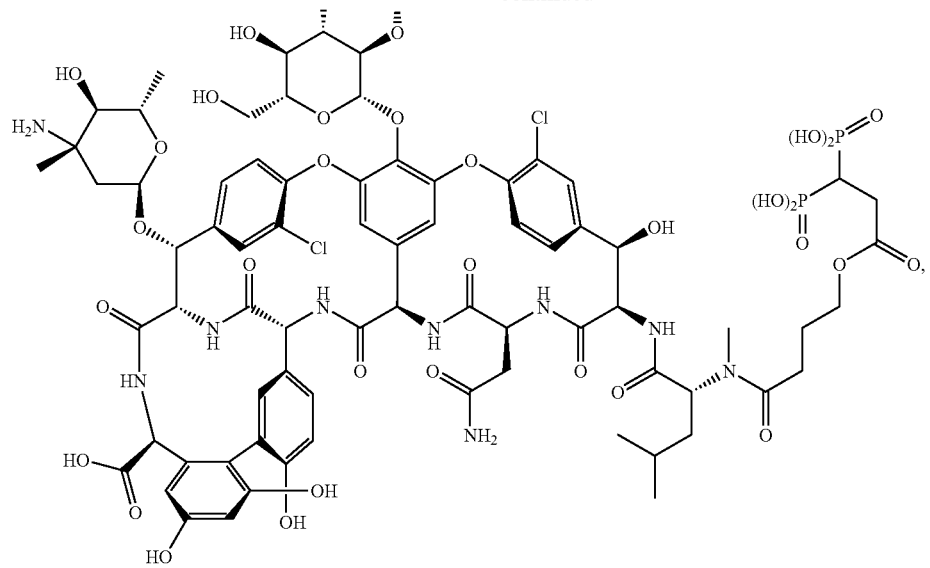
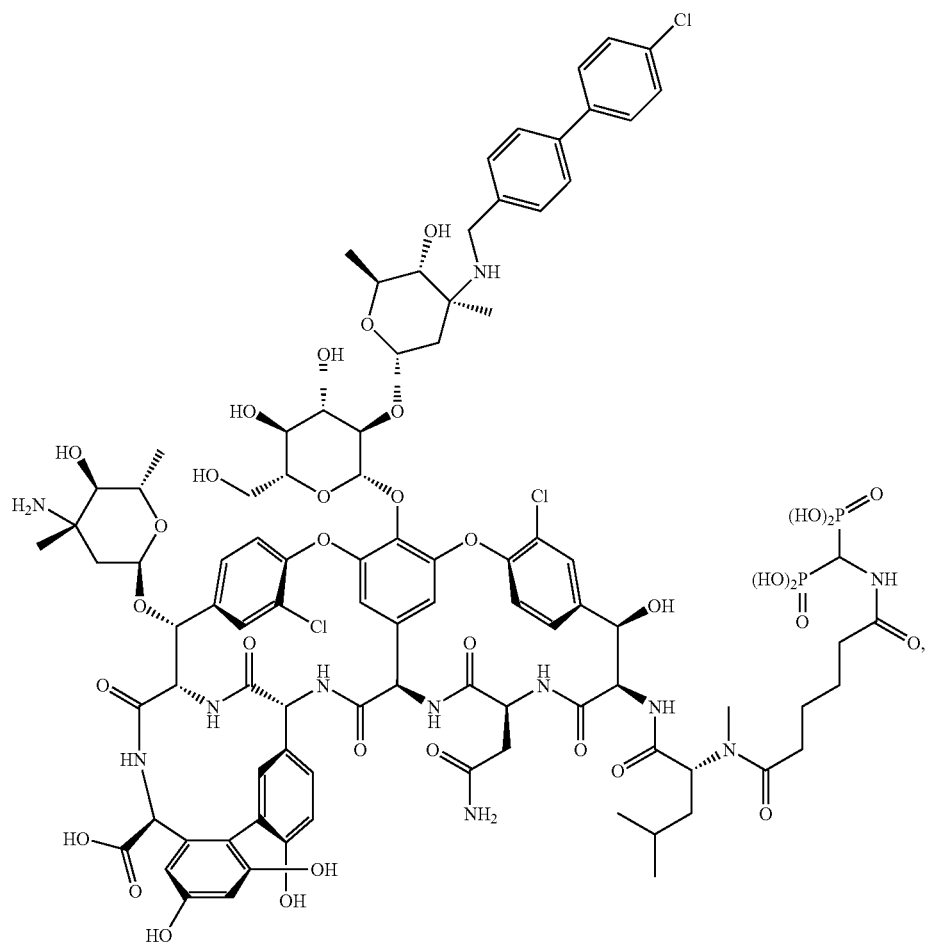

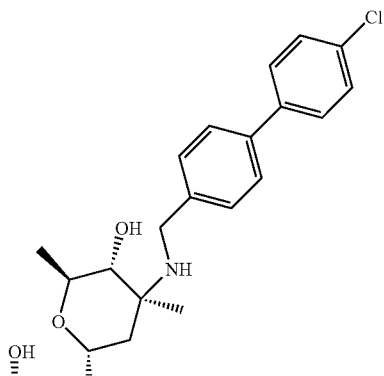
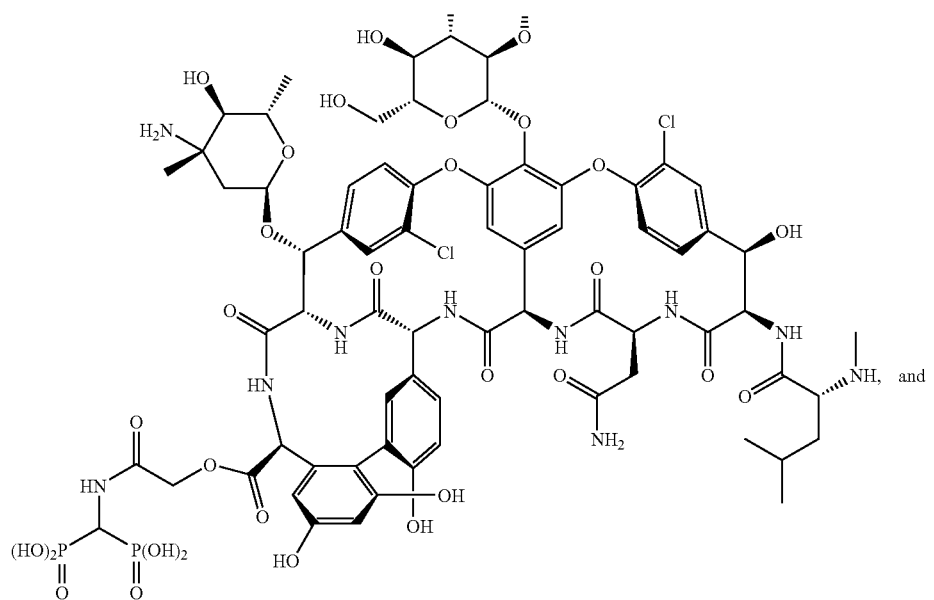
and
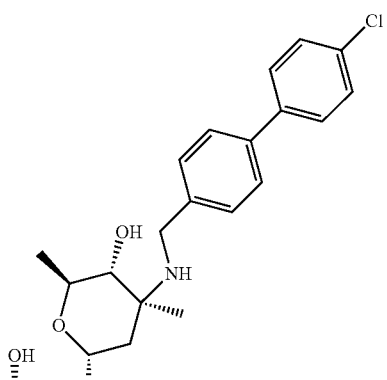

-continued

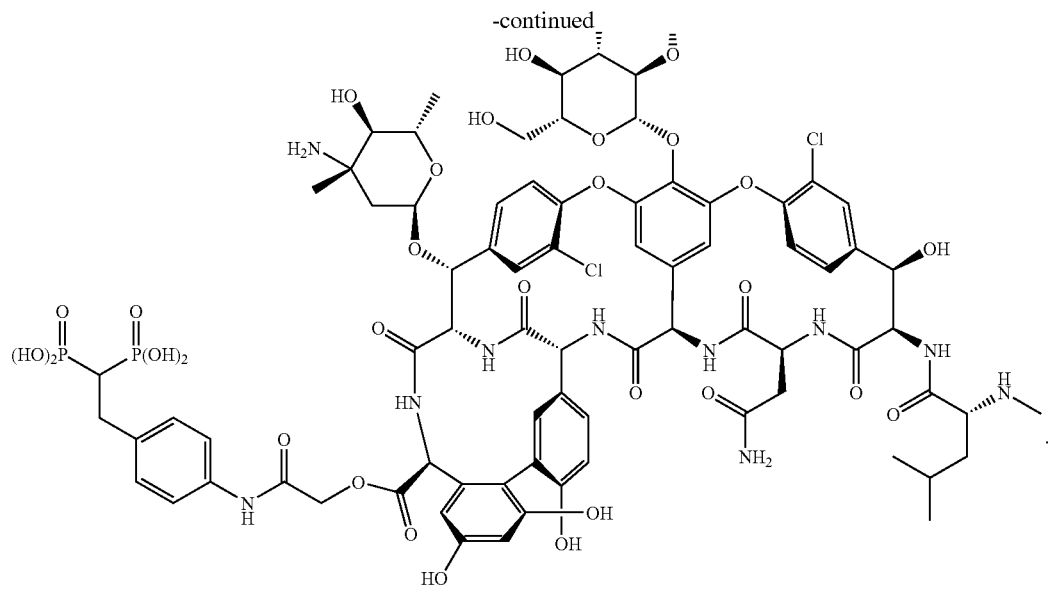

In another aspect of the present invention there are disclosed pharmaceutical compositions comprising one or more of the compounds as defined herein and a pharmaceutically acceptable carrier or excipient.

The present invention encompasses methods for treating a bacterial infection in a subject, comprising administering to a subject having a bacterial infection or otherwise in need of such treatment a pharmaceutically effective amount of one or more of the compounds as defined herein, or a pharmaceutical composition as defined herein. The subject may be an animal, preferably a mammal, more preferably a human.

The present invention also encompasses methods for preventing a bacterial infection in a subject, comprising administering to a subject at risk for developing a bacterial infection or otherwise in need of such prevention a pharmaceutically effective amount of one or more of the compounds as defined herein, or a pharmaceutical composition as defined herein. The subject may be an animal, preferably a mammal, more preferably a human.

The present invention further encompasses methods of prophylaxis for a bacterial infection in a subject, comprising administering to a subject in need of such prophylaxis a prophylactically effective amount of one or more of the compounds as defined herein, or a pharmaceutical composition as defined herein. The prophylactically effective amount of the compounds or pharmaceutical composition may be administered, for example, to a subject prior to, during, or after an invasive medical treatment. The subject may be an animal, preferably a mammal, more preferably a human.

The present invention encompasses methods for treating a bacterial infection in a subject, comprising administering to a subject having a bacterial infection or otherwise in need of such treatment a pharmaceutically effective amount of one or more of the compounds as defined herein, or a pharmaceutical composition as defined herein, and concurrently administering a second therapeutic agent. The subject may be an animal, preferably a mammal, more preferably a human.

The present invention also encompasses methods for preventing a bacterial infection in a subject, comprising administering to a subject at risk for developing a bacterial infection or otherwise in need of such prevention a pharmaceutically effective amount of one or more of the compounds as defined herein, or a pharmaceutical composition as defined herein, and concurrently administering a second therapeutic agent. The subject may be an animal, preferably a mammal, more preferably a human.

The present invention further encompasses methods of prophylaxis for a bacterial infection in a subject, comprising administering to a subject in need of such prophylaxis a prophylactically effective amount of one or more of the compounds as defined herein, or a pharmaceutical composition as defined herein, and concurrently administering a second therapeutic agent. The prophylactically effective amount of the compounds or pharmaceutical composition, and the second therapeutic agent, may be administered, for example, to a subject prior to, during, or after an invasive medical treatment. The subject may be an animal, preferably a mammal, more preferably a human.

Preferably the second therapeutic agent is an antibiotic. More preferably the second therapeutic agent is an antibiotic selected from the group consisting of tetracycline, a tetracycline derived antibacterial agent, glycylcycline, a glycylcycline derived antibacterial agent, minocycline, a minocycline derived antibacterial agent, an oxazolidinone antibacterial agent, an aminoglycoside antibacterial agent, a quinolone antibacterial agent, vancomycin, a vancomycin derived antibacterial agent, a teicoplanin, a teicoplanin derived antibacterial agent, eremomycin, an eremomycin derived antibacterial agent, chloroeremomycin, a chloroeremomycin derived antibacterial agent, daptomycin, a daptomycin derived antibacterial agent, Rifamycin, a Rifamycin derived antibacterial agent, Rifampin, a Rifampin derived antibacterial agent, Rifalazil, a Rifalazil derived antibacterial agent, Rifabutin, a Rifabutin derived antibacterial agent, Rifapentin, a Rifapentin derived antibacterial agent, Rifaximin and a Rifaximin derived antibacterial agent.

The invention also provides a method of accumulating a glycopeptide or lipoglycopeptide antimicrobial molecule in a bone of a subject, comprising administering to a subject one or more of the compounds as defined herein, or a pharmaceutical composition as defined herein, whereby the compound or pharmaceutical composition binds osseous tissue and accumulates in the bone of the subject. The subject may be an animal, preferably a mammal, more preferably a human.

The invention further provides a method for prolonging the presence of a glycopeptide or lipoglycopeptide antimicrobial molecule in a bone of a subject, comprising administering to a subject one or more of the compounds as defined herein, or a pharmaceutical composition as defined herein, whereby the compound or pharmaceutical composition binds osseous tissue and accumulates in the bone of the subject, and whereby cleavage of the linker of the compounds is gradual within the bone, thereby prolonging the presence of the glycopeptide or lipoglycopeptide antimicrobial molecule in the bone. The subject may be an animal, preferably a mammal, more preferably a human.

In a further aspect of the present invention there are provided processes for the preparation of phosphonated glycopeptide and lipoglycopeptide antimicrobial molecule, preferably glycopeptide and lipoglycopeptide antimicrobial molecule of Formula (I) and/or Formula (II) as defined herein.

An advantage of the invention is that it provides antimicrobial compounds having an increased binding affinity for bone. The invention also provides methods for the unmet medical need of prevention and treatment of bone and joint infections.

Additional objects, advantages and features of the present invention will become more apparent upon reading of the following non-restrictive description of preferred embodiments with reference to the accompanying drawings which are exemplary and should not be interpreted as limiting the scope of the present invention.

DETAILED DESCRIPTION OF THE INVENTION

A) General Overview of the Invention

The present invention discloses phosphonated derivatives of glycopeptide and lipoglycopeptide antibiotics of structural Formula I and Formula II as defined above. These compounds are useful antimicrobial agents effective against a number of human and veterinary pathogens.

The essence of the invention lies in the presence of a phosphonated group attached to a glycopeptide and lipoglycopeptide antibiotic. Since phosphonic acid derivatives are known to have a high affinity to bone due to their ability to bind the $Ca^{2+}$ ions found in the hydroxyapatite forming bone tissues, the present inventors have hypothesized that it would be possible to increase the binding affinity, adsorption and retention of glycopeptide and lipoglycopeptide antibiotics by the bones by tethering a phosphonated group to such an antibiotic. Achieving high concentrations of glycopeptide and lipoglycopeptide antibiotics in vascularized bone (in comparison with the concentrations achieved by administration of a non-phosphonated antibiotic), could prove to increase the concentration of the antibiotic in contiguous devascularized bones (sequestrum) to a level sufficient to eradicate microbes present in this locus of treatment resistance.

Actually, the present inventors have synthesized such phosphonated derivatives of glycopeptide and lipoglycopeptide antibiotics and demonstrated that these derivatives have an increased affinity for bony materials. The present inventors have also shown that these phosphonated derivatives accumulate in bones of mammals in amounts greater than amounts of a non-phosphonated equivalent of glycopeptide and lipoglycopeptide antimicrobials and that it is possible to prolong the presence of glycopeptide and lipoglycopeptide antimicrobials in the bones by administering such phosphonated derivatives. Accordingly, the compounds of the invention are particularly useful for the prevention and/or the treatment of bone-related infections and bone-related diseases such as osteomyelitis.

The present invention discloses phosphonated glycopeptide and lipoglycopeptide antimicrobial molecules, in particular, those phosphonated compounds defined in Formula (I) and Formula (II) as defined above and hereinafter. These compounds are useful antimicrobial agents effective against a number of human and veterinary pathogens. A phosphonated group is reversibly coupled to a glycopeptide and lipoglycopeptide antimicrobial molecule via a cleavable linker.

Phosphonated glycopeptide and lipoglycopeptide antimicrobial molecules have been synthesized and demonstrated to have an increased affinity for osseous materials. In vivo, these phosphonated compounds accumulate in bones in amounts greater than amounts of non-phosphonated equivalents. The presence of glycopeptide and lipoglycopeptide antimicrobial molecules in the bones can be prolonged by administering phosphonated derivatives of glycopeptide and lipoglycopeptide antimicrobial molecules according to the invention. Accordingly, the compounds of the invention are particularly useful for the prevention, prophylaxis and/or treatment of bone and joint-related infections and bone-related diseases such as osteomyelitis.

B) Definitions

In order to provide an even clearer and more consistent understanding of the invention, including the scope given herein to particular terms, the following general definitions are provided:

The term "alkyl" refers to saturated aliphatic groups including straight-chain, branched-chain, cyclic groups, and combinations thereof, having the number of carbon atoms specified, or if no number is specified, having 1 to 12 carbon atoms (preferably 1 to 6). Examples of alkyl groups include, but are not limited to groups such as methyl, ethyl, n-propyl, isopropyl, n-butyl, isobutyl, sec-butyl, t-butyl, n-pentyl, neopentyl, cyclopropyl, cyclobutyl, cyclopentyl, cyclohexyl, cyclobutylmethyl, cyclobutylethyl, cyclopentylmethyl, cyclopentylethyl, and adamantyl.

The term "cycloalkyl" refers to cyclic alkyl groups (e.g. cycloalkyl or heterocycloalkyl) consisting of one ring, including, but not limited to, groups such as cycloheptyl, or multiple fused rings, including, but not limited to, groups such as adamantyl or norbornyl.

The term "alkylaryl" refers to an alkyl group having the number of carbon atoms designated, appended to one, two, or three aryl groups.

The term "N-alkylaminocarbonyl" refers to the radical —C(O)NHR where R is an alkyl group.

The term "N,N-dialkylaminocarbonyl" refers to the radical —C(O)NR$_a$R$_b$ where R$_a$ and R$_b$ are each independently an alkyl group.

The term "alkylthio" refers to the radical —SR where R is an alkyl group.

The term "alkoxy" as used herein refers to an alkyl, alkenyl, or alkynyl linked to an oxygen atom and having the number of carbon atoms specified, or if no number is specified, having 1 to 12 carbon atoms (preferably 1 to 6). Examples of alkoxy groups include, but are not limited to, groups such as methoxy, ethoxy, tert-butoxy, and allyloxy. The term "alkoxycarbonyl" refers to the radical —C(O)OR where R is an alkyl. The term "alkylsulfonyl" refers to the radical —SO$_2$R where R is an alkyl group.

The term "alkylene" means a saturated divalent aliphatic group including straight-chain, branched-chain, cyclic groups, and combinations thereof, having the number of carbon atoms specified, or if no number is specified, having 1 to 12 carbon atoms (preferably 1 to 6). Examples of alkylene groups include, but are not limited to groups such as methylene, 2,2-dimethyletylene, ethylene, n-propylene, isopropylene, n-butylene, isobutylene, sec-butylene, t-butylene, n-pentylene, neopentylene, cyclopropylene, cyclobutylene, cyclopentylene, cyclohexylene, cyclobutylmethylene, cyclobutylethylene, cyclopentylmethylene, cyclopentylethylene, and adamantylene.

The term "cycloalkylene" refers to cyclic alkylene groups (e.g. cycloalkylene or heterocycloalkylene) consisting of one ring, including, but not limited to, groups such as cycloheptylene, or multiple fused rings, including, but not limited to, groups such as adamantylene or norbornylene.

The term "substituted alkyl" means an alkyl group as defined above that is substituted with one or more substituents, preferably one to three substituents selected from the group consisting of halogen, alkyl, aryl, alkoxy, acyloxy, amino, mono or dialkylamino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. The phenyl group may optionally be substituted with one to three substituents selected from the group consisting of halogen, alkyl, aryl, alkoxy, acyloxy, amino, mono or dialkylamino, hydroxyl, mercapto, carboxy, benzyloxy, benzyl, cyano, nitro, thioalkoxy, carboxaldehyde, carboalkoxy and carboxamide. Examples of substituted alkyl groups include, but are not limited to —$CF_3$, —$CF_2$—$CF_3$, hydroxymethyl, 1- or 2-hydroxyethyl, methoxymethyl, 1- or 2-ethoxyethyl, carboxymethyl, 1- or 2-carboxyethyl, methoxycarbonylmethyl, 1- or 2-methoxycarbonyl ethyl, benzyl, pyrdinylmethyl, thiophenylmethyl, imidazolinylmethyl, dimethylaminoethyl and the like.

The term "substituted alkylene" means an alkylene group as defined above that is substituted with one or more substituents, preferably one to three substituents, selected from the group consisting of halogen, alkyl, aryl, alkoxy, acyloxy, amino, mono or dialkylamino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. The phenyl group may optionally be substituted with one to three substituents selected from the group consisting of halogen, alkyl, aryl, alkoxy, acyloxy, amino, mono or dialkylamino, hydroxyl, mercapto, carboxy, benzyloxy, benzyl, cyano, nitro, thioalkoxy, carboxaldehyde, carboalkoxy and carboxamide. Examples of substituted alkyl groups include, but are not limited to —$CF_2$—, —$CF_2$—$CF_2$—, hydroxymethylene, 1- or 2-hydroxyethylene, methoxymethylene, 1- or 2-ethoxyethylene, carboxymethylene, 1- or 2-carboxyethylene, and the like.

The term "alkenyl" refers to unsaturated aliphatic groups including straight-chain, branched-chain, cyclic groups, and combinations thereof, having the number of carbon atoms specified, or if no number is specified, having 1 to 12 carbon atoms (preferably 1 to 6), which contain at least one double bond (—C═C—). Examples of alkenyl groups include, but are not limited to allyl vinyl, —$CH_2$—CH═CH—$CH_3$, —$CH_2$—$CH_2$-cyclopentenyl and —$CH_2$—$CH_2$-cyclohexenyl where the ethyl group can be attached to the cyclopentenyl, cyclohexenyl moiety at any available carbon valence.

The term "alkenylene" refers to unsaturated divalent aliphatic groups including straight-chain, branched-chain, cyclic groups, and combinations thereof, having the number of carbon atoms specified, or if no number is specified, having 1 to 12 carbon atoms (preferably 1 to 6), which contain at least one double bond (—C═C—). Examples of alkenylene groups include, but are not limited to —CH═CH—, —$CH_2$—CH═CH—$CH_2$—, —$CH_2$—CH(cyclopentenyl)- and the like.

The term "alkynyl" refers to unsaturated aliphatic groups including straight-chain, branched-chain, cyclic groups, and combinations thereof, having the number of carbon atoms specified, or if no number is specified, having 1 to 12 carbon atoms (preferably 1 to 6), which contain at least one triple bond (—C≡C—). Examples of alkynyl groups include, but are not limited to acetylene, 2-butynyl, and the like.

The term "alkynylene" refers to unsaturated divalent aliphatic groups including straight-chain, branched-chain, cyclic groups, and combinations thereof, having the number of carbon atoms specified, or if no number is specified, having 1 to 12 carbon atoms (preferably 1 to 6), which contain at least one triple bond (—C≡C—). Examples of alkynylene groups include, but are not limited to —C≡C—, —C≡C—$CH_2$—, and the like.

The term "substituted alkenyl" or "substituted alkynyl" refers to the alkenyl and alkynyl groups as defined above that are substituted with one or more substituents selected from the group consisting of halogen, alkyl, aryl, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of substituted alkenyl and alkynyl groups include, but are not limited to —CH═$CF_2$, methoxyethenyl, methoxypropenyl, bromopropynyl, and the like.

The term "substituted alkenylene" or "substituted alkynylene" refers to the alkenylene and alkynylene groups as defined above that are substituted with one or more substituents selected from the group consisting of halogen, alkyl, aryl, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

The term "aryl" or "Ar" refers to an aromatic carbocyclic group of 6 to 14 carbon atoms having a single ring (including but not limited to groups such as phenyl) or multiple condensed rings (including but not limited to groups such as naphthyl or anthryl), and includes both unsubstituted and substituted aryl groups. Substituted aryl is an aryl group that is substituted with one or more substituents, preferably one to three substituents, selected from the group consisting of alkyl, aryl, alkenyl, alkynyl, halogen, alkoxy, acyloxy, amino, mono or dialkylamino, hydroxyl, mercapto, carboxy, benzyloxy, phenyl, aryloxy, benzyl, cyano, nitro, thioalkoxy, carboxaldehyde, carboalkoxy and carboxamide, or a functionality that can be suitably blocked, if necessary for purposes of the invention, with a protecting group. Representative examples include, but are not limited to naphthyl, phenyl, chlorophenyl, iodophenyl, methoxyphenyl, carboxyphenyl, and the like. The term "aryloxy" refers to an aryl group linked to an oxygen atom at one of the ring carbons. Examples of alkoxy groups include, but are not limited to, groups such as phenoxy, 2-, 3-, or 4-methylphenoxy, and the like. The term "arylthio group" refers to the radical —$SR_c$ where $R_c$ is an aryl group. The term "heteroarylthio group" refers to the radical —$SR_d$ where $R_d$ is a heteroaryl.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —$NH_2$.

The term "N-alkylamino" and "N,N-dialkylamino" means a radical —NHR and —NRR' respectively where R and R' independently represent an alkyl group as defined herein. Representative examples include, but are not limited to N,N-dimethylamino, N-ethyl-N-methylamino, N,N-di(1-methylethyl)amino, N-cyclohexyl-N-methylamino, N-cyclohexyl-N-ethylamino, N-cyclohexyl-N-propylamino, N-cyclohexylmethyl-N-methylamino, N-cyclohexylmethyl-N-ethylamino, and the like.

The term "thioalkoxy" means a radical —SR where R is an alkyl as defined above e.g., methylthio, ethylthio, propylthio, butylthio, and the like.

The term "acyl group" means a radical —C(O)R, where R is hydrogen, halogen, alkyl, aryl, heteroaryl, alkoxy, aryloxy, N-alkylamino, N,N-dialkylamino, N-arylamino, thioalkoxy, thioaryloxy or substituted alkyl wherein alkyl, aryl, heteroaryl, and substituted alkyl are as defined herein.

The term "thioacyl group" means a radical —C(S)R, where R is hydrogen, halogen, alkyl, aryl, heteroaryl, alkoxy, aryloxy, N-alkylamino, N,N-dialkylamino, N-arylamino, thioalkoxy, thioaryloxy or substituted alkyl wherein alkyl, aryl, heteroaryl, and substituted alkyl are as defined herein.

The term "sulfonyl group" means a radical —$SO_2$R, where R is hydrogen, halogen, alkyl, aryl, heteroaryl, alkoxy, aryloxy, N-alkylamino, N,N-dialkylamino, N-arylamino, thioalkoxy, thioaryloxy or substituted alkyl wherein alkyl, aryl, heteroaryl, and substituted alkyl are as defined herein.

The term "acyloxy" means a radical —OC(=O)R, where R is hydrogen, alkyl, aryl, heteroaryl or substituted alkyl wherein alkyl, aryl, heteroaryl, and substituted alkyl are as defined herein. Representative examples include, but are not limited to formyloxy, acetyloxy, cylcohexylcarbonyloxy, cyclohexylmethylcarbonyloxy, benzoyloxy, benzylcarbonyloxy, and the like.

The term "heteroalkyl," "heteroalkenyl," and "heteroalkynyl" refers to alkyl, alkenyl, and alkynyl groups respectively as defined above, that contain the number of carbon atoms specified (or if no number is specified, having 1 to 12 carbon atoms, preferably 1 to 6) which contain one or more heteroatoms, preferably one to three heteroatoms, as part of the main, branched, or cyclic chains in the group. Heteroatoms are independently selected from the group consisting of —NR—, —NRR, —S—, —S(O)—, —$S(O)_2$—, —O—, —SR, —S(O)R, —$S(O)_2$R, —OR—PR—, —PRR, —P(O)R— and —P(O)RR; (where each R is hydrogen, alkyl or aryl) preferably —NR where R is hydrogen or alkyl and/or O. Heteroalkyl, heteroalkenyl, and heteroalkynyl groups may be attached to the remainder of the molecule either at a heteroatom (if a valence is available) or at a carbon atom. Examples of heteroalkyl groups include, but are not limited to, groups such as —O—$CH_3$, —$CH_2$—O—$CH_3$, —$CH_2$—$CH_2$—O—$CH_3$, —S—$CH_2$—$CH_2$—$CH_3$, —$CH_2$—$CH(CH_3)$—S—$CH_3$, —$CH_2$—$CH_2$—NH—$CH_2$—$CH_3$, 1-ethyl-6-propylpiperidino, 2-ethylthiophenyl, piperazino, pyrrolidino, piperidino, morpholino, and the like. Examples of heteroalkenyl groups include, but are not limited to groups such as —CH=CH—$CH_2$—$N(CH_3)_2$, and the like.

The term "heteroaryl" or "HetAr" refers to an aromatic monovalent monocyclic, bicyclic, or tricyclic radical containing 4, 5, 6, 7, 8, 9, 10, 11, 12, 13, 14, 15, 16, 17, or 18-member ring atoms, including 1, 2, 3, 4, or 5 heteroatoms, preferably one to three heteroatoms including, but not limited to heteroatoms such as N, O, P, or S, within the ring. Representative examples include, but are not limited to single ring such as imidazolyl, pyrazolyl, pyrazinyl, pyridazinyl, pyrimidinyl, pyrrolyl, pyridyl, thiophene, and the like, or multiple condensed rings such as indolyl, quinoline, quinazoline, benzimidazolyl, indolizinyl, benzothienyl, and the like.

The heteroalkyl, heteroalkenyl, heteroalkynyl and heteroaryl groups can be unsubstituted or substituted with one or more substituents, preferably one to three substituents, selected from the group consisting of alkyl, alkenyl, alkynyl, benzyl, halogen, alkoxy, acyloxy, amino, mono or dialkylamino, hydroxyl, mercapto, carboxy, benzyloxy, phenyl, aryloxy, cyano, nitro, thioalkoxy, carboxaldehyde, carboalkoxy and carboxamide, or a functionality that can be suitably blocked, if necessary for purposes of the invention, with a protecting group. Examples of such substituted heteroalkyl groups include, but are not limited to, piperazine, pyrrolidine, morpholine, or piperidine, substituted at a nitrogen or carbon by a phenyl or benzyl group, and attached to the remainder of the molecule by any available valence on a carbon or nitrogen, —NH—S(=O)$_2$-phenyl, —NH—(C=O)O-alkyl, —NH—C(=O)O-alkyl-aryl, and the like. The heteroatom(s) as well as the carbon atoms of the group can be substituted. The heteroatom(s) can also be in oxidized form.

The term "heteroarylene" refers to the diradical group derived from heteroaryl (including substituted heteroaryl), as defined above, and is exemplified by the groups 2,6-pyridinylene, 2,4-pyridinylene, 1,2-quinolinylene, 1,8-quinolinylene, 1,4-benzofuranylene, 2,5-pyridinylene, 2,5-indolenylene, and the like.

The term "heteroalkylene", "heteroalkenylene", and "heteroalkynylene" refers to the diradical group derived from heteroalkyl, heteroalkenyl, and heteroalkynyl (including substituted heteroalkyl, heteroalkenyl, and heteroalkynyl) as defined above.

The term "carboxaldehyde" means —CHO.

The term "carboalkoxy" means —C(=O)OR where R is alkyl as defined above and include groups such as methoxycarbonyl, ethoxycarbonyl, and the like.

The term "carboxamide" means —C(=O)NHR or —C(=O)NRR' where R and R' are independently hydrogen, aryl or alkyl as defined above. Representative examples include groups such as aminocarbonyl, N-methylaminocarbonyl, N,N-dimethylaminocarbonyl, and the like.

The term "carboxy" refers to the radical —C(O)OH.

The term "carbamoyl" refers to the radical —C(O)$NH_2$.

The term "halogen" or "halo" as used herein refer to Cl, Br, F or I substituents, preferably fluoro or chloro.

The term "hydroxy" refers to a —OH radical.

"Isomers": Compounds that have the same molecular formula (or elemental composition) but differ in the nature or sequence of bonding of their atoms or the arrangement of their atoms in space are termed "isomers". Isomers in which the connectivity between atoms is the same but which differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example which is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either an individual enantiomer or as a mixture thereof. A mixture containing equal proportions of the enantiomers is called a "racemic mixture".

The compounds of this invention may possess one or more asymmetric centers. Such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The description is also intended to include all possible diastereomers and mixtures thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

"Affinity" represents the tendency of different forms of matter (particles, chemical elements, molecules, ions, supramolecular assemblies) to aggregate or bond. According to the present invention, phosphonated glycopeptide or lipoglycopeptides demonstrate affinity for osseous tissues. In preferred examples, the phosphonated glycopeptide or lipoglycopeptides demonstrate high affinity for osseous tissues. For example, compounds of the invention may bind rapidly and efficiently to bone powder, calcium phosphate or other bone component, such that after a duration of 10 min to 1 hour of their introduction to a suspension of osseous matter in an aqueous medium at a pH of between 5 and 9, greater than 50% of the amount of a compound of the invention is no longer freely found in solution. Such binding demonstrates high affinity for osseous tissues. Preferably, greater than 70% of the amount of the phosphonated glycopeptide or lipoglycopeptide molecule is bonded to bone one hour after its introduction to the suspension of osseous matter in the aqueous medium. Such binding demonstrates very high affinity for osseous tissues.

"Optically pure": As generally understood by those skilled in the art, an optically pure compound is one that is enantiomerically pure. As used herein, the term "optically pure" is intended to mean a compound which comprises at least a sufficient amount of a single enantiomer to yield a compound having the desired pharmacological activity. Preferably, "optically pure" is intended to mean a compound that comprises at least 90% of a single isomer (80% enantiomeric excess), preferably at least 95% (90% e.e.), more preferably at least 97.5% (95% e.e.), and most preferably at least 99% (98% e.e.). Preferably, the compounds of the invention are optically pure.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) Protective Groups in Organic Synthesis, 2nd Ed. (John Wiley & Sons, Inc., New York). Preferred amino protecting groups include, but are not limited to, benzyloxycarbonyl (CBz), t-butyloxycarbonyl (Boc), t-butyldimethylsilyl (TBDMS), 9-fluorenylmethyl-oxycarbonyl (Fmoc), or suitable photolabile protecting groups such as 6-nitroveratryloxy carbonyl (Nvoc), nitropiperonyl, pyrenylmethoxycarbonyl, nitrobenzyl, dimethyl dimethoxybenzil, 5-bromo-7-nitroindolinyl, and the like. Preferred hydroxyl protecting groups include acetyl (Ac), benzoyl (Bz), benzyl (Bn), Tetrahydropyranyl (THP), TBDMS, photolabile protecting groups (such as nitroveratryl oxymethyl ether (Nvom)), Mom (methoxy methyl ether), and Mem (methoxy ethoxy methyl ether). Particularly preferred protecting groups include NPEOC (4-nitrophenethyloxycarbonyl) and NPEOM (4-nitrophenethyloxy-methyloxycarbonyl).

"Prodrug": Phosphonated glycopeptide and lipoglycopeptide antimicrobial molecules of the present invention may be formulated as prodrugs. According to the present invention, a prodrug is an inactive (or significantly less active) form of any of the phosphonated glycopeptide and lipoglycopeptide antimicrobial molecule compounds of the present invention. Upon in vivo processing, prodrugs of the present invention release an active phosphonated glycopeptide and lipoglycopeptide antimicrobial molecule. Prodrugs of phosphonated glycopeptide and lipoglycopeptide antimicrobial molecules of the present invention may be prepared by modifying functional groups present on the phosphonated glycopeptide and lipoglycopeptide antimicrobial molecules in such a way that the modifications may be cleaved in vivo to release the phosphonated glycopeptide and lipoglycopeptide antimicrobial molecules.

Prodrugs include compounds of Formula (I) and/or Formula (II) wherein a hydroxyl, carboxyl or amino group in the glycopeptide and lipoglycopeptide antimicrobial molecule portion of the compound is bonded to any group that may be cleaved in vivo to regenerate the free hydroxyl, carboxyl or amino group, respectively. Such prodrug groups are in addition to the phosphonated linker that may be coupled to a hydroxy, carboxy and/or amino group of an glycopeptide and lipoglycopeptide antimicrobial molecule. Examples of prodrug groups include, but are not limited to, esters (e.g., acetate, formate, and benzoate derivatives) and carbamates (e.g., N,N-dimethylaminocarbonyl) on hydroxy functional groups of the glycopeptide and lipoglycopeptide antimicrobial molecule portion of the phosphonated compounds of the present invention. The present invention also includes those prodrugs requiring two or more events in prodrug cleavage. According to that embodiment, more complex compounds would release, upon cleavage, a prodrug of a phosphonated glycopeptide and lipoglycopeptide antimicrobial molecule, the latter prodrug being activatable to release a desired phosphonated glycopeptide and lipoglycopeptide antimicrobial molecule. The skilled artisan will understand that prodrugs of phosphonated glycopeptide and lipoglycopeptide antimicrobial molecules of the present invention may undergo two cleavage events, one of which cleaves the cleavable linker and thus releases the phosphonate group, the other of which results in the release of the prodrug group.

A "pharmaceutically acceptable prodrug" is intended to mean prodrug of phosphonated glycopeptide and lipoglycopeptide antimicrobial molecule, such as a prodrug of a compound of Formula (I) and/or Formula (II), in a formulation that may be administered to a subject, such as a mammal, preferably a human. For example, the prodrug may be in a formulation comprising a pharmaceutically acceptable carrier or excipient.

A "pharmaceutically acceptable active metabolite" is intended to mean a pharmacologically active product produced through metabolism in the body of a compound of Formula (I) or Formulae (II) as defined herein.

A "pharmaceutically acceptable solvate" is intended to mean a solvate that retains the biological effectiveness and properties of the biologically active components of compounds of Formula I and/or Formula II. Examples of pharmaceutically acceptable solvates include, but are not limited to water, isopropanol, ethanol, methanol, DMSO, ethyl acetate, acetic acid, and ethanolamine.

A "pharmaceutically acceptable carrier or excipient" means any compound, solution, substance or material that can be used in a formulation of the compounds of the present invention that may be administered to a subject. In particular, carriers and excipients of the present invention are those useful in preparing a pharmaceutical composition that is generally safe, non-toxic and neither biologically nor otherwise undesirable, and that may present pharmacologically favorable profiles and that includes carriers and excipient that are acceptable for veterinary use as well as human pharmaceutical use. Suitable pharmaceutically acceptable carriers and excipients are well known in art and can be determined by those of skill in the art as the clinical situation warrants. The skilled artisan will understand that diluents are included within the scope of the terms carriers and excipients. Examples of suitable carriers and excipients include saline, buffered saline, dextrose, water, glycerol, ethanol, more particularly: (1) Dulbecco's phosphate buffered saline, pH about 7.4, containing about 1 mg/ml to 25 mg/ml human serum albumin, (2) 0.9% saline (0.9% w/v NaCl), (3) 5% (w/v) dextrose, and (4) water.

A "pharmaceutically acceptable salt" is intended to mean a salt of phosphonated glycopeptide or lipoglycopeptide antimicrobial molecule, such as a salt of a compound of Formula (I) and/or Formula (II), in a formulation that may be administered to a subject, such as a mammal, preferably a human. For example, the salt may be in a formulation comprising a pharmaceutically acceptable carrier or excipient.

"Saccharide": represents saturated polyhydroxylated compounds. The term is sometimes limited to polyhydroxylated carbon chains possessing an aldehyde or a ketone moiety either free or masked as an acetal or a ketal functionality. In this case, it is intended to include monosaccharides, oligosaccharides and polysaccharides as well as substances derived from monosaccharides by reduction of the carbonyl group (alditols), by oxidation of one or more terminal groups to carboxylic acids, by oxidation of one or more secondary hydroxyl groups to ketones, by replacement of one or more hydroxy group(s) by a hydrogen atom, an amino group, an O-linked ester group, a C-linked ester group, an N-linked amide group, a C-linked amide group, an alkyl group, an aryl group, a thiol group or similar heteroatomic groups and/or by replacement of one or more of the hydrogens bonded to carbons by a C-linked ester group, a C-linked amide group, an alkyl group, an aryl group or other heteroatomic groups. It also includes oligomers of modified and unmodified monosaccharides as well as derivatives of these compounds.

Unmodified, oxidized, reduced or substituted saccharide monoradicals are covalently attached to the glycopeptide via any atom of the saccharide moiety, preferably a carbon. Representative saccharide include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose, 2-O-(α-L-vancosaminyl)-β-D-glucopyranose, 2-O-(α-L-3-epivancosaminyl)-β-D-glucopyranose, 2-O-(3-desmethyl-α-L-vancosaminyl)-β-D-glucopyranose, sucrose, lactose, or maltose; derivatives such as acetals, amines, acylated, sulfated and phosphorylated sugars; oligosaccharides having from 2 to 10 saccharide units. These saccharides are can be either in their open or preferably in their pyranose or furanose forms.

The saccharide may be linked to the aglycone of the glycopeptide or lipoglycopeptide antimicrobial agent indirectly via an additional spacer such as an ethylene, propylene, butylenes or phenylene group.

The term "amino-containing saccharide group" refers to a saccharide group having an amino substituent. Representative amino-containing saccharide include L-vancosamine, 3-desmethyl-vancosamine, 3-epi-vancosamine, 4-epi-vancosamine, acosamine, actinosamine, daunosamine, 3-epi-daunosamine, ristosamine, N-methyl-D-glucamine and the like.

"Salt": Phosphonated glycopeptide and lipoglycopeptide antimicrobial molecules of the present invention may be in the form of a salt. Salts of phosphonated glycopeptide and lipoglycopeptide antimicrobial molecules of the present invention means a salt that retains or improves the biological effectiveness and properties of the free acids and bases of the parent compound as defined herein or that takes advantage of an intrinsically charged functionality on the molecule and that is not biologically or otherwise undesirable. Such salts include the following:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 3-phenyl propionic acid, trimethylacetic acid, tertiary butylacetic acid, lauryl sulfuric acid, gluconic acid, glutamic acid, hydroxynapthoic acid, salicylic acid, stearic acid, muconic acid, and the like;

(2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like; or (3) salts formed when a charged functionality is present on the molecule and a suitable counterion is present, such as a tetraalkyl(aryl)ammonium functionality and an alkali metal ion, a tetraalkyl(aryl)phosphonium functionality and an alkali metal ion, an imidazolium functionality and an alkali metal ion, and the like.

As used herein, the terms "bone", "bone tissues" or "osseous tissues" refer to the dense, semi rigid, porous, calcified connective tissue forming the major portion of the skeleton of most vertebrates. It also encompasses teeth, osteoarticular tissues and calcifications that are frequently seen in the walls of atherosclerotic vessels.

The term "glycopeptide antimicrobial molecule" and "lipoglycopeptide antimicrobial molecule", and related terms, have the same meaning and refer to antimicrobial agents which are part of the well known class of "glycopeptides and lipoglycopeptides" as described in more detail herein.

The term "phosphonated group" is intended to mean any compound non-toxic to humans having at least one phosphorus atom bonded to at least three oxygen atoms and having a measurable affinity to osseous tissues as described hereinafter.

The term "antibacterial" includes those compounds that inhibit, halt or reverse growth of bacteria, those compounds that inhibit, halt, or reverse the activity of bacterial enzymes or biochemical pathways, those compounds that kill or injure bacteria, and those compounds that block or slow the development of a bacterial infection.

The terms "treating" and "treatment" are intended to mean at least the mitigation of a disease condition associated with a bacterial infection in a subject, including mammals such as a human, that is alleviated by a reduction of growth, replication, and/or propagation of any bacterium such as Gram-positive organisms, and includes curing, healing, inhibiting, relieving from, improving and/or alleviating, in whole or in part, the disease condition.

The term "prophylaxis" is intended to mean at least a reduction in the likelihood that a disease condition associated with a bacterial infection will develop in a mammal, preferably a human. The terms "prevent" and "prevention" are intended to mean blocking or stopping a disease condition associated with a bacterial infection from developing in a mammal, preferably a human. In particular, the terms are related to the treatment of a mammal to reduce the likelihood ("prophylaxis") or prevent the occurrence of a bacterial infection, such as bacterial infection that may occur during or following a surgery involving bone reparation or replacement. The terms also include reducing the likelihood ("prophylaxis") of or preventing a bacterial infection when the mammal is found to be predisposed to having a disease condition but not yet diagnosed as having it. For example, one can reduce the likelihood or prevent a bacterial infection in a mammal by administering a compound of Formula (I) and/or Formula (II), or a pharmaceutically acceptable prodrug, salt, active metabolite, or solvate thereof, before occurrence of such infection.

The term "subject" is intended to mean an animal, such as a mammal, including humans and animals of veterinary importance, such as dogs, cats, horses, sheep, goats, and cattle.

C) Compounds of the Invention

As will be described hereinafter in the Exemplification section, the inventors have prepared phosphonated derivatives of glycopeptide or lipoglycopeptide antimicrobial molecules having a high binding affinity to osseous tissues.

In one embodiment, the compounds of the invention are represented by the general Formula (I):

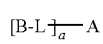
(I)

as well as pharmaceutically acceptable salts, esters and prodrugs thereof, wherein:
B is a phosphonated group, preferably having a high affinity to osseous tissues;
L is a bond or a linker, preferably covalently coupling B to A;
α is 1, 2, 3, 4, 5, 6 or 7, preferably 1, 2 or 3; and
A is a glycopeptide or lipoglycopeptide antimicrobial molecule;

As mentioned previously, the essence of the invention lies in the presence of a phosphonated group attached to a glycopeptide or lipoglycopeptide antibiotic for increasing the affinity, binding, accumulation and/or retention time of the glycopeptide or lipoglycopeptide antibiotic to or within the bones.

Phosphonates

All non-toxic phosphonated groups having an affinity, preferably a high affinity or a very high affinity, to bone due to their ability to bind the $Ca^{2+}$ ions found in the hydroxyapatite forming the bone tissues are suitable according to the present invention. Suitable examples of phosphonated groups can be found in WO 04/026315 (Ilex Oncology Research), U.S. Pat. No. 6,214,812 (MBC research), U.S. Pat. No. 5,359,060 (Pfizer), U.S. Pat. No. 5,854,227 and U.S. Pat. No. 6,333,424 (Elizanor), U.S. Pat. No. 6,548,042 (Arstad and Skattelbol) and WO 2004/089925 (Semaphore Pharmaceuticals). Examples of bisphosphonate and trisphosphonate groups suitable for the present invention include but are not limited to those having the formula:

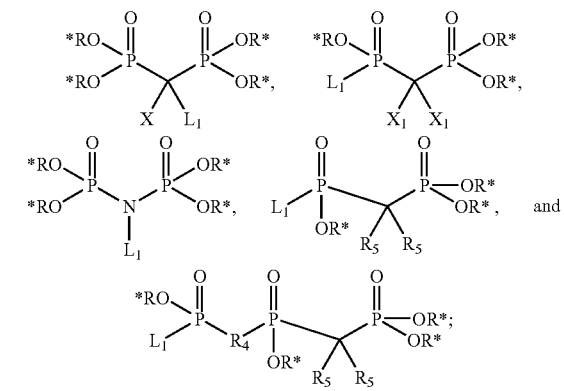

wherein:
each R* is independently selected from the group consisting of H, lower alkyl, cycloalkyl, aryl and heteroaryl, with the proviso that at least two, preferably three, R* are H;
$R_4$ is —$CH_2$—, —O—, —S—, or —NH—;
each $R_5$ is independently selected from the group consisting of H, $R_6$, $OR_6$, $NR_6$, and $SR_6$, wherein $R_6$ is H, lower alkyl, cycloalkyl, aryl, heteroaryl or $NH_2$;
X is H, OH, $NH_2$, or a halo group;
$X_1$ are both H, or each is independently selected from the group consisting of H, OH, $NH_2$, and a halo group; and
$L_1$ is the point of attachment to L.

Although monophosphonates, bisphosphonates, and tris- or tetraphosphonates could potentially be used, bisphosphonates are preferred. More preferably, the bisphosphonate group is the bisphosphonate —$CH(P(O)(OH)_2)_2$. As shown in Example 3 hereinafter, glycopeptide and lipoglycopeptide derivatives possessing such a bisphosphonate group have a strong binding affinity for hydroxyapatite powder. Of course, other types of phosphonated group could be selected and synthesized by those skilled in the art. For instance the phosphonated group may be an esterase-activated bisphosphonate radical (Vepsäläinen J., Current Medicinal Chemistry, 9, 1201-1208, 2002) or be any other suitable prodrug thereof. These and other suitable phosphonated groups are encompassed by the present invention.

Glycopeptide and Lipoglycopeptide Antibiotics

Glycopeptide and lipoglycopeptide antibiotics are a well known class of biologically produced or semi-synthetic Gram-positive antimicrobial agents (Williams, D. H et al, Angewandte Chemie International Edition in English (1999), 1999, 38; 1172-1193. Nicolaou, K. C. et al, Angewandte Chemie International Edition in English (1999), 38; 2097-2152. Kahne, D. et al Chemical Reviews (2005), 105; 425-448; Pace, J. L. et al, Biochemical Pharmacology (2006), 71; 968-980). Vancomycin and teicoplanin are certainly the best known compounds in this class. Both drugs were proven clinically and microbiologically to have potent activity against Gram-positive organisms. Oritavancin (U.S. Pat. No. 5,840,684), dalbavancin (U.S. Pat. No. 5,750,509) and telavancin (U.S. Pat. No. 6,635,618) are recent examples of this class of compounds possessing extremely attractive pharmacological profiles with potent activity against gram-positive organisms, including methicillin-resistant *Staphylococcus aureus*, intermediate and fully vancomycin-resistant *Staphylococcus aureus*, vancomycin-resistant *Enterococcus* spp., and *Streptococcus* spp. The present invention is not restricted to a specific glycopeptide or lipoglycopeptide antibiotic, but encompasses all kinds of glycopeptide or lipoglycopeptide molecules having a suitable antimicrobial activity including, but not limited to, those disclosed in the above-listed US patents and PCT patent applications (incorporated herein by reference) and other glycopeptide or lipoglycopeptide antibiotic derivatives and hybrids such as glycopeptide-cephalosporin (as described in US patent application No 20050239691 for example).

According to a preferred embodiment, the term "glycopeptide and lipoglycopeptide antimicrobial molecule" includes all compounds having the Formula $A_1$ illustrated below:

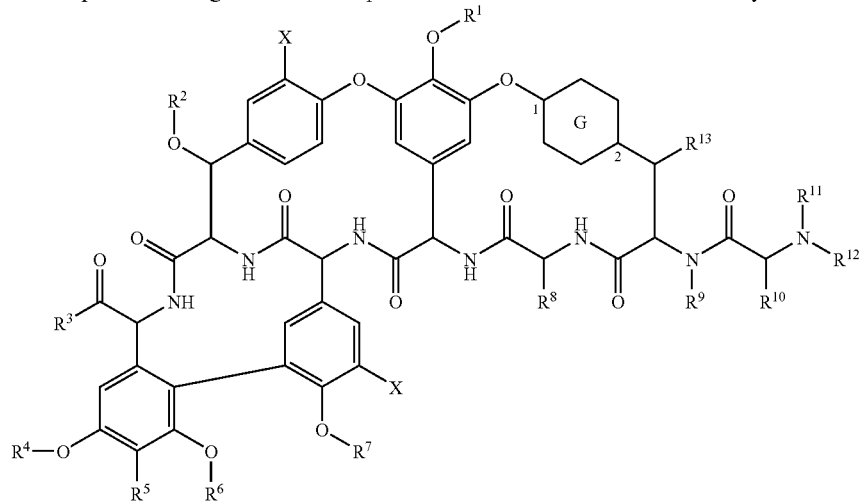

as well as pharmaceutically acceptable salts, esters and prodrugs thereof, where:

$R^1$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and $-R^a-Y-R^b-(Z)_x$; or $R^1$ is a saccharide group optionally substituted with $-R^a-Y-R^b-(Z)_x$, $-R^f$, $-C(O)R^f$, or $-C(O)-R^a-Y-R^b-(Z)_x$;

$R^2$ is hydrogen or a saccharide group optionally substituted with $-R^a-Y-R^b-(Z)_x$, $-R^f$, $-C(O)R^f$, or $-C(O)-R^a-Y-R^b-(Z)_x$;

$R^3$ is $-OR^e$, $-NR^cR^e$, $-O-R^a-Y-R^b-(Z)_x$, $-NR^c-R^a-Y-R^b-(Z)_x$, $-NR^cR^e$, or $-O-R^e$;

$R^4$ is selected from the group consisting of hydrogen, alkyl, substituted alkyl, alkenyl, substituted alkenyl, alkynyl, substituted alkynyl, $-R^a-Y-R^b-(Z)_x$, $-C(O)R^d$ and a saccharide group optionally substituted with $-R^a-Y-R^b-(Z)_x$, $-R^f$, or $-C(O)-R^aY-R^b-(Z)_x$, or $R^4$ and $R^5$ can be joined, together with the atoms to which they are attached, to form a heterocyclic ring optionally substituted with $-NR^c-R^a-Y-R^b-(Z)_x$;

$R^5$ is selected from the group consisting of hydrogen, halo, $-CH(R^c)-NR^cR^e$, $-CH(R^c)-NR^cR^e$, $-CH(R^c)-NR^c-R^a-Y-R^b-(Z)_x$, $-CH(R^c)-R^x$, and $-CH(R^c)-NR^c-R^a-C(O)-R^x$;

$R^6$ is selected from the group consisting of hydrogen, alkyl, substituted alkyl, alkenyl, substituted alkenyl, alkynyl, substituted alkynyl, $-R^a-Y-R^b-(Z)_x$, $-C(O)R^d$ and a saccharide group optionally substituted with $-R^a-Y-R^b-(Z)_x$, $-R^f$, $-C(O)R^f$, or $-C(O)-R^a-Y-R^b-(Z)_x$, or $R^5$ and $R^6$ can be joined, together with the atoms to which they are attached, to form a heterocyclic ring optionally substituted with $-NR^c-R^a-Y-R^b-(Z)_x$;

$R^7$ is selected from the group consisting of hydrogen, alkyl, substituted alkyl, alkenyl, substituted alkenyl, alkynyl, substituted alkynyl, $-R^a-Y-R^b-(Z)_x$, and $-C(O)R^d$;

$R^8$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and $-R^a_{(T)}-Y-R^b-(Z)_x$;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^{10}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or $R^8$ and $R^{10}$ are joined to form $-Ar^1-O-Ar^2-$, where $Ar^1$ and $Ar^2$ are independently arylene or heteroarylene;

$R^{11}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic, or $R^{10}$ and $R^{11}$ are joined, together with the carbon and nitrogen atoms to which they are attached, to form a heterocyclic ring;

$R^{12}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —C(O)R$^d$, —C(NH)R$^d$, —C(O)NR$^c$R$^c$, —C(O)OR$^d$, —C(NH)NR$^c$R$^c$, —R$^a$—Y—R$^b$—(Z)$_x$, and —C(O)—R$^b$—Y—R$^b$—(Z)$_x$, or R$^{11}$ and R$^{12}$ are joined, together with the nitrogen atom to which they are attached, to form a heterocyclic ring;

R$^{13}$ is hydrogen or —OR$^{14}$;

R$^{14}$ is hydrogen, —C(O)R$^d$ or a saccharide group;

R$^a$ is each independently selected from the group consisting of alkylene, substituted alkylene, alkenylene, substituted alkenylene, alkynylene and substituted alkynylene;

R$^b$ is each independently selected from the group consisting of a covalent bond, alkylene, substituted alkylene, alkenylene, substituted alkenylene, alkynylene and substituted alkynylene;

R$^c$ is each independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^d$;

R$^d$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

R$^e$ is each a saccharide group;

R$^f$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, and heterocyclic;

R$^x$ is an N-linked amino saccharide or an N-linked heterocycle;

X is each independently selected from the group consisting of hydrogen, fluoro, chloro, bromo and iodo;

Y is each independently selected from the group consisting of, —CH$_2$—, —O—, —S—, —S—S—, —NR$^c$—, —S(O)—, —SO$_2$—, —NR$^c$C(O)—, —OSO$_2$—, —OC(O)—, —N(R$^c$)SO$_2$—, —C(O)NR$^c$—, —C(O)O—, —SO$_2$NR$^c$—, —SO$_2$O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^c$C(O)O—, —NR$^c$C(O)NR$^c$—, —OC(O)NR$^c$—, —C(O)—, and —N(R$^c$)SO$_2$NR$^c$—;

Z is each independently selected from the group consisting of hydrogen, aryl, cycloalkyl, cycloalkenyl, heteroaryl, heterocyclic; and a saccharide;

x is 1 or 2; and

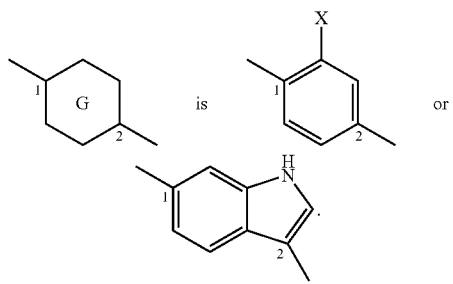

Those skilled in the art will readily identify, isolate and/or prepare the suitable glycopeptide or lipoglycopeptide antimicrobial molecules according to the invention. If necessary they could refer to the numerous literature found in the art, including the US patents and PCT patent applications listed hereinbefore, and more particularly to U.S. Pat. Nos. 5,840,684, 5,750,509 and 6,635,618.

According to one embodiment, the glycopeptide or lipoglycopeptide antimicrobial molecule is a derivative of vancomycin. According to another embodiment, the glycopeptide or lipoglycopeptide antimicrobial molecule is a derivative of teicoplanin. According to a third embodiment, the glycopeptide or lipoglycopeptide antimicrobial molecule is a derivative of chloroeremomycin. According to a fourth embodiment, the glycopeptide or lipoglycopeptide antimicrobial molecule is a derivative of oritavancin. According to a fifth embodiment, the glycopeptide or lipoglycopeptide antimicrobial molecule is a derivative of dalbavancin. According to a sixth embodiment, the glycopeptide or lipoglycopeptide antimicrobial molecule is a derivative of telavancin. The chemical structures of these six molecules are illustrated hereinafter. Arrows indicate preferred sites for attachment of the phosphonated group (direct attachment or via an optional linker), but those skilled in the art will recognize that all hydroxyl amino, amido and carboxyl groups may be possible sites for attachment:

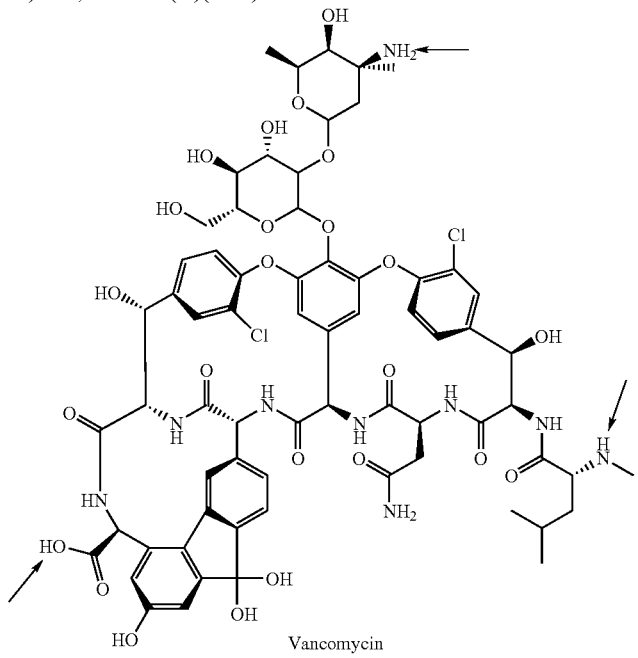

Vancomycin

-continued
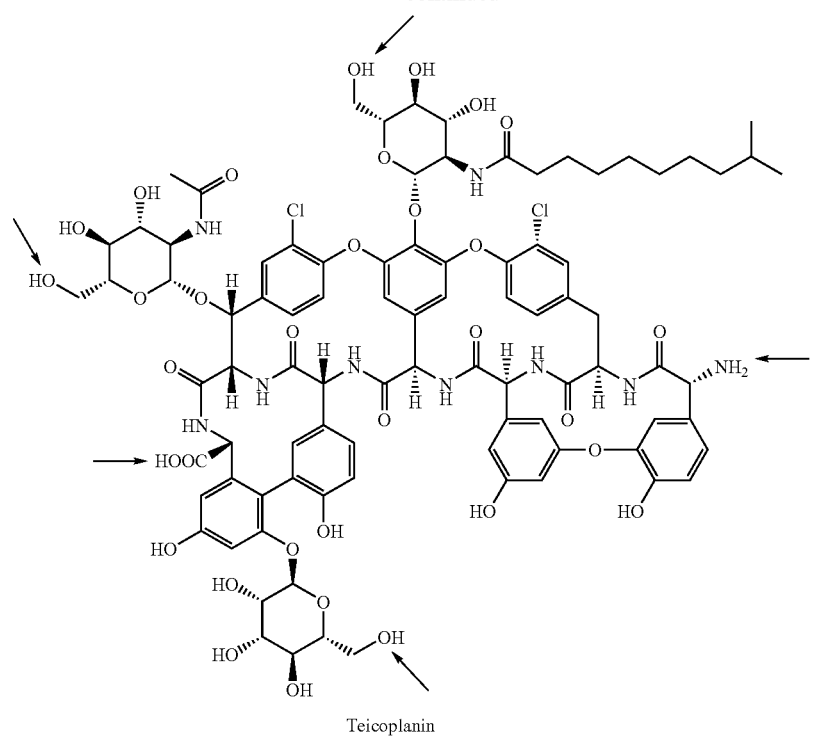
Teicoplanin
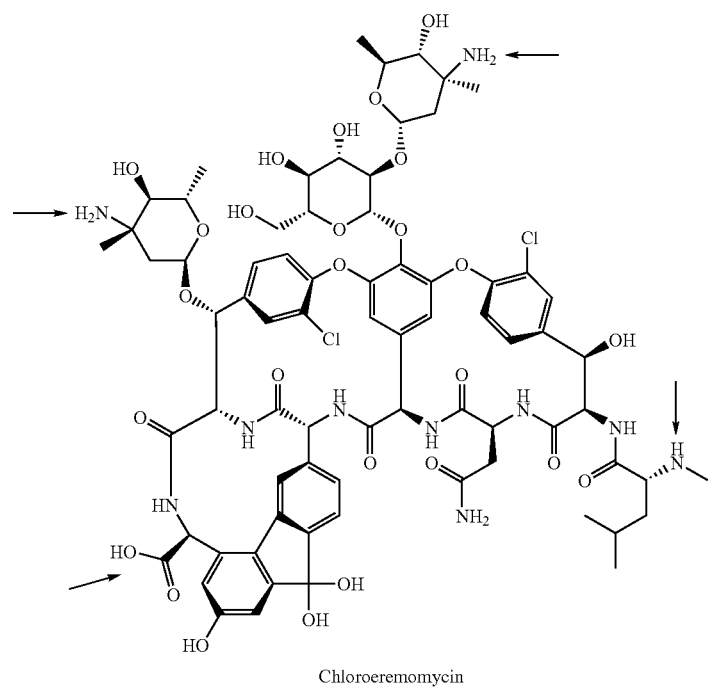
Chloroeremomycin

-continued
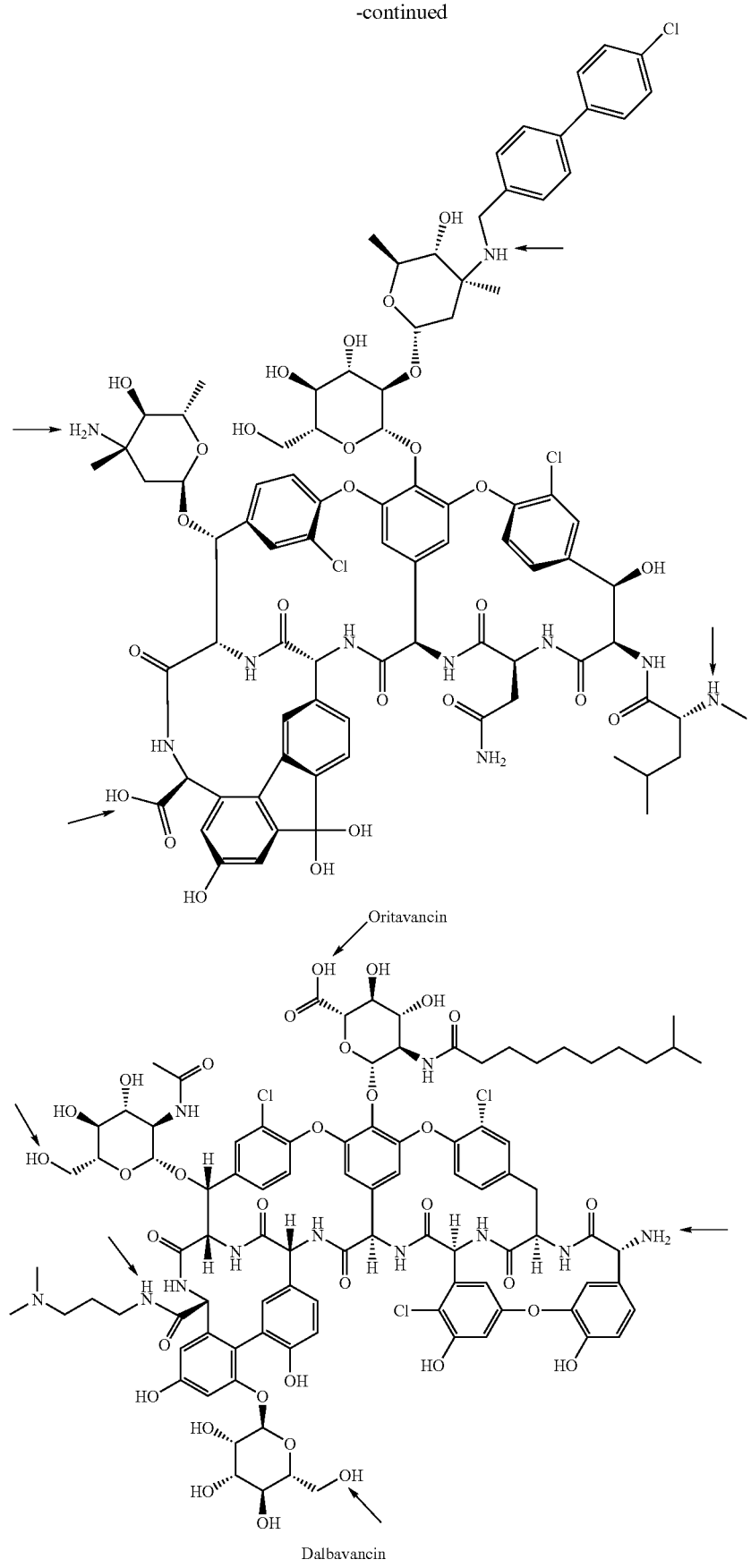
Oritavancin
Dalbavancin

-continued

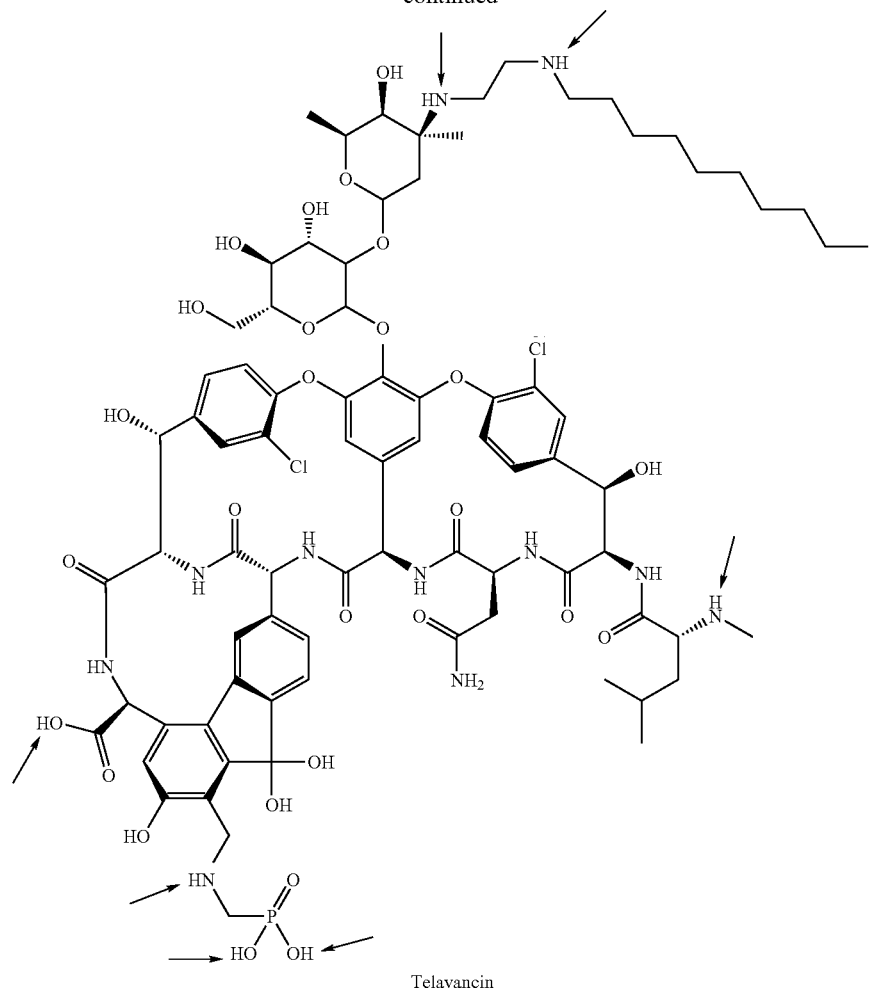

Telavancin

Specific examples of vancomycin and oritavancin derivatives according to the invention are shown in the Exemplification section. Even though in the examples phosphonated groups have not been attached to all the preferred attachment sites shown by the arrows, the results presented in the Exemplification section confirm that it is possible to synthesize phosphonated biologically active glycopeptide and lipoglycopeptide derivatives having a highly increased affinity for bony materials. Similarly, although not tested, the invention encompasses phosphonated glycopeptide and lipoglycopeptide derivatives having more than just one phosphonated group (one at the carboxy and one at one of the amino groups on the oritavancin molecule for instance). As mentioned previously, the above identified sites of attachment are only preferred sites for tethering a phosphonated group and all other potential sites (on any of the hydroxyl groups for instance) are covered by the present invention.

Linkers

A cleavable linker L covalently and reversibly couples the phosphonated group B to glycopeptide or lipoglycopeptide antimicrobial molecules A. As used herein, the term "cleavable" refers to a group that is chemically or biochemically unstable under physiological conditions. The chemical instability preferably results from spontaneous decomposition due to a reversible chemical process, an intramolecular chemical reaction or hydrolysis (i.e. splitting of the molecule or group into two or more new molecules or groups due to the net insertion of one or more water molecules) when it depends on an intermolecular chemical reaction.

Cleavage of the linker may range from being very rapid to being very slow. For instance, the half-life of the cleavable liker may be of about 1 minute, about 15 minutes, about 30 minutes, about 1 hour, about 5 hours, about 10 hours, about 15 hours, about 1 day or about 48 hours. The cleavable linker may be an enzyme-sensitive linker that is cleavable only by selected specific enzymes (e.g. amidase, esterase, metalloproteinase, etc) or may be susceptible to cleavage by other chemical means, such as but not limited to acid/base catalysis or self-cleavage. For instance, it is conceivable according to the invention to have an esterase-sensitive linker that is cleavable only by bone-specific esterases (Goding et al. Biochim Biophys Acta (2003), 1638(1):1-19) or bone-specific metalloproteinase (MMP) (Kawabe et al., Clin Orthop. (1986) 211:244-51; Tuckermann et al., Differentiation (2001), 69(1): 49-57; Sellers et al., Biochem J. (1978) 171(2):493-6) or by the action of alkaline phosphatases thereby releasing the glycopeptide or lipoglycopeptide antibiotic at its desired site of action. Similarly, it is conceivable to use a cleavable linker which is not too easily cleavable in the plasma, thereby permitting a sufficient amount of the phosphonated glycopeptide or lipoglycopeptide antimicrobial molecules to reach and accumulate within the osseous tissues before being cleaved to release the glycopeptide or lipoglycopeptide antimicrobial molecules. For instance, the linker may be selected such that only 1%, 5%, 10%, 15%, 20%, 25%, 30%, 35%, 40%, 50%, 60%, or 70% of the bone-bonded antibiotic is released through a time period extending to 1 minute, 15 minutes, 30 minutes, 1 hour, 5 hours, 10 hours, 15 hours, 1 day, 2 days, 3 days, 4 days, 5 days, 6 days 7 days, one week, two weeks, three weeks or more following administration of the compound of the invention. Preferably, the linker is selected such that only about 1% to about 25% of the bone-bound glycopeptide or lipoglycopeptide antimicrobial molecule is released per day. The choice of the linker may vary according to factors such as (i) the site of attachment of the phosphonated group to the glycopeptide or lipoglycopeptide antimicrobial molecule, (ii) the type of phosphonated group used; (iii) the type of glycopeptide or lipoglycopeptide antimicrobial molecule used, and (iv) the desired ease of cleavage of the linker and associated release of the glycopeptide or lipoglycopeptide antimicrobial molecule.

Preferably, the linker L couples the phosphonated group B to a glycopeptide or lipoglycopeptide antimicrobial molecule A through one or more hydroxyl groups on A, through one or more nitrogen atoms on A, through one or more carboxyl groups on A, or a combination of one or more hydroxyl groups, one or more nitrogen atoms, and/or one or more carboxyl groups, on A. Between 1 and 7 phosphonated groups may be coupled to A through any combination of linkers L.

The linker is facultative because its presence is dependent upon (i) the site of attachment of the phosphonated group to the glycopeptide or lipoglycopeptide molecule, (ii) the type of phosphonated group used; (iii) the type of glycopeptide or lipoglycopeptide used, and (iv) the desired ease of cleavage of the linker and associated release of the glycopeptide or lipoglycopeptide antibiotic. For instance, it is possible to avoid the linker and tether a phosphonated group directly to the carboxyl group of oritavancin.

Preferably, the bisphosphonated-linker substructure is described by the formula $BL_1$:

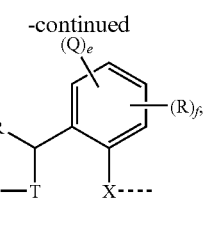

wherein:
$A_a$ indicates the point of attachment to the glycopeptide or lipoglycopeptide antimicrobial molecule A;
W is a covalent bond or is selected from the group of

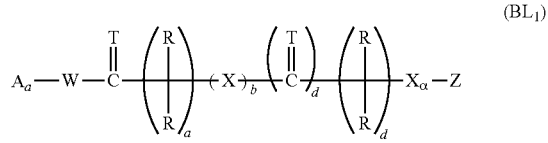

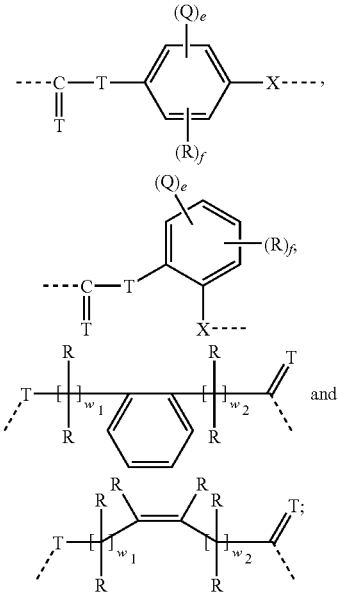

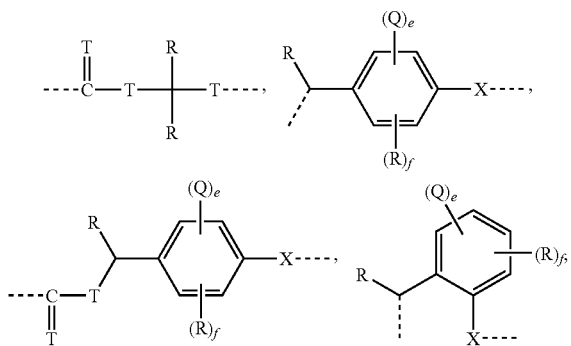

T is oxygen or sulfur;
each R is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, amino, substituted amino, hydroxyl, alkoxy, substituted alkoxy, aryloxy, substituted aryloxy, and —$R^a$—Y—$R^b$—Y—$R^b$—B;
each $R^a$ is independently selected from the group consisting of a covalent bond, alkylene, substituted alkylene, alkenylene, substituted alkenylene, alkynylene, substituted alkynylene, arylene, substituted arylene, —(CO)-alkylene-, substituted —(CO)-alkylene-, —(CO)-alkenylene-, substituted —(CO)-alkenylene-, —(CO)-alkynylene-, substituted —(CO)-alkynylene-, —(CO)-arylene- and substituted —(CO)-arylene-;
each $R^b$ is independently selected from the group consisting of a covalent bond, alkylene, substituted alkylene, alkenylene, substituted alkenylene, alkynylene, substituted alkynylene, arylene and substituted arylene;
each Y is independently selected from the group consisting of a covalent bond, —$CH_2$—, —O—, —S—, —S—S—, —$NR^c$—, —S(O)—, —$SO_2$—, —$NR^c$C(O)—, —$OSO_2$—, —OC(O)—, —N($R^c$)$SO_2$—, —C(O)$NR^c$—, —C(O)O—, —$SO_2NR^c$—, —$SO_2O$—, —P(O)(O$R^c$)O—, —P(O)(O$R^c$)$NR^c$—, —OP(O)(O$R^c$)O—, —OP(O)(O$R^c$)$NR^c$—, —OC(O)O—, —$NR^c$C(O)O—, —$NR^c$C(O)$NR^c$—, —OC(O)$NR^c$—, —C(O)—, and —N($R^c$)$SO_2NR^c$—;
each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^d$—;

and R$^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

B is a phosphonated group;

each Q is independently selected from the group consisting of nitro, chloro, bromo, iodo and fluoro;

each X is independently selected from the group consisting of —O—, —S—, and —N(R)—;

Z is selected from the group consisting of hydrogen, acyl, substituted acyl, aroyl, substituted aroyl, alkoxycarbonyl, substituted alkoxycarbonyl, aryloxycarbonyl, substituted aryloxycarbonyl,

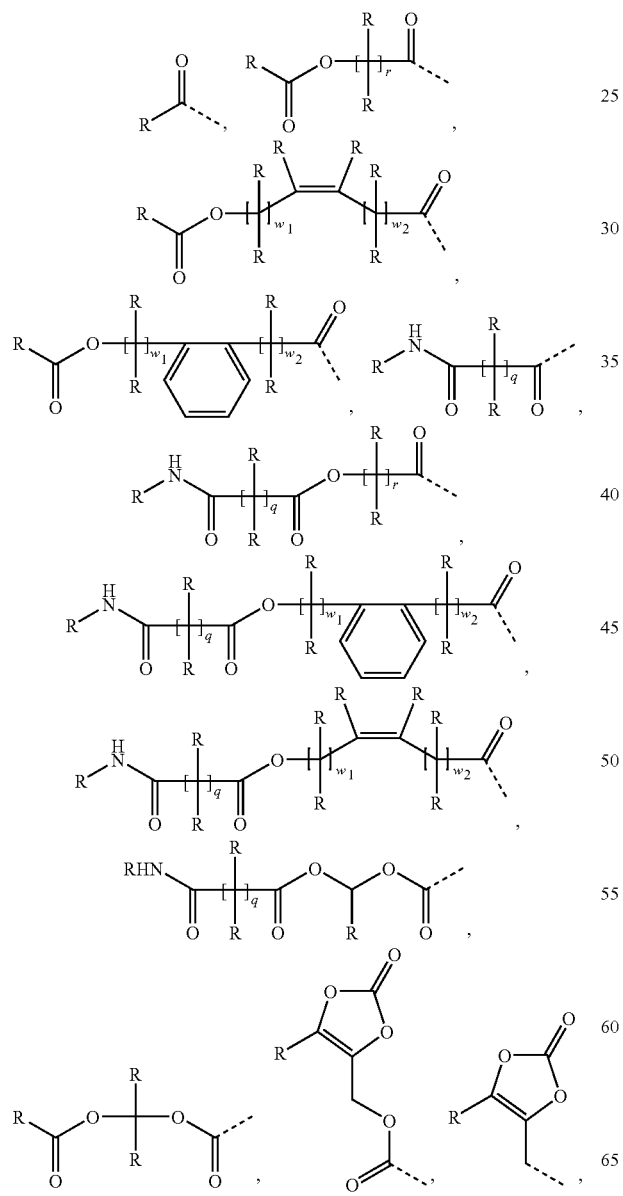

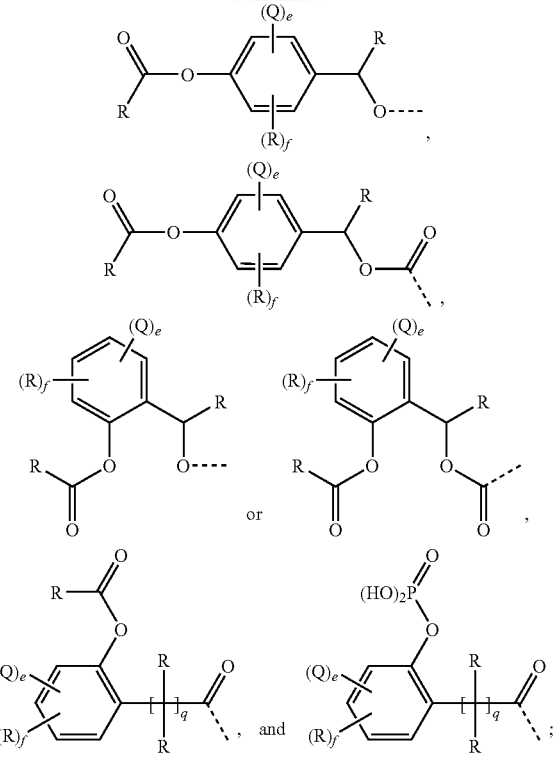

q is 2 or 3;

r is 1, 2, 3, 4 or 5;

$w_1$ and $w_2$ are each integers ≥0 such that their sum ($w_1+w_2$) is 1, 2 or 3;

a, b, c, d are integers ≥0 such that a+b+c+d≤7 or null;

e and f are integers ≥0 such that e+f=4;

α is 0 or 1.

When L couples B to A through a hydroxyl group on A, preferably L is one or more of the following linkers:

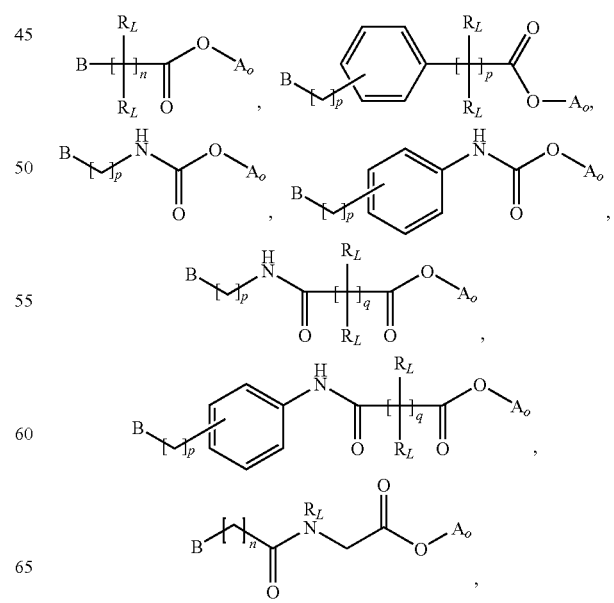

-continued

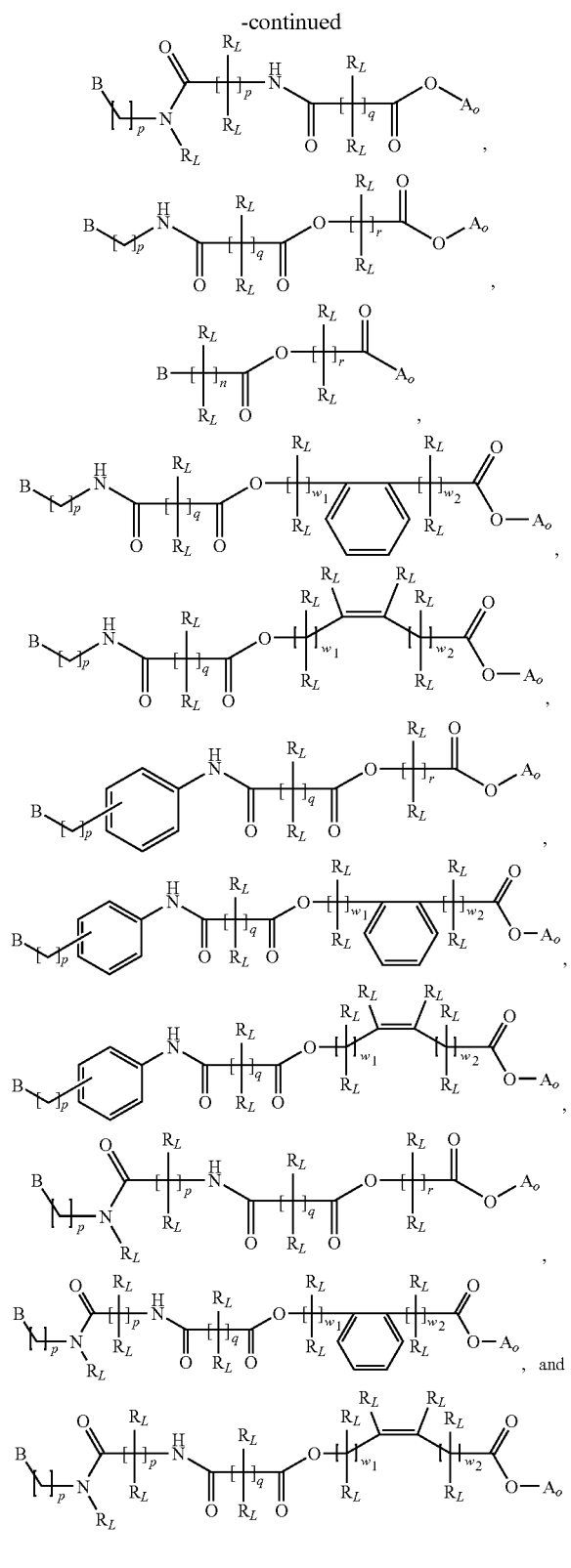

wherein:
  n is an integer ≤10, preferably 1, 2, 3 or 4, more preferably 1 or 2;
  each p is independently 0 or an integer ≤10, preferably 0, 1, 2, 3 or 4, more preferably 0 or 1;
  q is 2 or 3
  r is 1, 2, 3, 4 or 5

$w_1$ and $w_2$ are integers ≥0 such that their sum ($w_1+w_2$) is 1, 2 or 3
  each $R_L$ is independently selected from the group consisting of H, ethyl and methyl, preferably H;
  B represents the phosphonated group; and
  the substructure

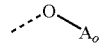

of the linker represents the hydroxyl moiety of A.

When L couples B to A through a nitrogen atom on A, preferably L is one or more of the following linkers:

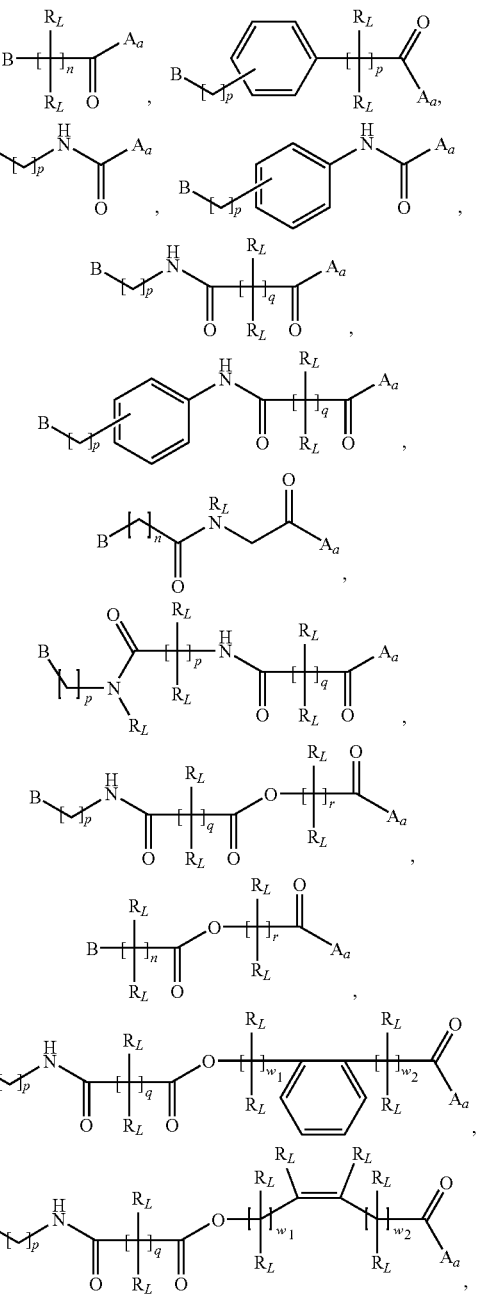

-continued
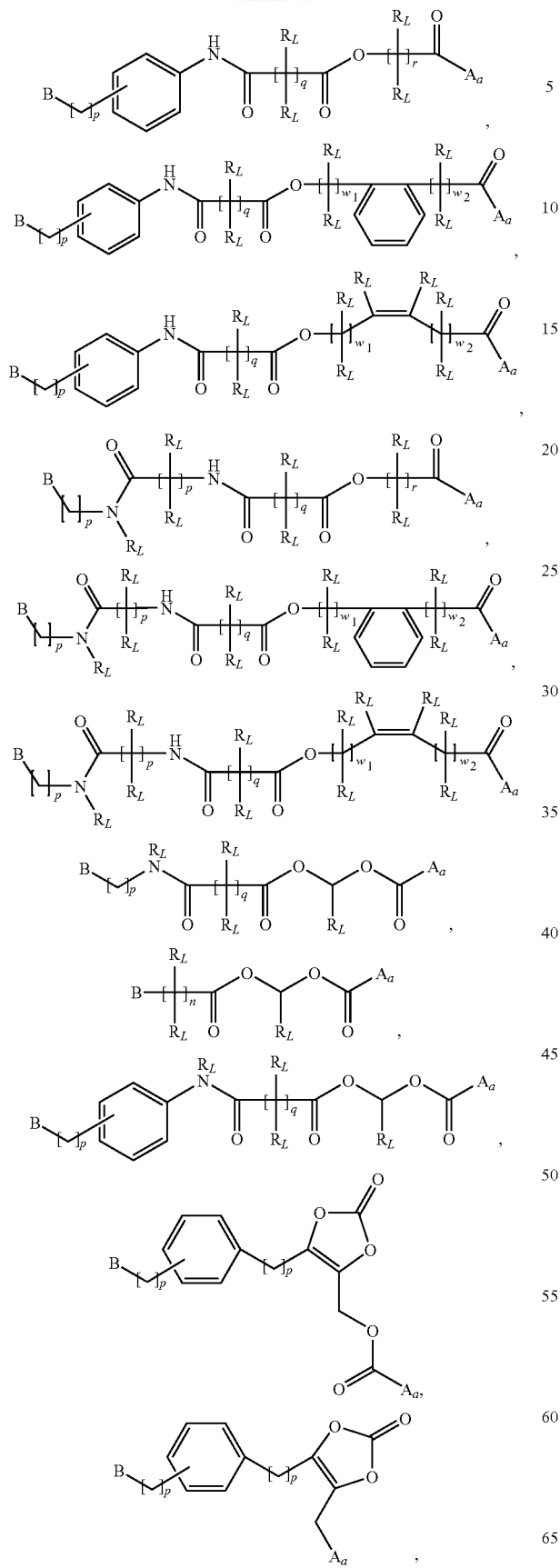
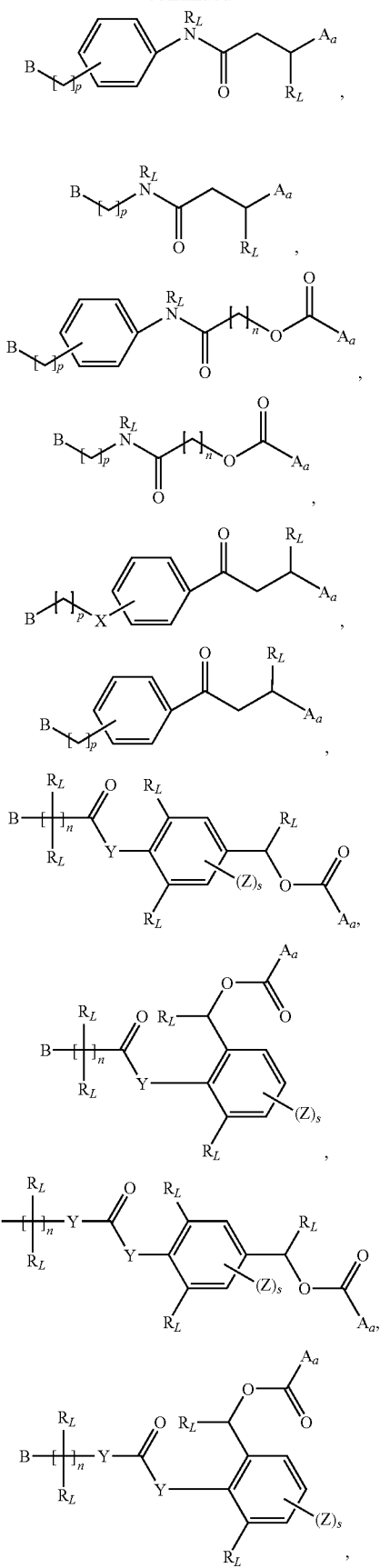

-continued

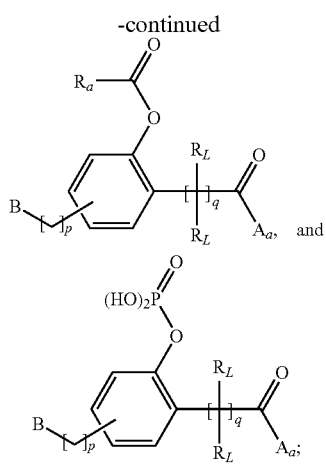

and

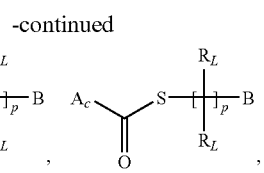

wherein:
  B represents said phosphonated group;
  n is an integer ≤10;
  each p is independently 0 or an integer ≤10;
  each $R_L$ is independently selected from the group consisting of H, ethyl and methyl;
  q is 2 or 3;
  r is 1, 2, 3, 4 or 5;
  $w_1$ and $w_2$ are each integers ≥0 such that their sum ($w_1 + w_2$) is 1, 2 or 3.
  X is —$CH_2$—, —$CONR_L$—, —CO—O—$CH_2$—, or —CO—O—; and
  each Y is independently selected from the group consisting of —O—, —S— and —$NR_L$—;
  each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro, wherein s is 1, 2, 3 or 4; and
  $R_a$ is $C_xH_y$ where x is an integer of 0 to 20 and y is an integer of 1 to 2x+1.
  B represents said phosphonated group; and
  $A_a$ represents the nitrogen atom on A.

When L couples B to A through the carbonyl of a carboxyl group on A, preferably L is one or more of the following linkers:

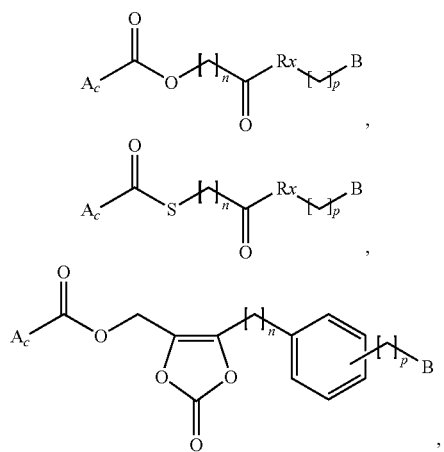

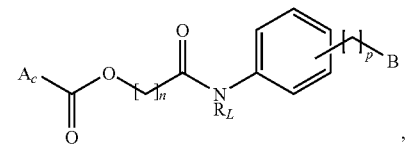

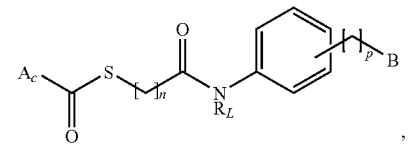

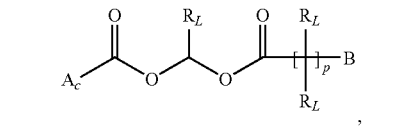

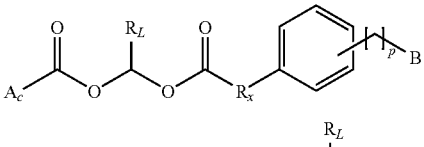

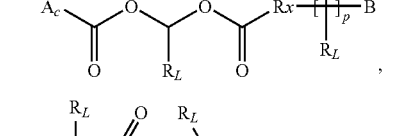

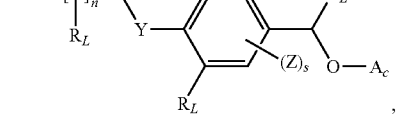

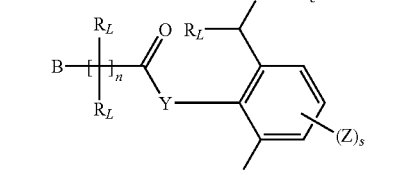

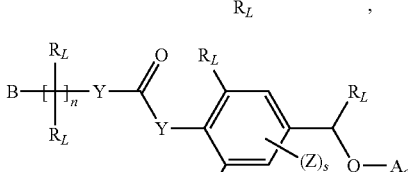

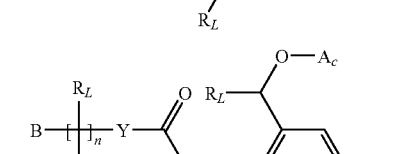

-continued

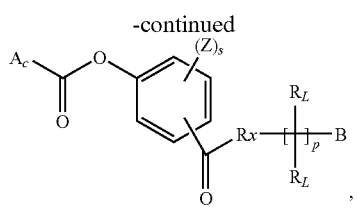

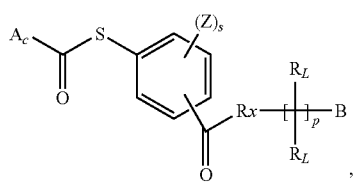

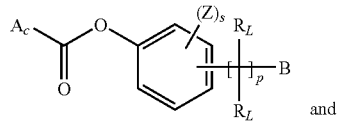

and

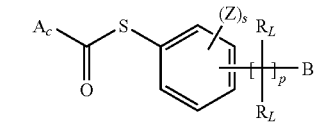

wherein:

n is an integer ≤10, preferably 1, 2, 3 or 4, more preferably 1 or 2;

p is 0 or an integer ≤10, preferably 0, 1, 2, 3 or 4, more preferably 0 or 1;

$R_L$ is H, ethyl or methyl, preferably H;

$R_x$ is —S—, —C($R_L$)$_2$—, —N$R_L$— or —O—; preferably —N$R_L$—, more preferably —NH—;

each Y is independently selected from the group consisting of —O—, —S—, and —N$R_L$—;

each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro; wherein s is 1, 2, 3 or 4; and B represents the phosphonated group; and the substructure

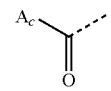

of the linker represents the carbonyl of a carboxylate group

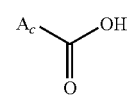

of A.

According to another particular embodiment, the compounds of the invention are represented by Formula (II):

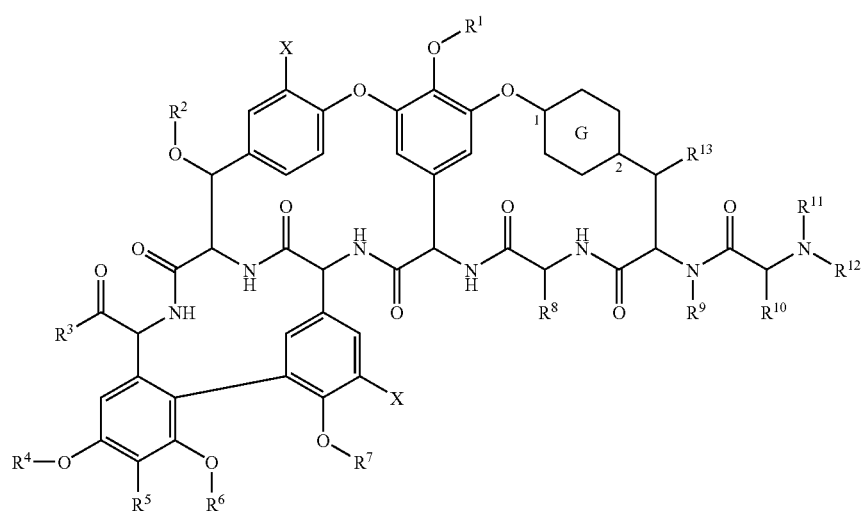

as well as pharmaceutically acceptable salts, esters and prodrugs thereof, where:

$R^1$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —$R^a$—Y—$R^b$—$(Z)_x$, and -$L^1$; or $R^1$ is a saccharide group optionally substituted with —$R^a$—Y—$R^b$—$(Z)_x$, —$R^f$, —C(O)$R_f$, —C(O)—$R^a$—Y—$R^b$—$(Z)_x$, —C($NL^2$)$R_f$, or —C($NL^3$)-$R^a$—Y—$R^b$—$(Z)_x$;

$R^2$ is hydrogen, -$L^4$ or a saccharide group optionally substituted with —$R^a$—Y—$R^b$—$(Z)_x$, —$R^f$, —C(O)$R^f$, —C(O)—$R^a$—Y—$R^b$—$(Z)_x$, —C($NL^5$)$R^f$, or —C($NL^6$)-$R^a$—Y—$R^b$—$(Z)_x$;

$R^3$ is selected from the group consisting of —$OR^c$, —$NR^cR^c$, —O—$R^a$—Y—$R^b$—$(Z)_x$, —$NR^c$—$R^a$—Y—$R^b$—$(Z)_x$, —$NR^cR^e$, —O—$R^e$, —$OL^7$, —$NL^8R^c$, and —$NL^9R^e$;

$R^4$ is selected from the group consisting of hydrogen, alkyl, substituted alkyl, alkenyl, substituted alkenyl, alkynyl, substituted alkynyl, -$L^{10}$, —$R^a$—Y—$R^b$—$(Z)_x$, —C(O)$R^d$, —C($NL^{11}$)$R^d$ and a saccharide group optionally substituted with —$R^a$—Y—$R^b$—$(Z)_x$, —$R^f$, —C(O)—$R^a$—Y—$R^b$—$(Z)_x$, or C($NL^{12}$)—$R^a$—Y—$R^b$—$(Z)_x$, or $R^4$ and $R^5$ can be joined, together with the atoms to which they are attached, to form a heterocyclic ring optionally substituted with —$NR^c$—$R^a$—Y—$R^b$—$(Z)_x$ or —$NL^{13}$-$R^a$—Y—$R^b$—$(Z)_x$;

$R^5$ is selected from the group consisting of hydrogen, halo, —CH($R^c$)—$NR^cR^c$, —CH($R^c$)—$NR^cR^e$, —CH($R^c$)—$NR^c$—$R^a$—Y—$R^b$—$(Z)_x$, —CH($R^c$)—$R^x$, —CH($R^c$)—$NR^c$—$R^a$—C(O)—$R^x$, —CH($R^c$)—$NL^{14}R^c$, —CH($R^c$)—$NL^{15}R^e$, —CH($R^c$)—$NL^{16}$-$R^a$—Y—$R^b$—$(Z)_x$, —CH($R^c$)—$NL^{17}$-$R^a$—C(O)—$R^x$ and —CH($R^c$)—$NR^c$—$R^a$—C($NL^{18}$)-$R^x$;

$R^6$ is selected from the group consisting of hydrogen, alkyl, substituted alkyl, alkenyl, substituted alkenyl, alkynyl, substituted alkynyl, -$L^{19}$, —$R^a$—Y—$R^b$—$(Z)_x$, —C(O)$R^d$, —C($NL^{20}$)$R^d$ and a saccharide group optionally substituted with —$R^a$—Y—$R^b$—$(Z)_x$, —$R^f$, —C(O)$R^f$, —C(O)—$R^a$—Y—$R^b$—$(Z)_x$, —C($NL^{21}$)$R^f$, or —C($NL^{22}$)-$R^a$—Y—$R^b$—$(Z)_x$; or $R^5$ and $R^6$ can be joined, together with the atoms to which they are attached, to form a heterocyclic ring optionally substituted with —$NR^c$—$R^a$—Y—$R^b$—$(Z)_x$ or —$NL^{23}$-$R^a$—Y—$R^b$—$(Z)_x$;

$R^7$ is selected from the group consisting of hydrogen, alkyl, substituted alkyl, alkenyl, substituted alkenyl, alkynyl, substituted alkynyl, -$L^{24}$, —$R^a$—Y—$R^b$—$(Z)_x$, —C(O)$R^d$, and —C($NL^{25}$)$R^d$;

$R^8$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$R^a$—Y—$R^b$—$(Z)_x$;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic; and -$L^{26}$;

$R^{10}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or $R^8$ and $R^{10}$ are joined to form —$Ar^1$—O—$Ar^2$—, where $Ar^1$ and $Ar^2$ are independently arylene or heteroarylene which may optionally be substituted with —$OL^{27}$;

$R^{11}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, and -$L^{28}$; or $R^{10}$ and $R^{11}$ are joined, together with the carbon and nitrogen atoms to which they are attached, to form a heterocyclic ring which may optionally be substituted with —$OL^{29}$, —$CO_2L^{30}$ or —$NL^{31}R^c$;

$R^{12}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, -$L^{32}$, —C(O)$R^d$, —C(NH)$R^d$, —C(O)$NR^cR^c$, —C(O)$OR^d$, —C(NH)$NR^cR^c$, —$R^a$—Y—$R^b$—$(Z)_x$, and —C(O)—$R^b$—Y—$R^b$—$(Z)_x$, —C($NL^{33}$)$R^d$, —C(O)$NL^{34}R^c$, —C(O)$OL^{35}$, —C(NH)$NL^{36}R^c$, —C($NL^{37}$)$NR^cR^c$, and —C($NL^{38}$)—$R^b$—Y—$R^b$—$(Z)_x$; or $R^{11}$ and $R^{12}$ are joined, together with the nitrogen atom to which they are attached, to form a heterocyclic ring which may optionally be substituted with —$OL^{39}$, —$CO_2L^{40}$ or —$NL^{41}R^c$;

$R^{13}$ is hydrogen or —$OR^{14}$;

$R^{14}$ is selected from the group consisting of hydrogen, -$L^{42}$, —C(O)$R^d$, —C($NL^{43}$)$R^d$ and a saccharide group optionally substituted with —$R^a$—Y—$R^b$—$(Z)_x$, —$R^f$, —C(O)$R^f$, —C(O)—$R^a$—Y—$R^b$—$(Z)_x$, —C($NL^{44}$)$R^f$, or —C($NL^{45}$)—$R^a$—Y—$R^b$—$(Z)_x$;

$R^a$ is each independently selected from the group consisting of alkylene, substituted alkylene, alkenylene, substituted alkenylene, alkynylene and substituted alkynylene;

$R^b$ is each independently selected from the group consisting of a covalent bond, alkylene, substituted alkylene, alkenylene, substituted alkenylene, alkynylene and substituted alkynylene;

$R^c$ is each independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

$R^d$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^e$ is each a saccharide group optionally substituted with —$R^a$—Y—$R^b$—$(Z)_x$, —$R^f$, —C(O)$R^f$, —C(O)—$R^a$—Y—$R^b$—$(Z)_x$, —C($NL^{46}$)$R^f$, or —C($NL^{47}$)—$R^a$—Y—$R^b$—$(Z)_x$;

$R^f$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, and heterocyclic;

$R^x$ is an N-linked amino saccharide or an N-linked heterocycle, either of which may be optionally substituted with —$R^a$—Y—$R^b$—$(Z)_x$, —$R^f$, —C(O)$R_f$, —C(O)—$R^a$—Y—$R^b$—$(Z)_x$, —C($NL^{48}$)$R_f$, or —C($NL^{49}$)—$R^a$—Y—$R^b$—$(Z)_x$;

X is each independently selected from the group consisting of hydrogen, fluoro, chloro, bromo and iodo;

Y is each independently selected from the group consisting of —$CH_2$—, —O—, —S—, —S—S—, —$NR^c$—, —S(O)—, —SO$_2$—, —NR$^c$C(O)—, —OSO$_2$—, —OC(O)—, —N(R$^c$)SO$_2$—, —C(O)NR$^c$—, —C(O)O—, —SO$_2$NR$^c$—, —SO$_2$O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^c$C(O)O—, —NR$^c$C(O)NR$^c$—, —OC(O)NR$^c$, —C(O)—, —N(R$^c$)SO$_2$NR$^c$—, —NL$^{50}$-, —NL$^{51}$C(O)—, —OSO$_2$—, —OC(O)—, —N(L$^{52}$)SO$_2$—, —C(O)NL$^{53}$-, —SO$_2$NL$^{54}$-, —P(O)(OL$^{55}$)O—, —P(O)(OL$^{56}$)NR$^c$—, —P(O)(OR$^c$)NL$^{57}$-, —OP(O)(OL$^{58}$)O—, —OP(O)(OL$^{59}$)NR$^c$—, —OP(O)(OR$^c$)NL$^{60}$-, —NL$^{61}$C(O)O—, —NL$^{62}$C(O)NR$^c$—, —NR$^c$C(O)NL$^{63}$-, —OC(O)NL$^{64}$-, —N(L$^{65}$)SO$_2$NR$^c$— and —N(R$^c$)SO$_2$NL$^{66}$-;

Z is each independently selected from the group consisting of hydrogen, aryl, cycloalkyl, cycloalkenyl, heteroaryl, heterocyclic, a saccharide, -L$^{67}$, -L$^{68}$ and -L$^{69}$;

x is 1 or 2; and

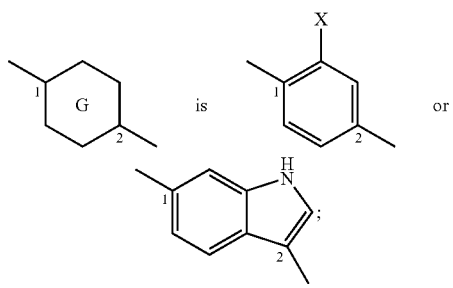

each L$^1$, L$^4$, L$^{10}$, L$^{19}$, L$^{24}$, L$^{27}$, L$^{29}$, L$^{39}$, L$^{42}$, and L$^{67}$ is a linker independently selected from the group consisting of

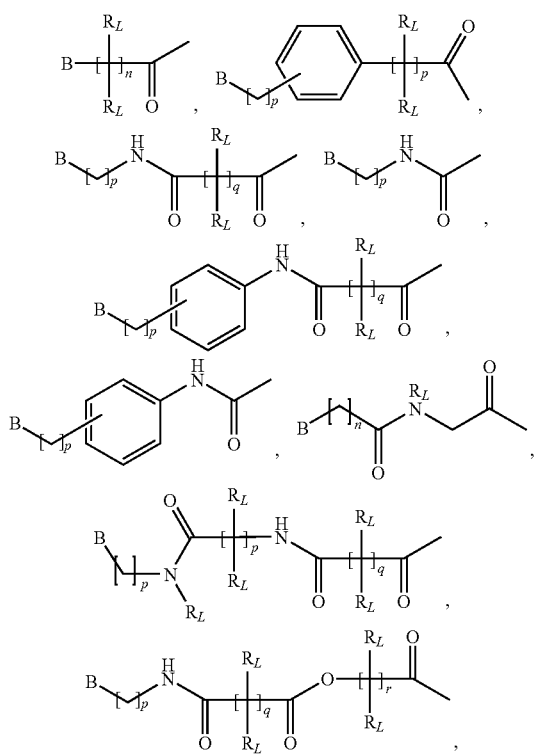

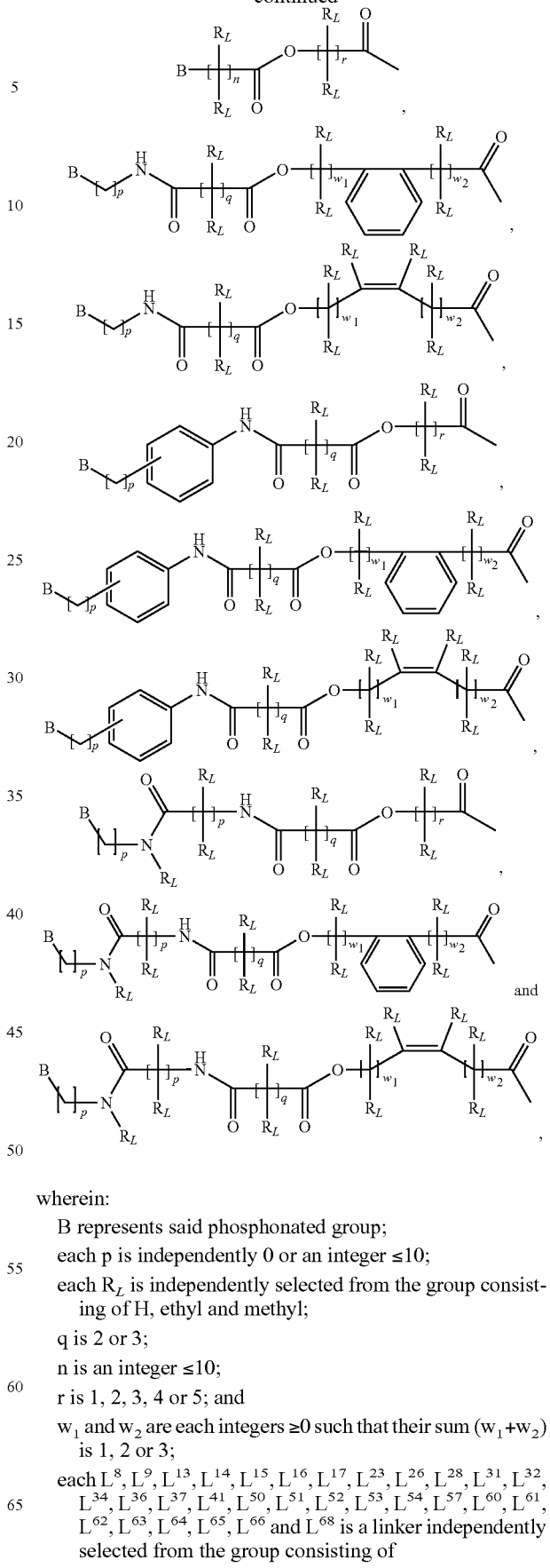

wherein:
B represents said phosphonated group;
each p is independently 0 or an integer ≤10;
each R$_L$ is independently selected from the group consisting of H, ethyl and methyl;
q is 2 or 3;
n is an integer ≤10;
r is 1, 2, 3, 4 or 5; and
w$_1$ and w$_2$ are each integers ≥0 such that their sum (w$_1$+w$_2$) is 1, 2 or 3;
each L$^8$, L$^9$, L$^{13}$, L$^{14}$, L$^{15}$, L$^{16}$, L$^{17}$, L$^{23}$, L$^{26}$, L$^{28}$, L$^{31}$, L$^{32}$, L$^{34}$, L$^{36}$, L$^{37}$, L$^{41}$, L$^{50}$, L$^{51}$, L$^{52}$, L$^{53}$, L$^{54}$, L$^{57}$, L$^{60}$, L$^{61}$, L$^{62}$, L$^{63}$, L$^{64}$, L$^{65}$, L$^{66}$ and L$^{68}$ is a linker independently selected from the group consisting of

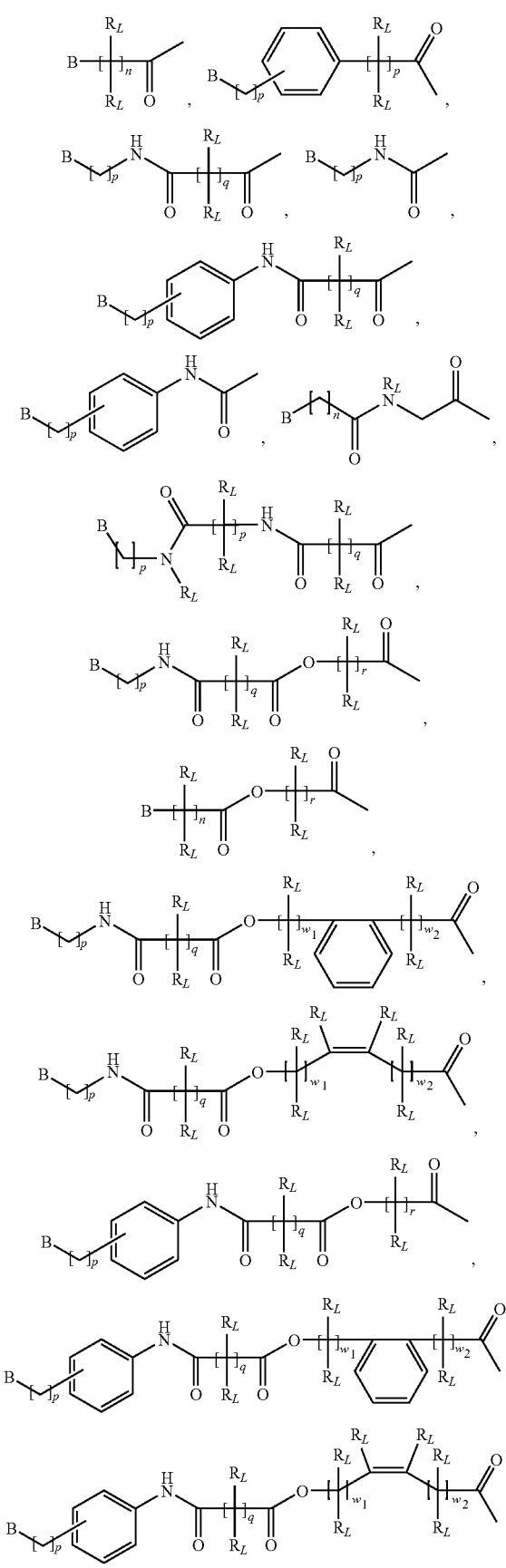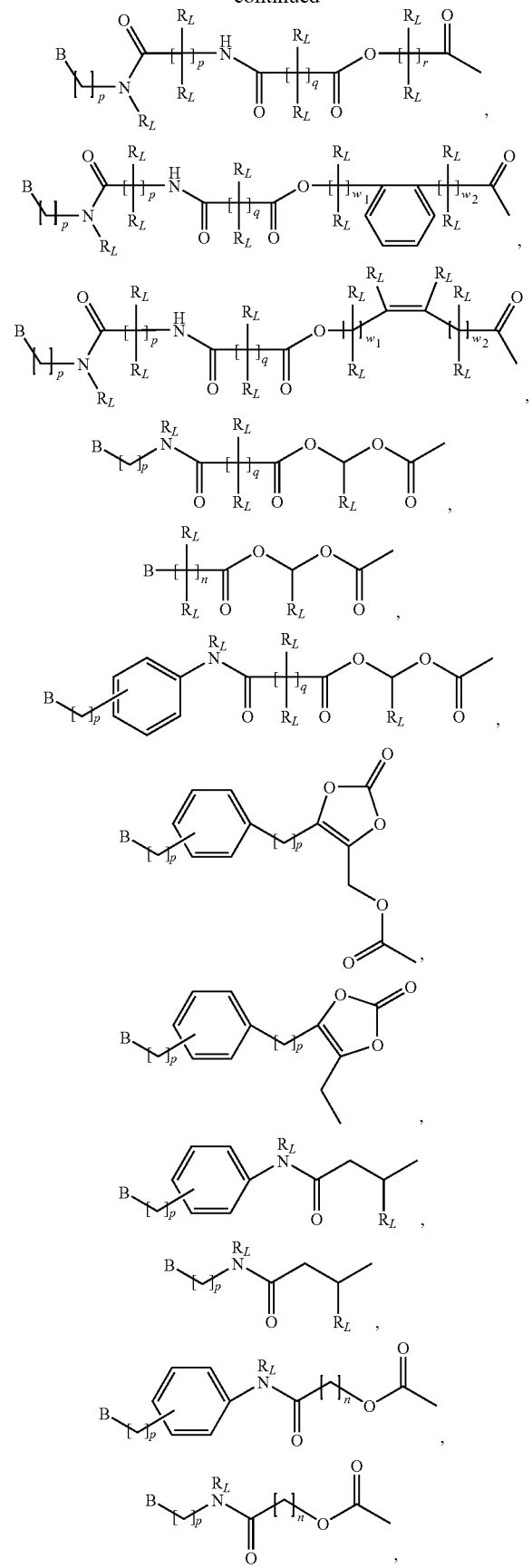

-continued

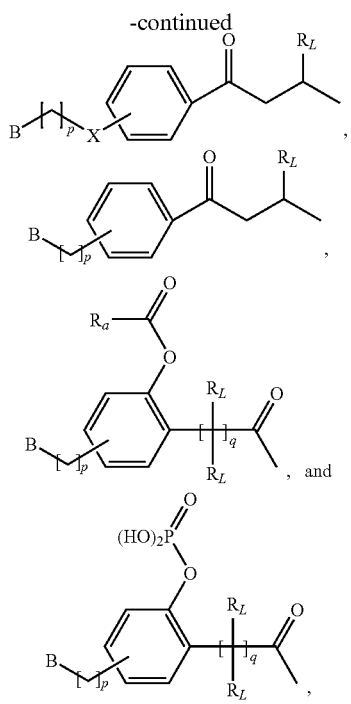

wherein:
B represents said phosphonated group;
n is an integer ≤10;
each p is independently 0 or an integer ≤10;
each $R_L$ is independently selected from the group consisting of H, ethyl and methyl;
q is 2 or 3;
r is 1, 2, 3, 4 or 5;
$w_1$ and $w_2$ are each integers ≥0 such that their sum $(w_1+w_2)$ is 1, 2 or 3;
X is —$CH_2$—, —$CONR_L$—, —CO—O—$CH_2$—, or —CO—O—; and
$R_a$ is $C_xH_y$, where x is an integer of 0 to 20 and y is an integer of 1 to 2x+1;
each $L^7, L^{30}, L^{35}, L^{40}, L^{55}, L^{56}, L^{58}, L^{59}$ and $L^{69}$ is a linker independently selected from the group consisting of

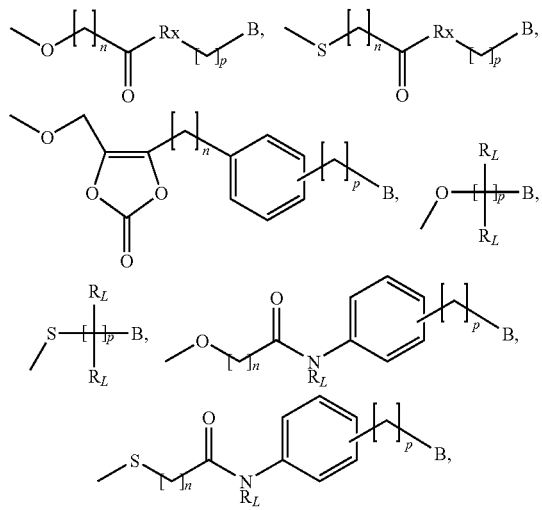

-continued

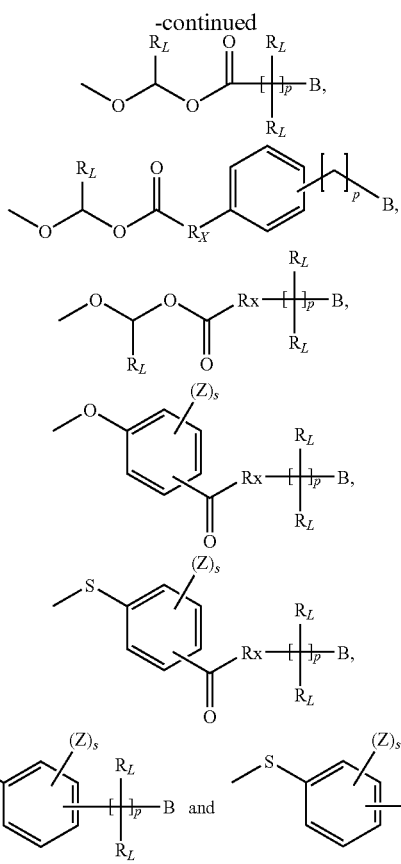

wherein:
n is an integer ≤10, preferably 1, 2, 3 or 4, more preferably 1 or 2;
p is 0 or an integer ≤10, preferably 0, 1, 2, 3 or 4, more preferably 0 or 1;
$R_L$ is H, ethyl or methyl, preferably H;
$R_x$ is —S—, —$C(R_L)_2$—, —$NR_L$— or —O—; preferably —$NR_L$—, more preferably —NH—;
each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro, wherein s is 1, 2, 3 or 4; and
B represents the phosphonated group;
each $L^2, L^3, L^5, L^6, L^{11}, L^{12}, L^{18}, L^{20}, L^{21}, L^{22}, L^{25}, L^{33}, L^{38}, L^{43}, L^{44}, L^{45}, L^{46}, L^{47}, L^{48}$ and $L^{49}$ is a linker independently

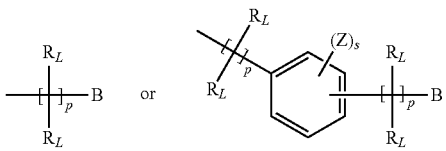

wherein:
p is 0 or an integer ≤10, preferably 0, 1, 2, 3 or 4, more preferably 0 or 1;
$R_L$ is H, ethyl or methyl, preferably H;
each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro, wherein s is 1, 2, 3 or 4; and B represents the phosphonated group;

with the proviso that at least one of $L^1, L^2, L^3, L^4, L^5, L^6, L^7, L^8, L^9, L^{10}, L^{11}, L^{12}, L^{13}, L^{14}, L^{15}, L^{16}, L^{17}, L^{18}, L^{19}, L^{20}, L^{21}, L^{22}, L^{23}, L^{24}, L^{25}, L^{26}, L^{27}, L^{28}, L^{29}, L^{30}, L^{31}, L^{32}, L^{33}, L^{34}, L^{35}, L^{36}, L^{37}, L^{38}, L^{39}, L^{40}, L^{41}, L^{42}, L^{43}, L^{44}, L^{45}, L^{46}, L^{47}, L^{48}, L^{49}, L^{50}, L^{51}, L^{52}, L^{53}, L^{54}, L^{55}, L^{56}, L^{57}, L^{58}, L^{59}, L^{60}, L^{61}, L^{62}, L^{63}, L^{64}, L^{65}, L^{66}, L^{67}, L^{68}$ and $L^{69}$ is present.

In a preferred embodiment of formula (II), B is a phosphonated group selected from the group consisting of:

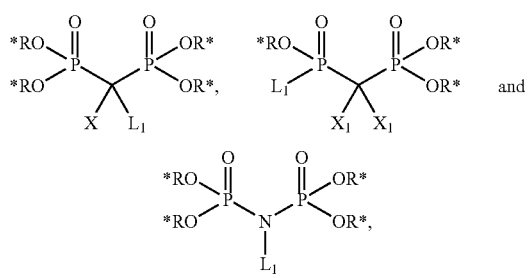

wherein:
each R* is independently selected from the group consisting of H, lower alkyl, cycloalkyl, aryl and heteroaryl, with the proviso that at least two R* are H;

X is H, OH, $NH_2$, or a halo group;

$X_1$ are both H, or each is independently selected from the group consisting of H, OH, $NH_2$, and a halo group; and $L_1$ is the point of attachment to L.

It is also conceivable according to the invention to couple a single phosphonated group to two or more antibacterial molecules. In such circumstances, the antibacterial molecules may be the same (e.g. two molecules of oritavancin) or different (e.g. one molecule of the fluoroquinolone antibacterial ciprofloxacin (Cipro®; U.S. Pat. No. 4,670,444) and one molecule of oritavancin). The phosphonated group may also be tethered to similar groups (e.g. the amino groups) or to different groups (e.g. the carboxyl group of one fluoroquinolone molecule and the amino group of a glycopeptide or lipoglycopeptide antimicrobial molecule). Examples of potentially useful, cleavable, multi-antibacterial linkers according to the invention include, but are not limited to, those having the structures:

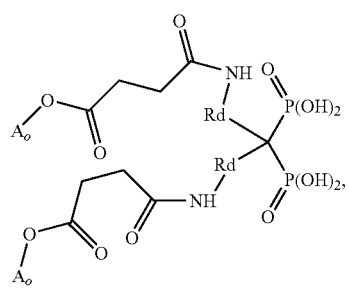

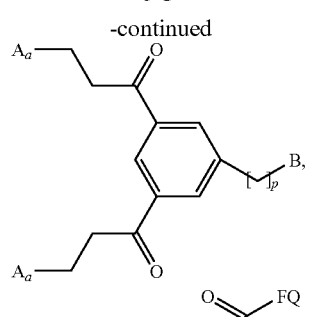

wherein:
each $R_d$ is independently an alkyl or an aryl group;
p is 0 or an integer ≤10, preferably 0, 1, 2, 3 or 4, more preferably 0 or 1;
the substructure

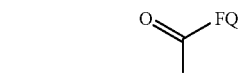

of the linker represents the hydroxyl moiety of the glycopeptide or lipoglycopeptide antimicrobial molecule A;

$A_a$ represents an amine group of the glycopeptide or lipoglycopeptide antimicrobial molecule A;

the substructure

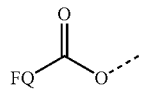

of the linker represents the carboxylic moiety of a fluoroquinolone antimicrobial.

Because of its high affinity osseous tissues, the phosphonated group B will likely remain bond to the bones for an extended period of times (up to several years). Therefore, it is very important that the phosphonated group be endowed with low or no measurable toxicity. According to another embodiment, the phosphonated group B and the linker L are selected such that the linker is hydrolyzed or cleaved in vivo (preferably mostly in osseous tissues) thereby releasing: (i) the glycopeptide or lipoglycopeptide antimicrobial molecule A and (ii) a chosen non-toxic phosphonated molecule having a proven bone therapeutic activity. Such compounds would thus have a double utility that is to: 1) provide locally to the bones for an extended period of time and/or at increased concentrations, an antibiotic useful in preventing and/or treating a bacterial bone infection, and 2) provide to the bones a drug stimulating bone regeneration or inhibiting bone resorption, thereby facilitating bone recovery from damages caused by an infection or other injury. Suitable phosphonated molecules with proven bone therapeutic activity useful according to the invention include but are not limited to pamidronate, alendronate and incadronate as well as others such as risedronate, olpadronate, etidronate, ibandronate, zolendronate or neridronate, these molecules being well known bisphosphonate bone resorption inhibitors commonly used for the treatment of osteoporosis.

The scheme below illustrates the principles of that embodiment:

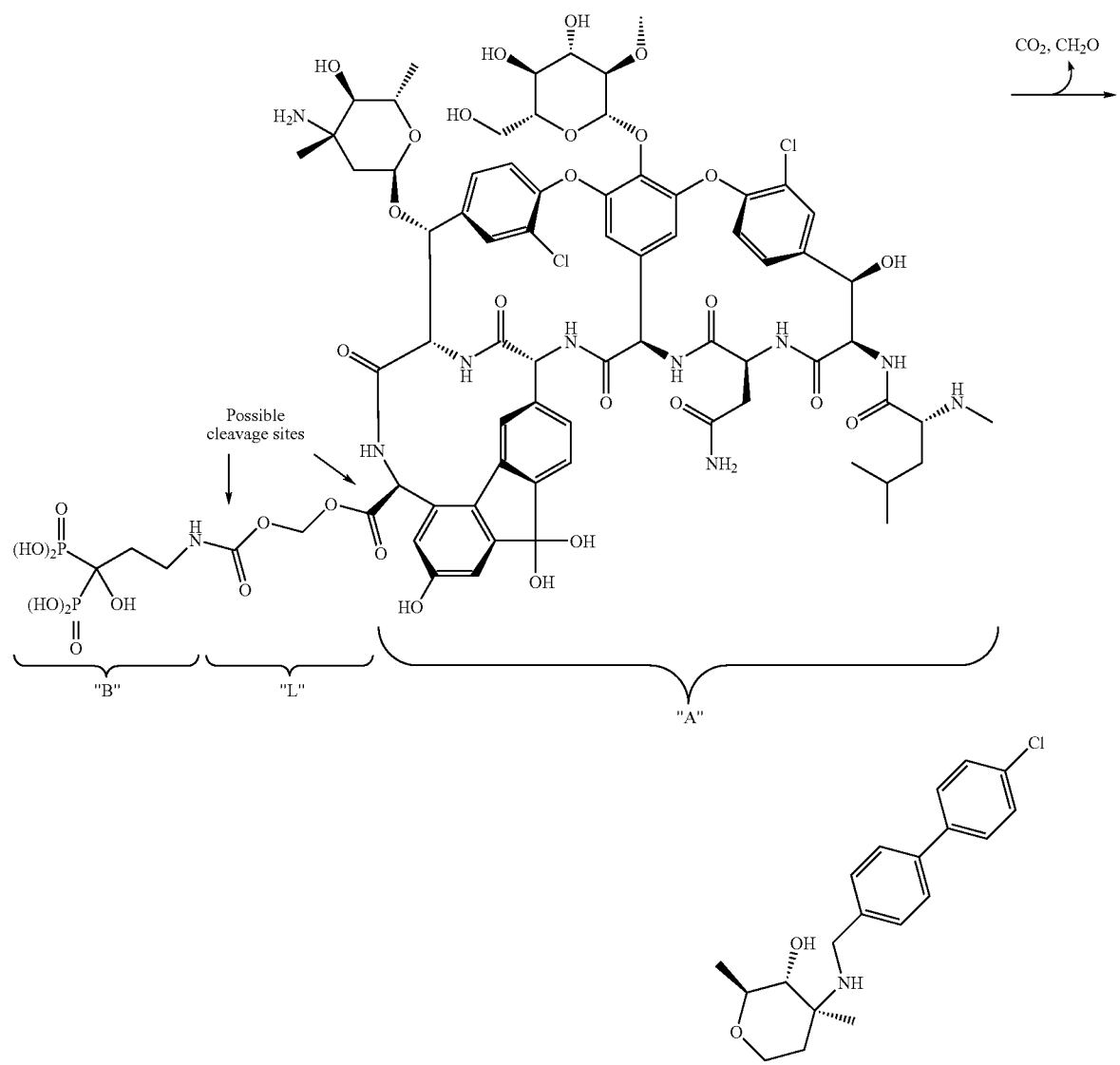

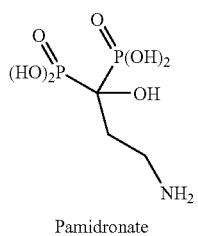
Pamidronate
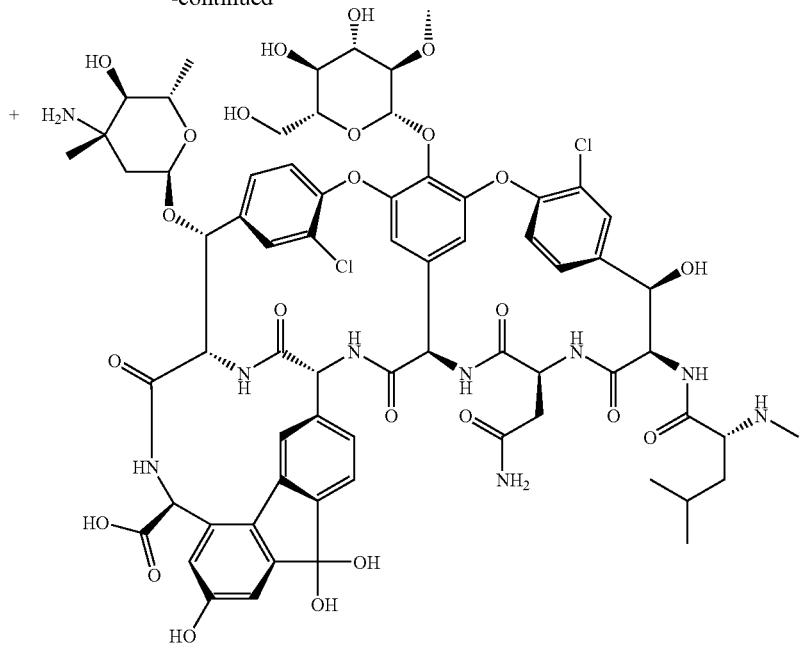
Oritavancin
Additional specific examples of bisphosphonate derivatives according to the invention derived from pamidronate and alendronate are shown hereinafter:
pamidronate
From  $NH_2$:
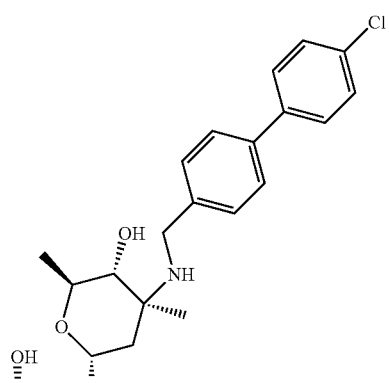

-continued
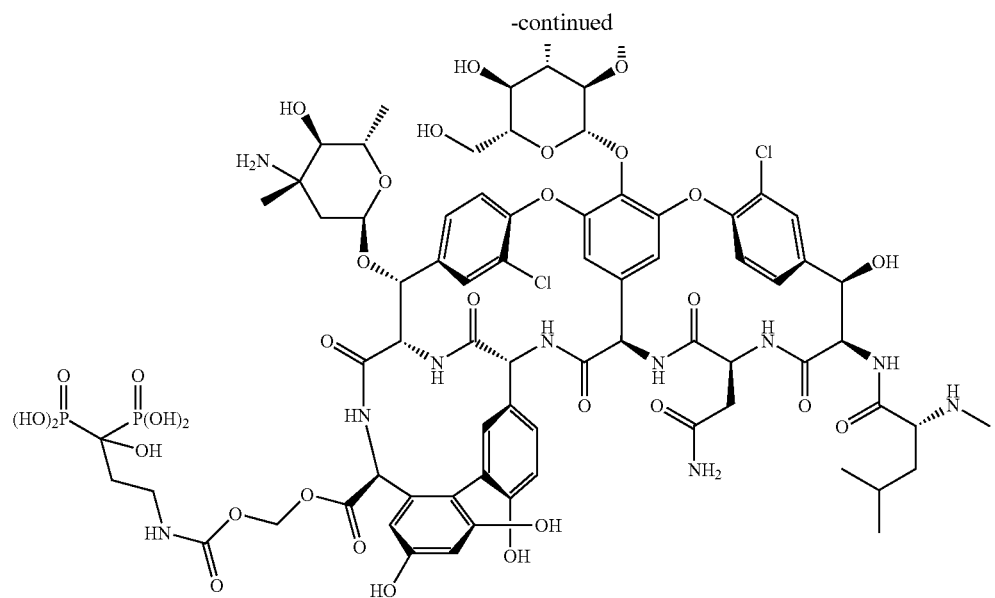
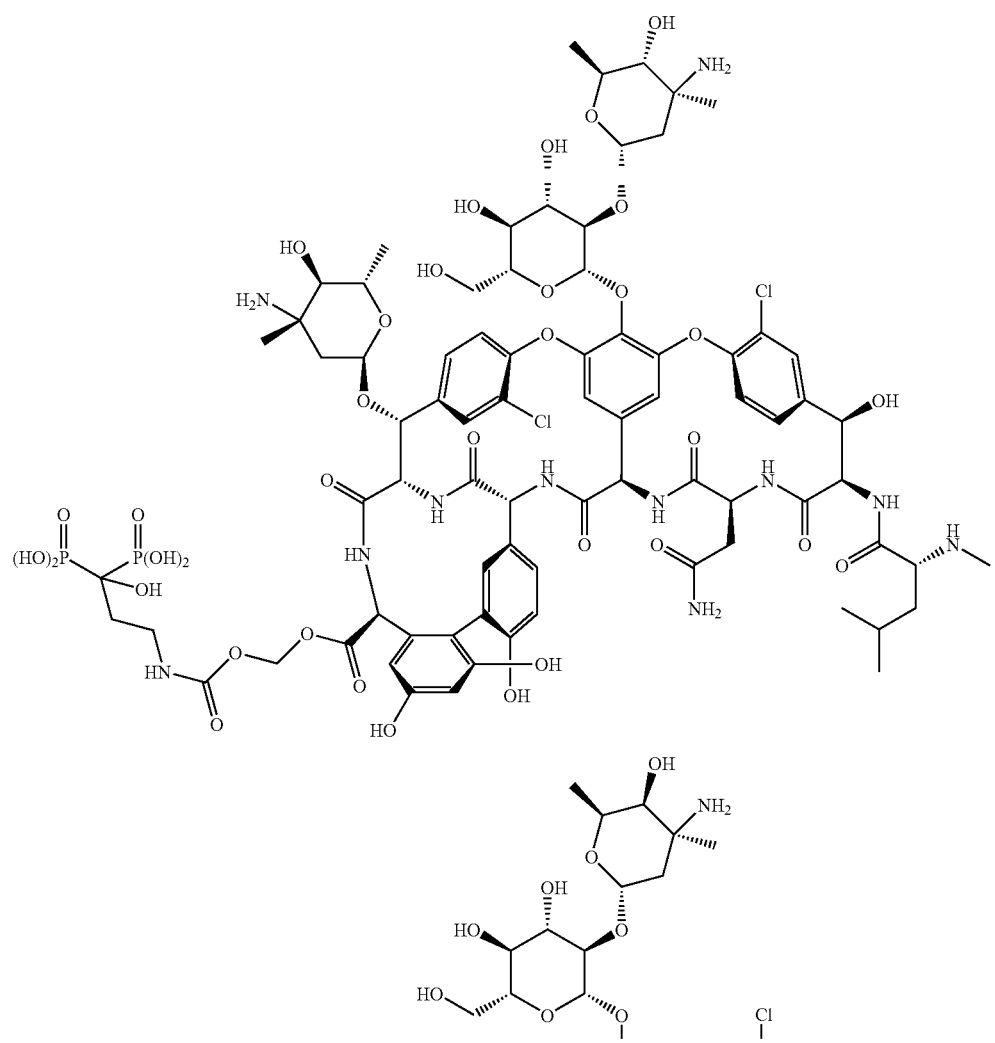

-continued
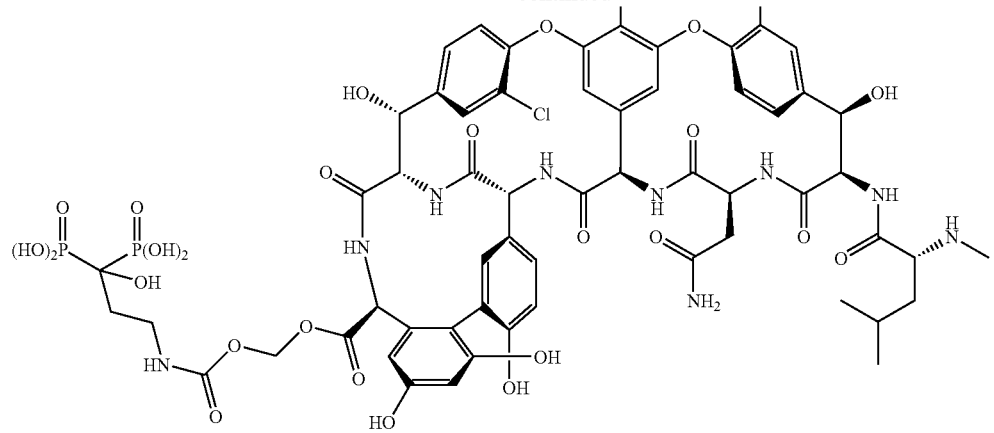
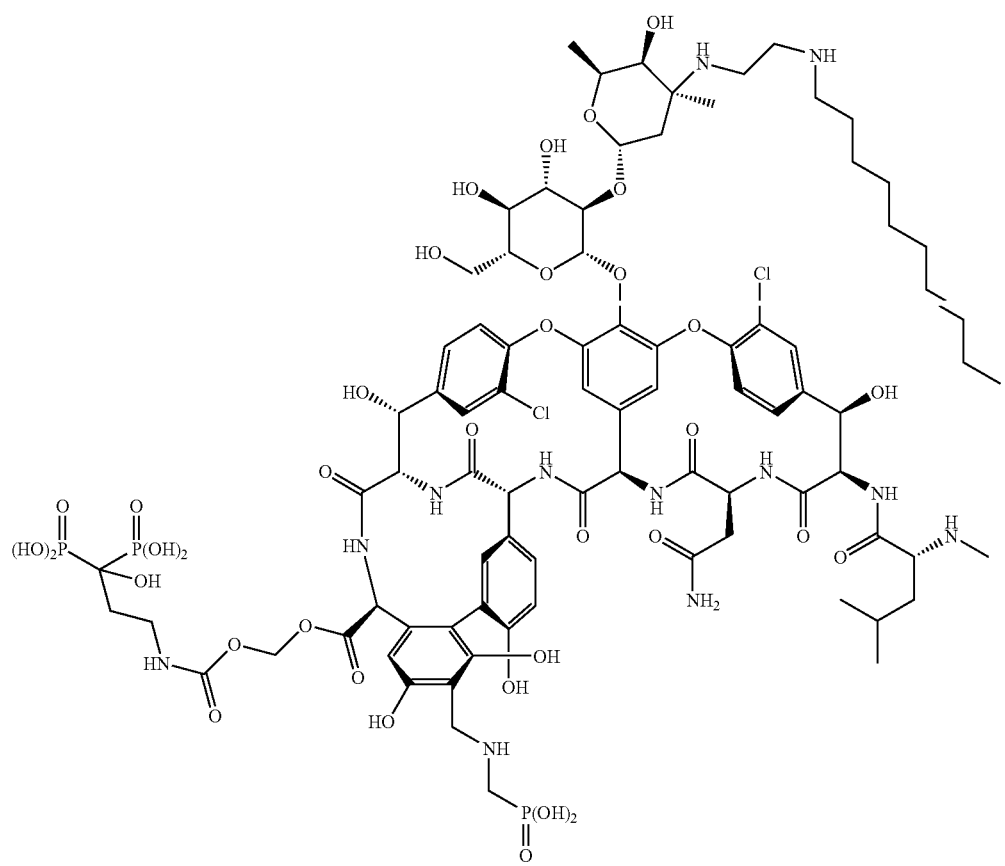

107
108
-continued
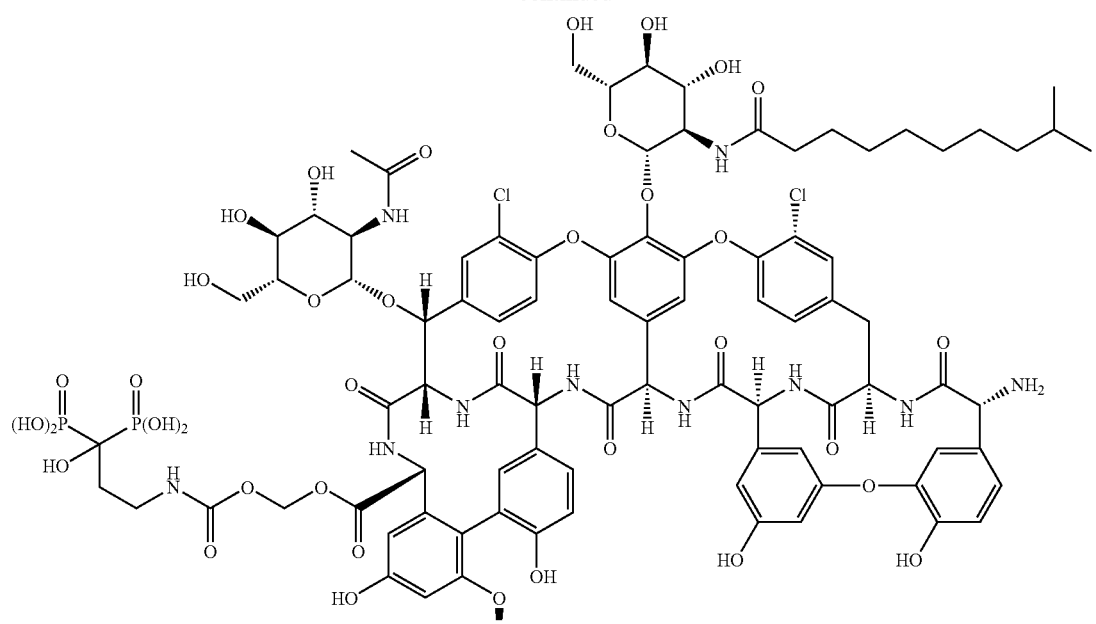
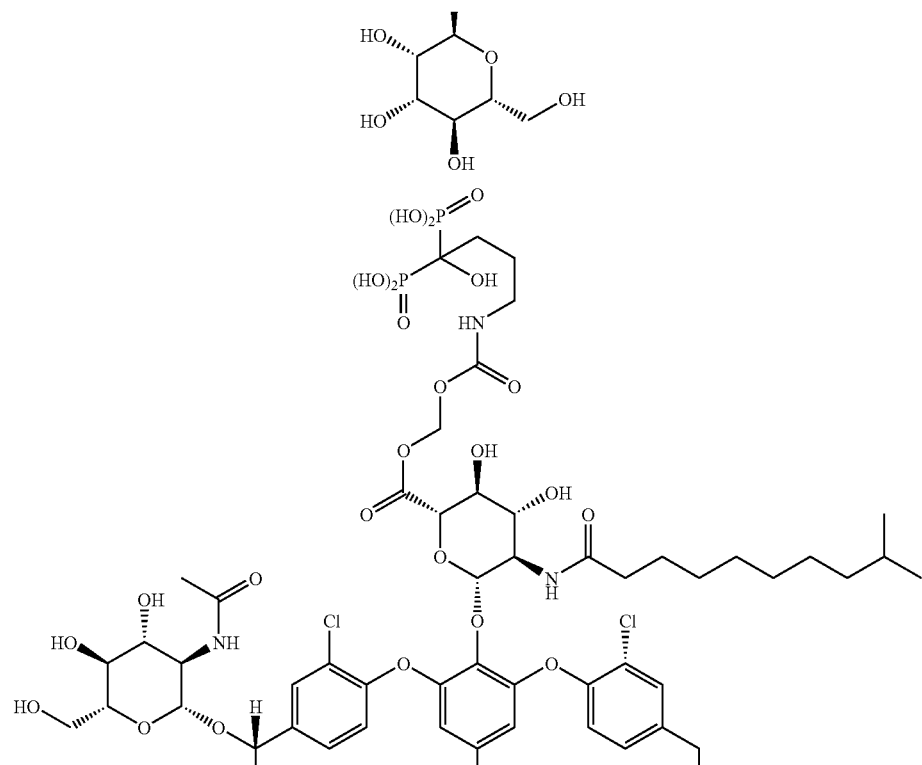

-continued
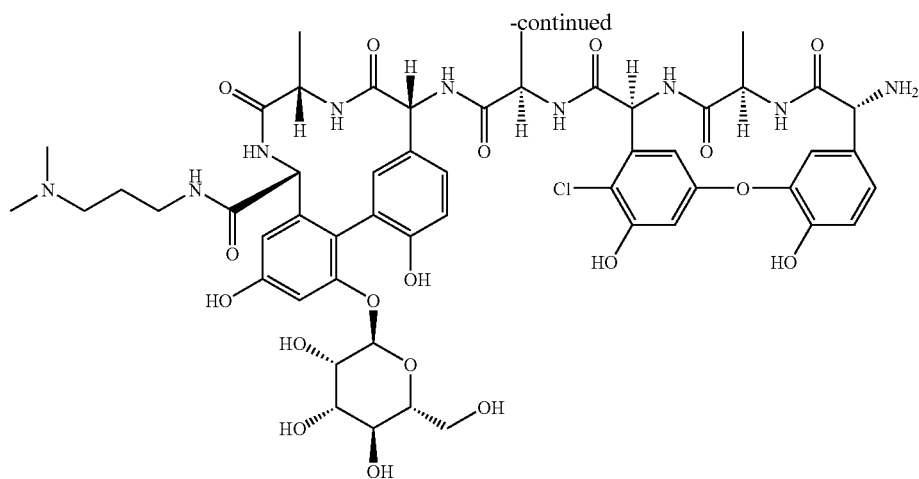
From 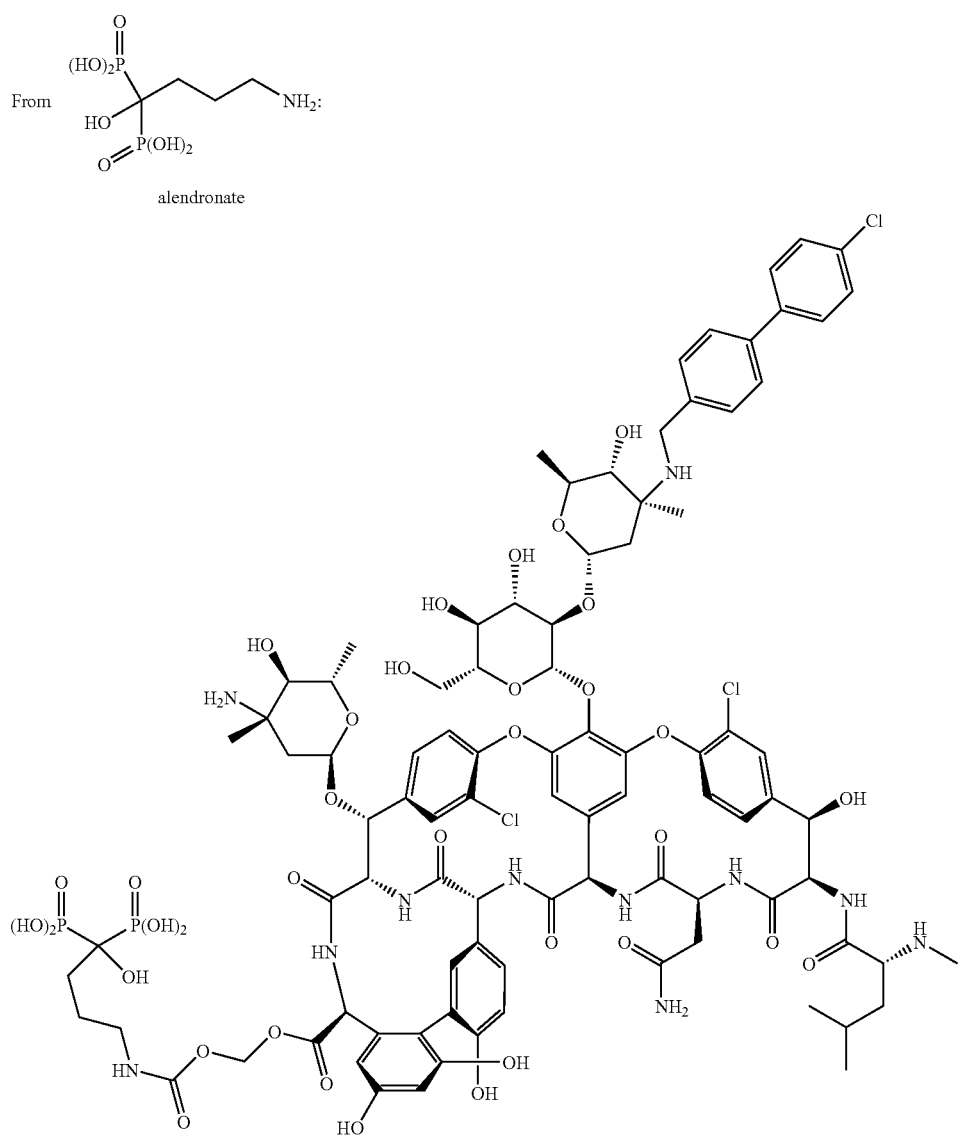
alendronate

-continued
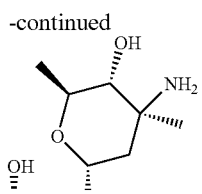
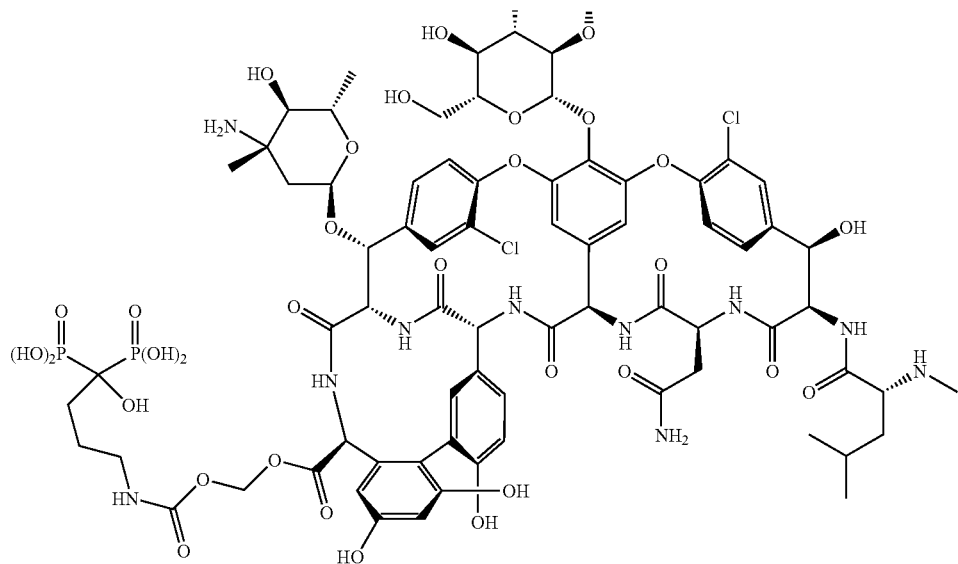
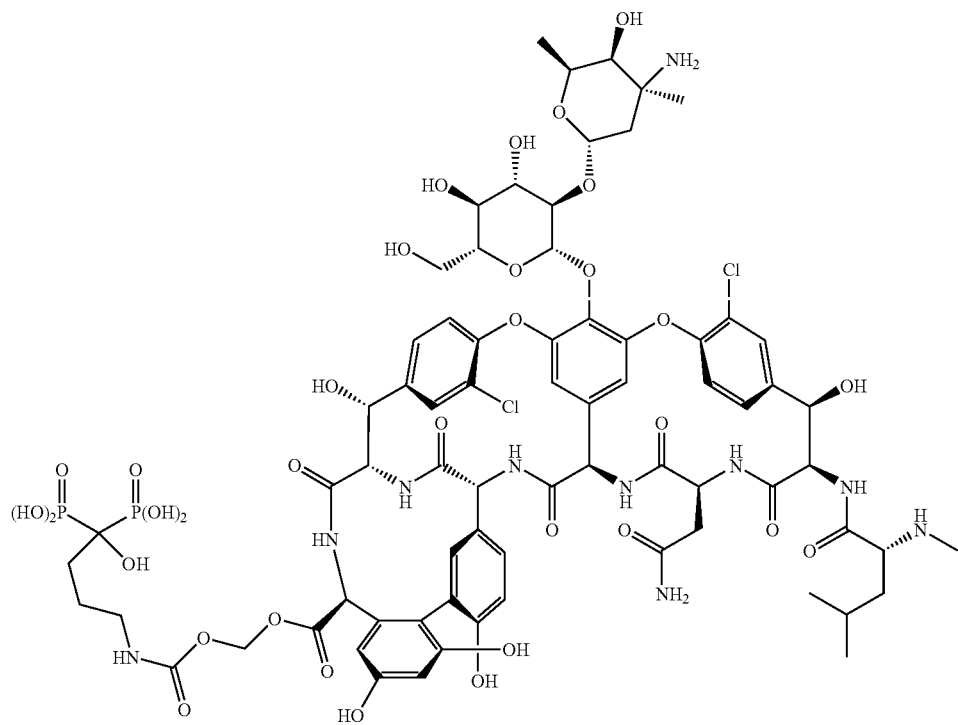

-continued
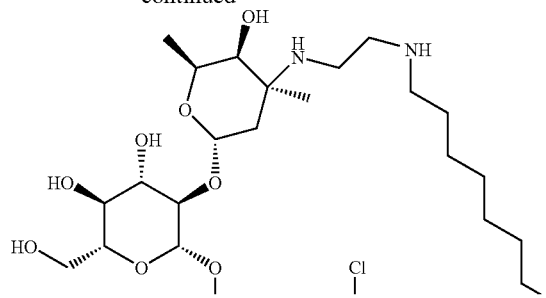
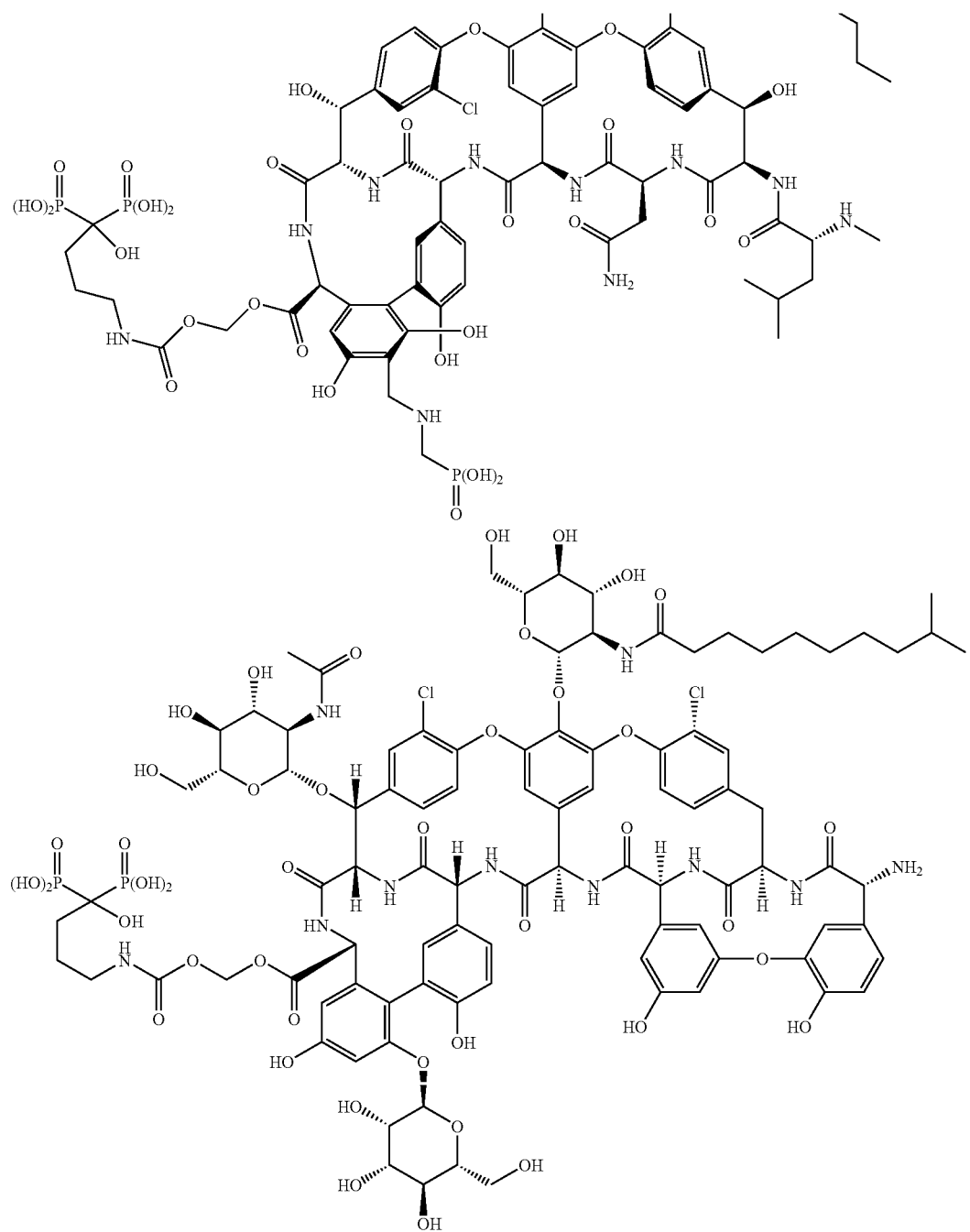

-continued

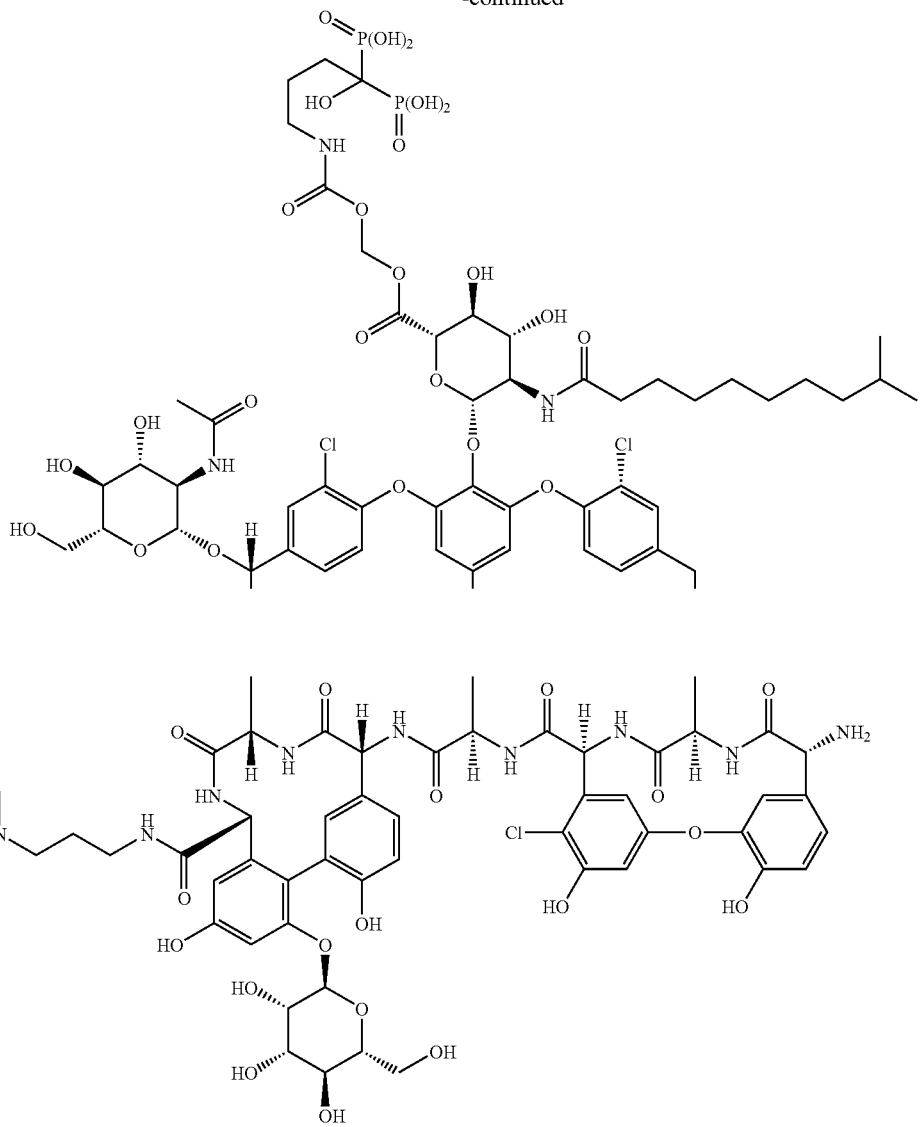

It is also conceivable according to the present invention to use a pH-sensitive linker that is cleaved only at a predetermined range of pH. In one embodiment, the pH-sensitive linker is a base-sensitive linker that is cleaved at a basic pH ranging from about 7 to about 9. According to another embodiment, the linker is an acid-sensitive linker that is cleaved at an acidic pH ranging from about 7.5 to about 4, preferably from about 6.5 and lower. It is hypothesized that such an acid-sensitive linker would allow a specific release of the glycopeptide or lipoglycopeptide antibiotic mostly at a site of bacterial infection because it is known that, acidification of tissues commonly occurs during infection (O'Reilley et al., Antimicrobial Agents and Chemotherapy (1992), 36(12): 2693-97).

A covalent bond or a non-cleavable linker may also covalently couple the phosphonated group B to the glycopeptide or lipoglycopeptide A. Such bond or linker would be selected such that it would not be cleaved or would be cleaved mainly by the bacteria present at the actual site of infection. It is hypothesized that for such compounds the phosphonated group would remain tethered to the glycopeptide or lipoglycopeptide antibiotic and the whole compound would gradually be released from the bone and absorbed by the bacteria, thereby exerting its antibacterial effect.

Of course, other types of linkers could be selected and synthesized by those skilled in the art. For instance the linker may also contain an in vivo hydrolysable phosphonated group having an affinity to bones as disclosed by Ilex Oncology Research in WO 04/026315. The linker may also contain an active group (e.g. a releasable group stimulating bone formation or decreasing bone resorption). These and other suitable linkers are encompassed by the present invention.

In addition to those compounds described hereinbefore and in the Exemplification section, additional compounds having the formula

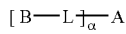

according to the invention include, but are not limited to, those having the following formulae:

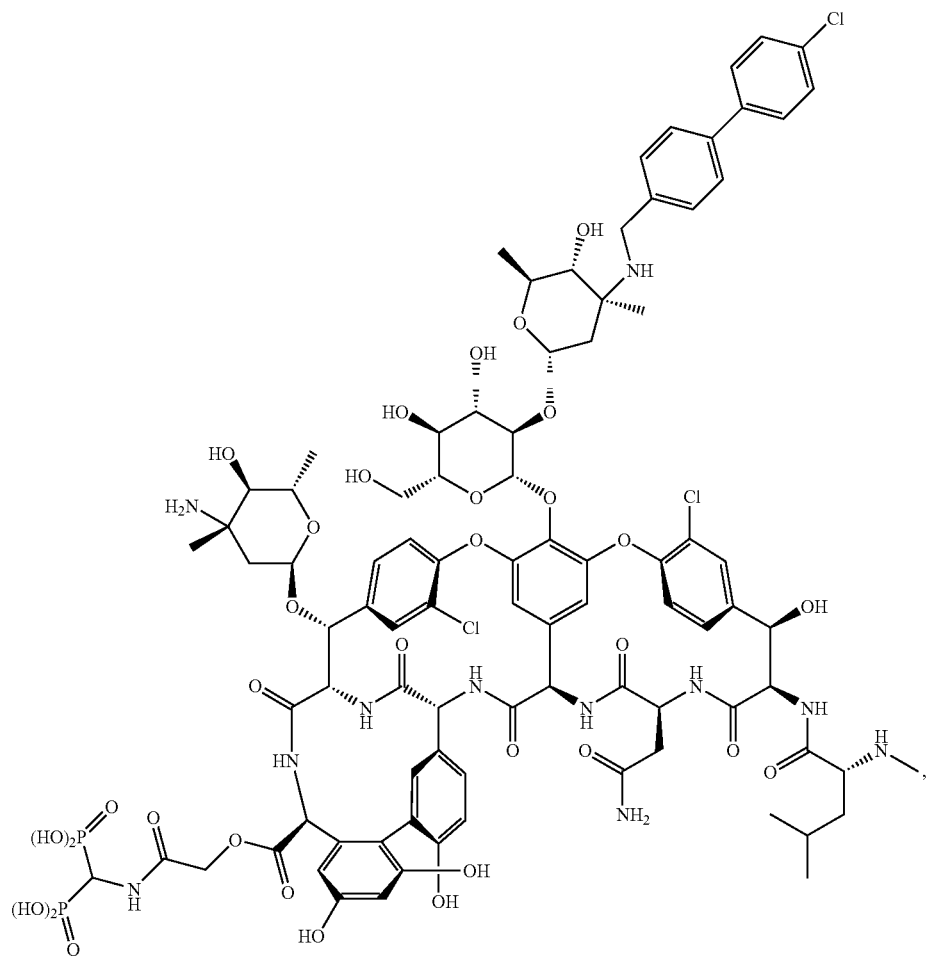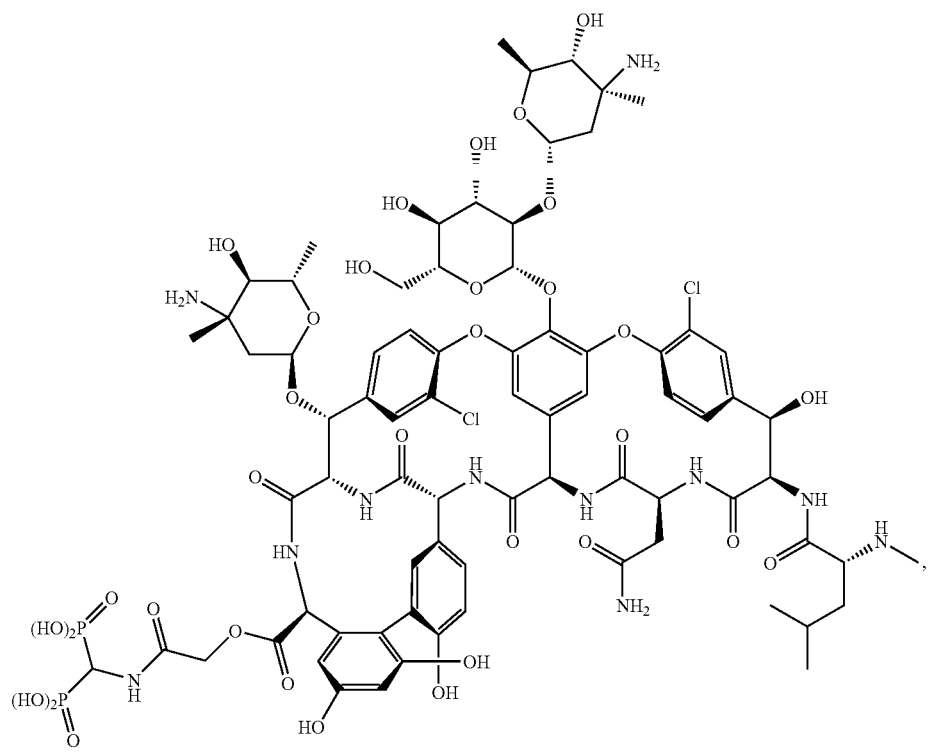

-continued
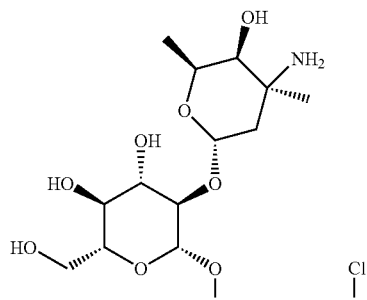
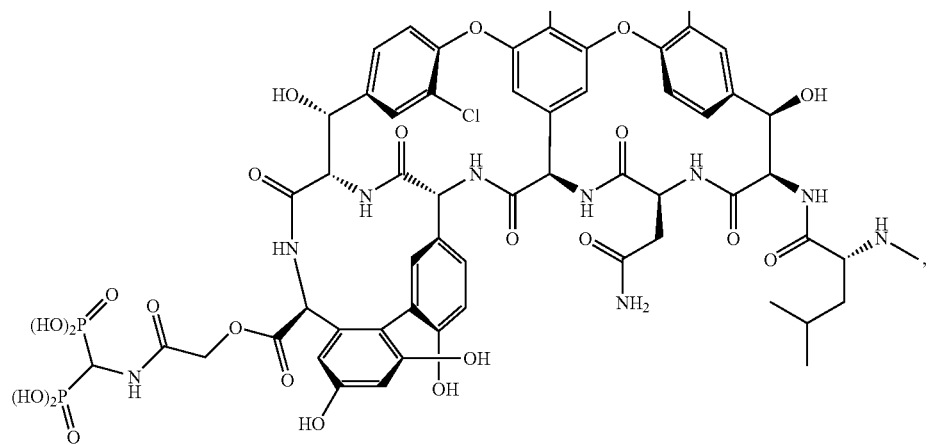
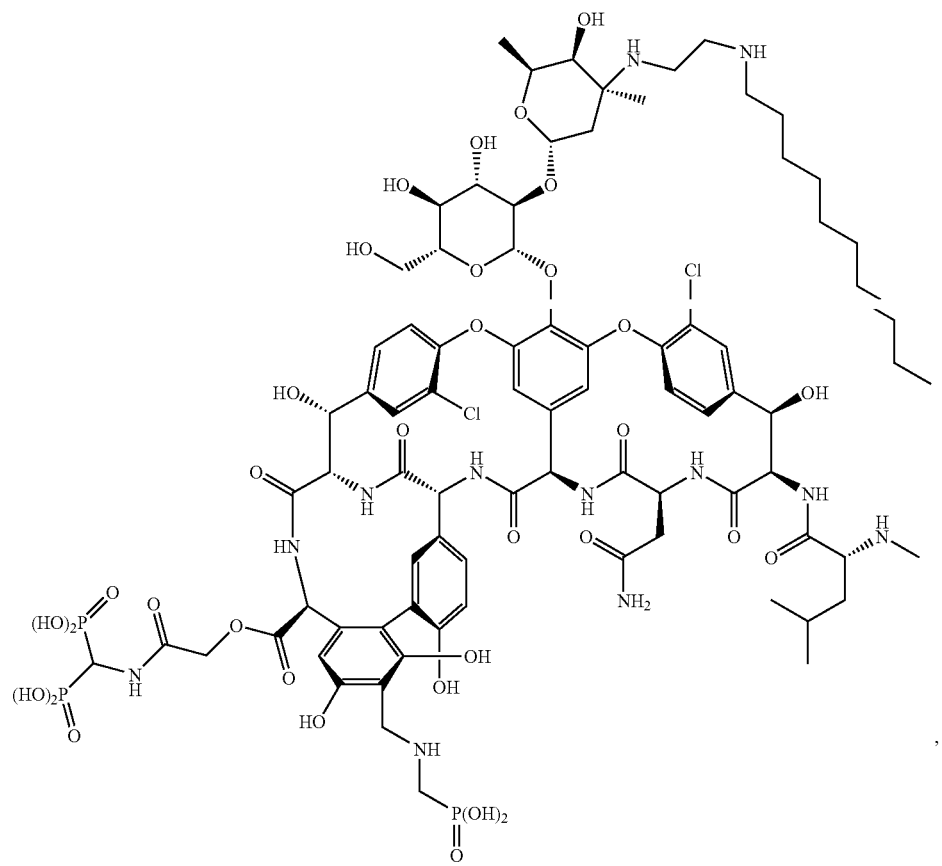

-continued
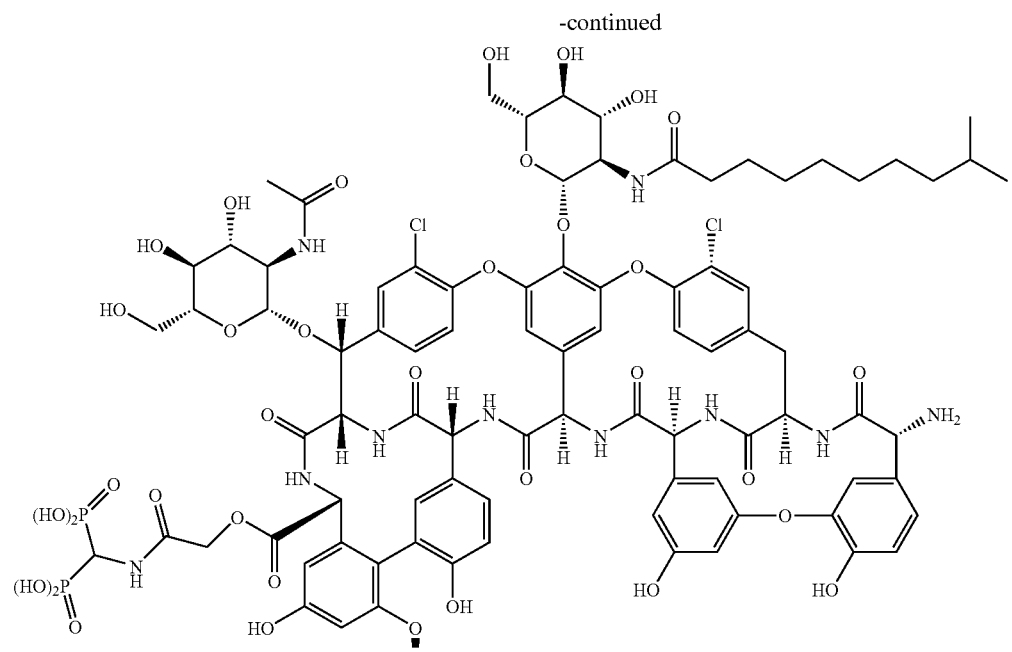
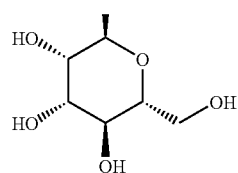
,
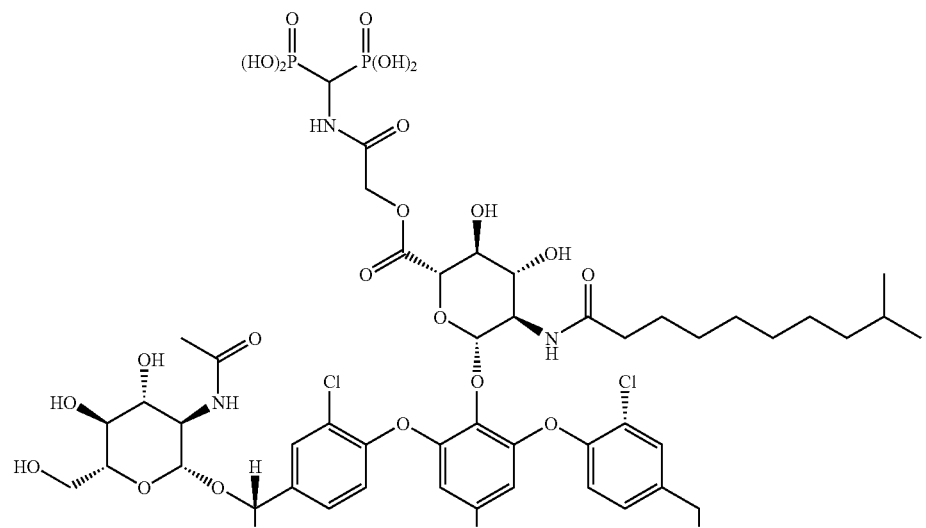

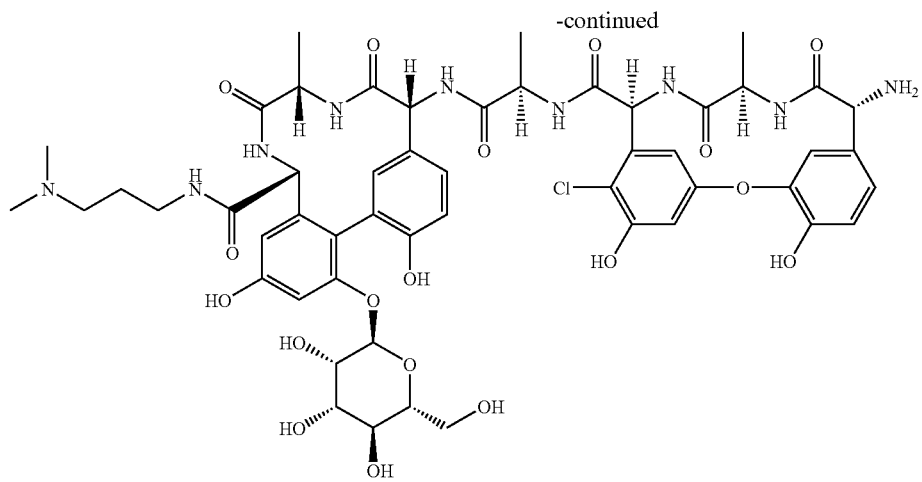
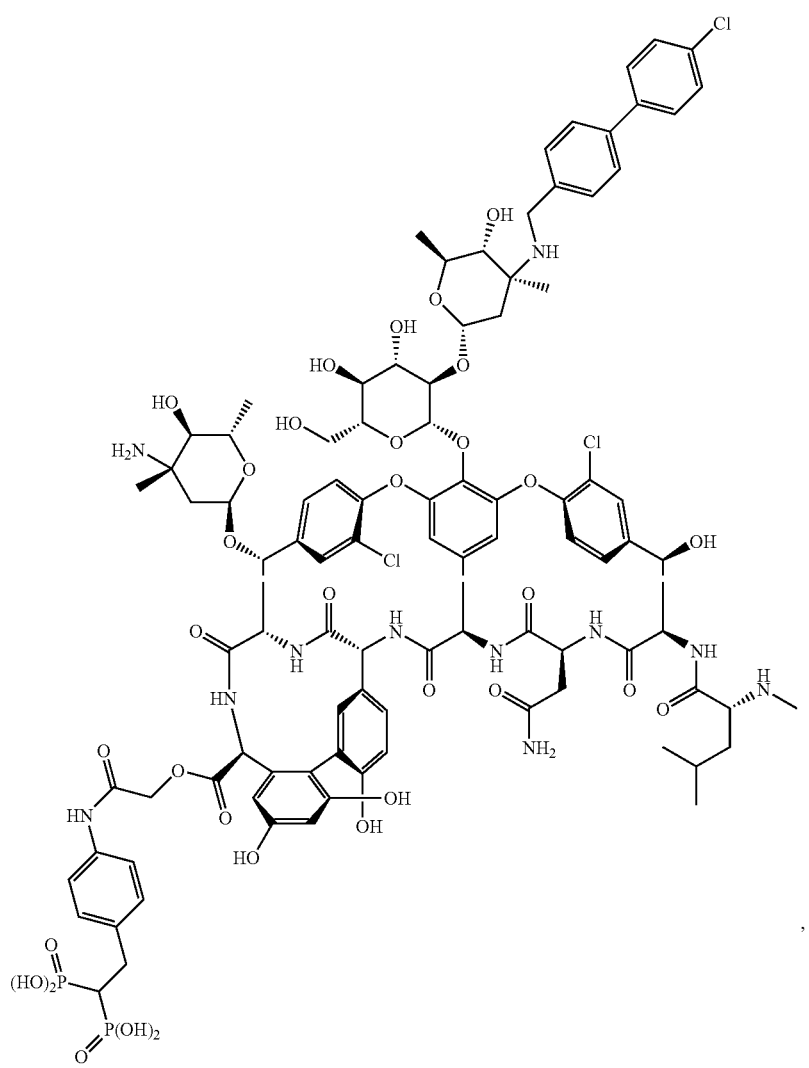

-continued
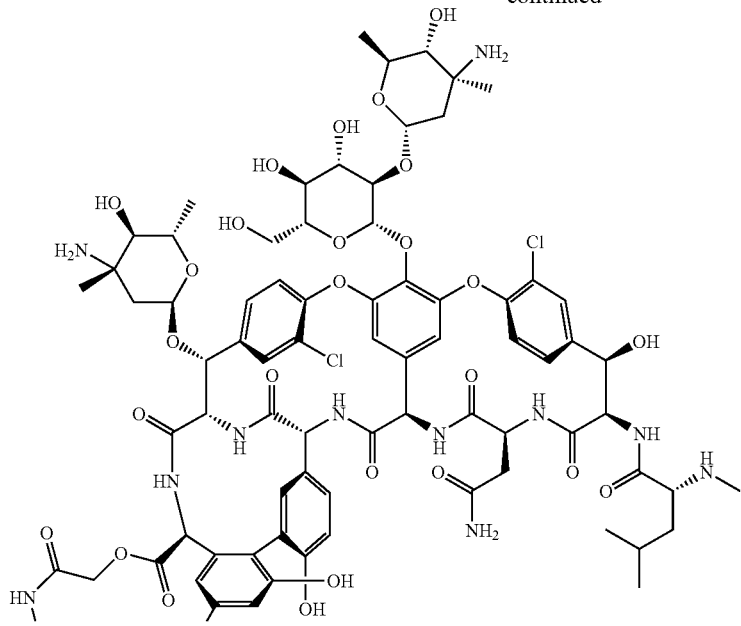
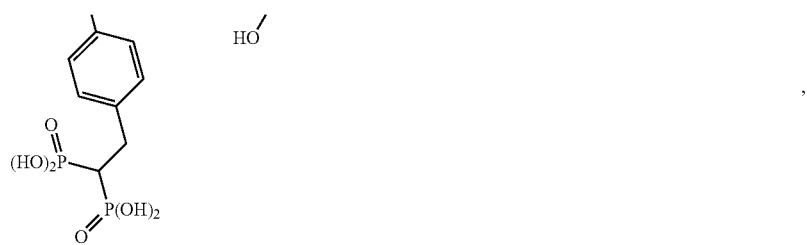
,
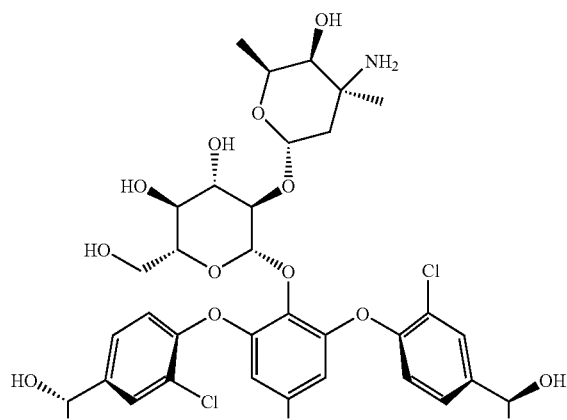

127
-continued
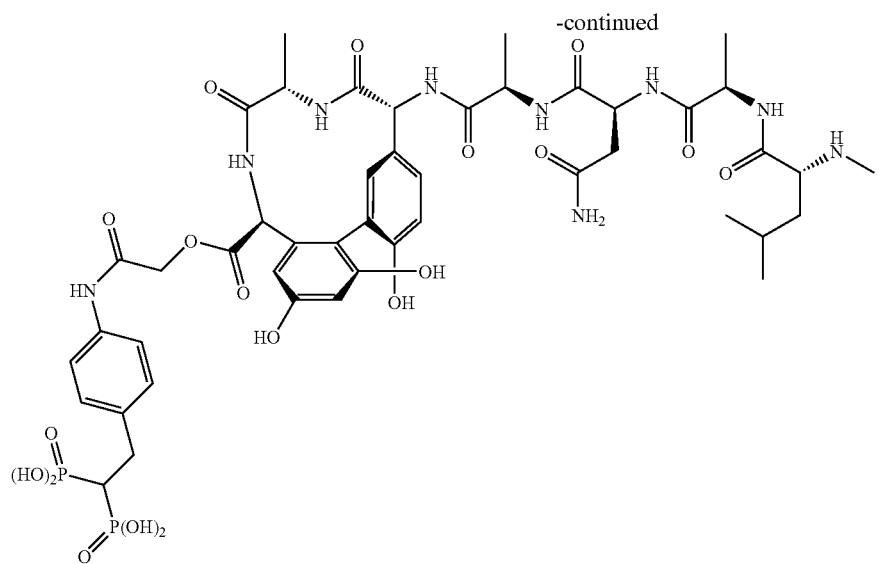
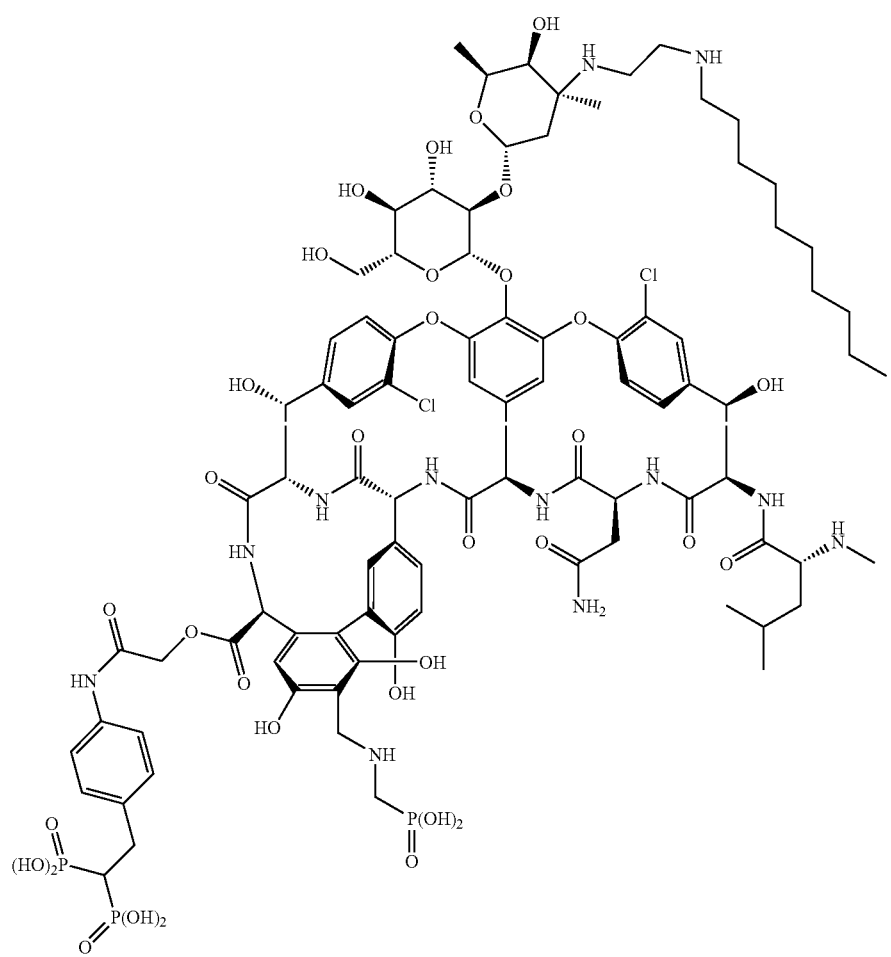

-continued
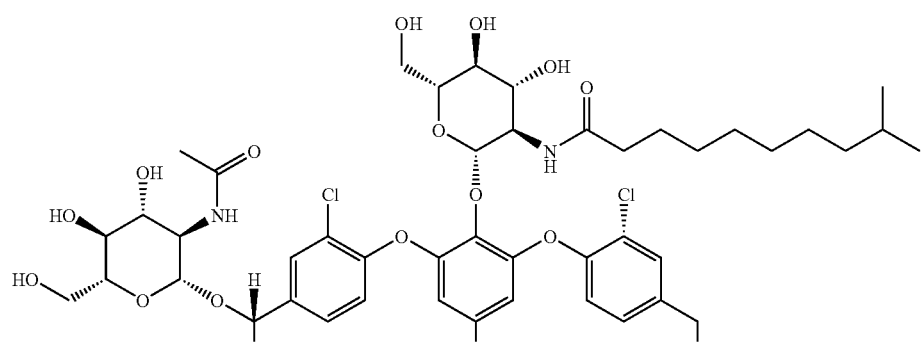
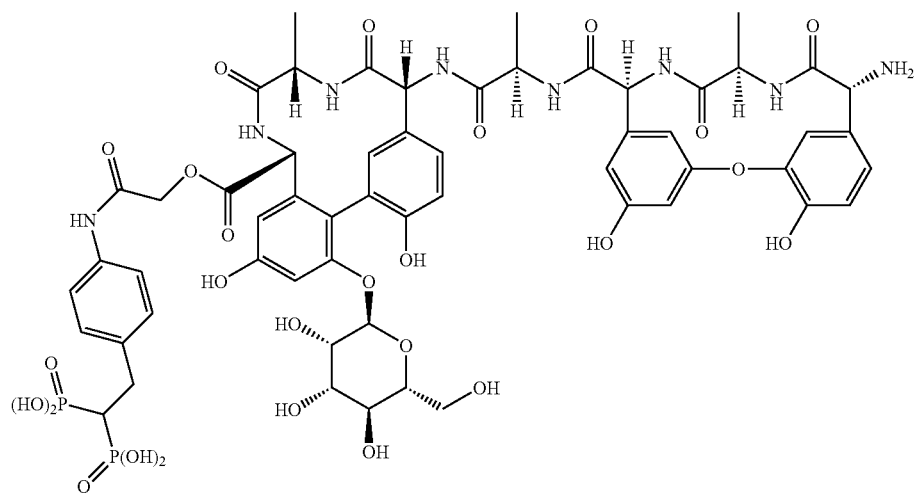
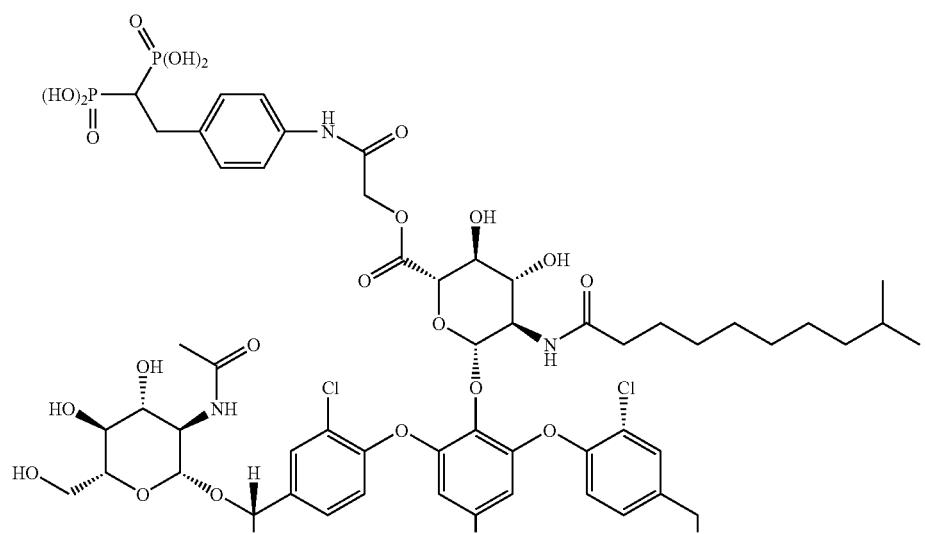

-continued
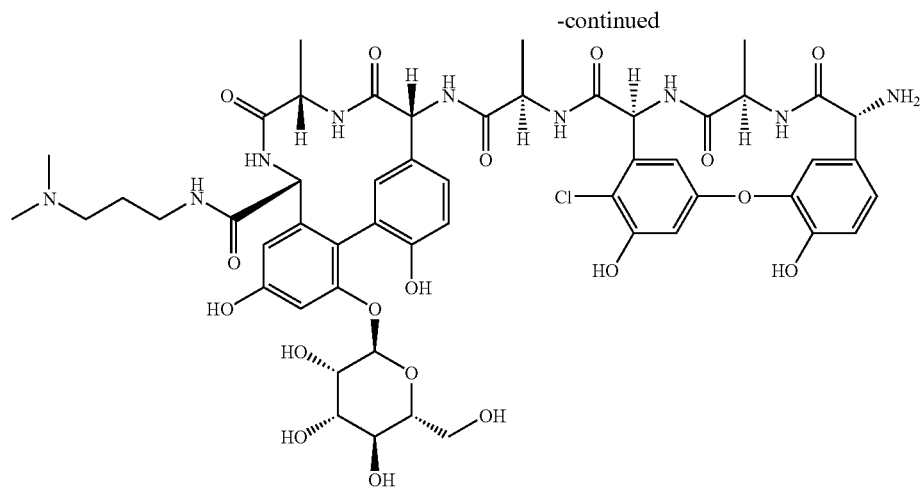
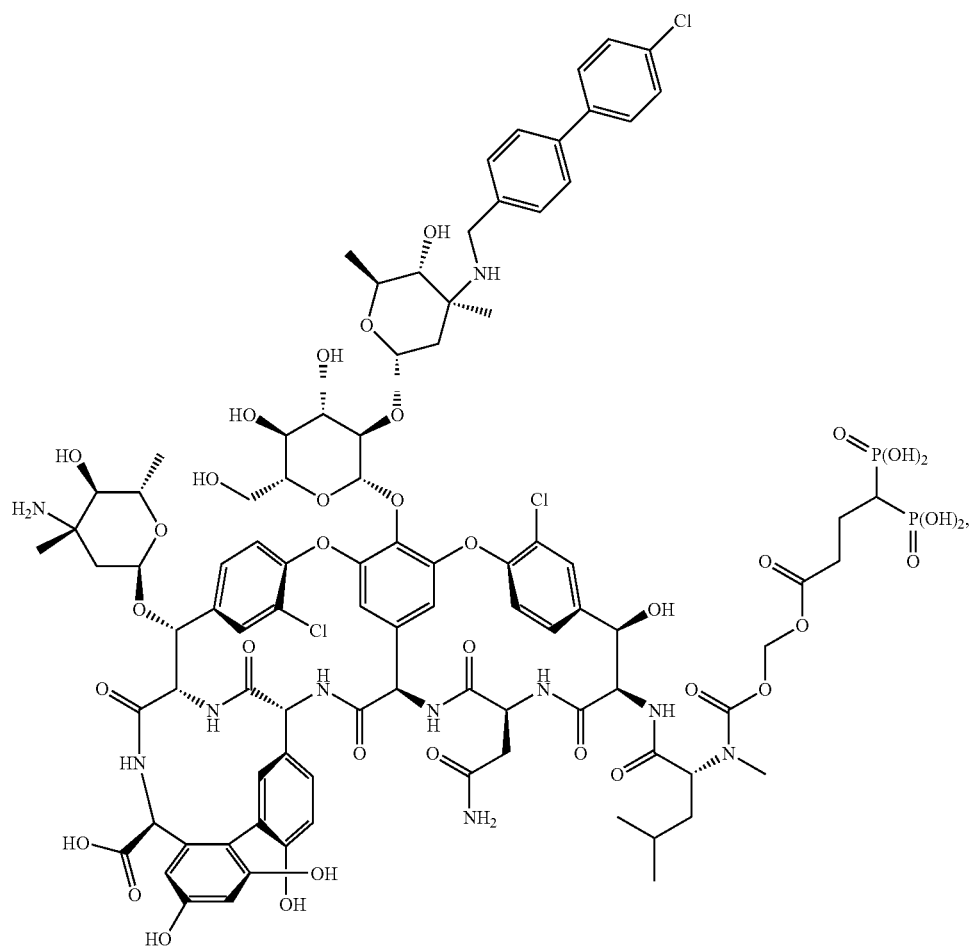

-continued
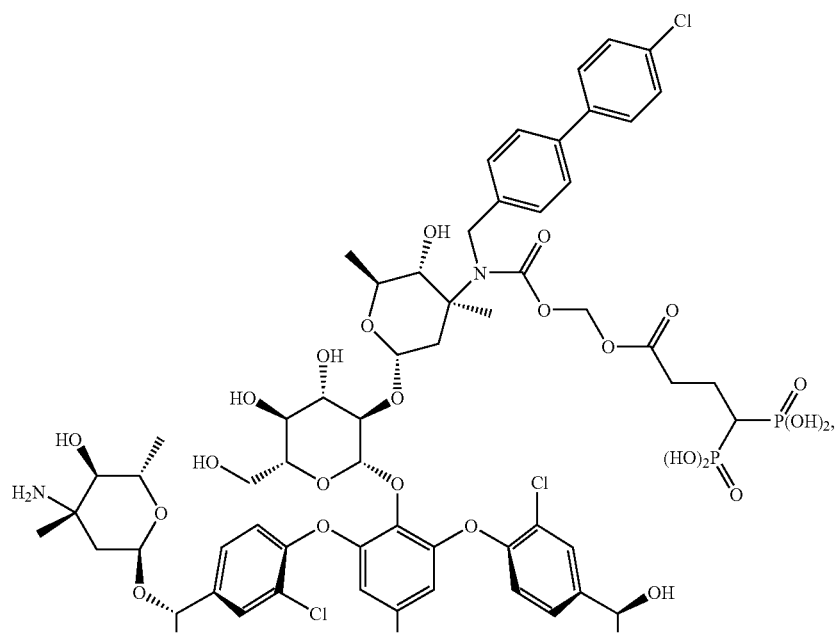
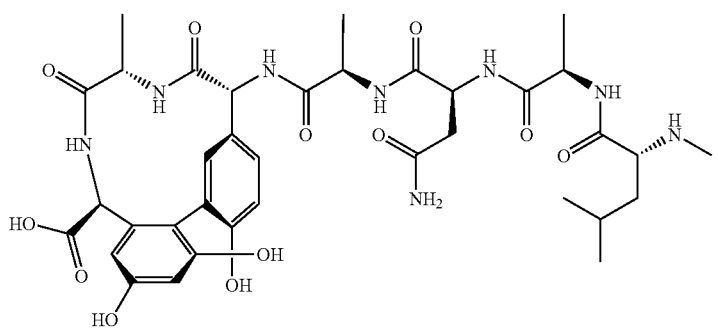
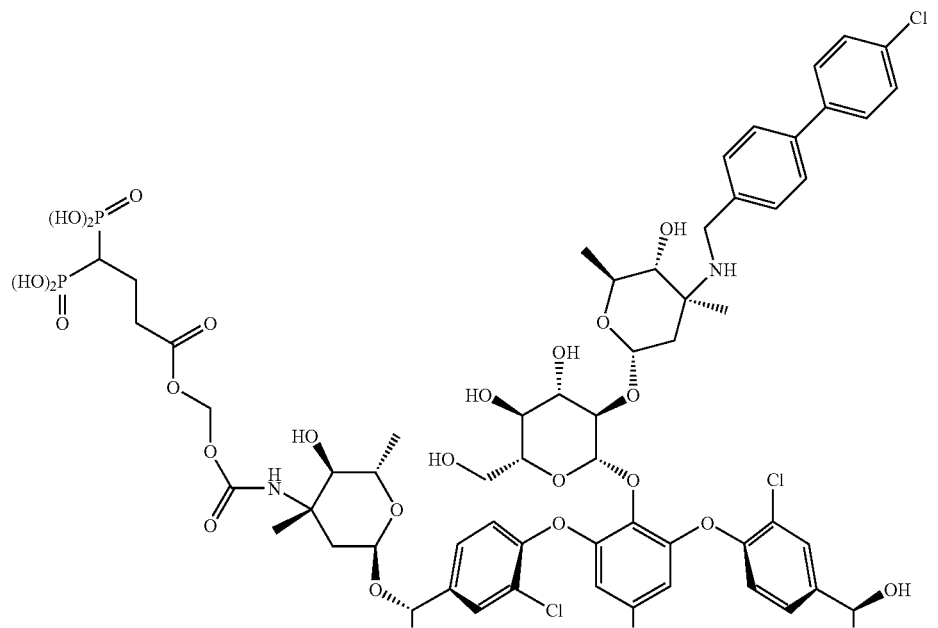

-continued
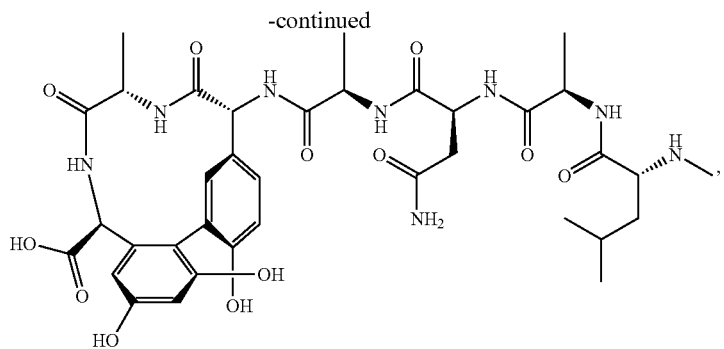
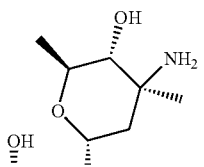
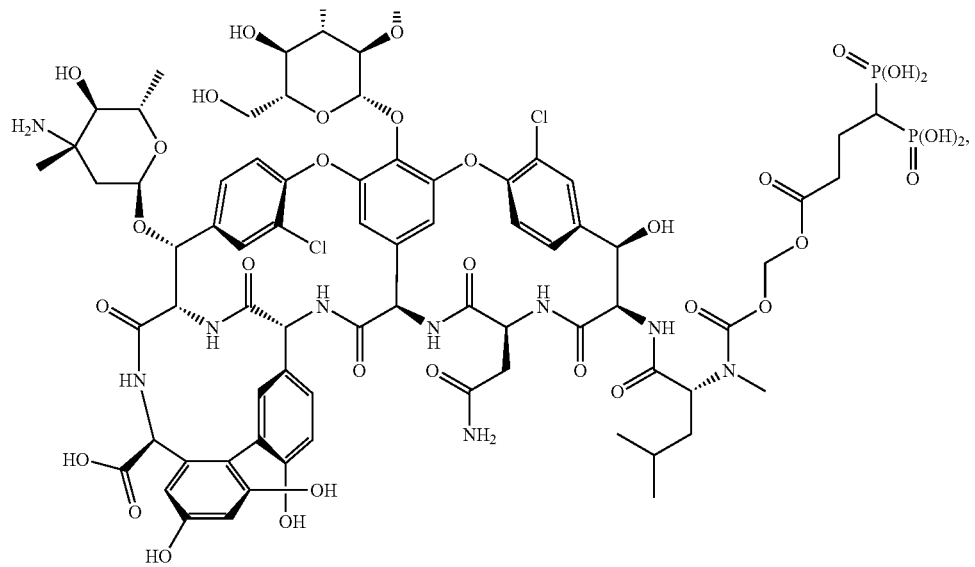
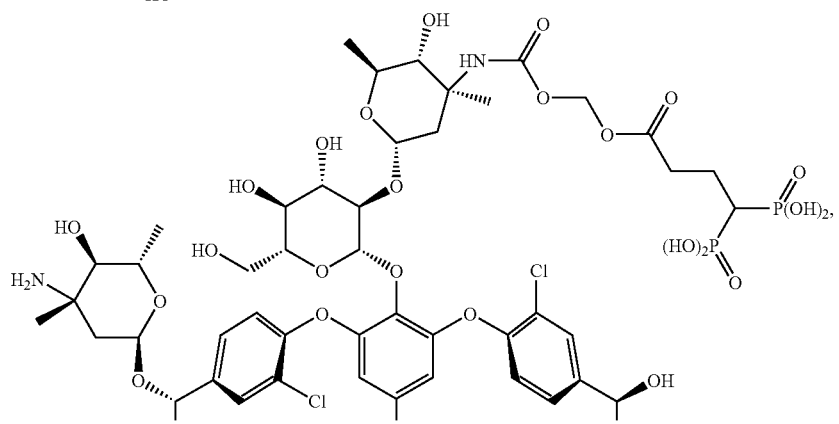

137
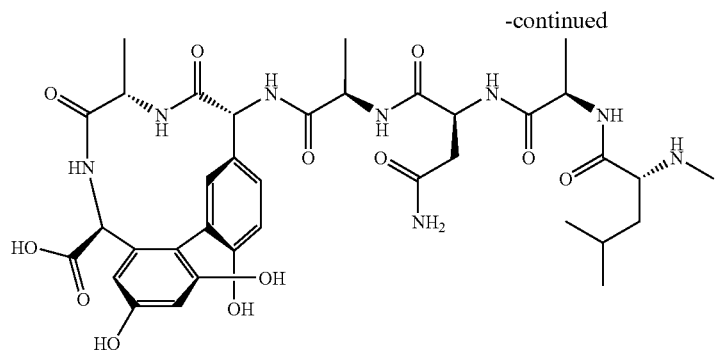
138
-continued
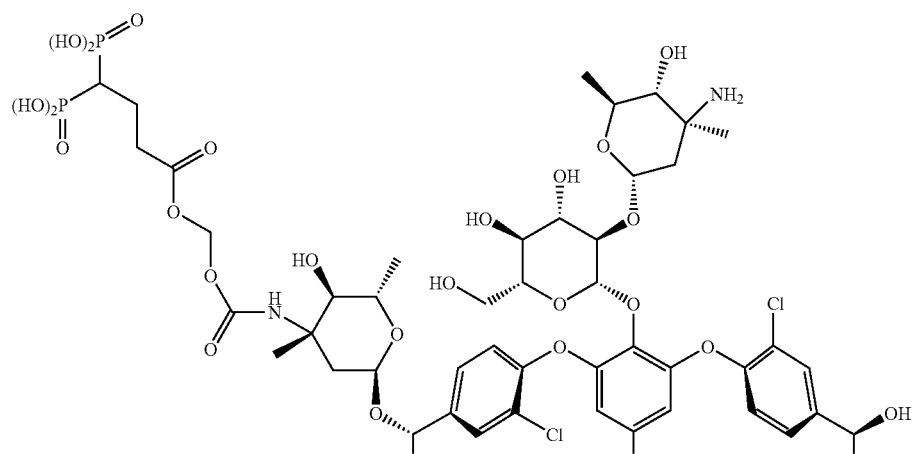
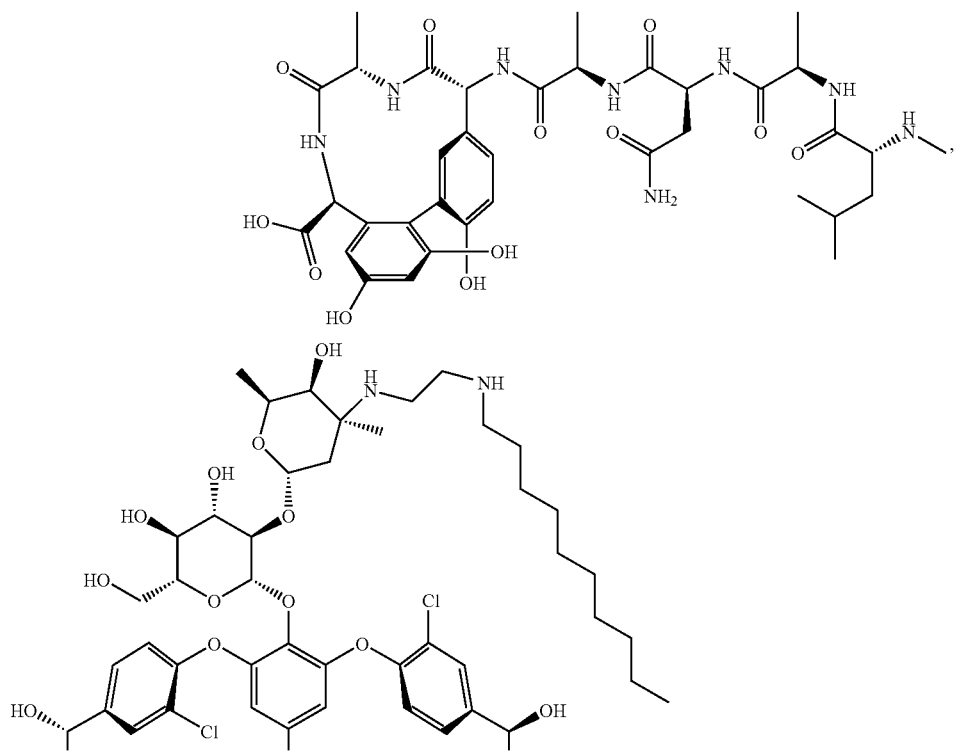

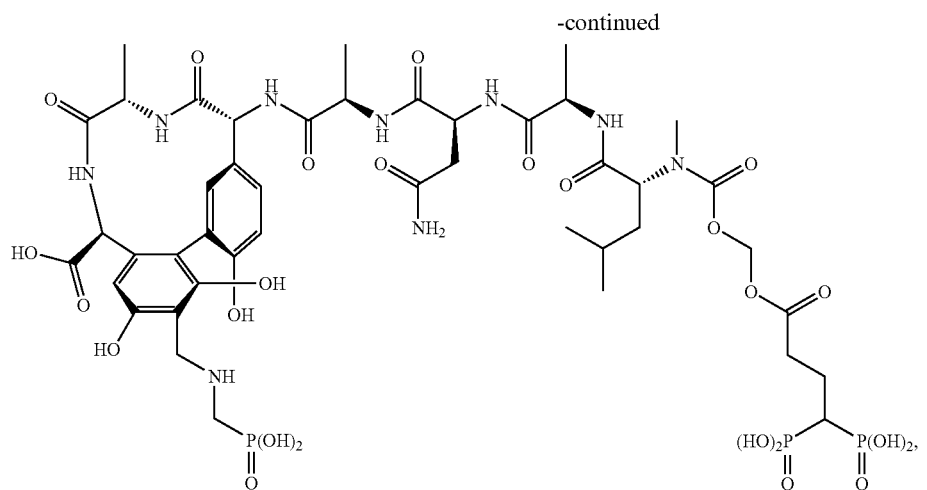
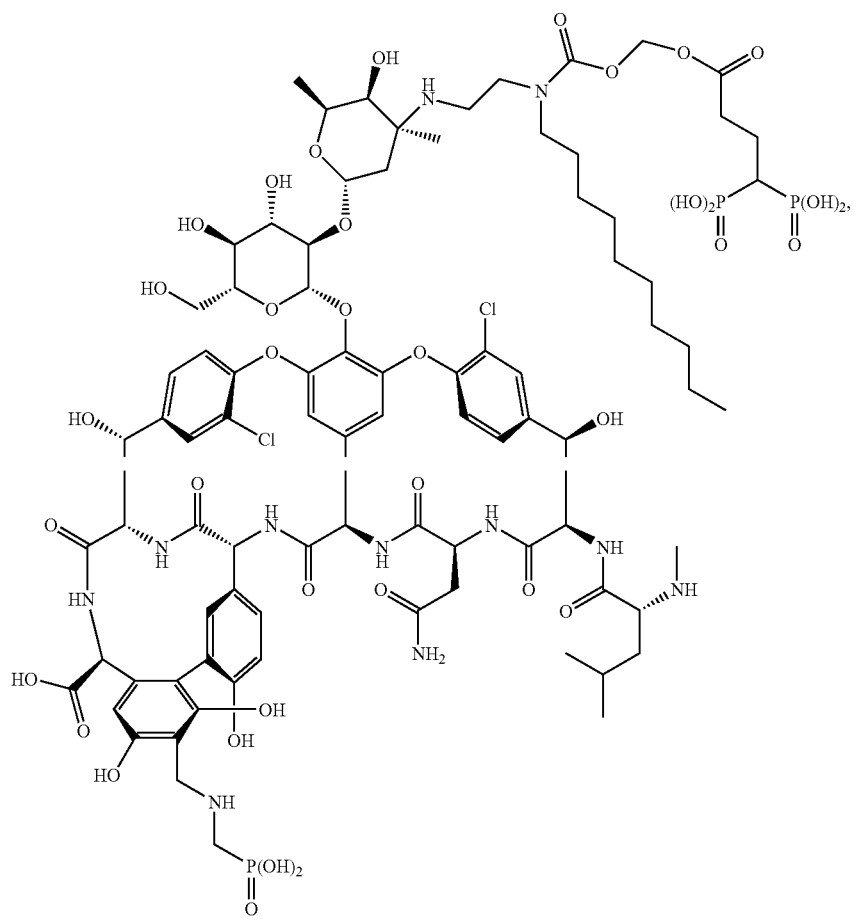

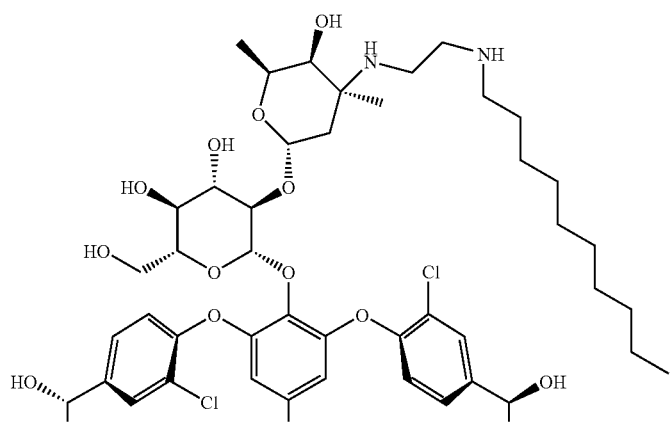
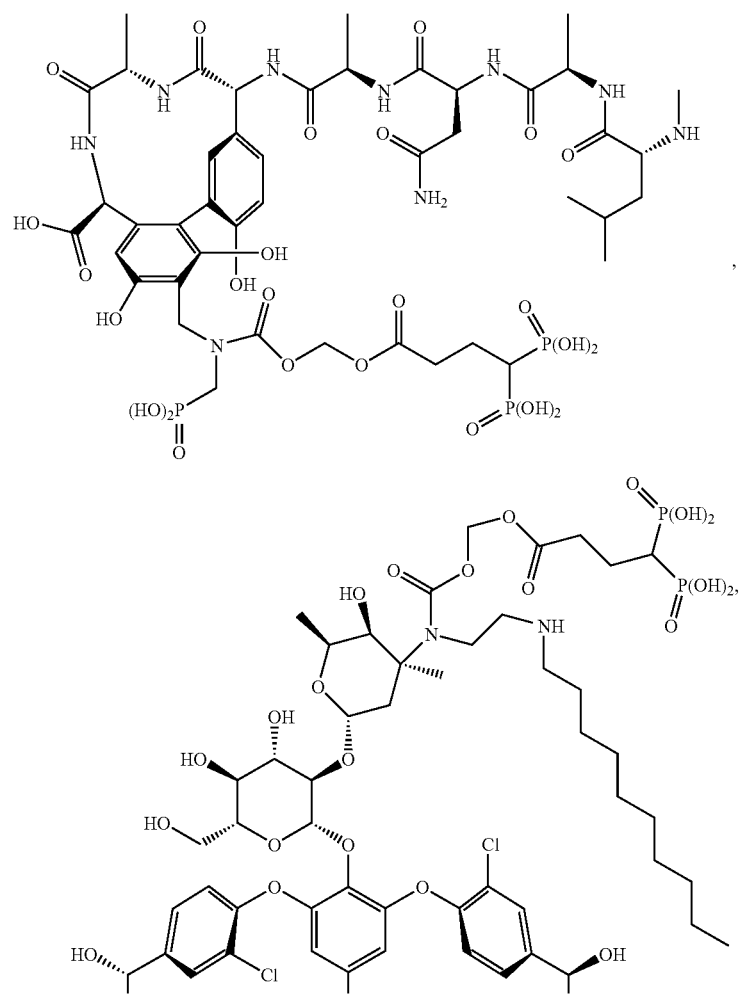

143
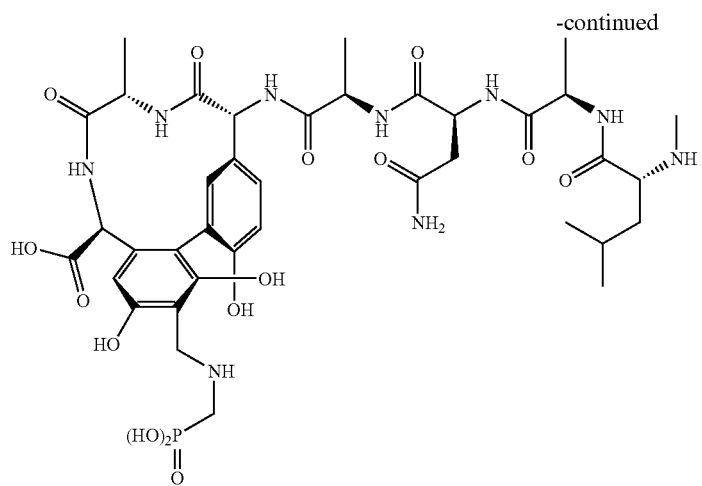
-continued
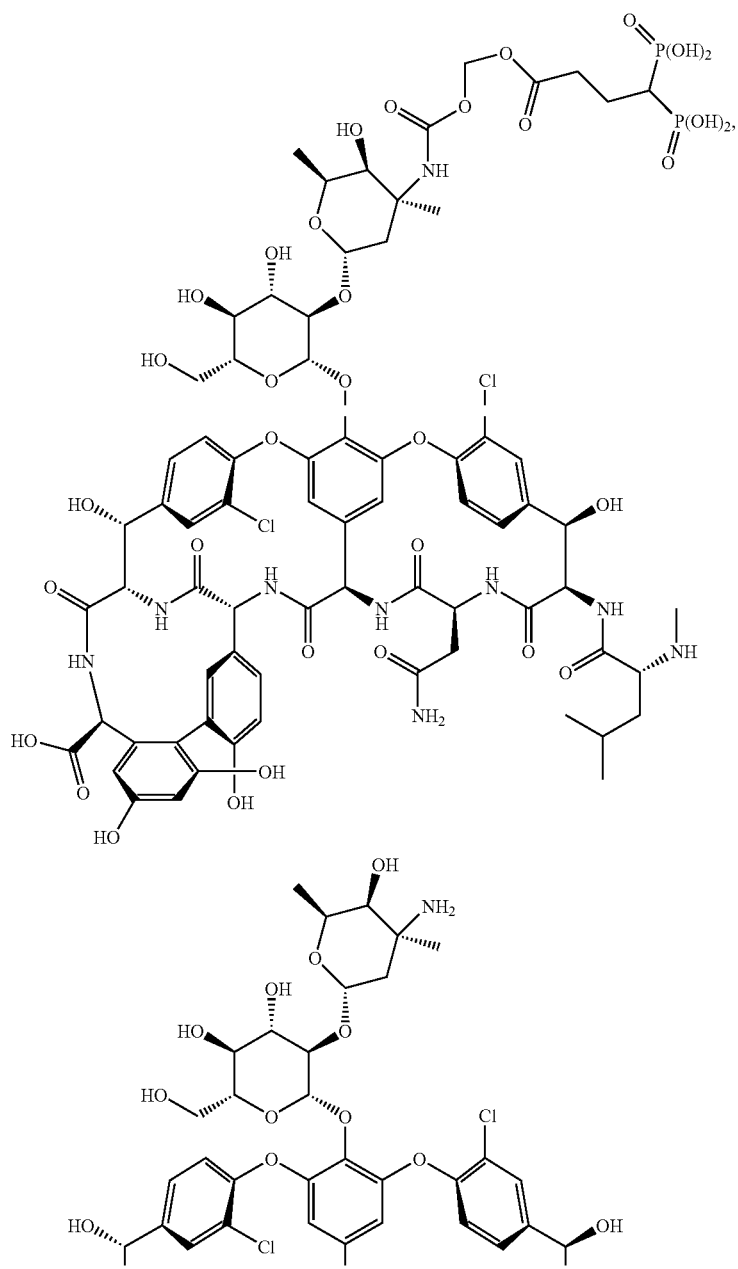

145
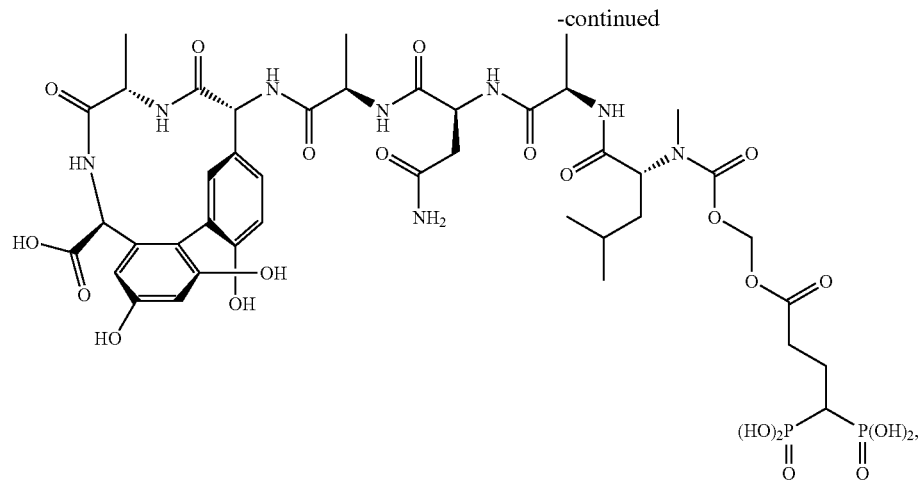
146
-continued
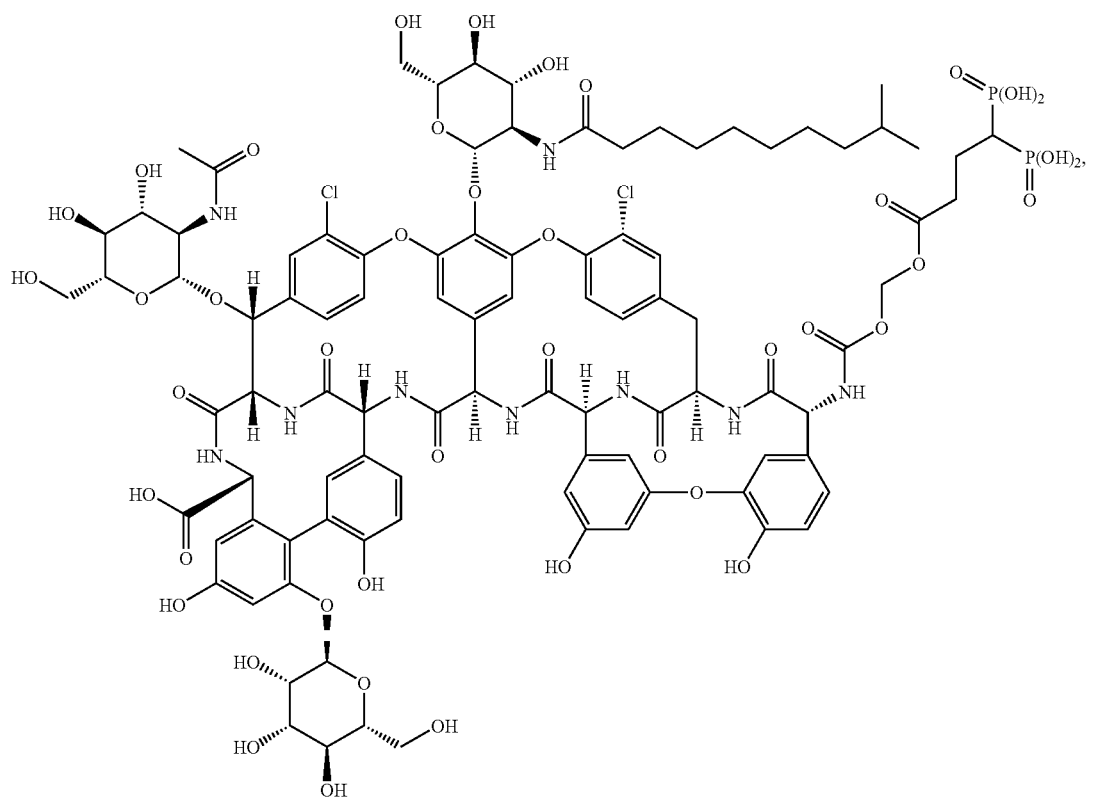

-continued
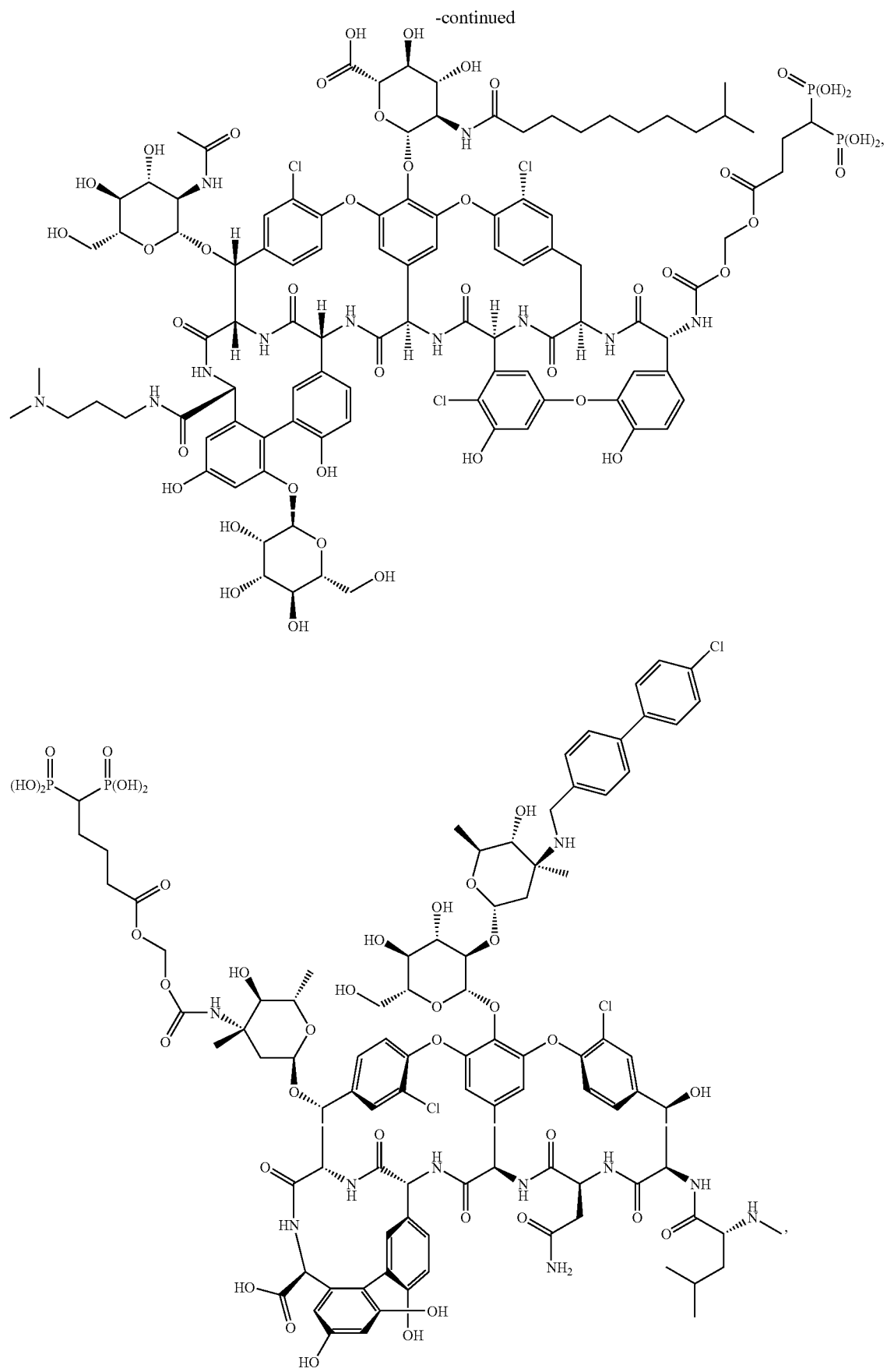

-continued
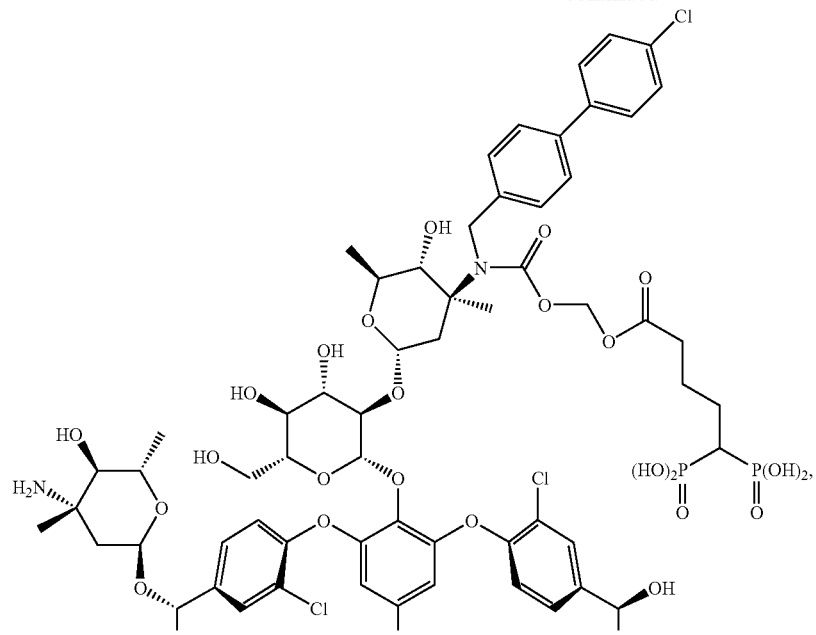
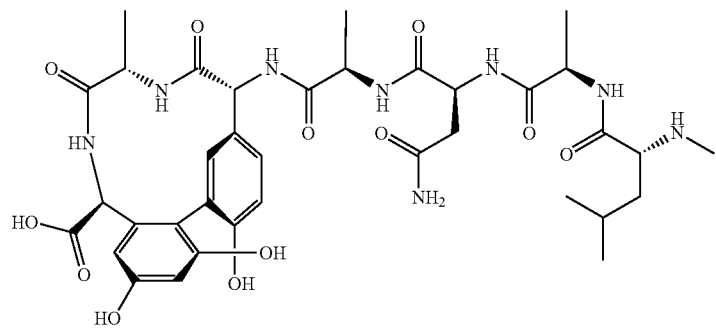
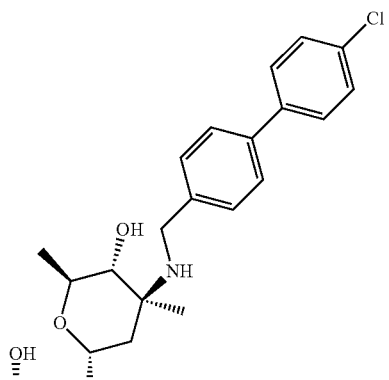

151
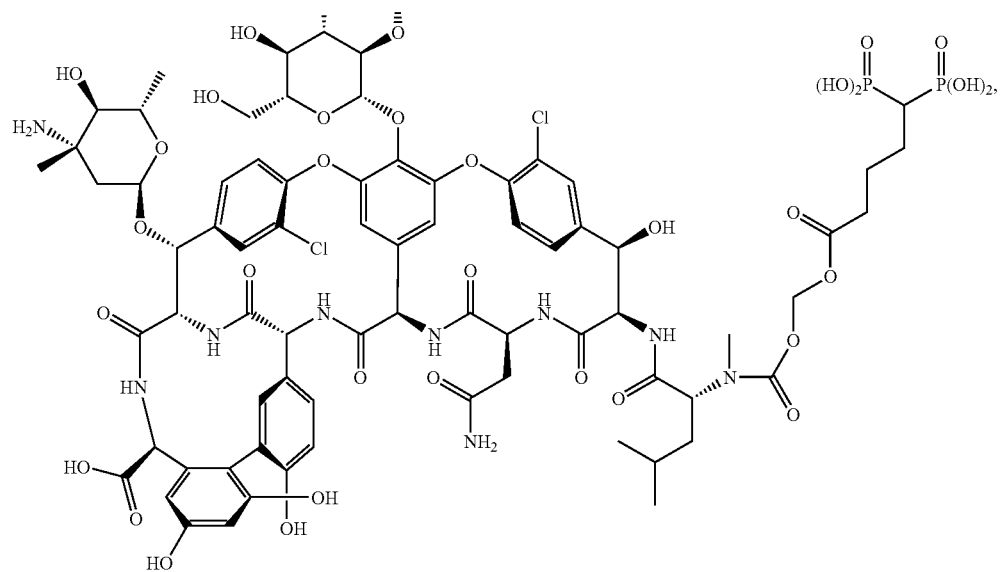
152
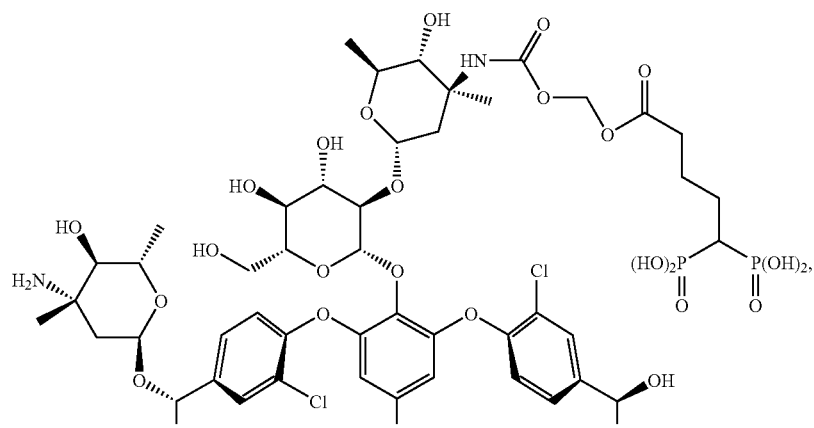
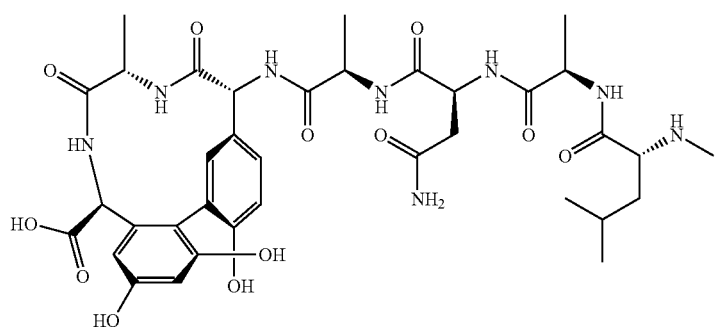

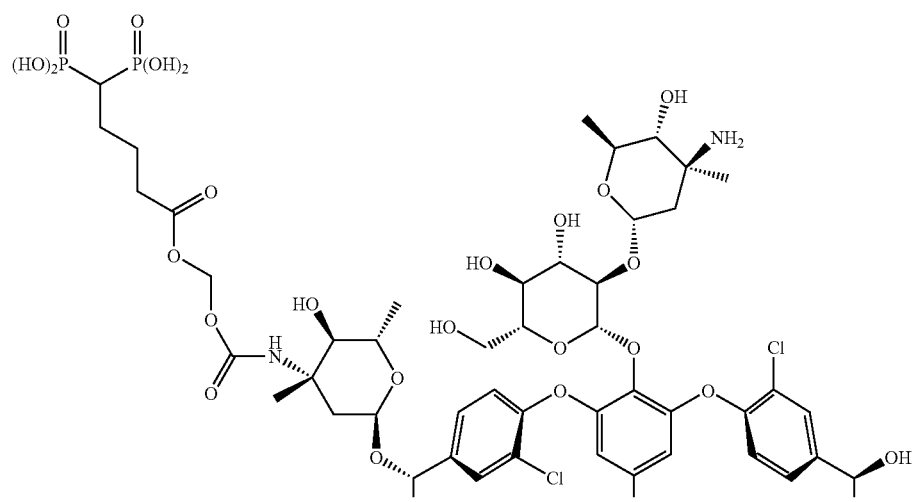
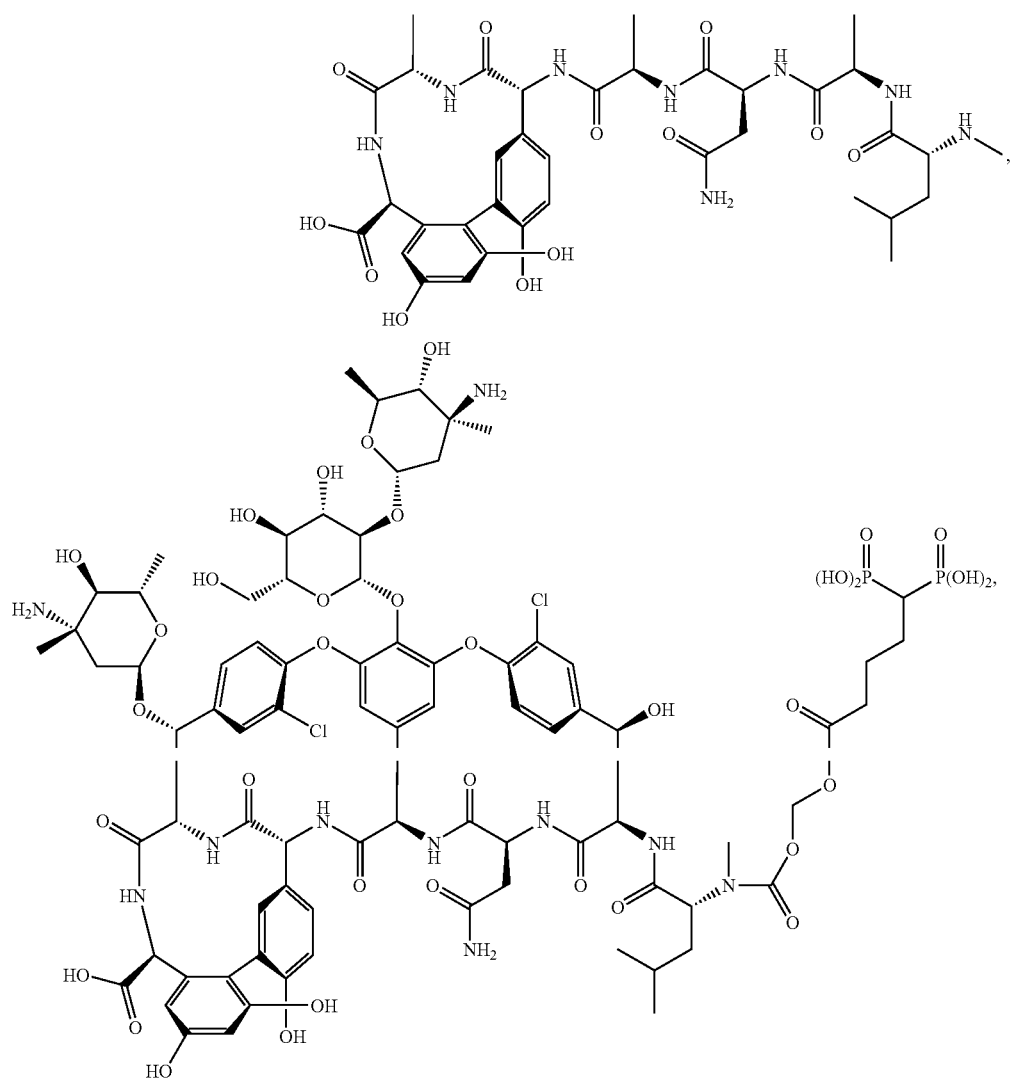

-continued
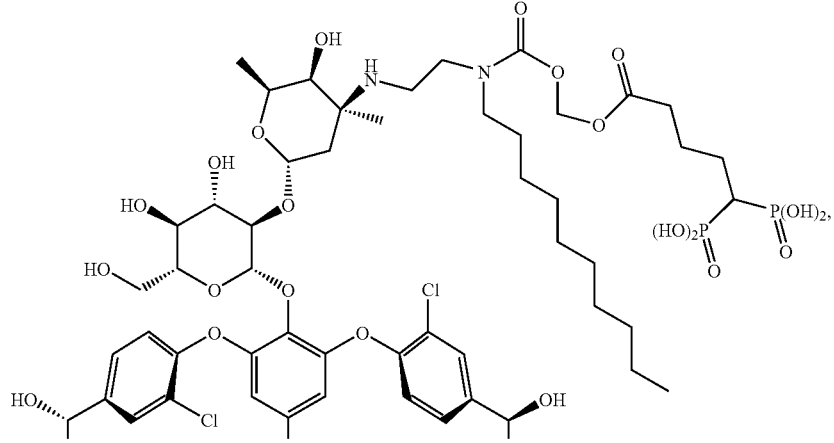
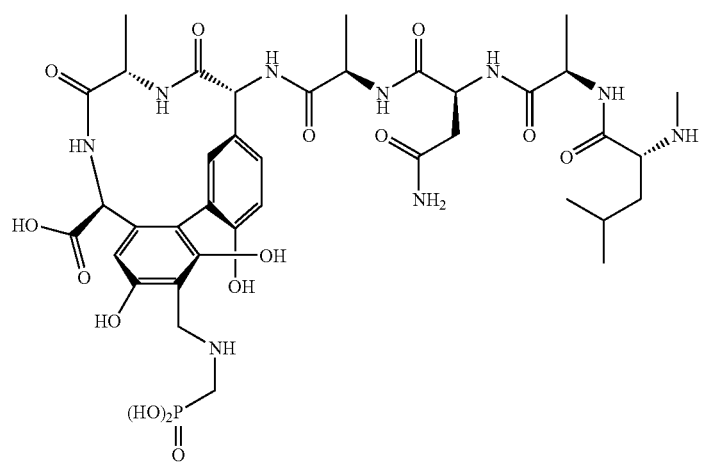
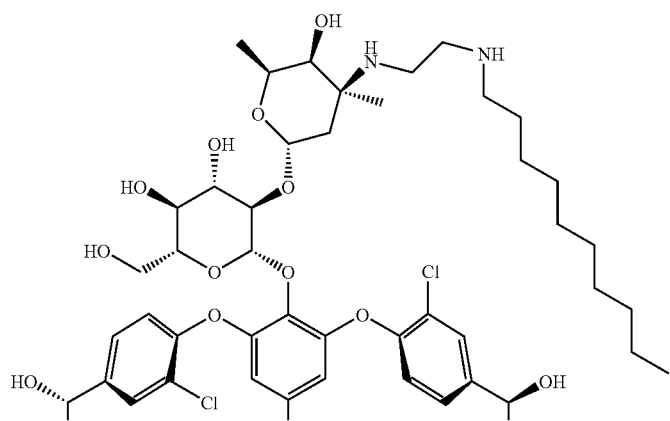

157
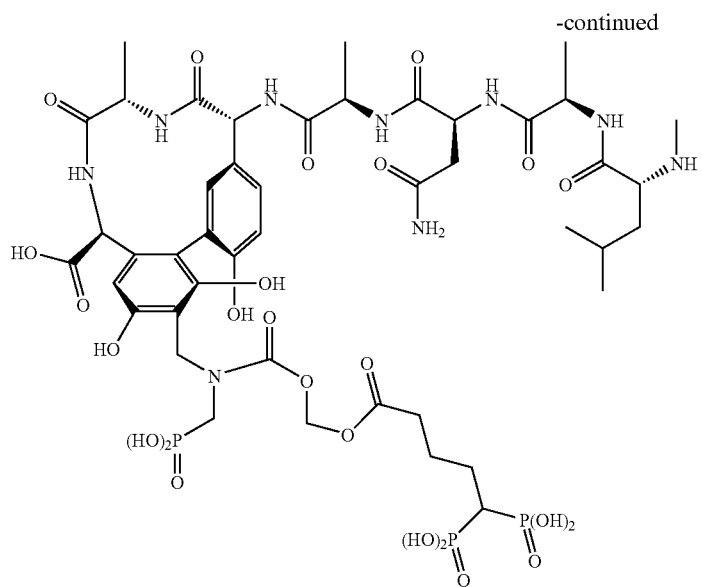
-continued
158
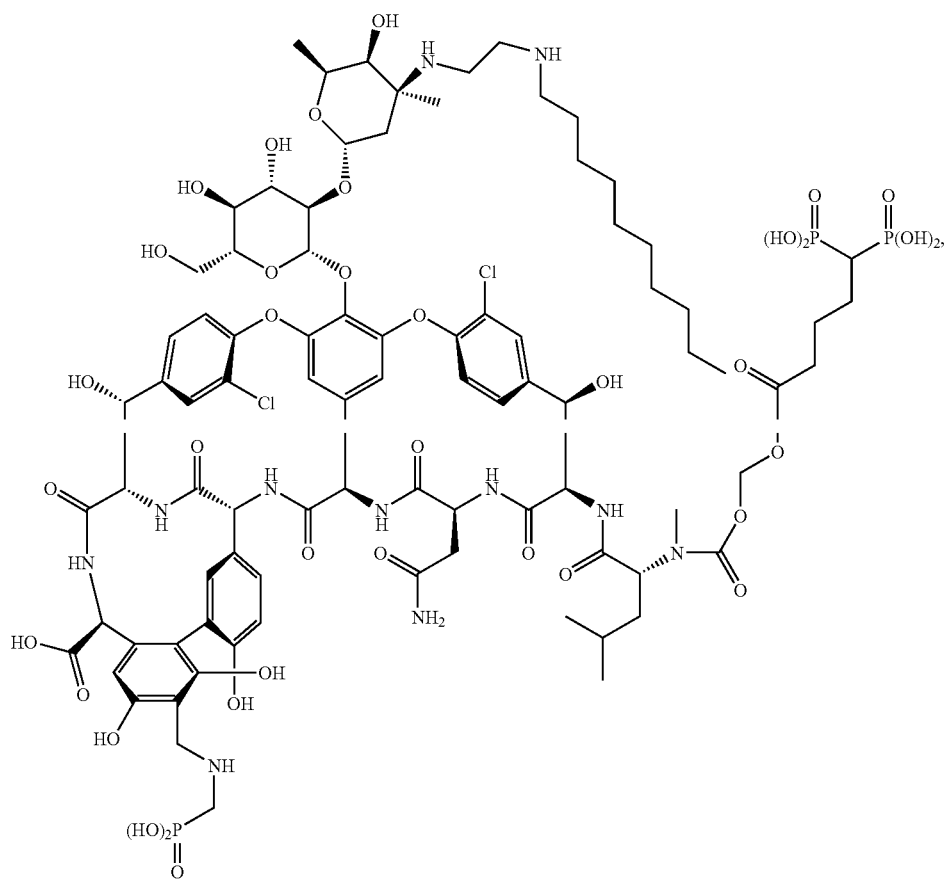

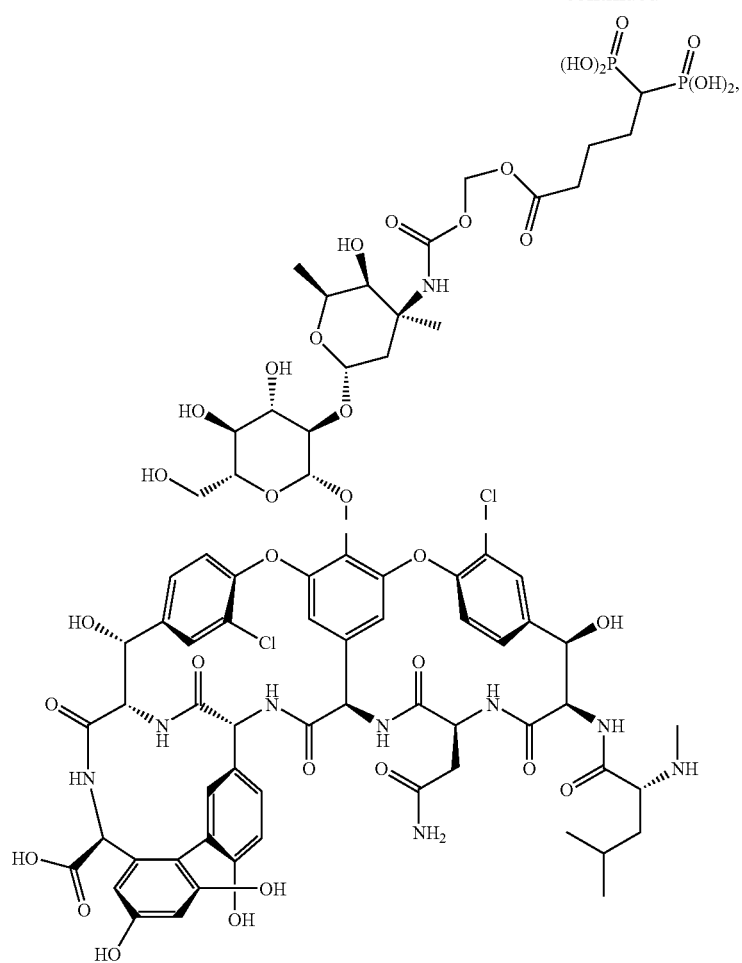
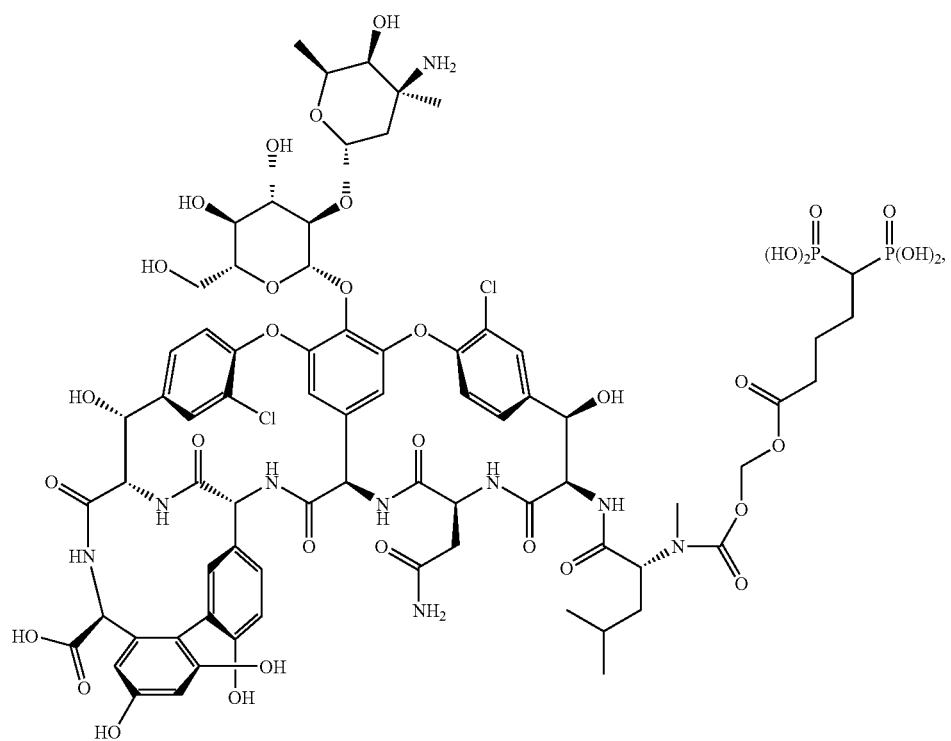

161
162
-continued
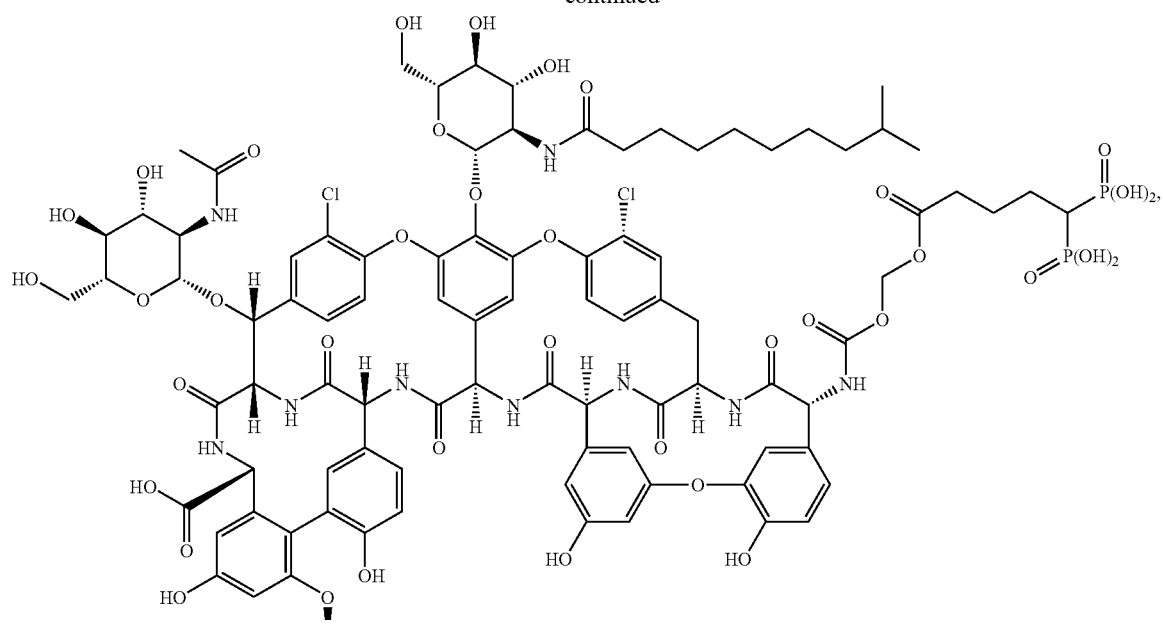
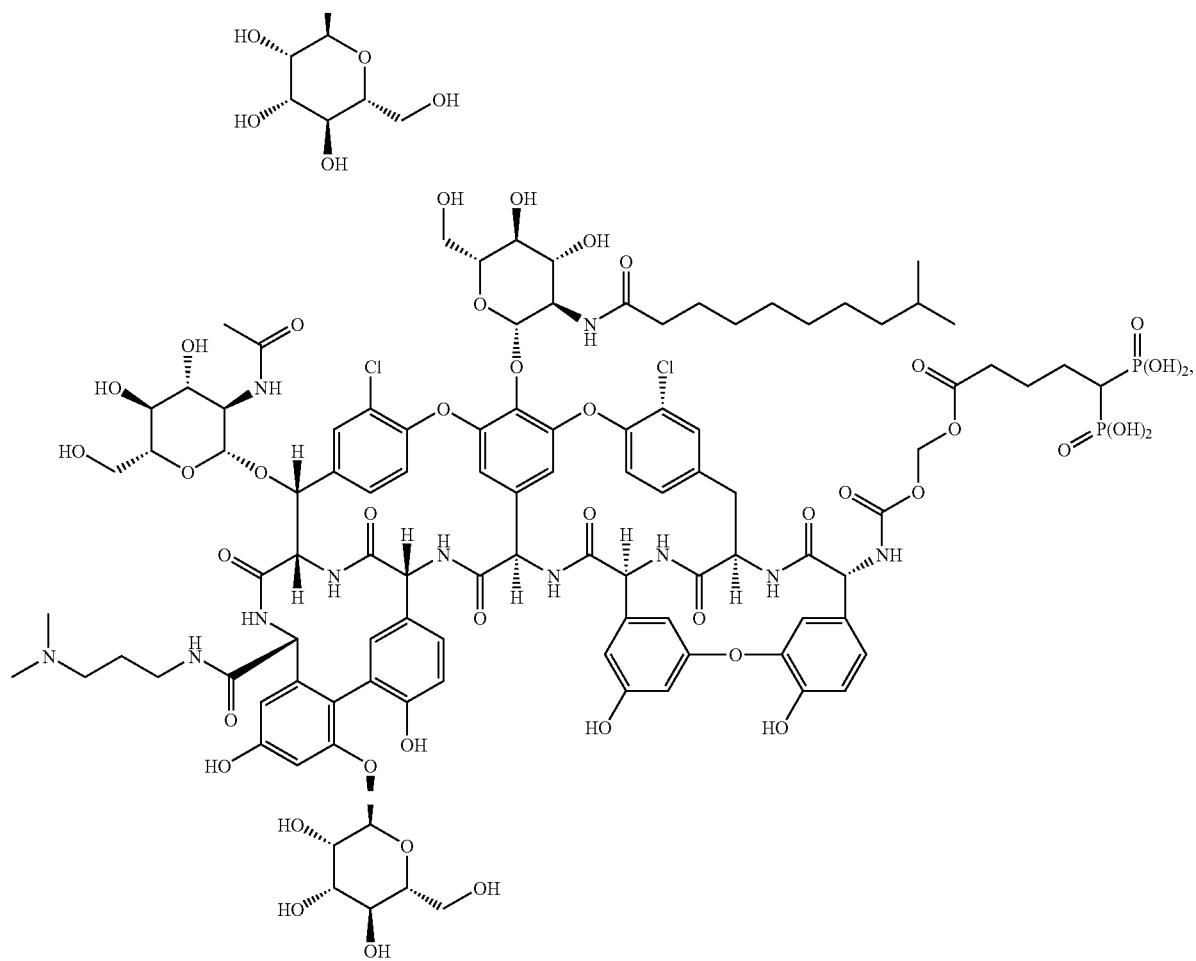

163
-continued
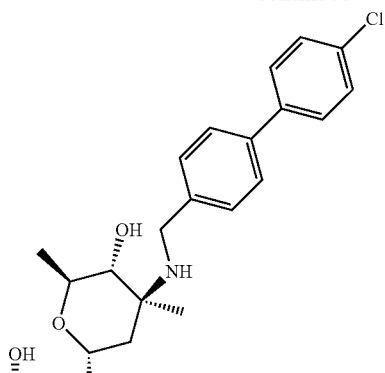
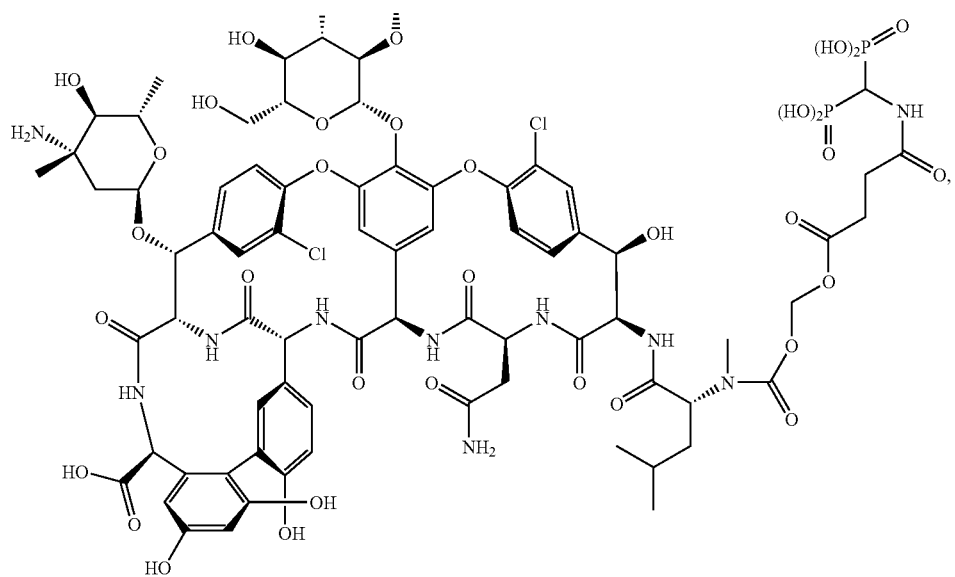
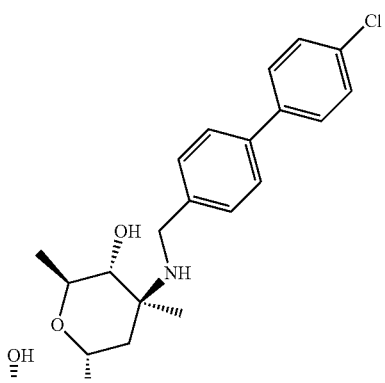

165
166
-continued
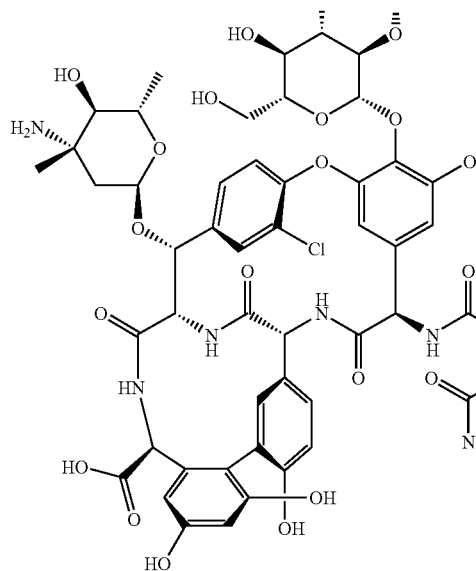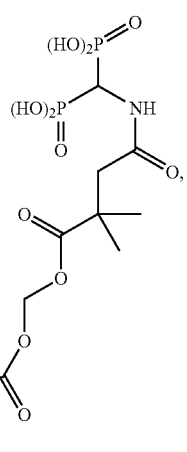
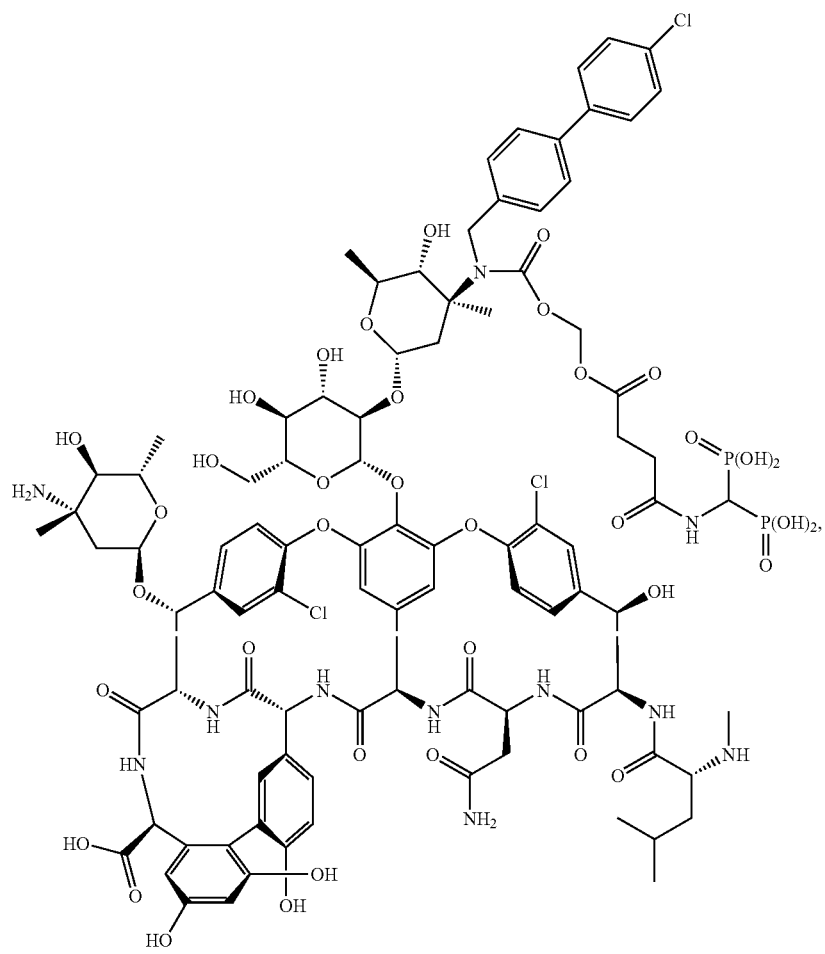

-continued
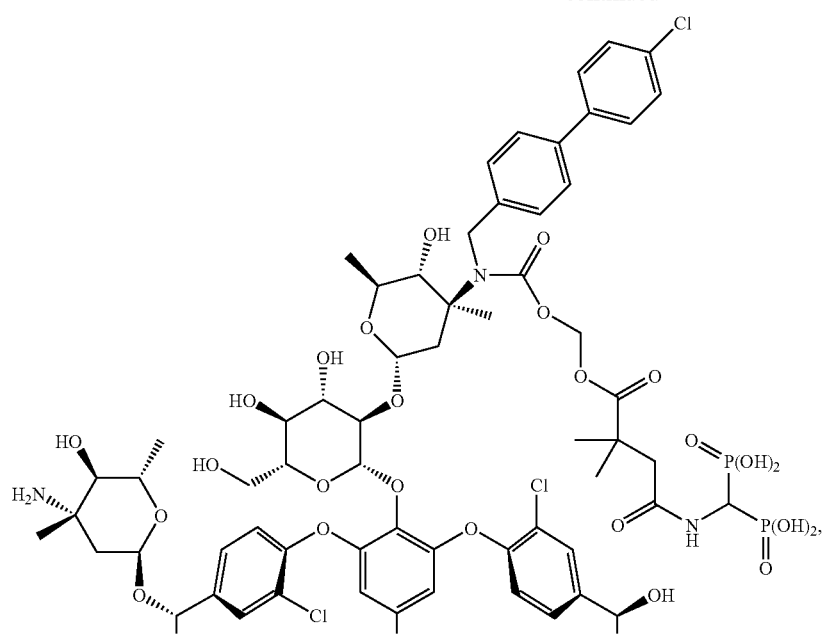
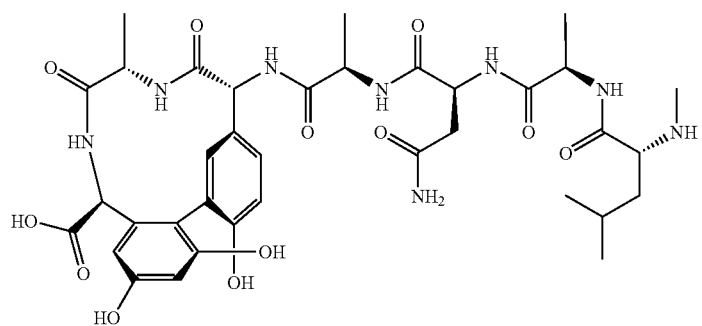
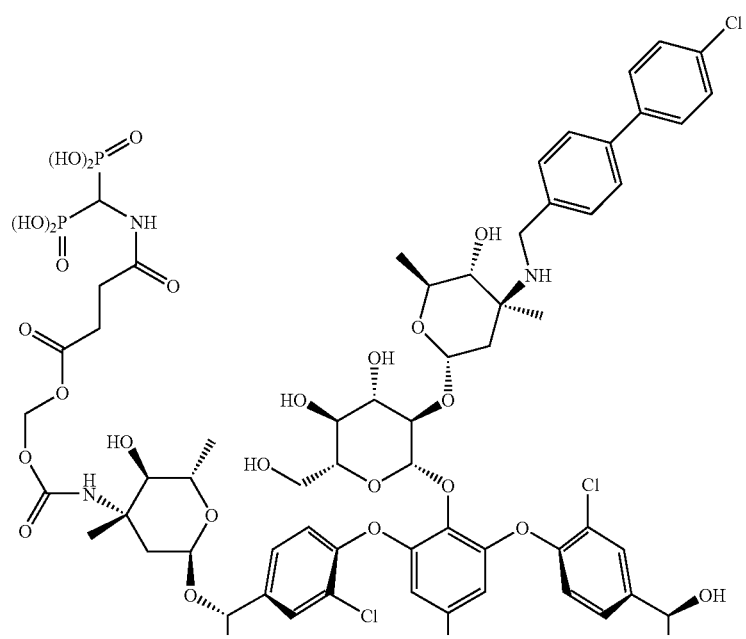

-continued
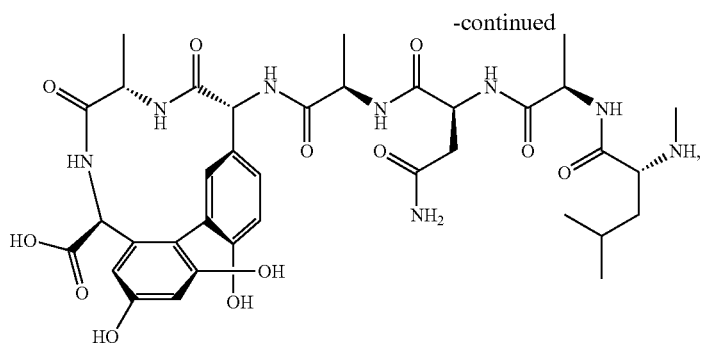
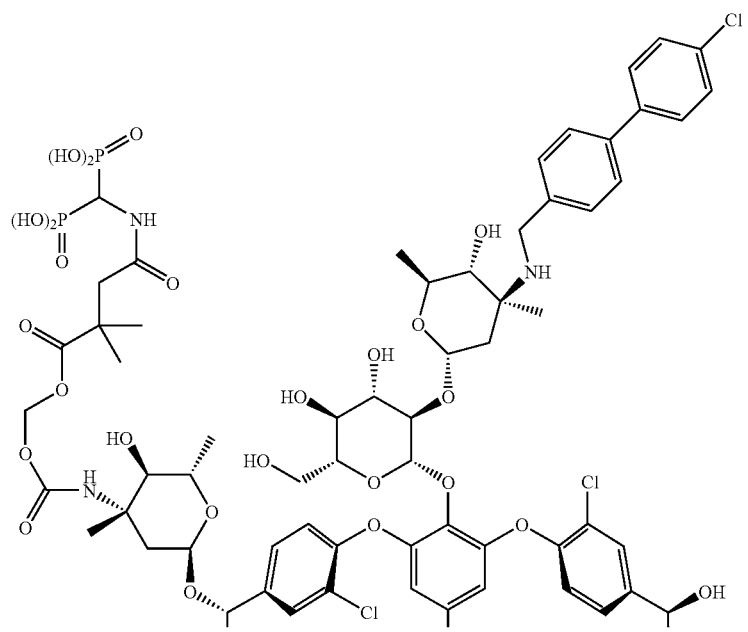
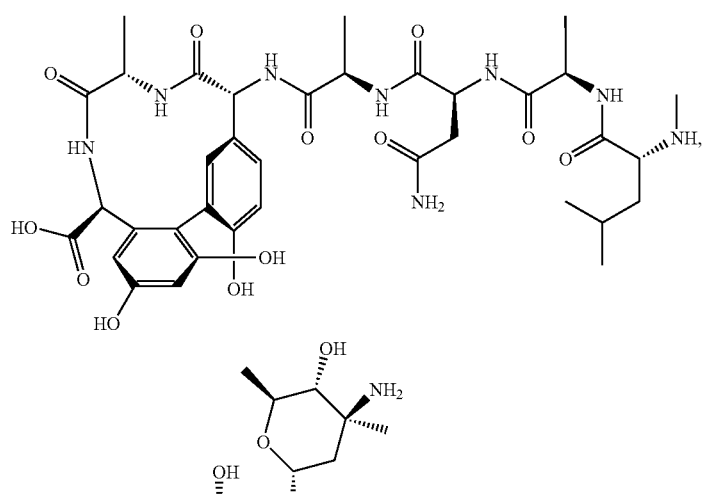

-continued
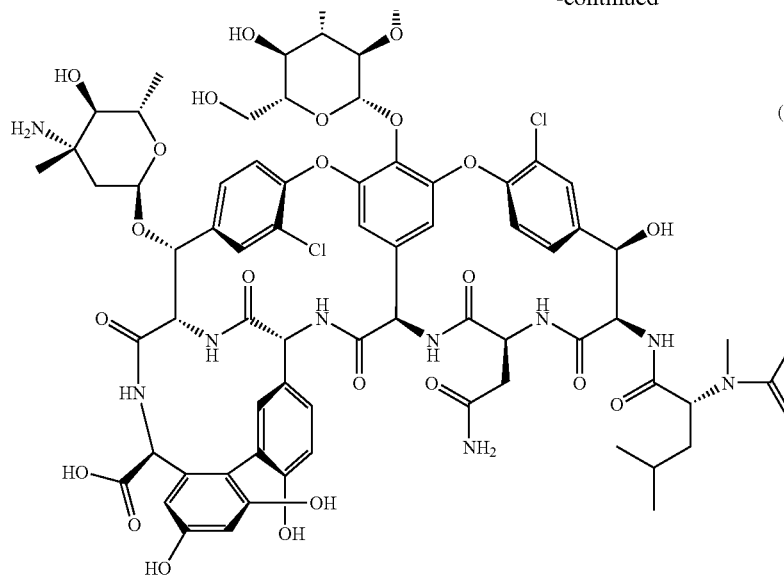
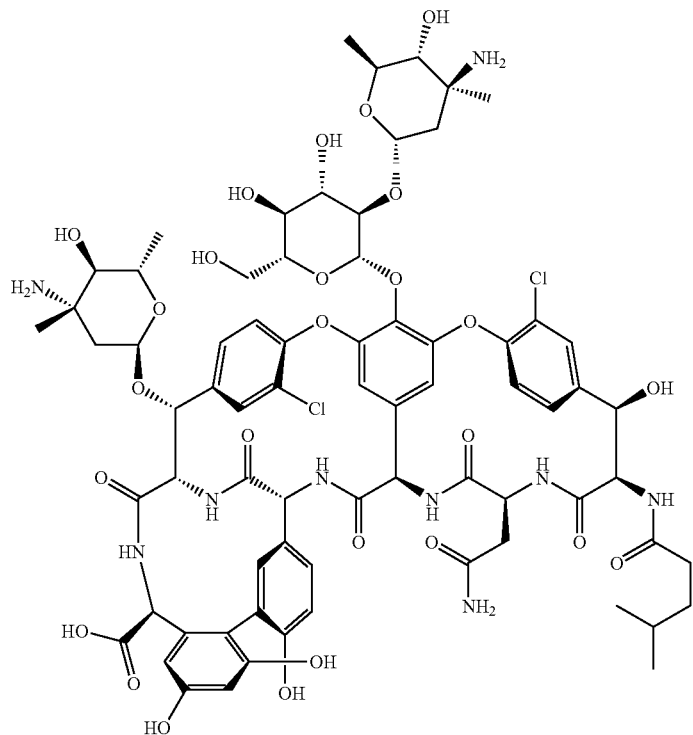
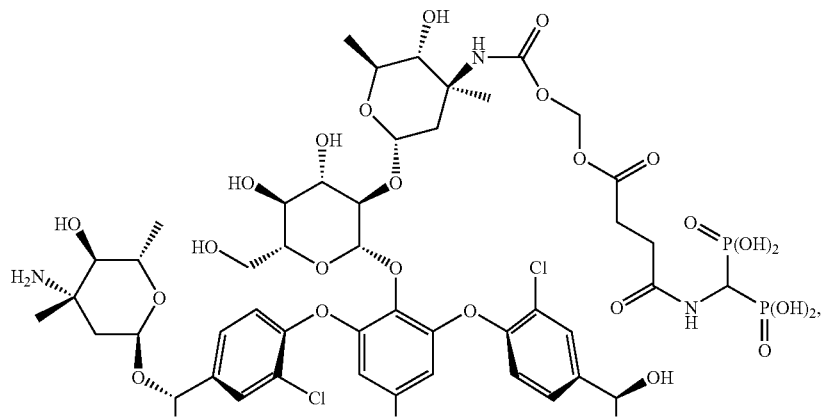

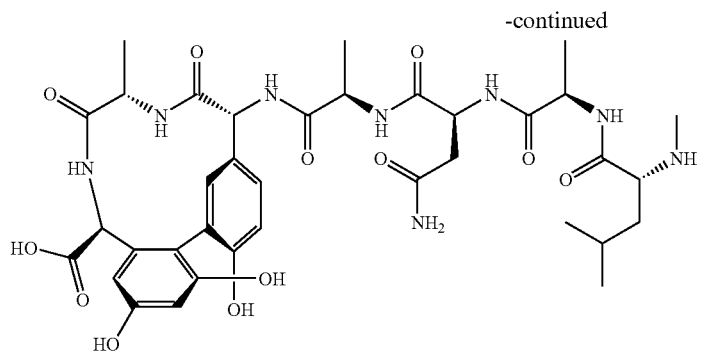
-continued
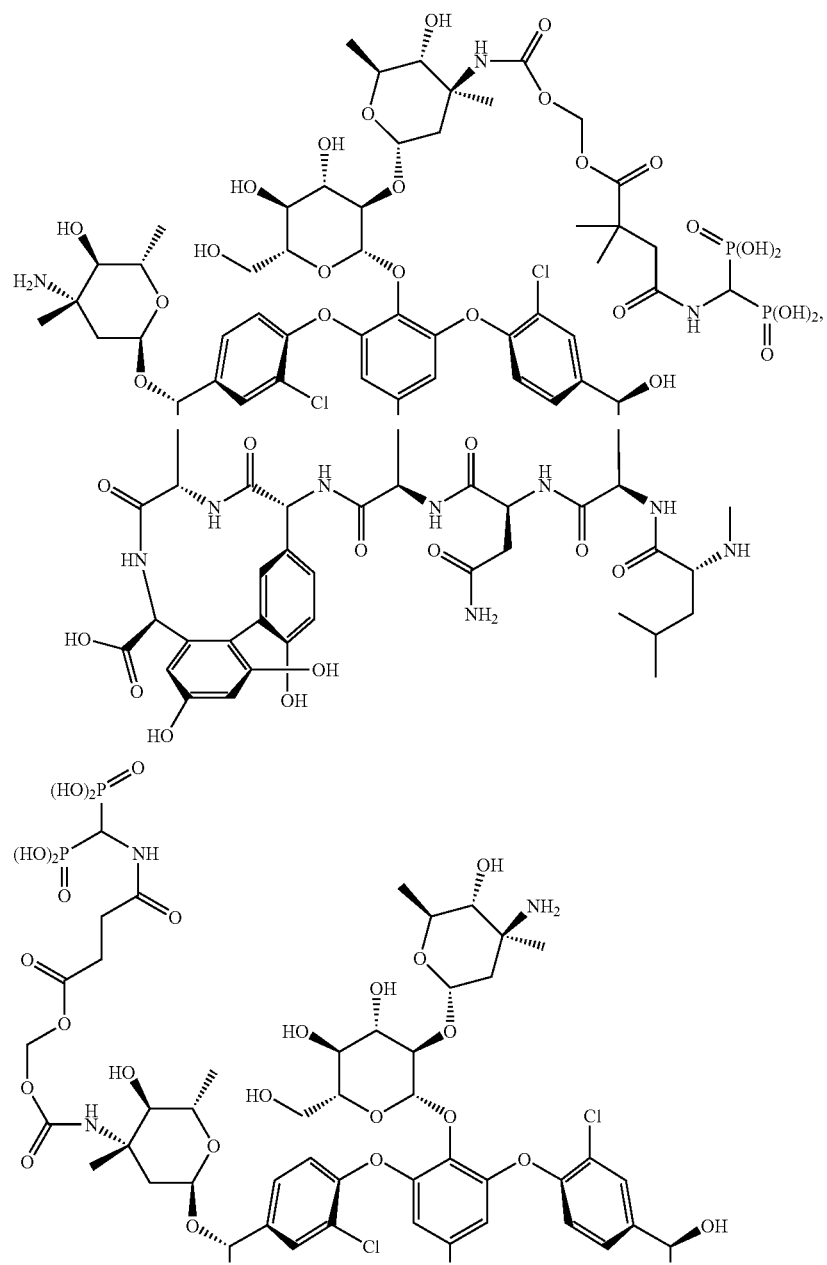

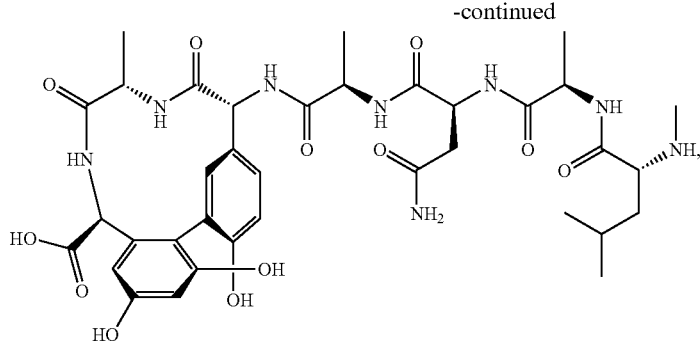
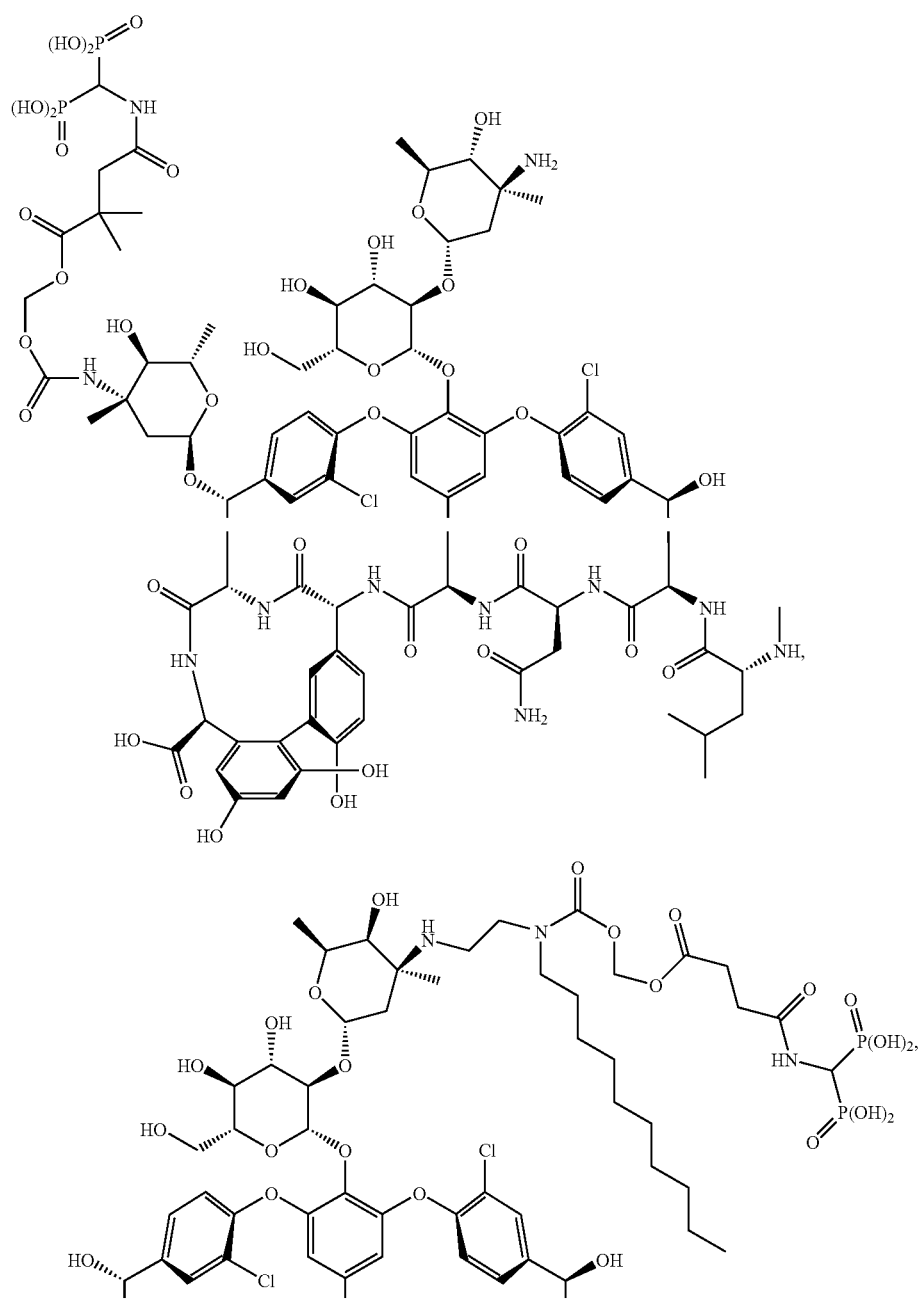

177
-continued
178
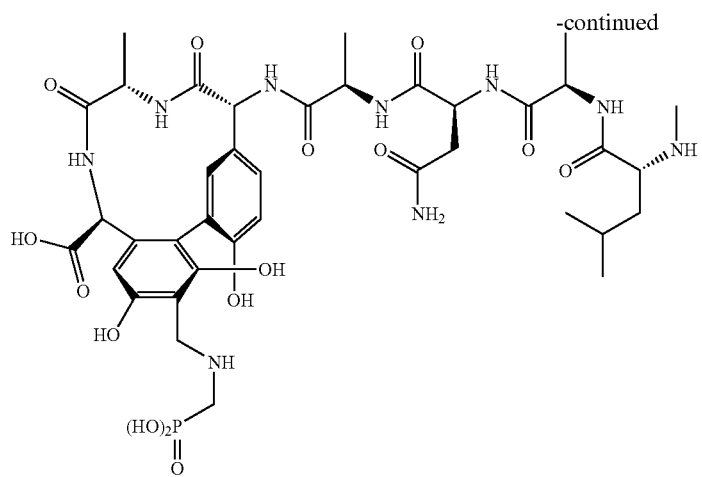
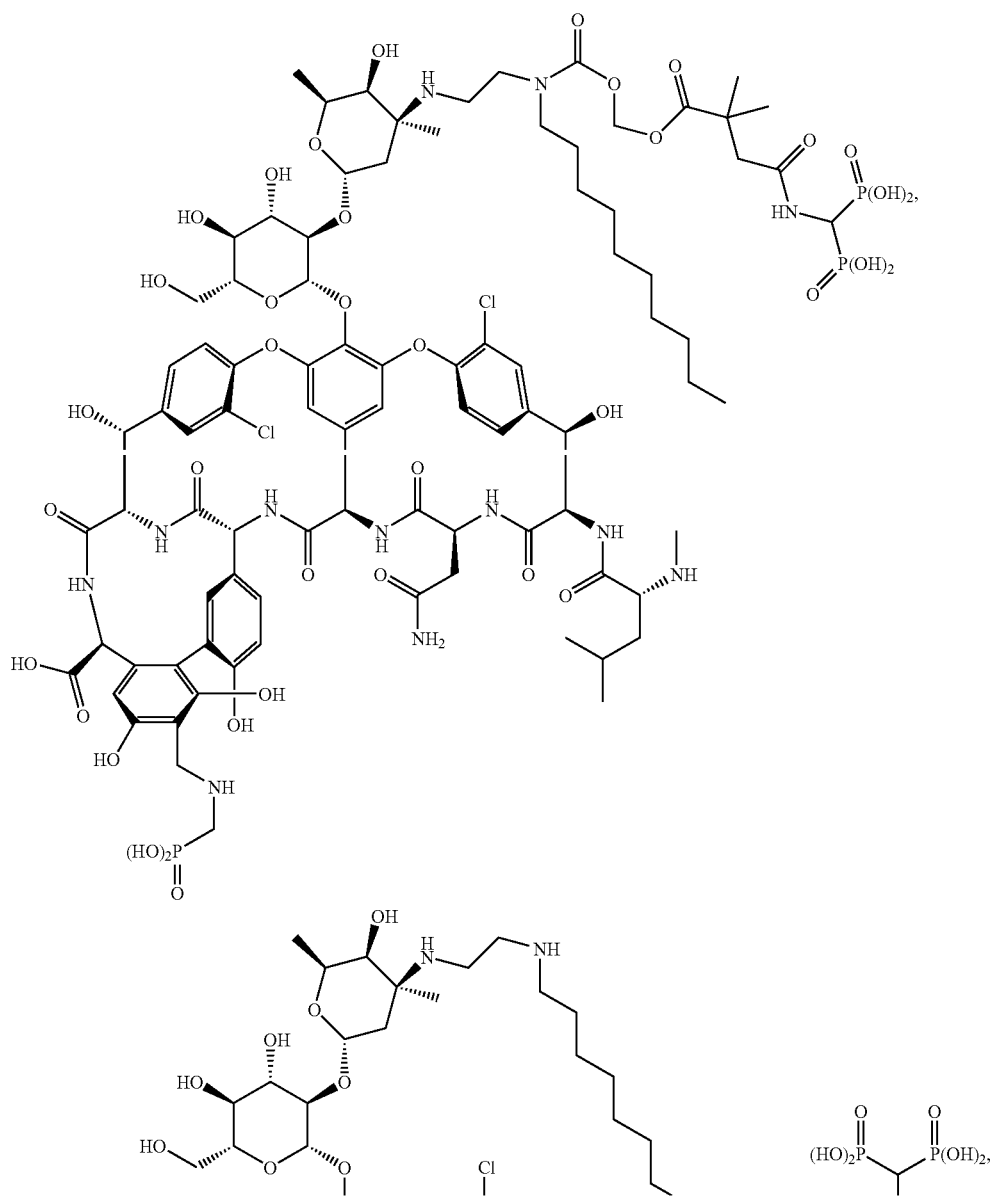

179
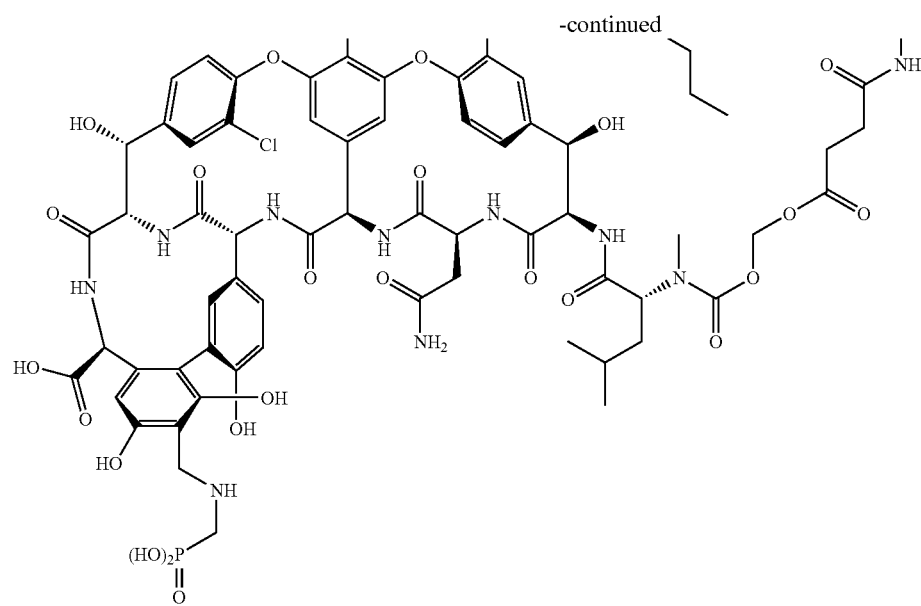
-continued
180
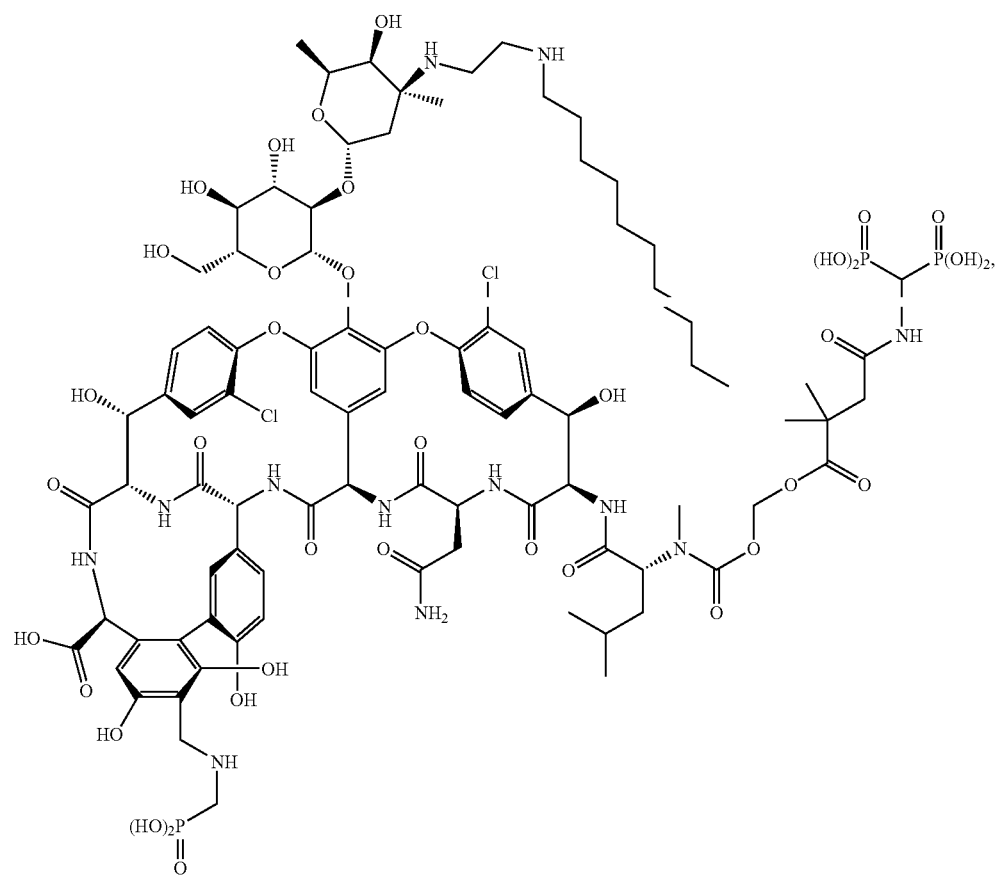

-continued
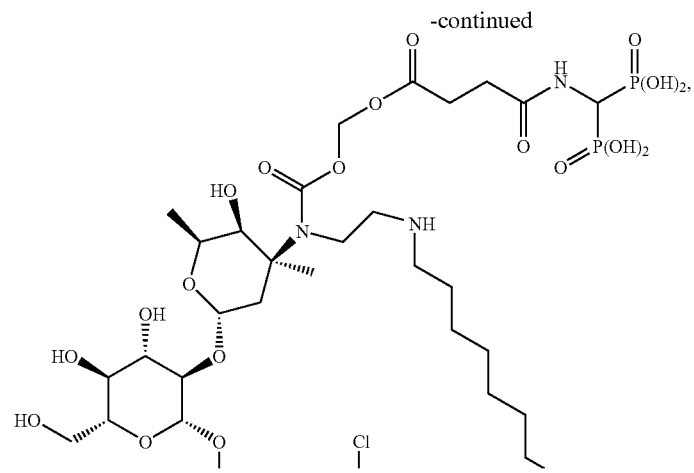
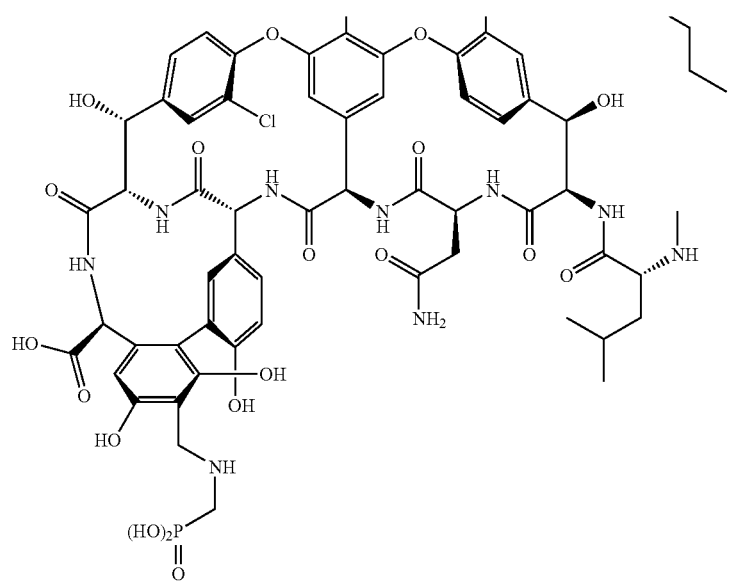
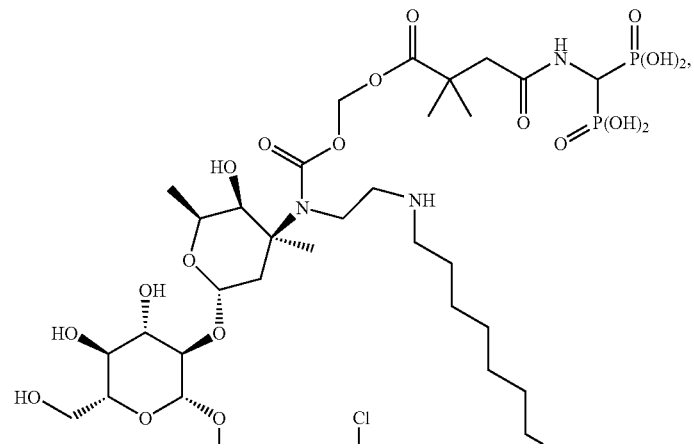

183
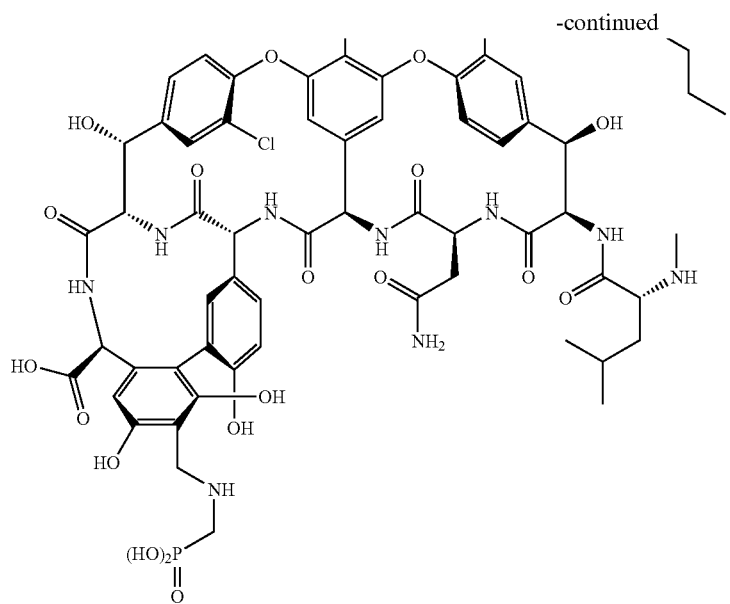
-continued
184
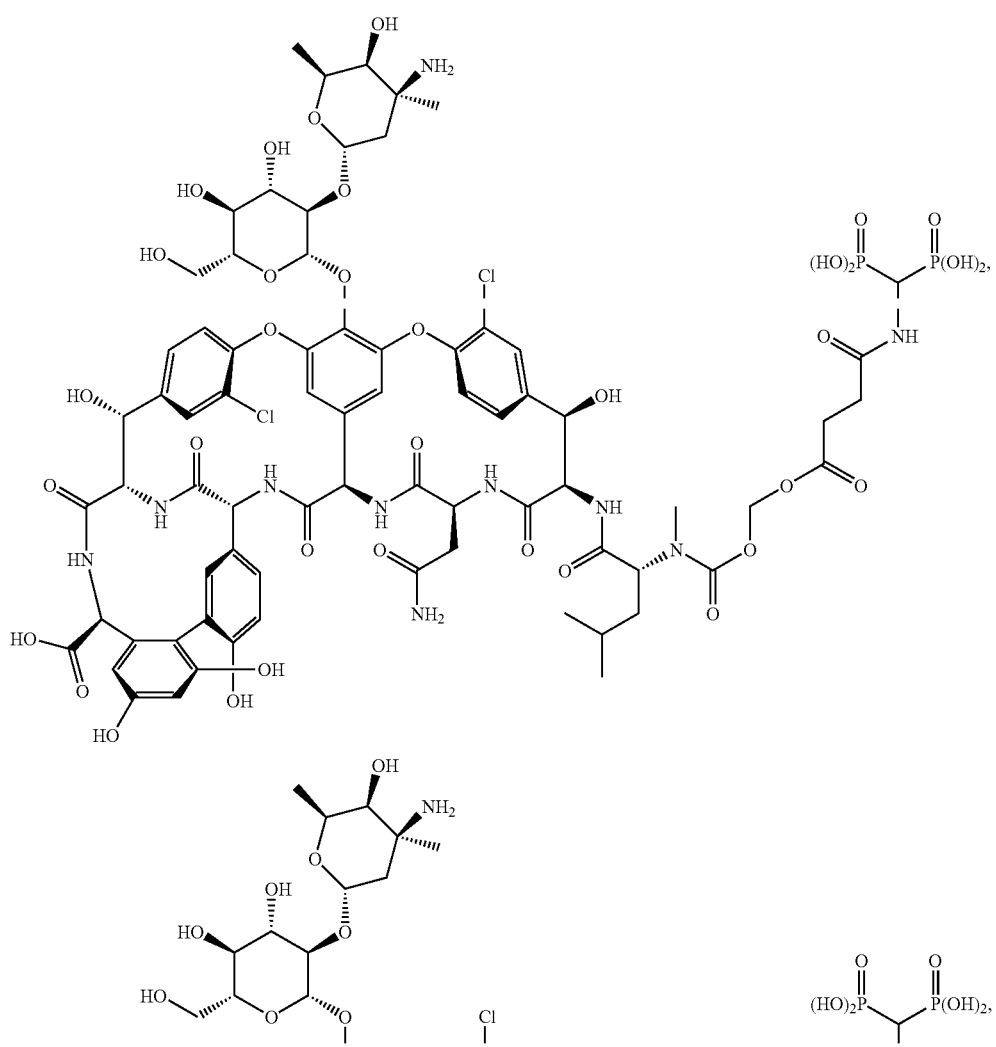

185 186
-continued
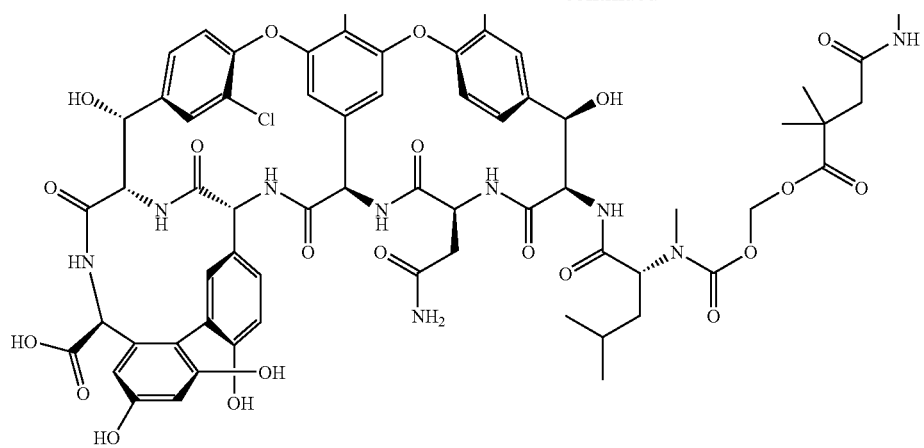
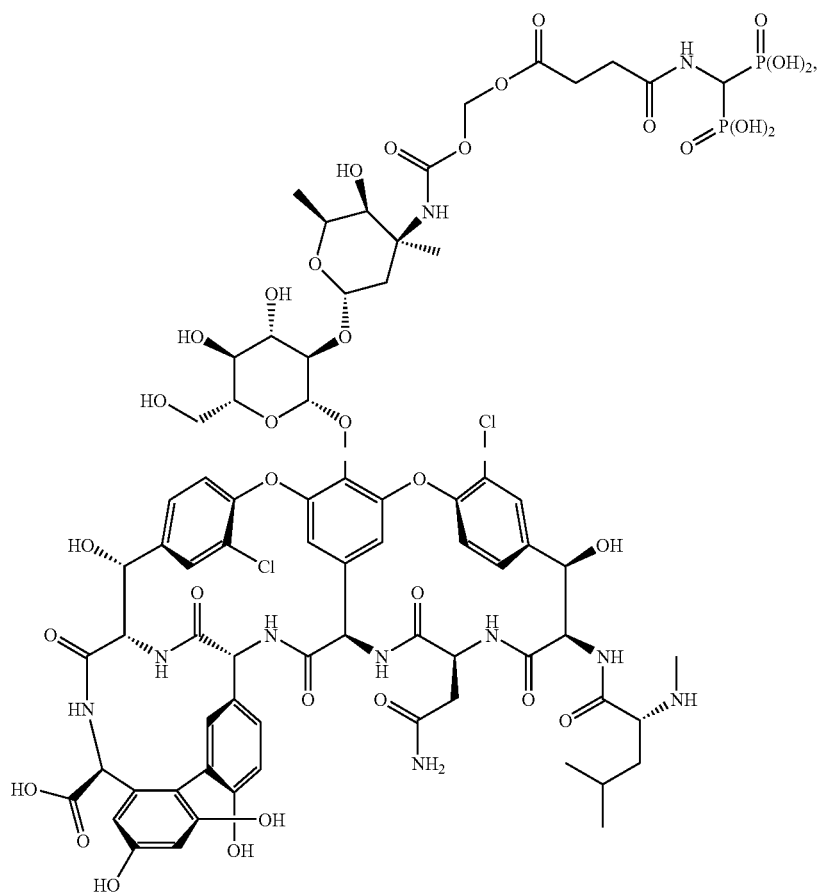

-continued
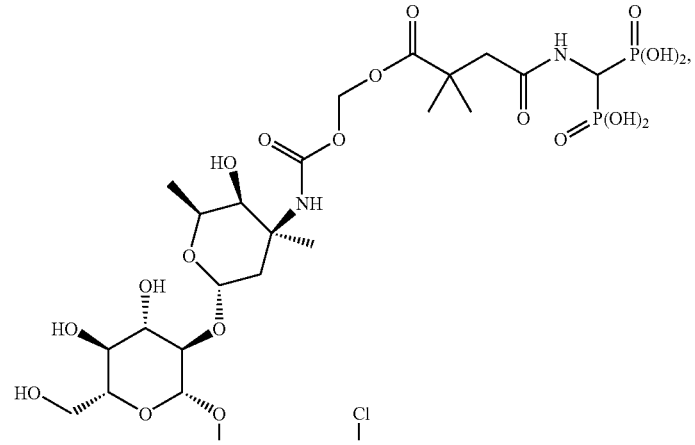
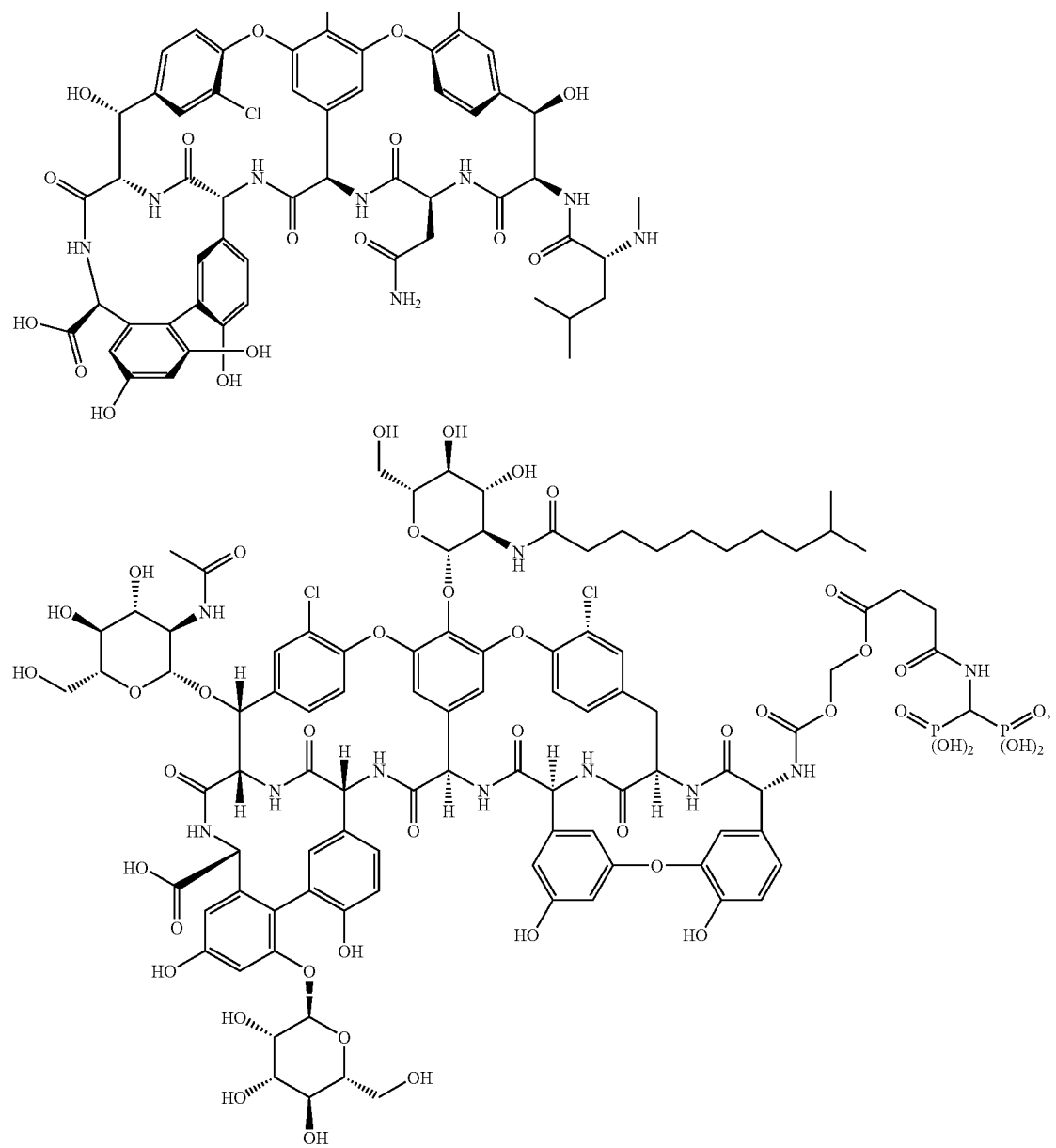

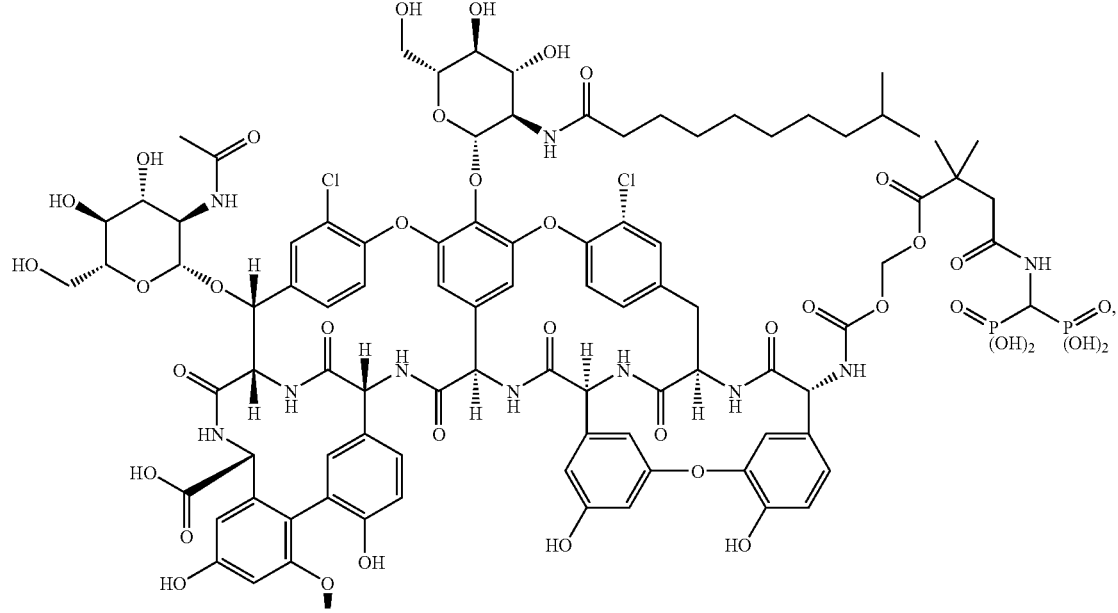
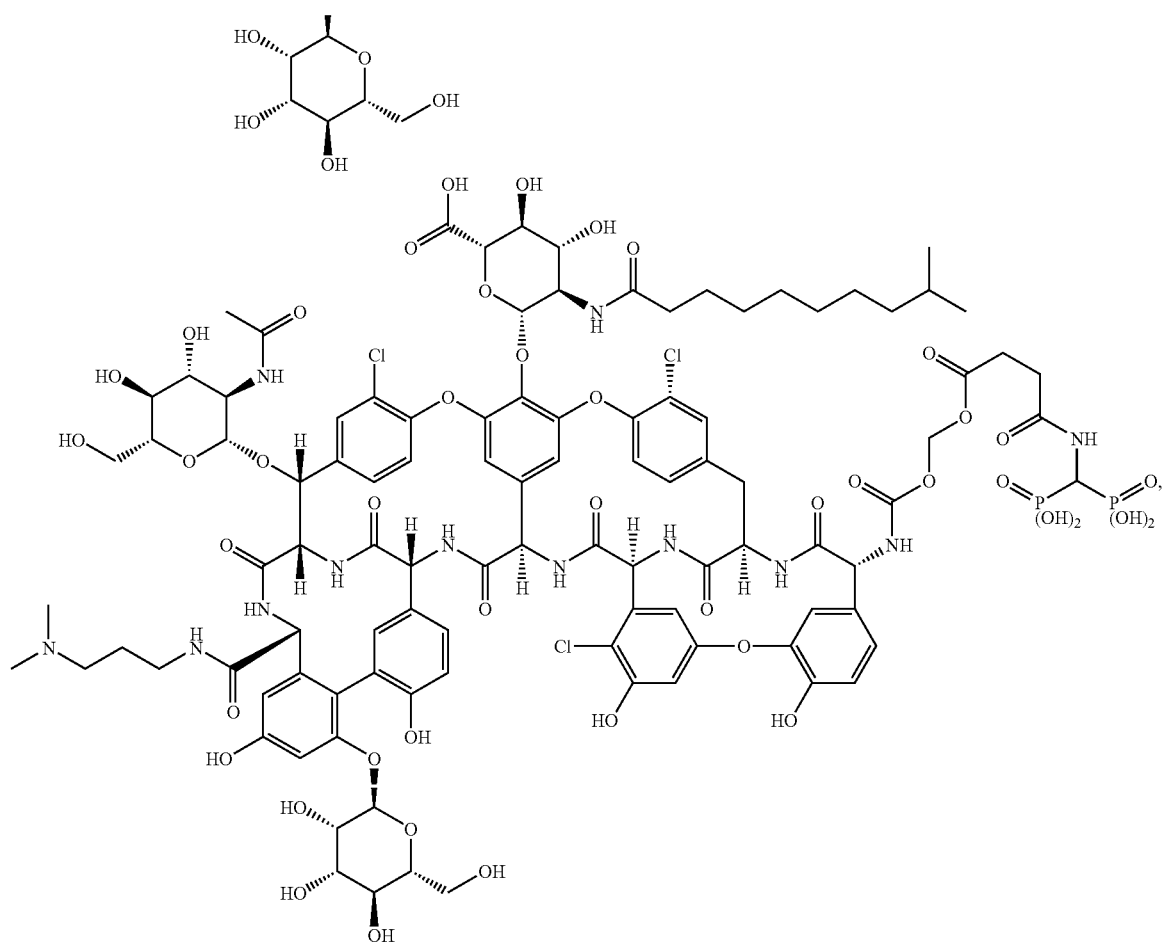

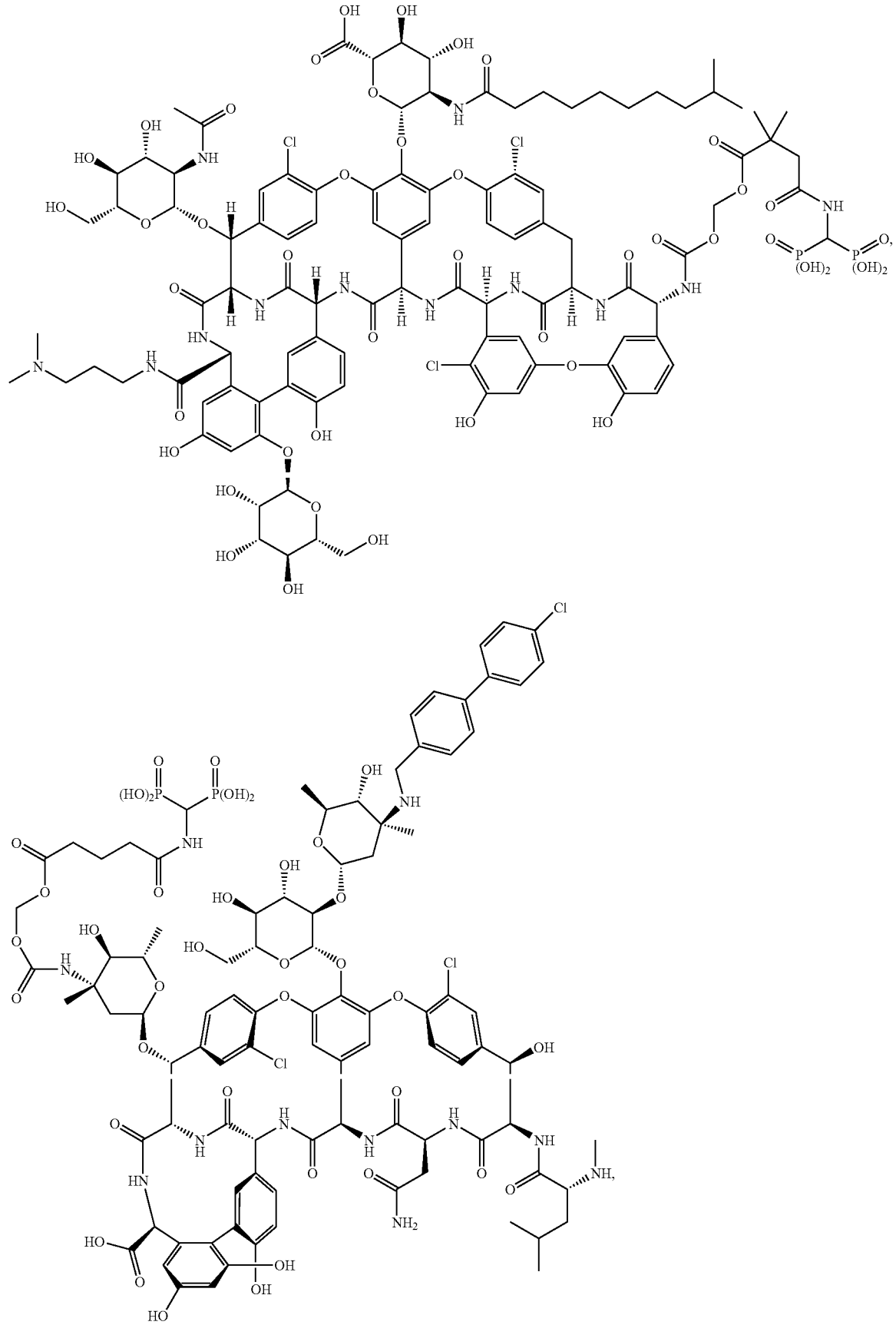

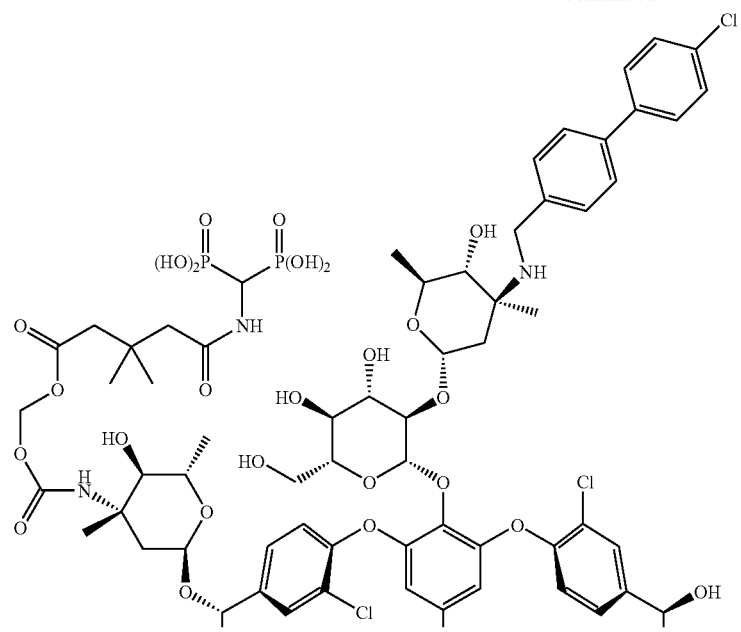
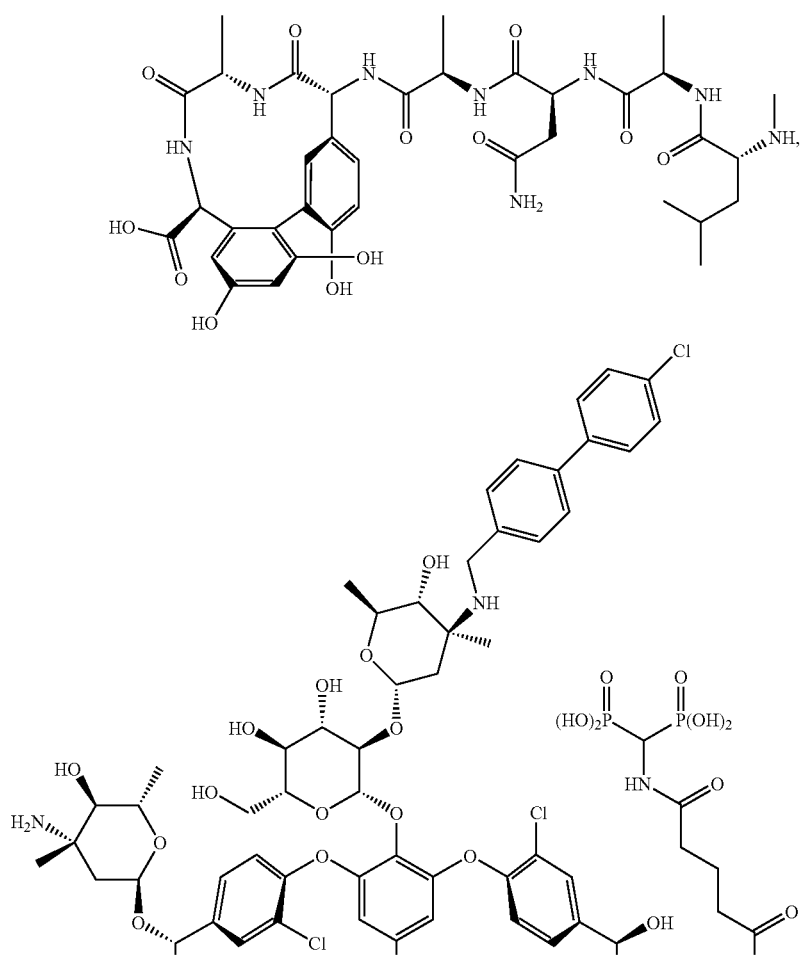

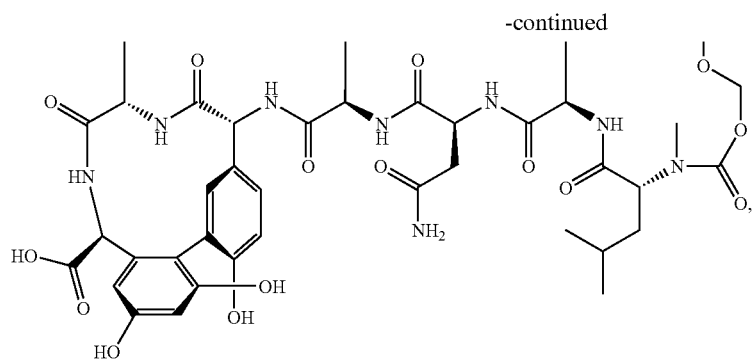
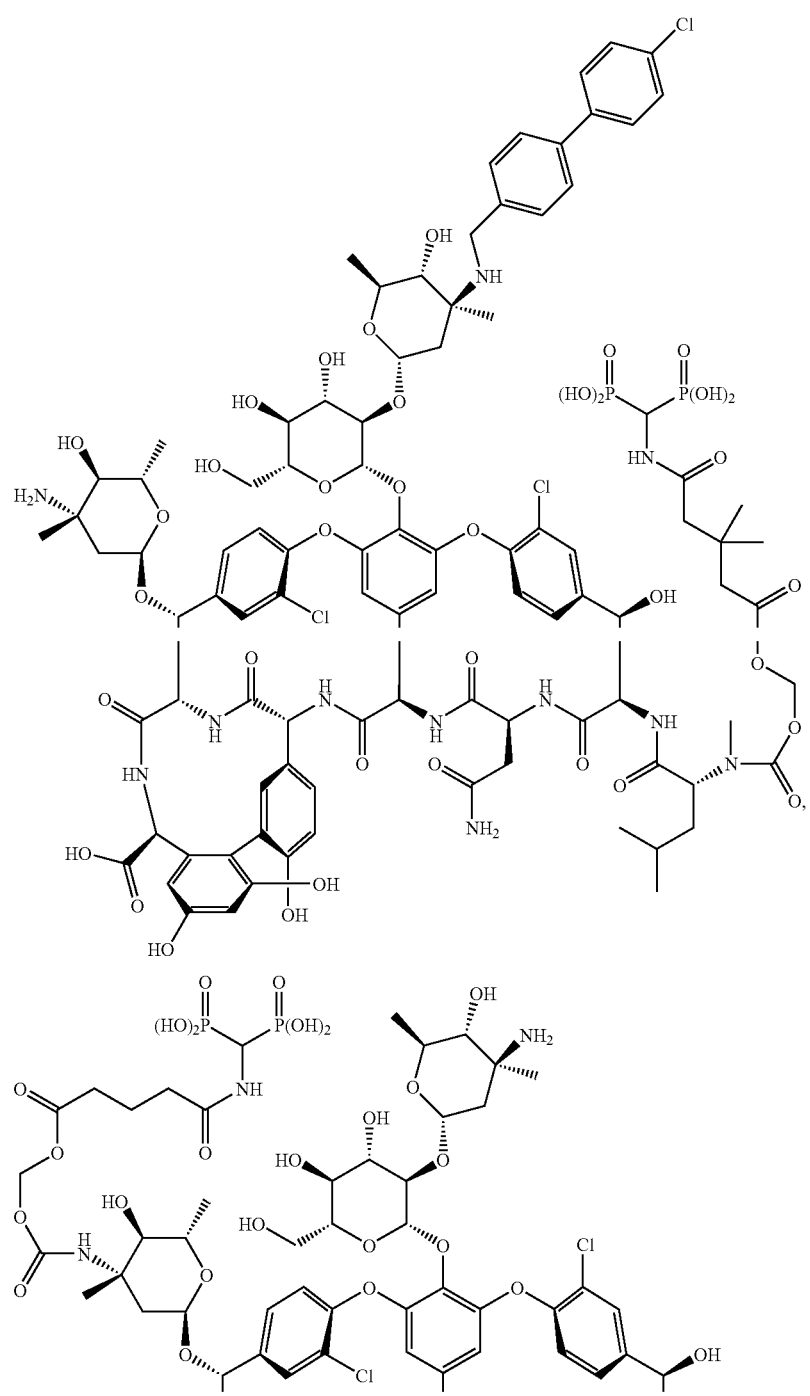

197
-continued
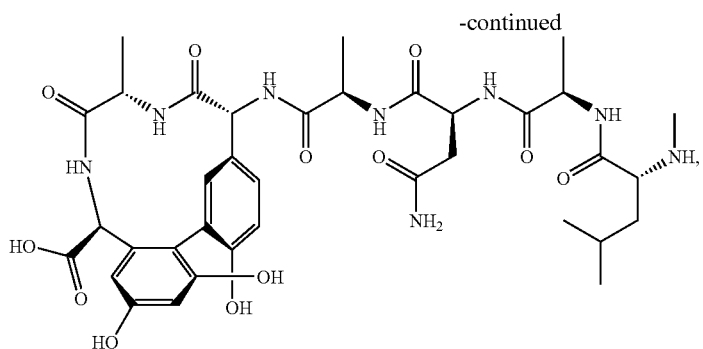
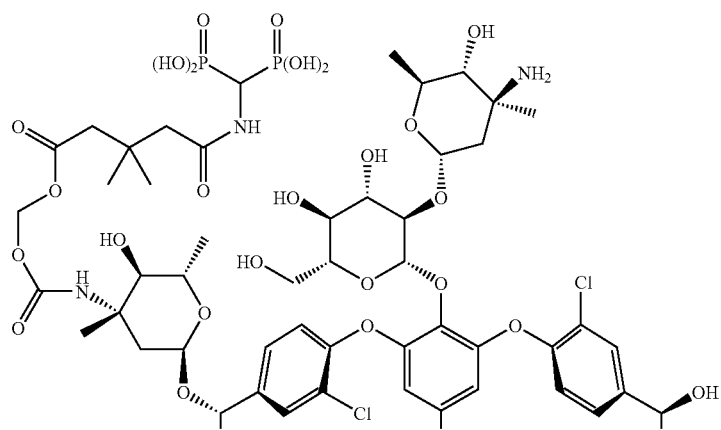
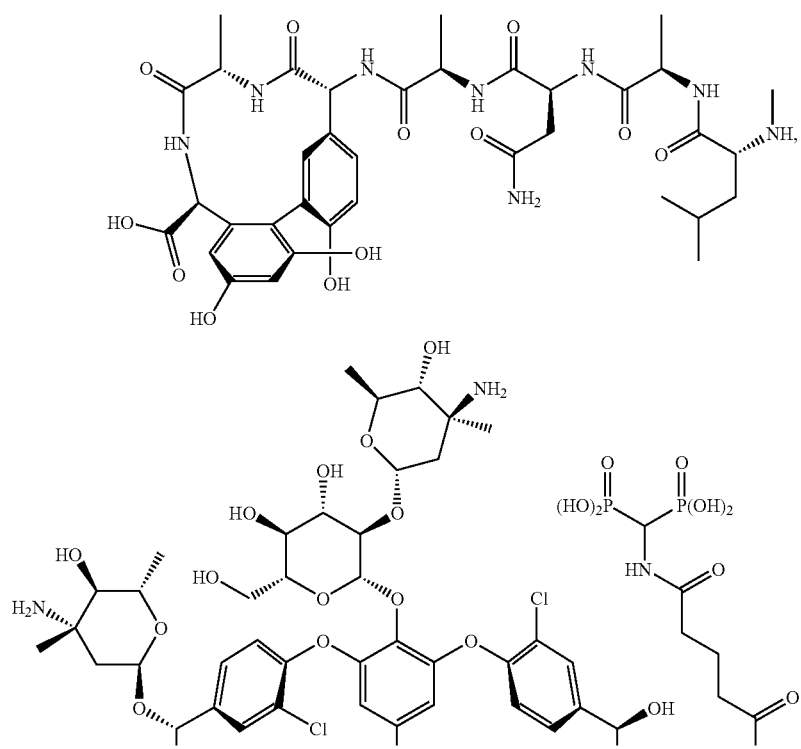

199
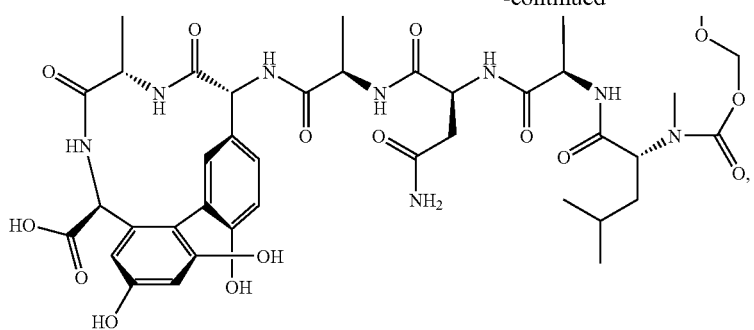
-continued
200
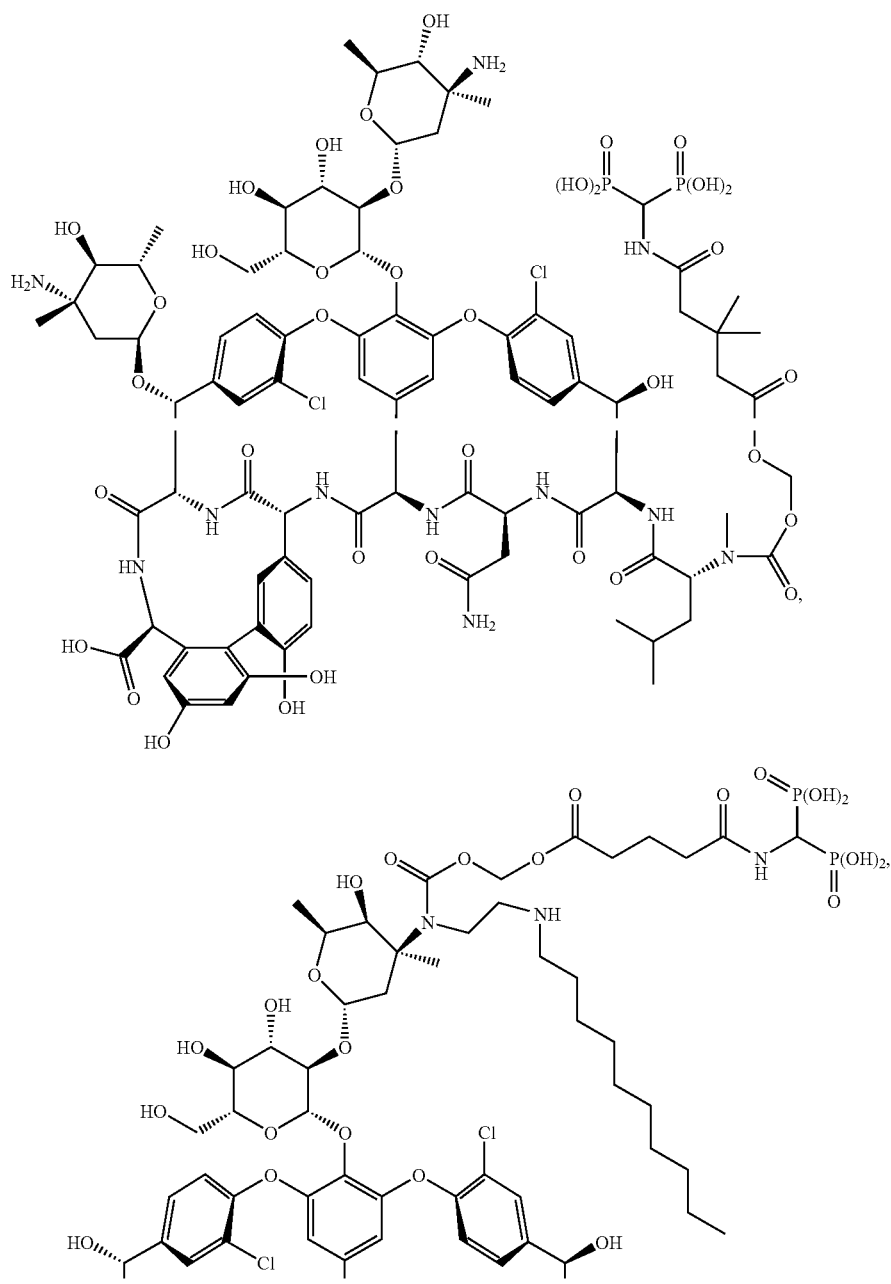

201
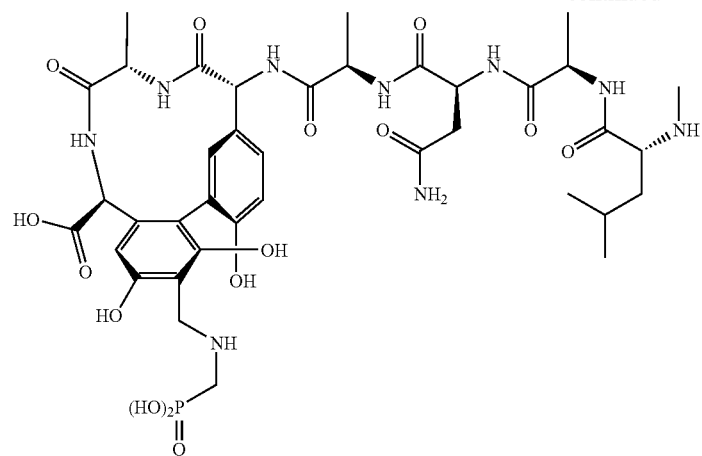
-continued
202
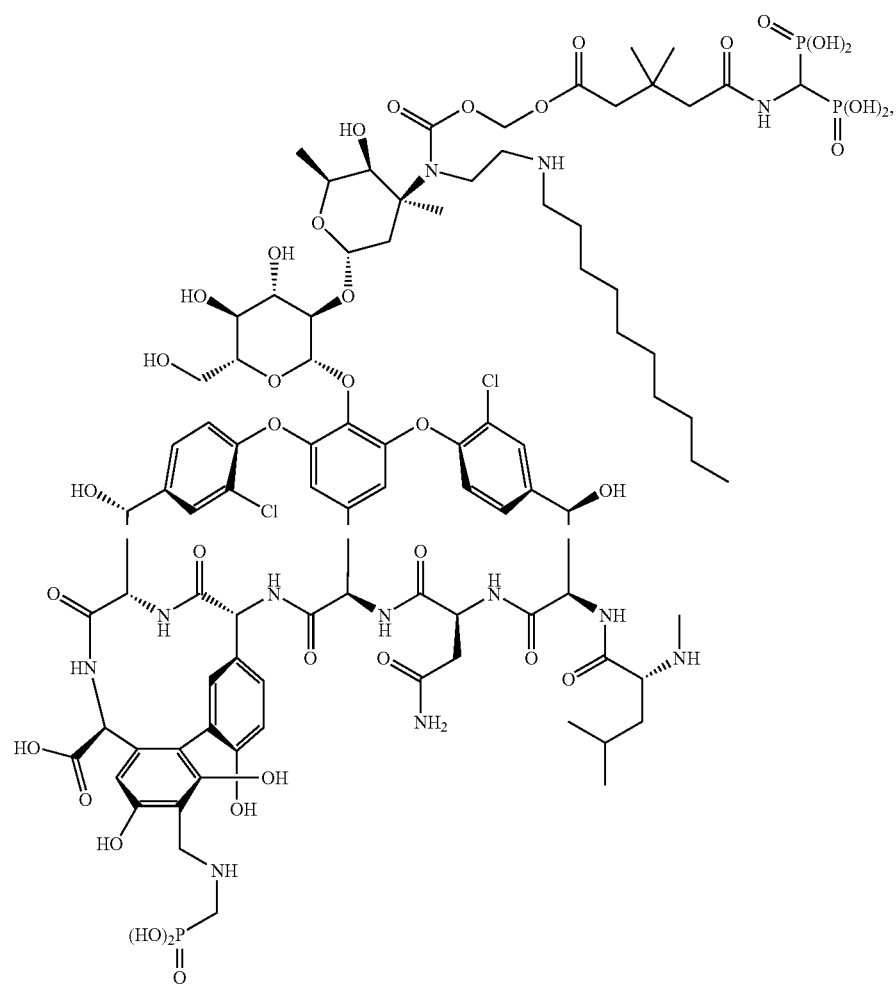

203
204
-continued
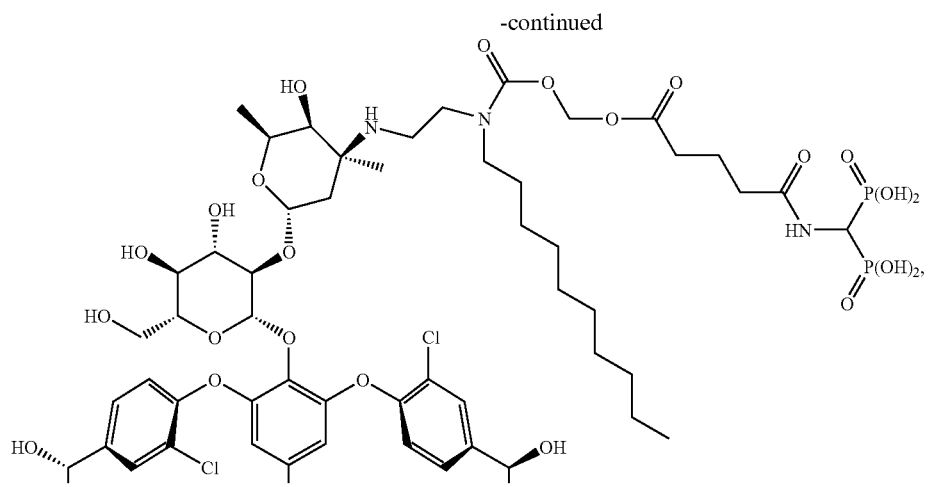
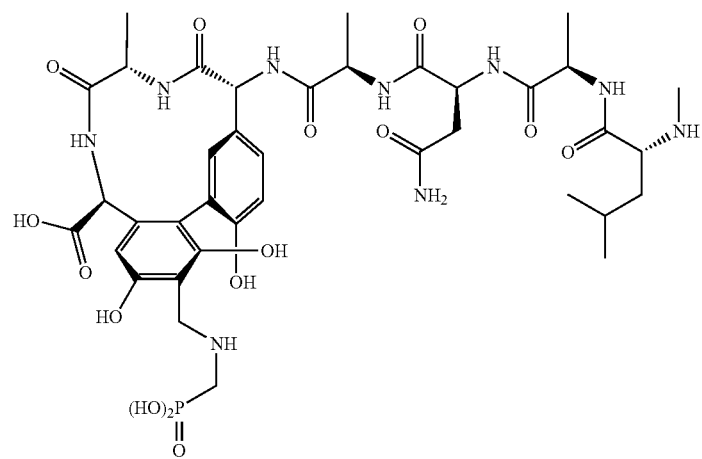
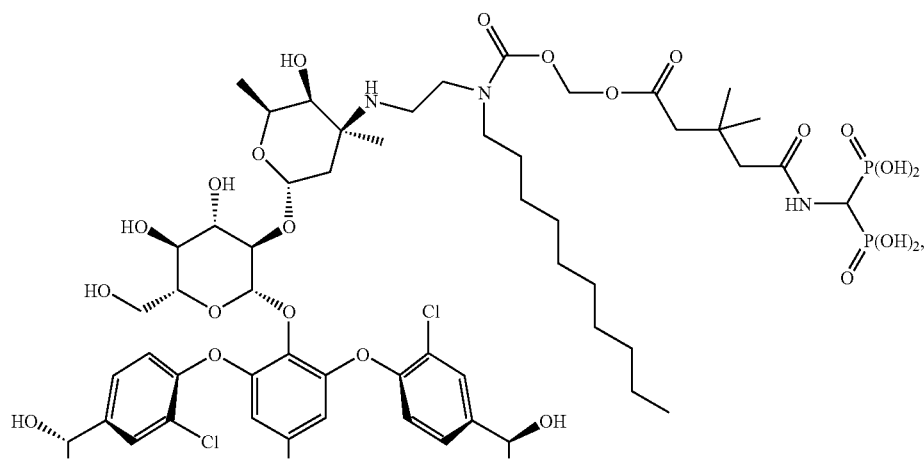

205
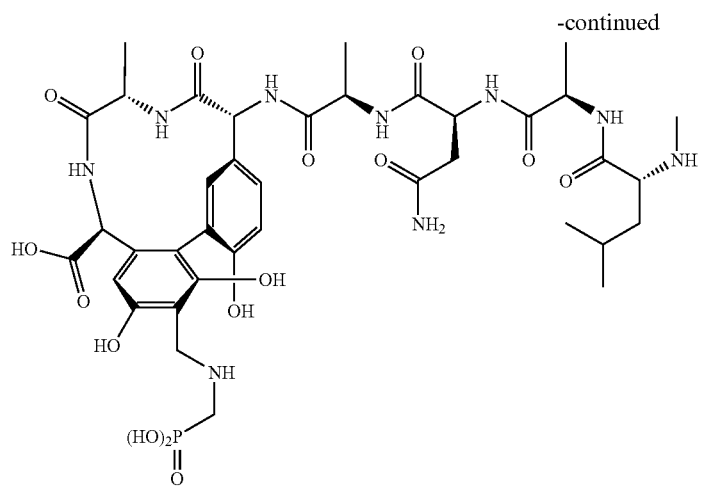
-continued
206
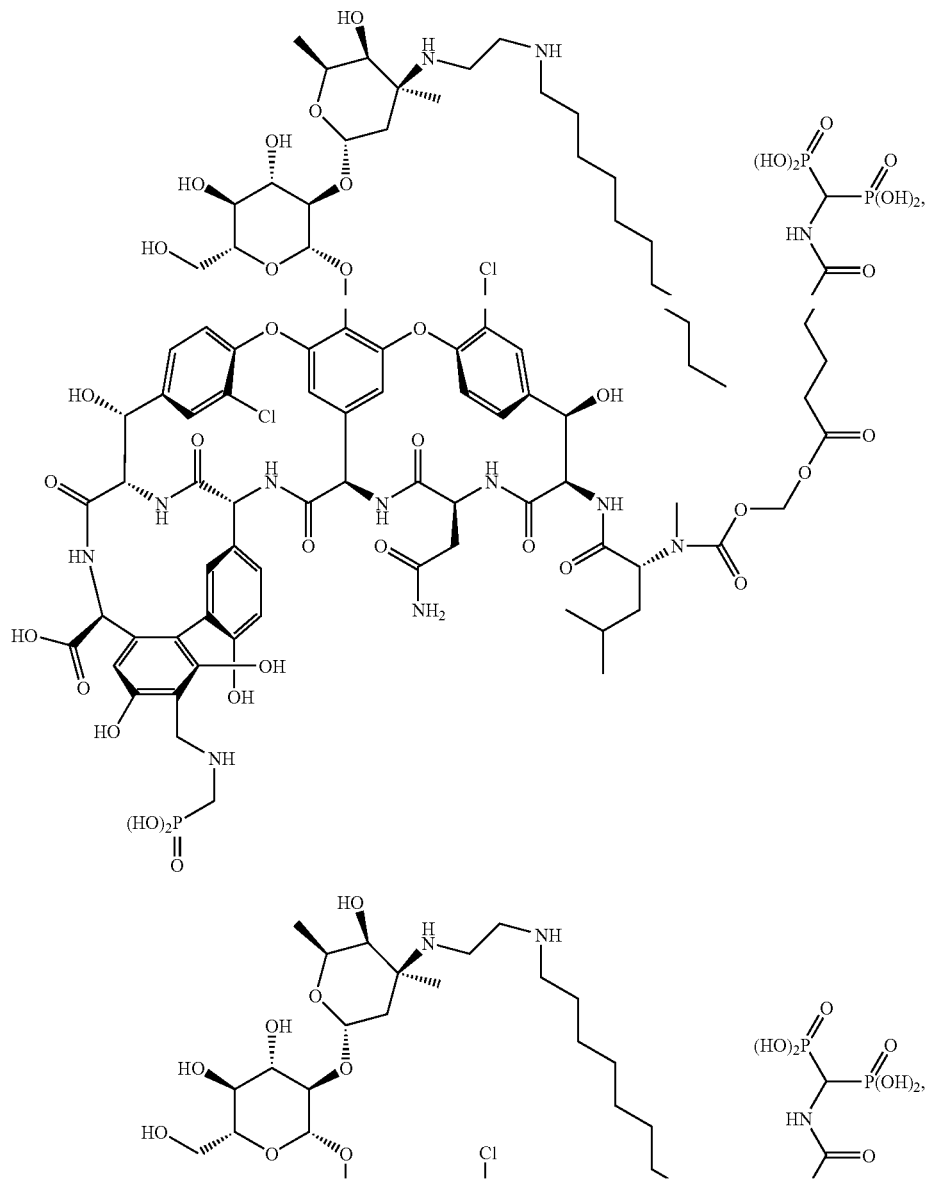

207
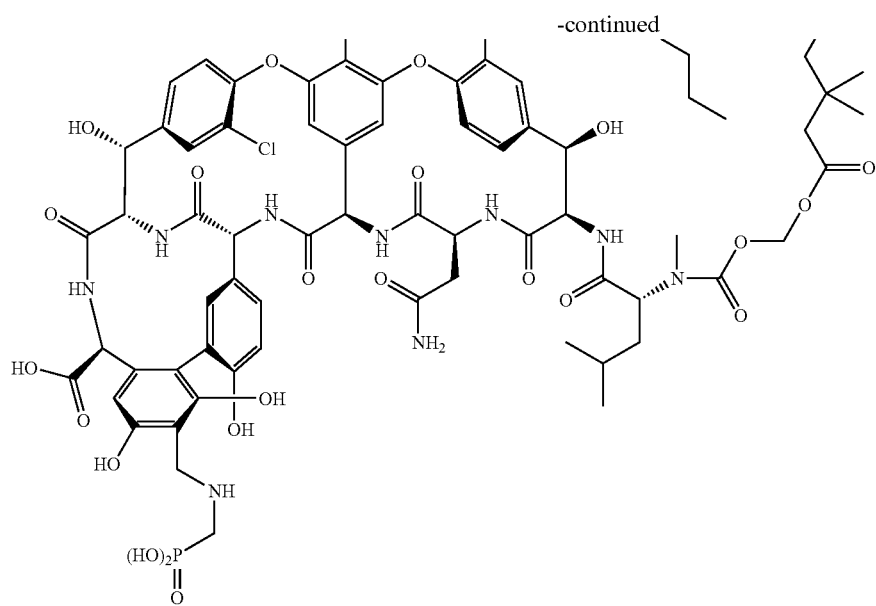
-continued
208
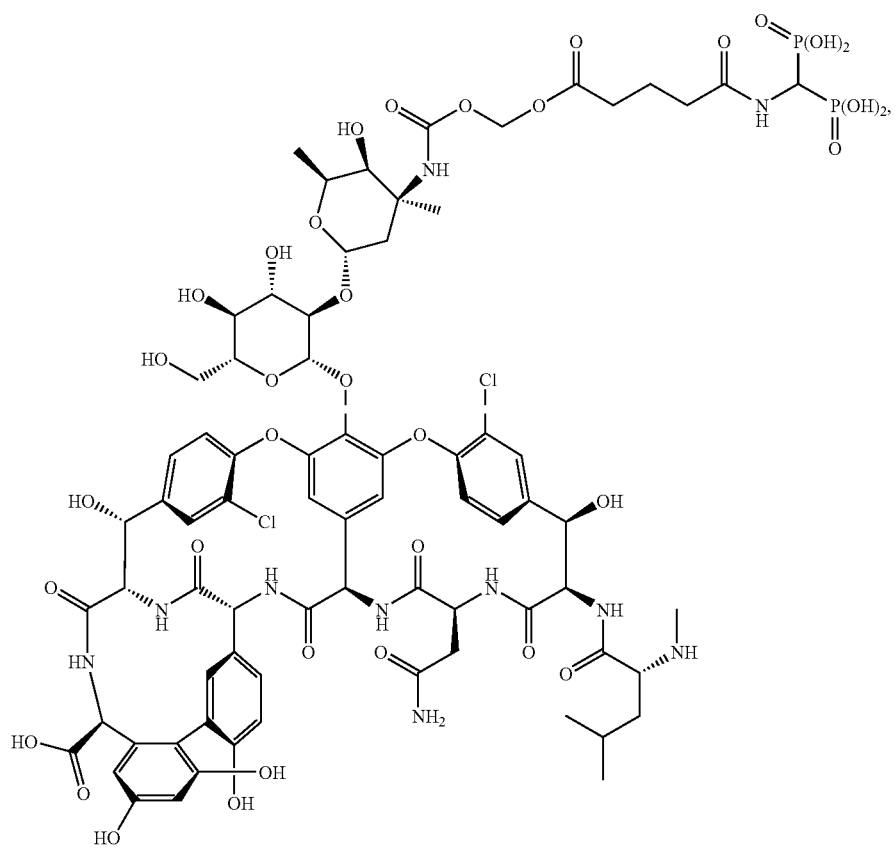

-continued
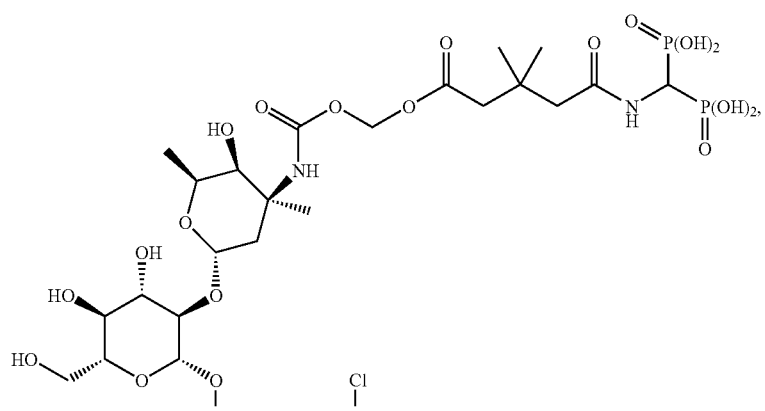
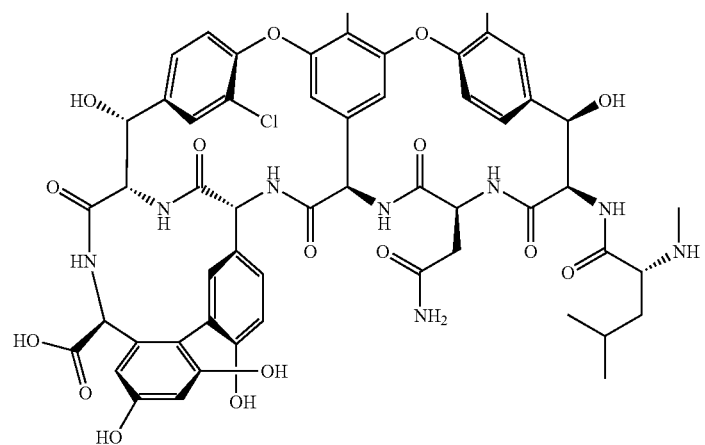
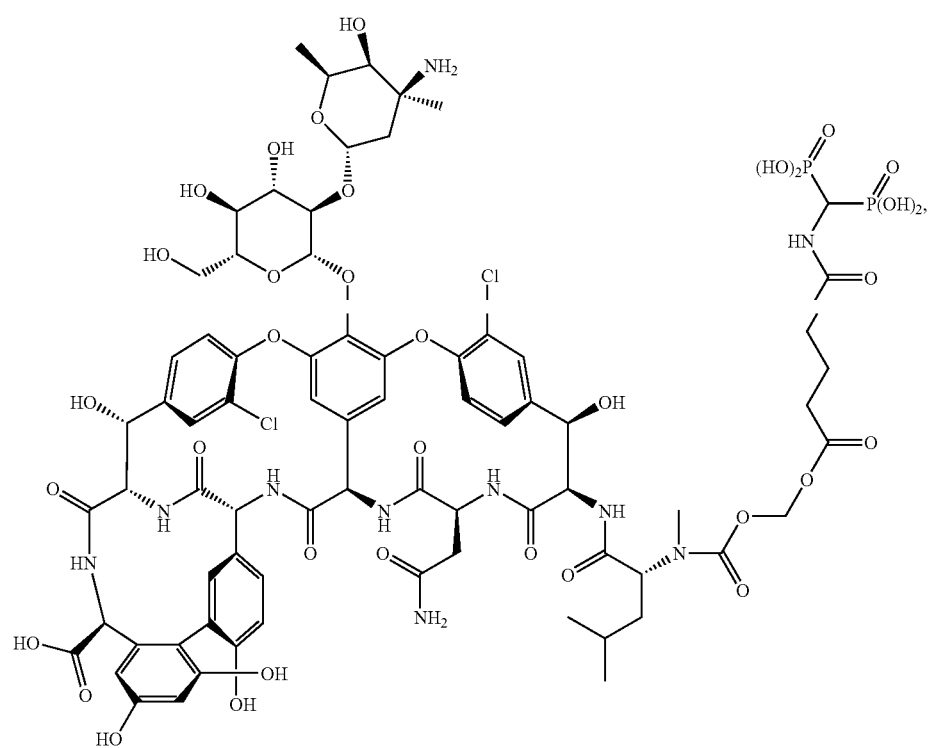

211
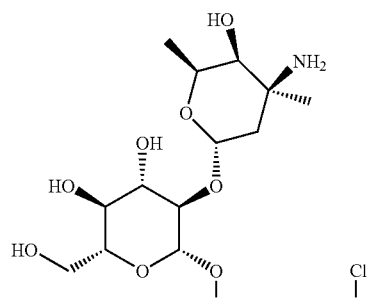
212
-continued
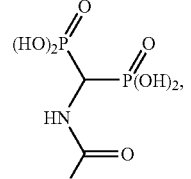
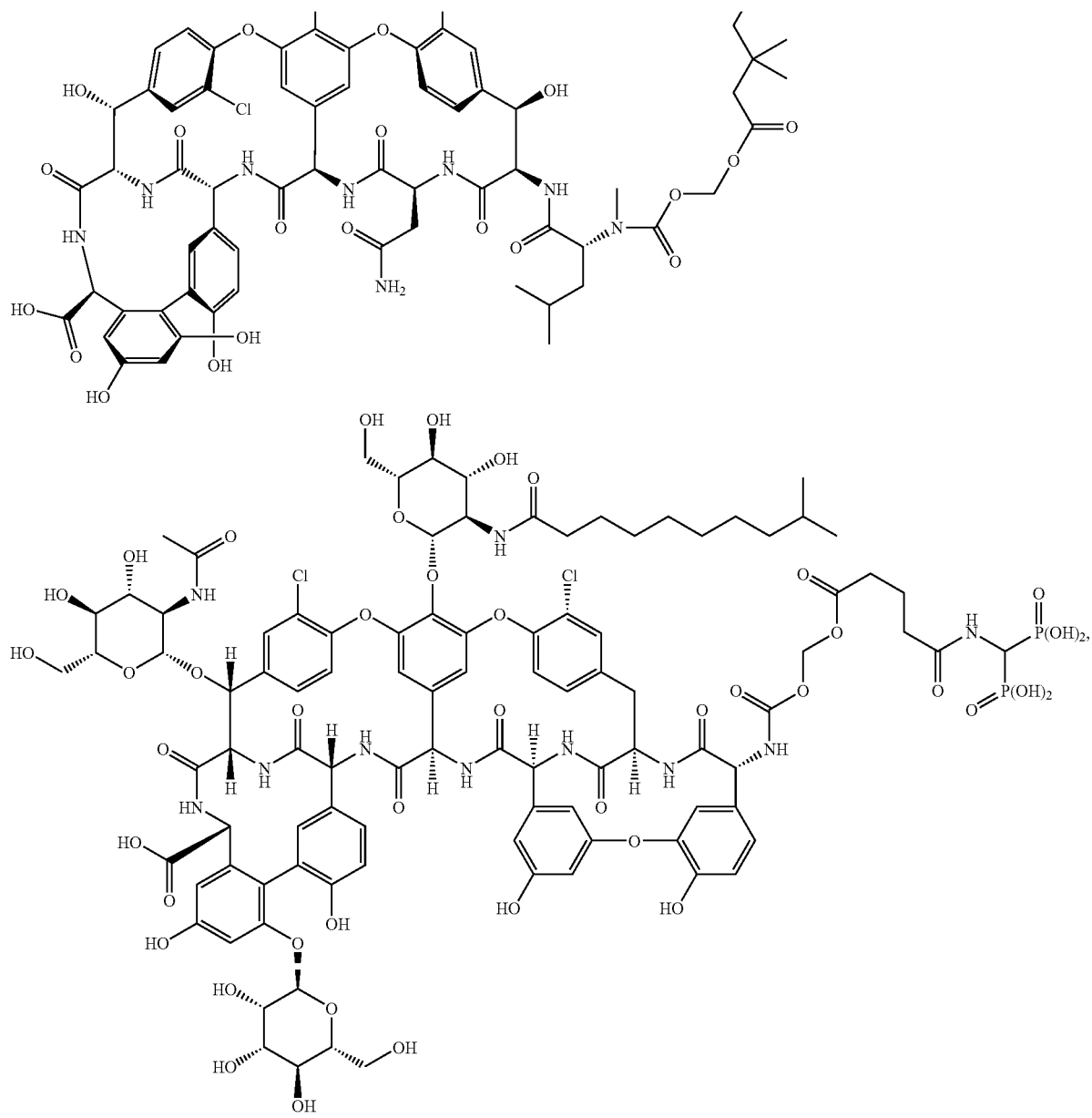

213
-continued
214
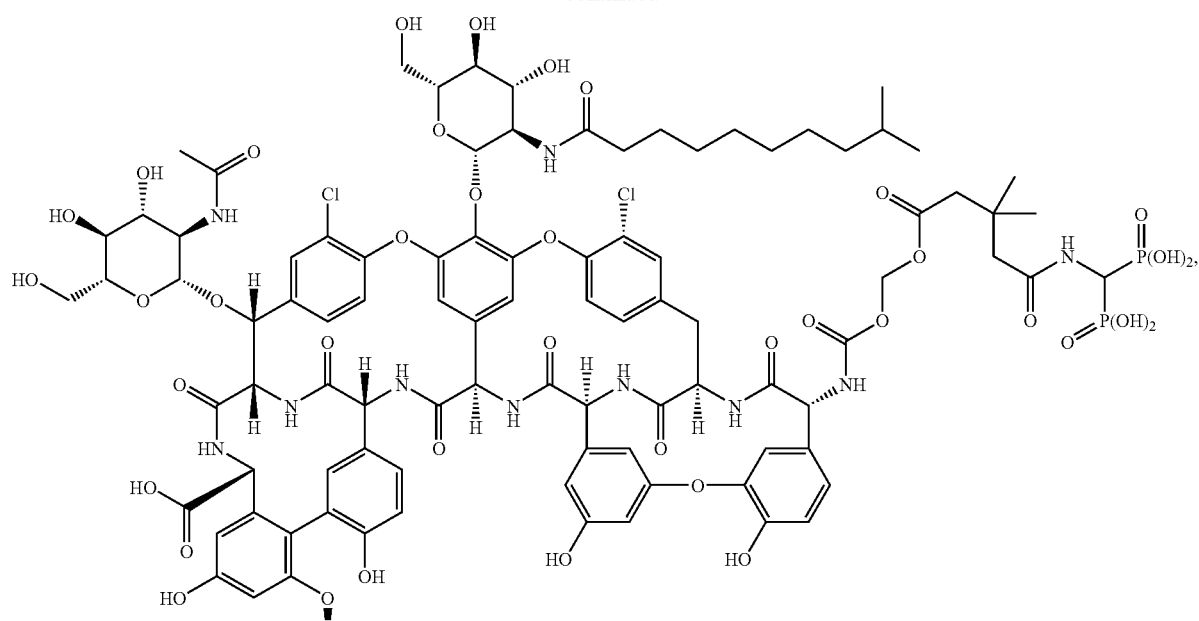
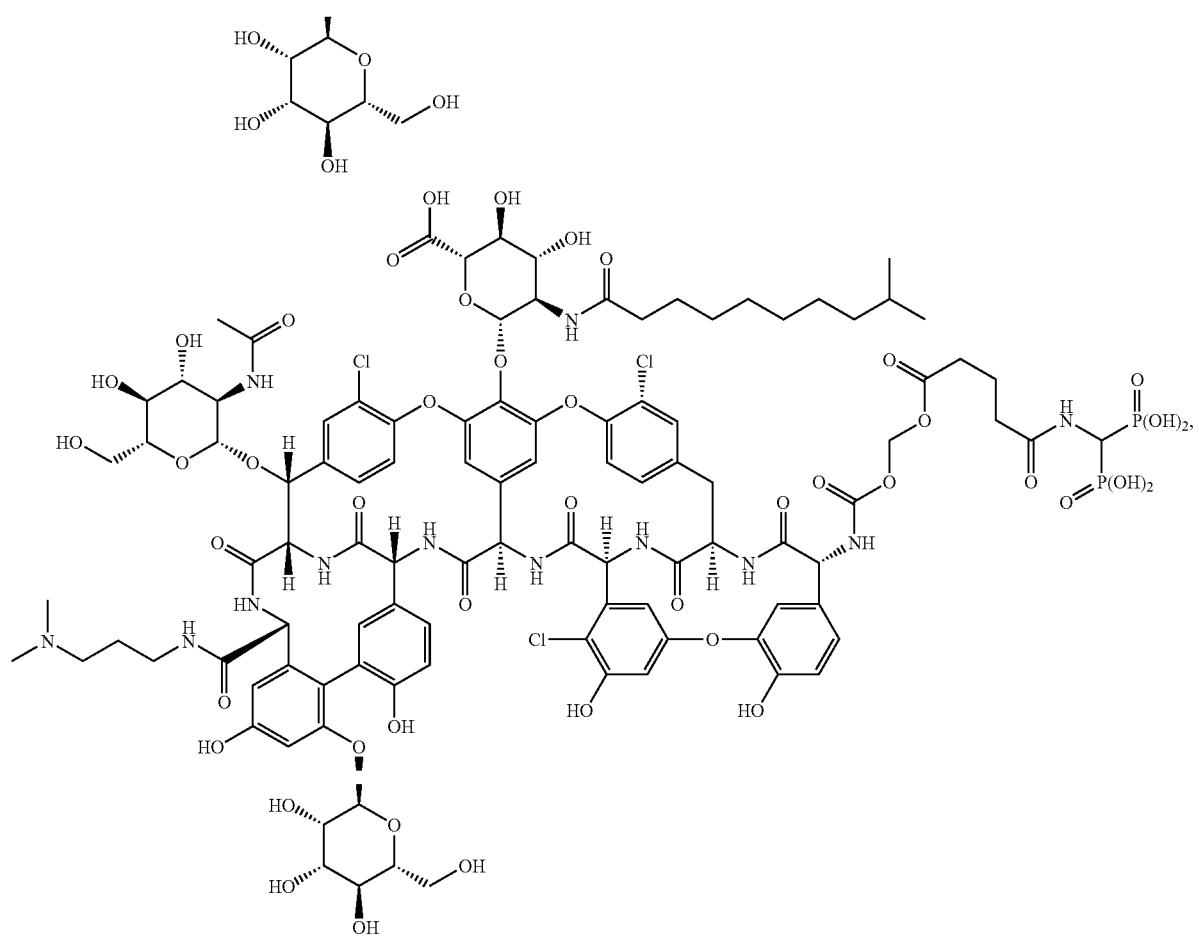

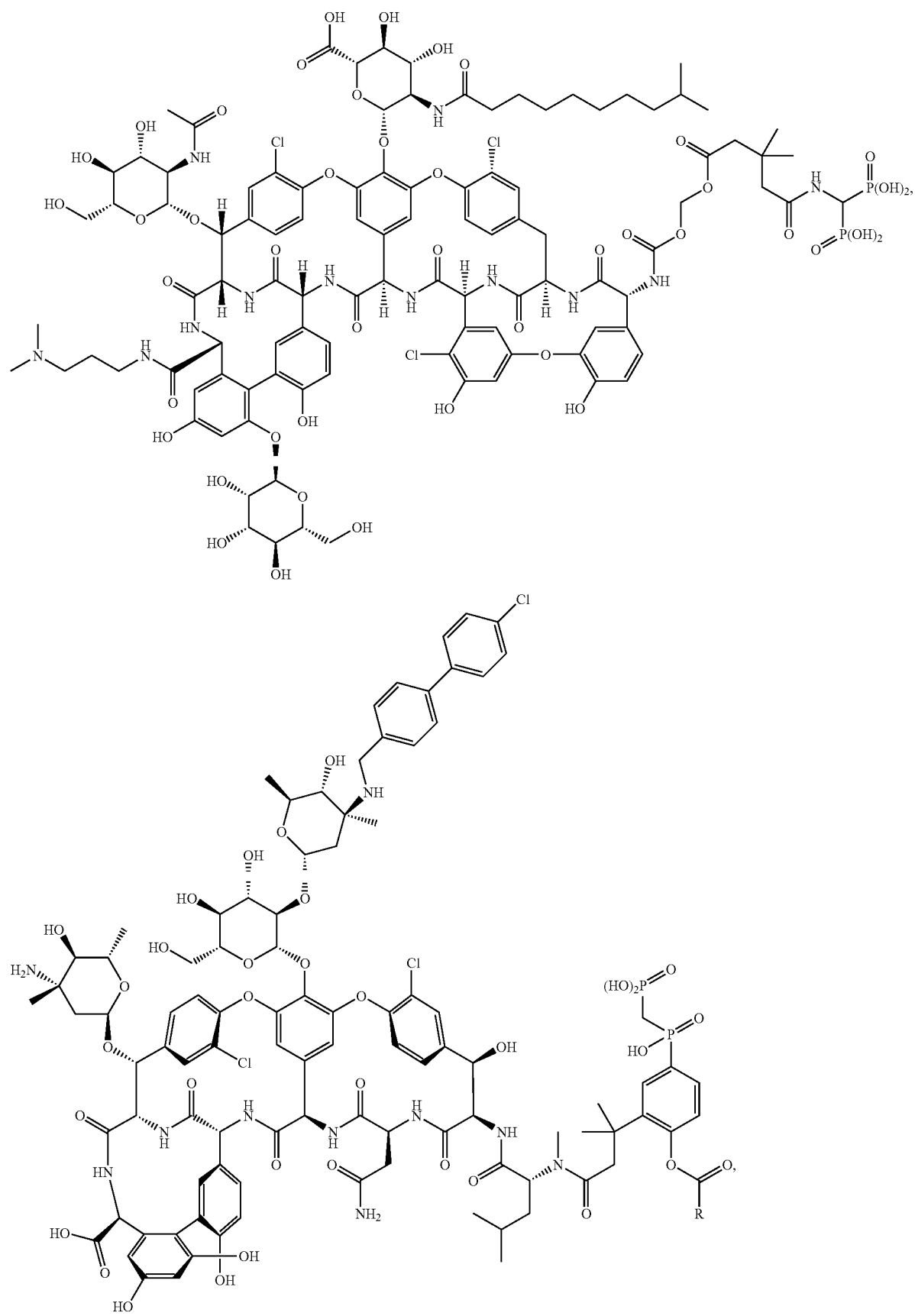

-continued
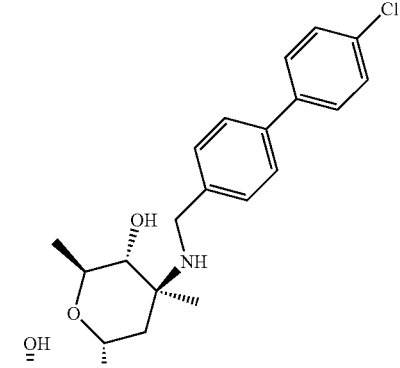
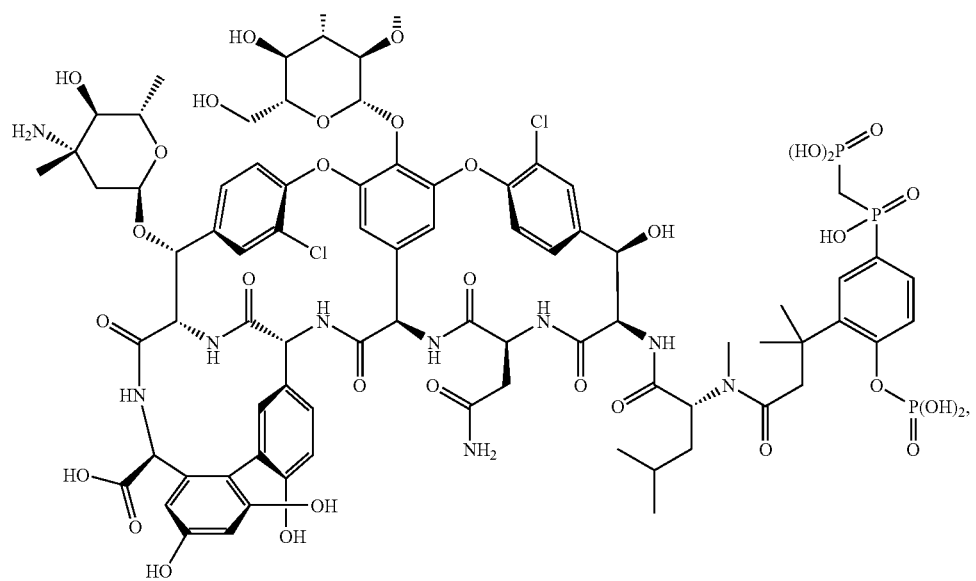
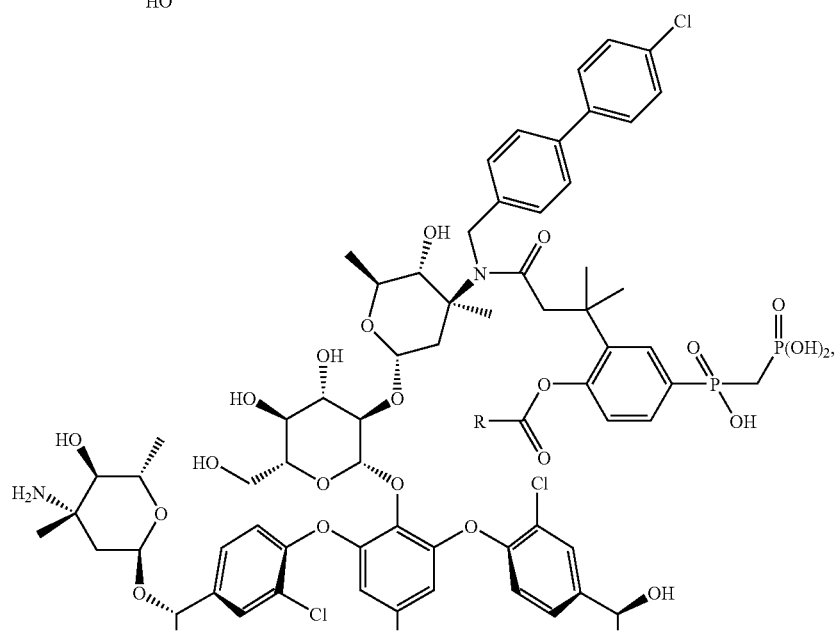

-continued
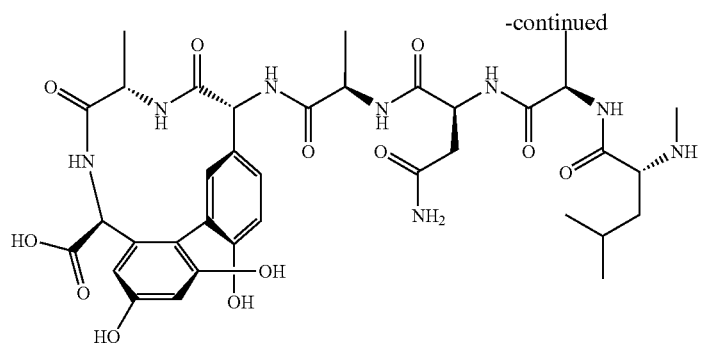
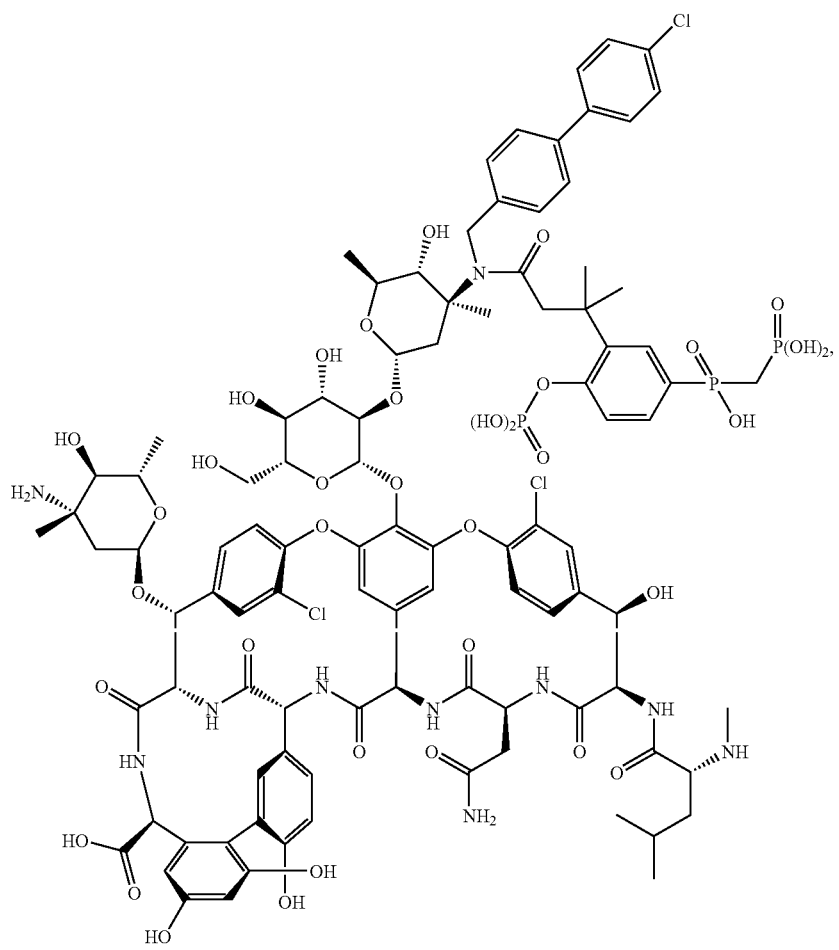

221 222
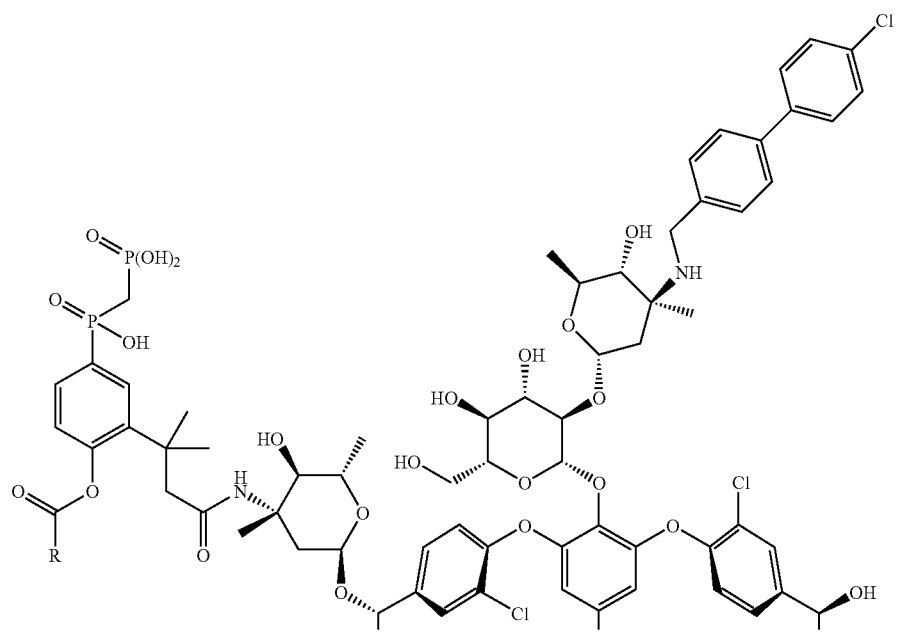
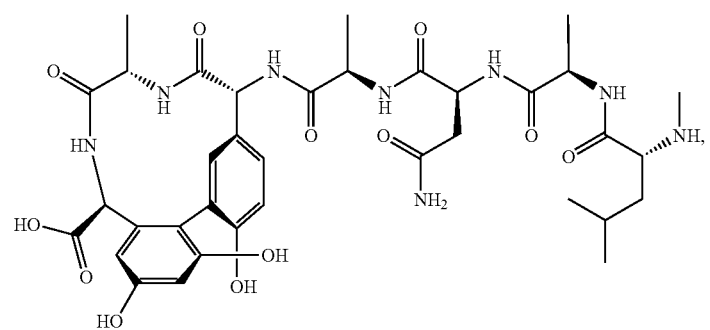
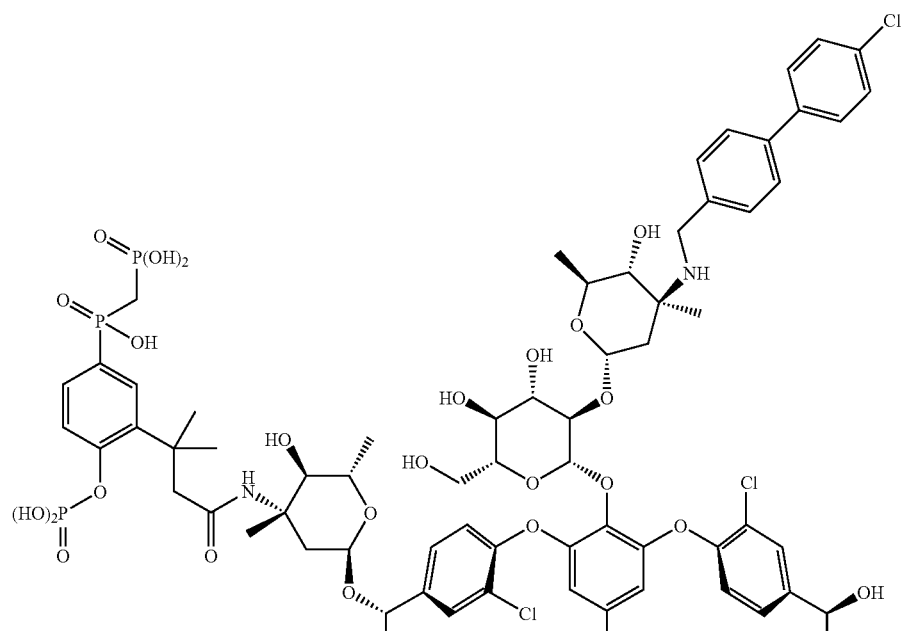

223                                    224
-continued
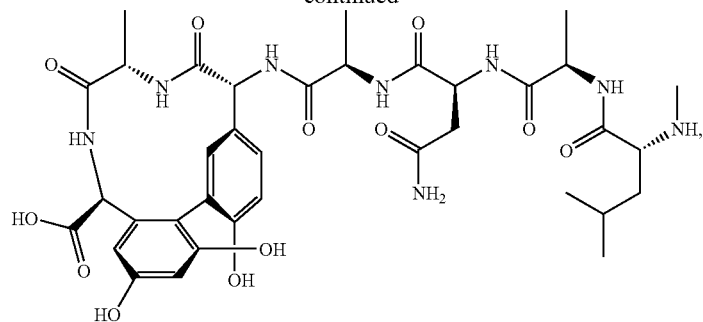
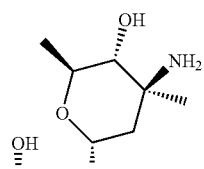
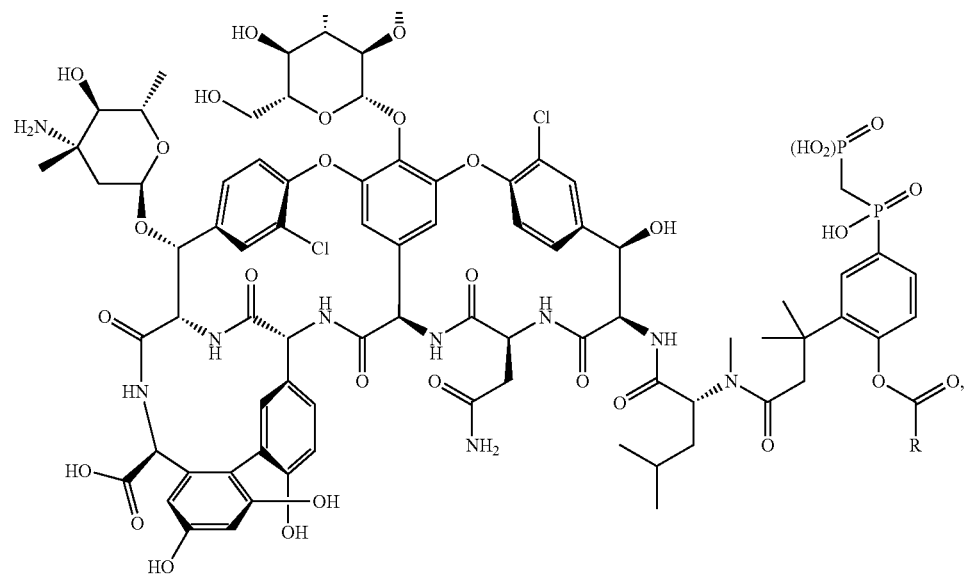
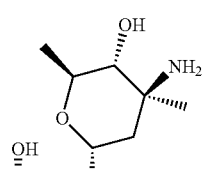

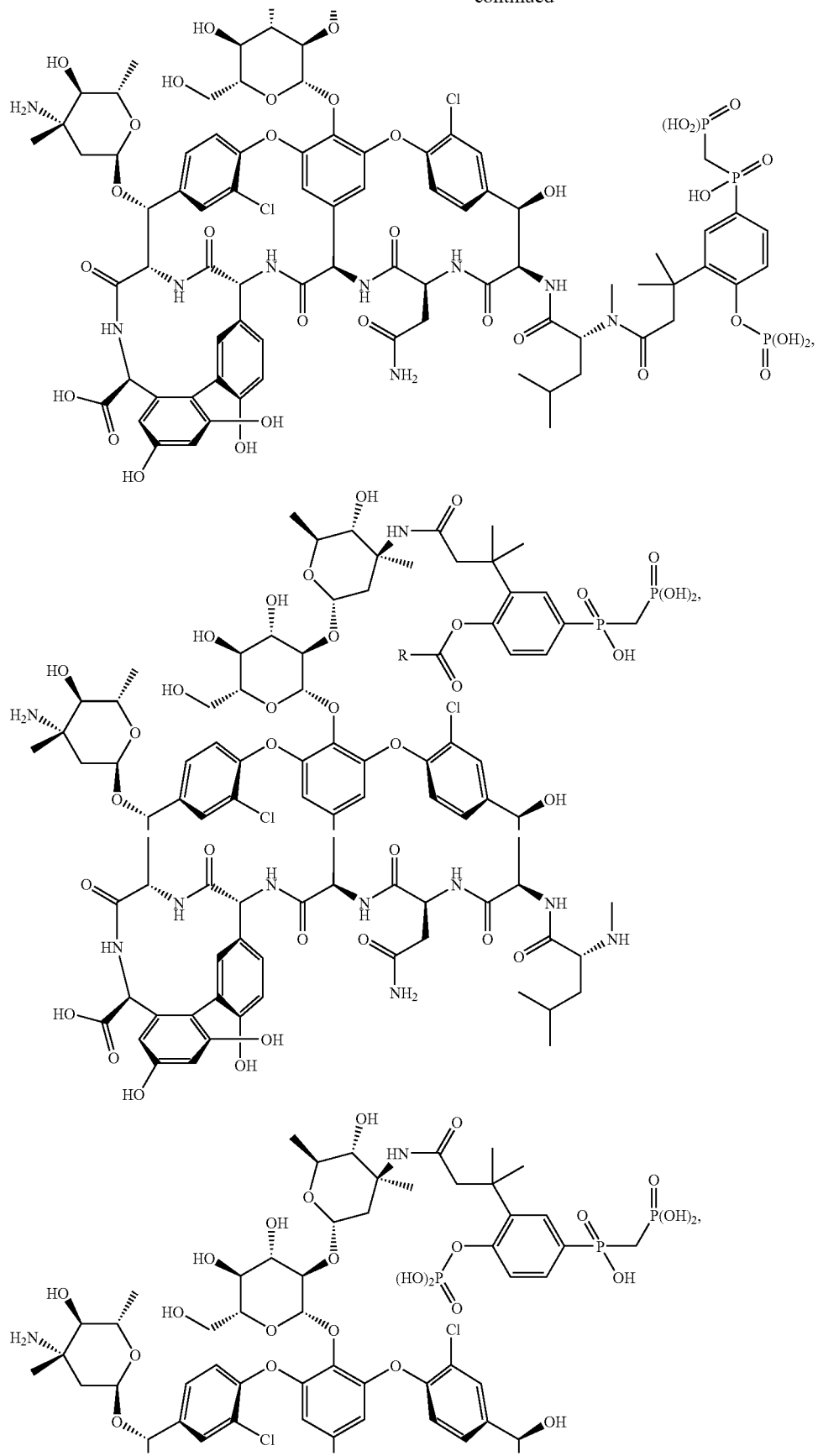

227
-continued
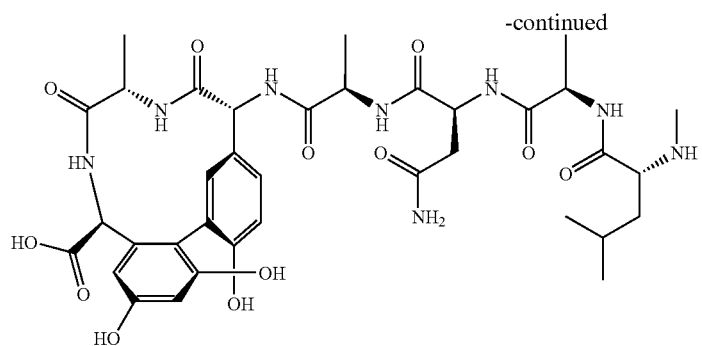
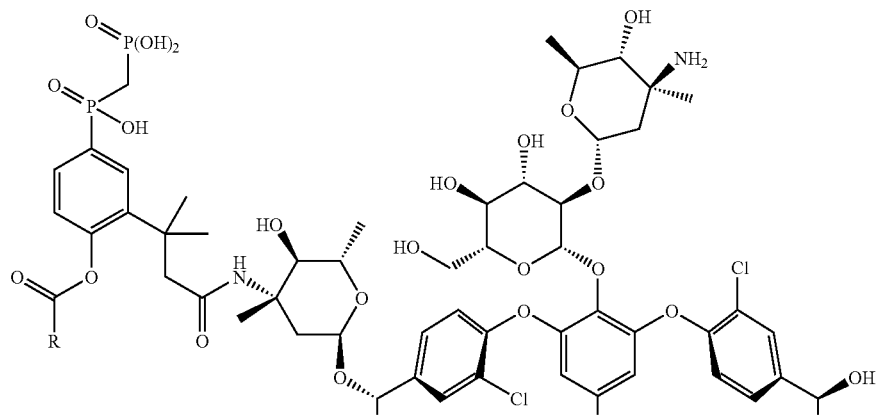
228
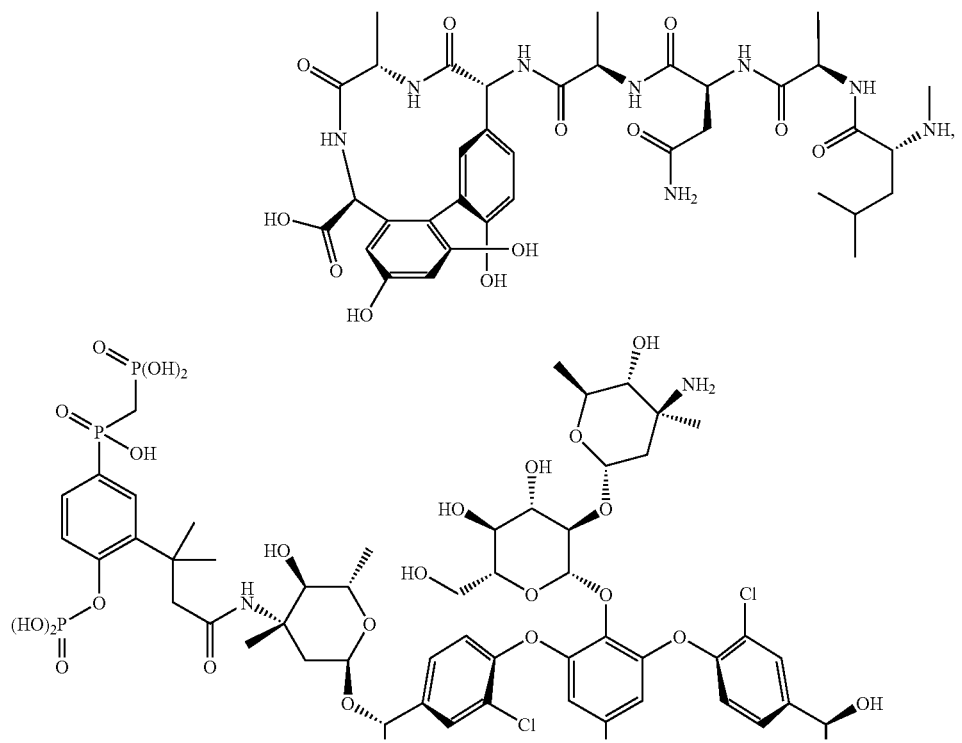

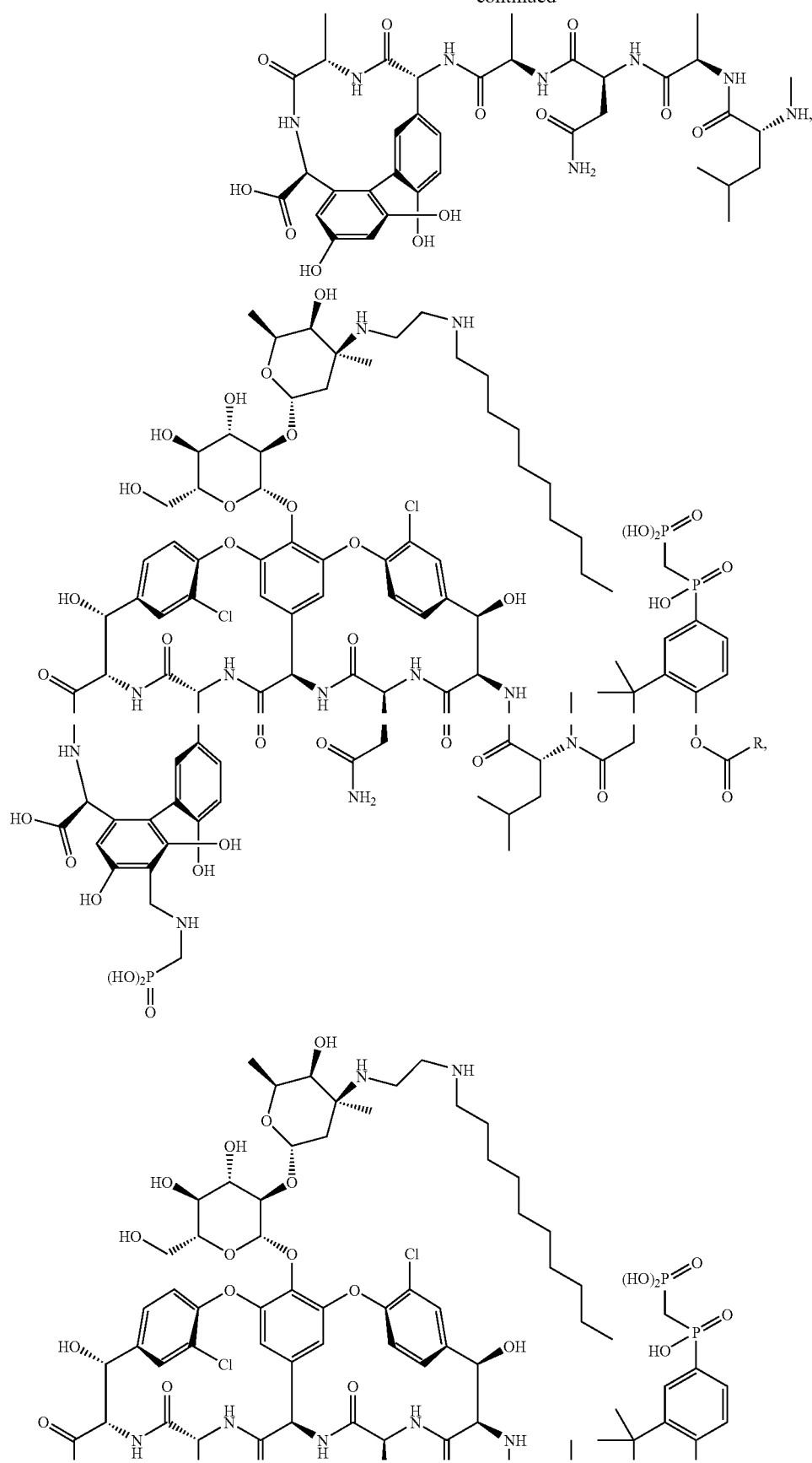

231
232
-continued
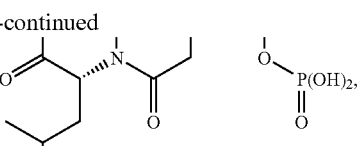
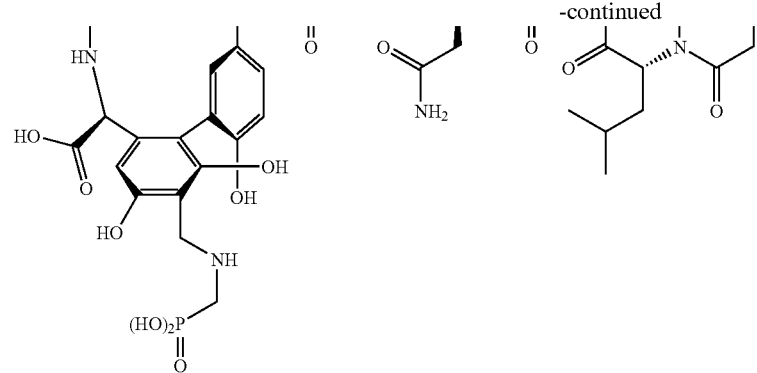
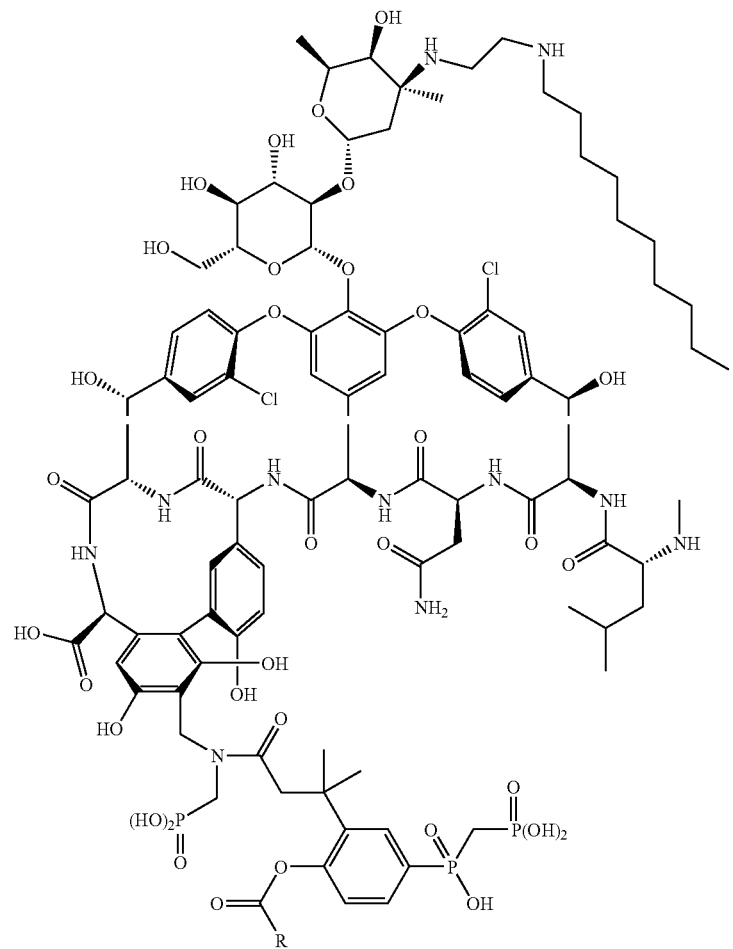
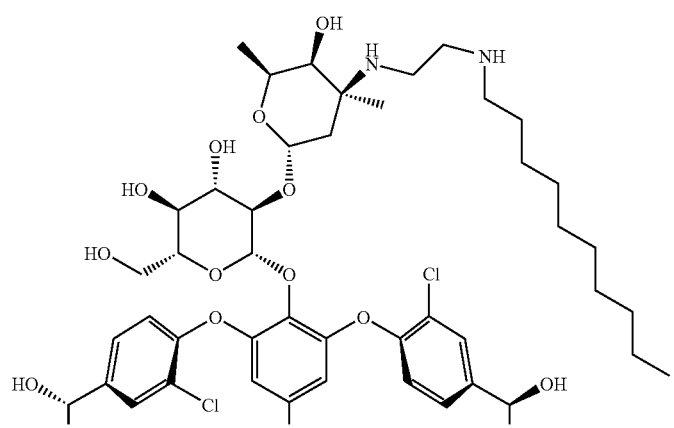

233
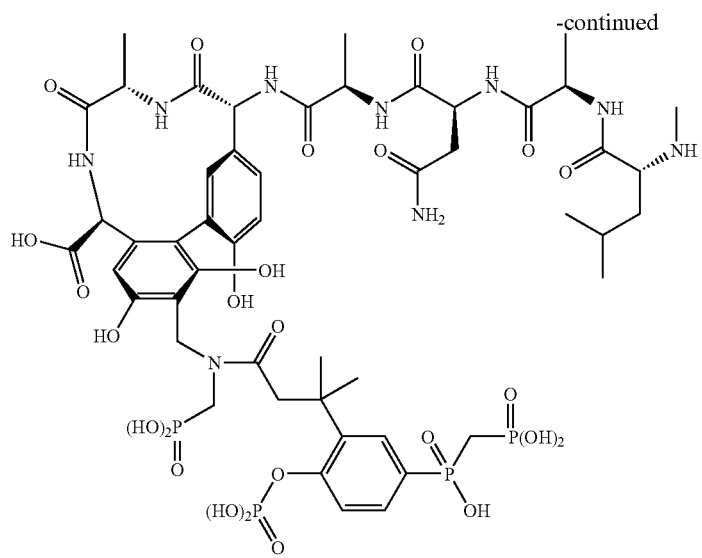
-continued
234
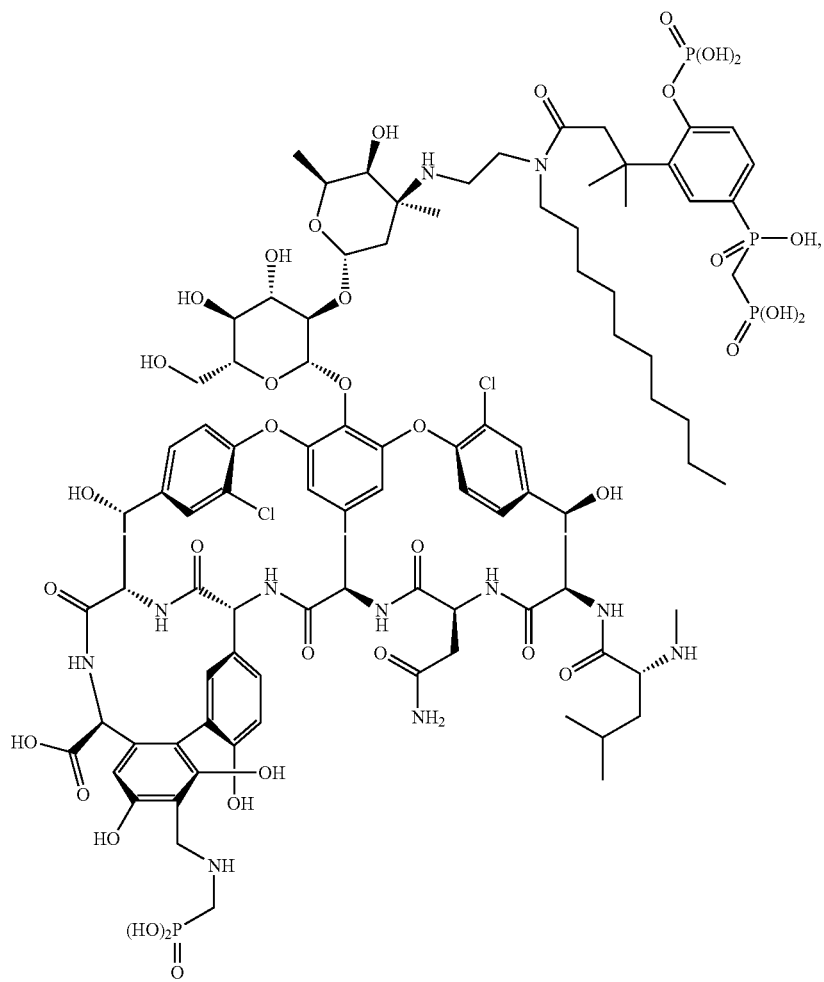

-continued
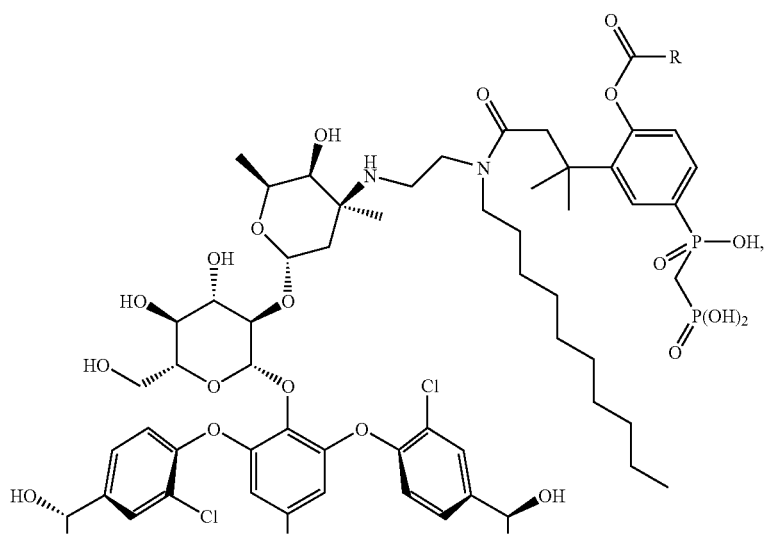
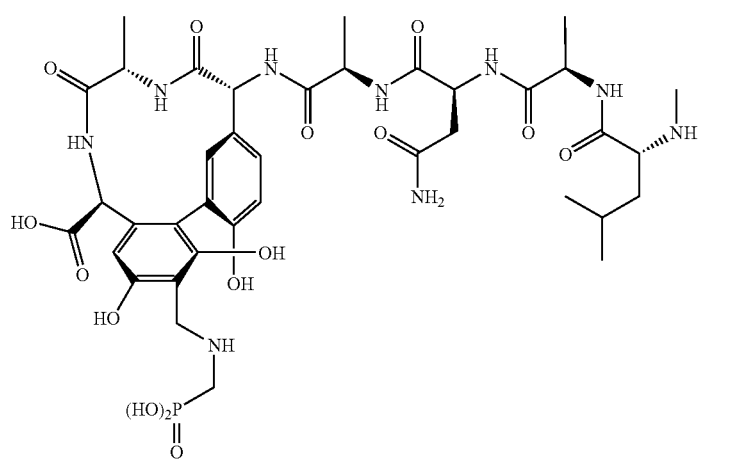
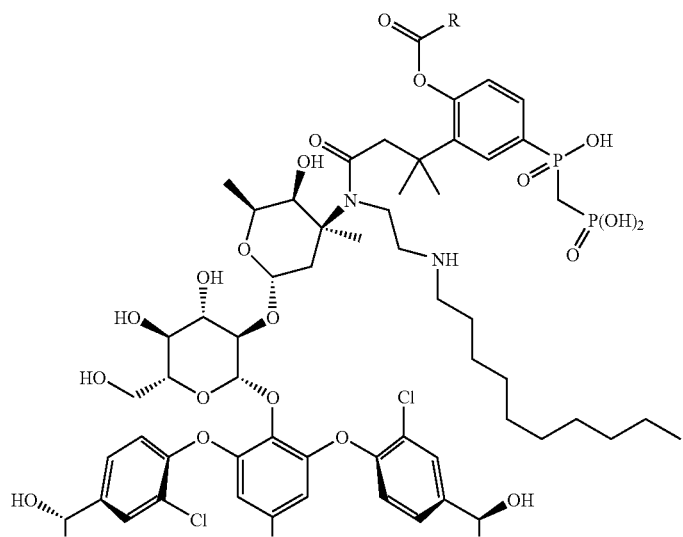

237
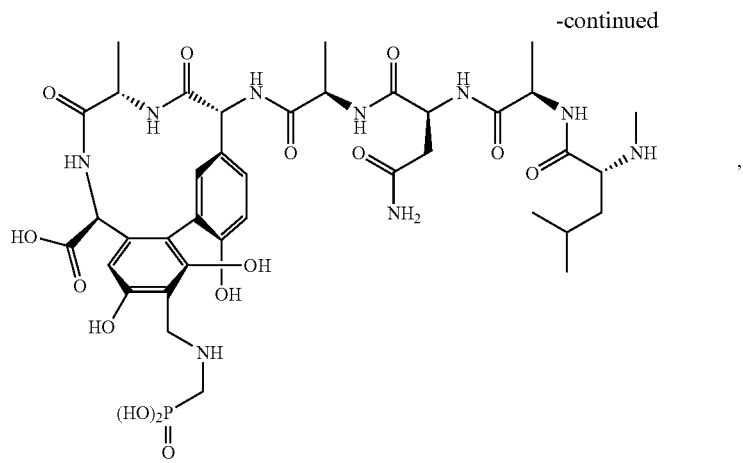
-continued
238
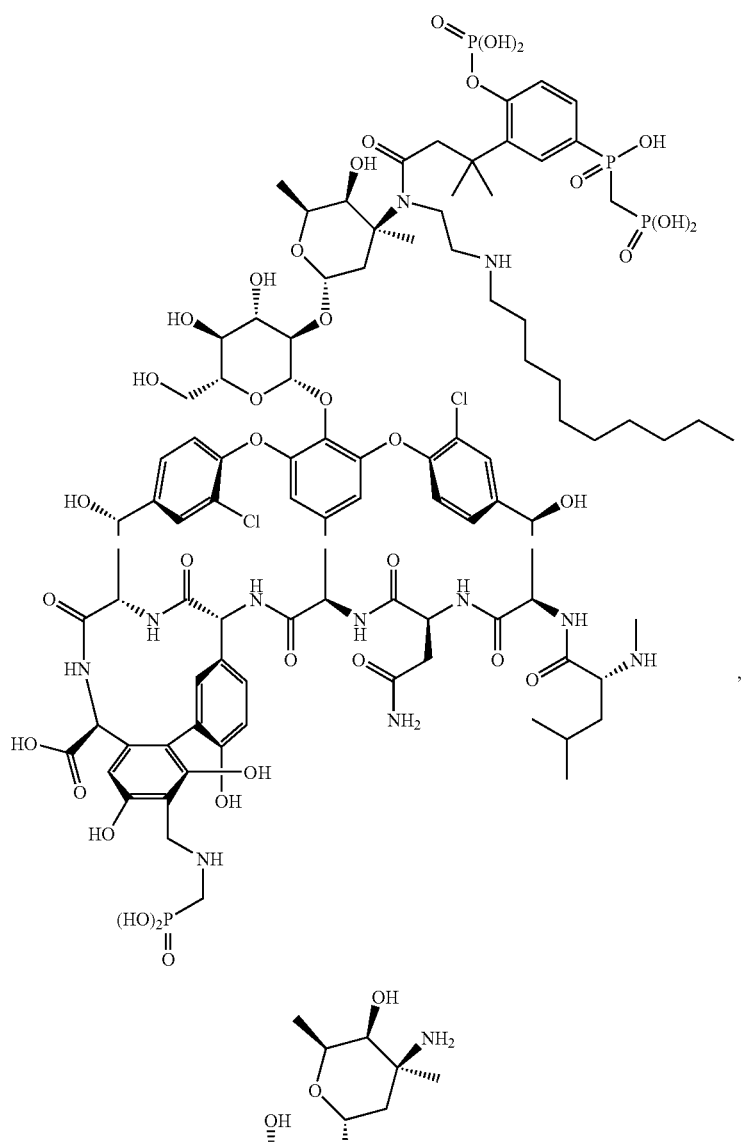

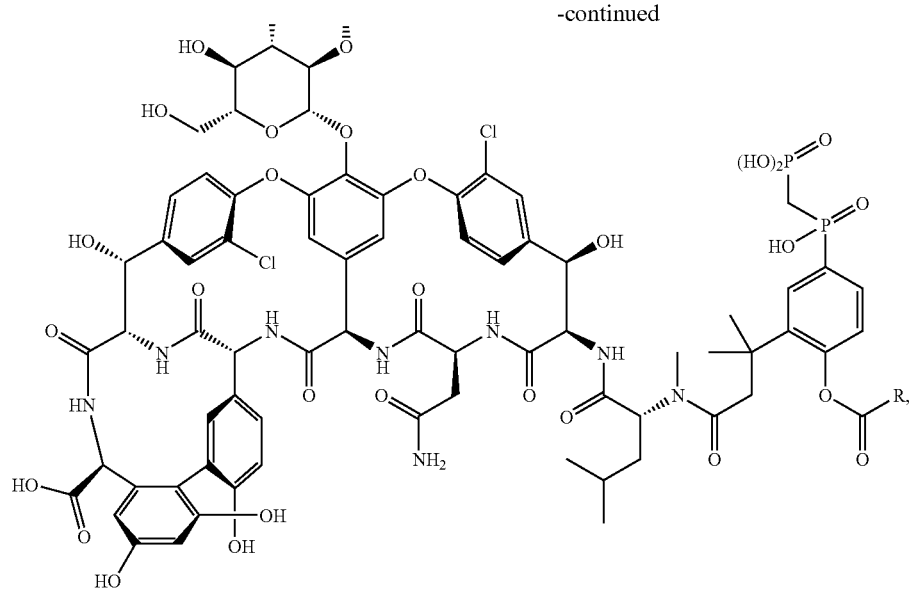
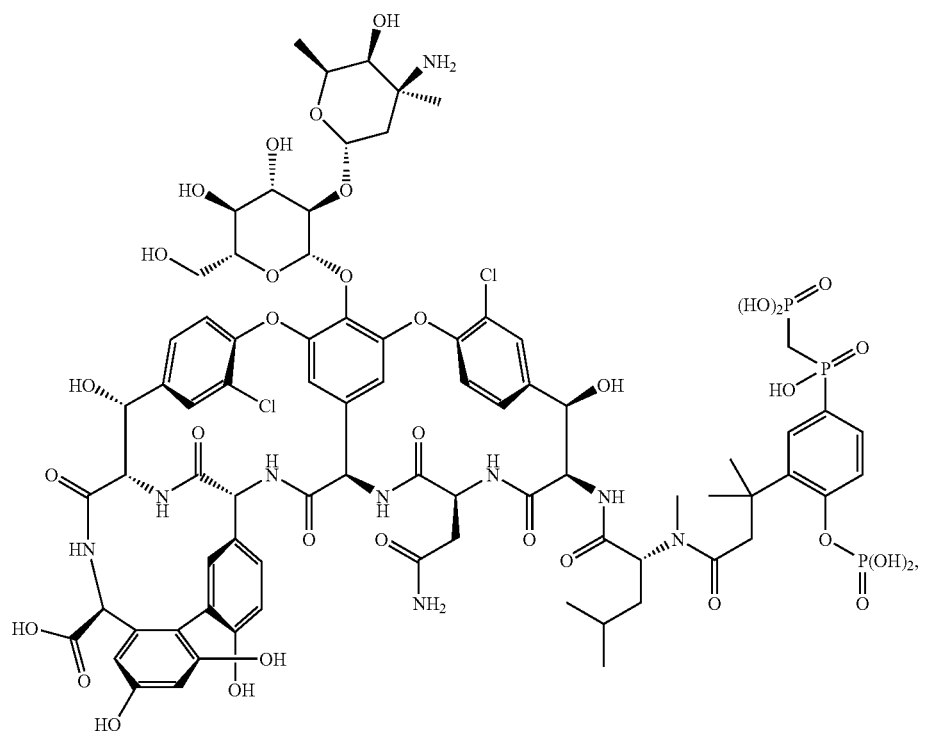

-continued
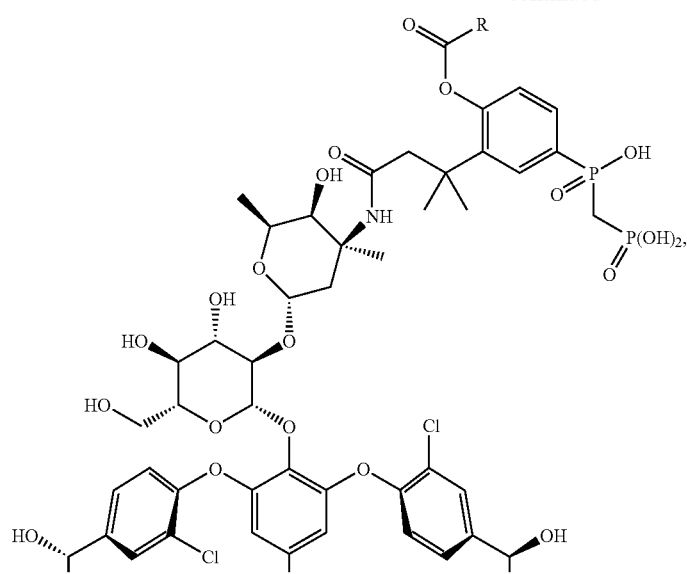
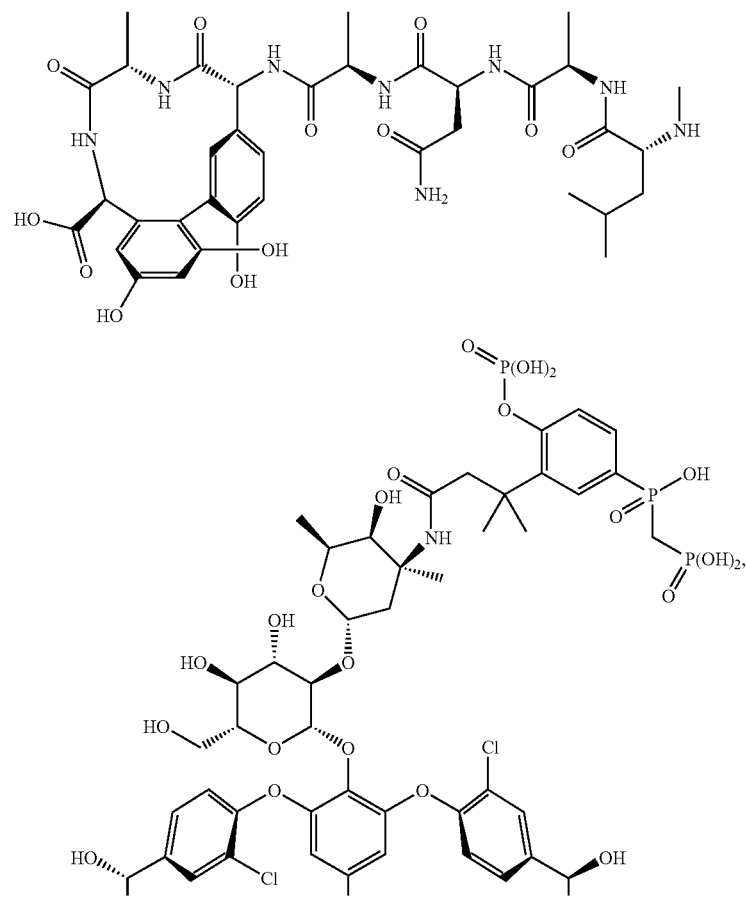

243
-continued
244
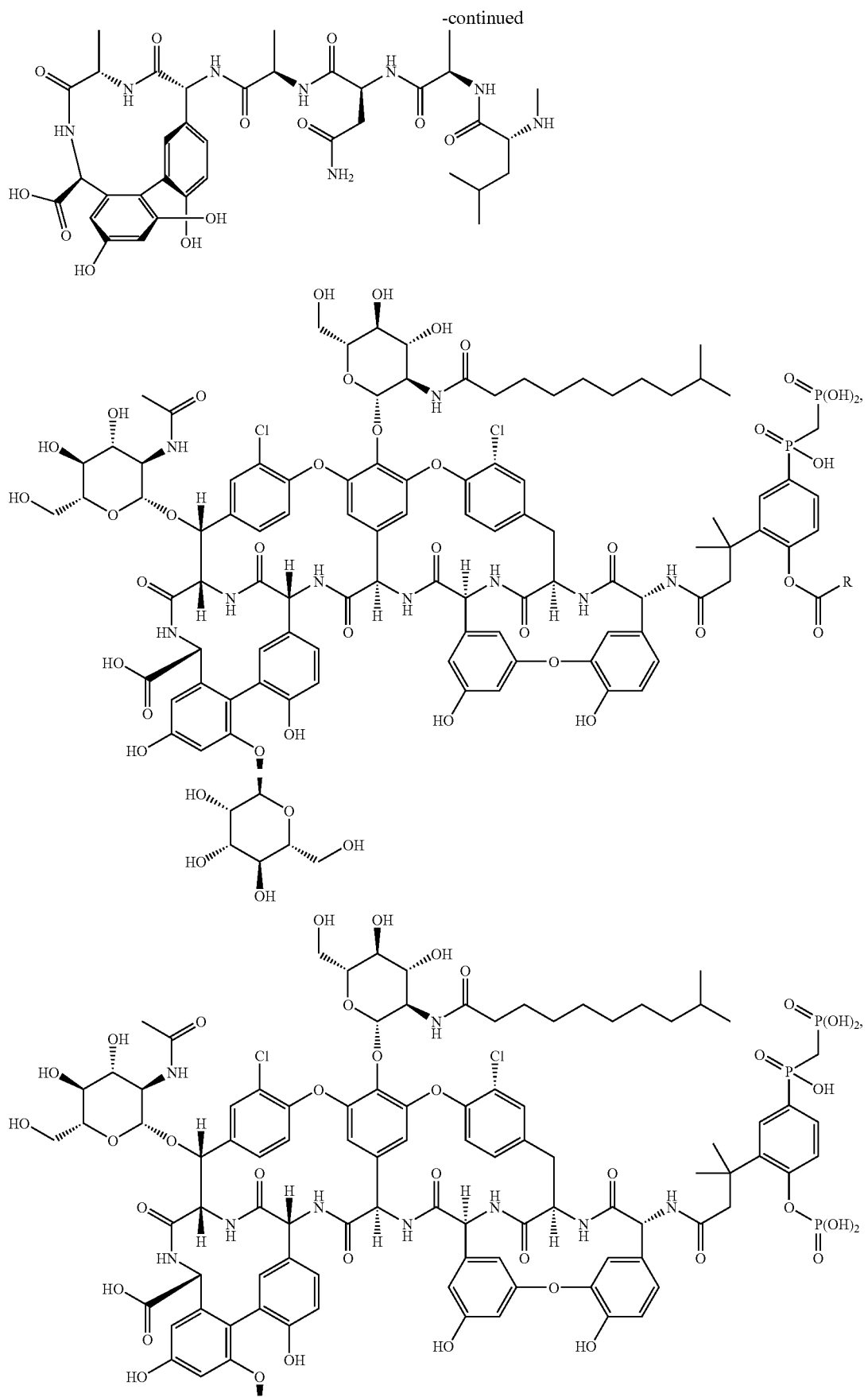

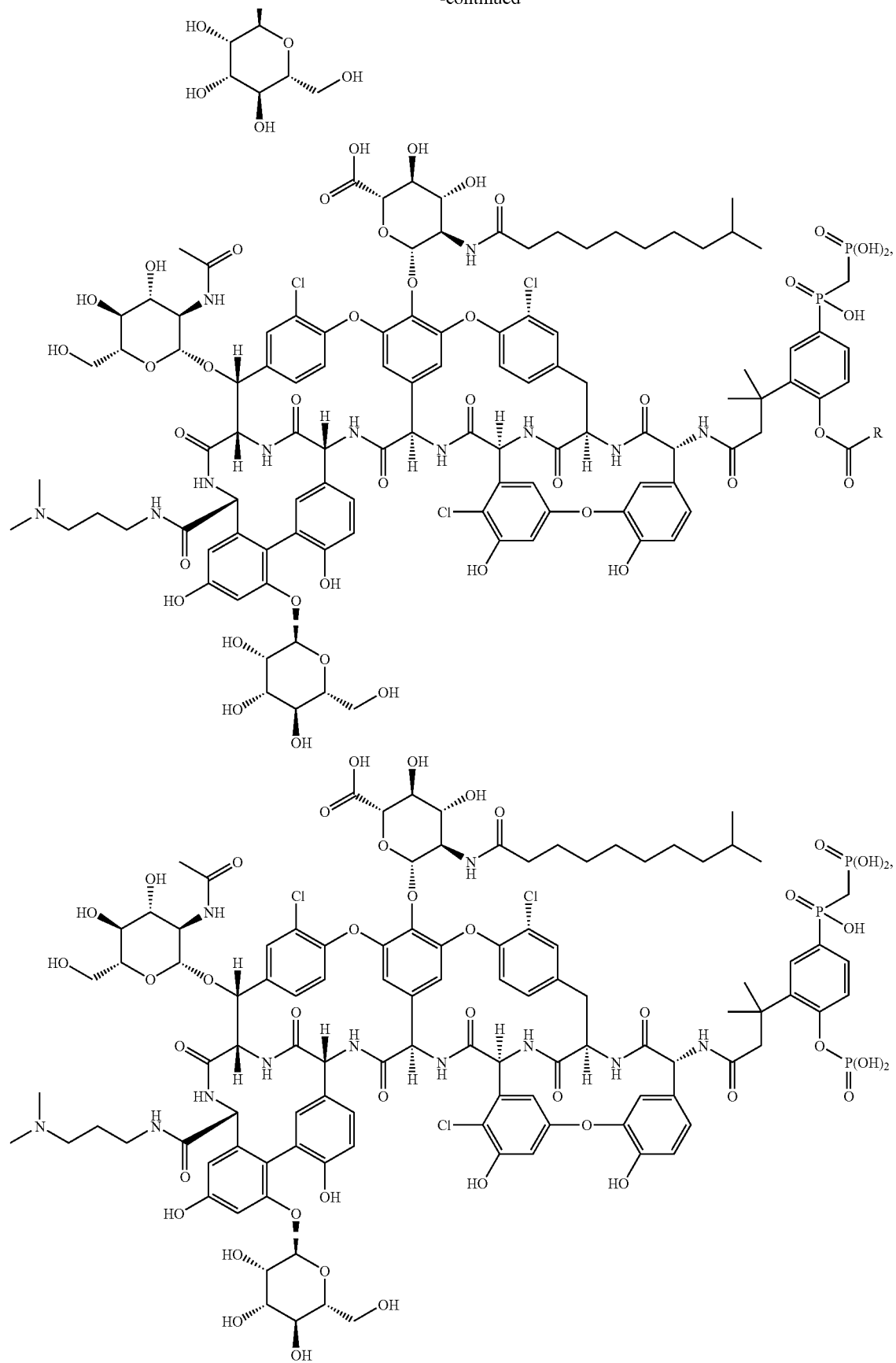

-continued
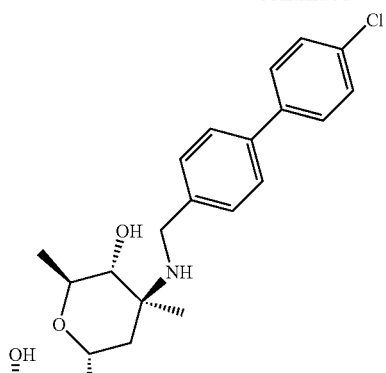
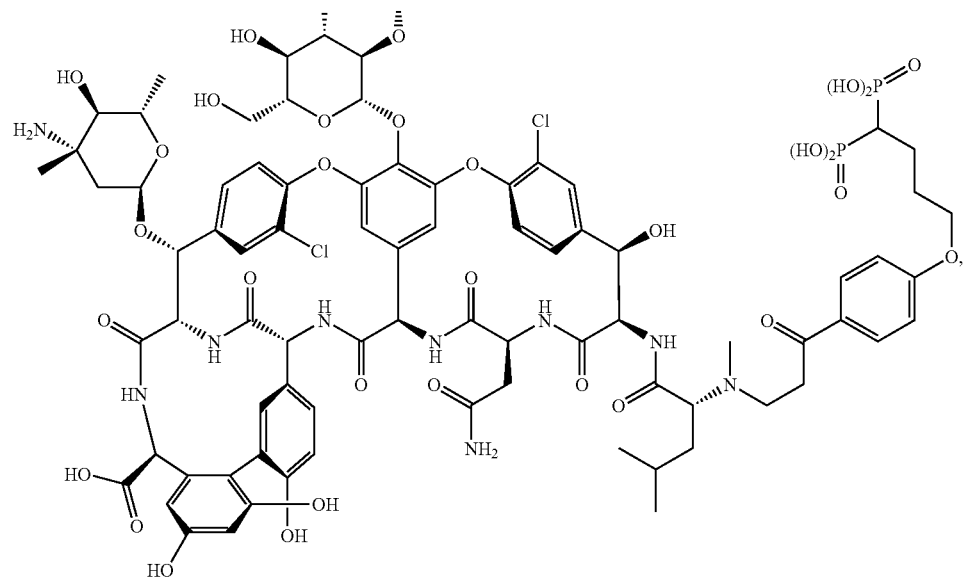
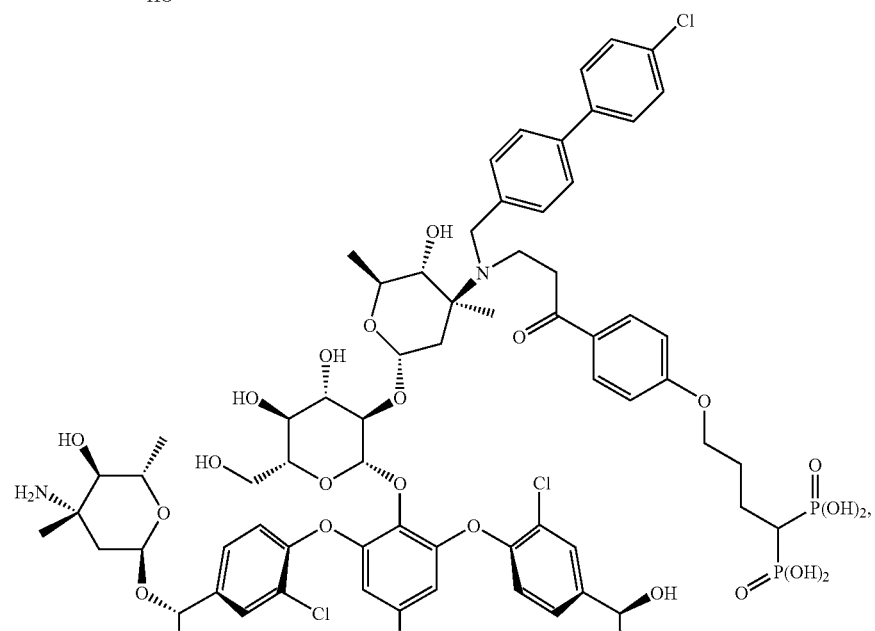

249
-continued
250
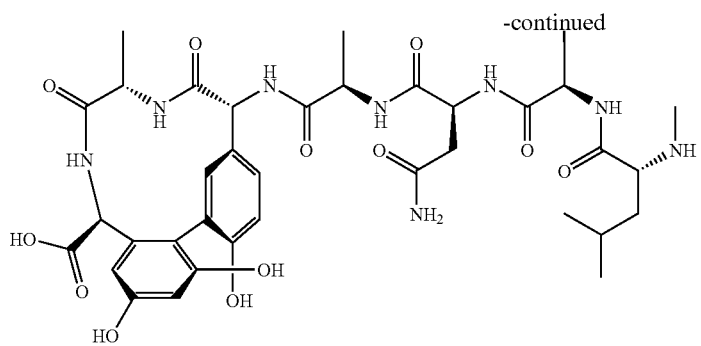
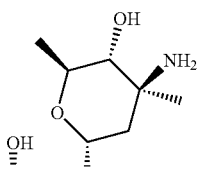
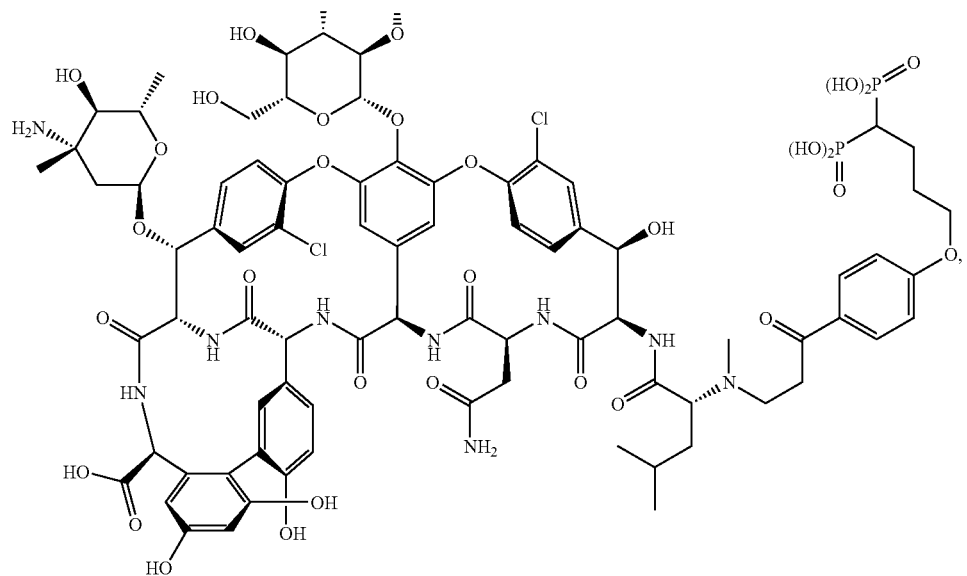
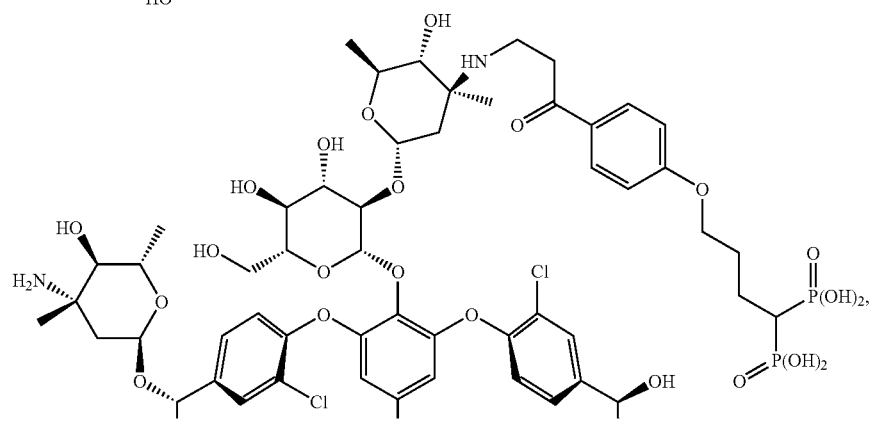

251
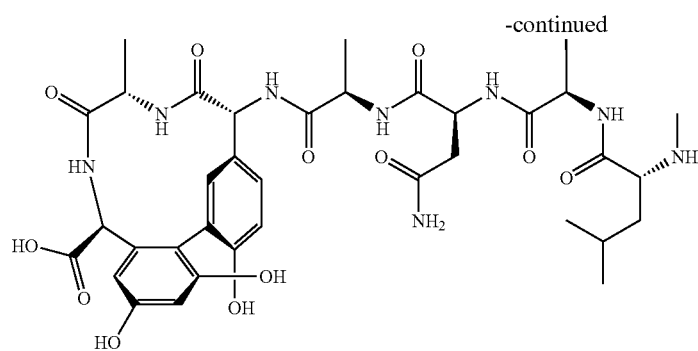
-continued
252
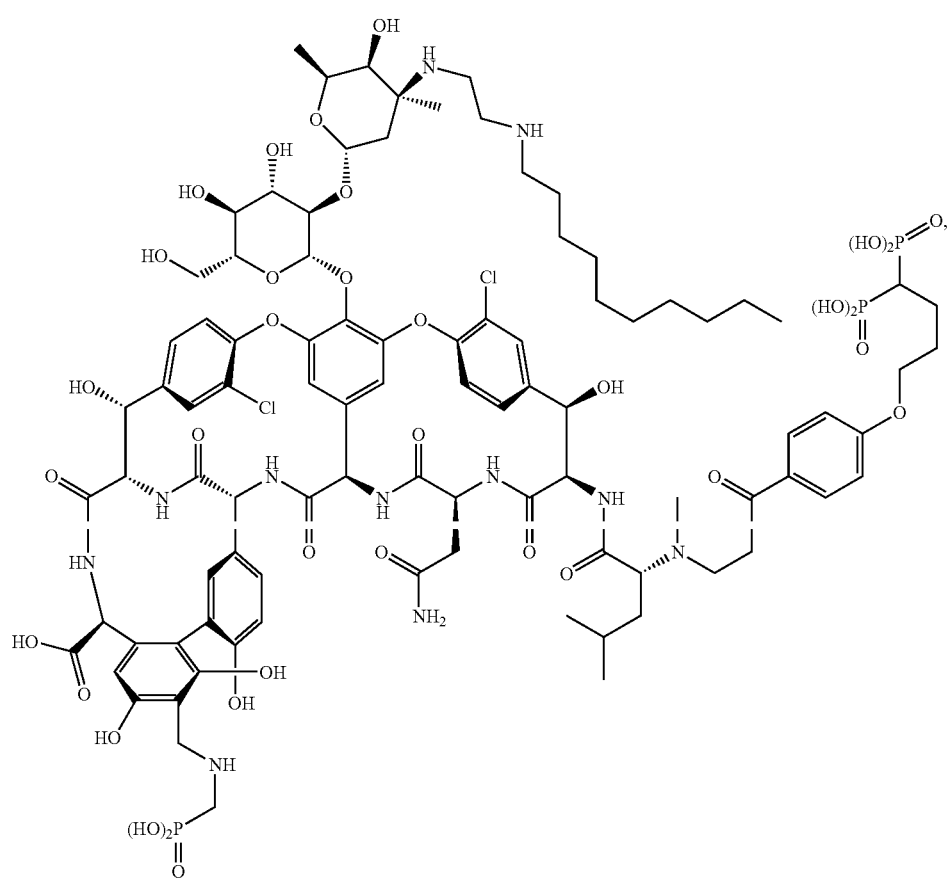

-continued
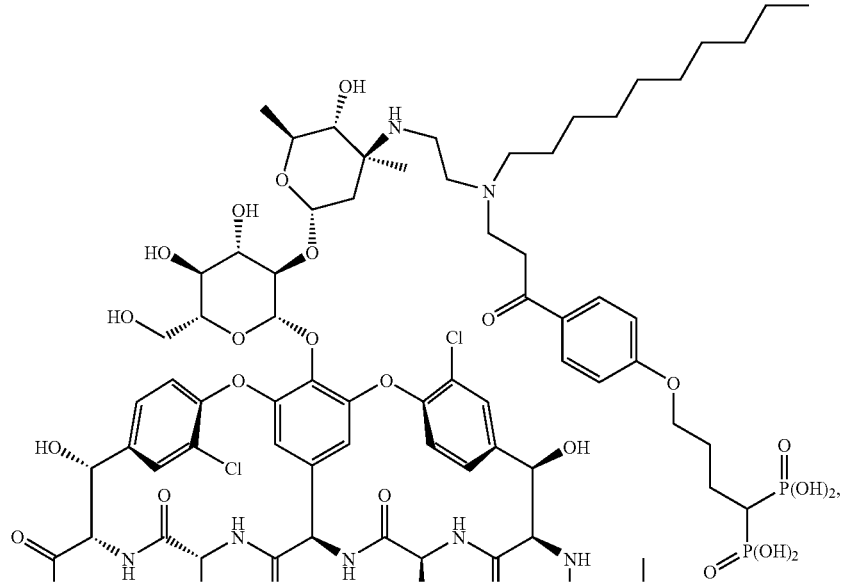
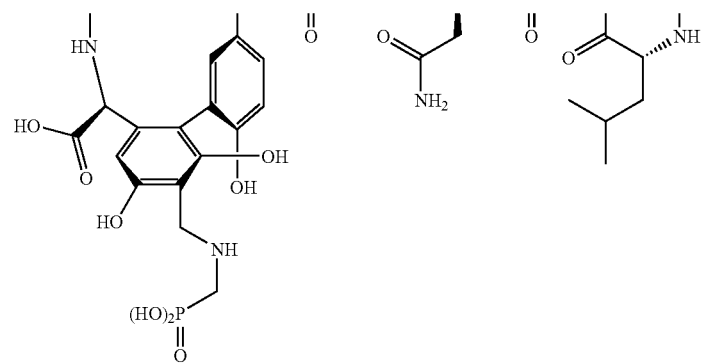
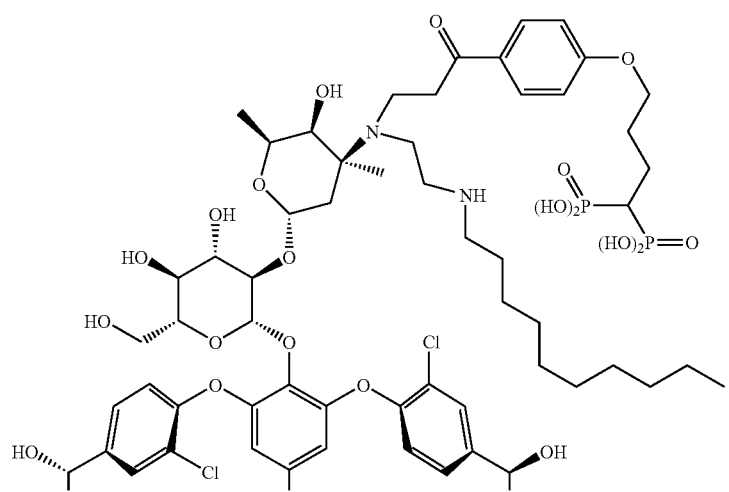

255
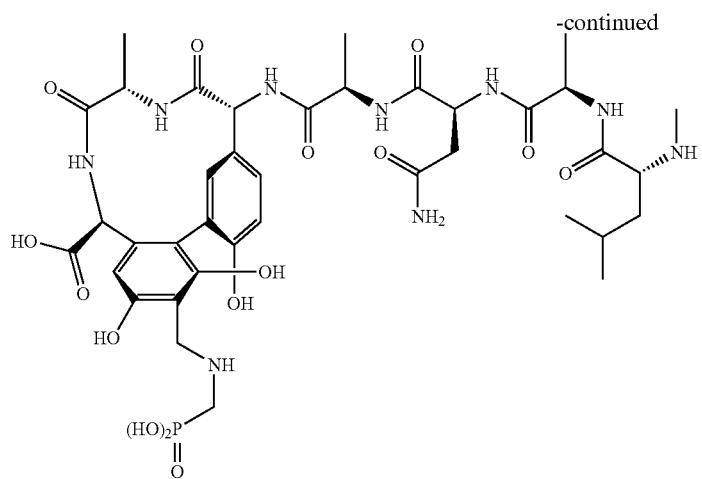
-continued
256
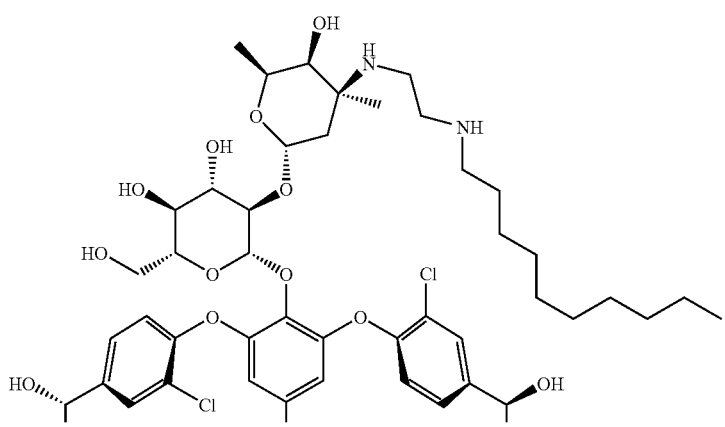
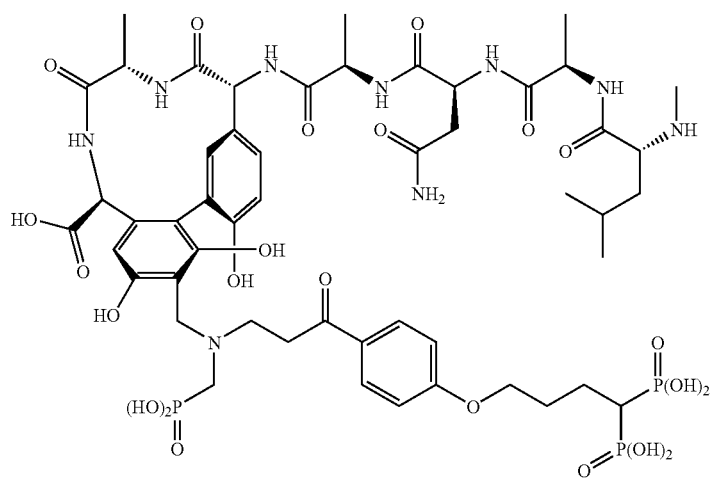
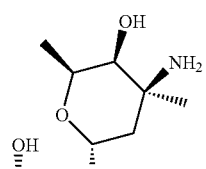

257
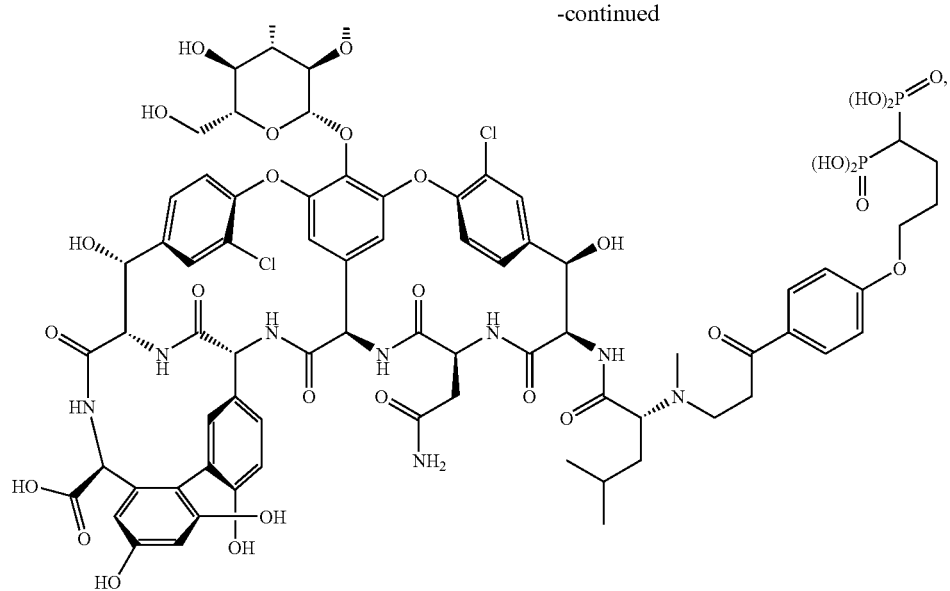
258
-continued
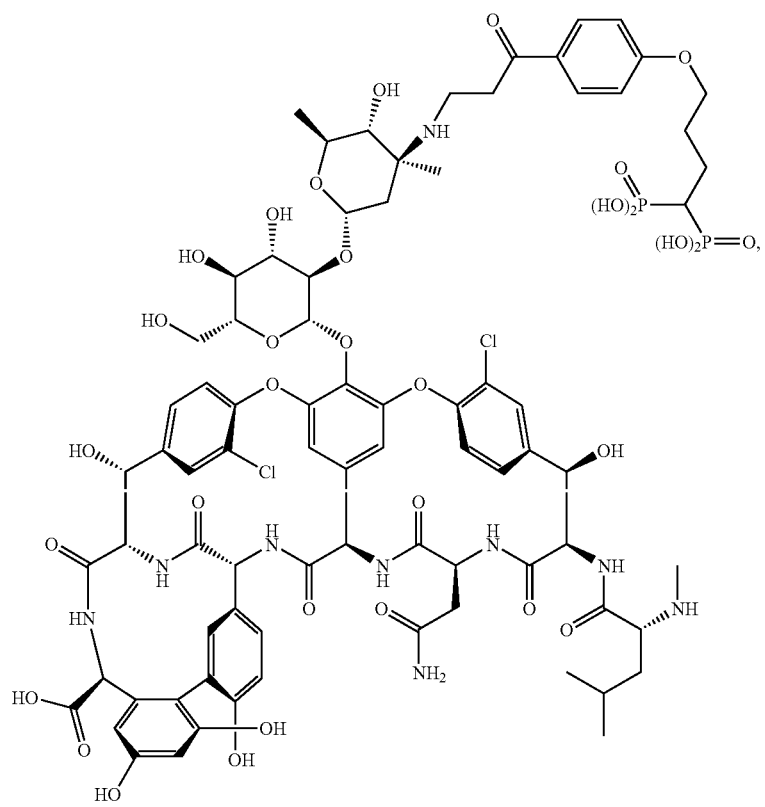

-continued
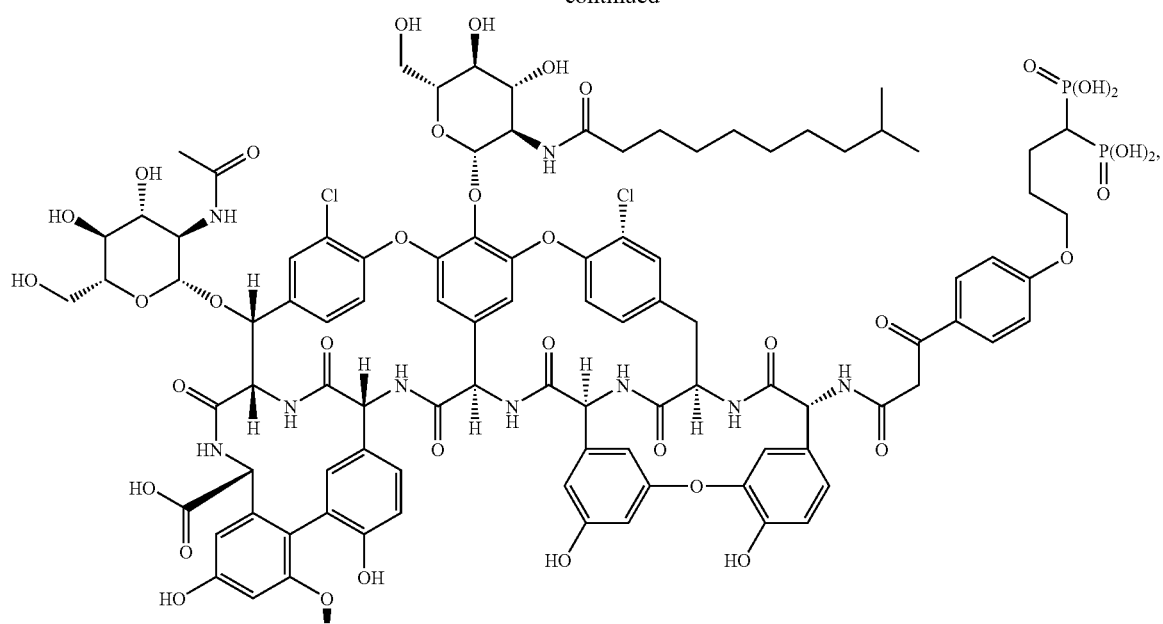
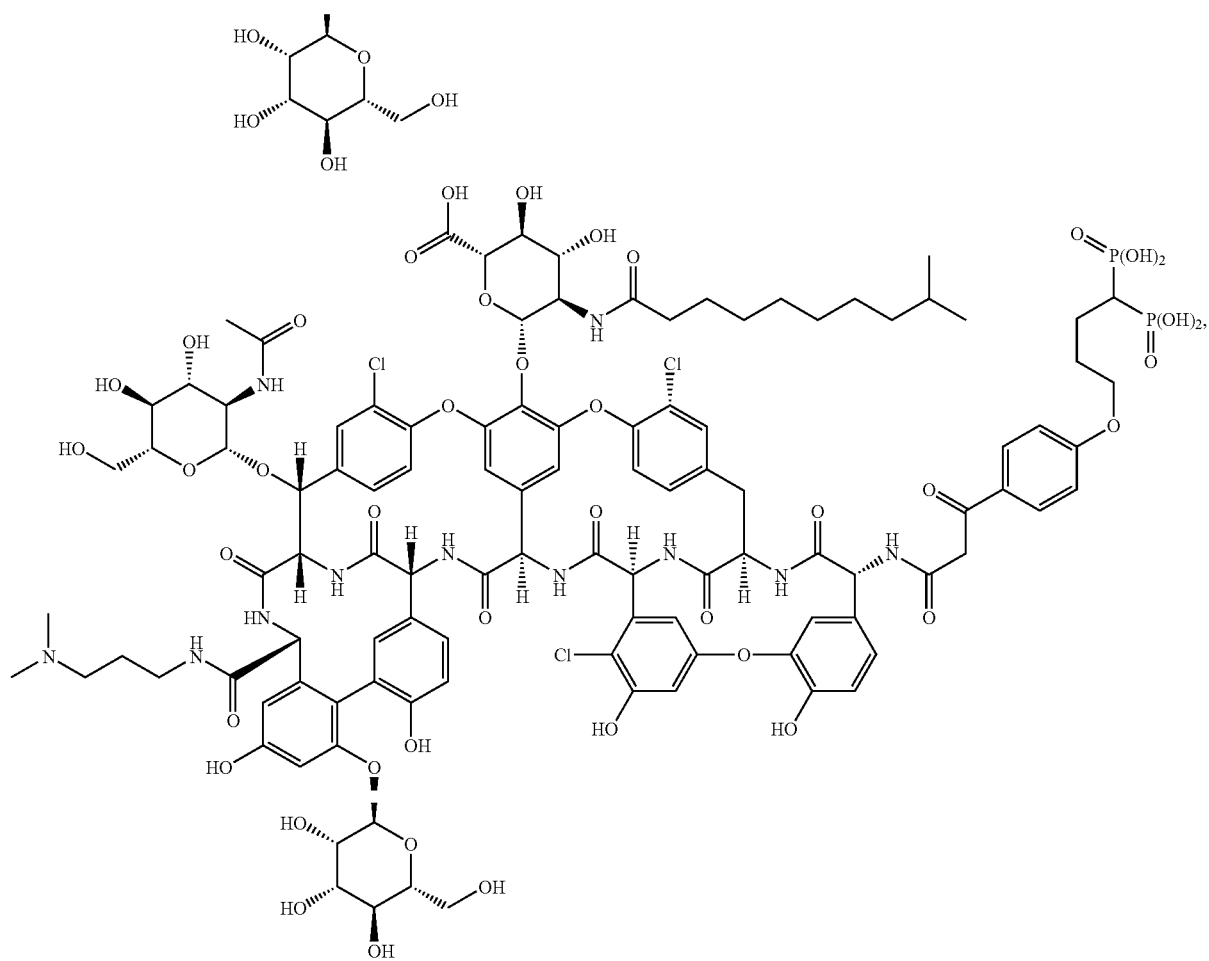

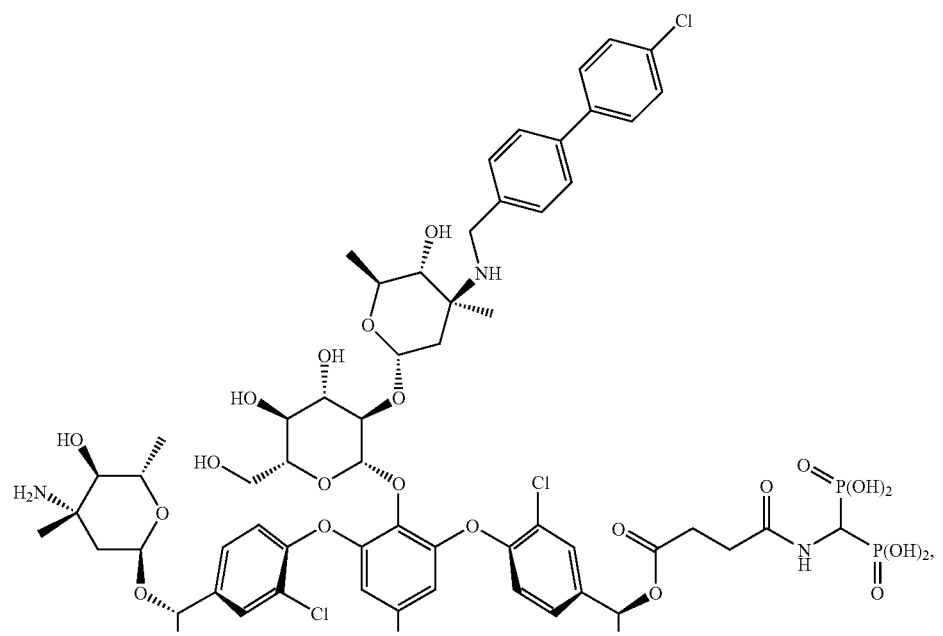
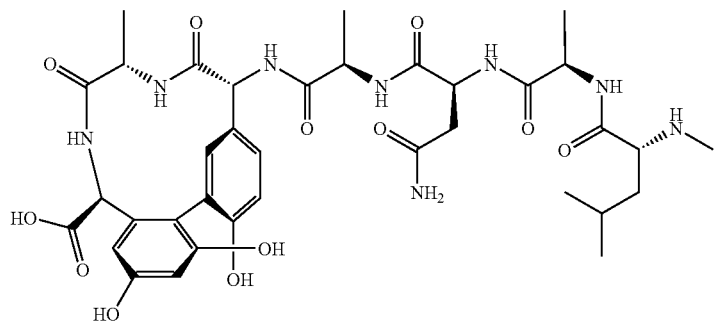
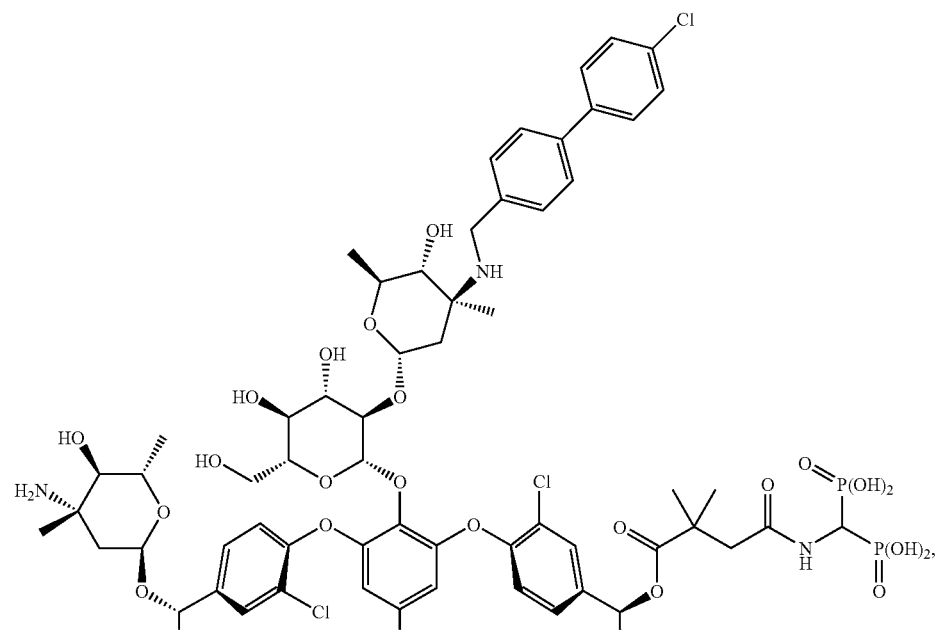

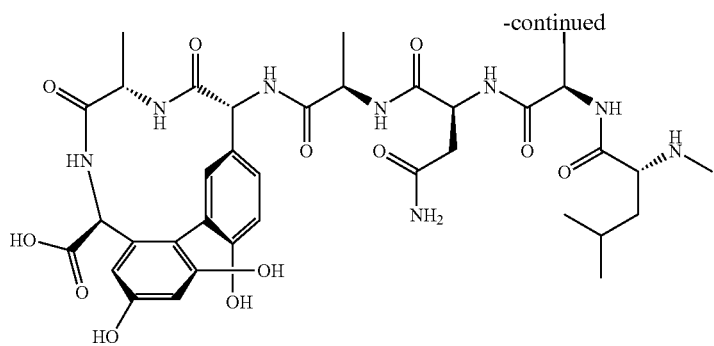
-continued
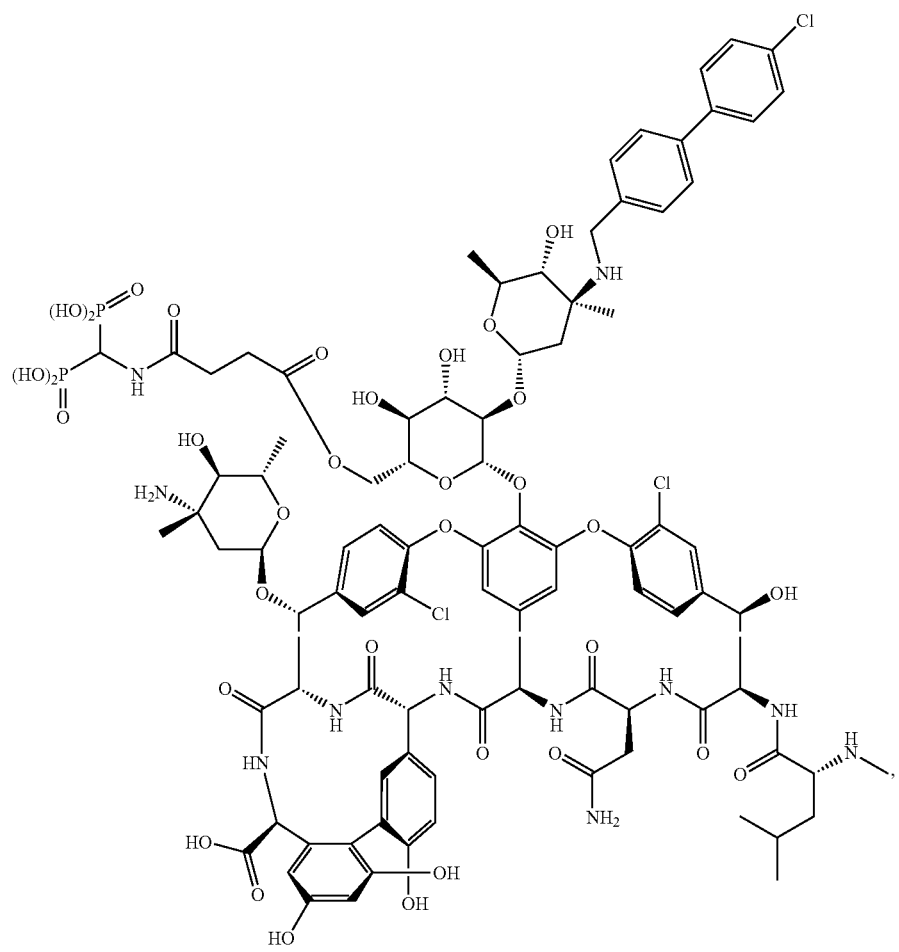

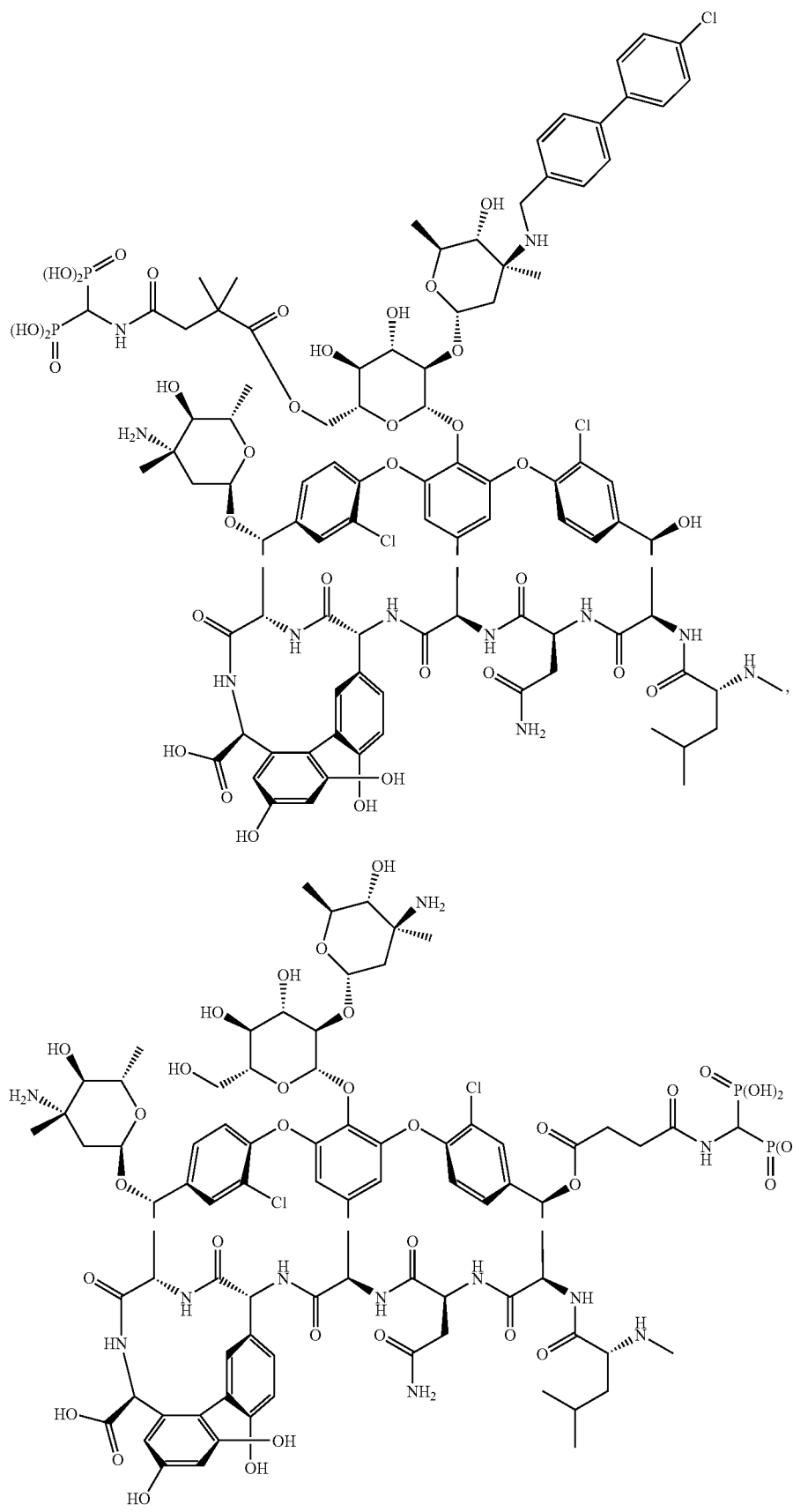

-continued
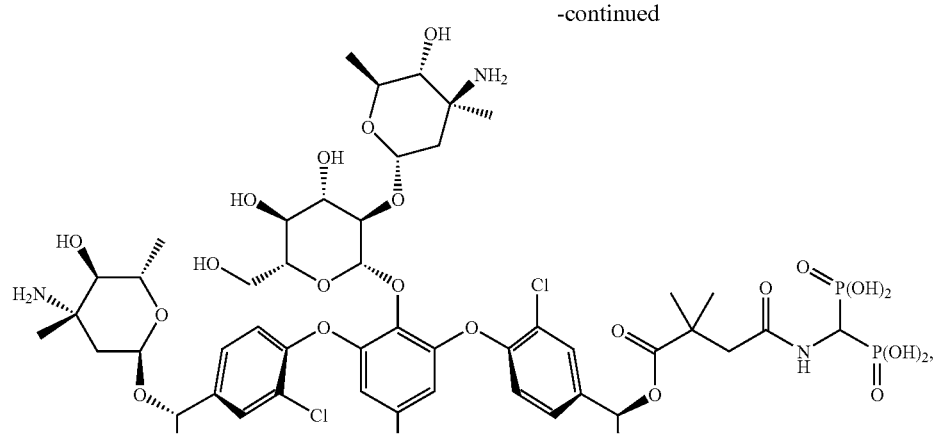
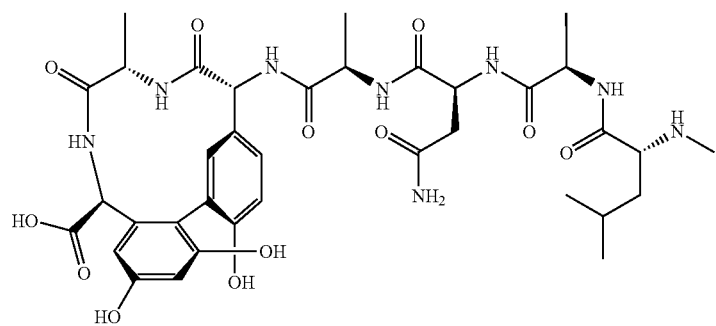
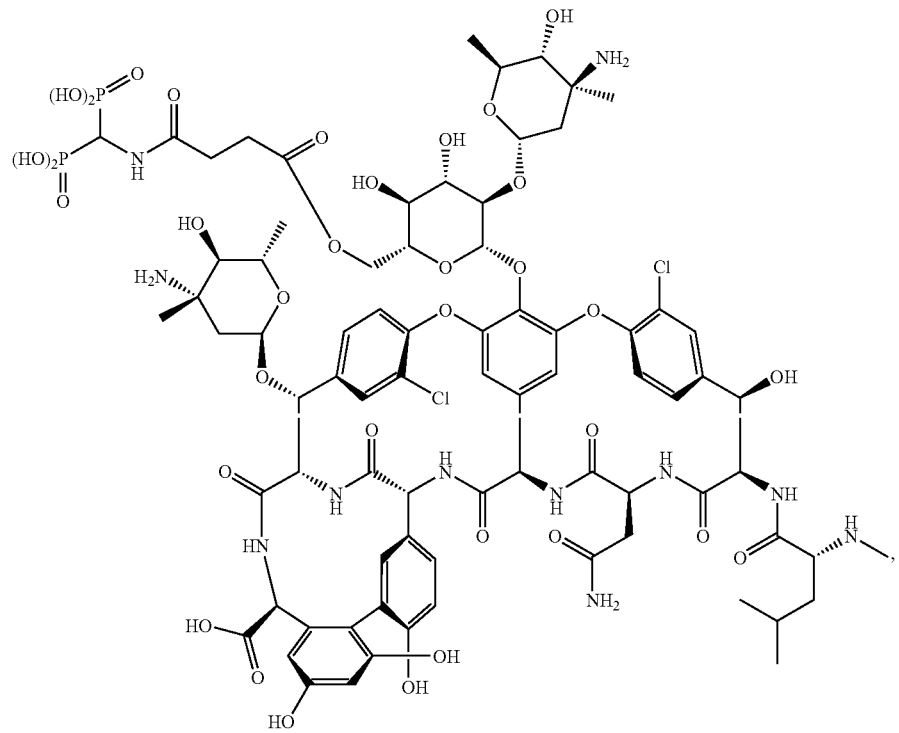

-continued
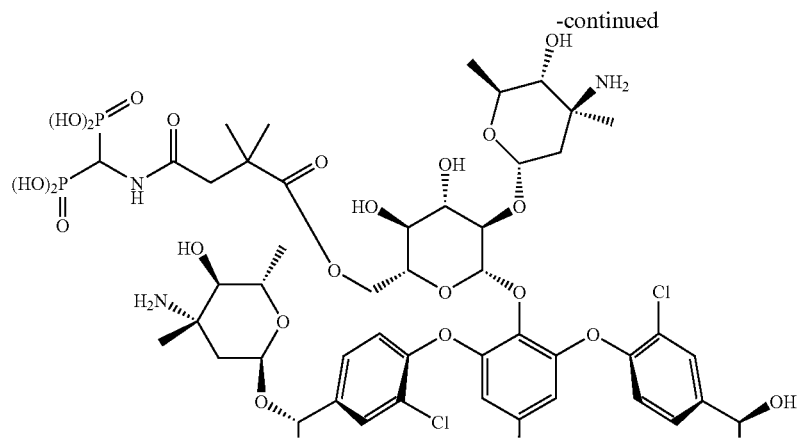
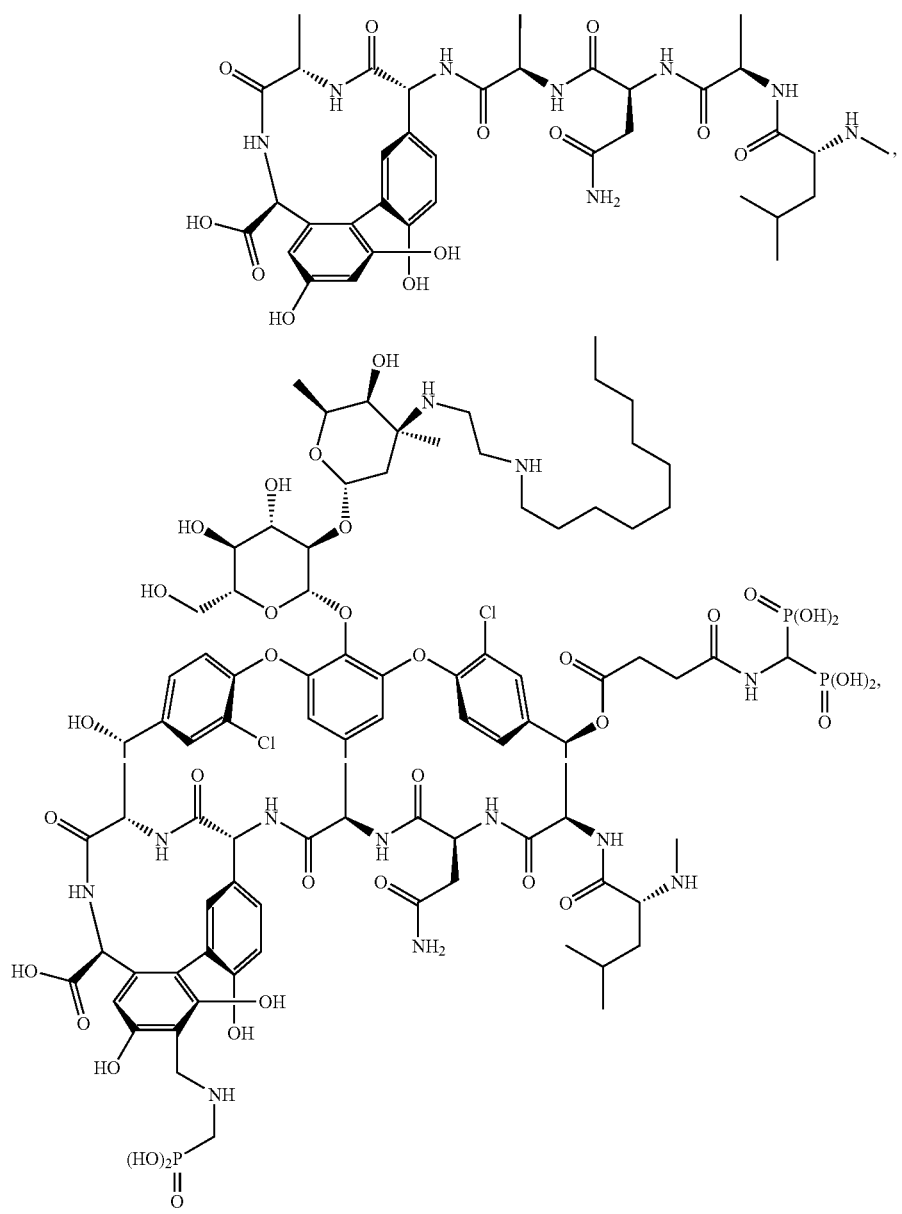

-continued
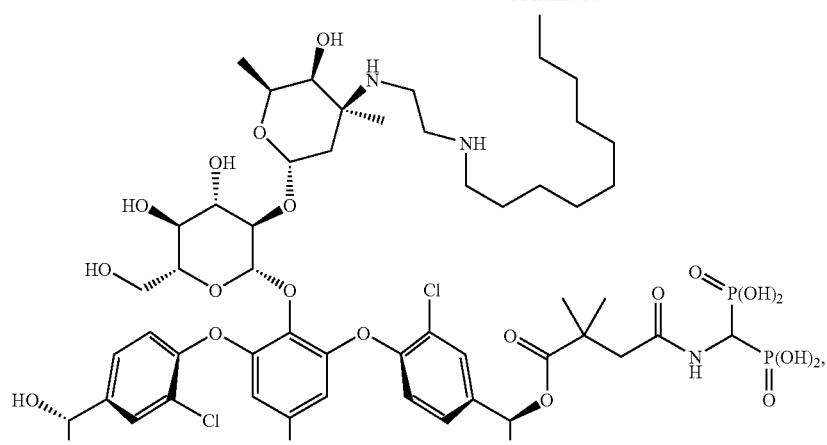
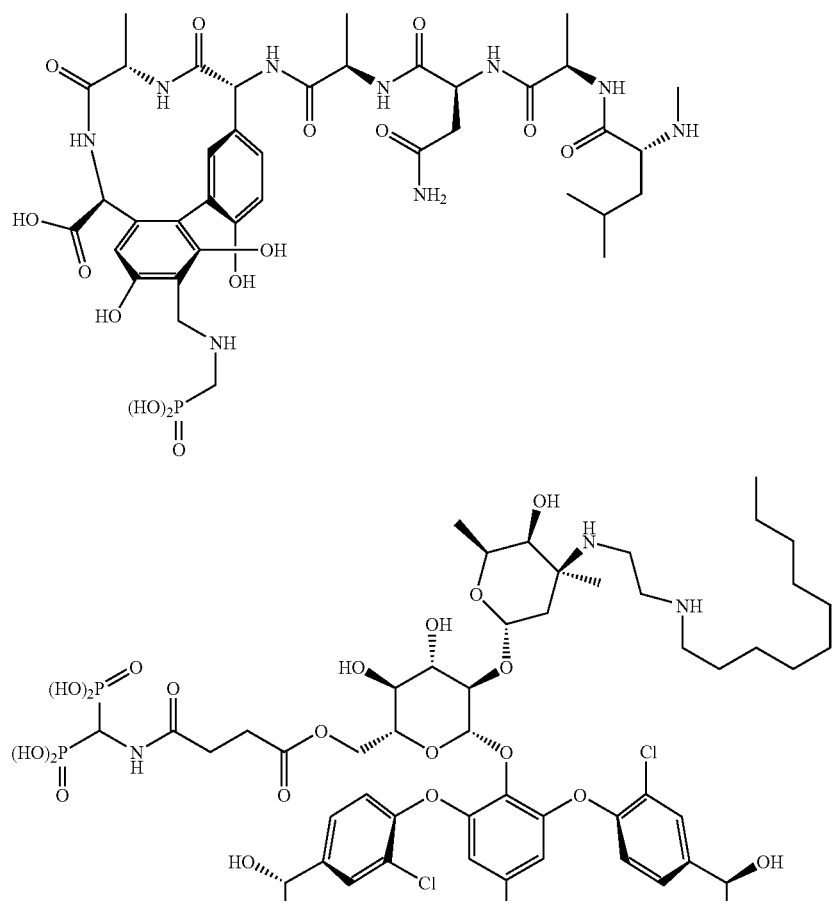

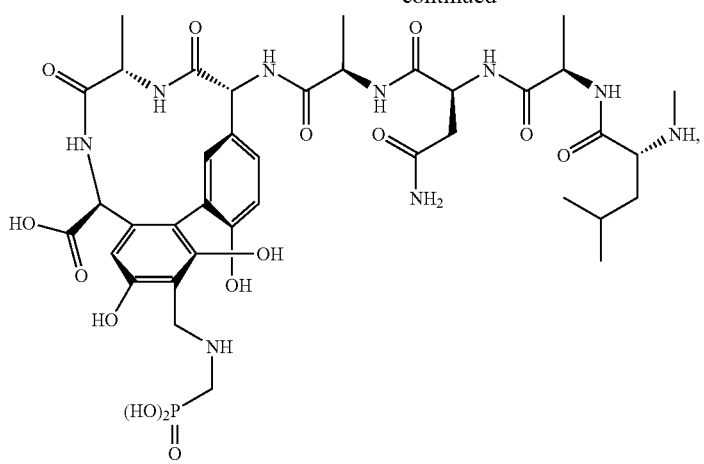
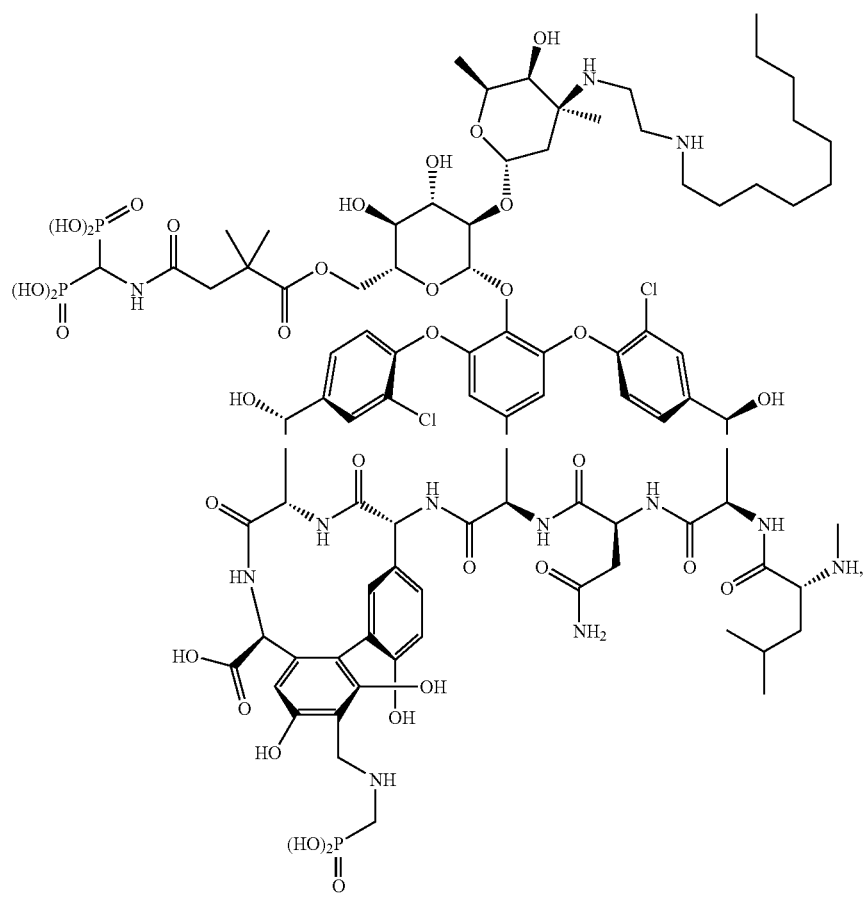

-continued
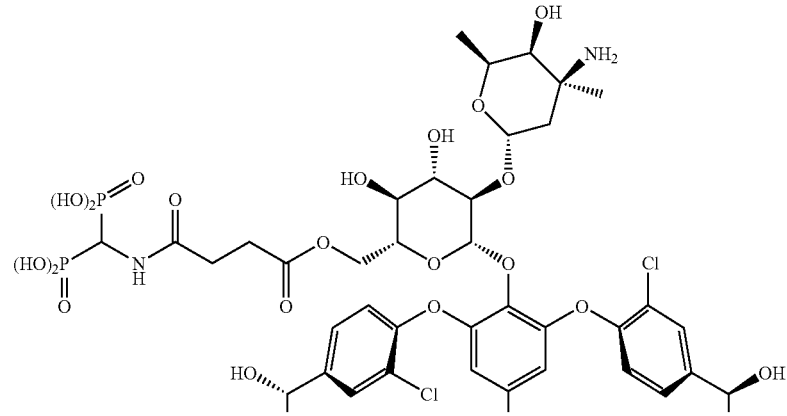
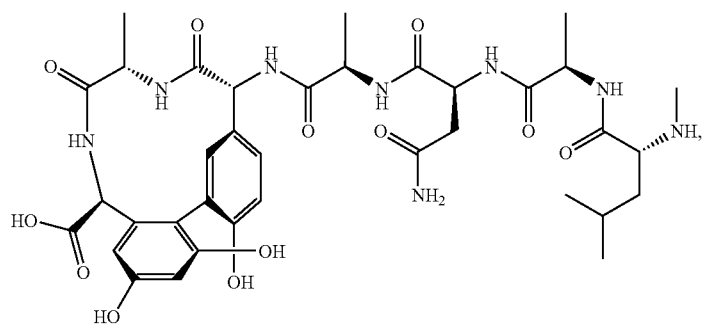

-continued
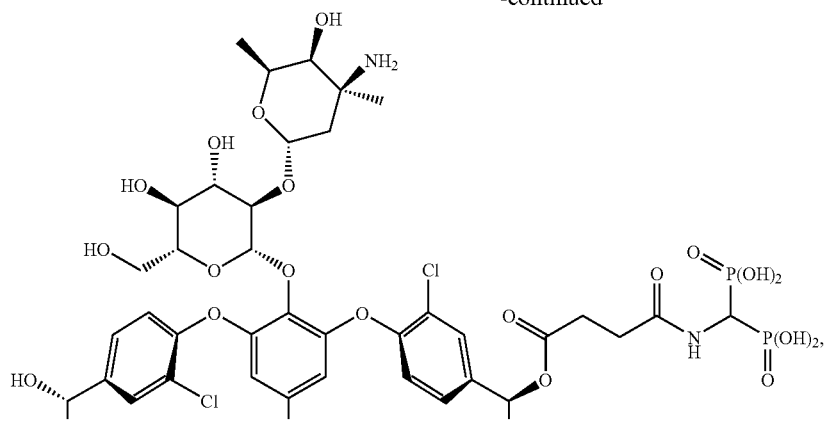
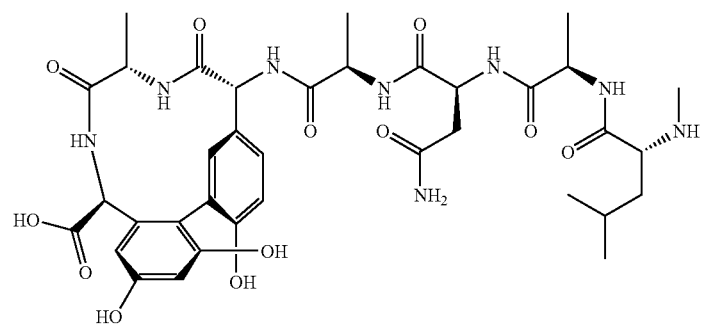
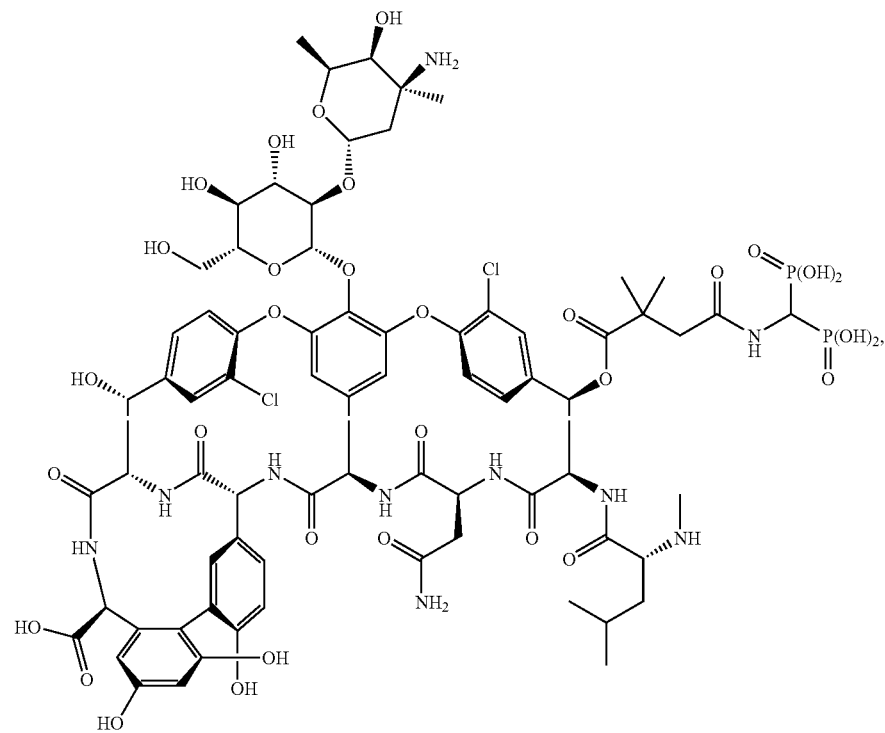

-continued
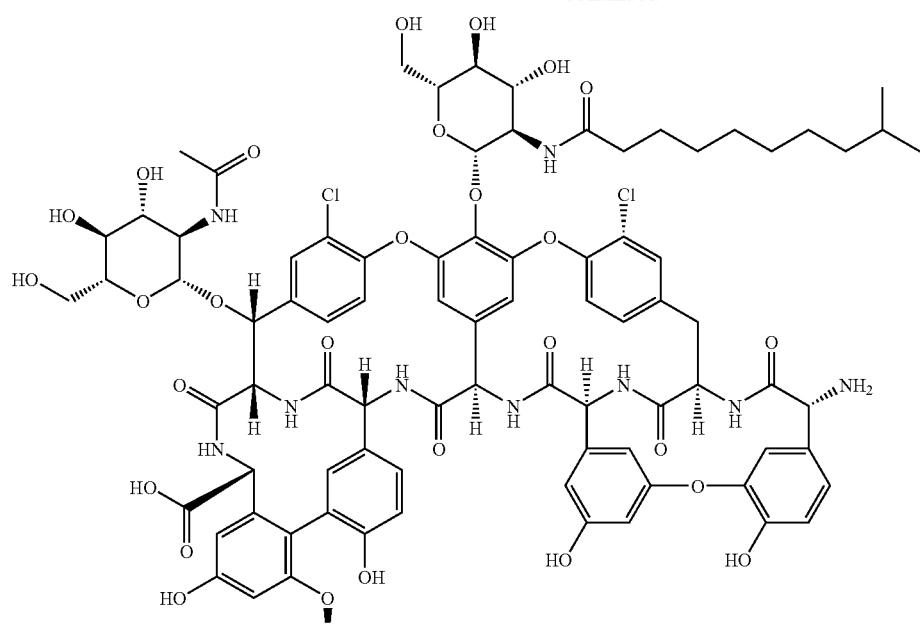
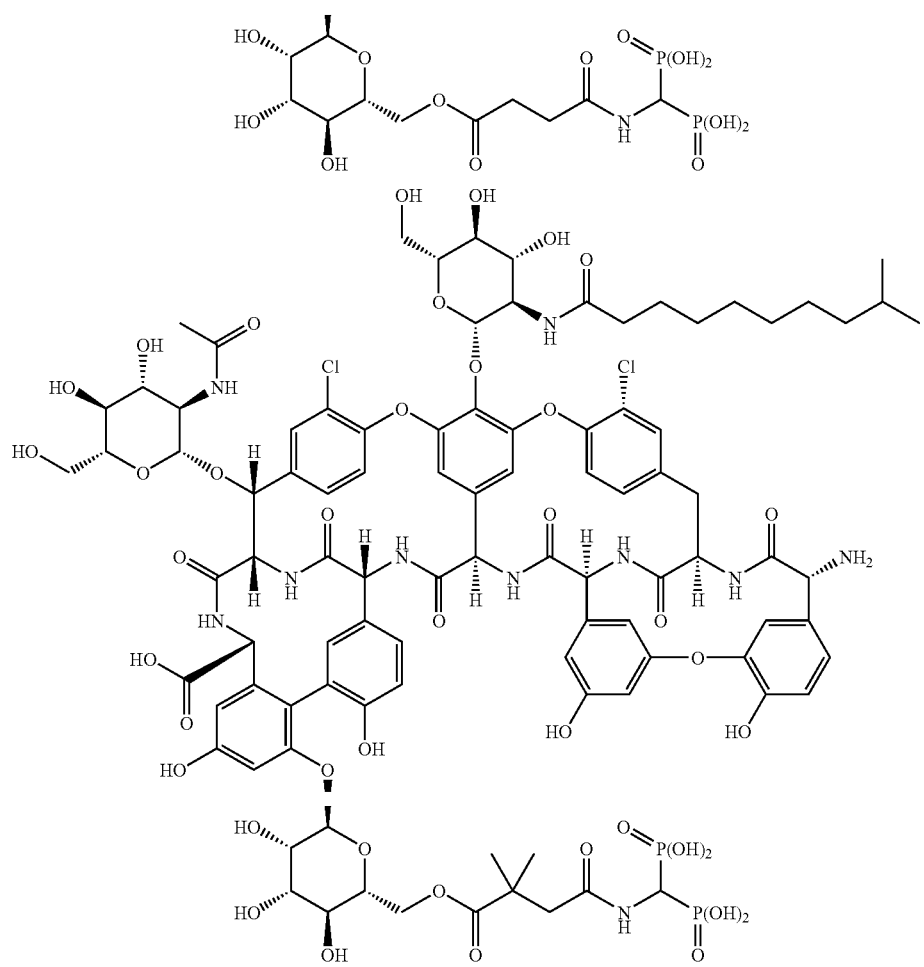

-continued
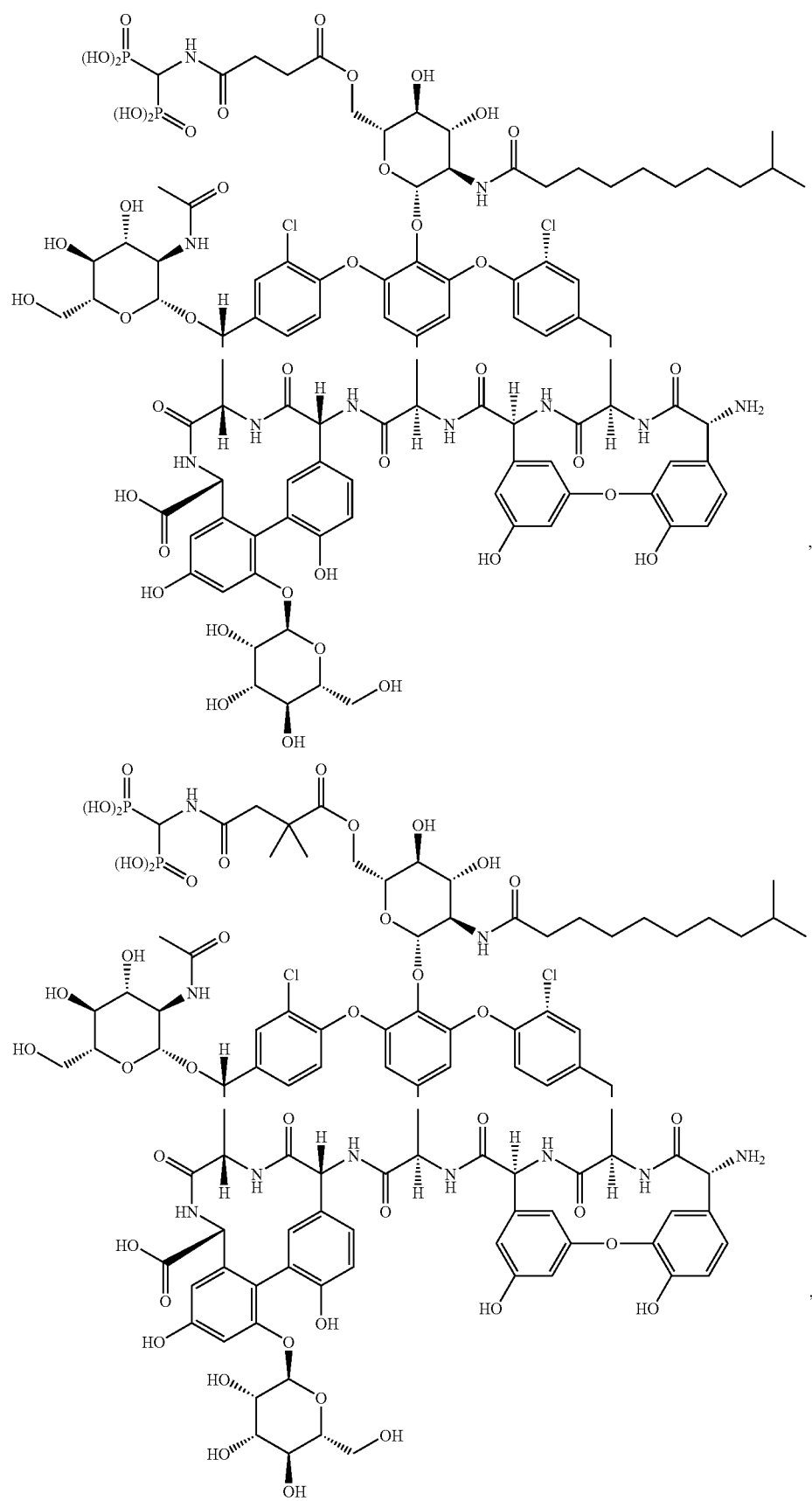

283
284
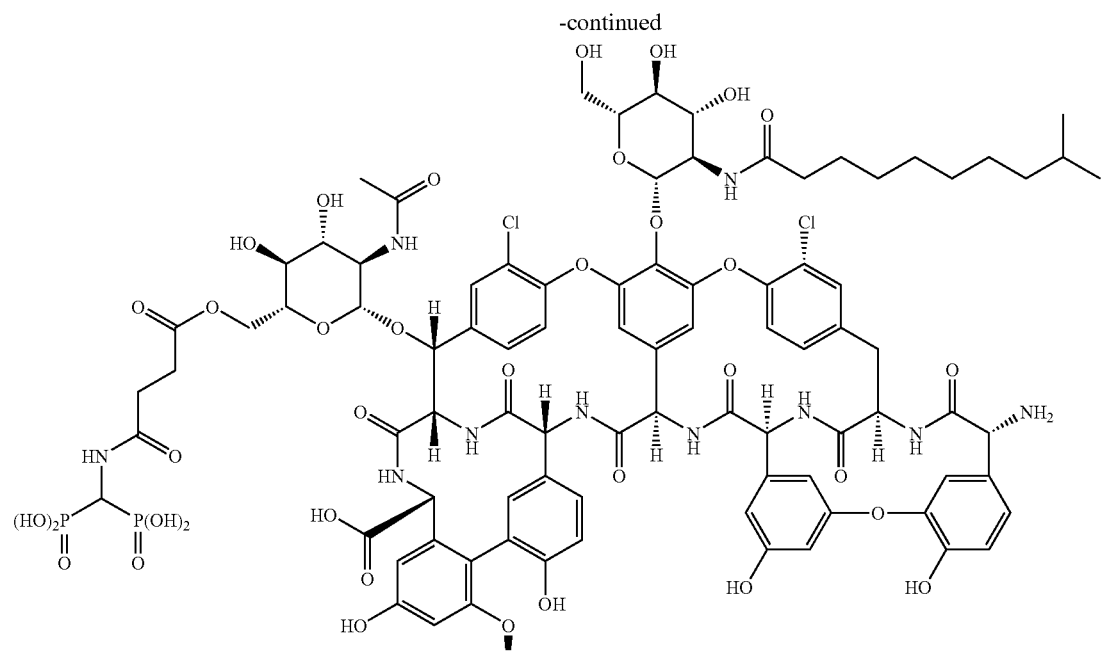
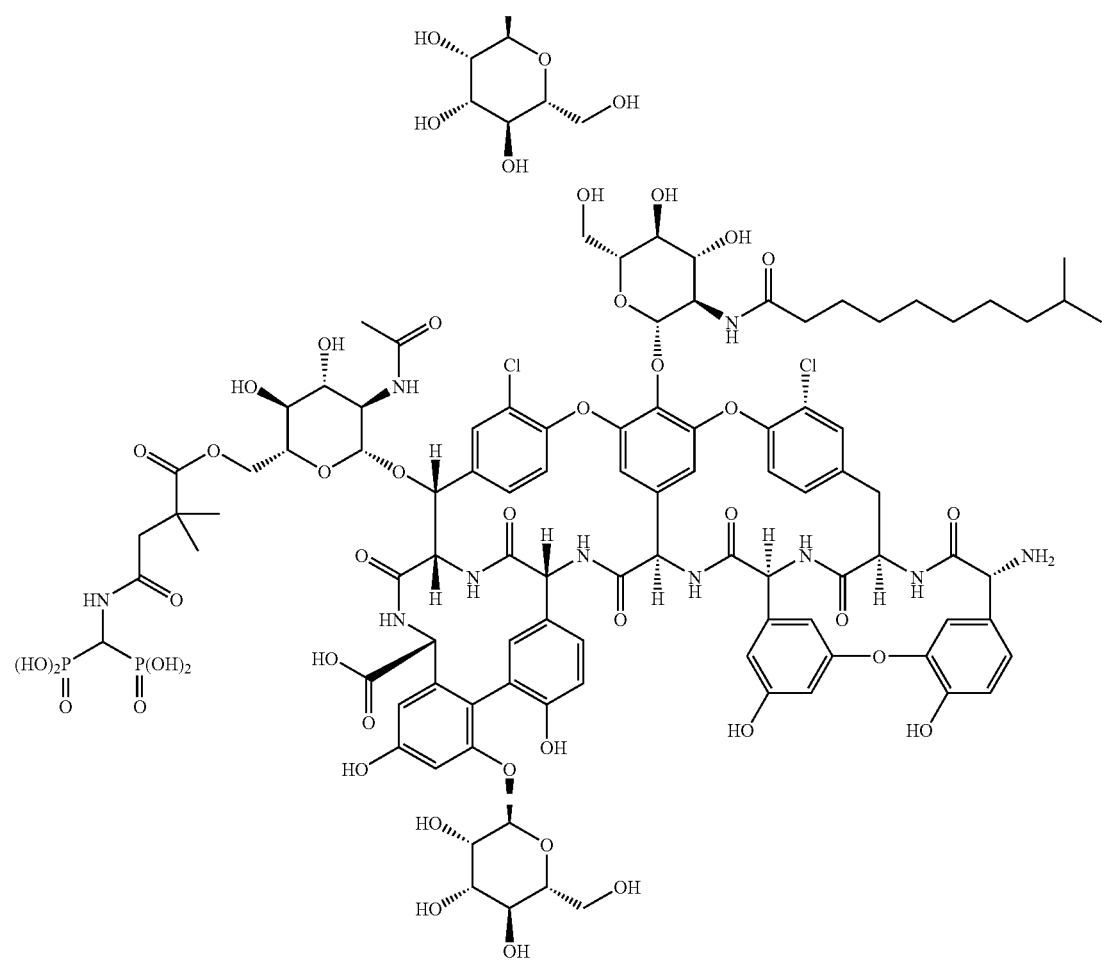

285
-continued
286
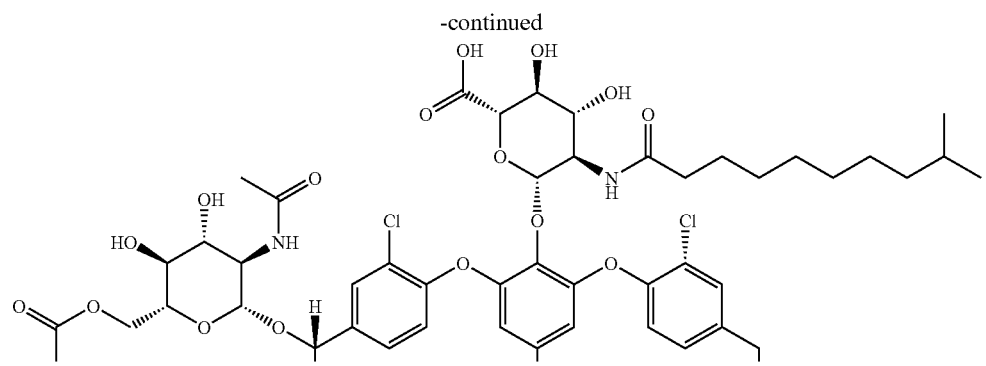
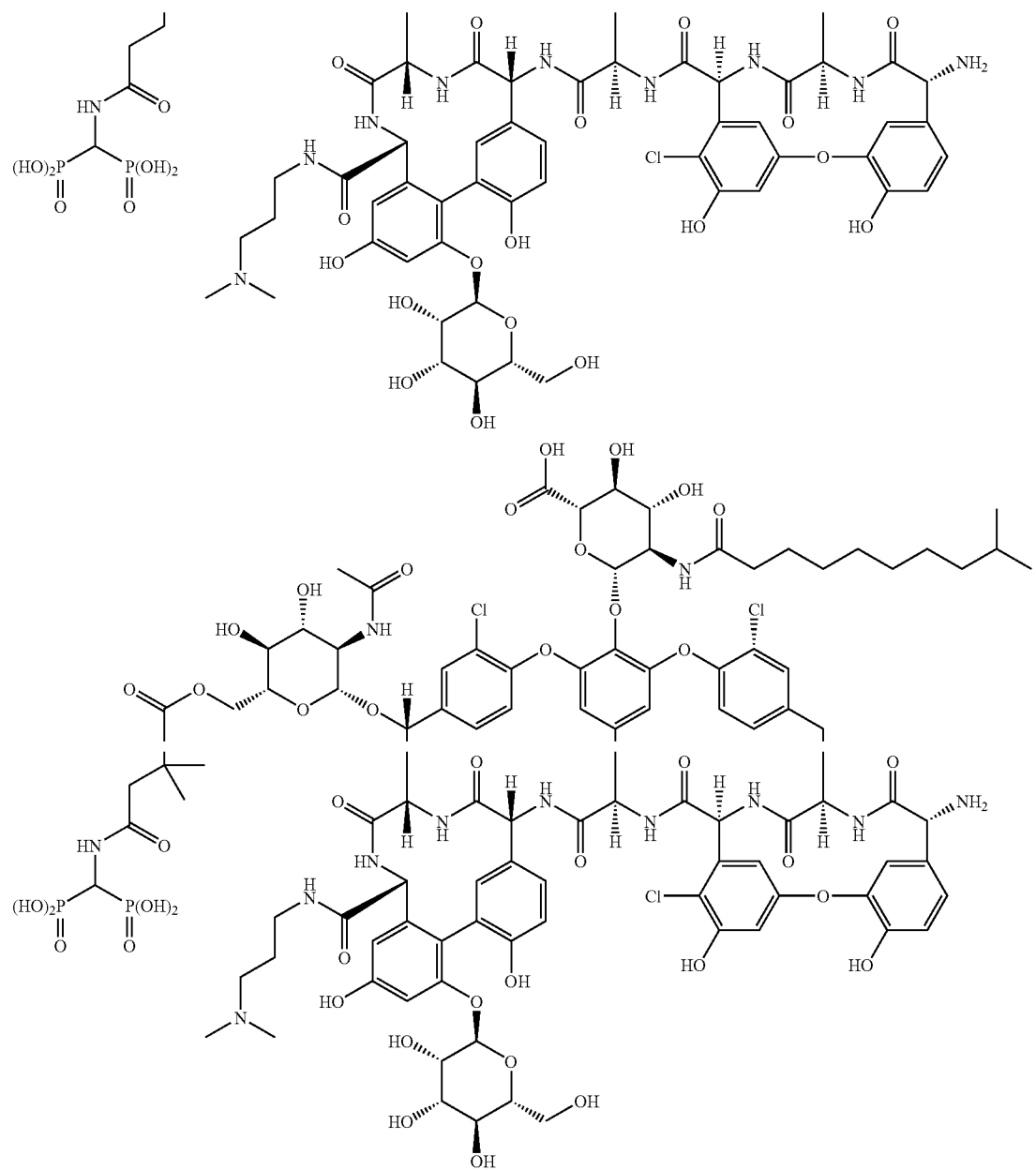

-continued
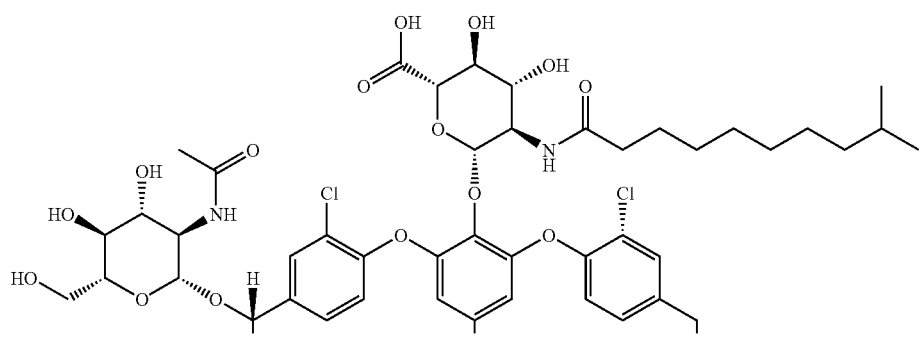
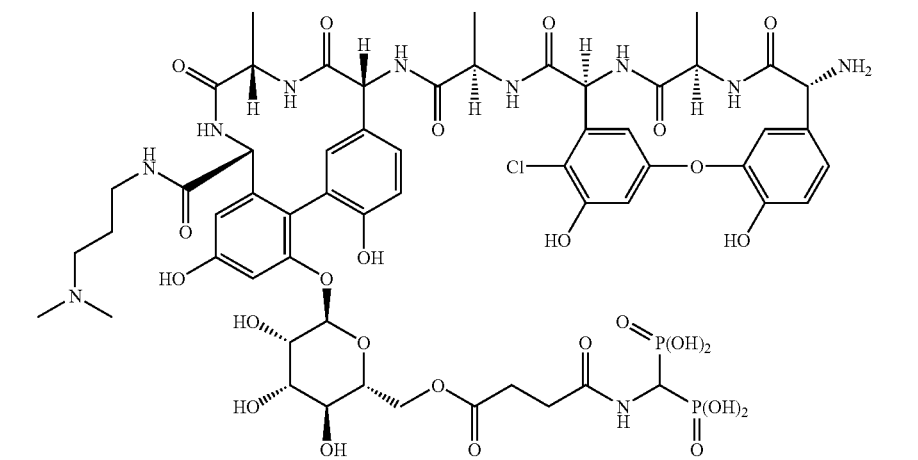
,
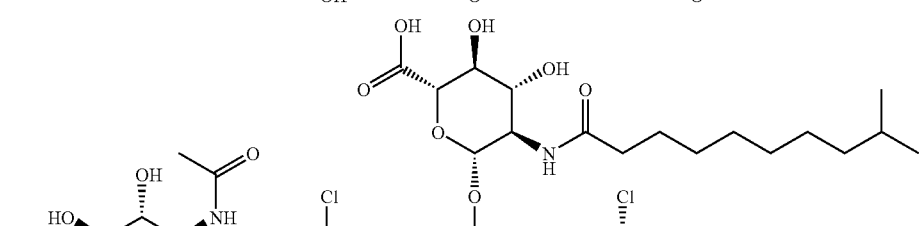
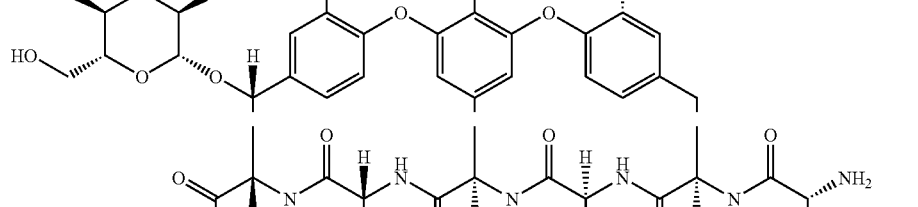
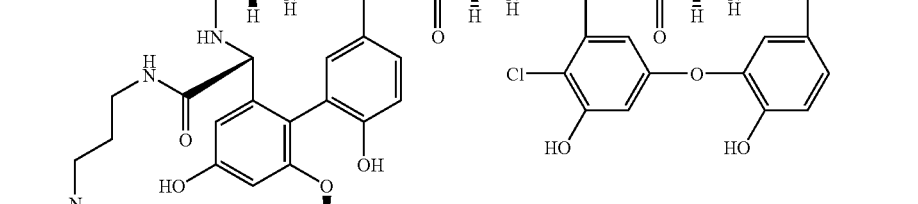
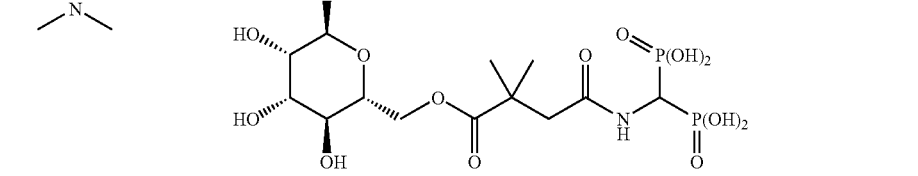
,

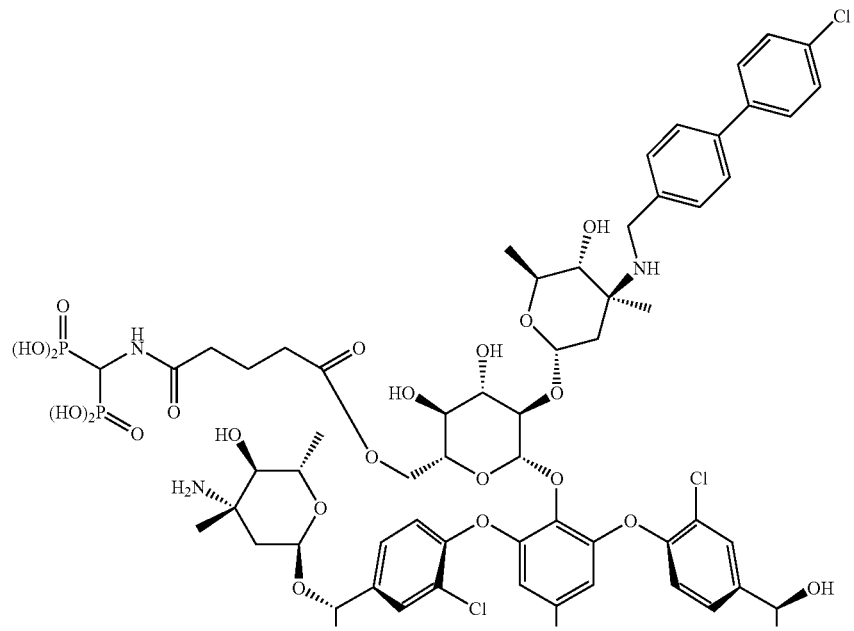
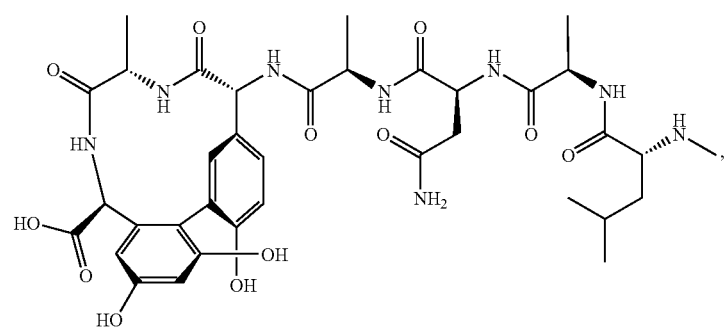
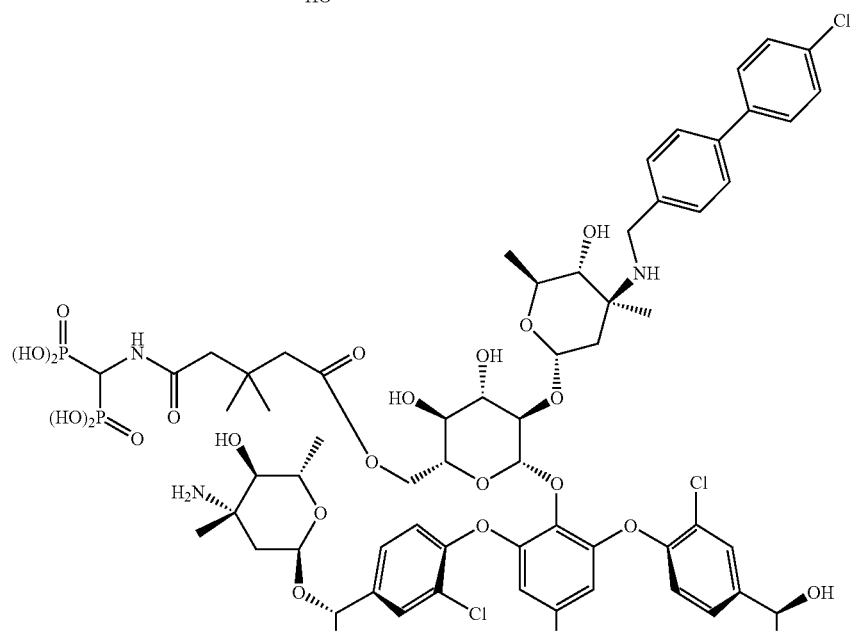

291
-continued
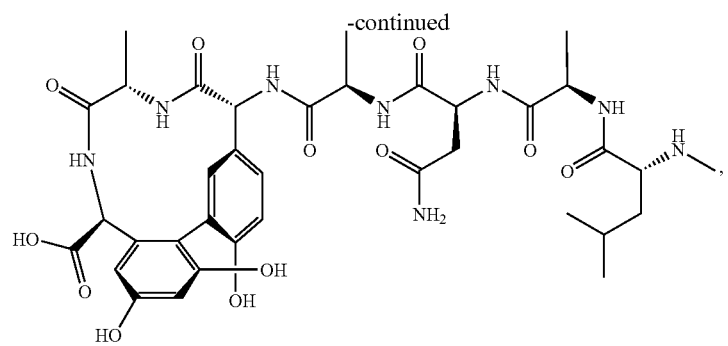
292
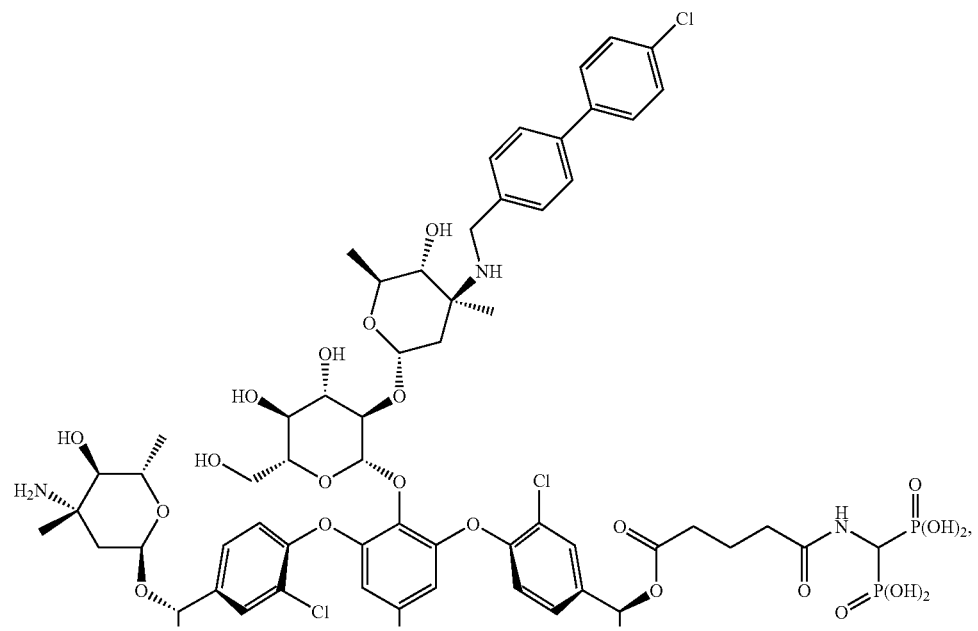
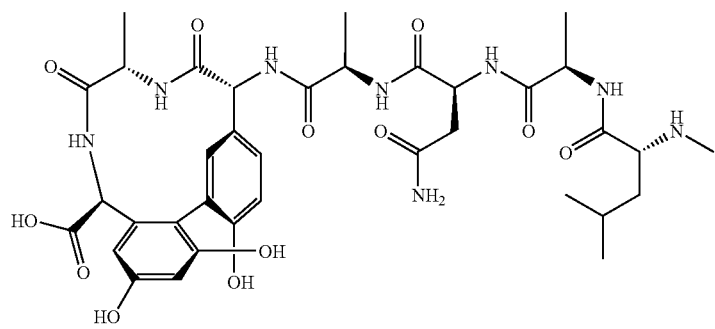

-continued
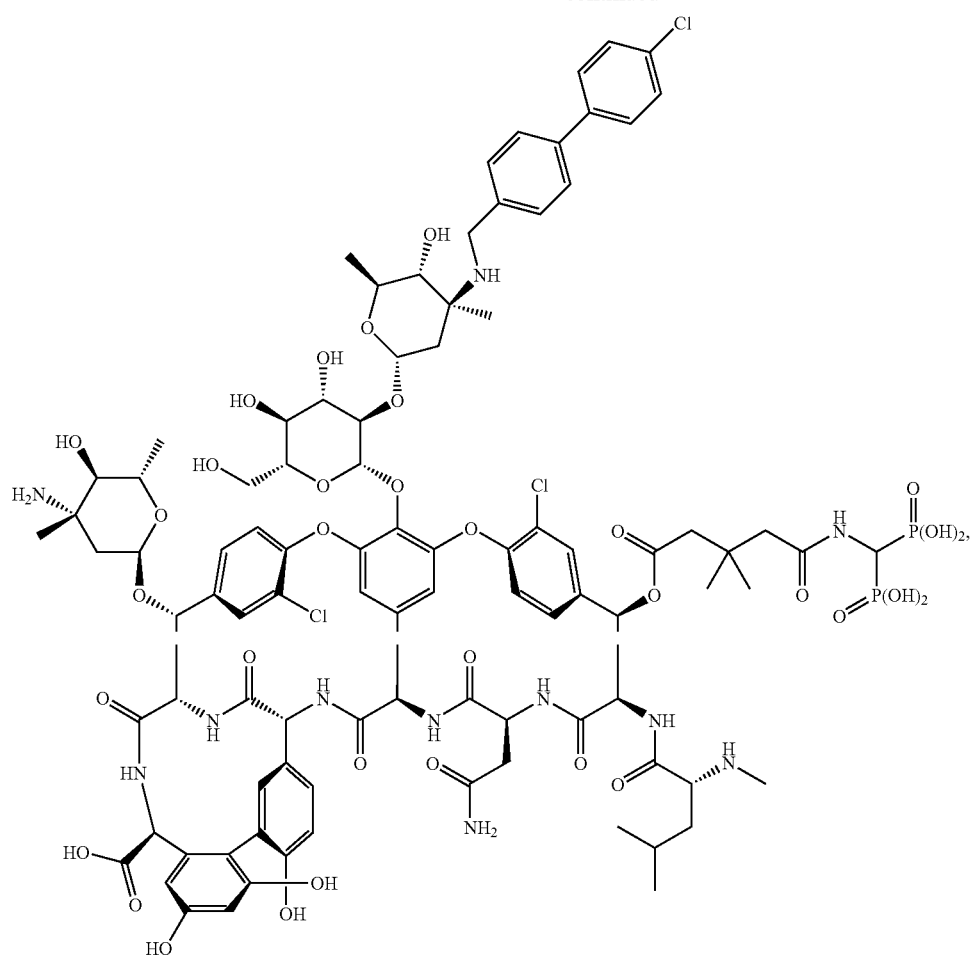
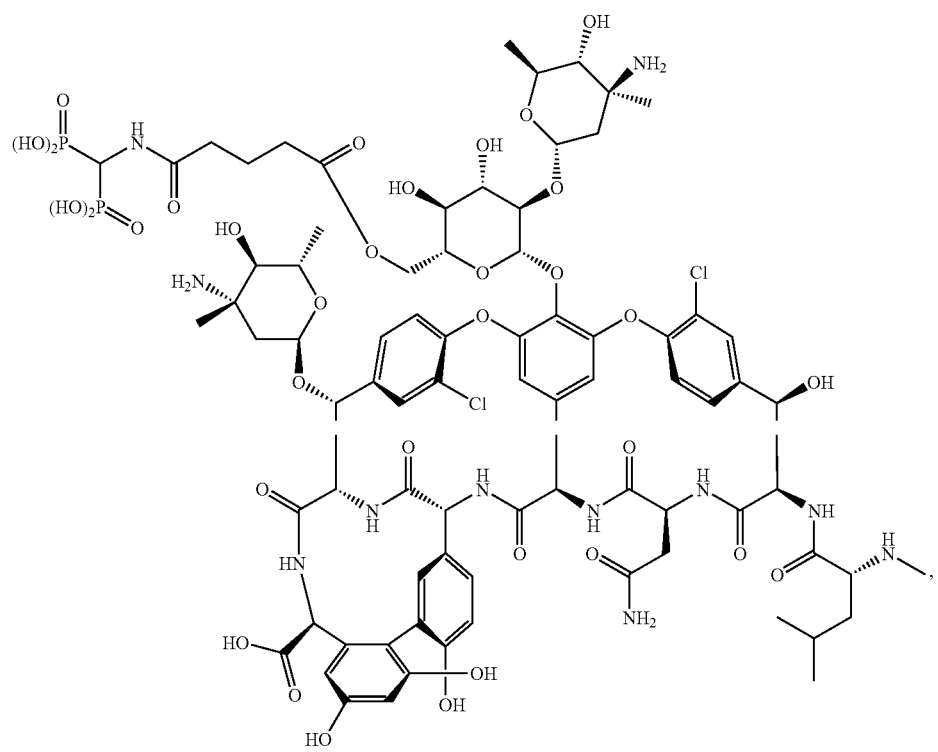

-continued
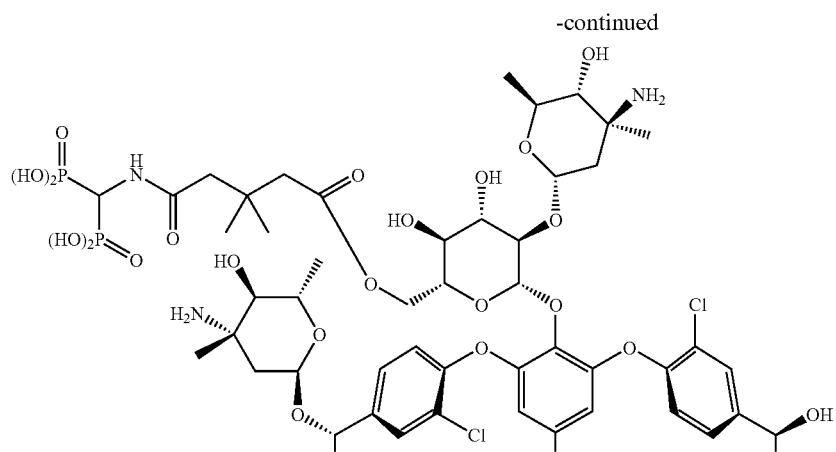
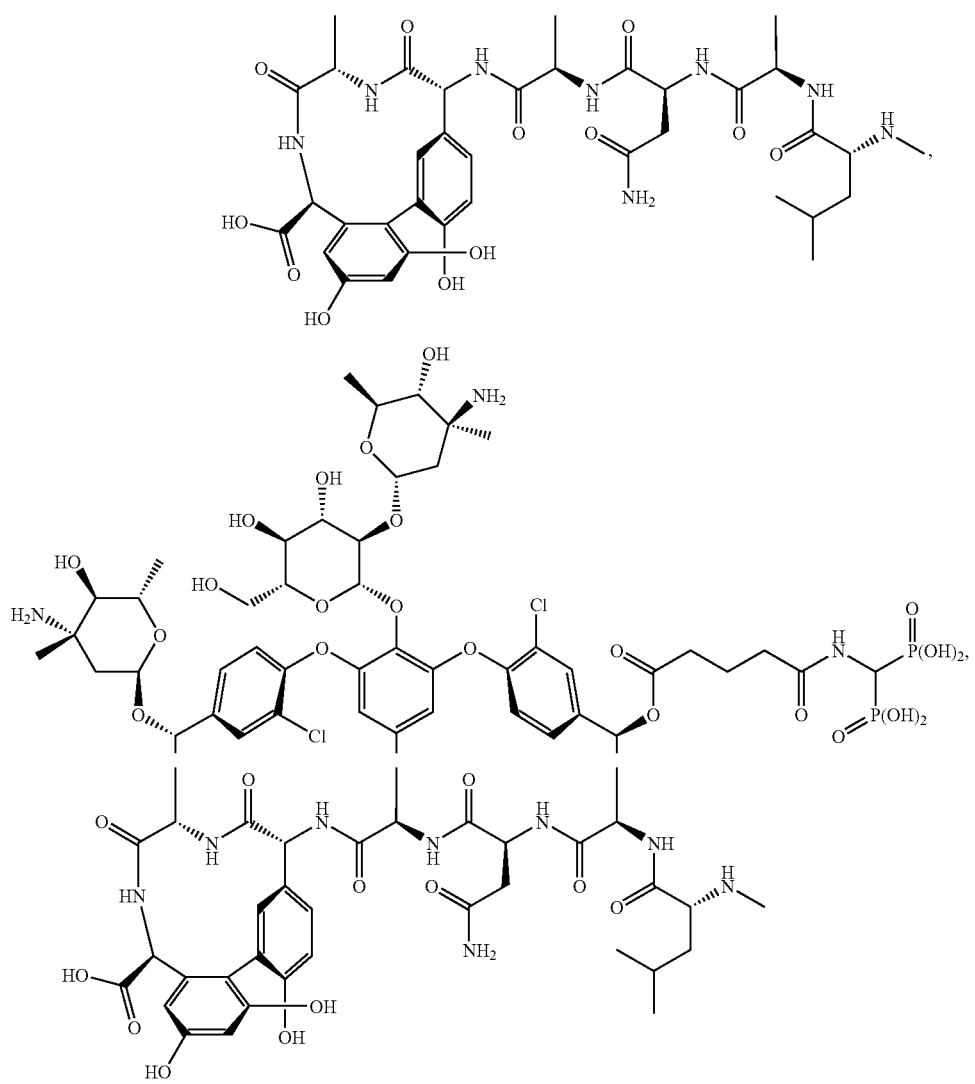

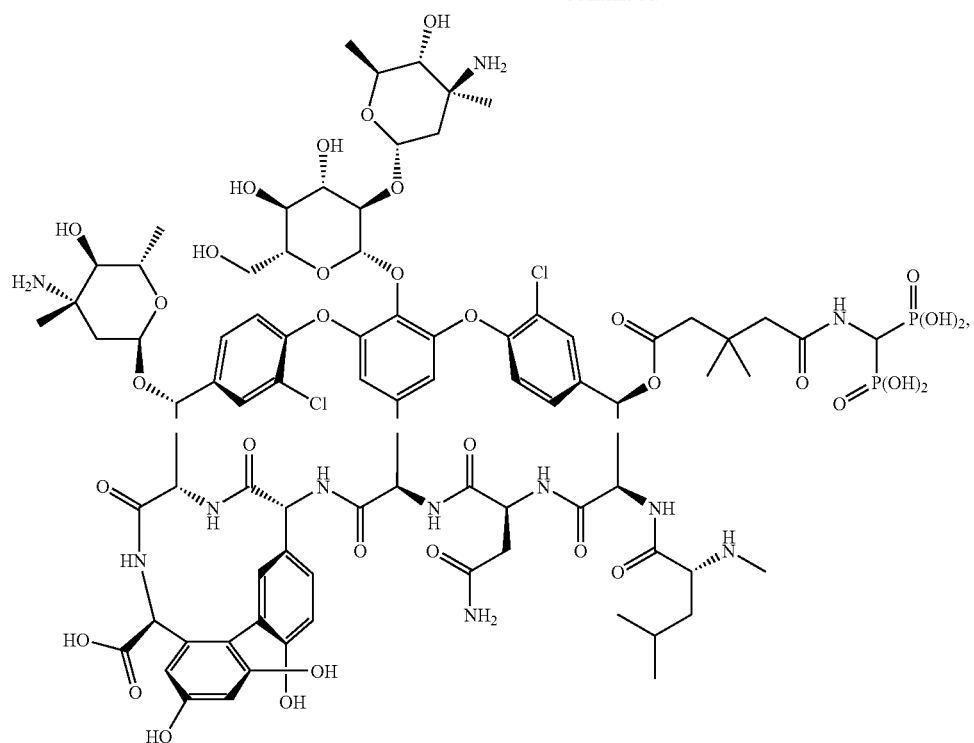
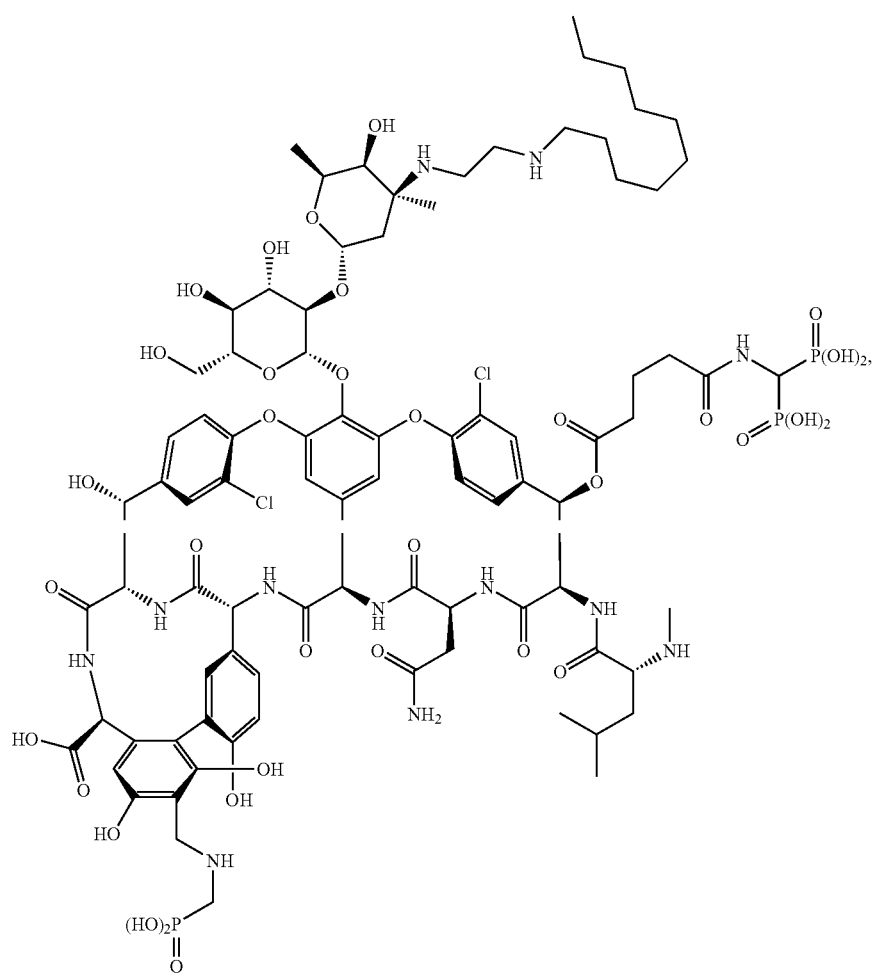

-continued
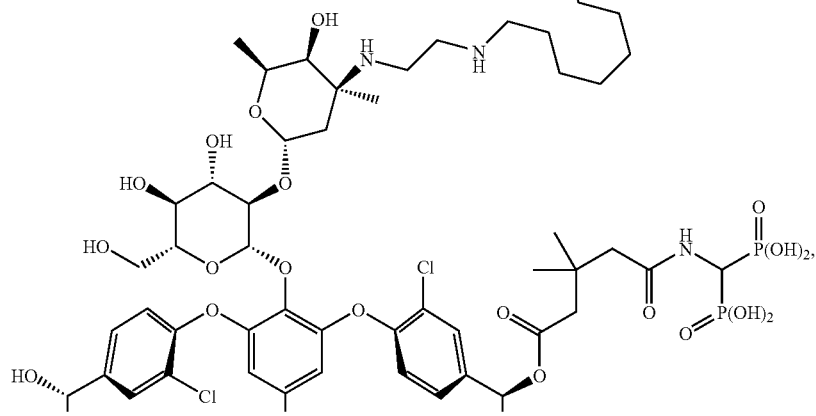
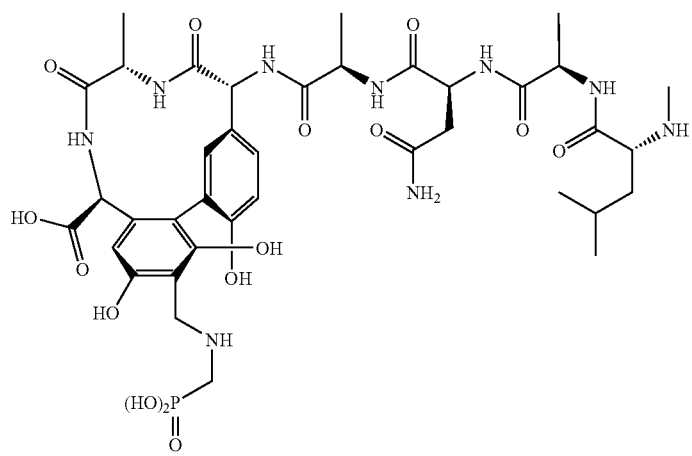
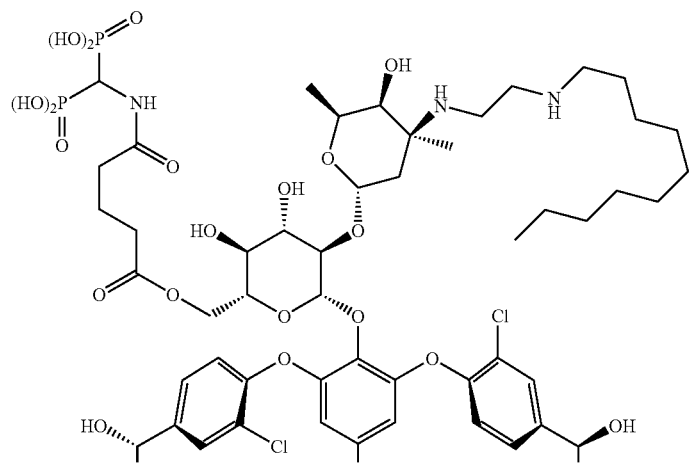

301
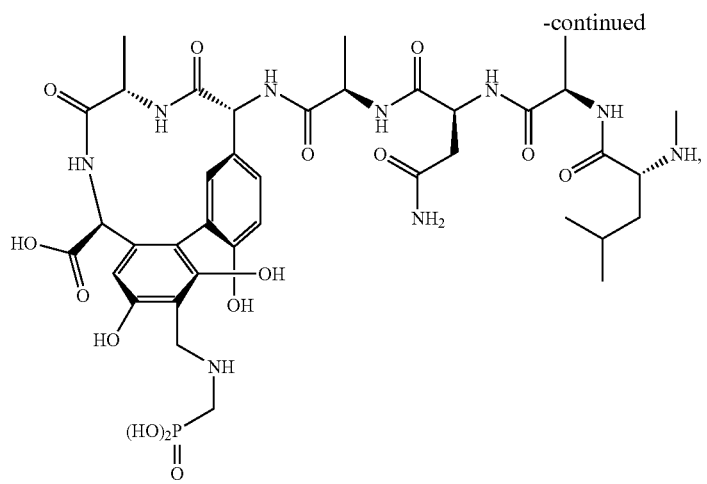
-continued
302
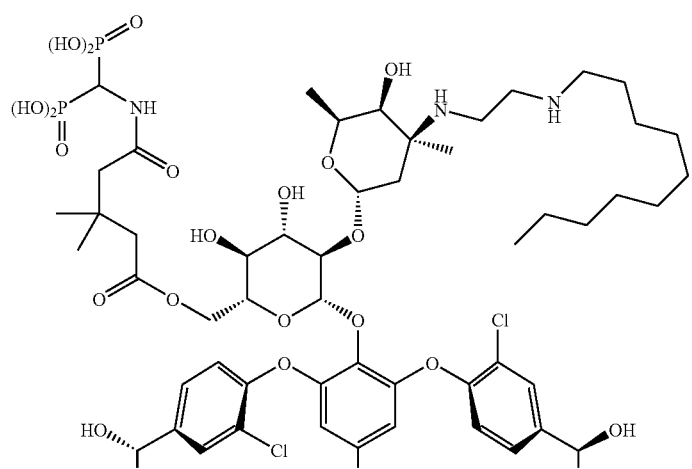
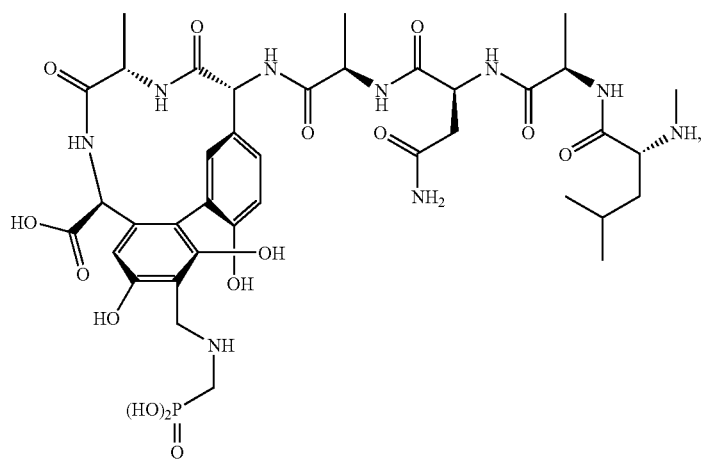

-continued
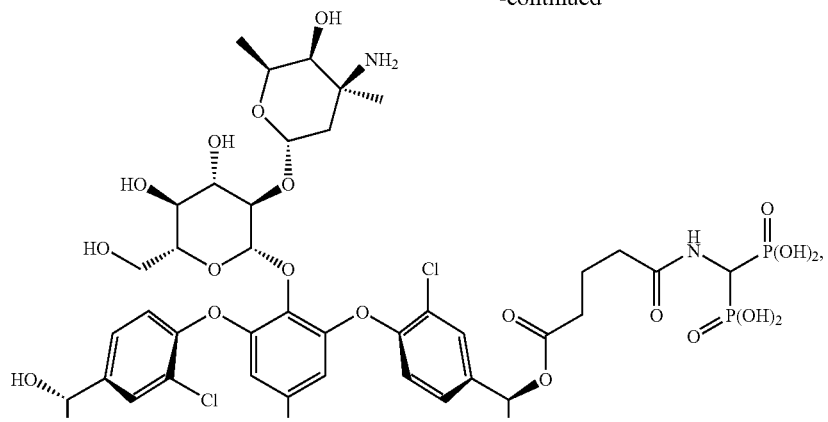
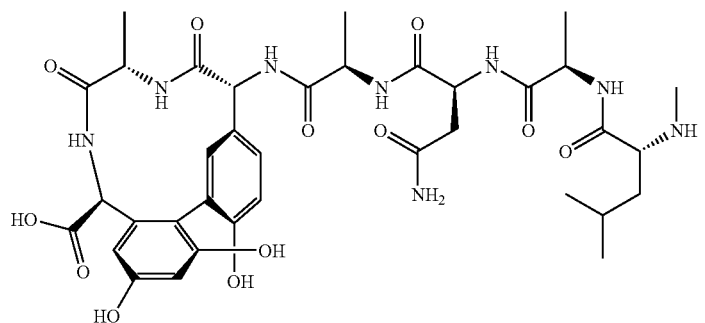
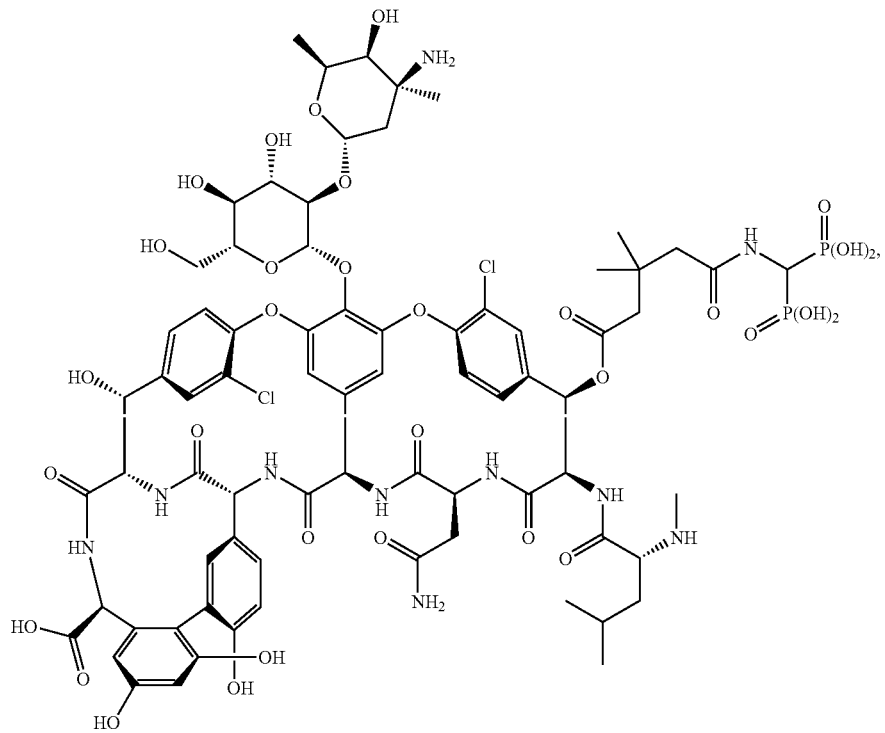

-continued
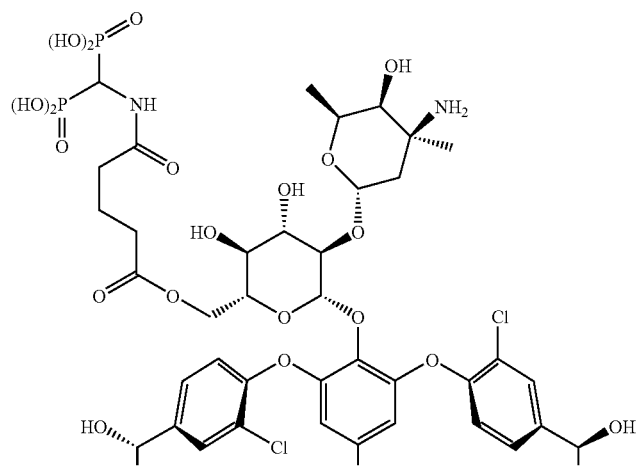
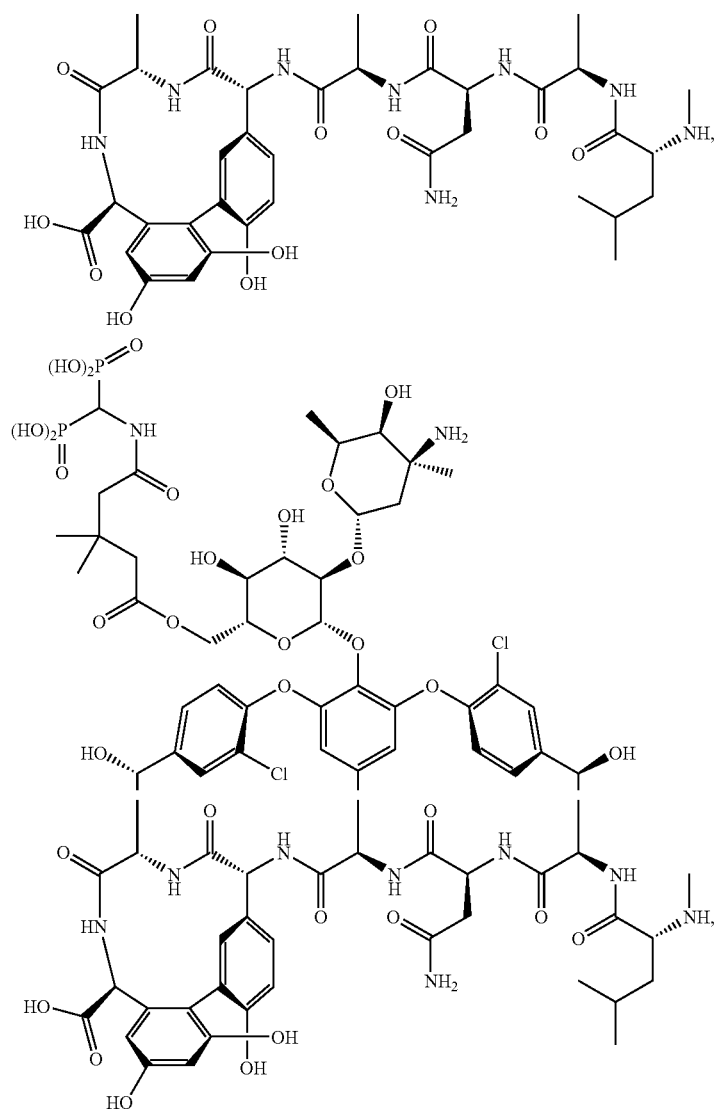

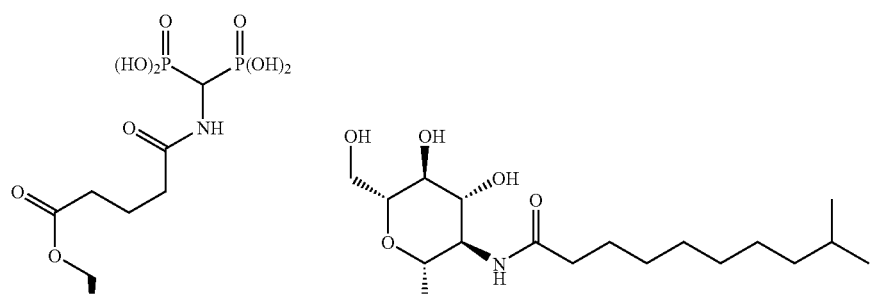
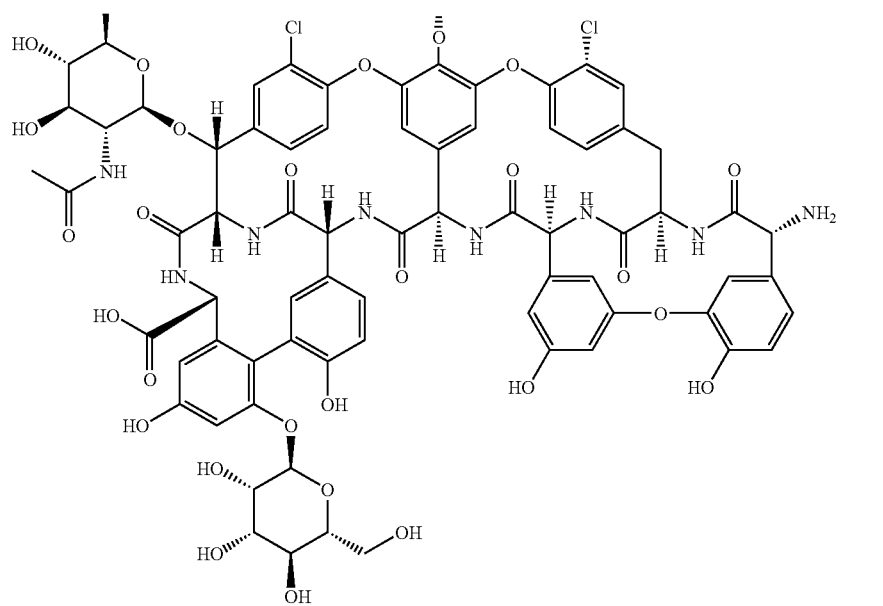
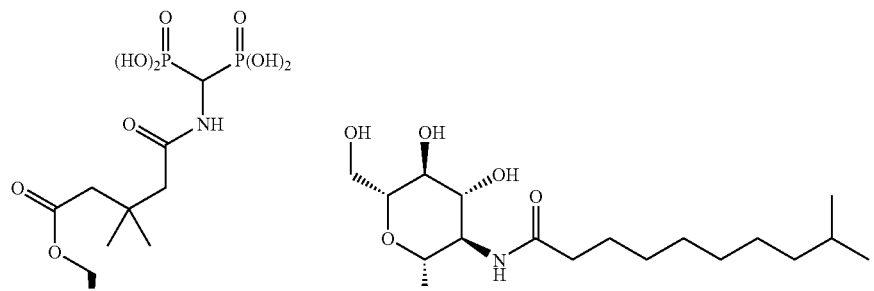

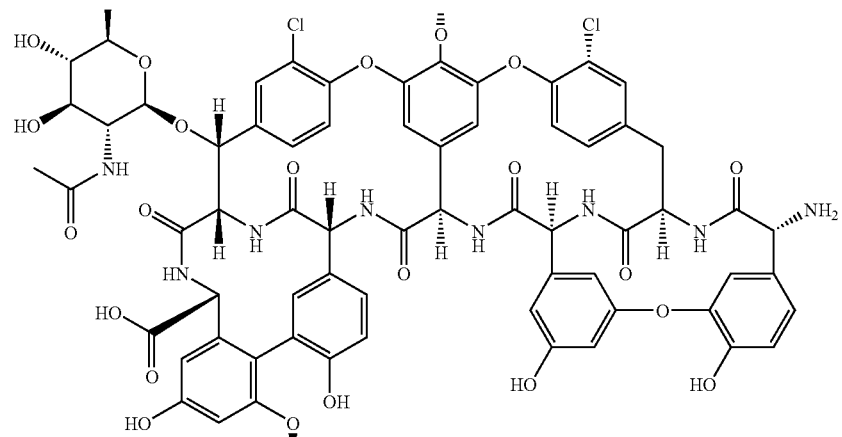
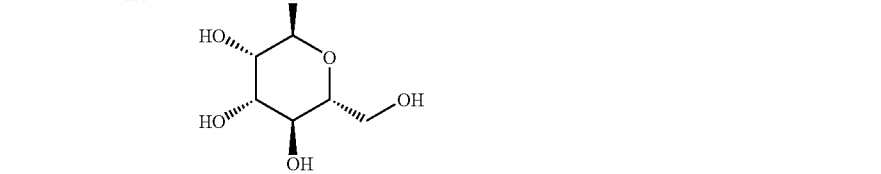
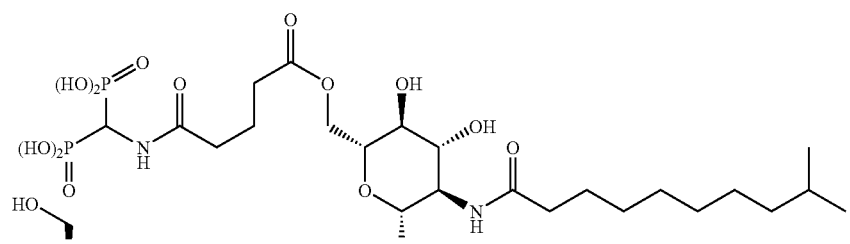
-continued
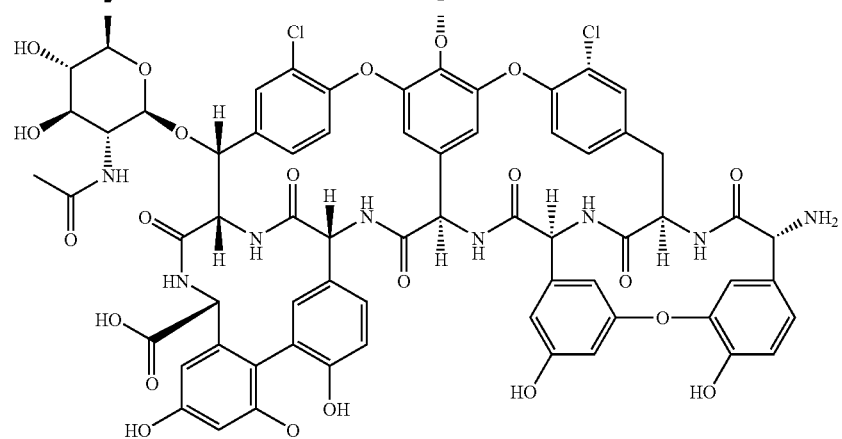
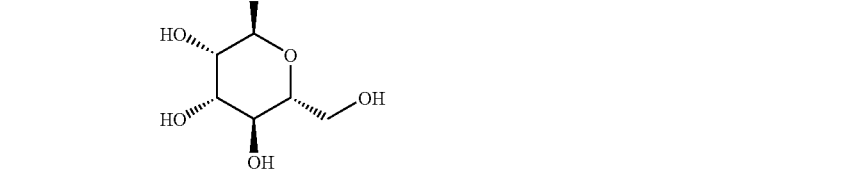
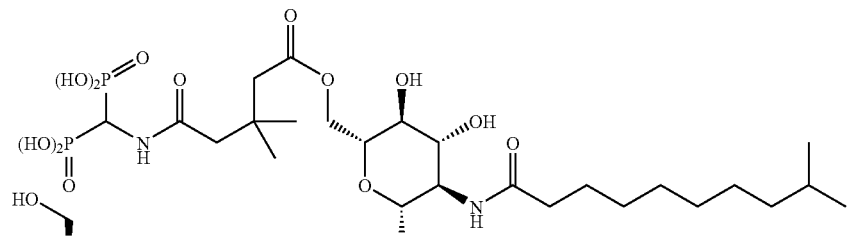

311
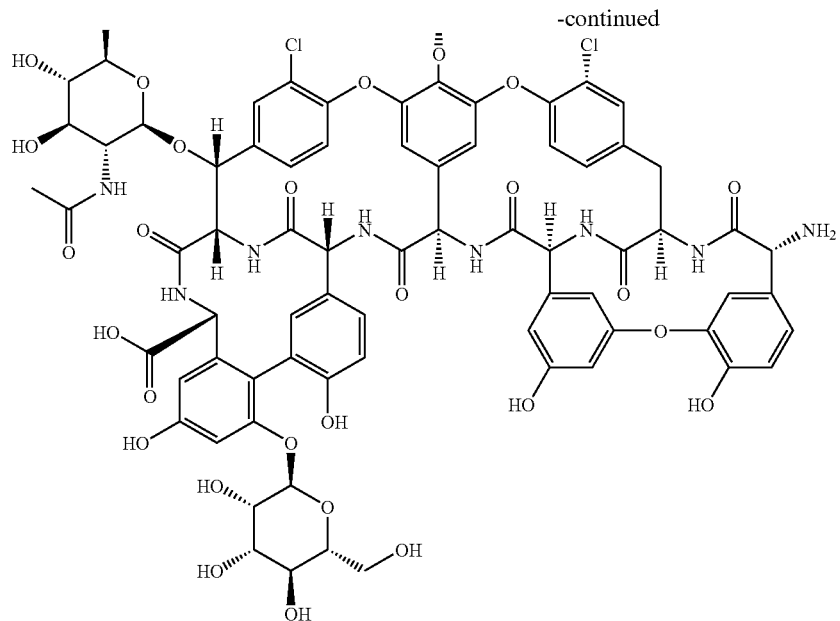
-continued
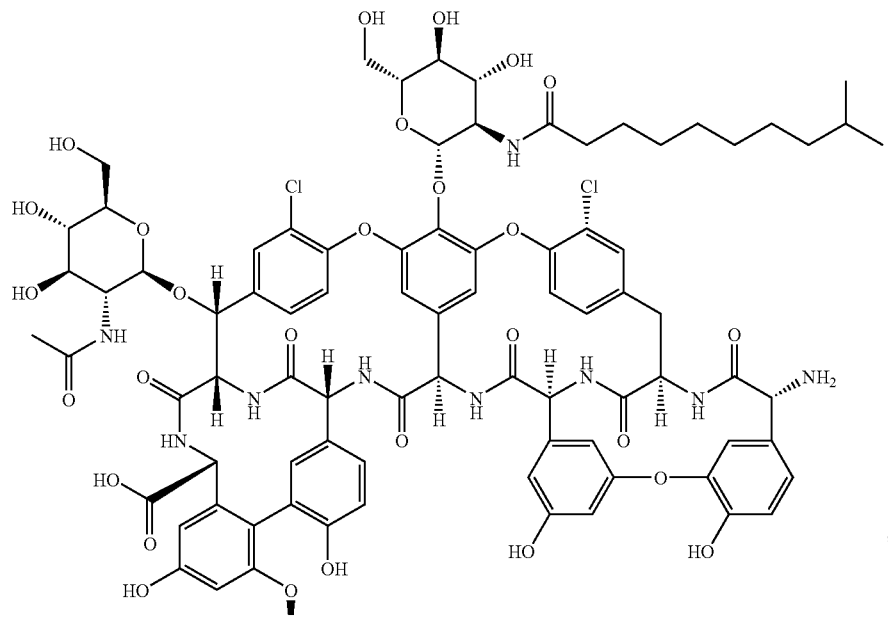
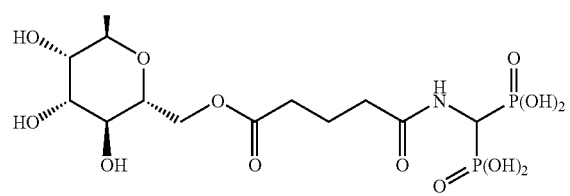

-continued
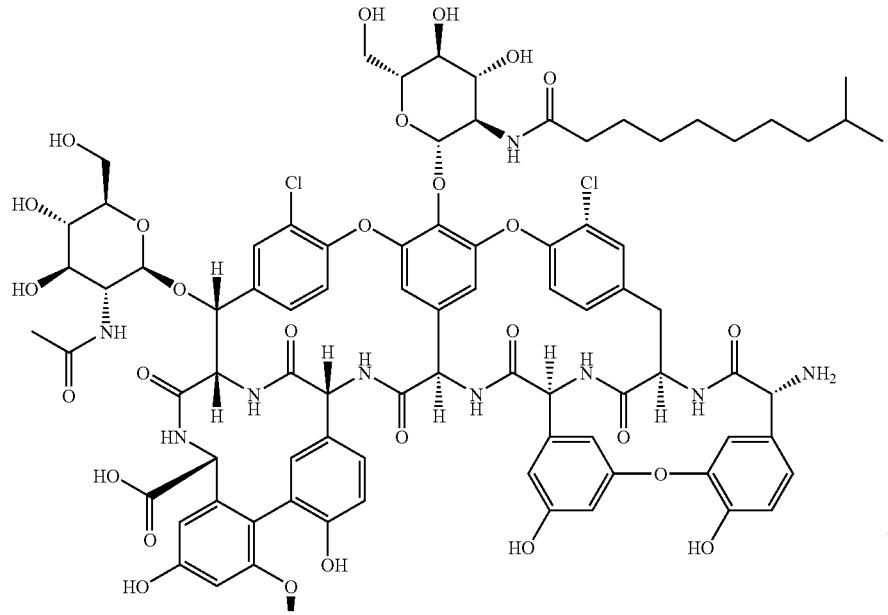
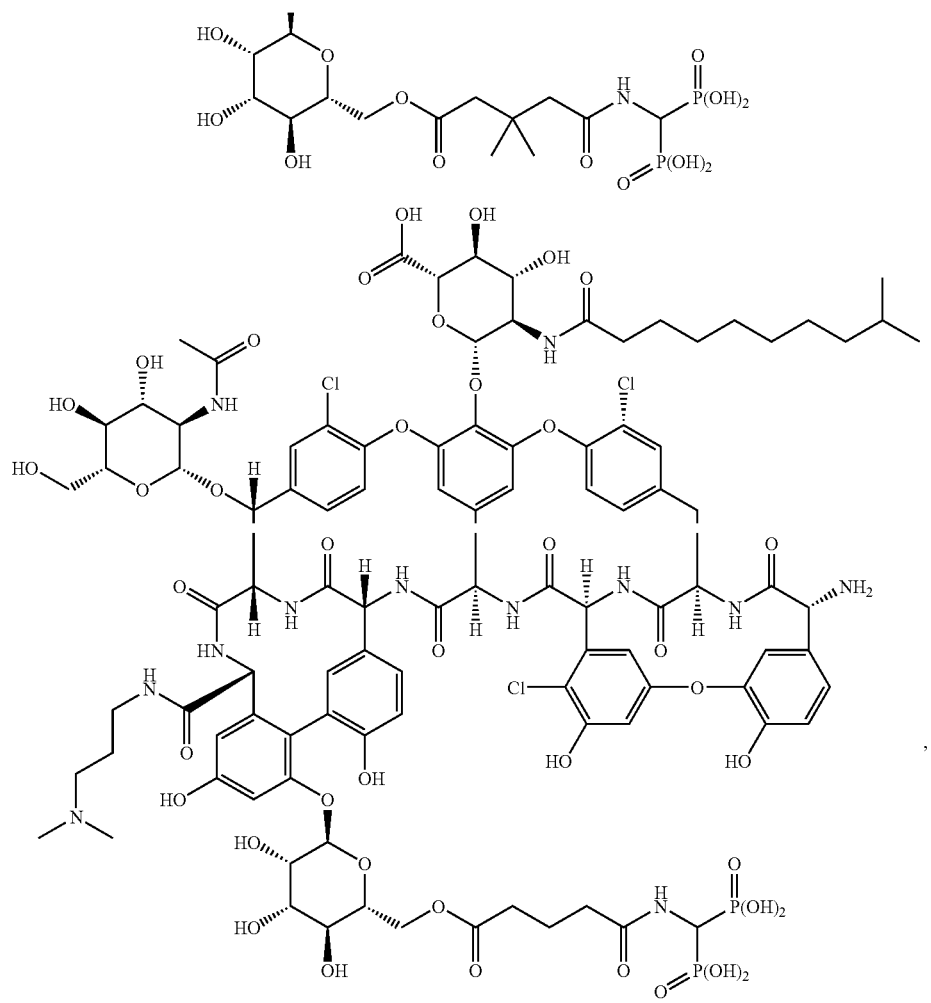

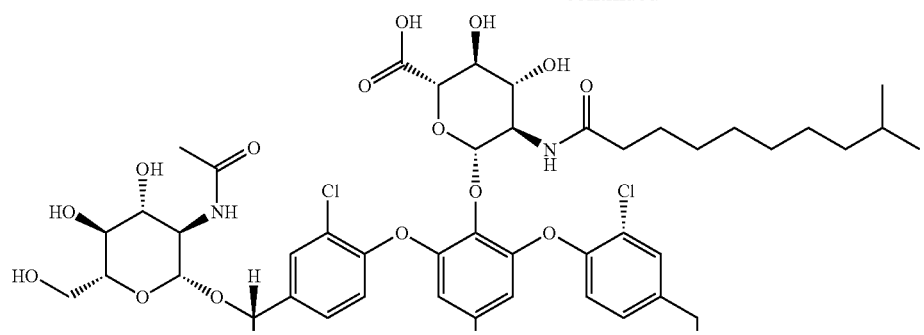
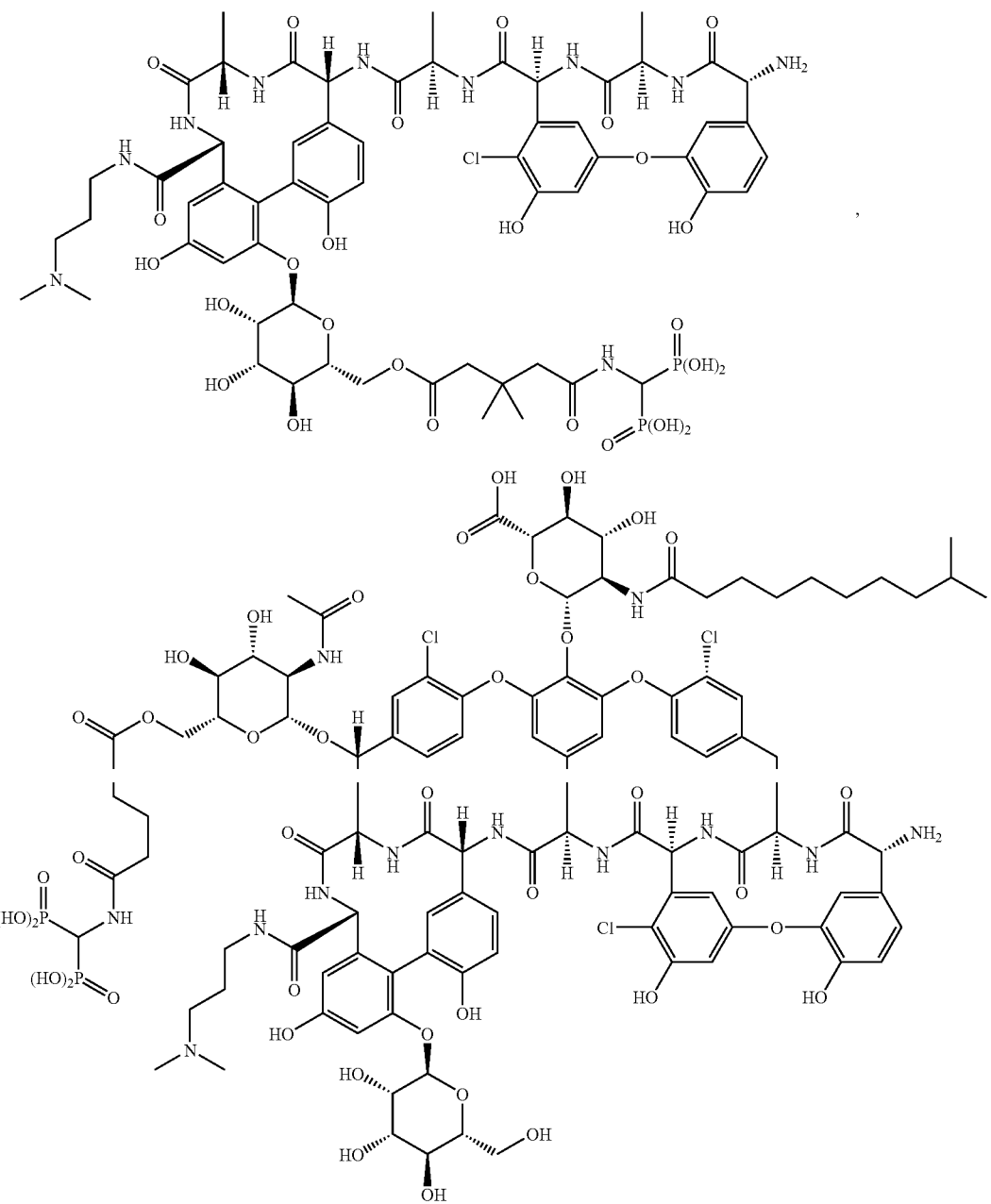

-continued
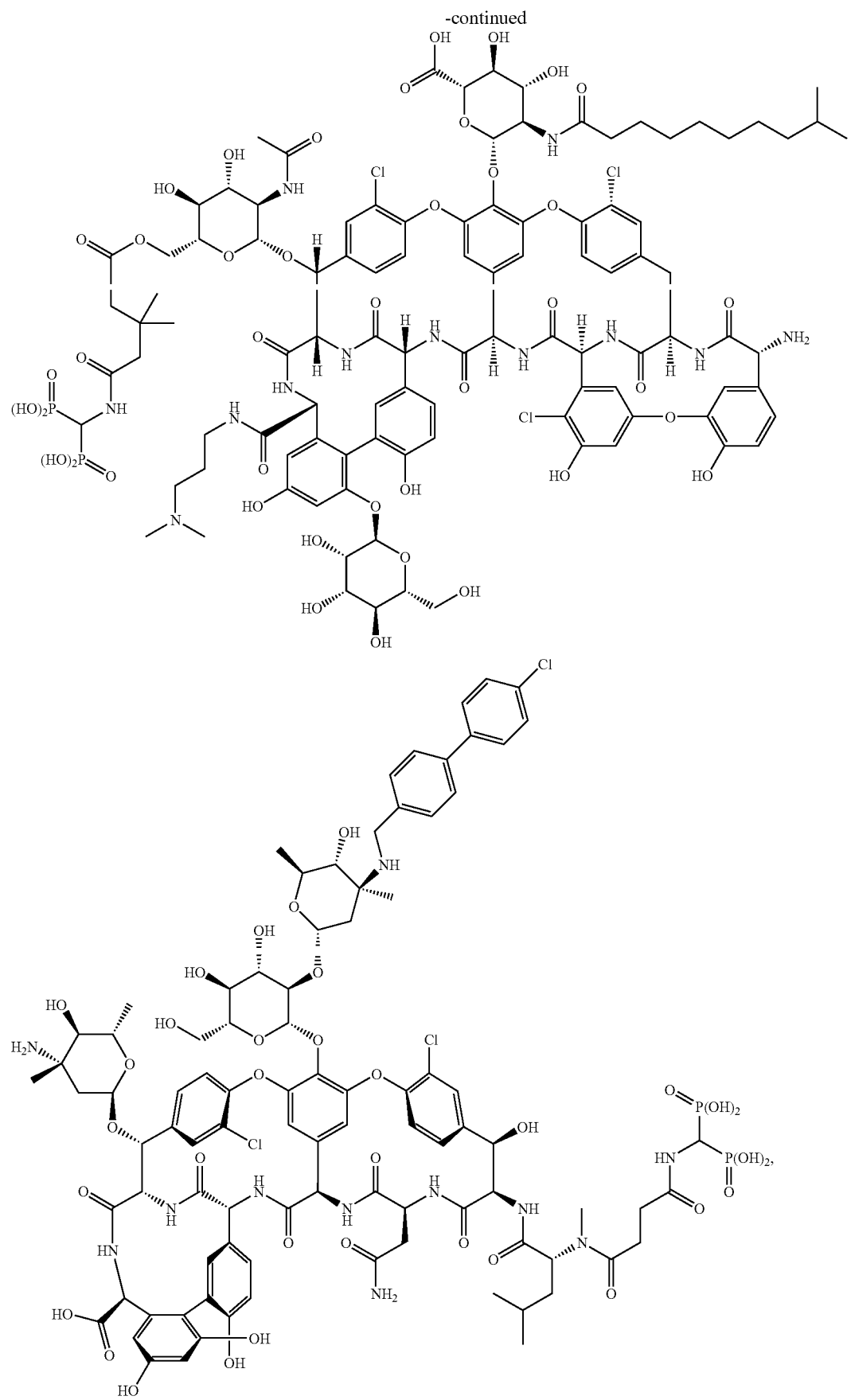

-continued
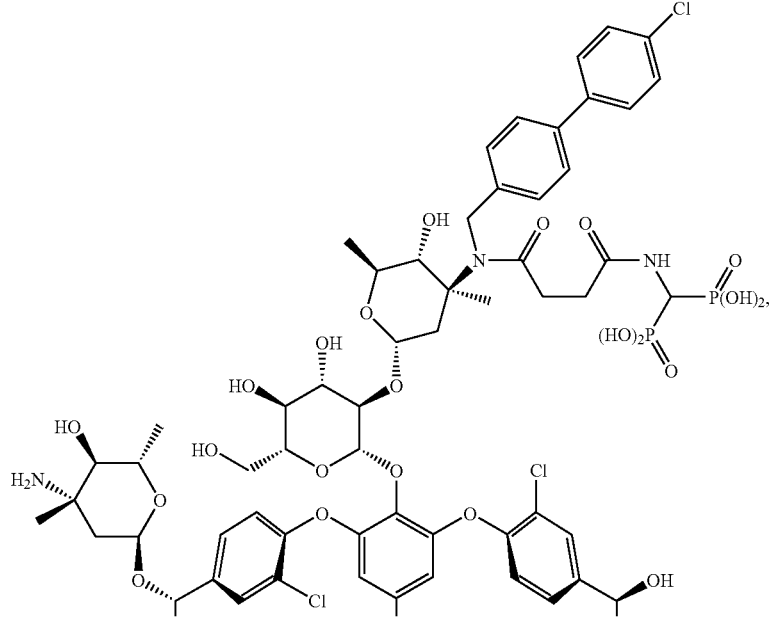
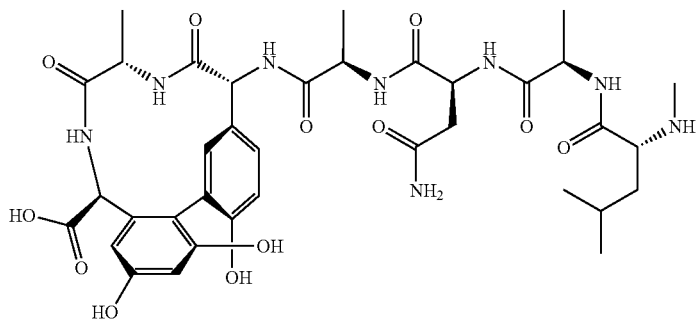
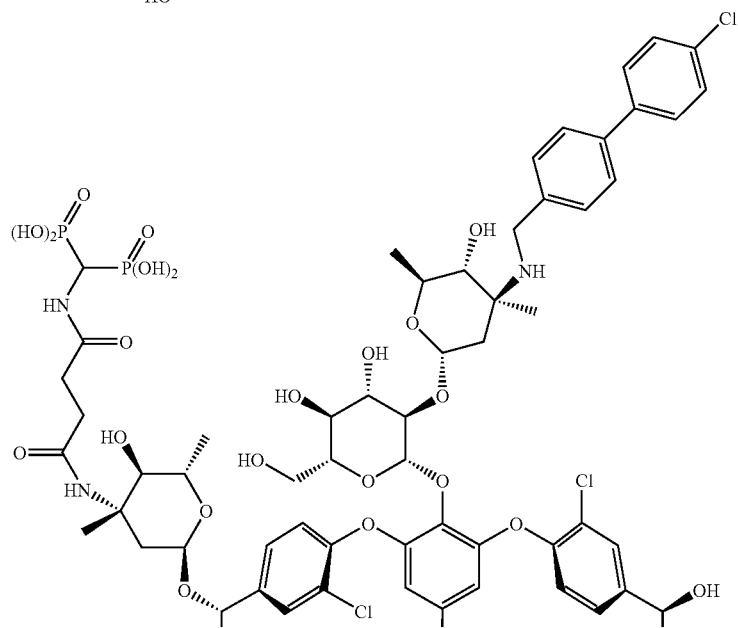

321
-continued
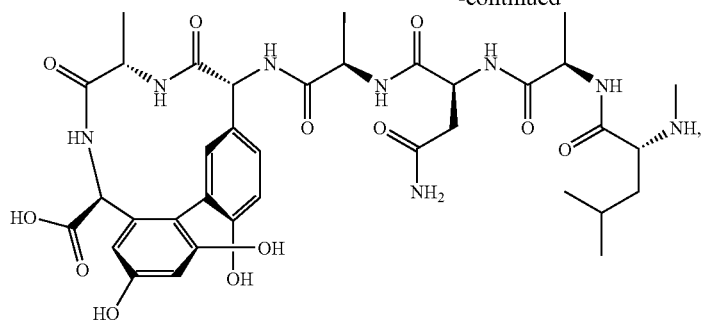
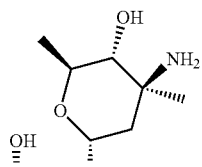
322
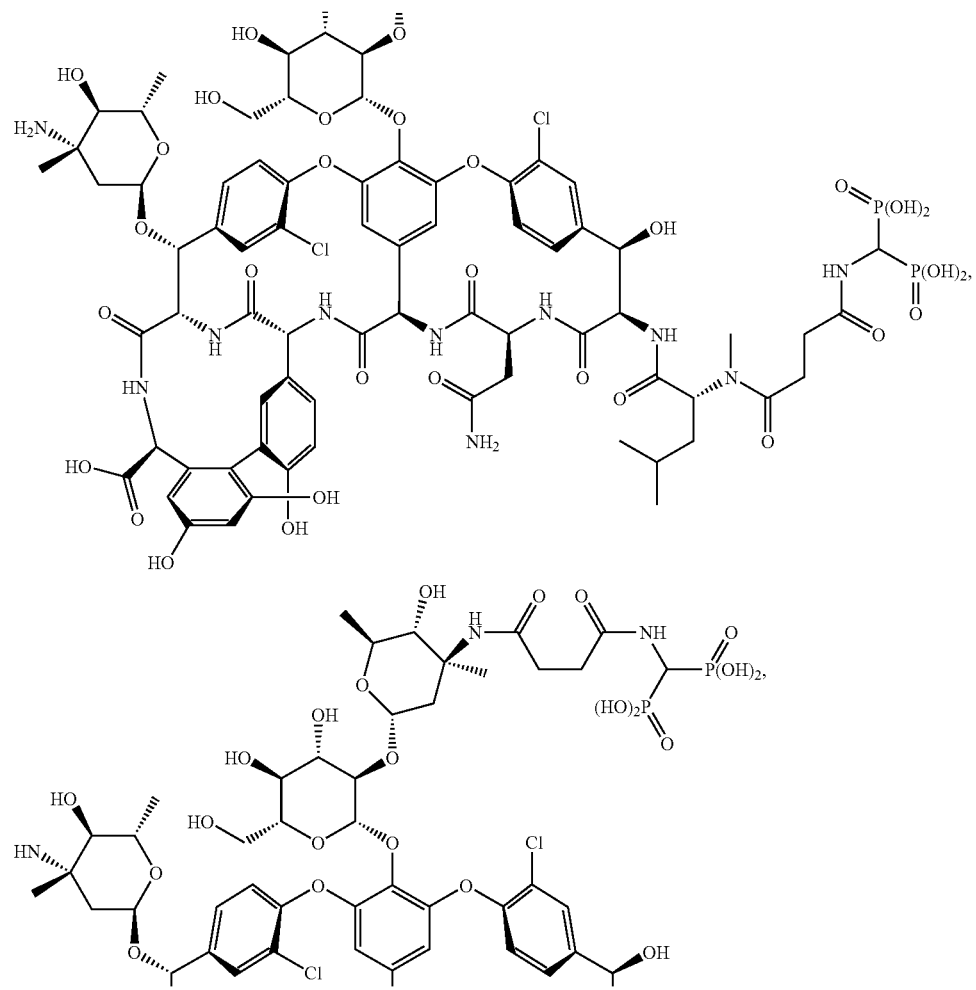

323
-continued
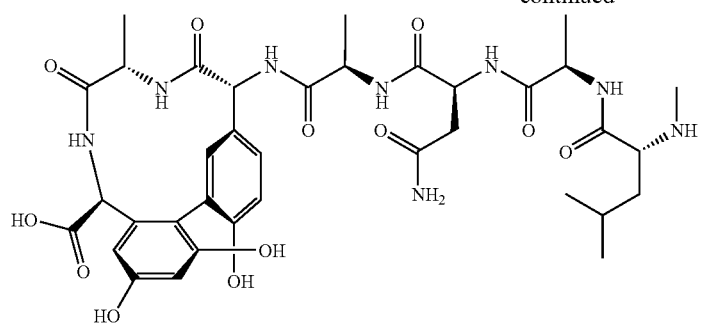
324
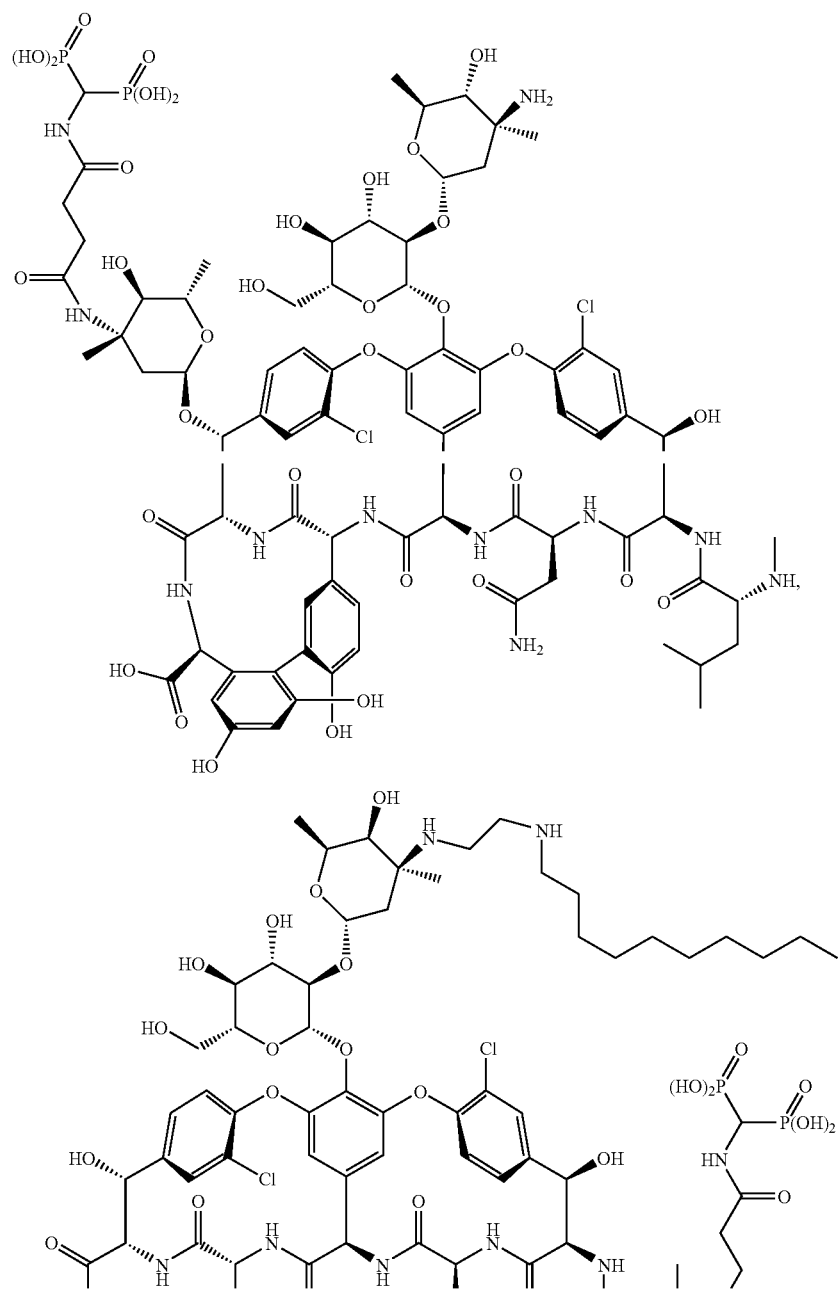

325
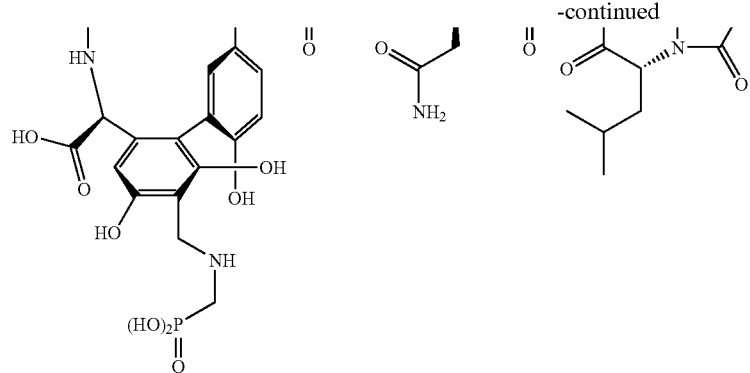
326 -continued
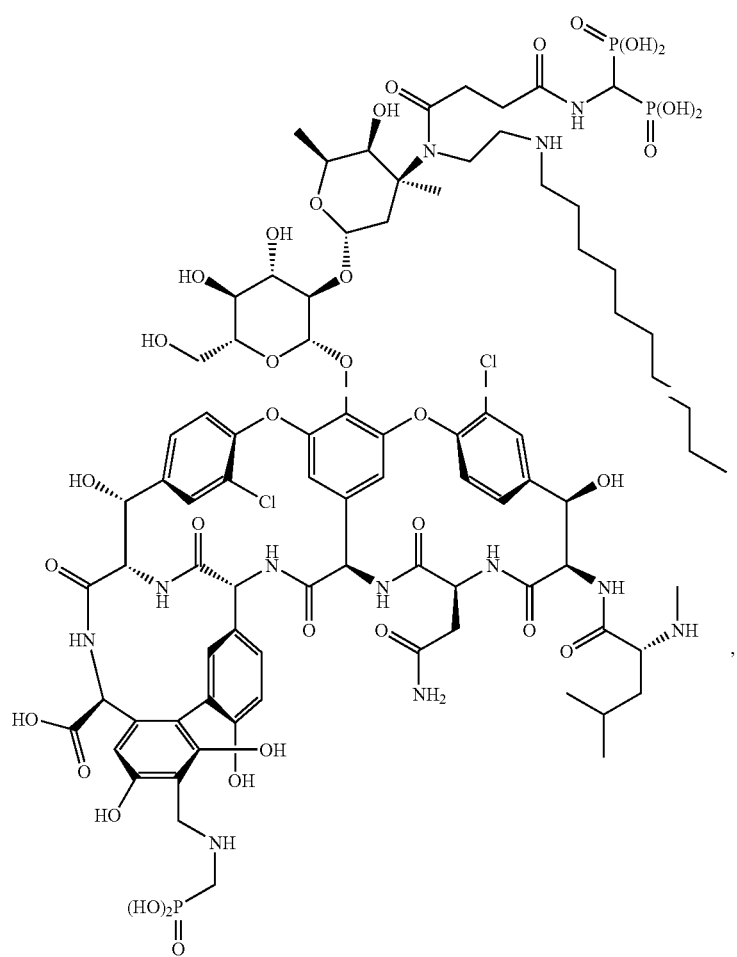
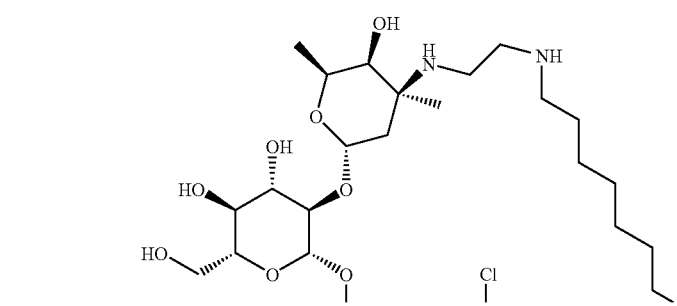

327
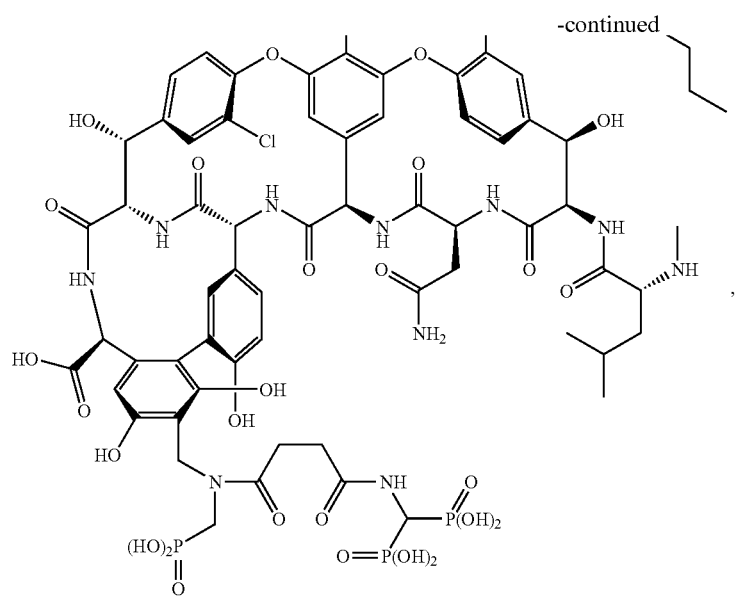
328
-continued
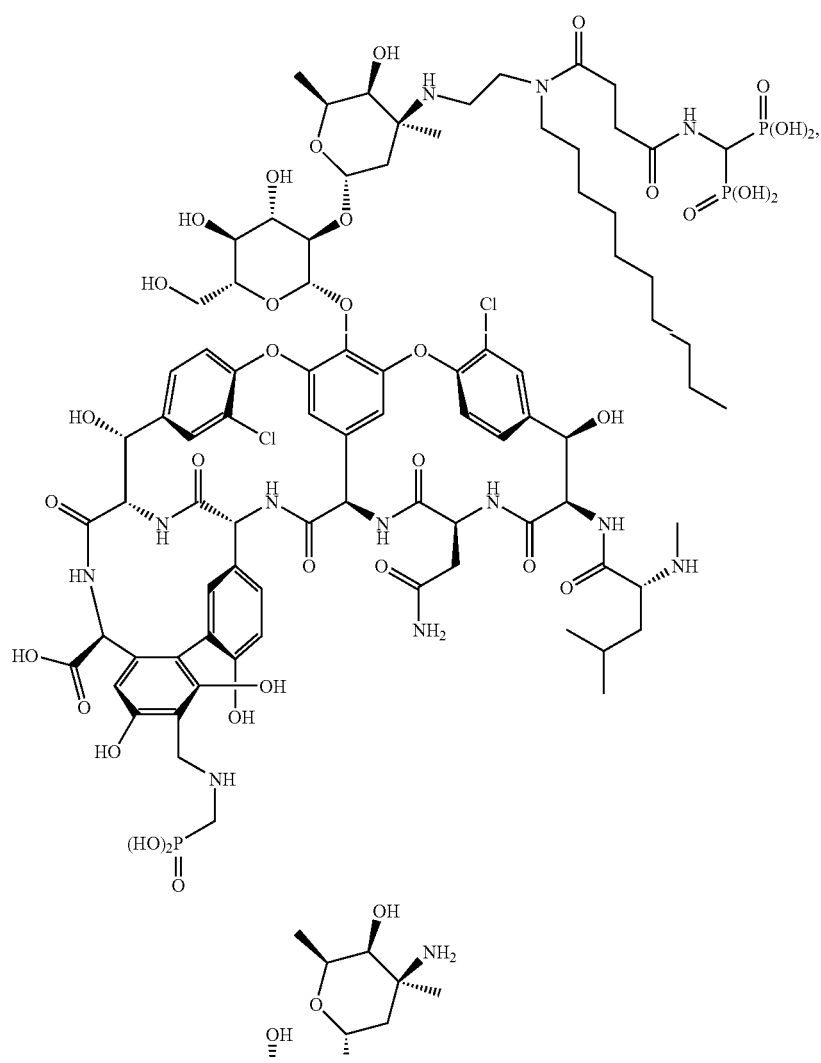

-continued
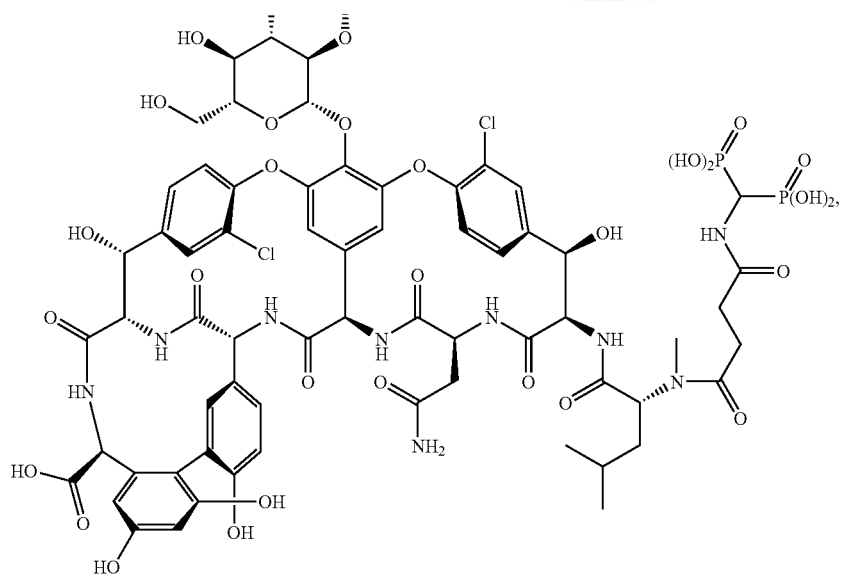
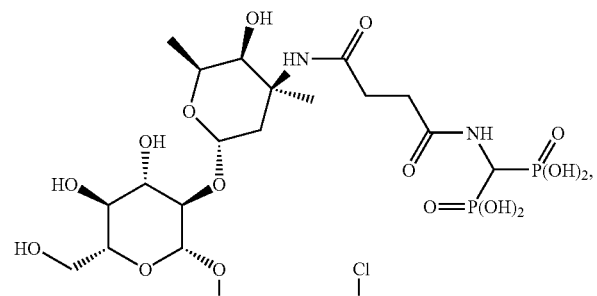
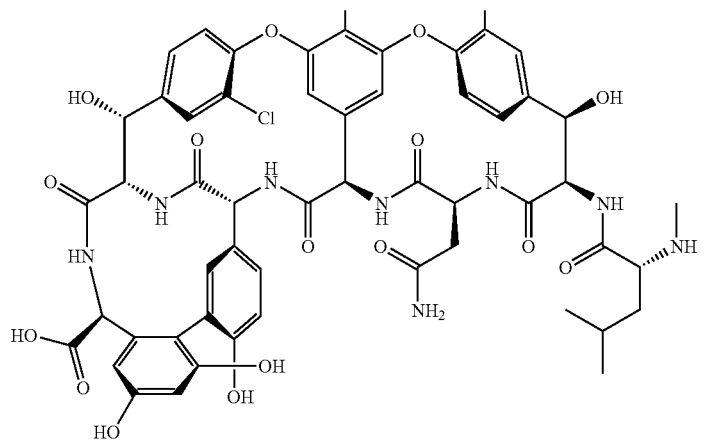

-continued
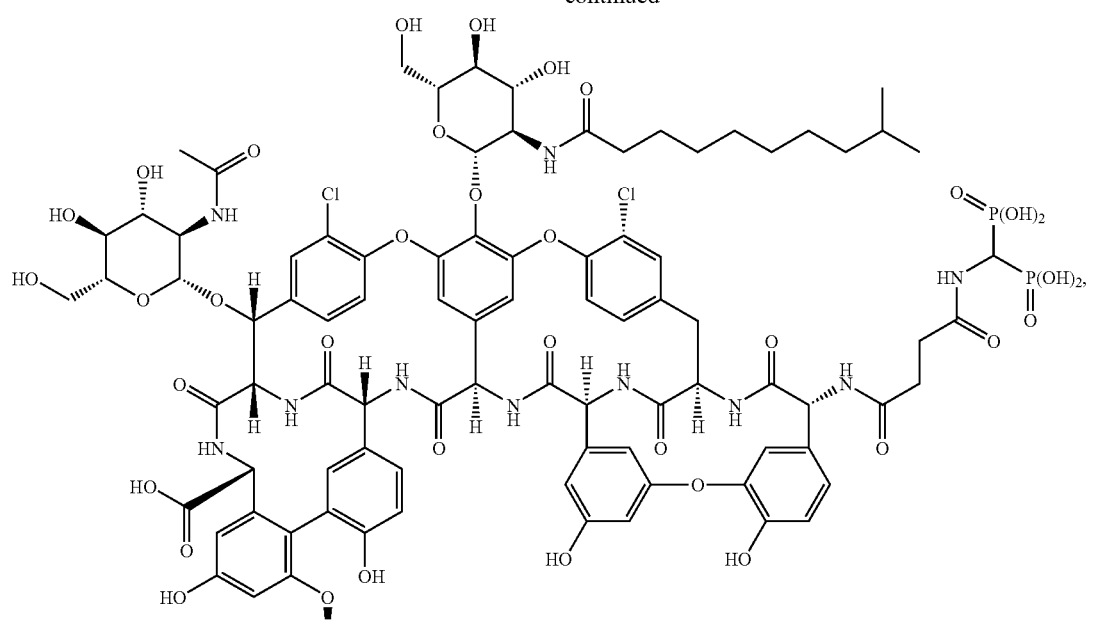
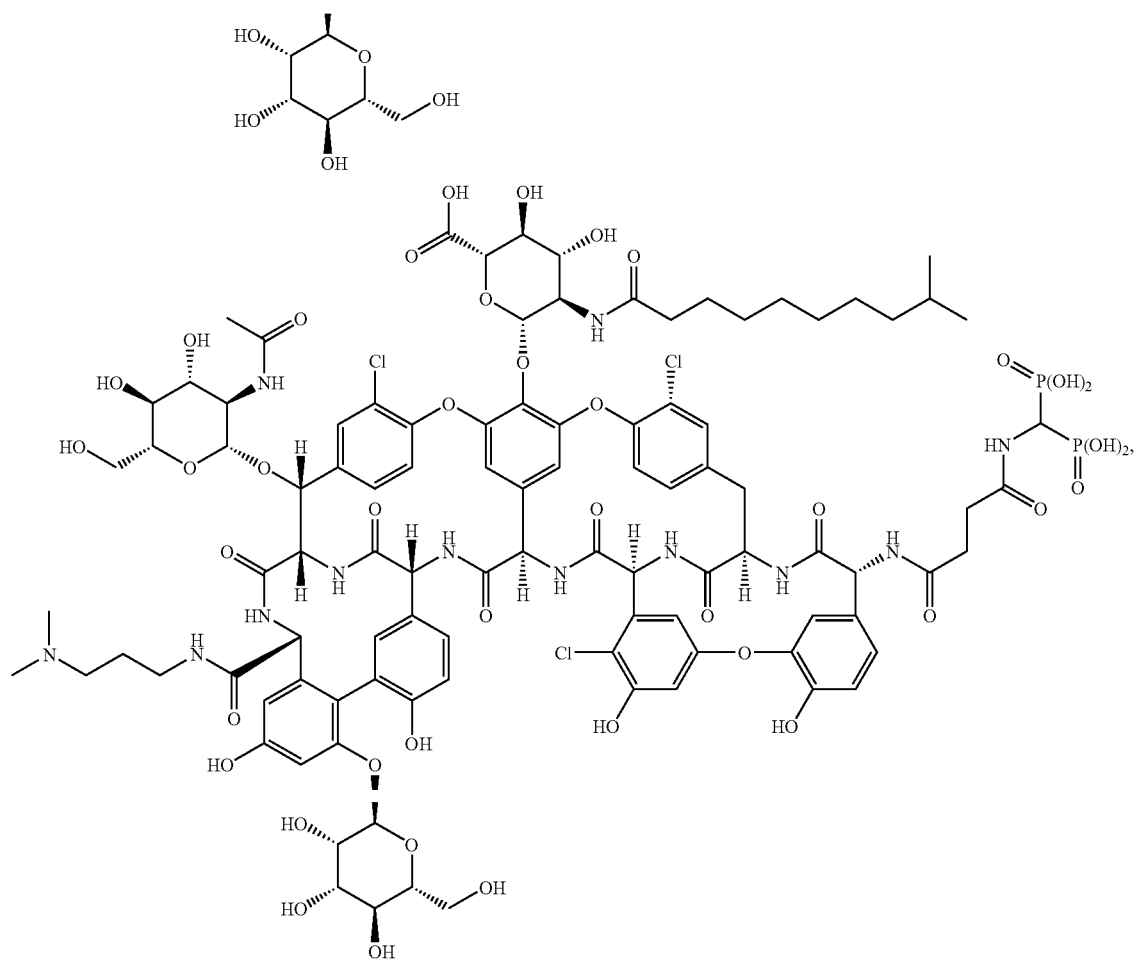

-continued
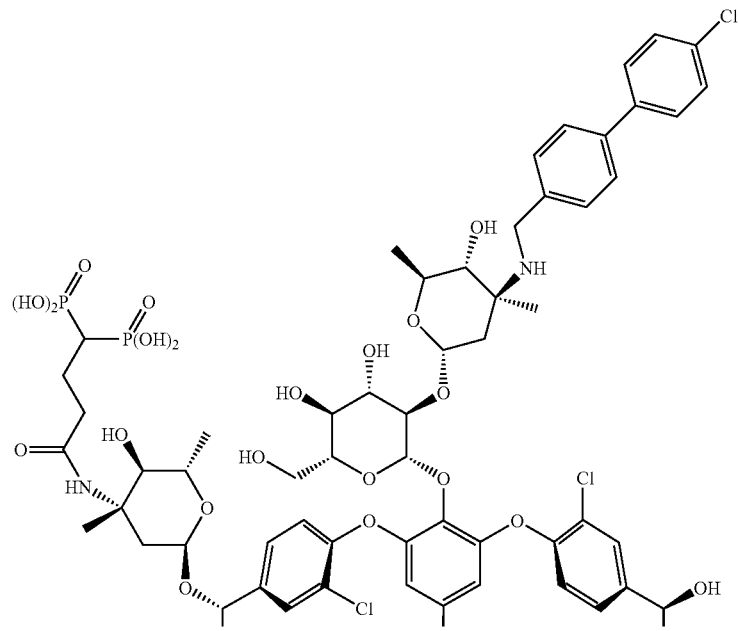
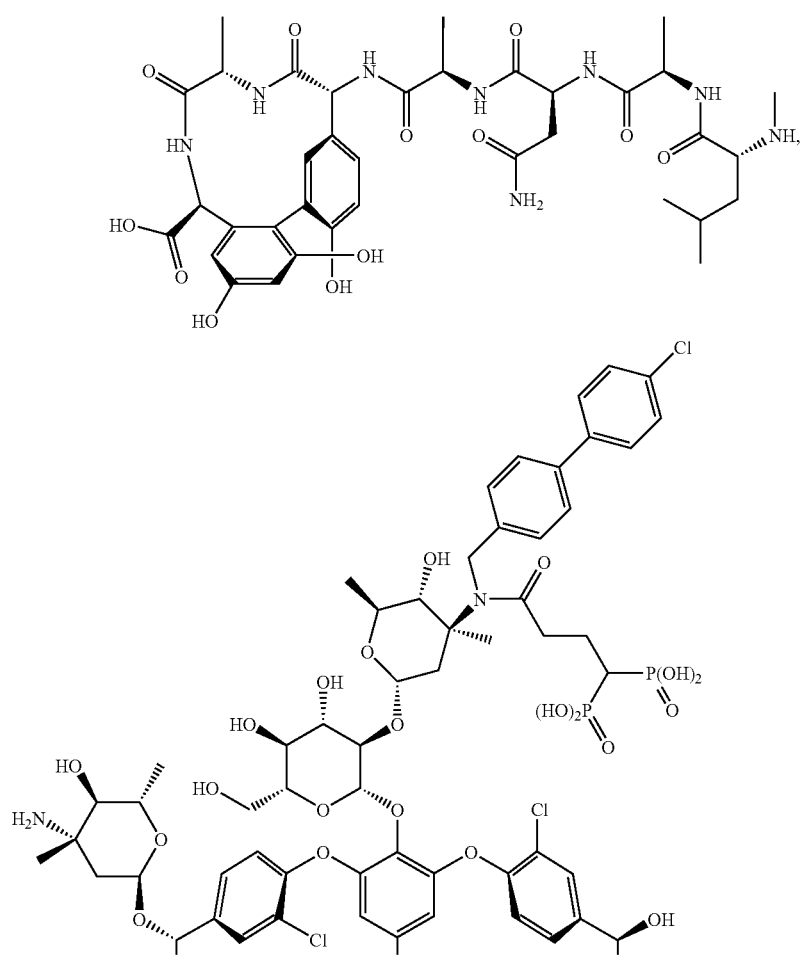

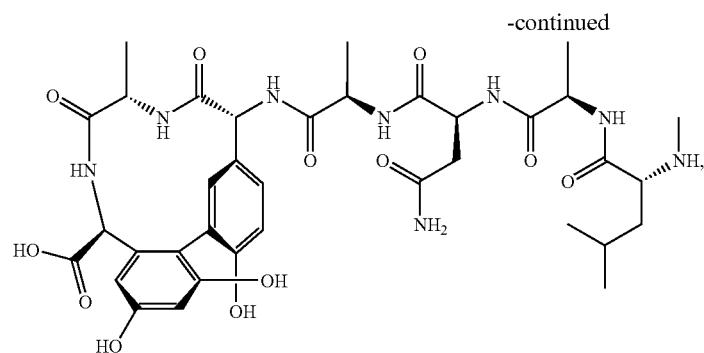
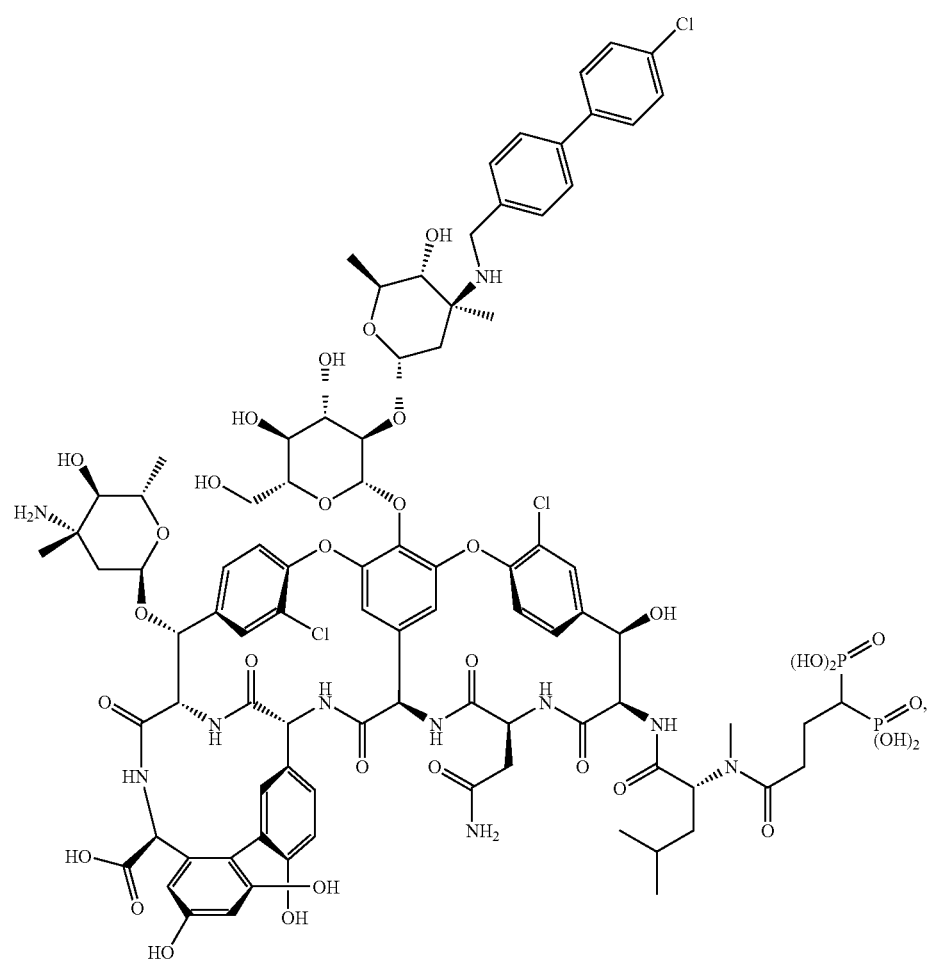
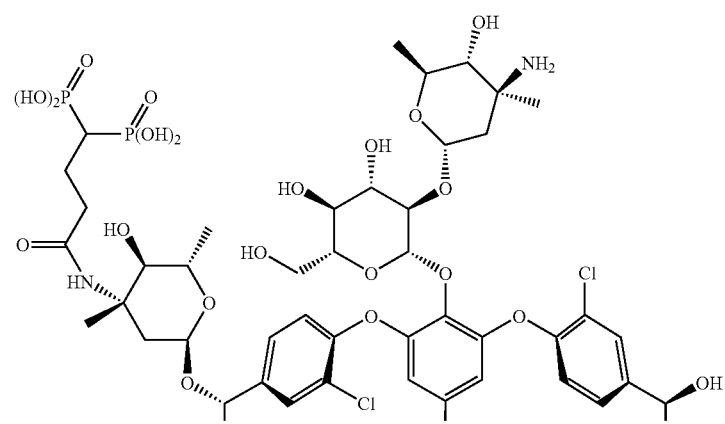

337
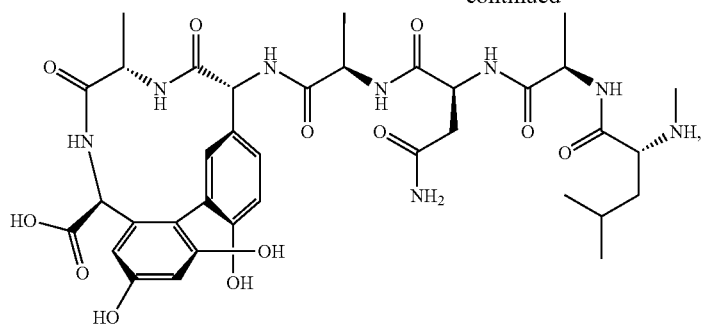
-continued
338
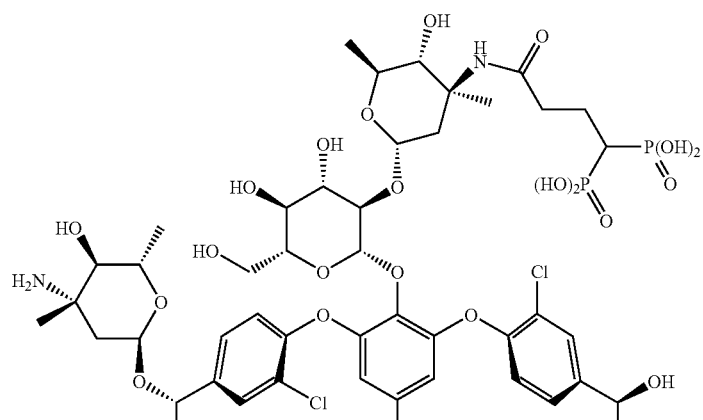
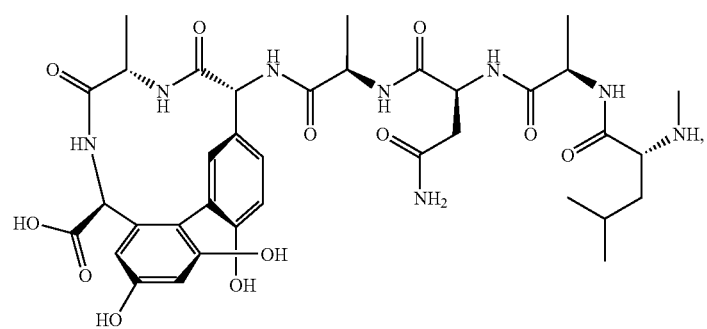
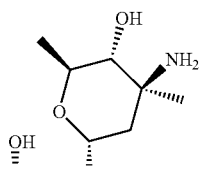

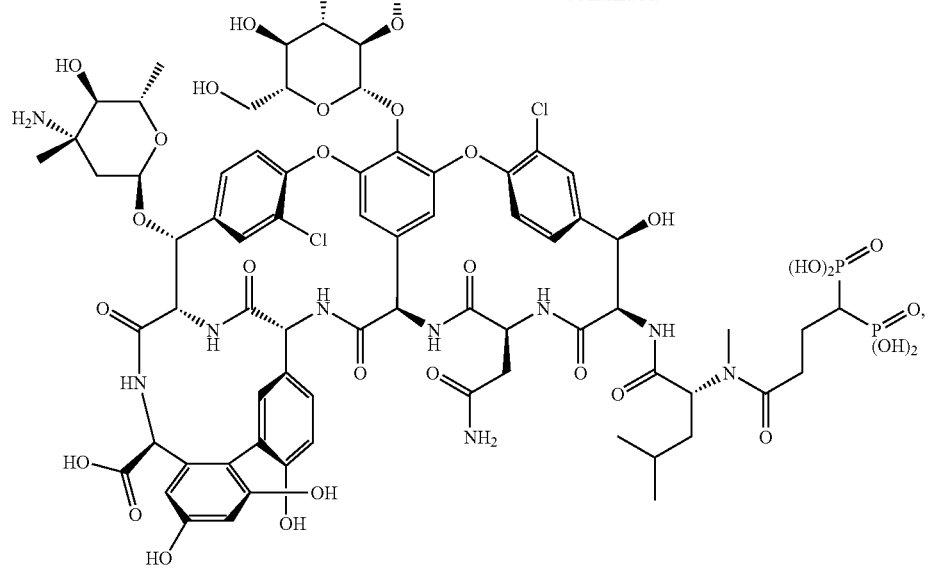
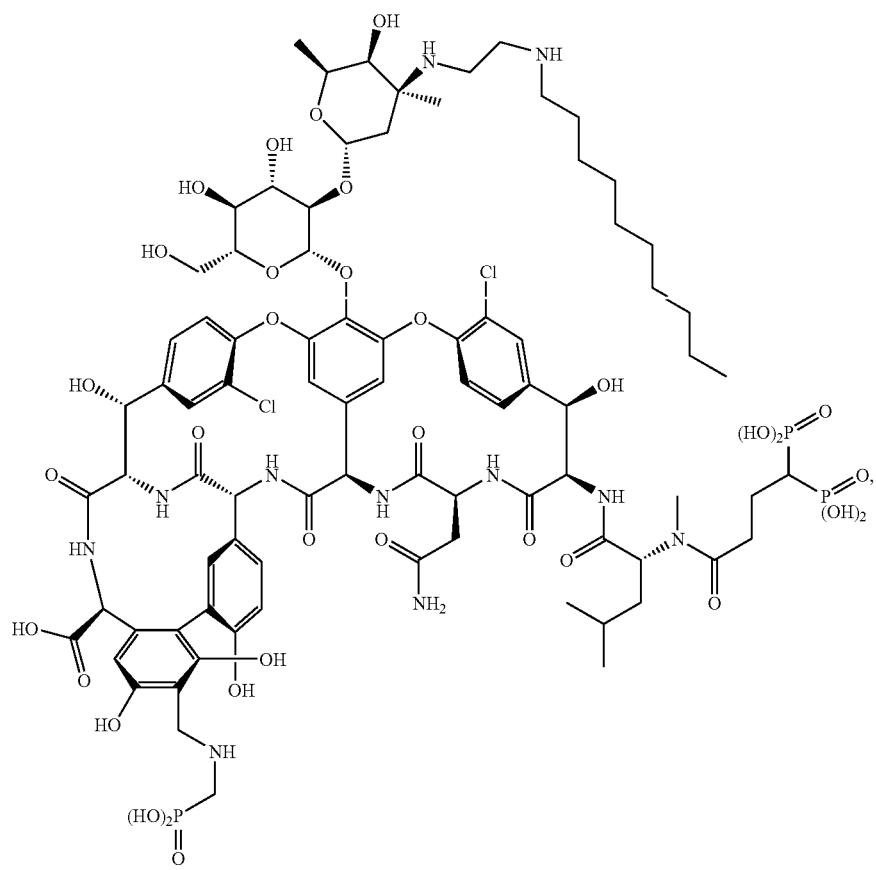

-continued
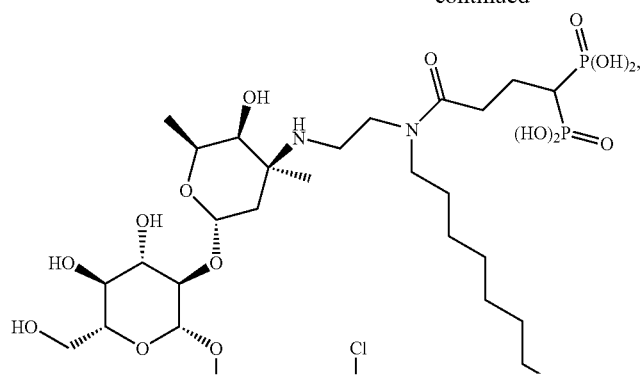
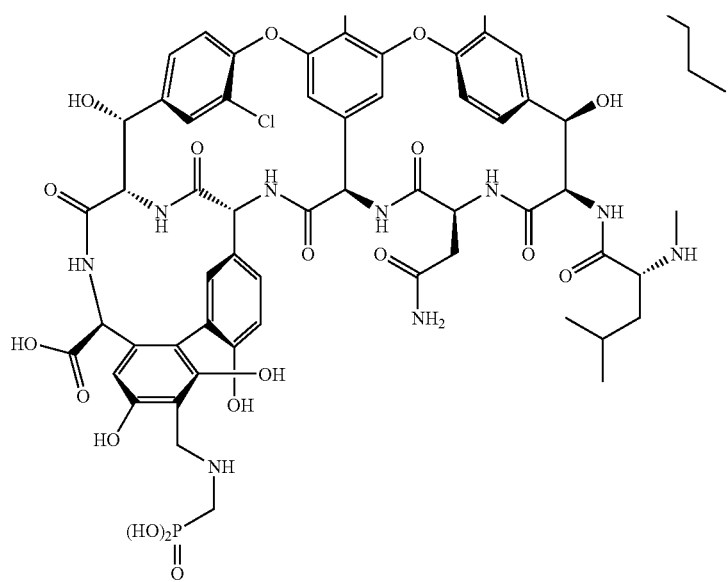
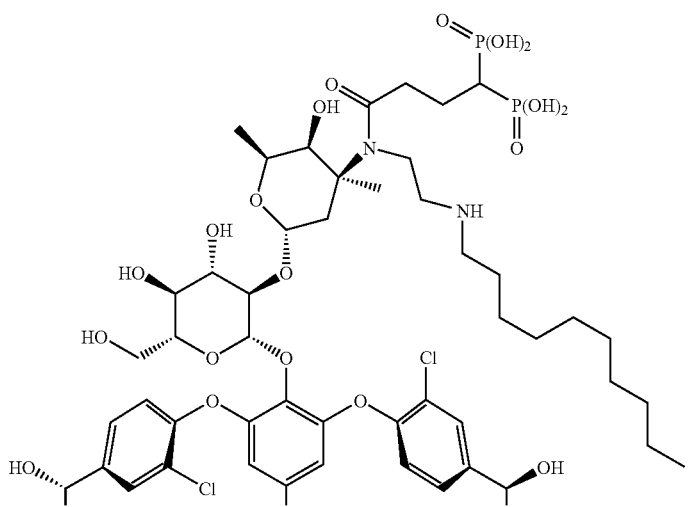

343
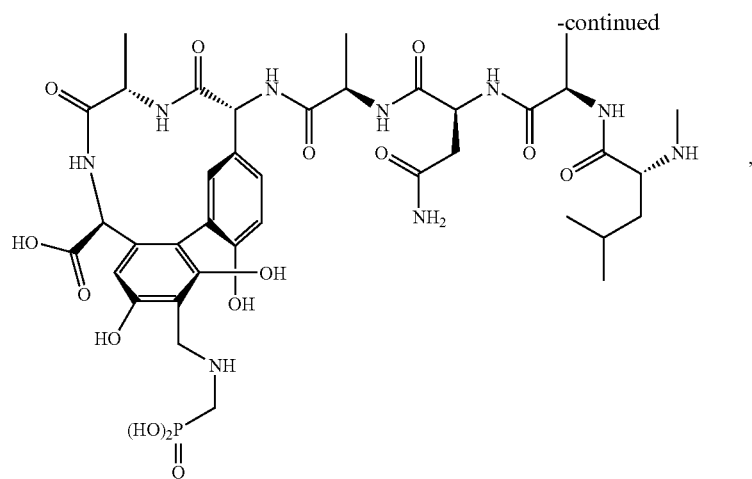
344
-continued
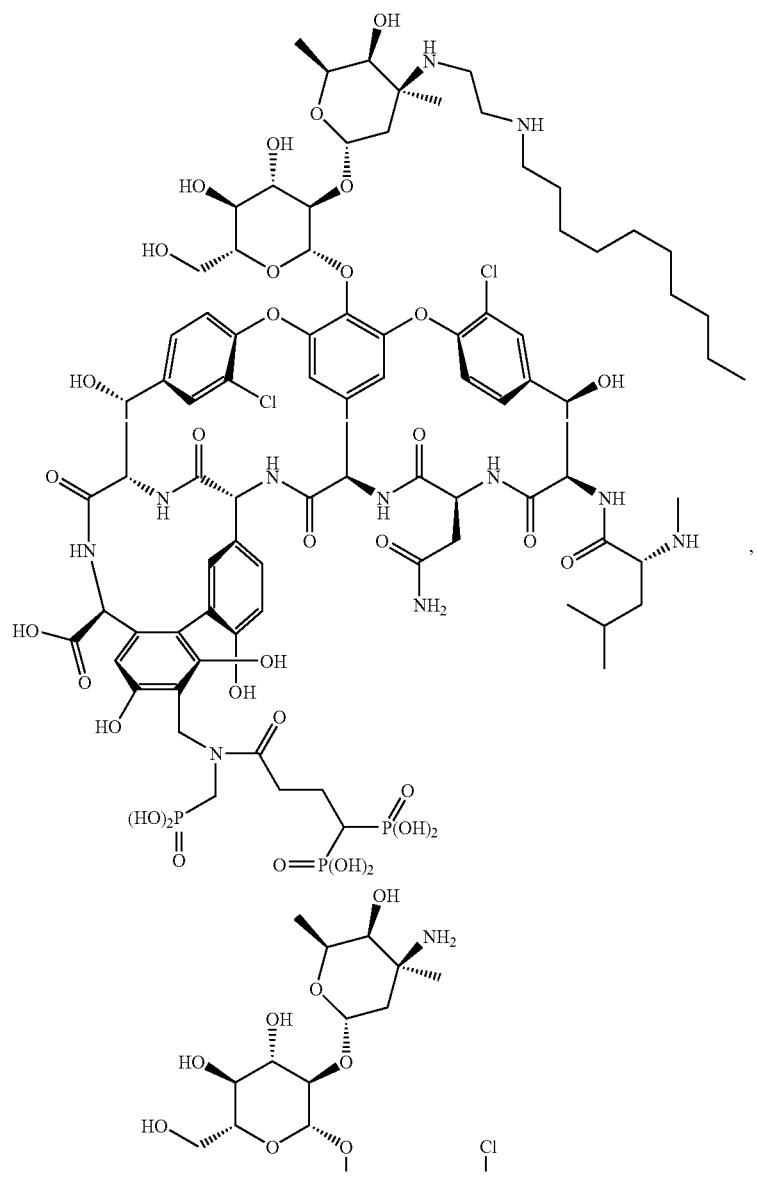

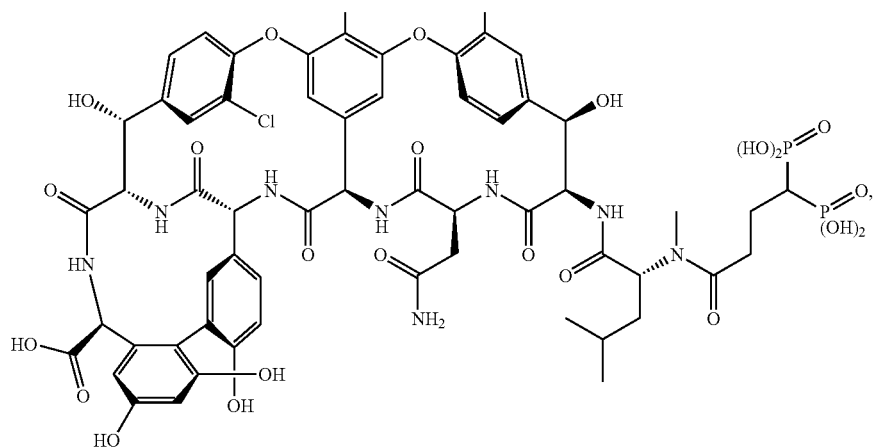
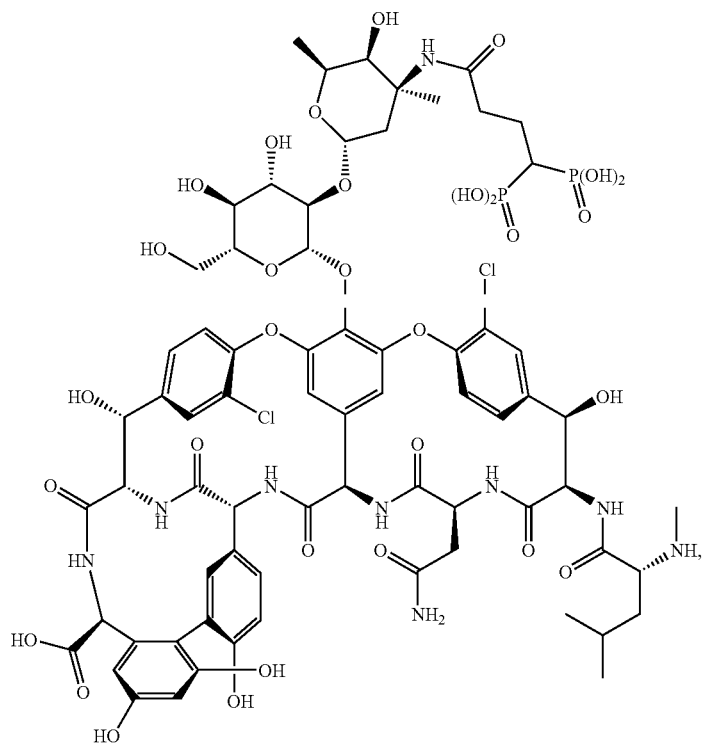

-continued
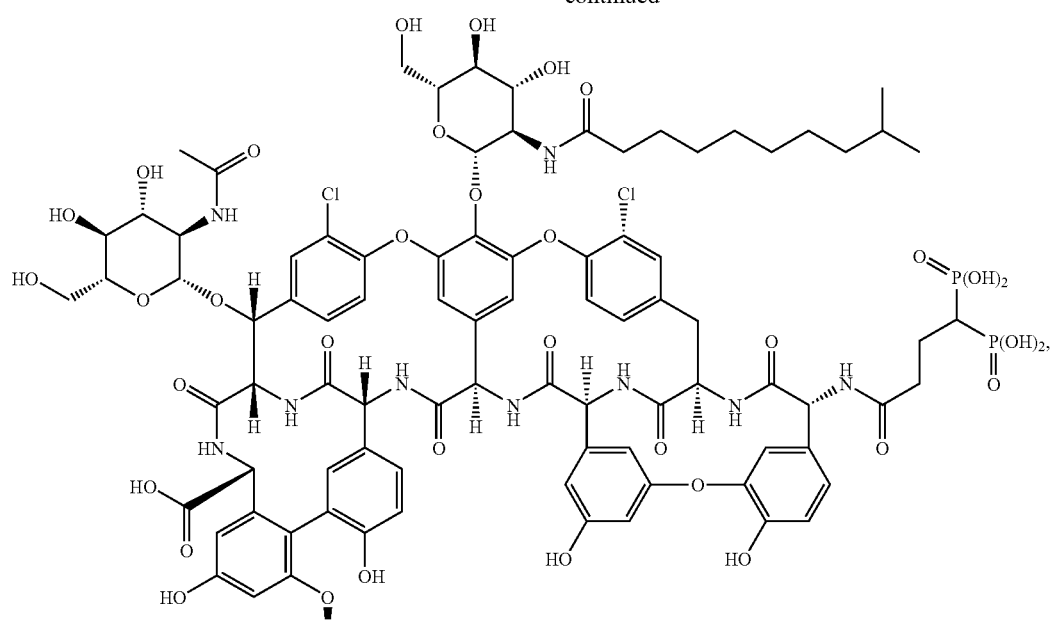
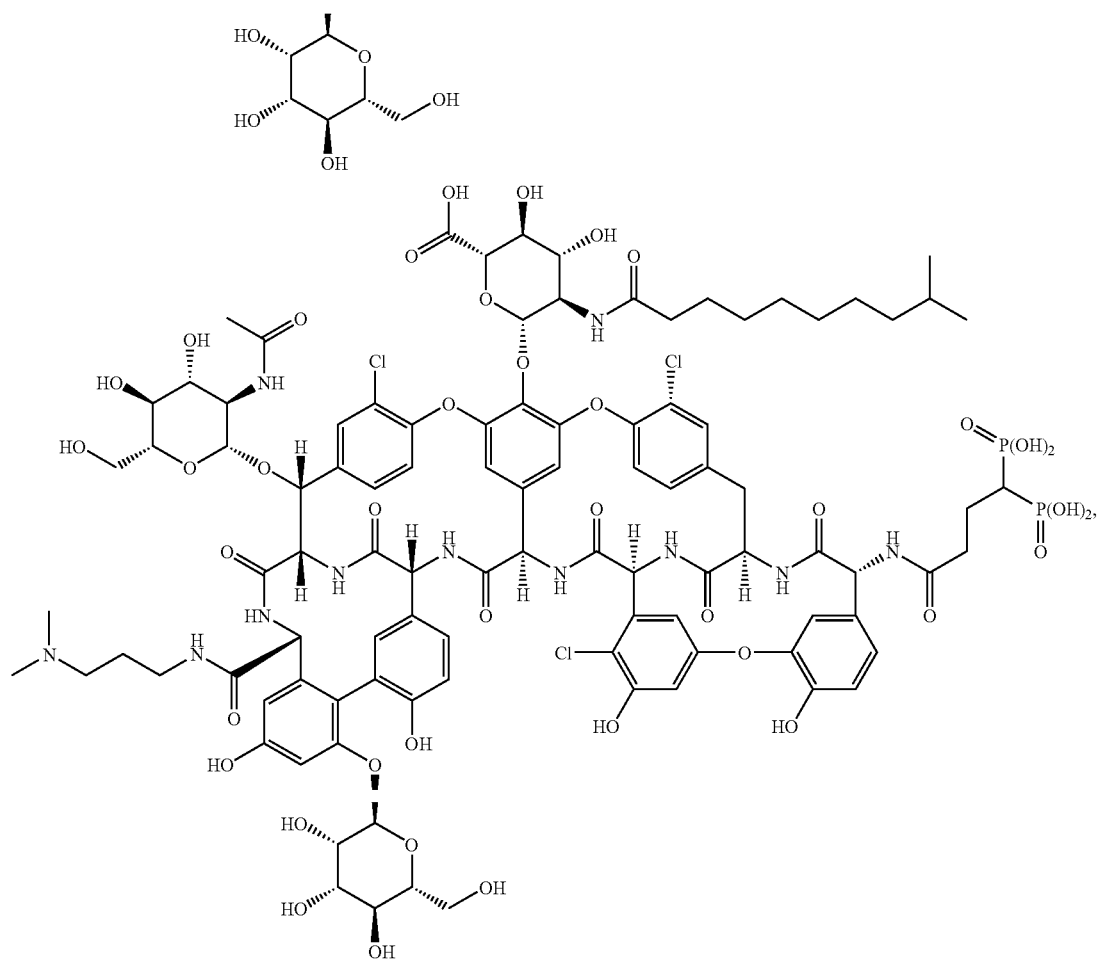

-continued
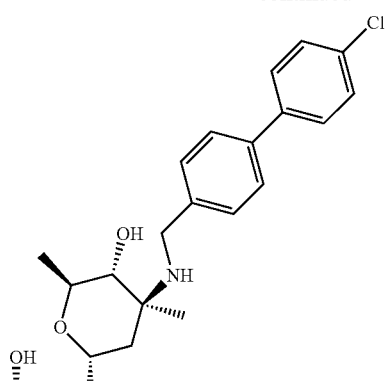
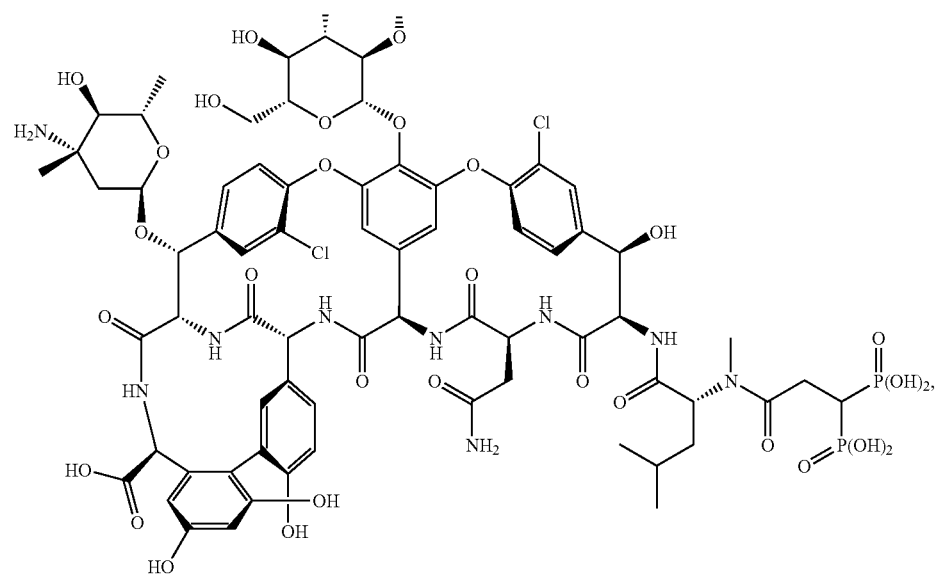
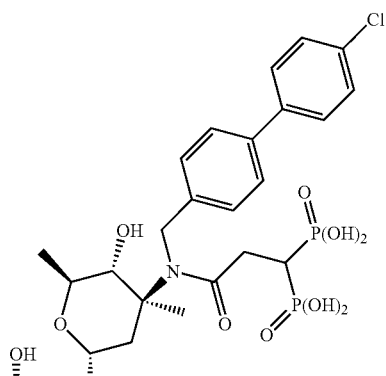

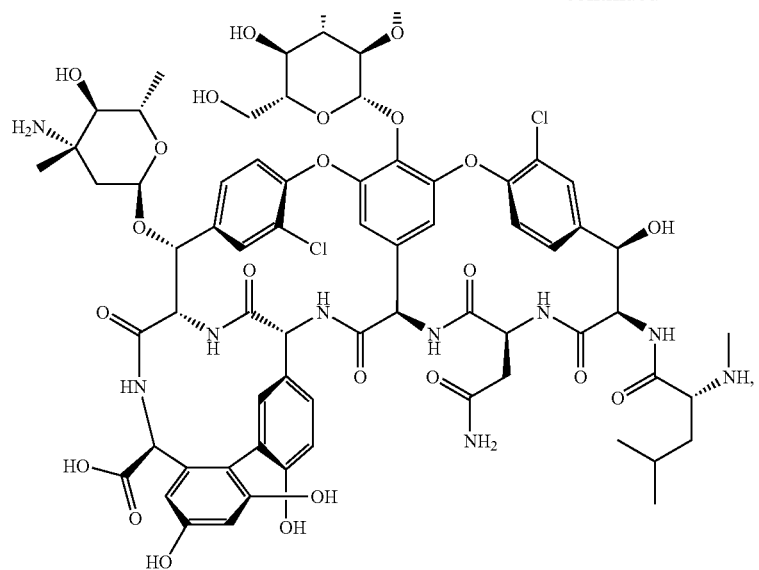
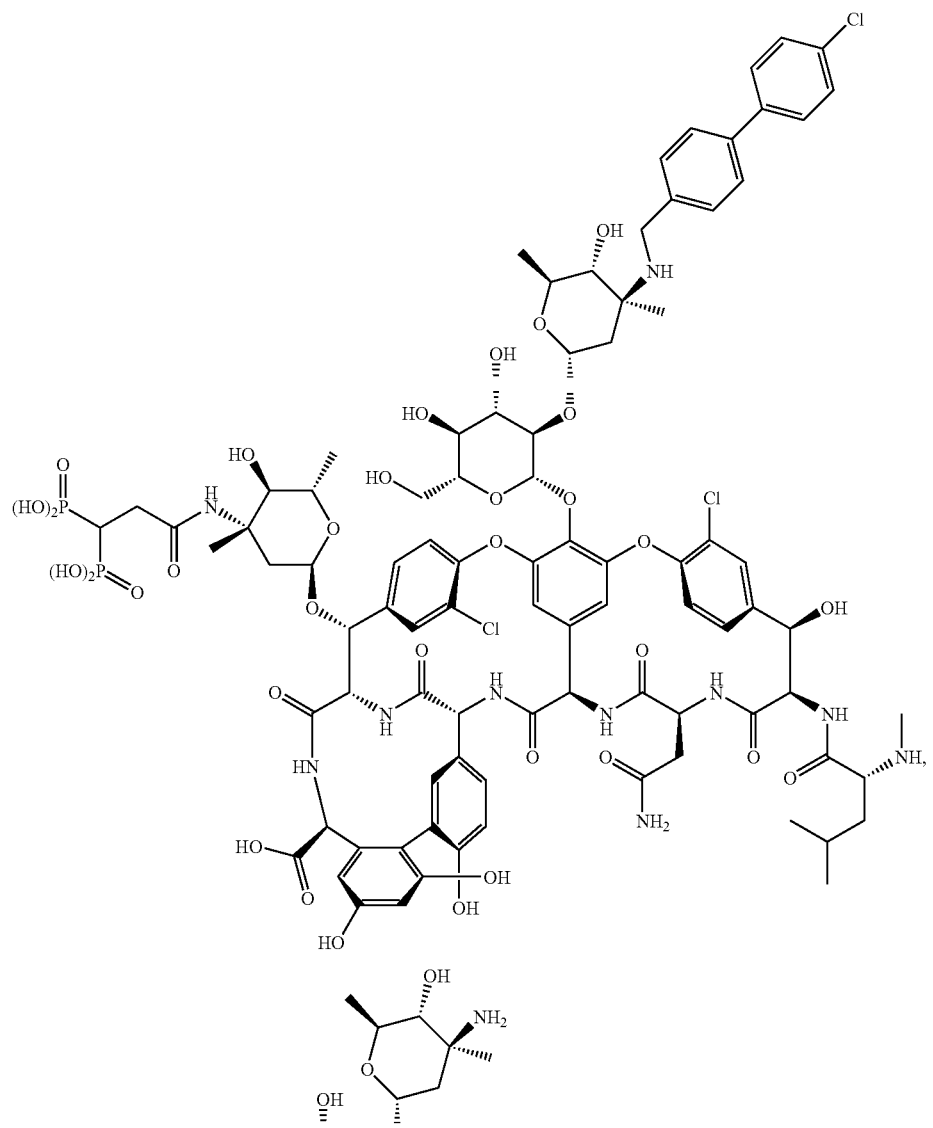

-continued
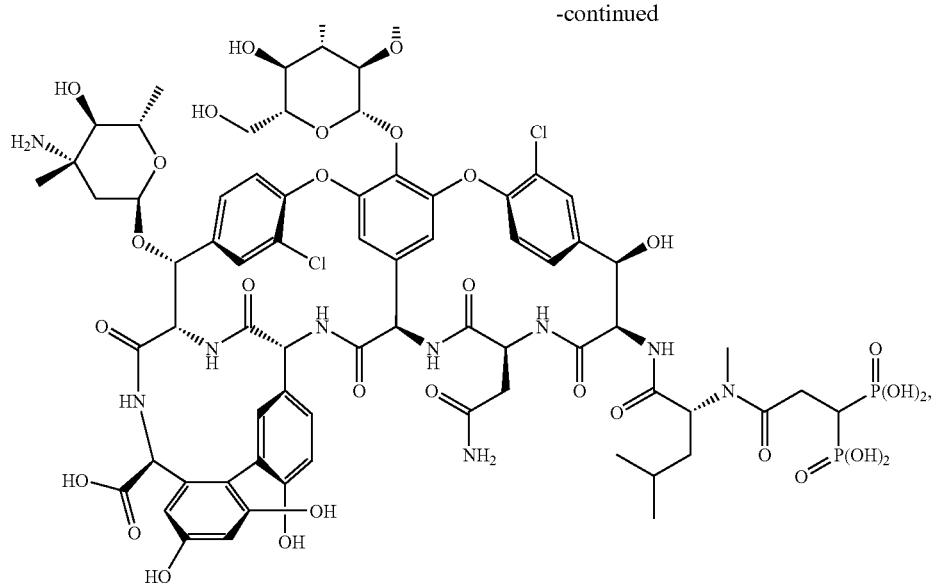
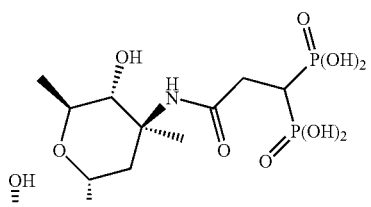
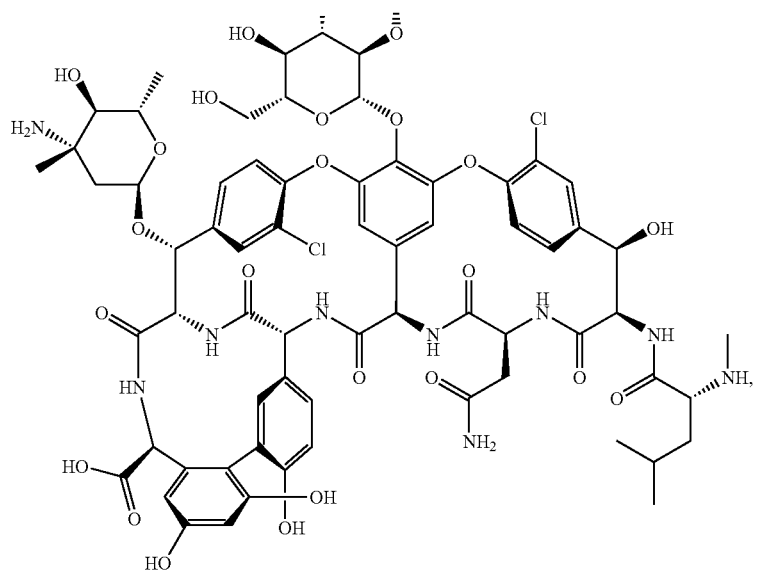
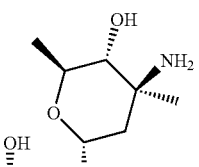

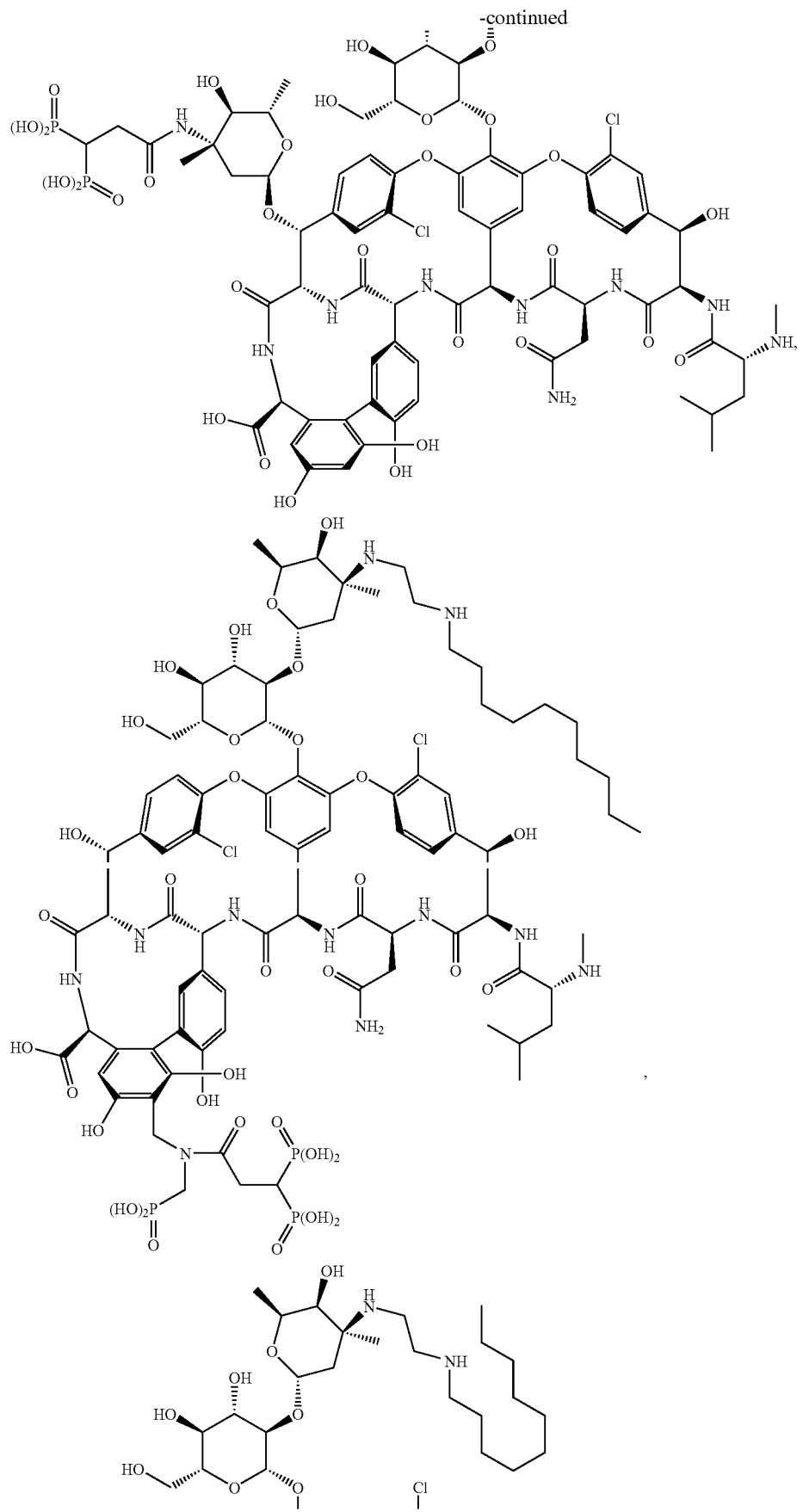

357
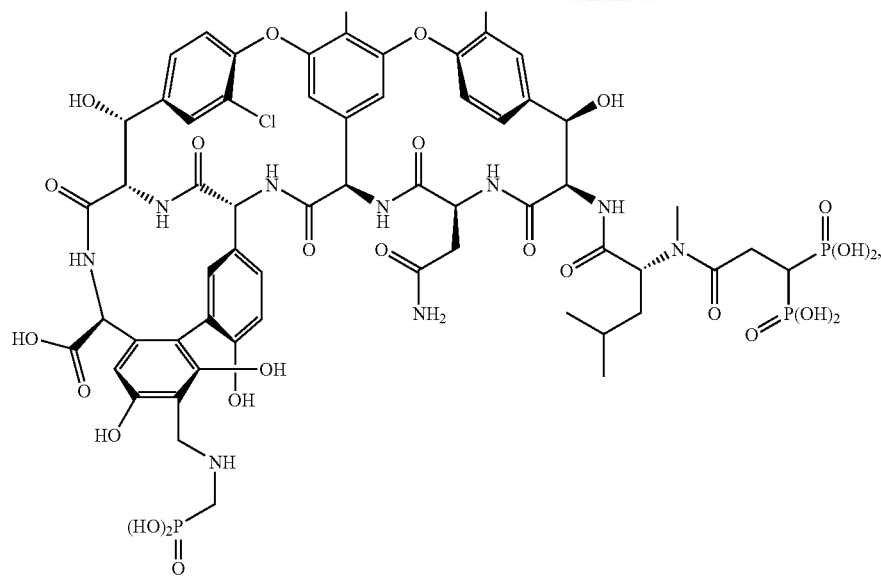
-continued
358
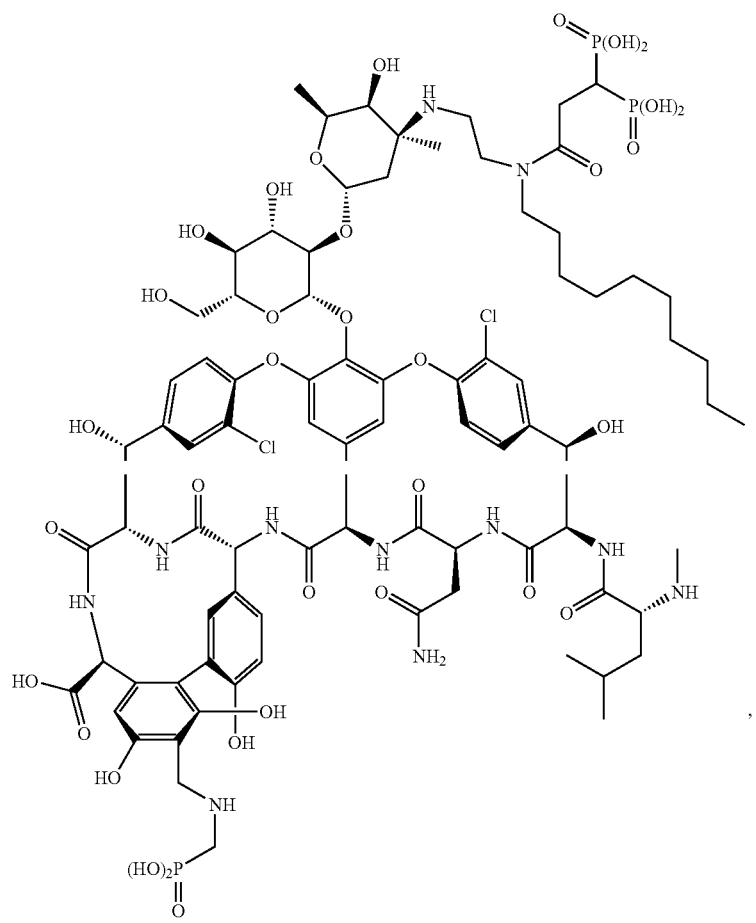

-continued
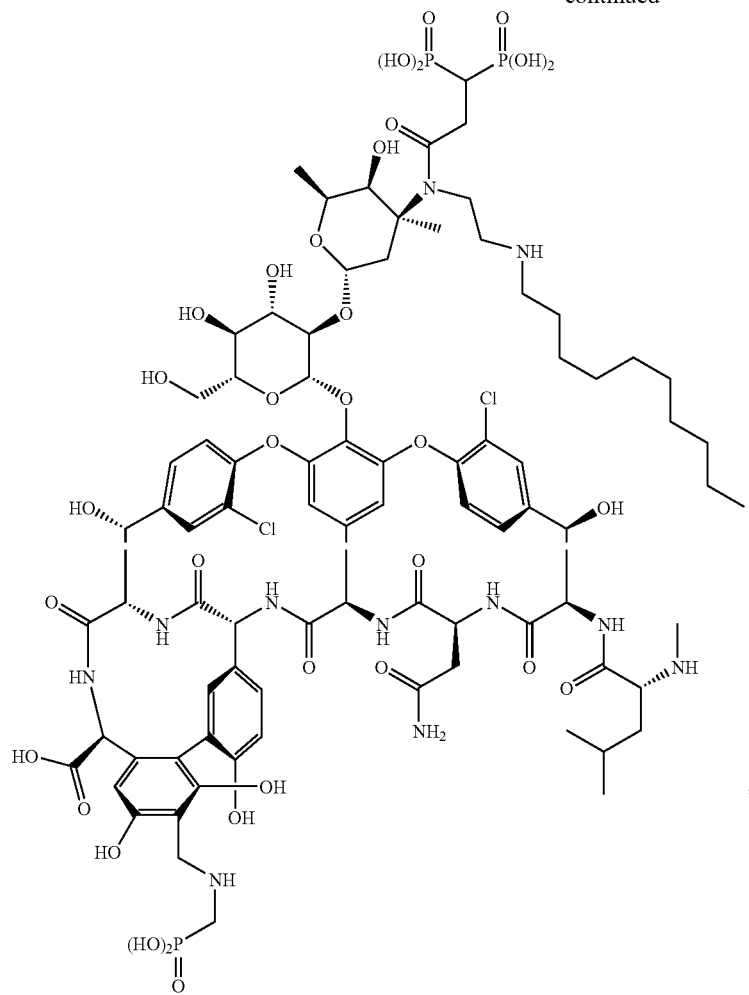
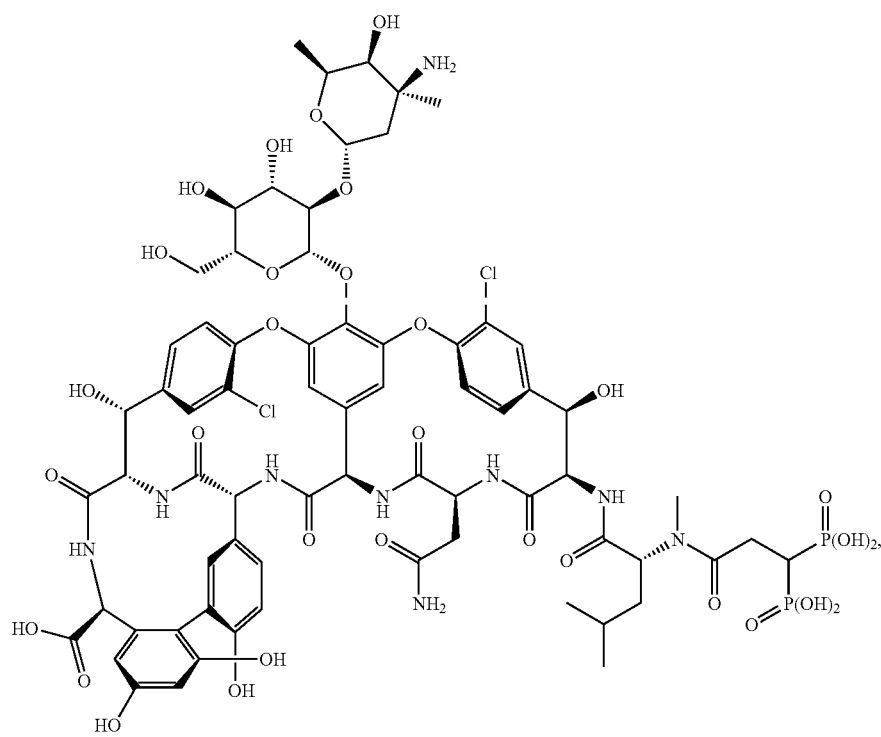

-continued
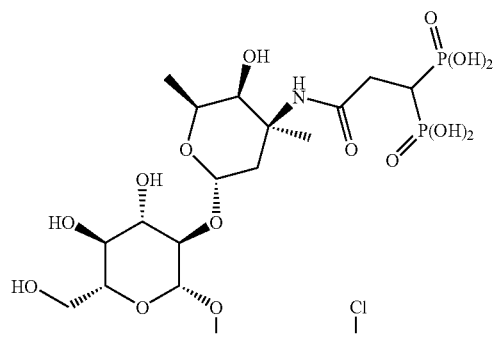
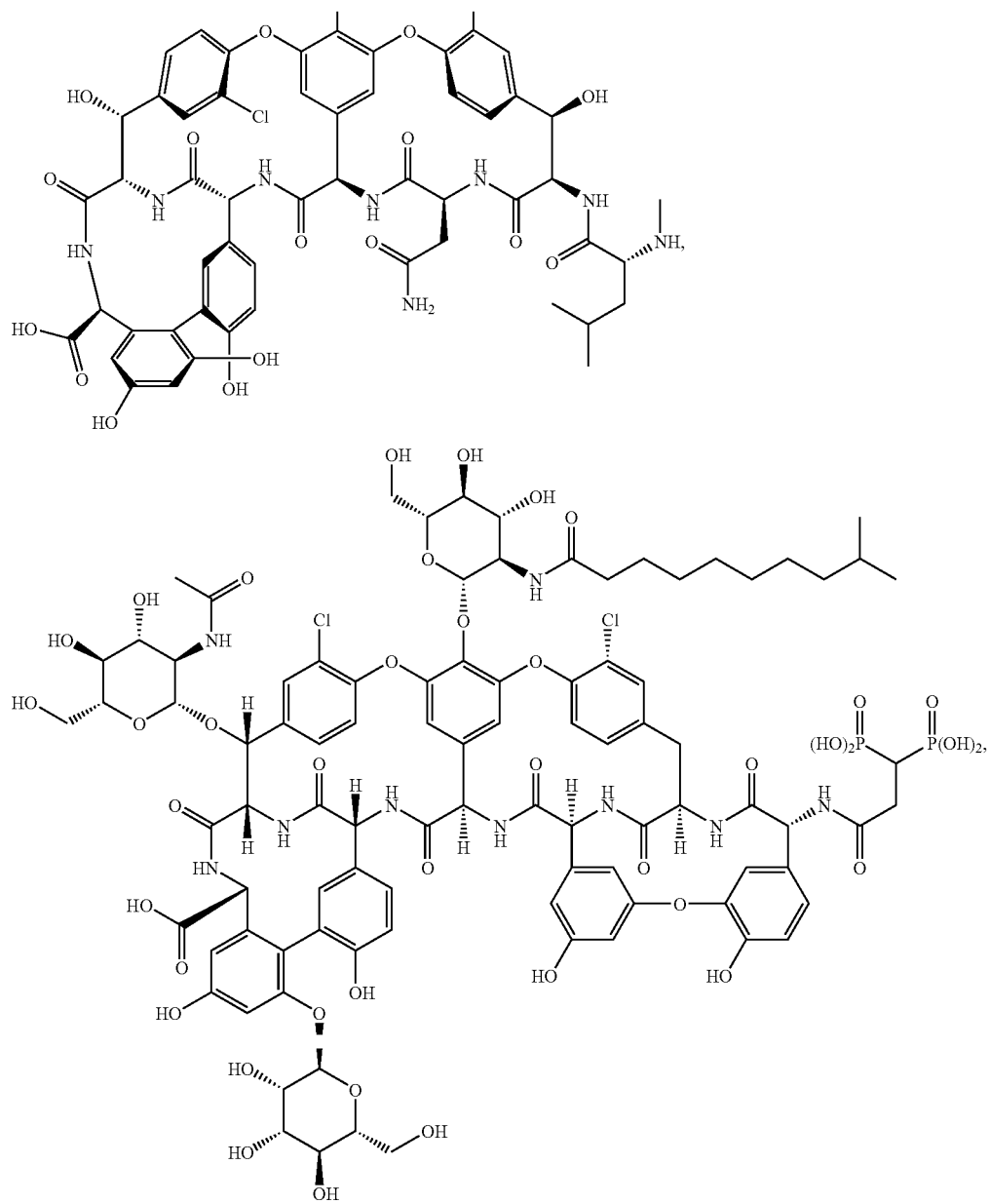

363
364
-continued
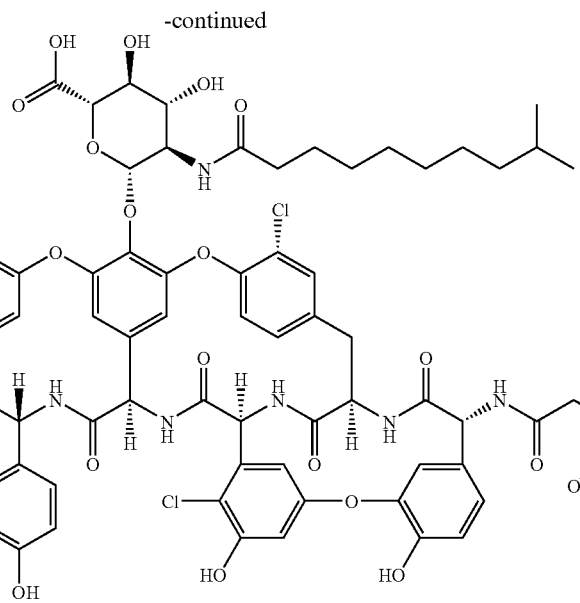
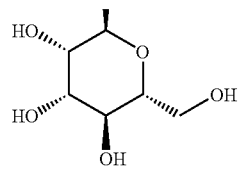
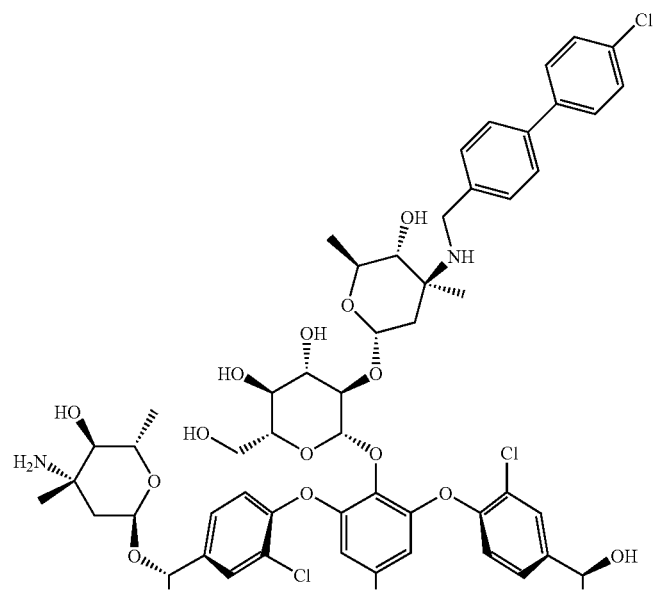

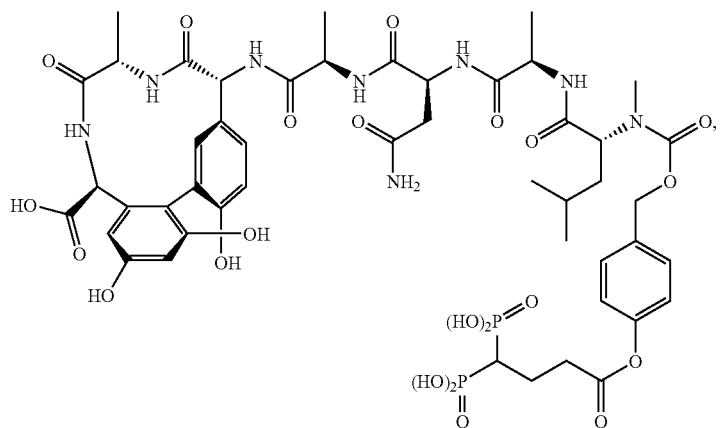
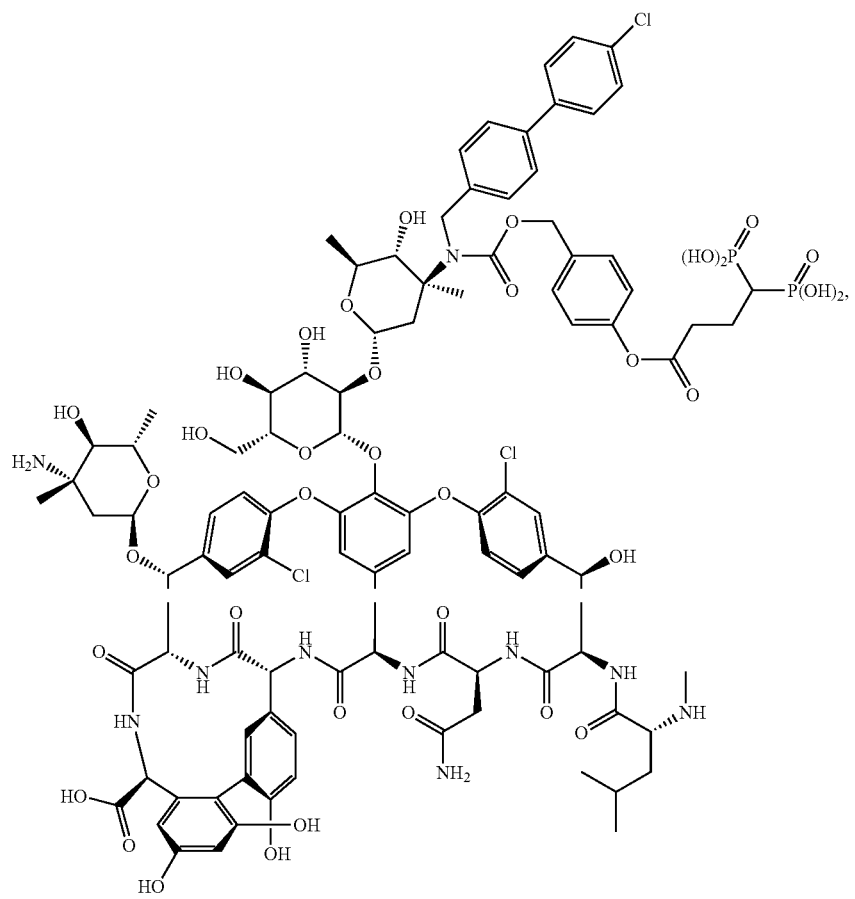

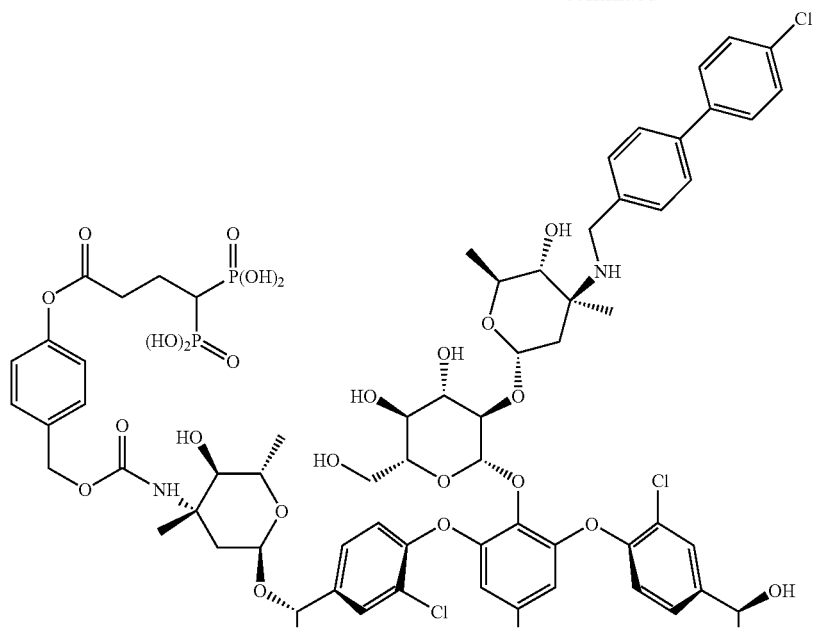
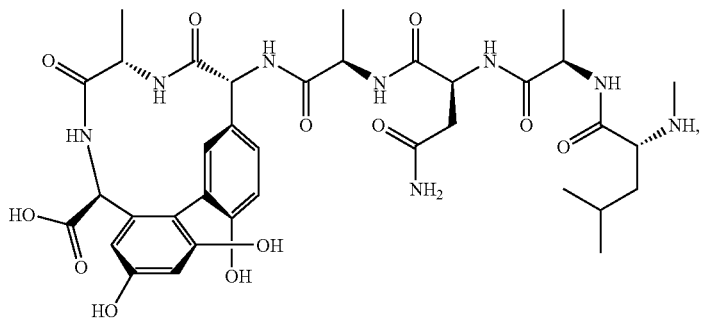
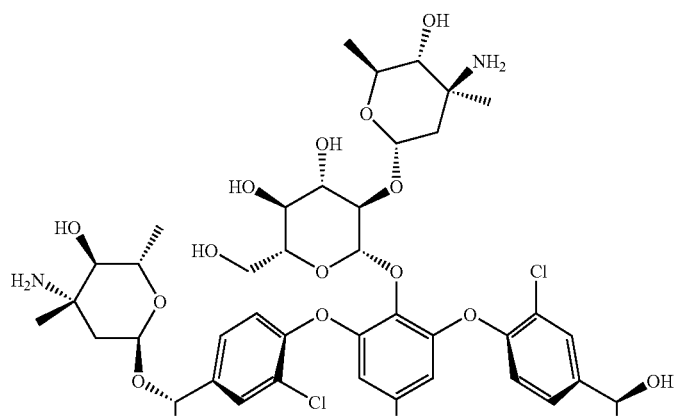

-continued
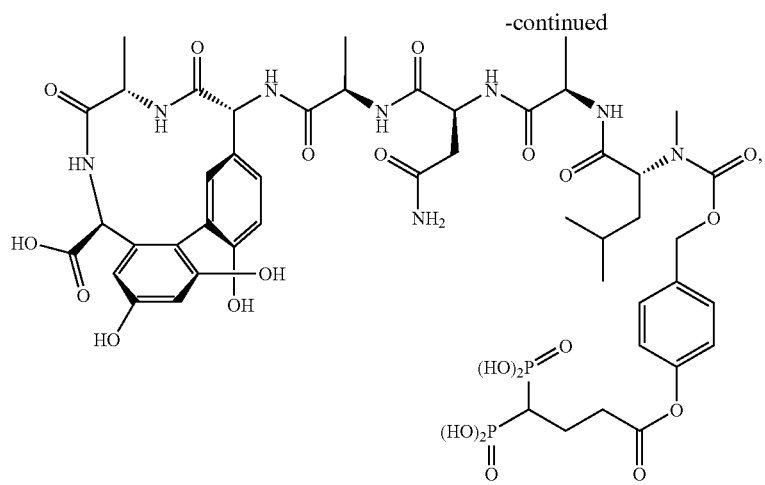
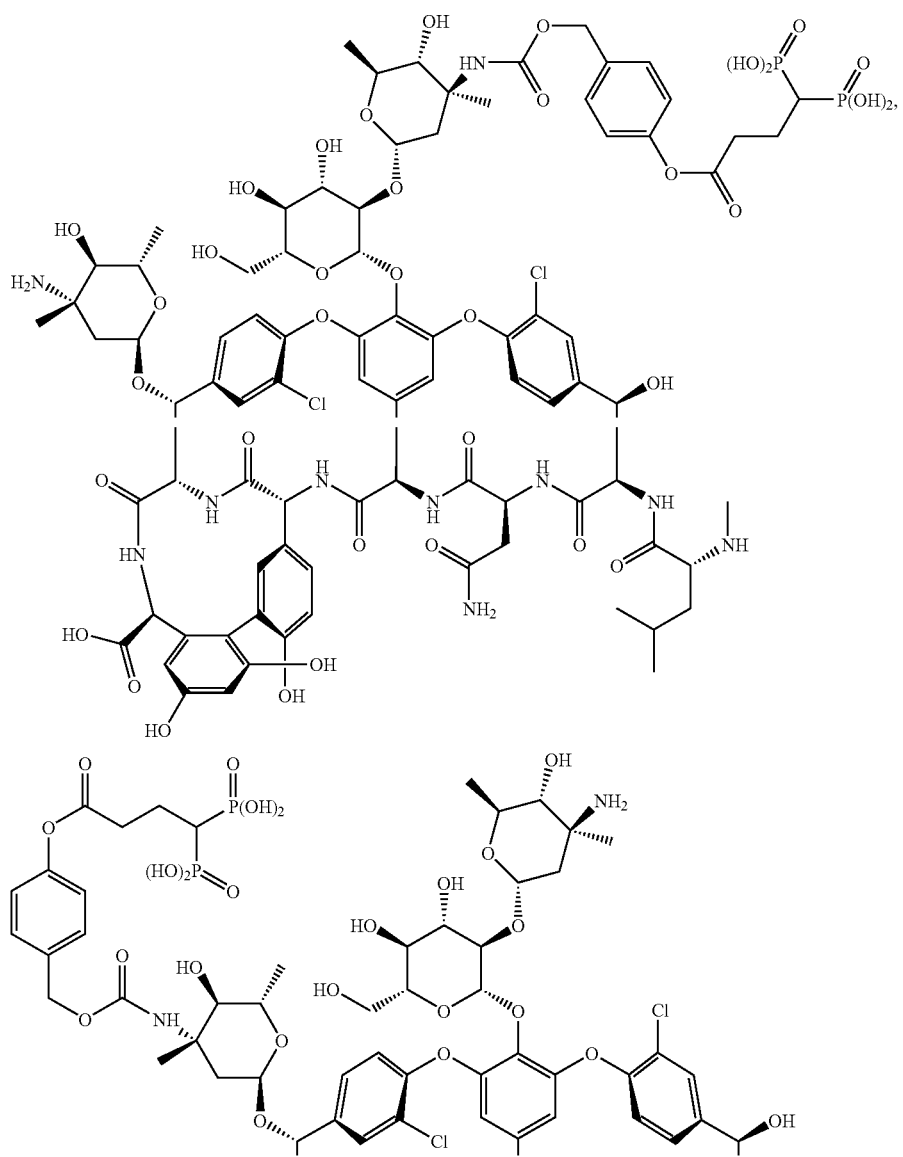

371
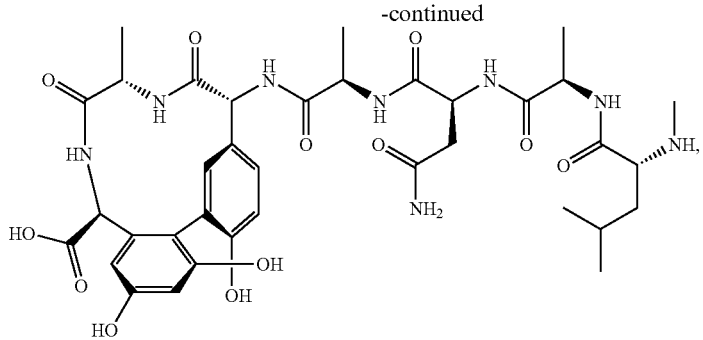
-continued
372
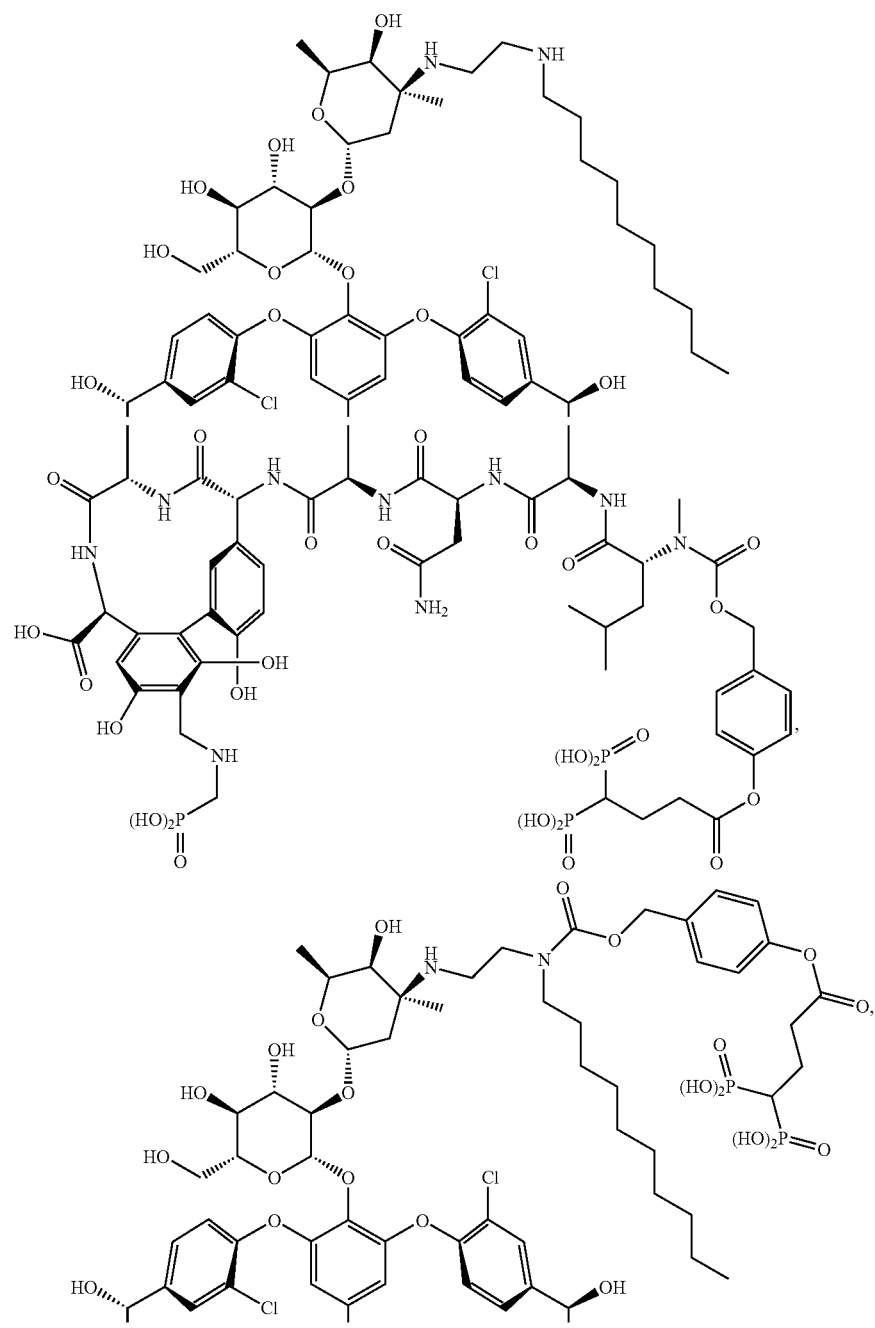

373
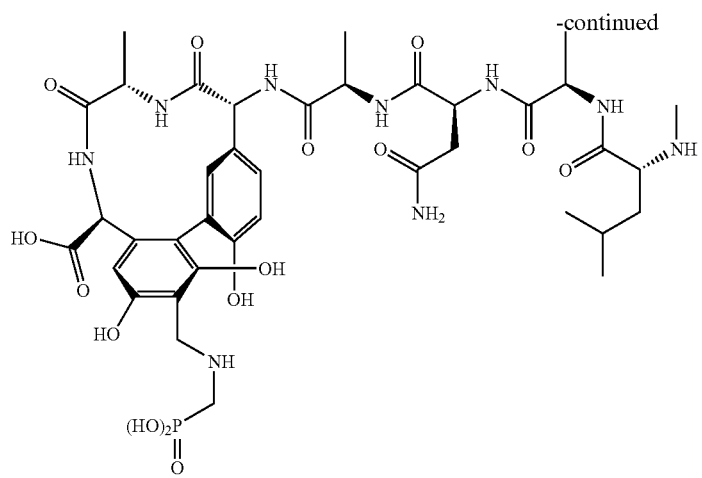
-continued
374
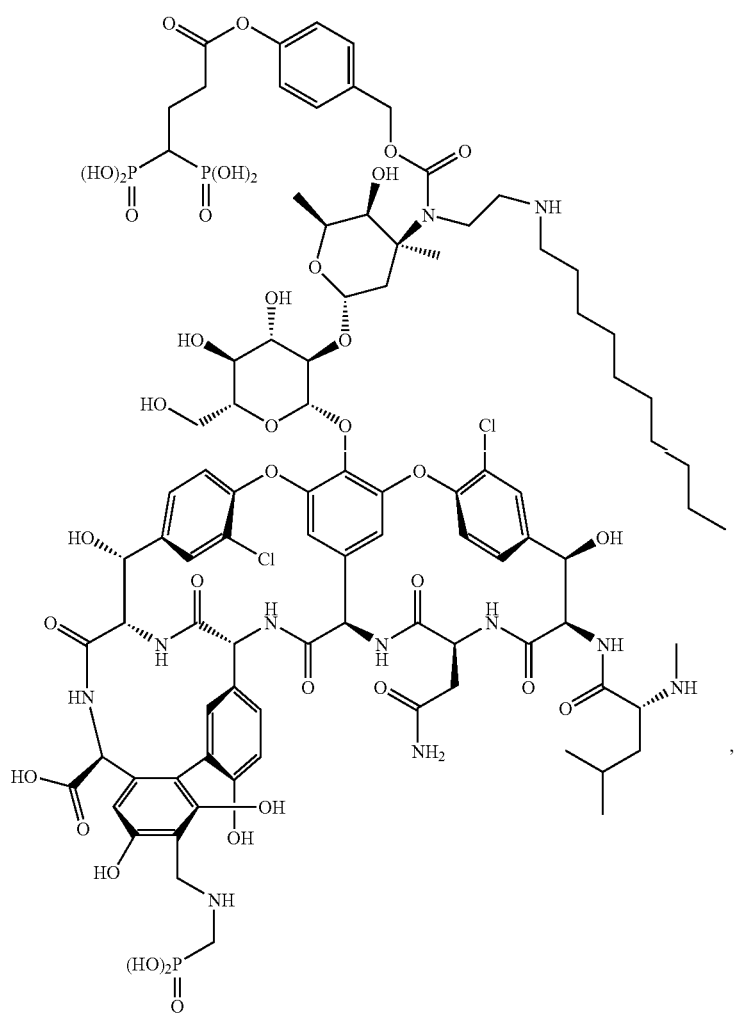

-continued
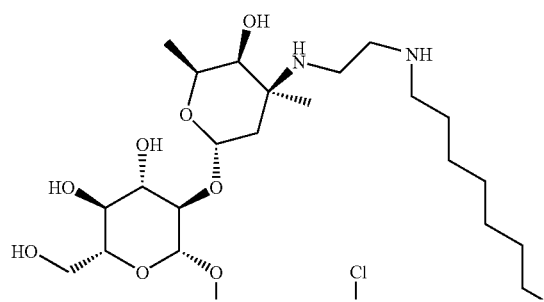
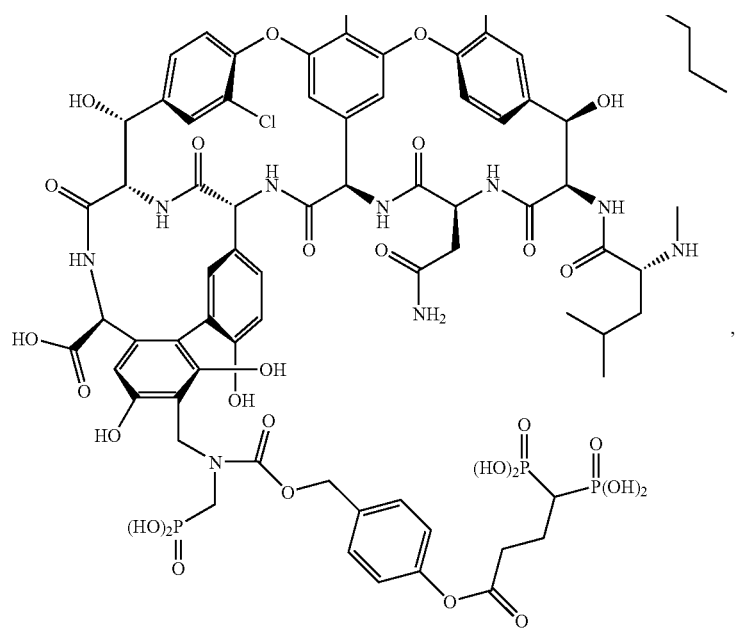
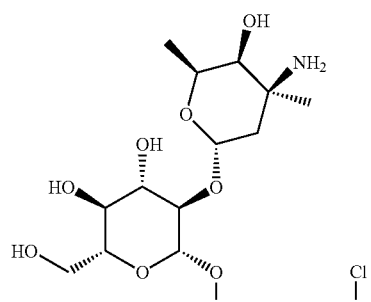

-continued
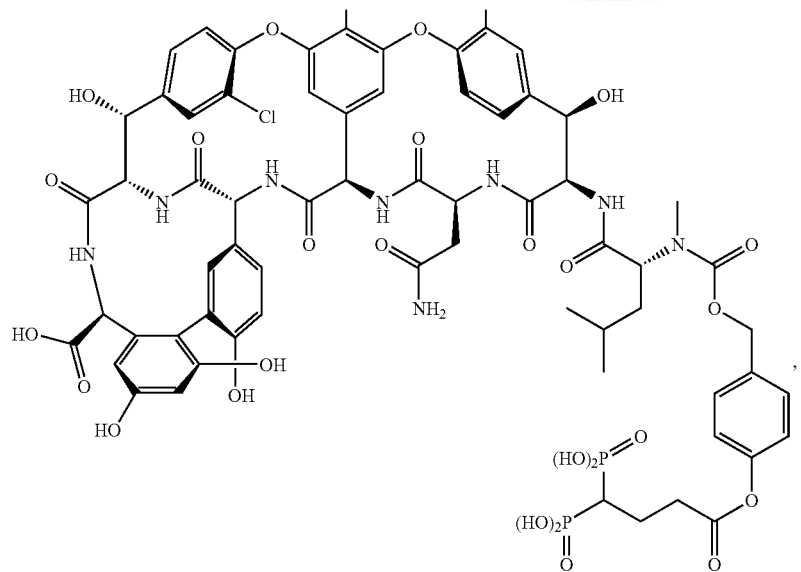
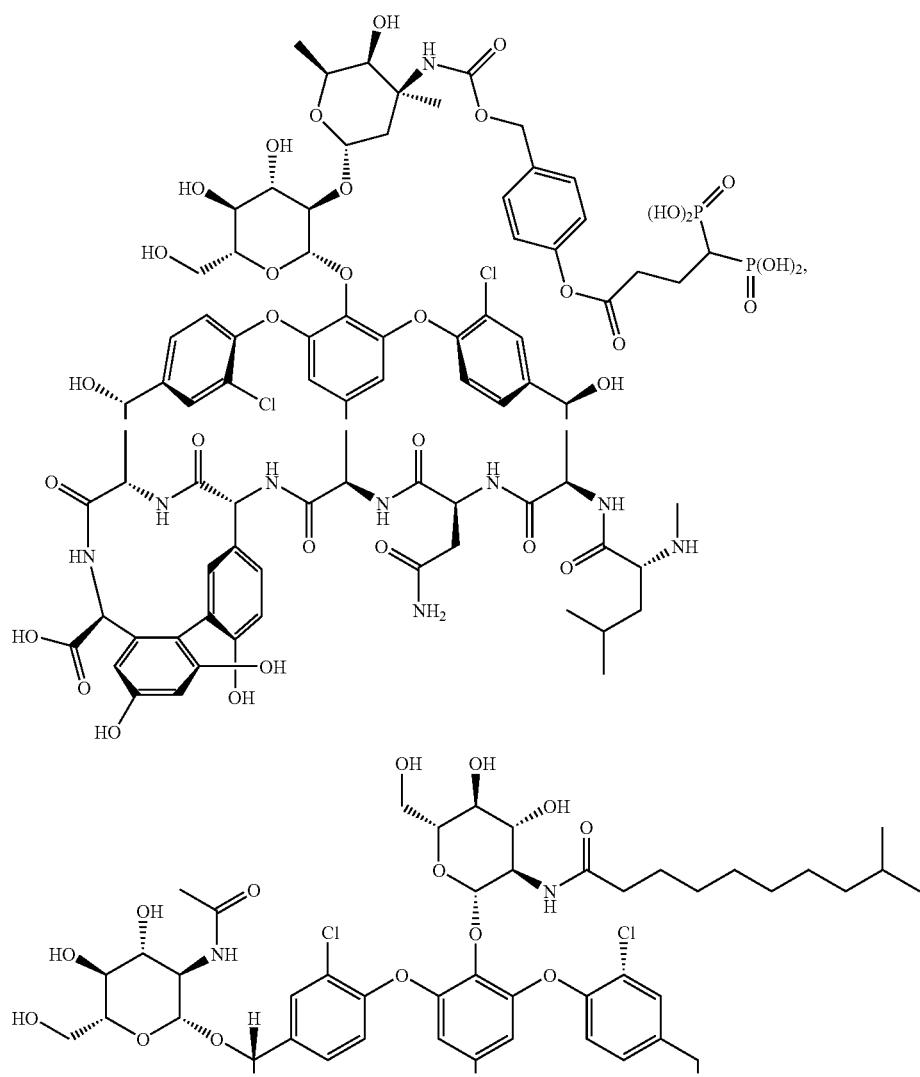

-continued
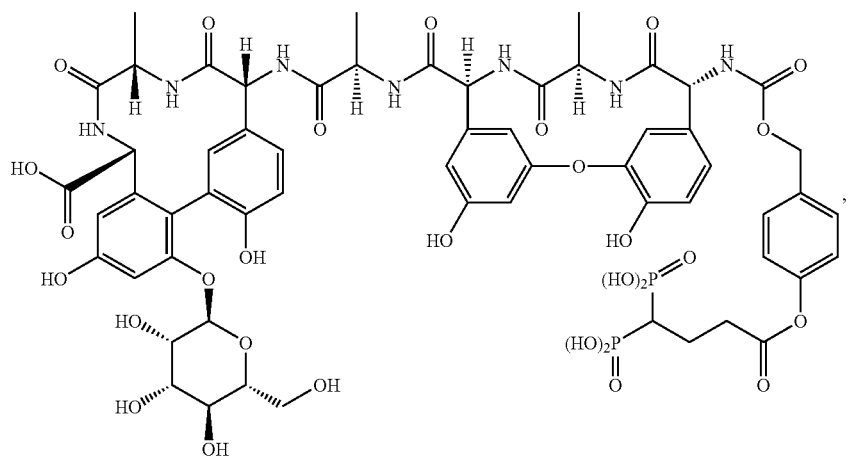
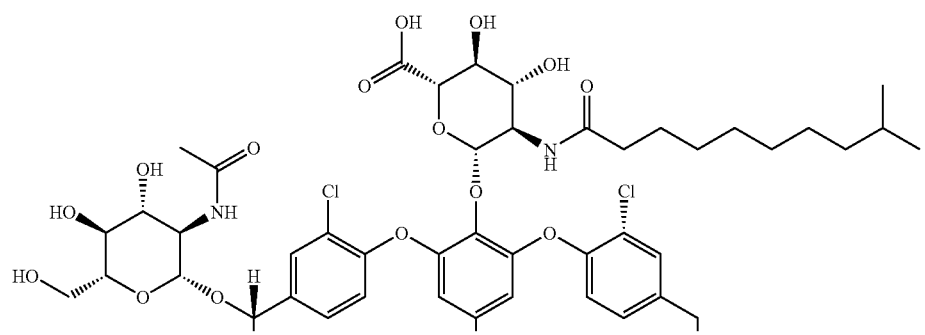
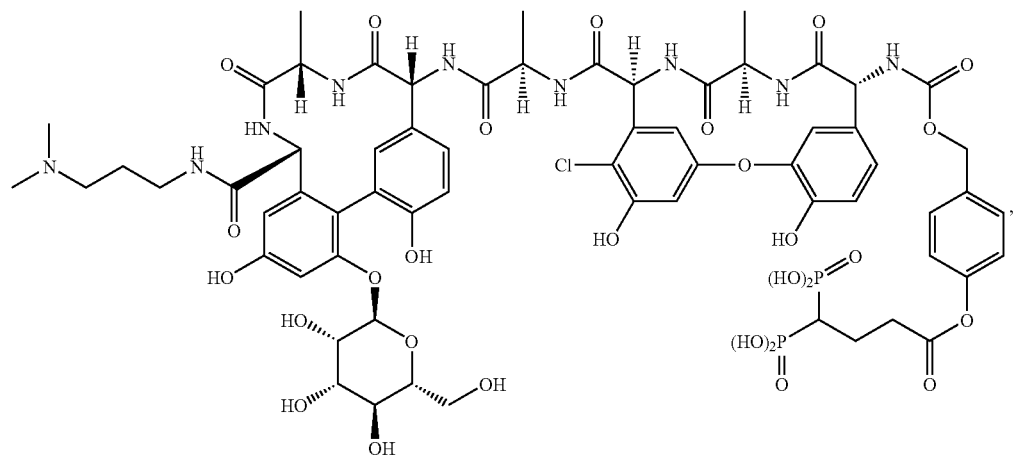

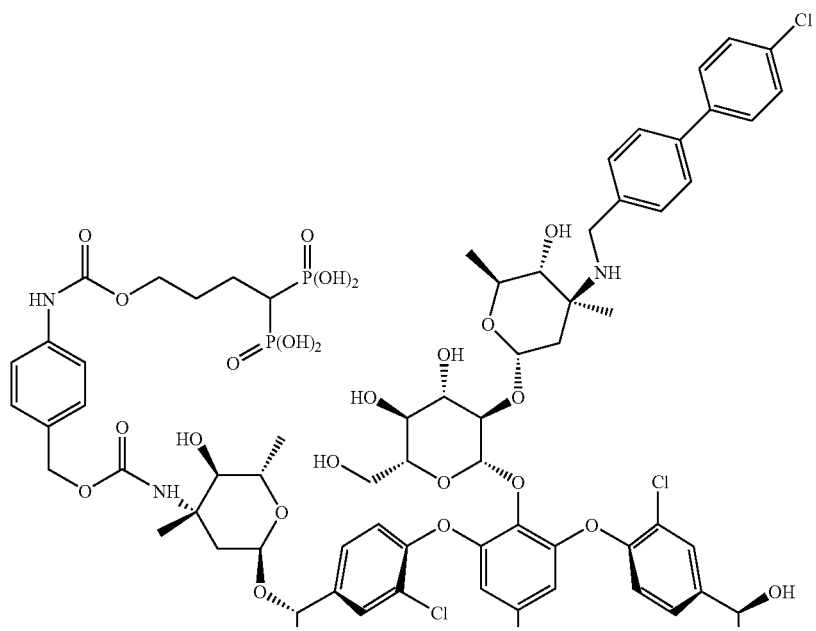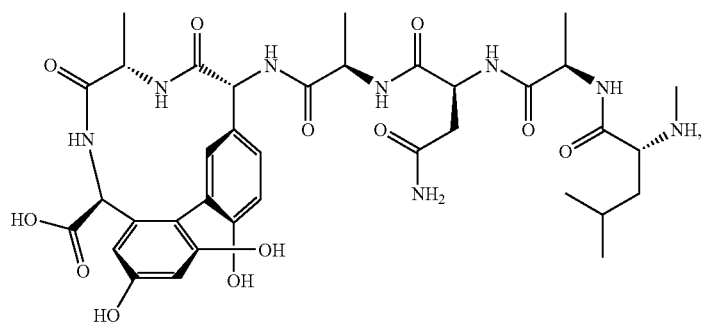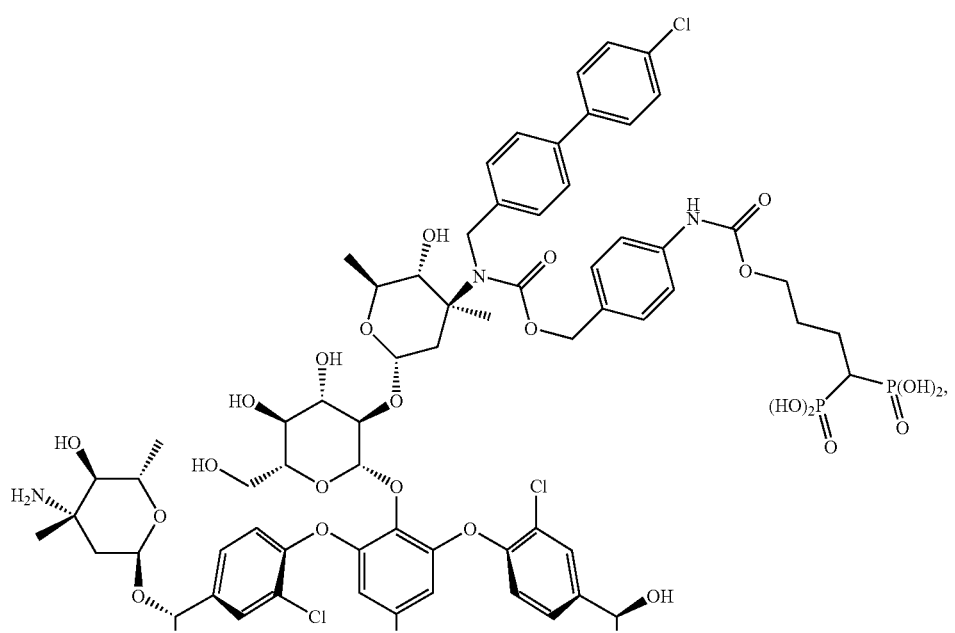

383
-continued
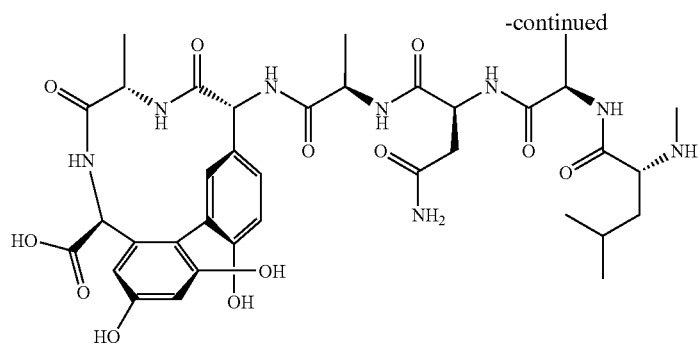
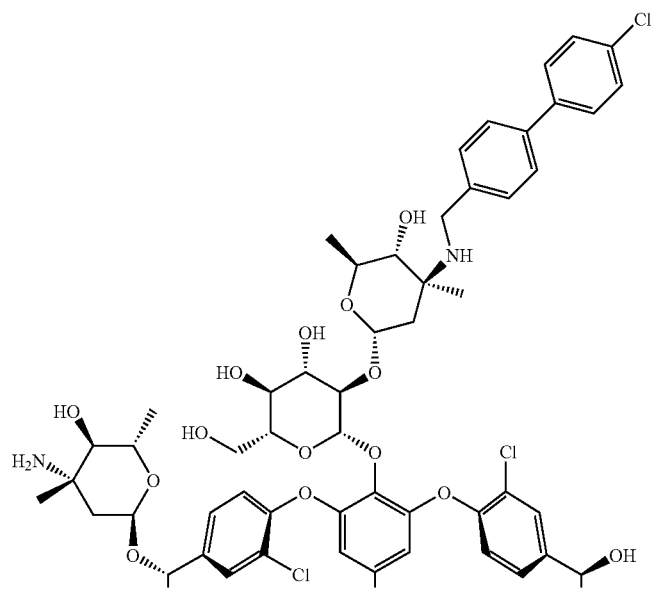
384
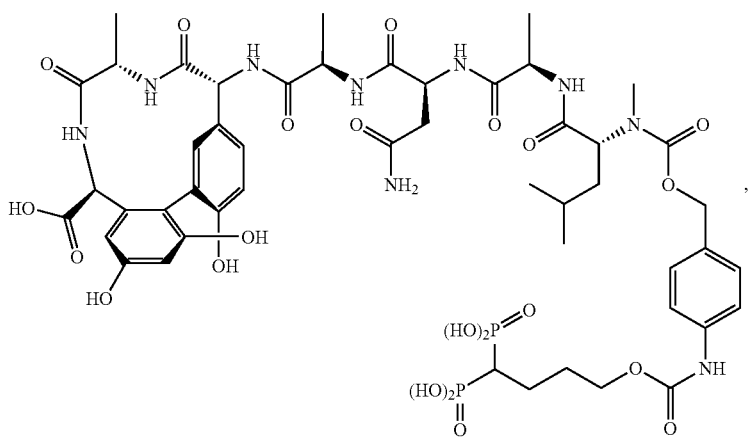

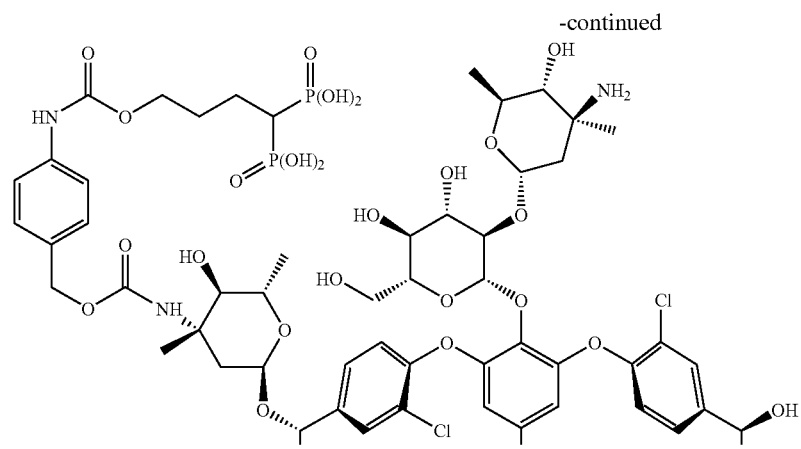
-continued
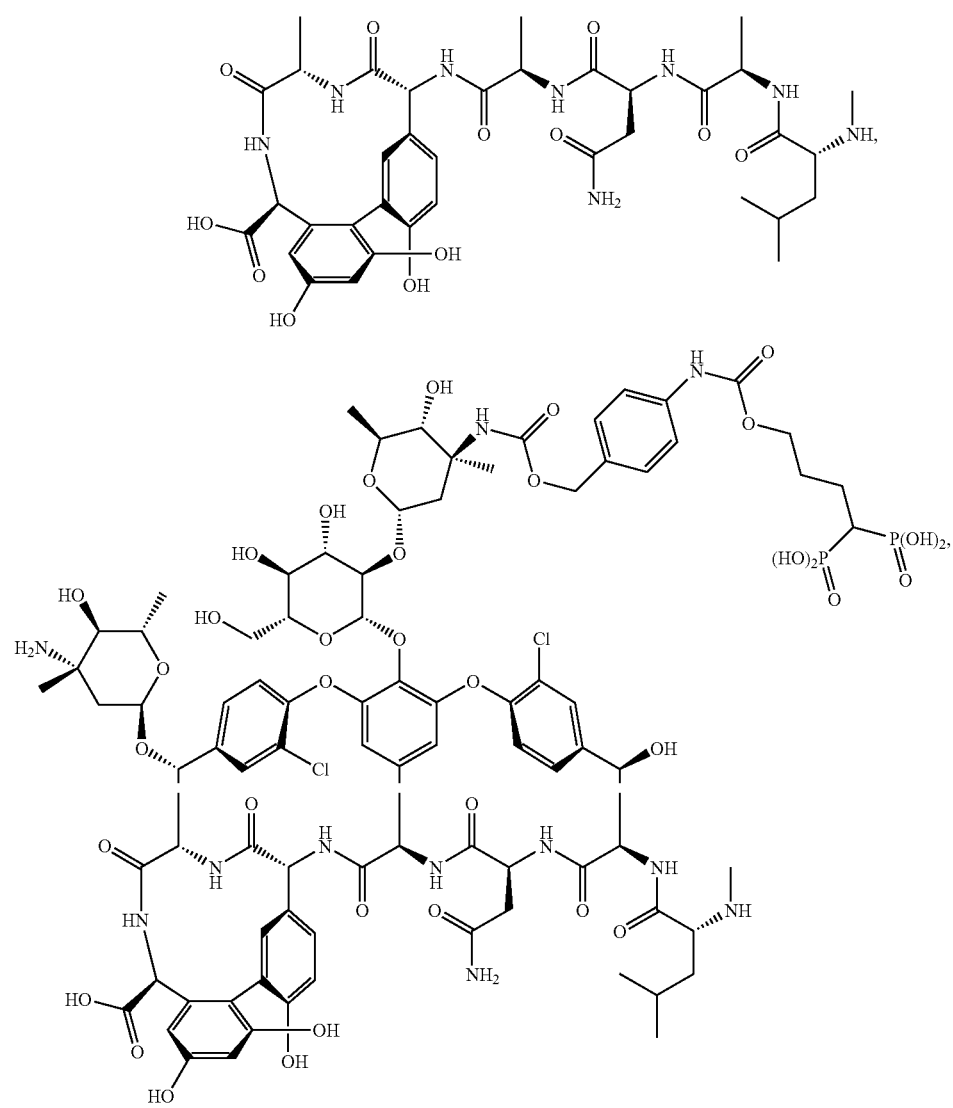

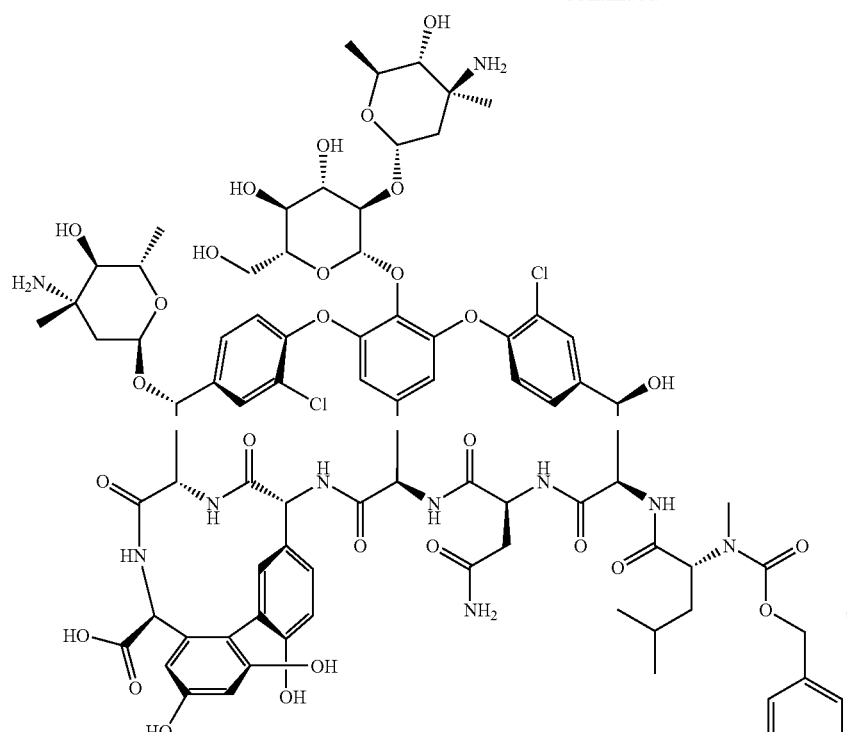
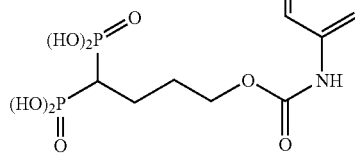
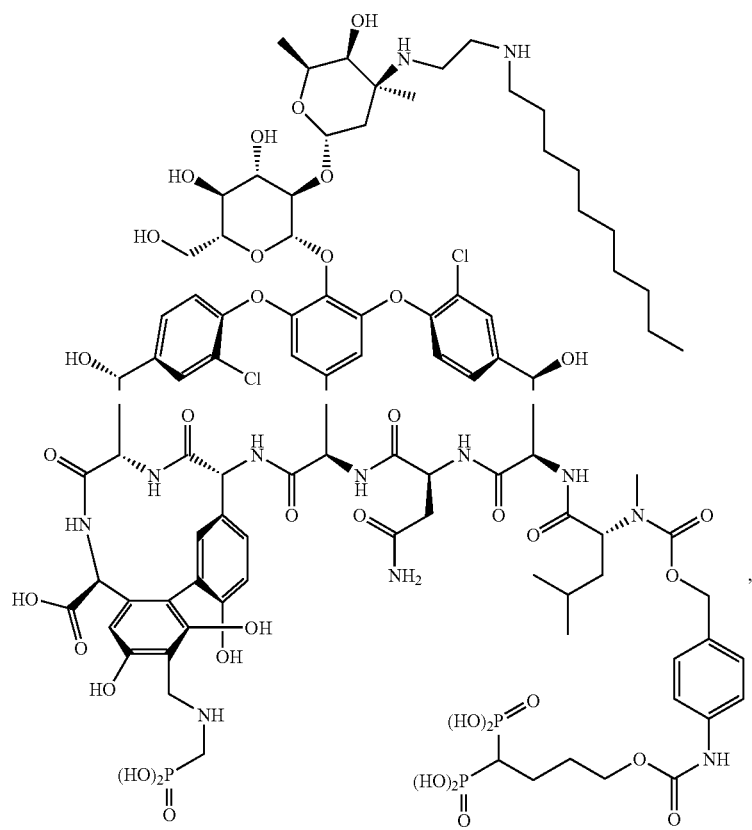
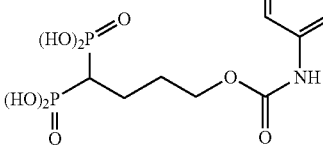

-continued
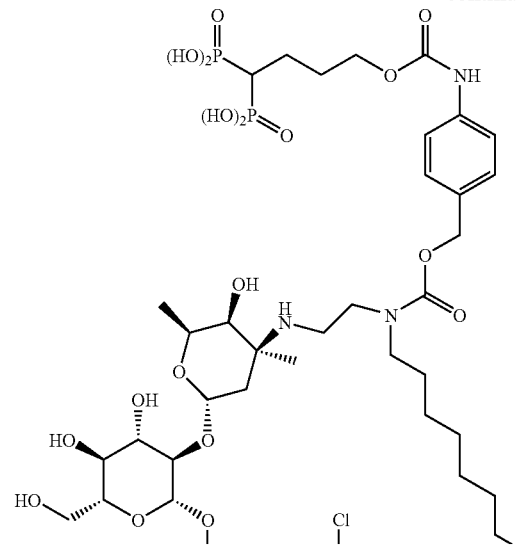
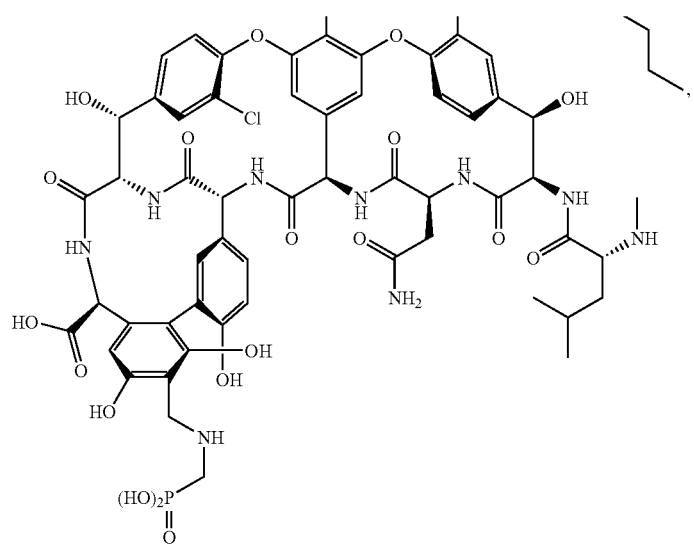
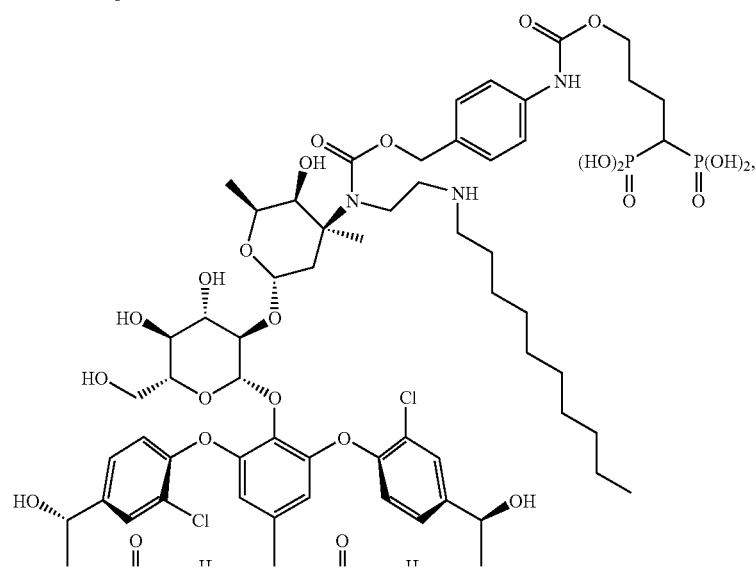

391
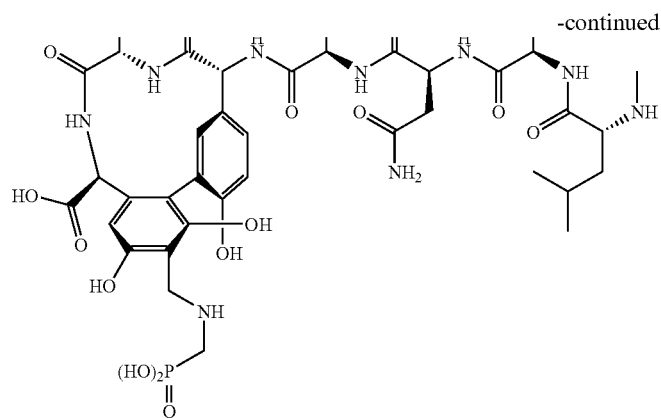
-continued
392
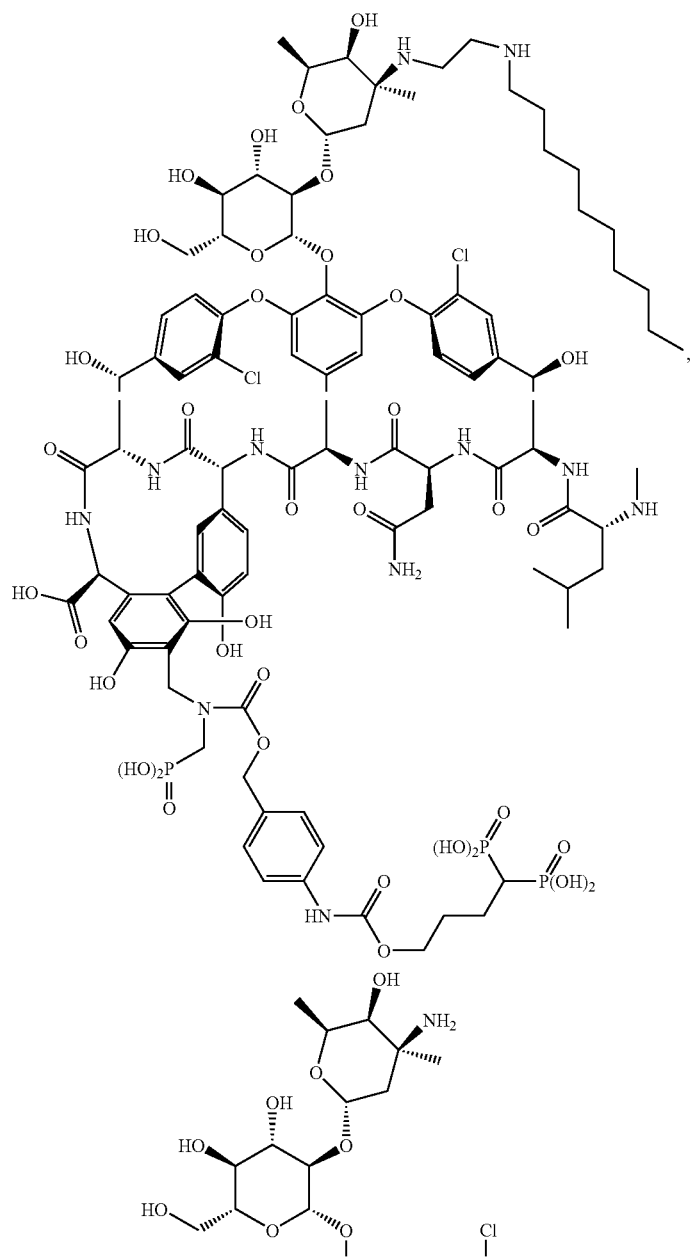

-continued
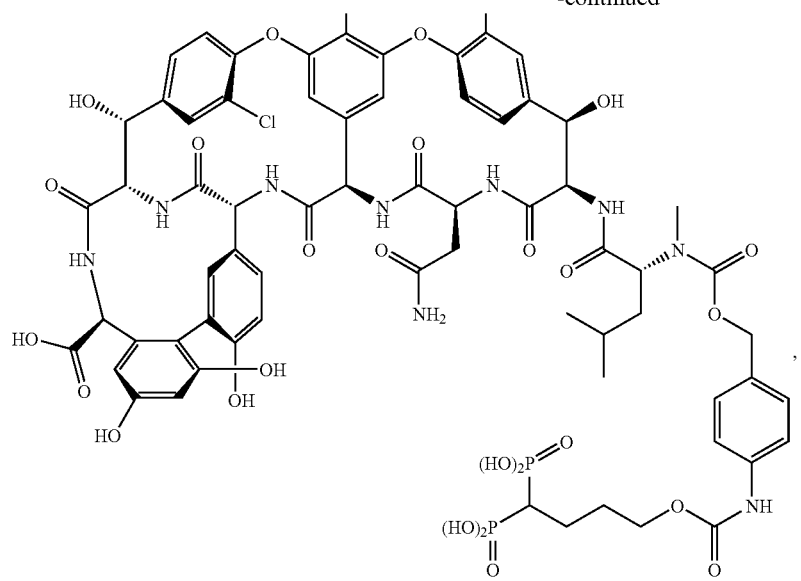
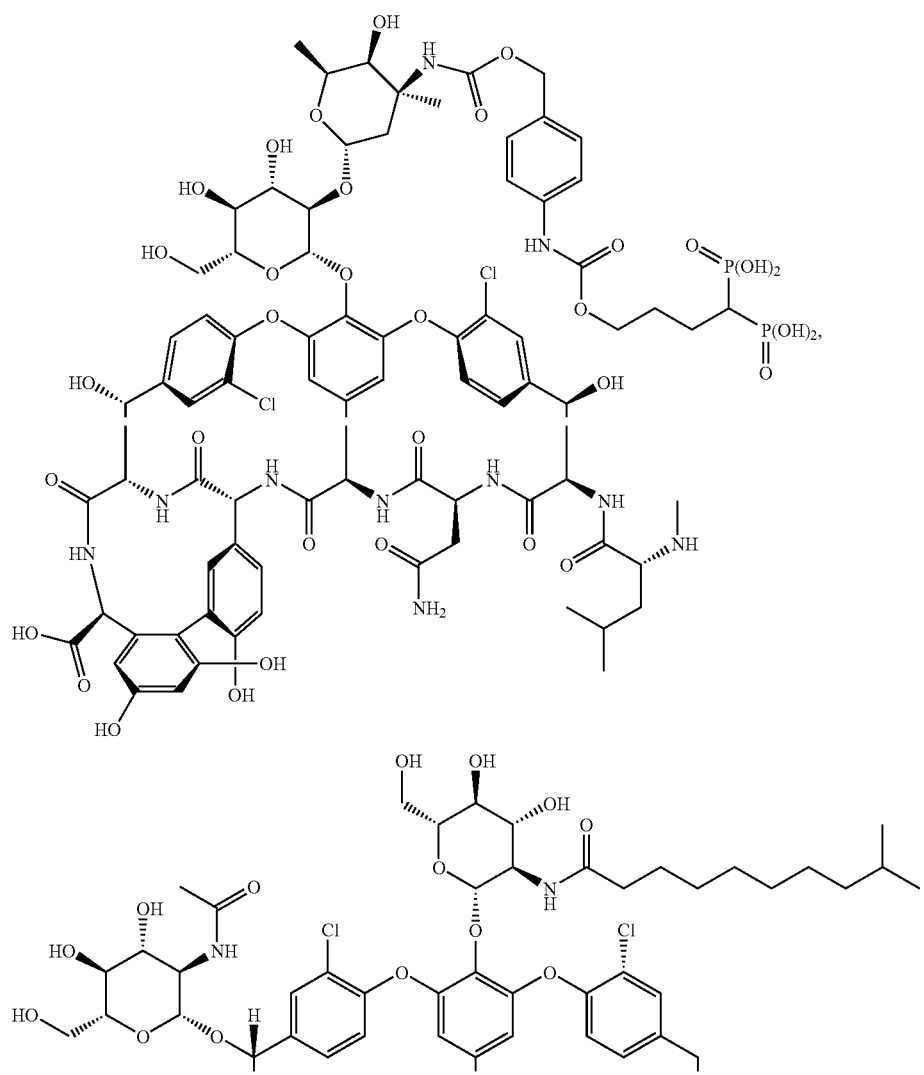

395 396
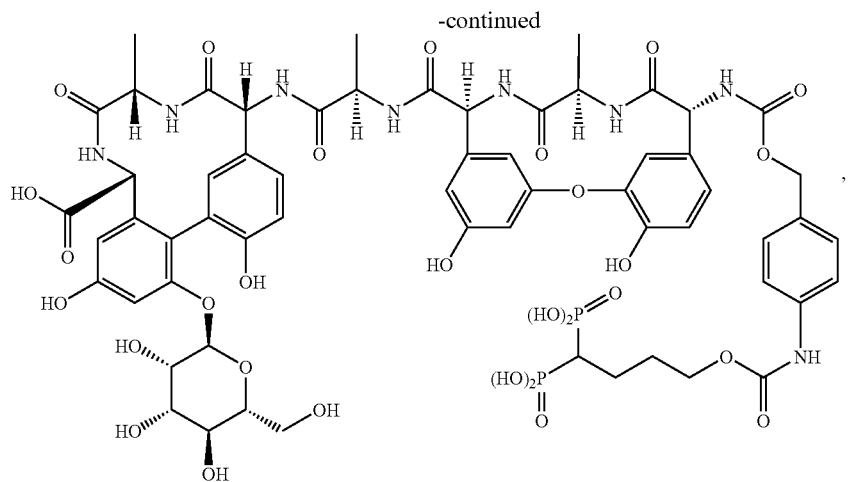
-continued
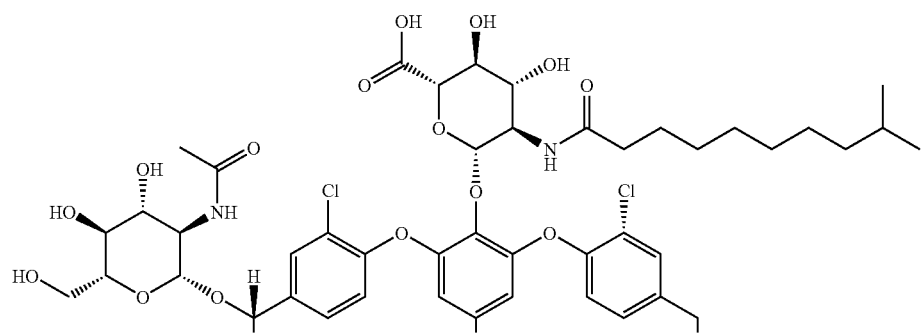
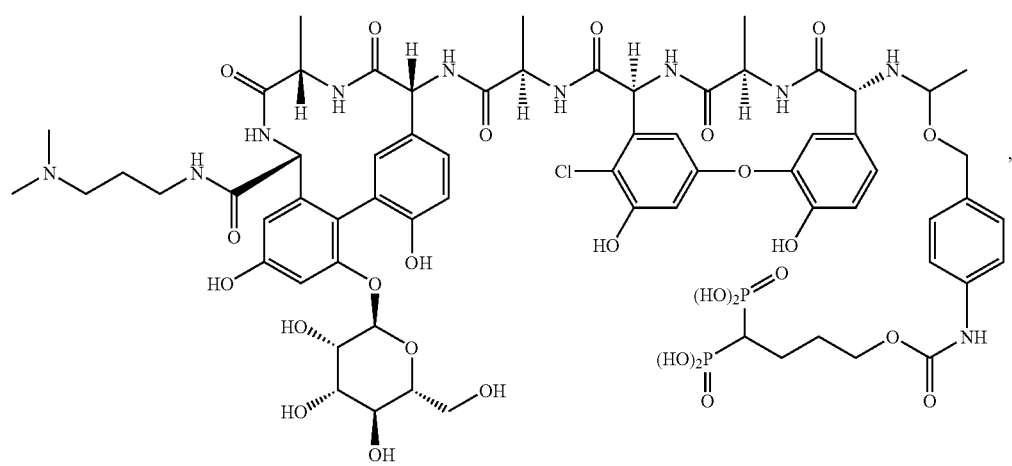

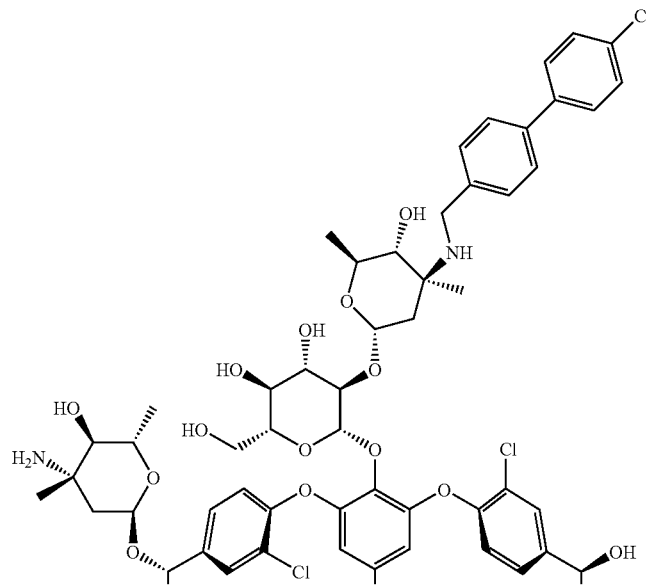
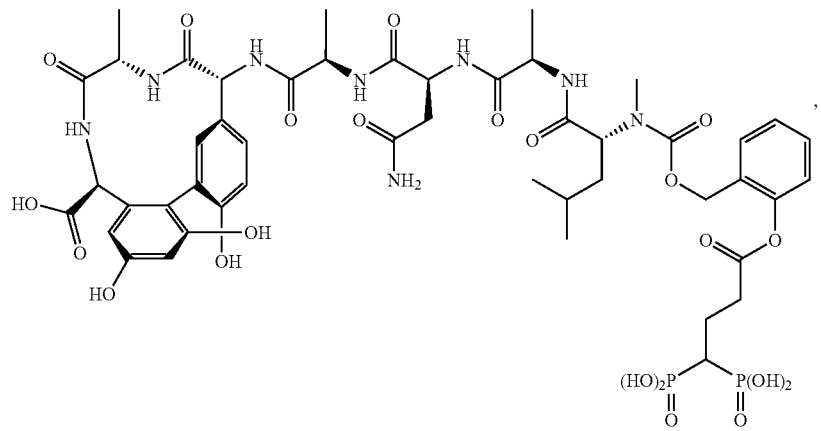
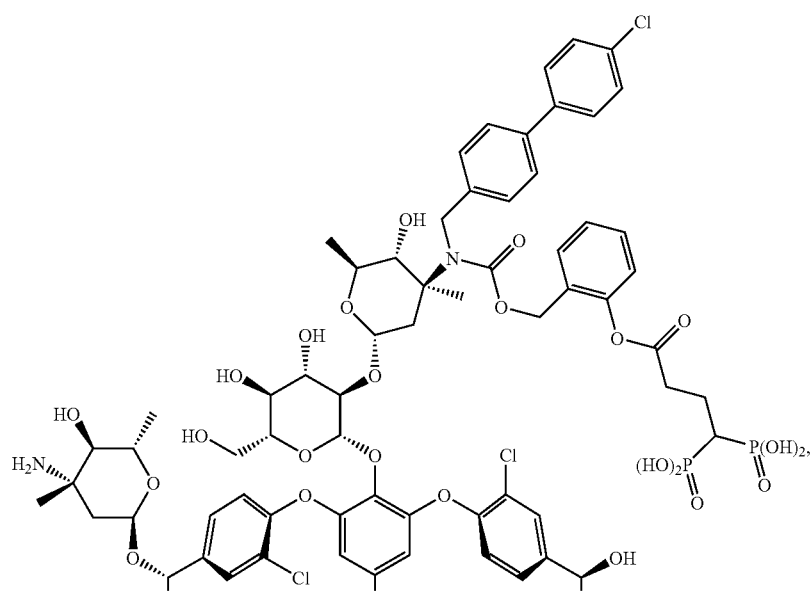

-continued
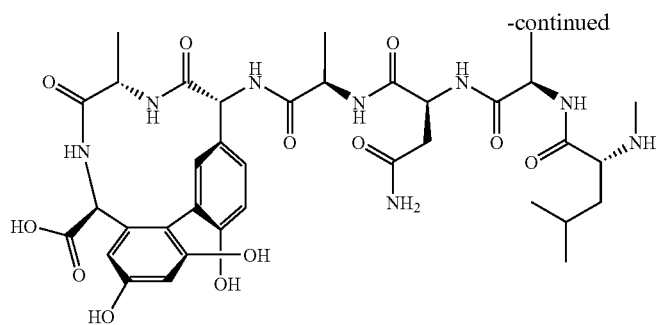
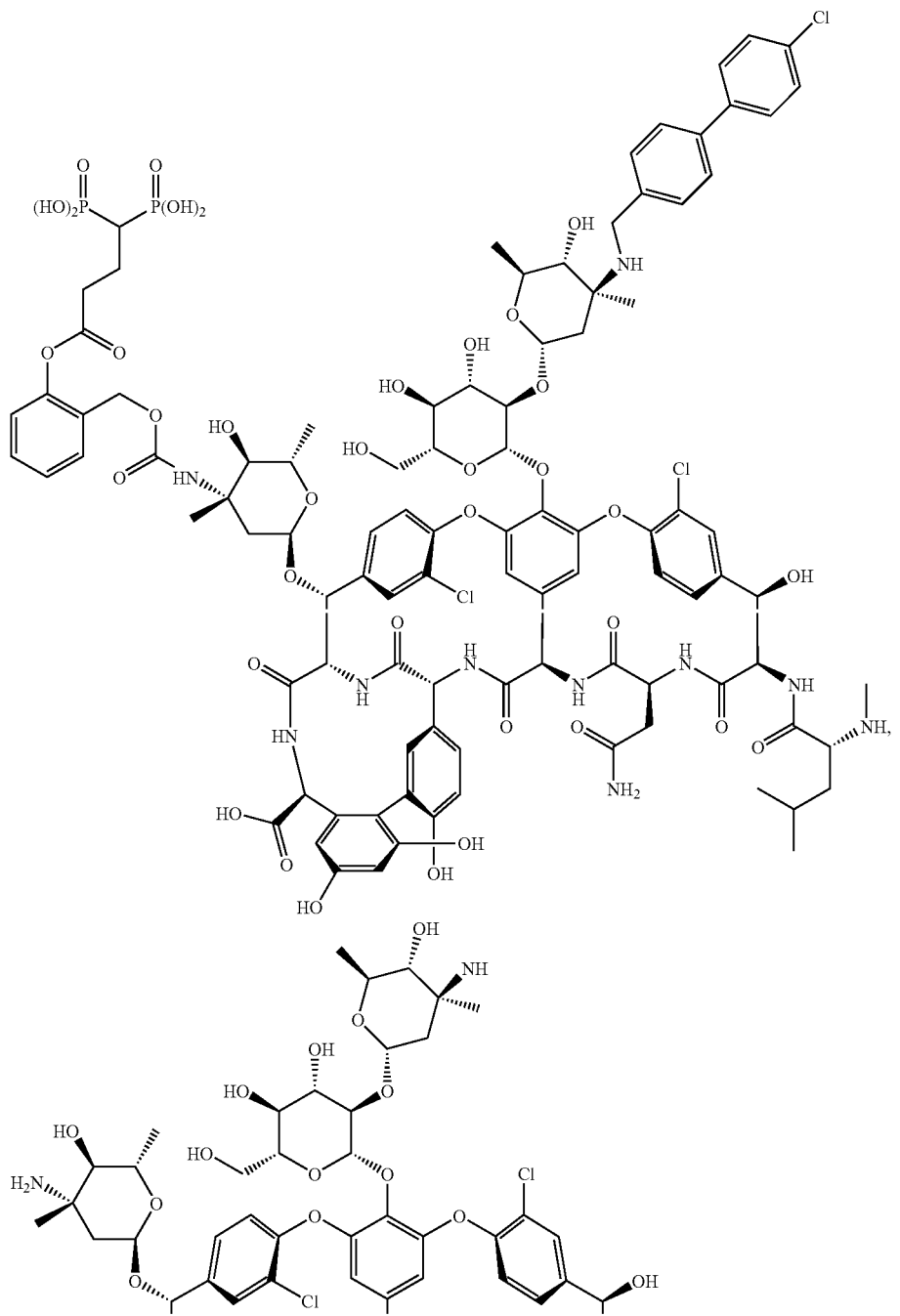

401
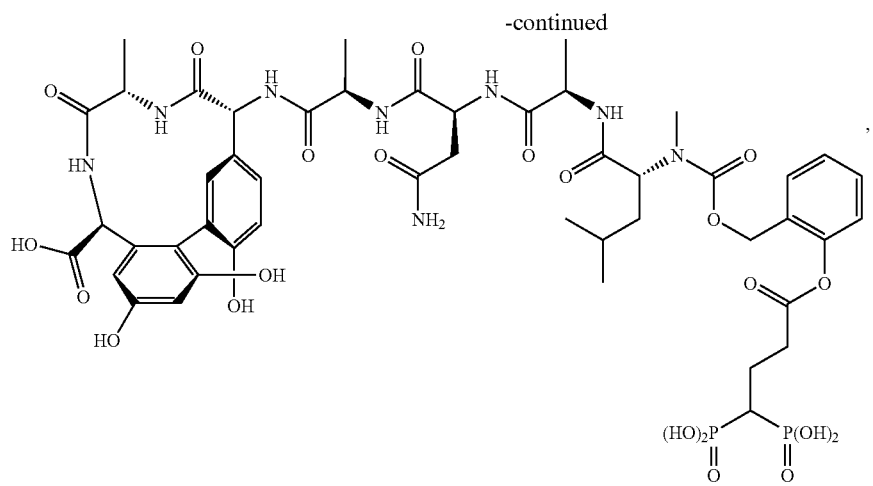
-continued
402
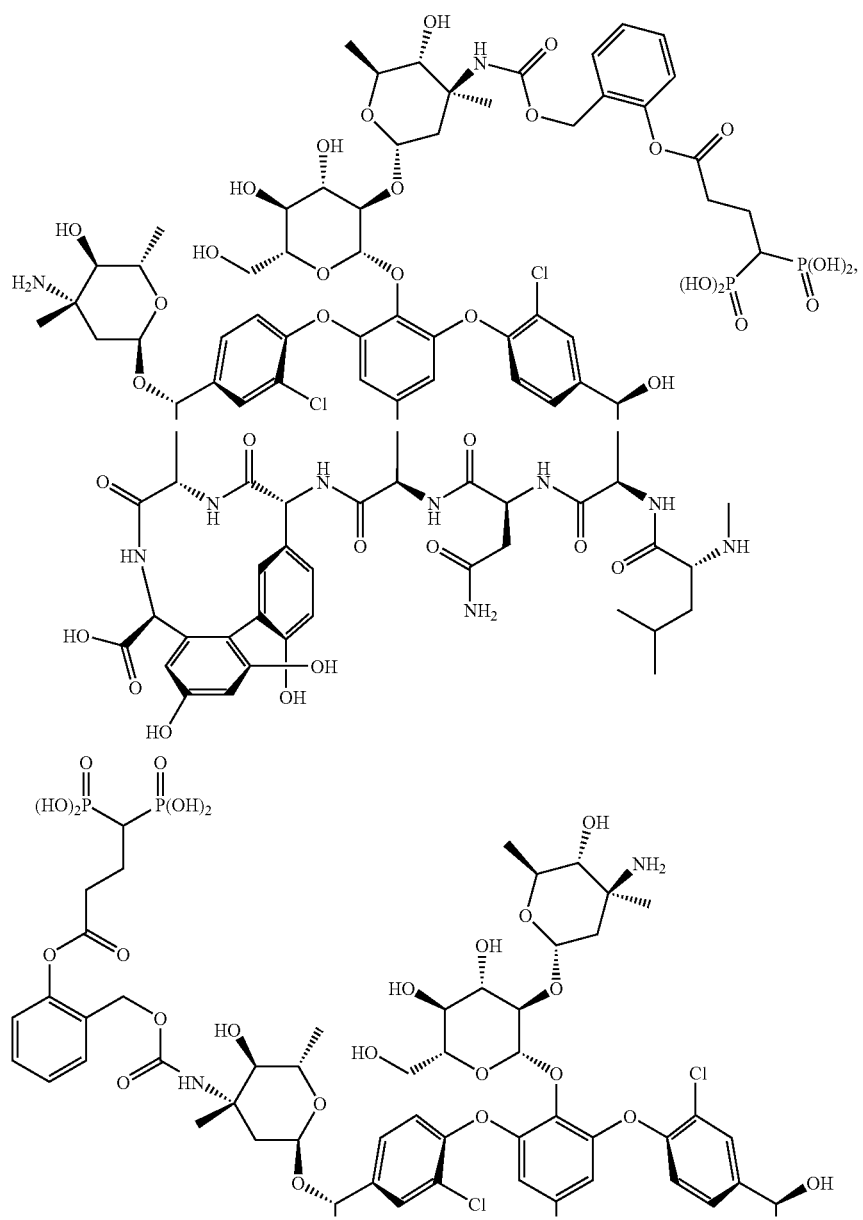

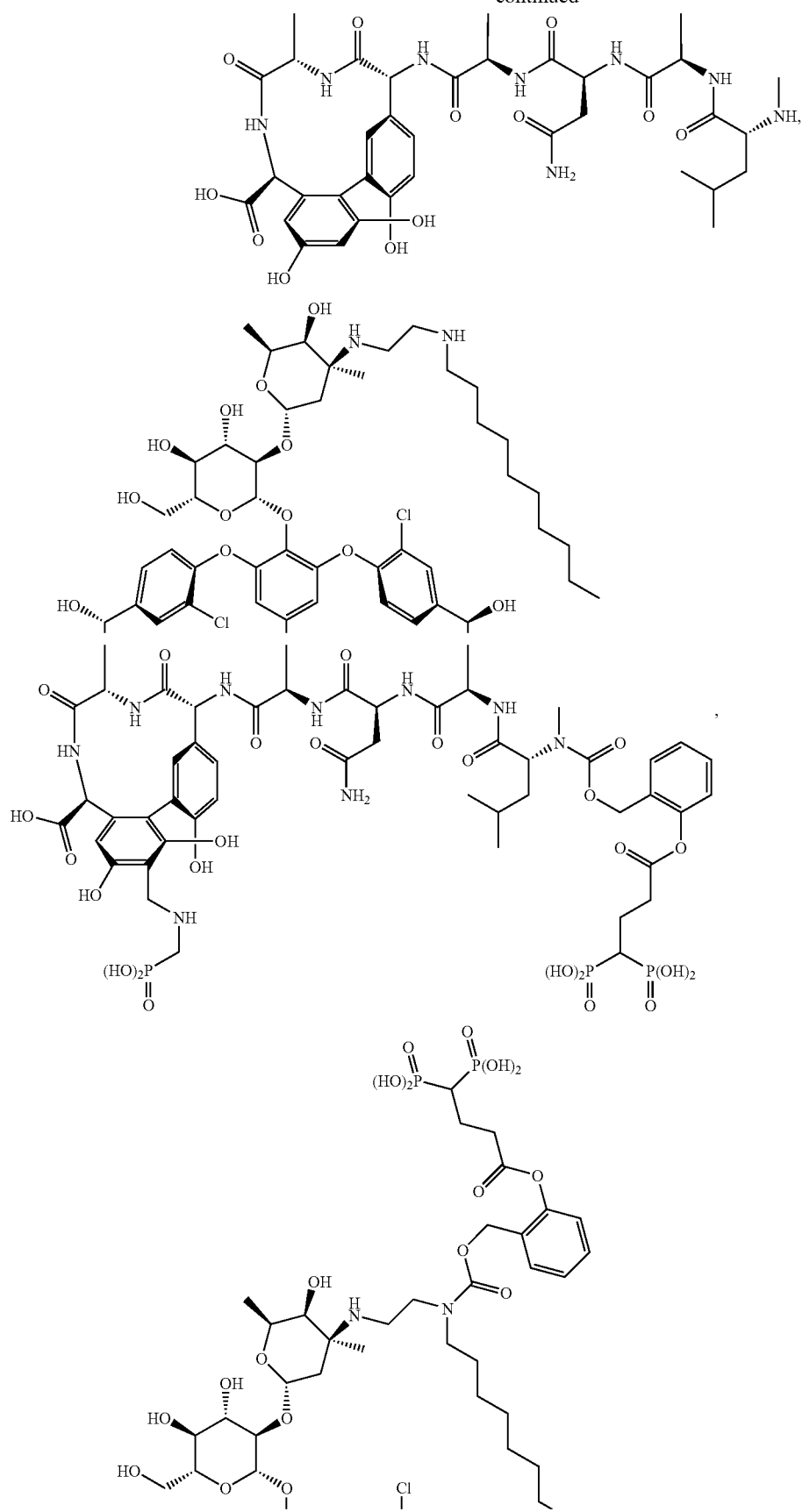

405
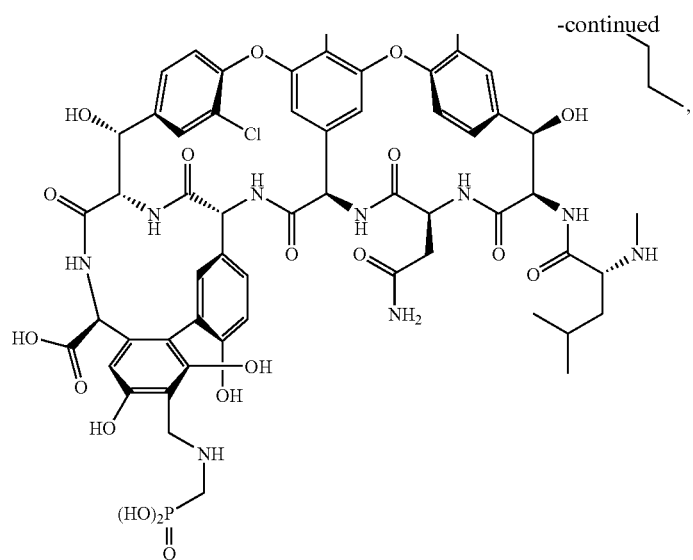
406
-continued
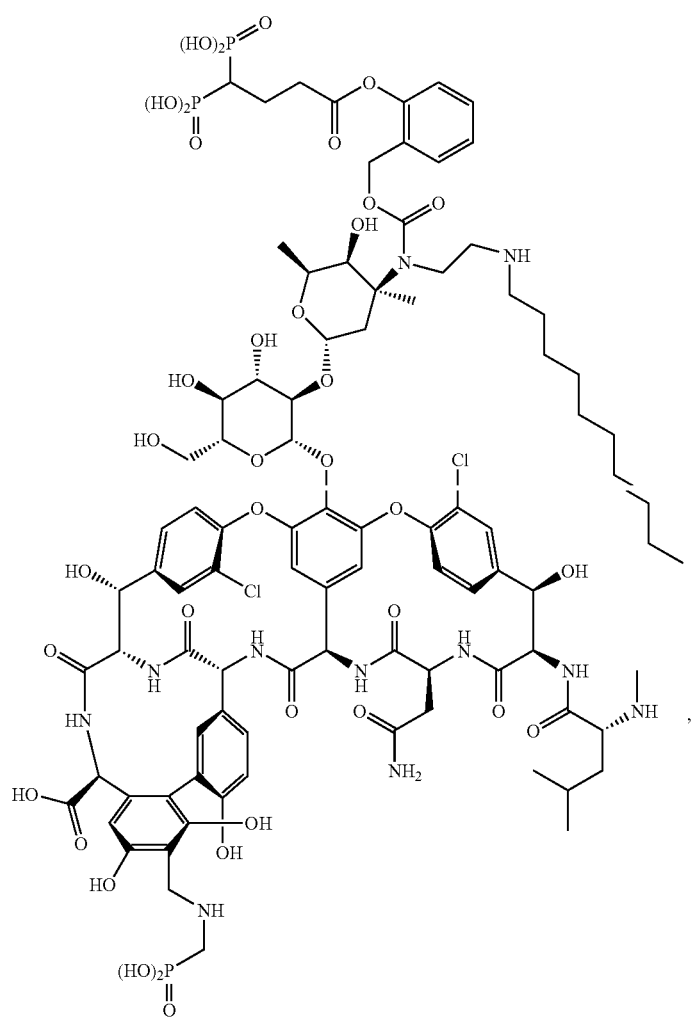

407
-continued
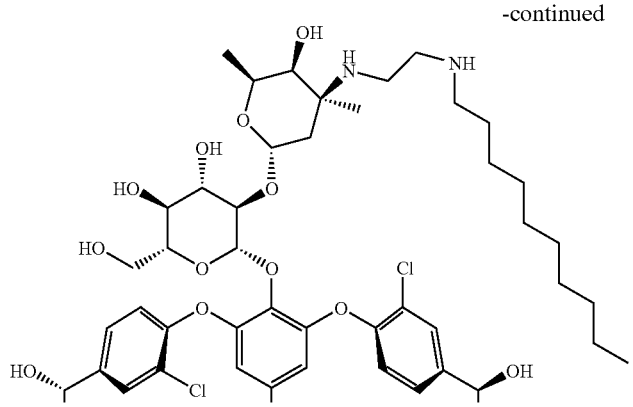
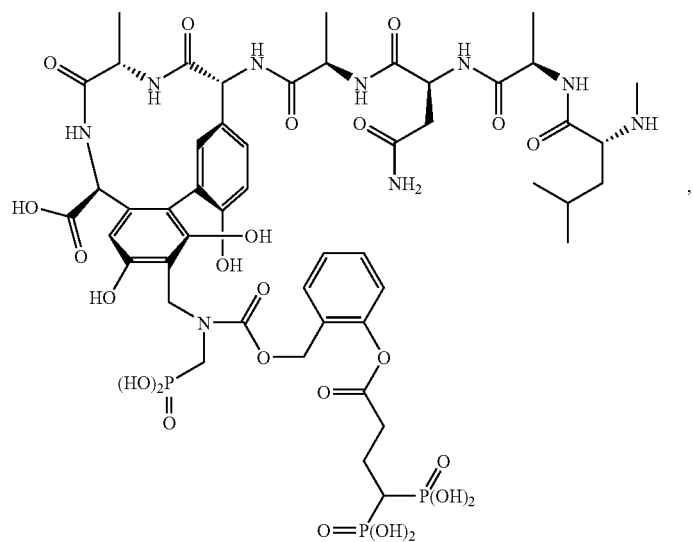
408
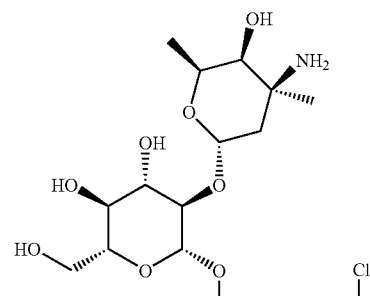

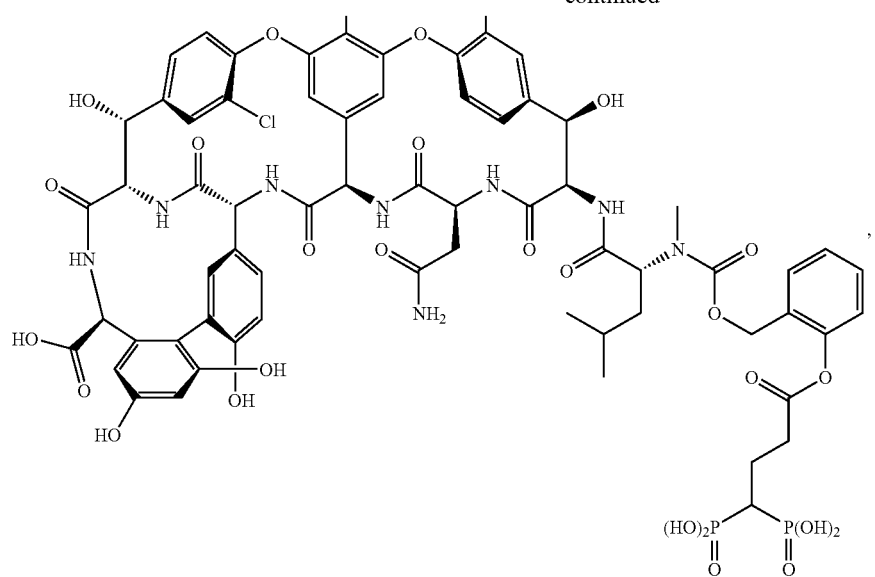
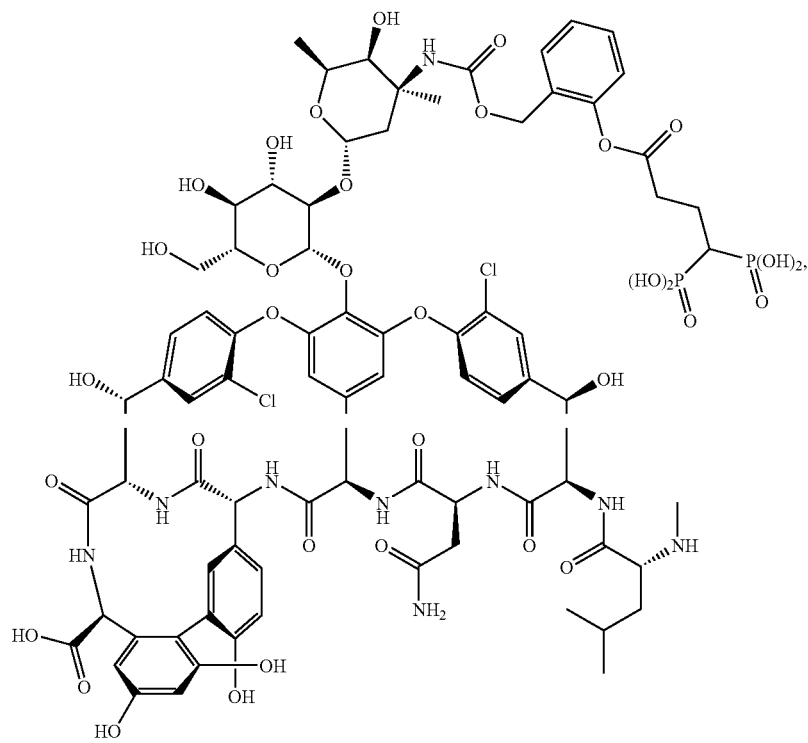

411
412
-continued
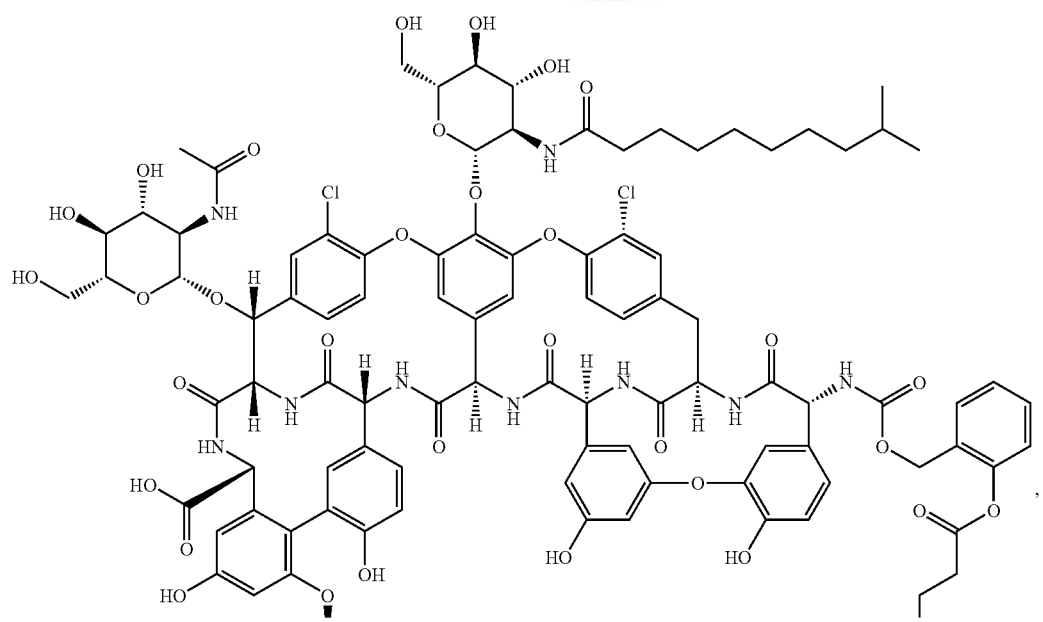
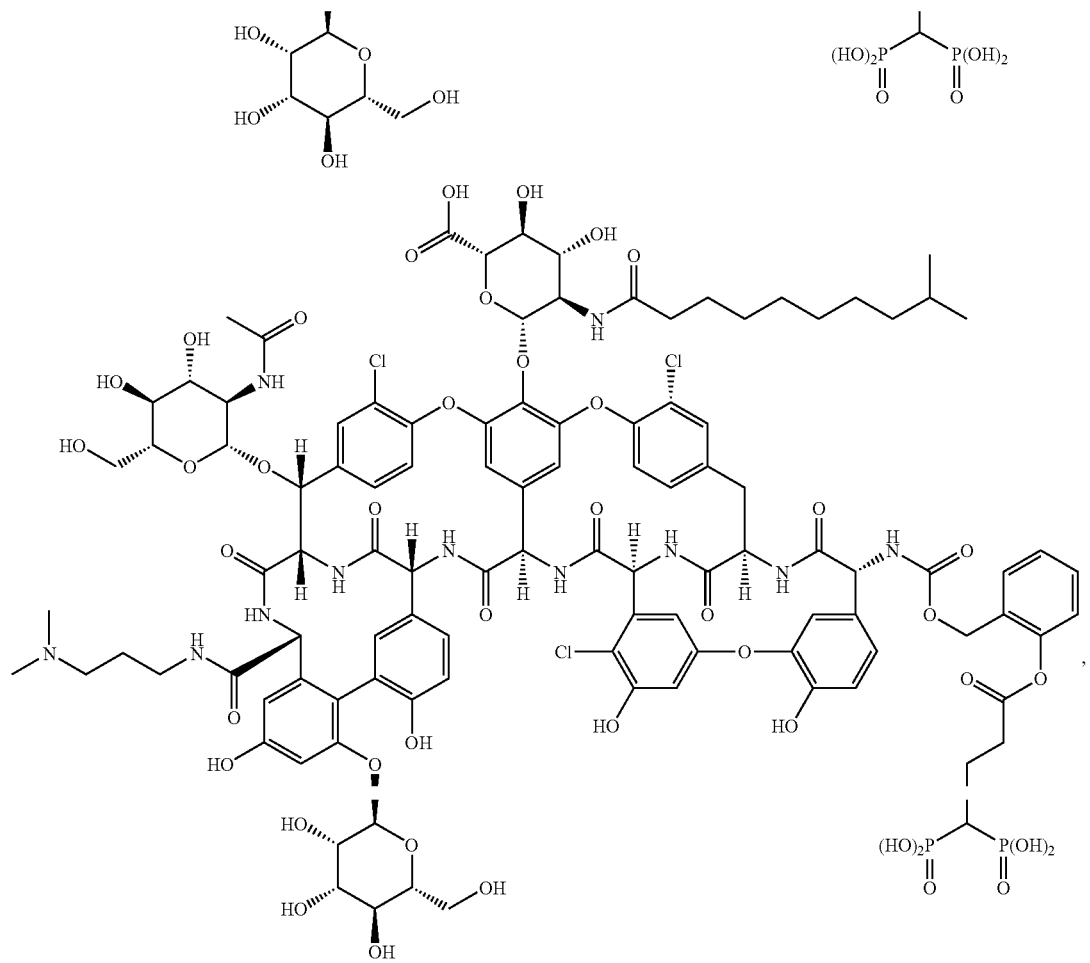

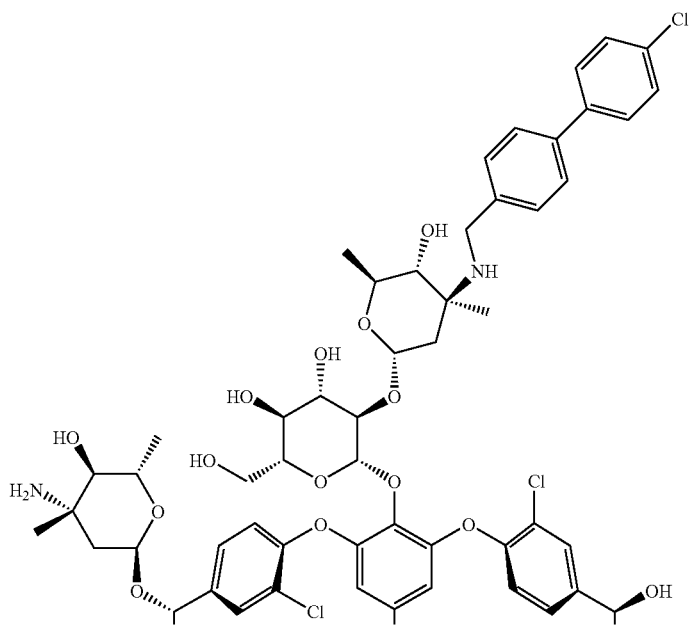
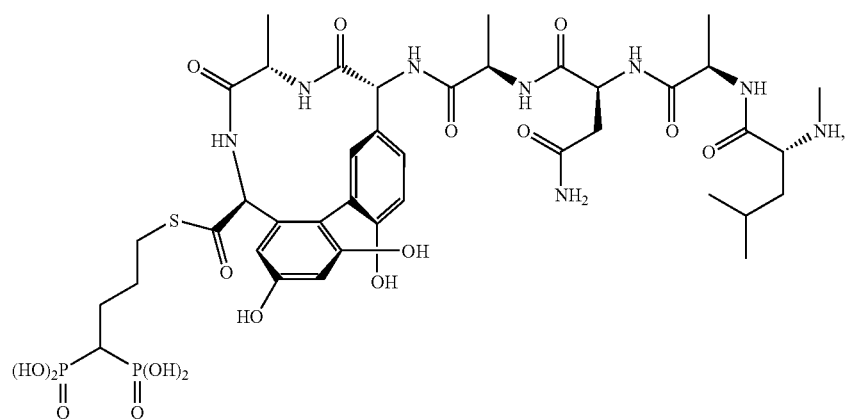
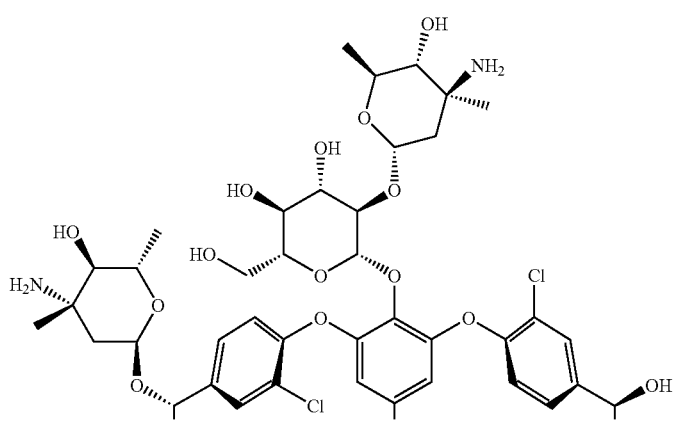

415
416
-continued
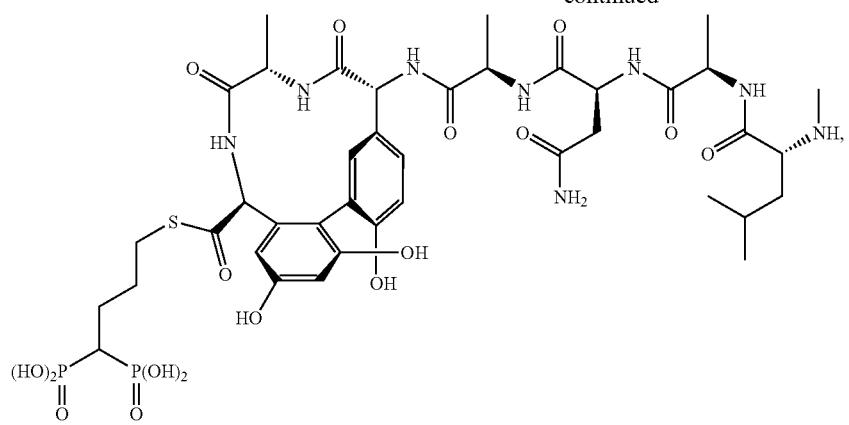
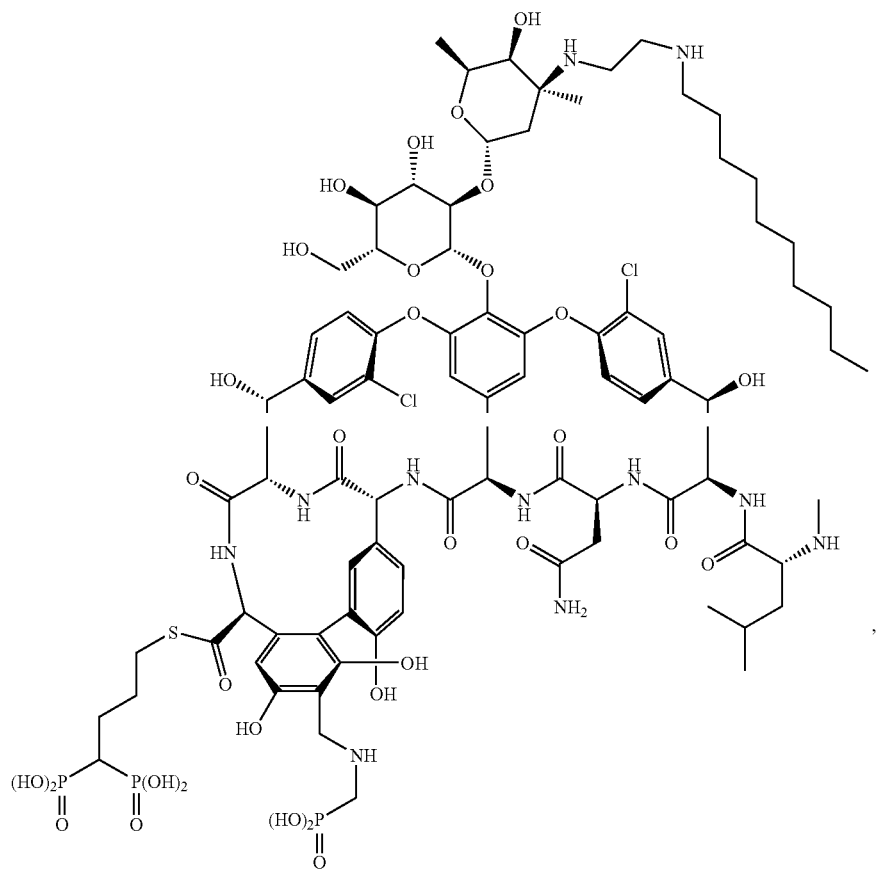
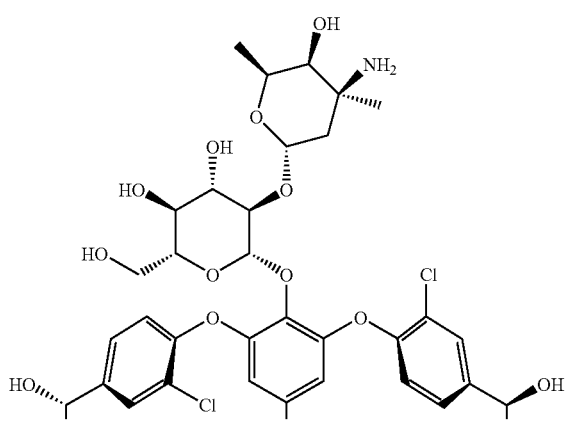

417
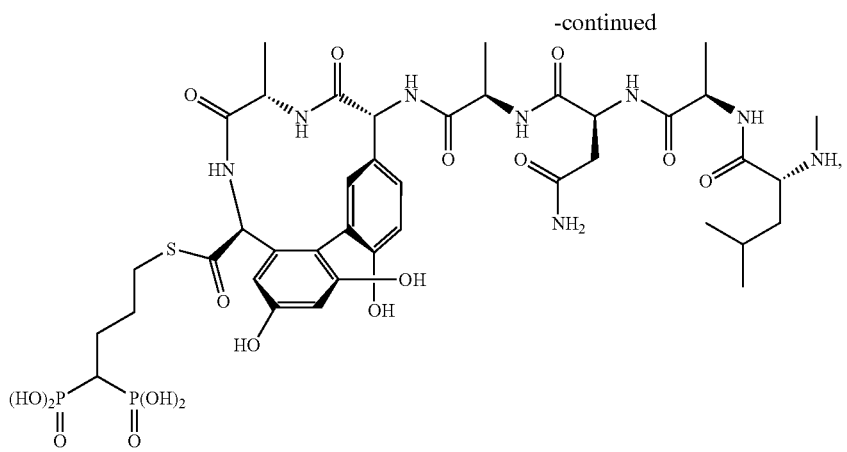
-continued
418
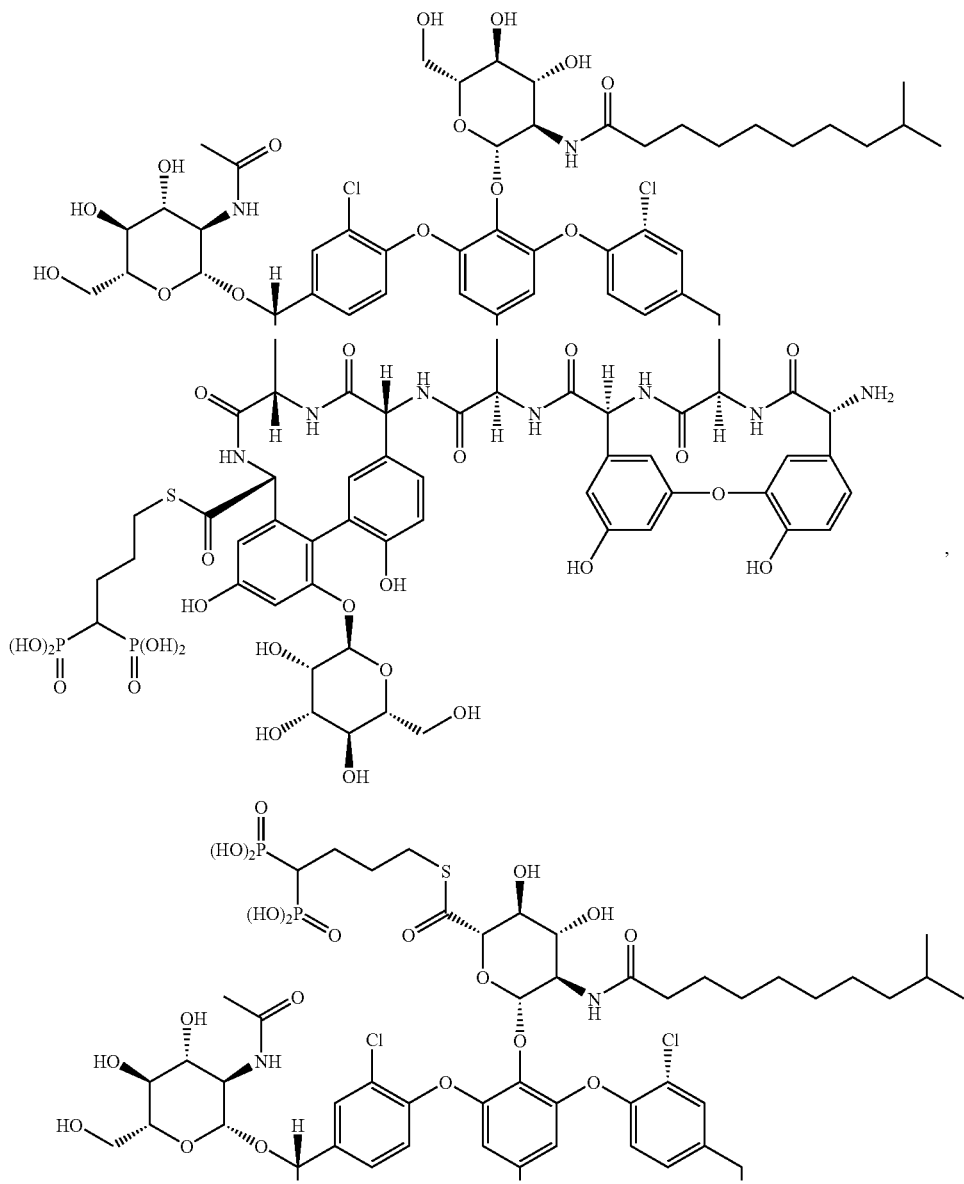
,

419
-continued
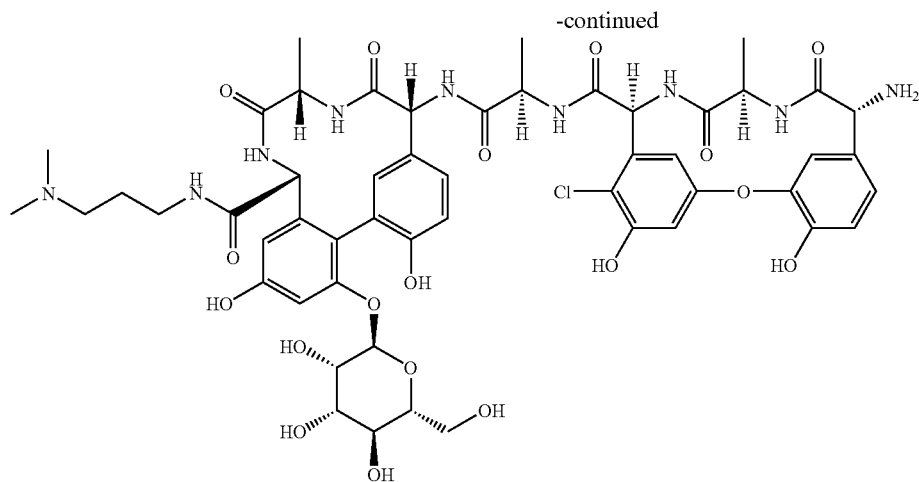
420
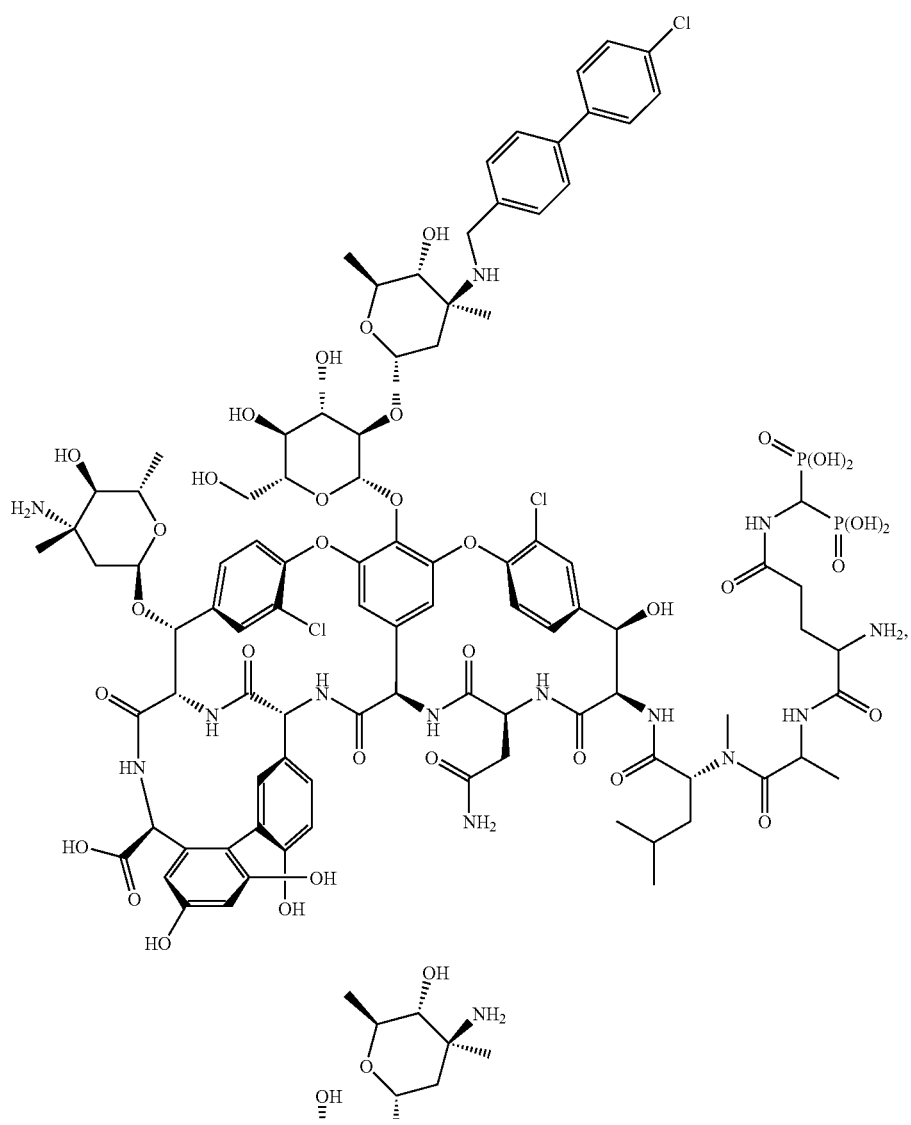
,

421
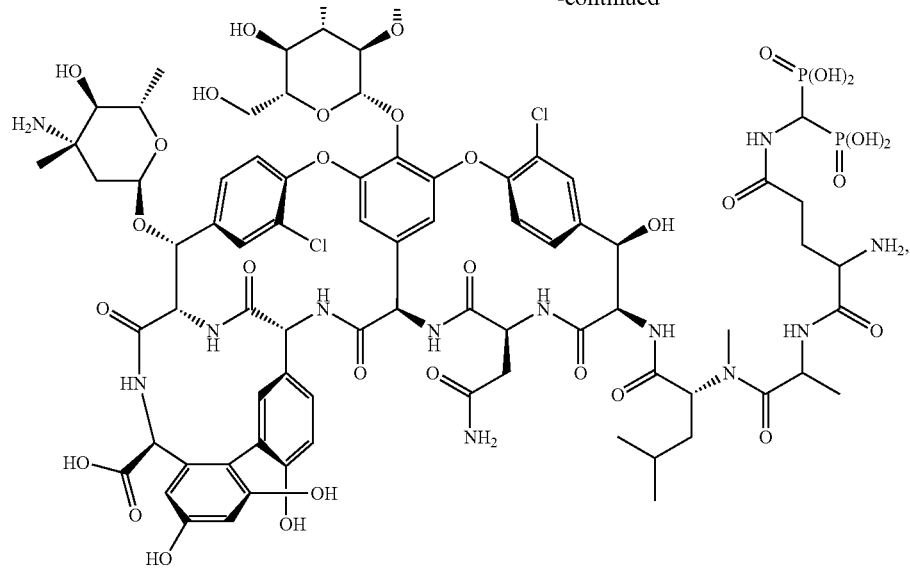
422
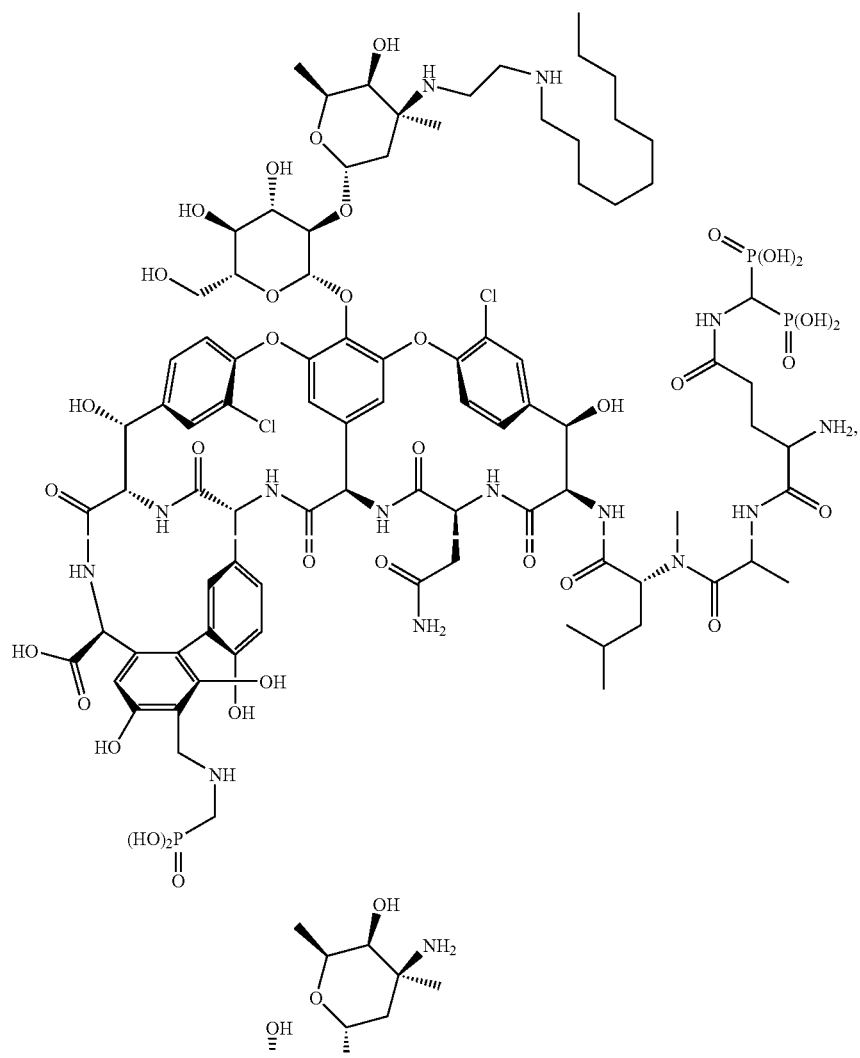

-continued
423
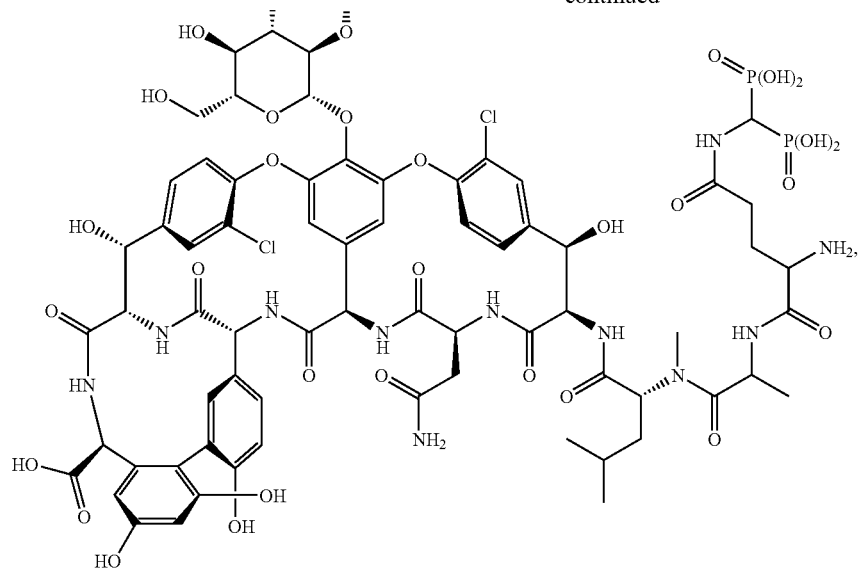
424
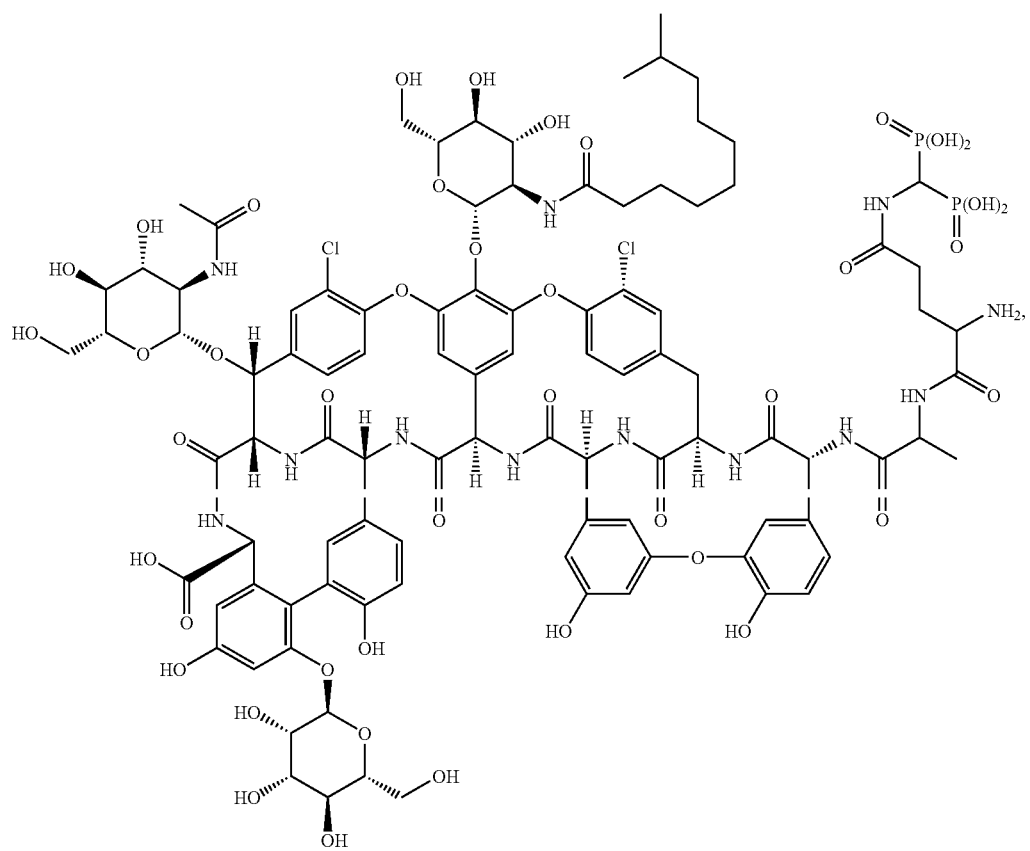

425 426
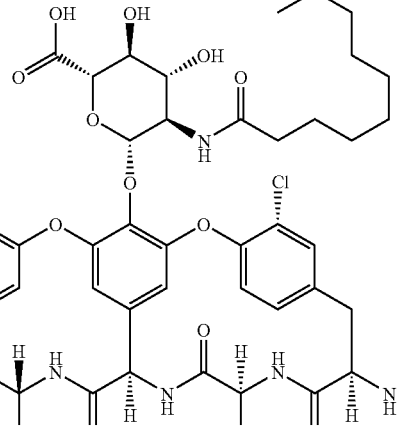
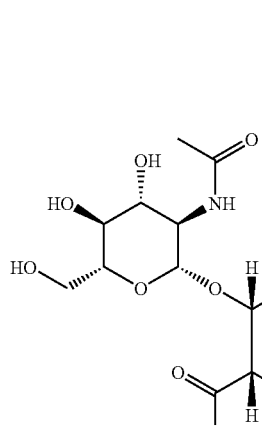
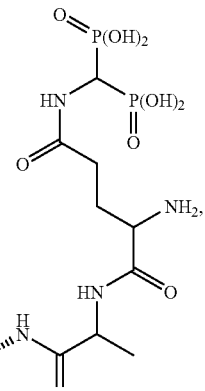
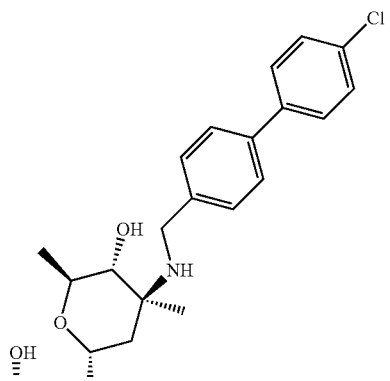

427
428
-continued
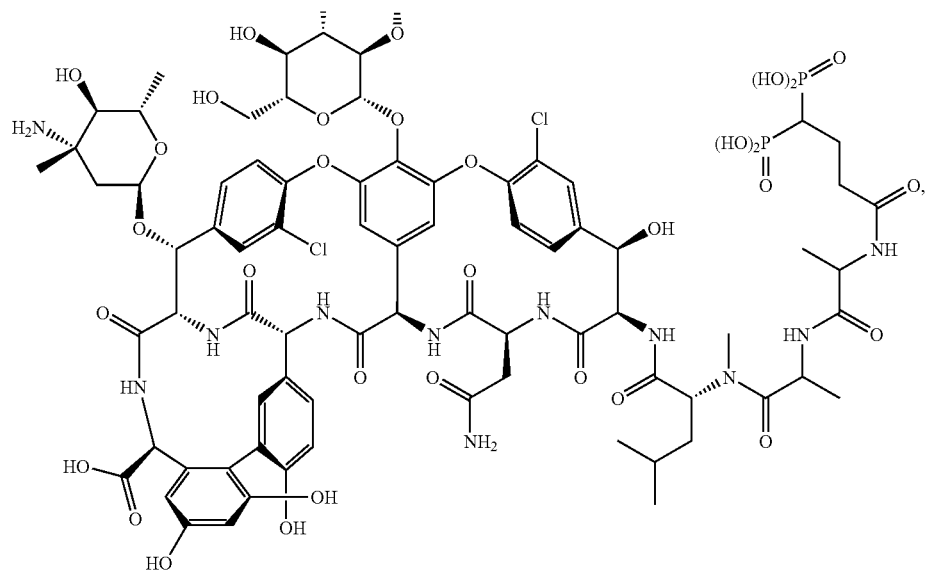
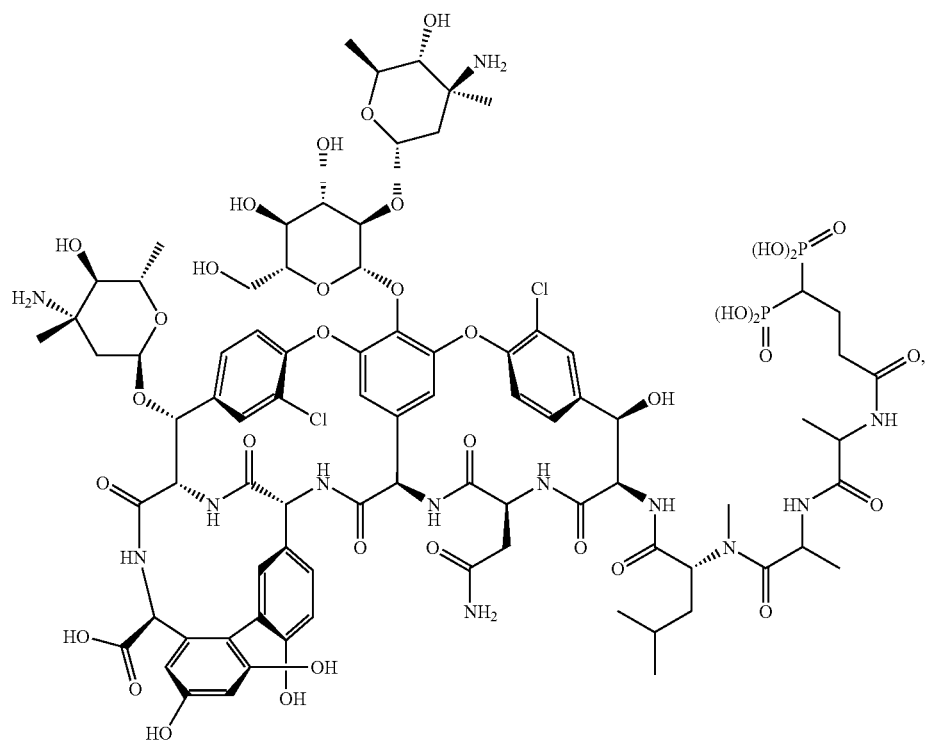

-continued
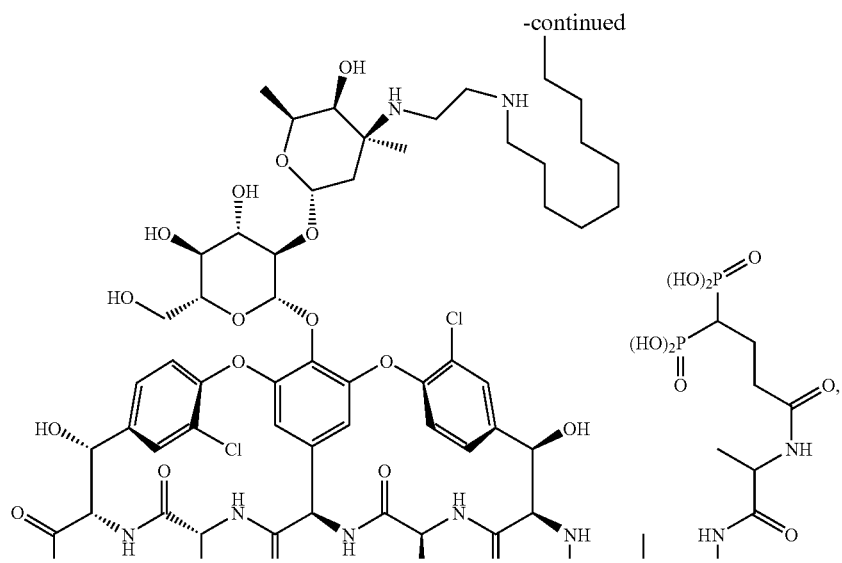
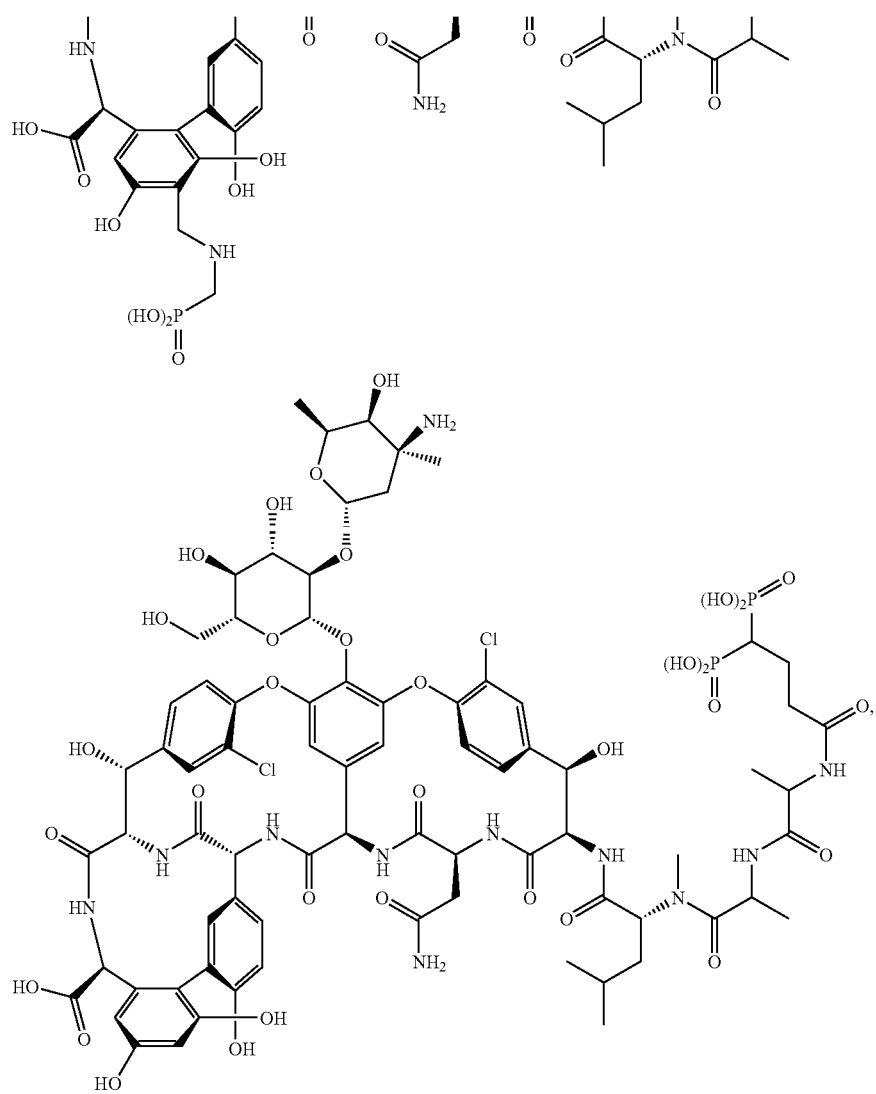

431
-continued
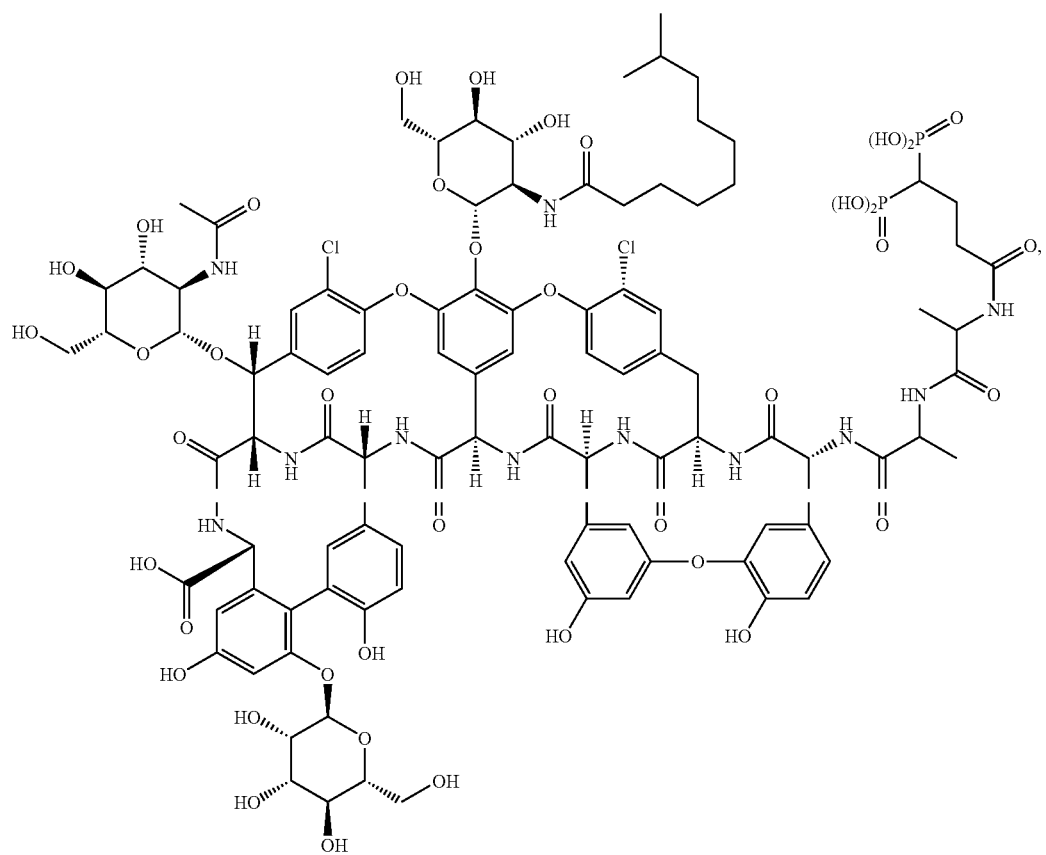
432
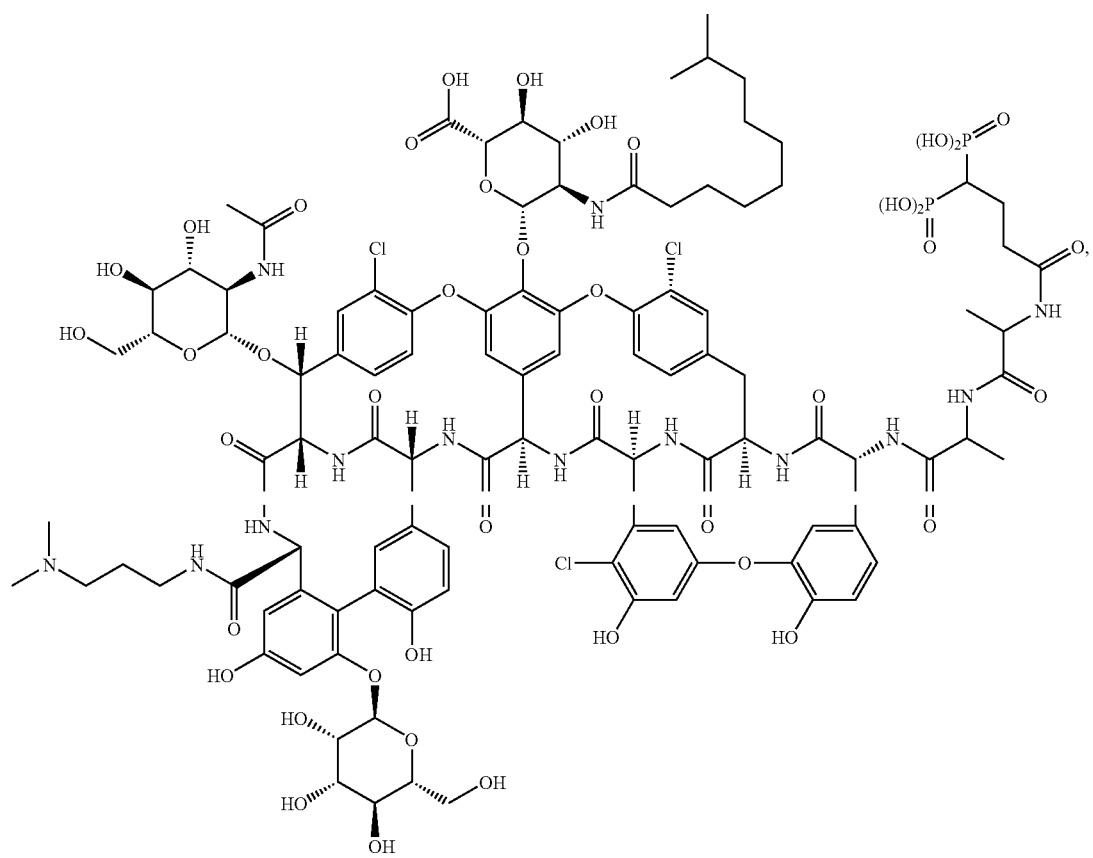

-continued
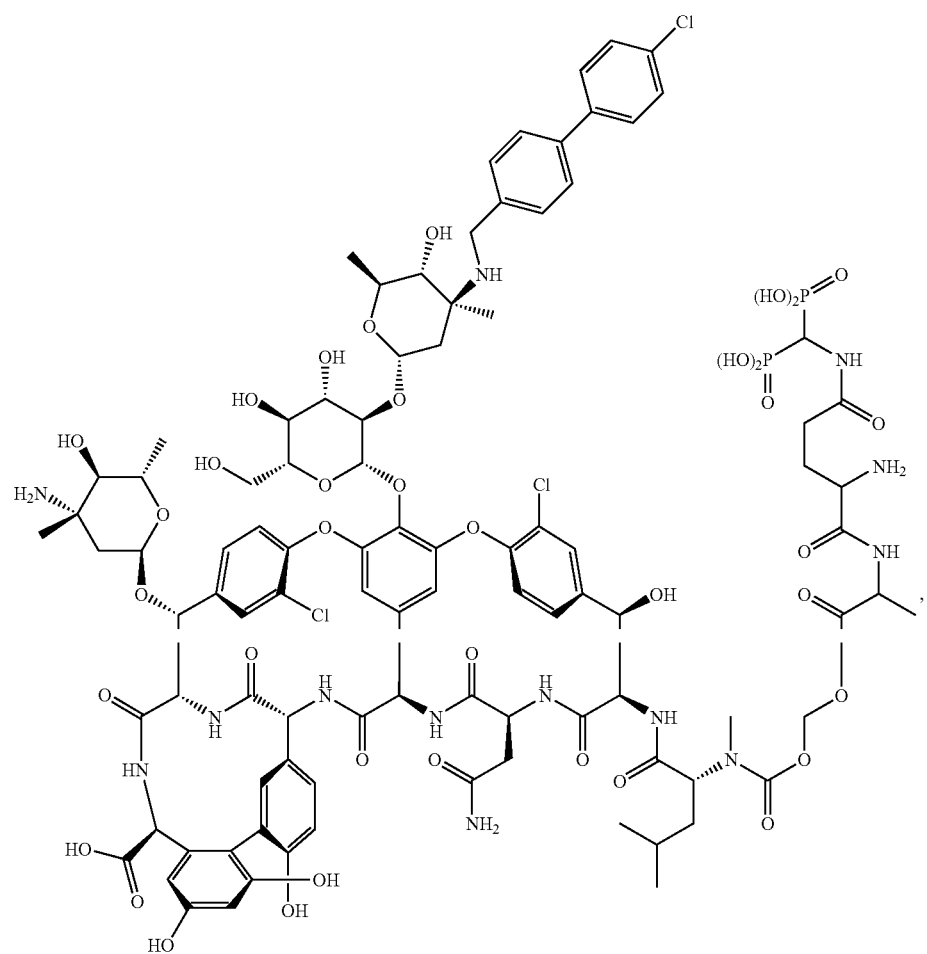
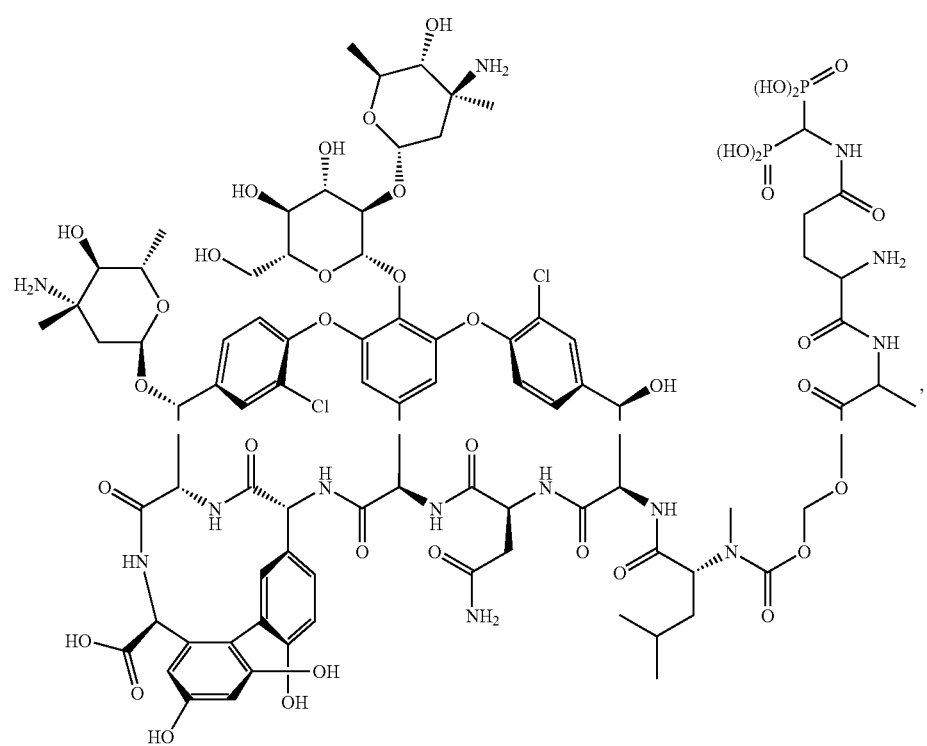

-continued
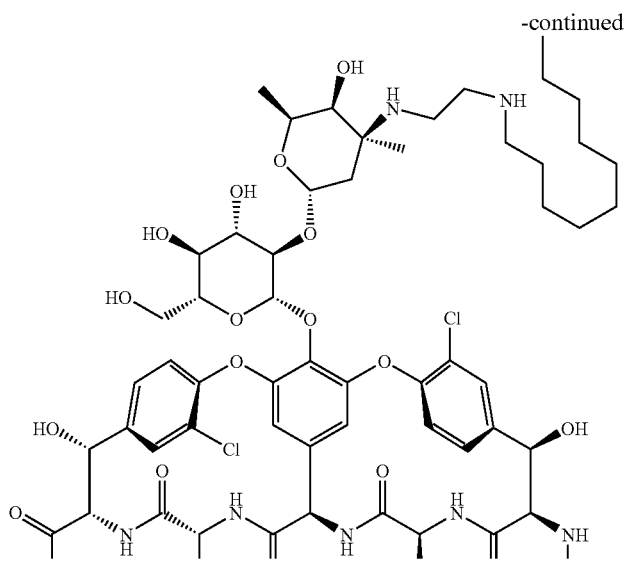
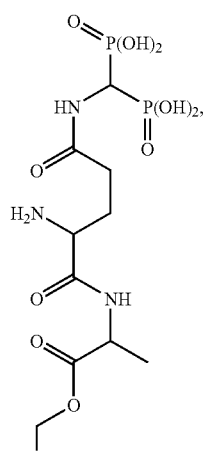
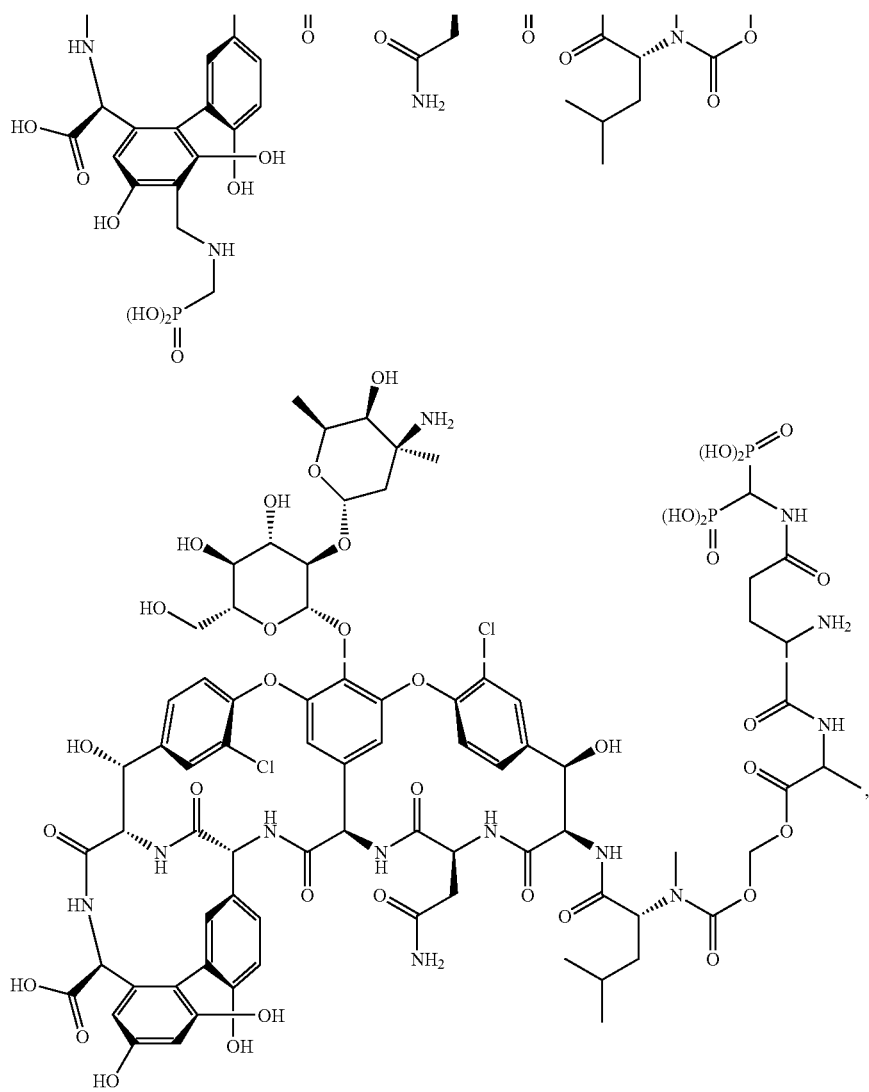

437
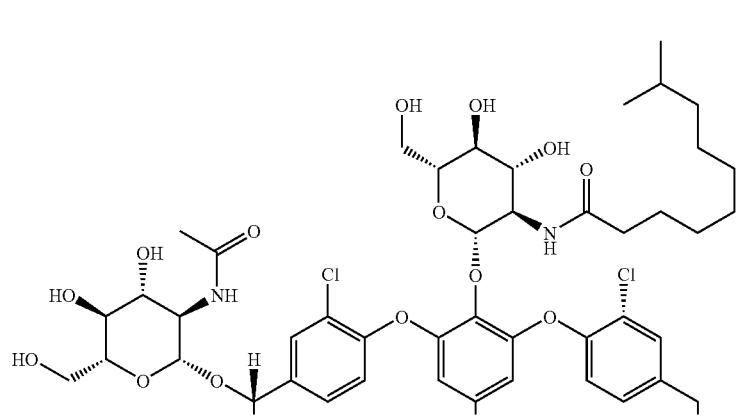
438
-continued
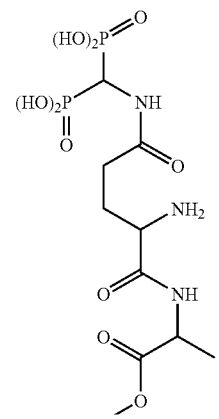
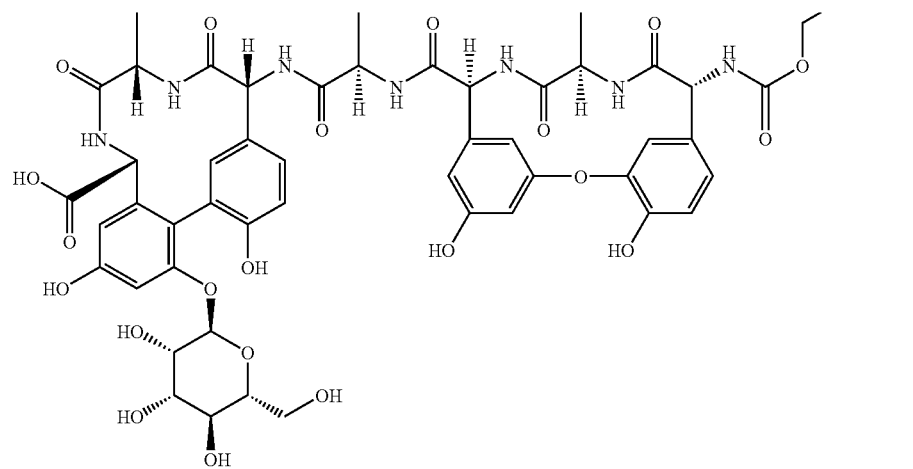
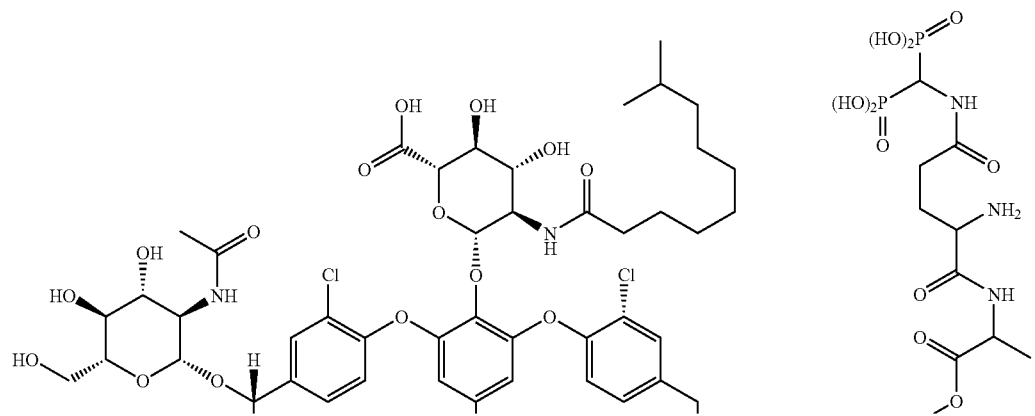

439
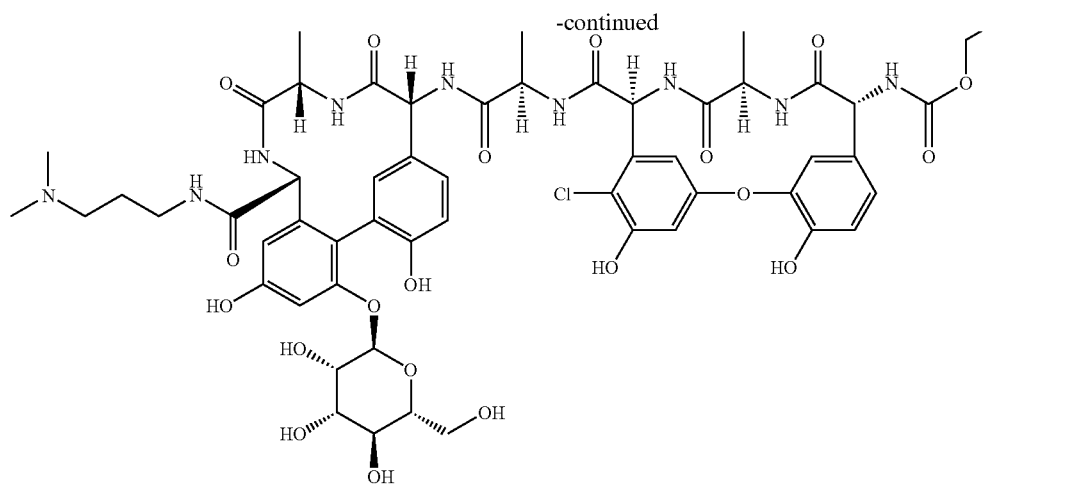
-continued
440
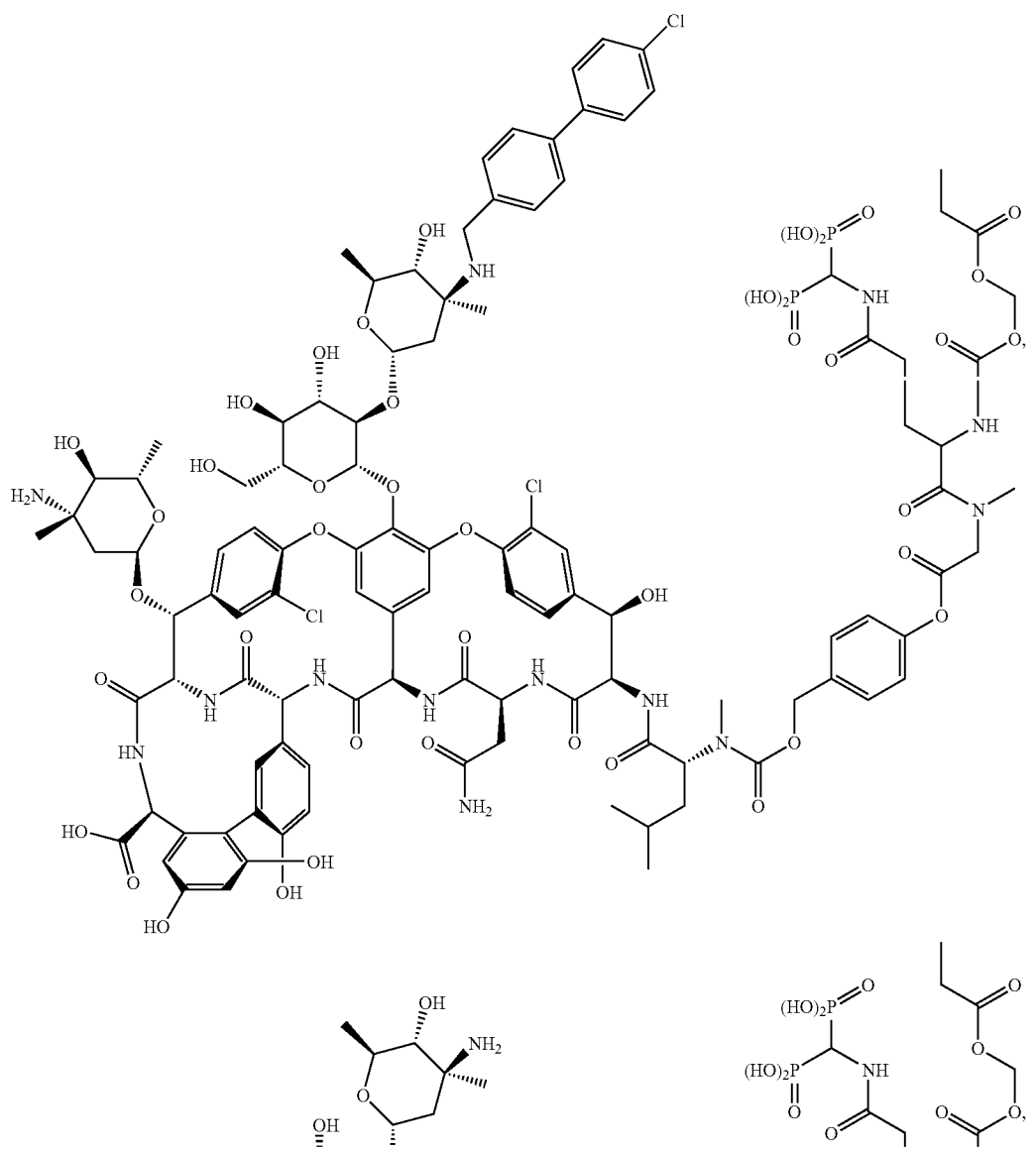

441 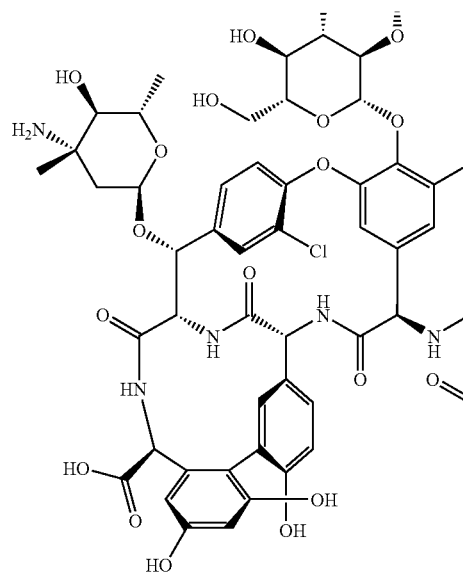 442 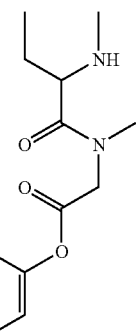
-continued
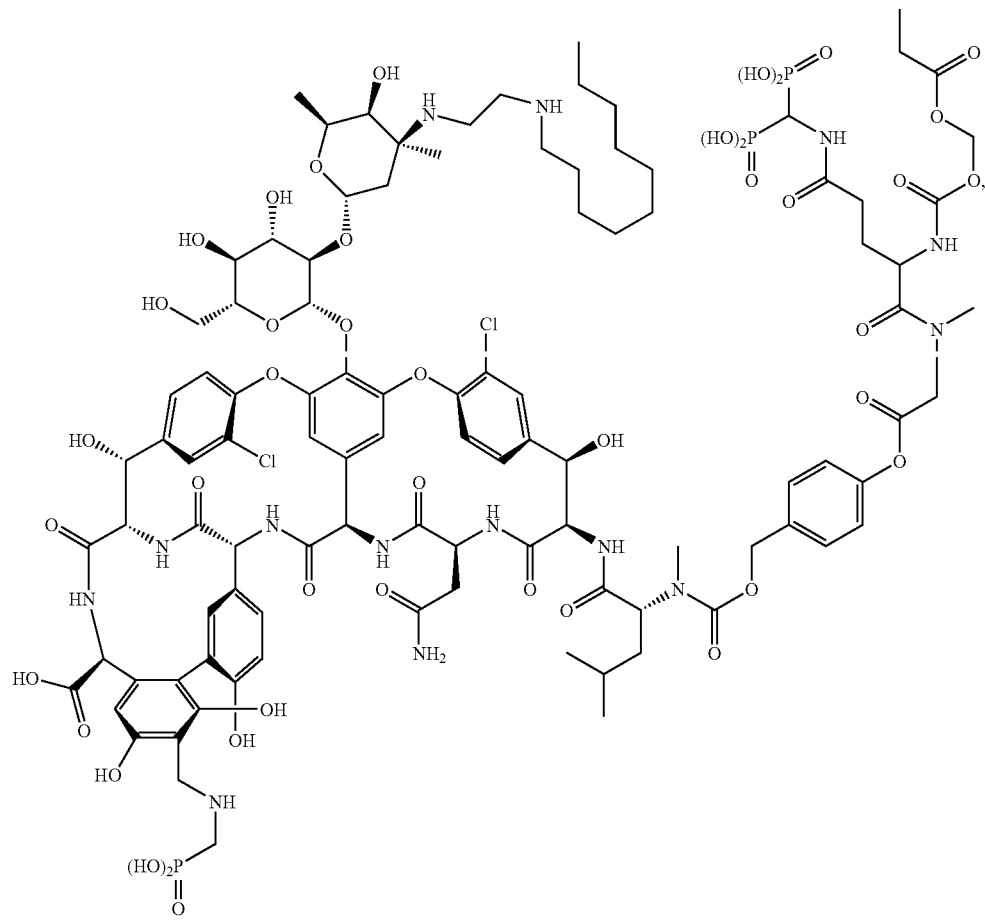

443
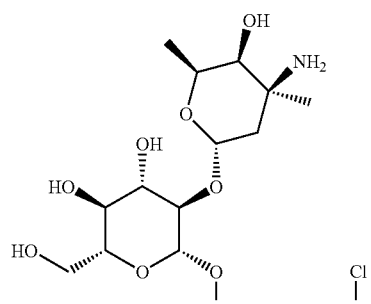
444
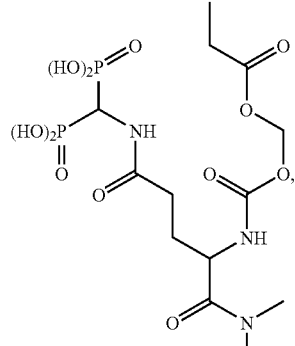
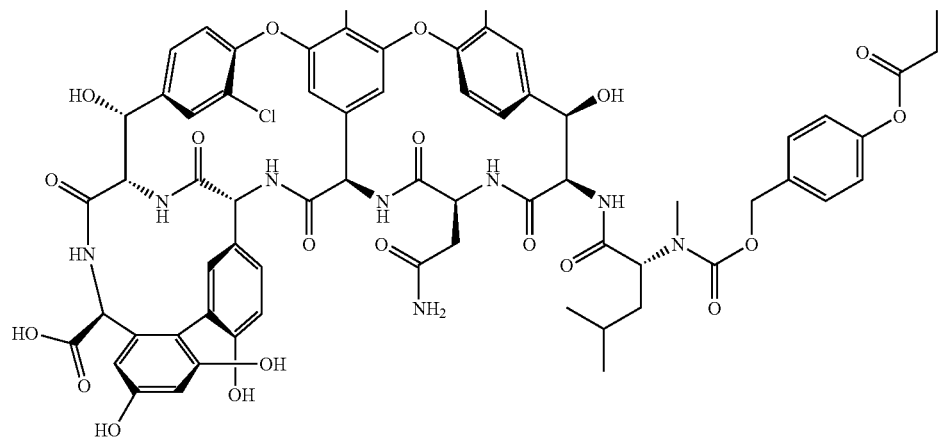
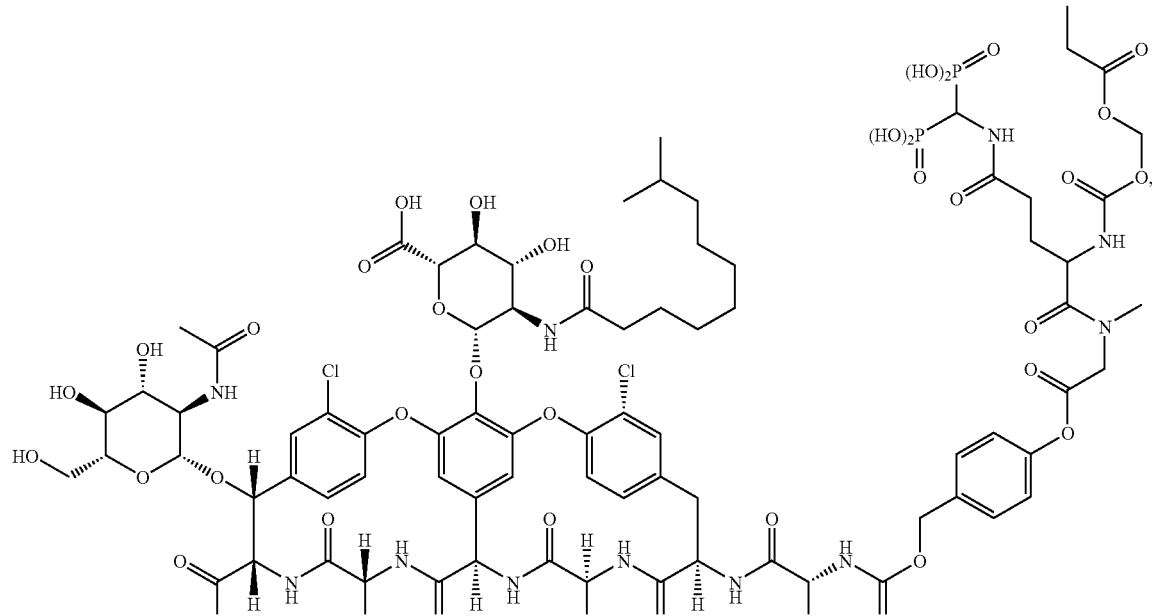

445
446
-continued
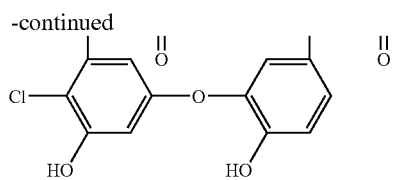
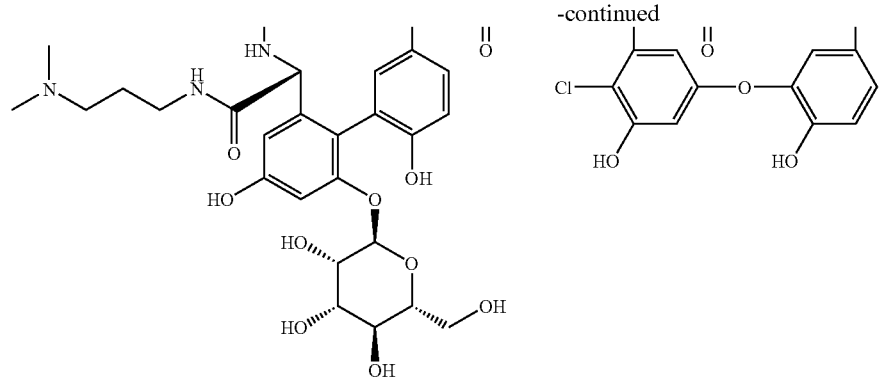
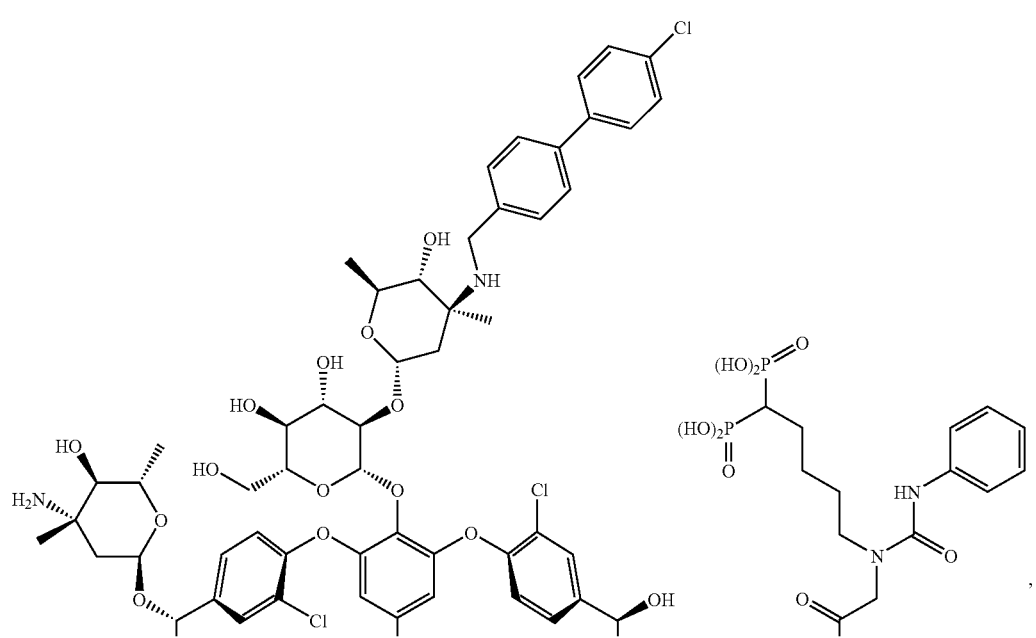
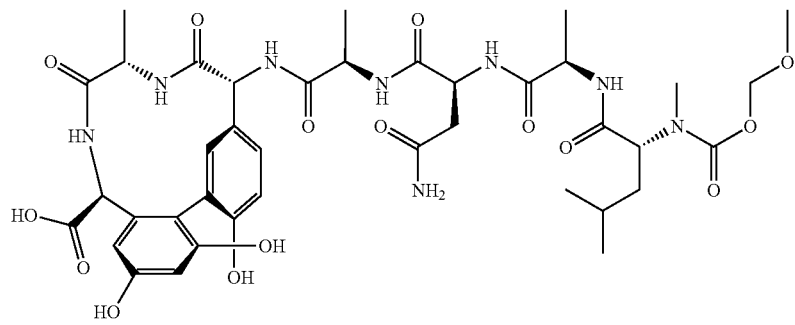

447 448
-continued
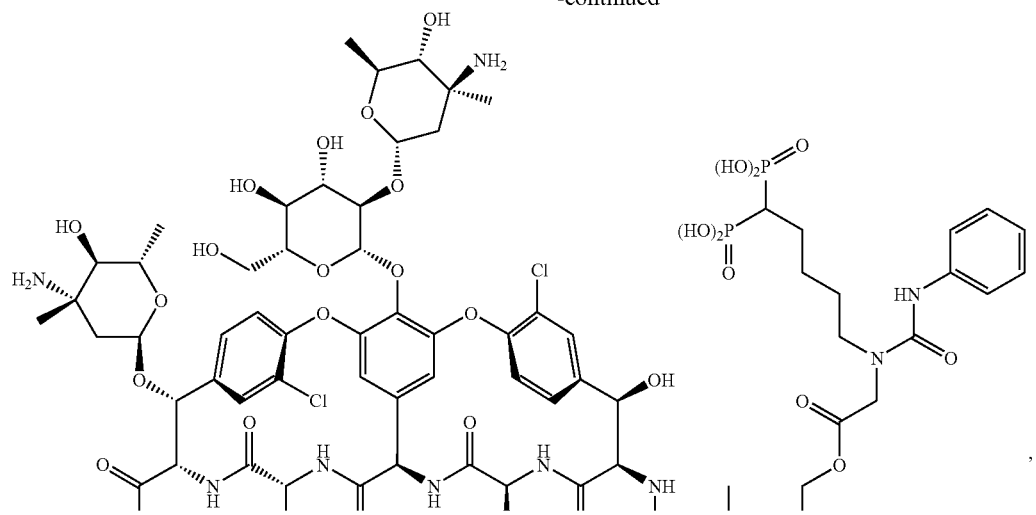
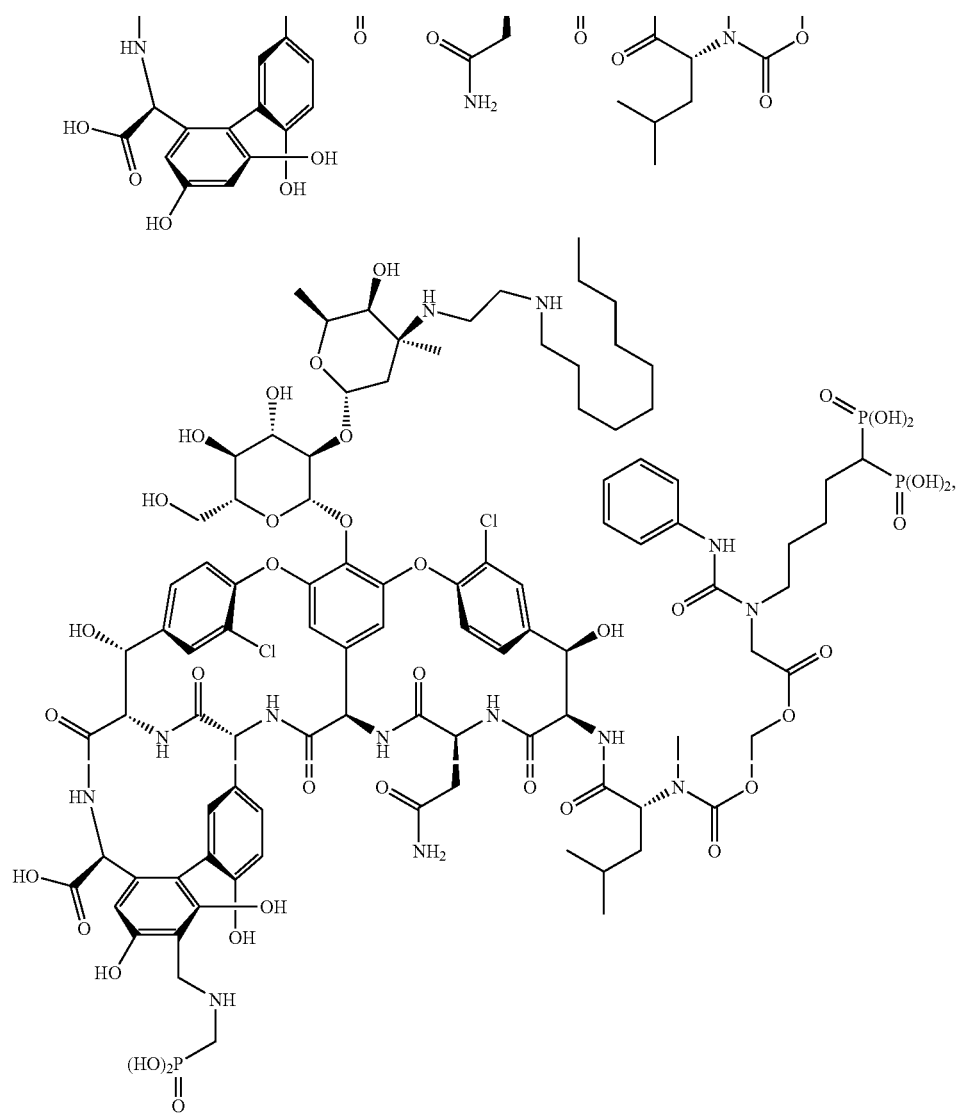

449
450
-continued
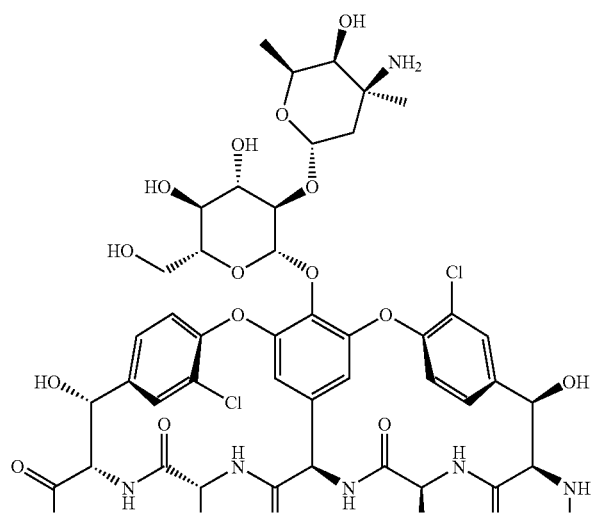
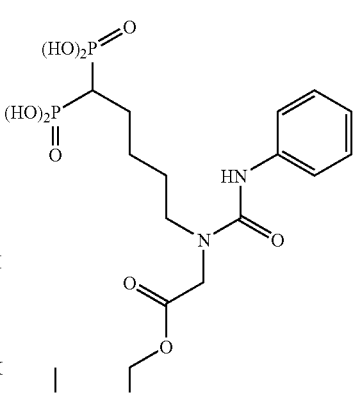
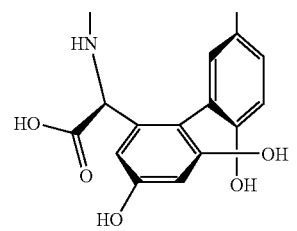
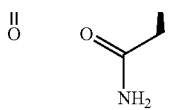
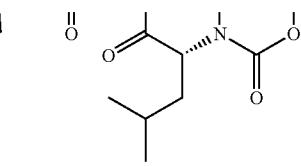
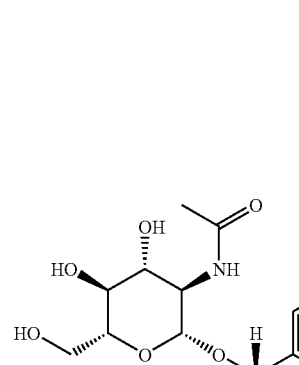
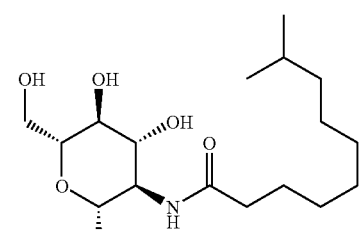
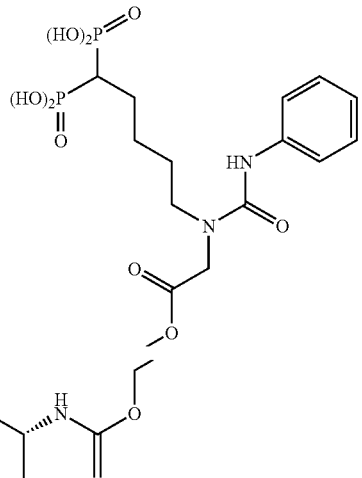
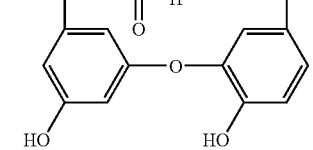
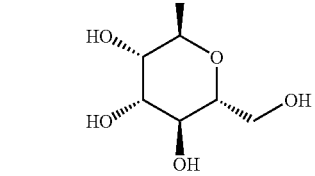

451 -continued 452
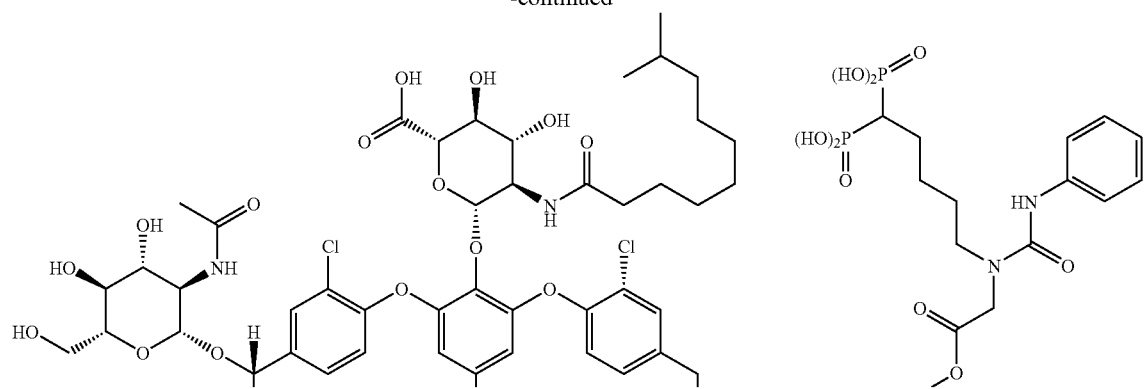
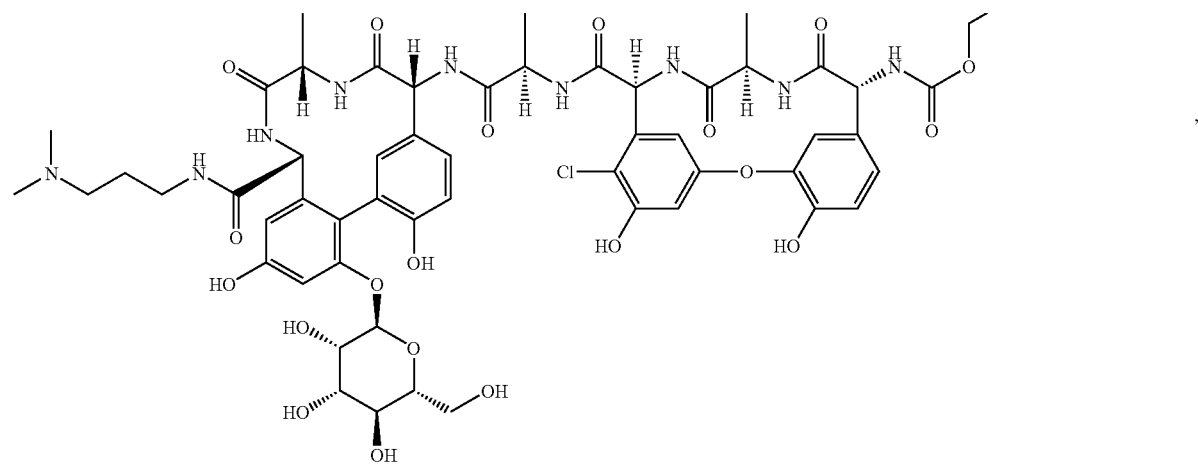
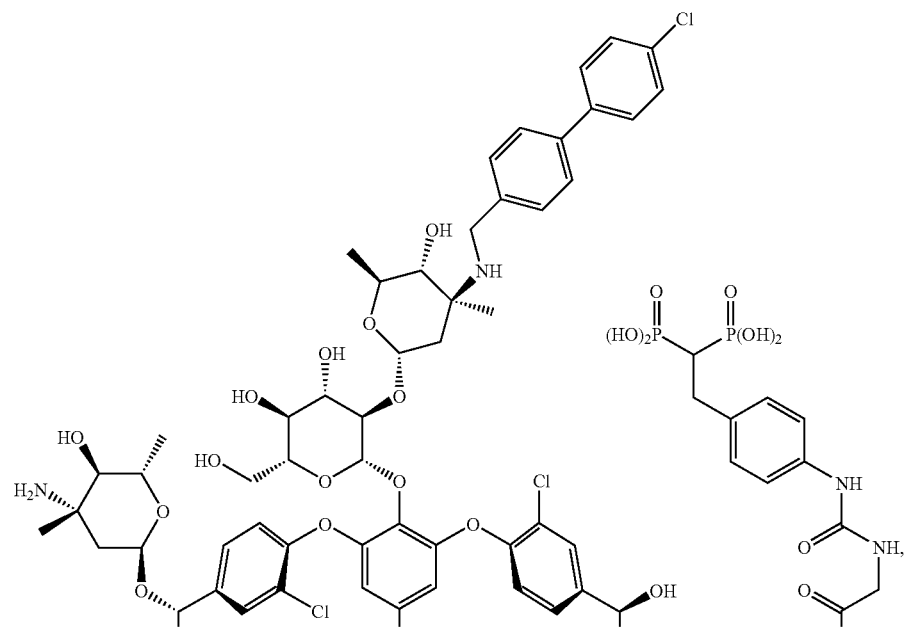

453
-continued
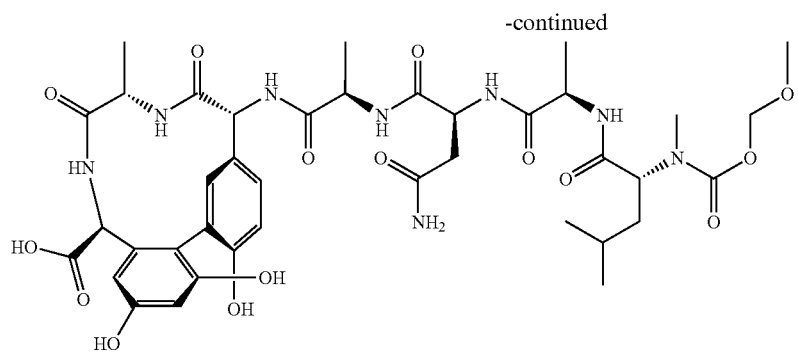
454
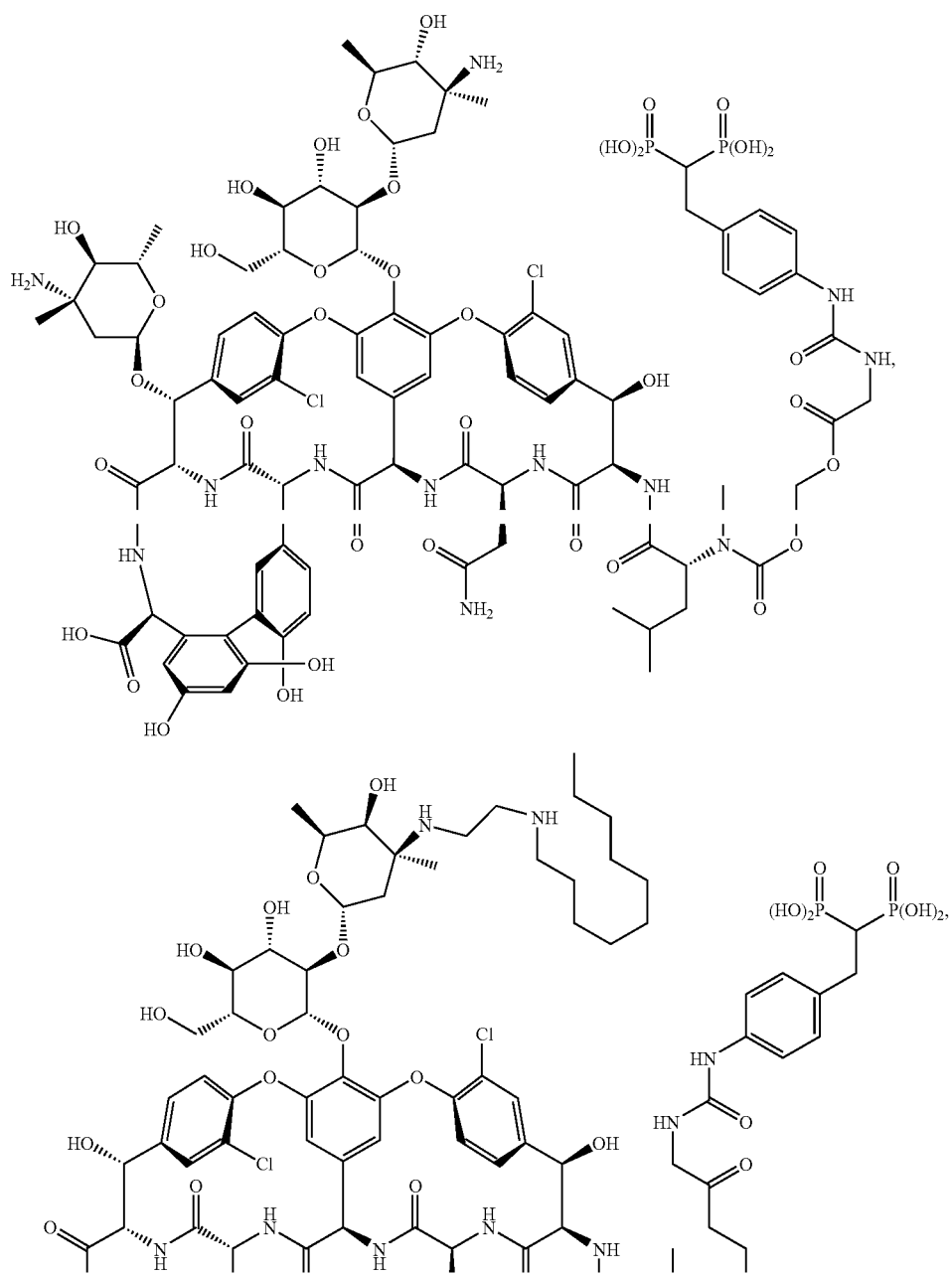

455
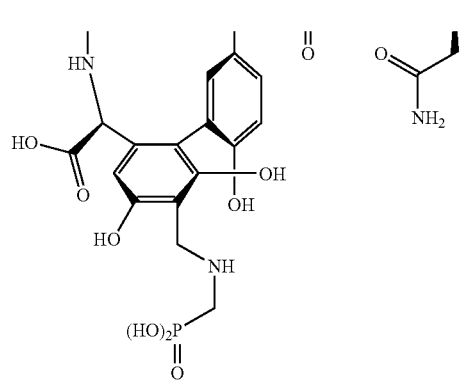
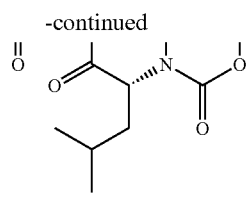
-continued
456
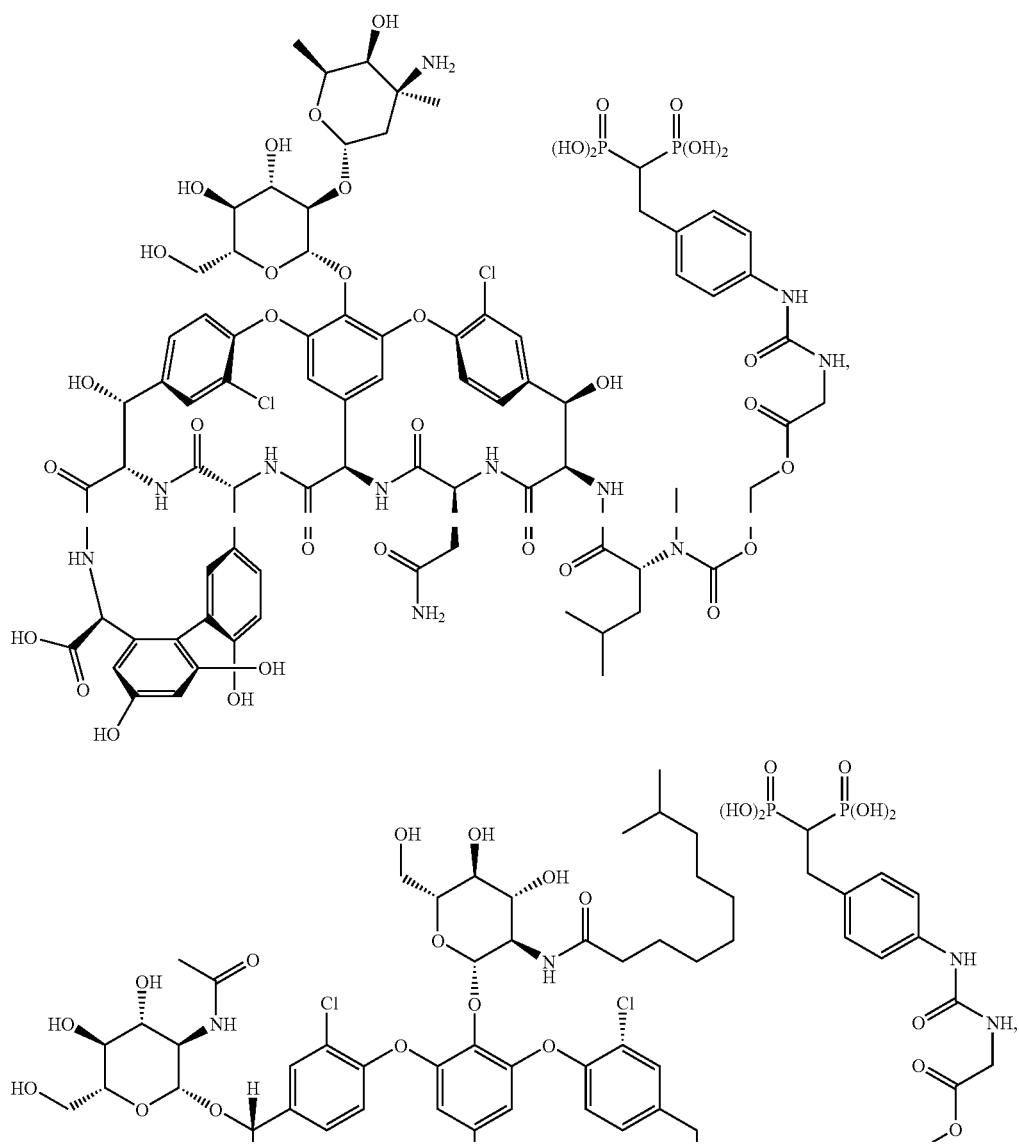

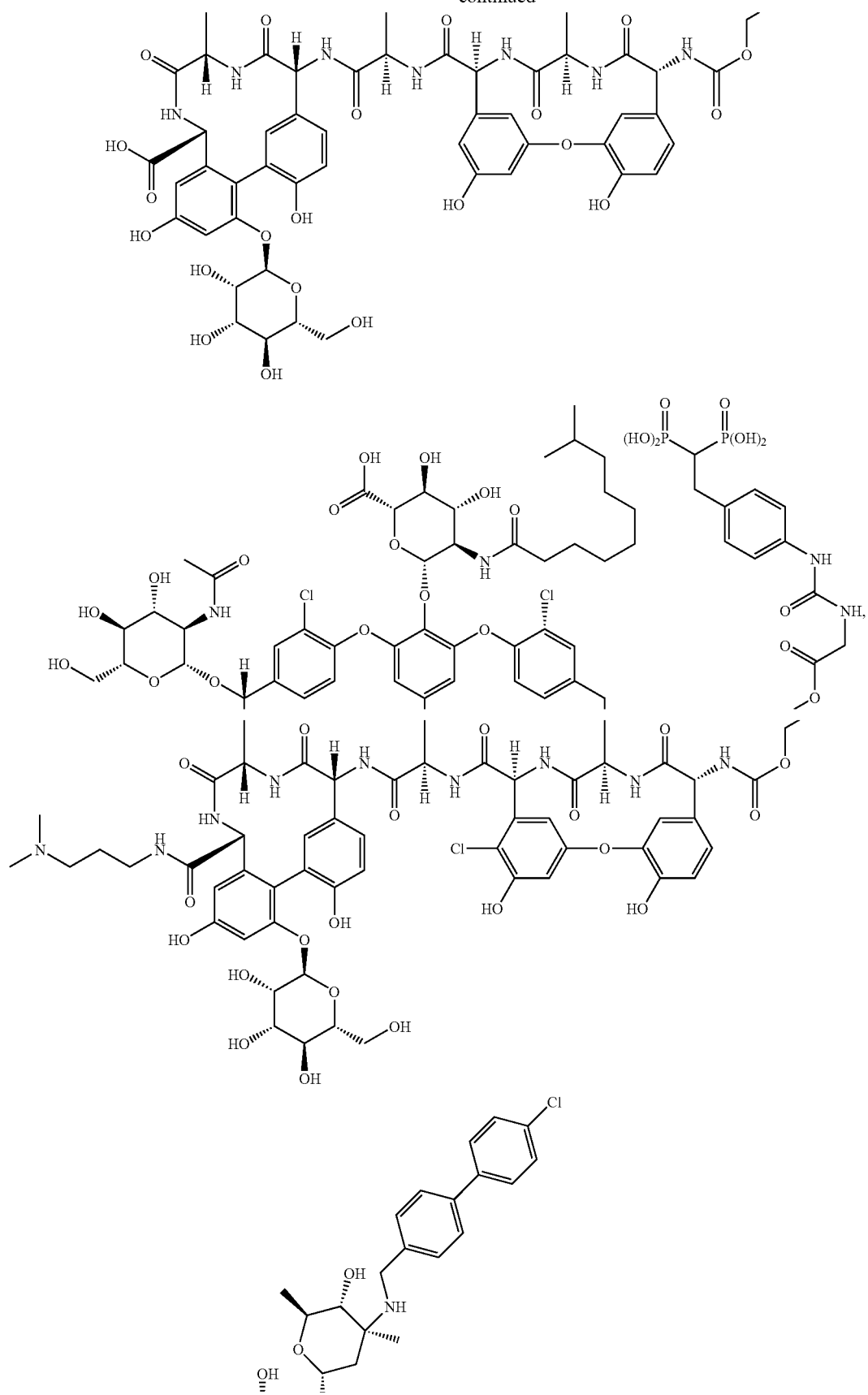

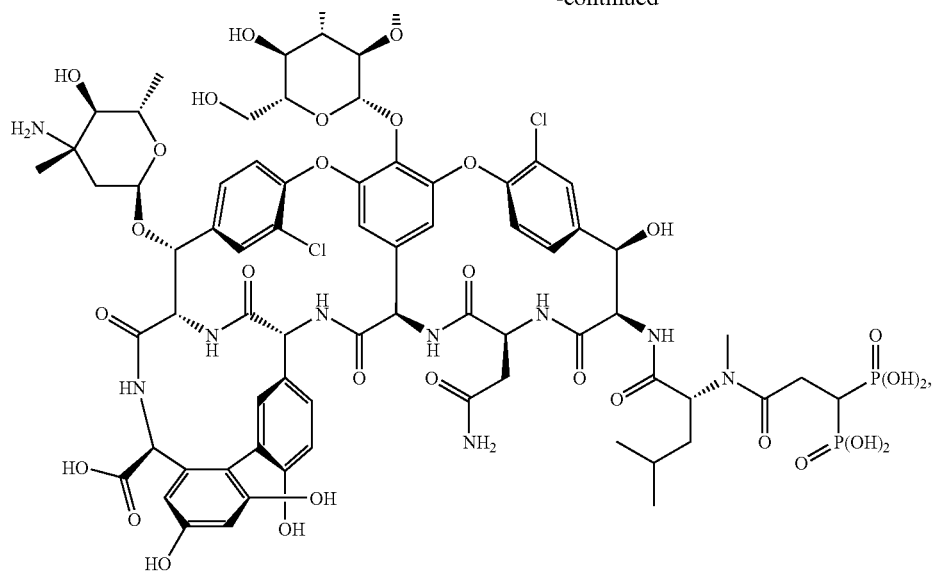
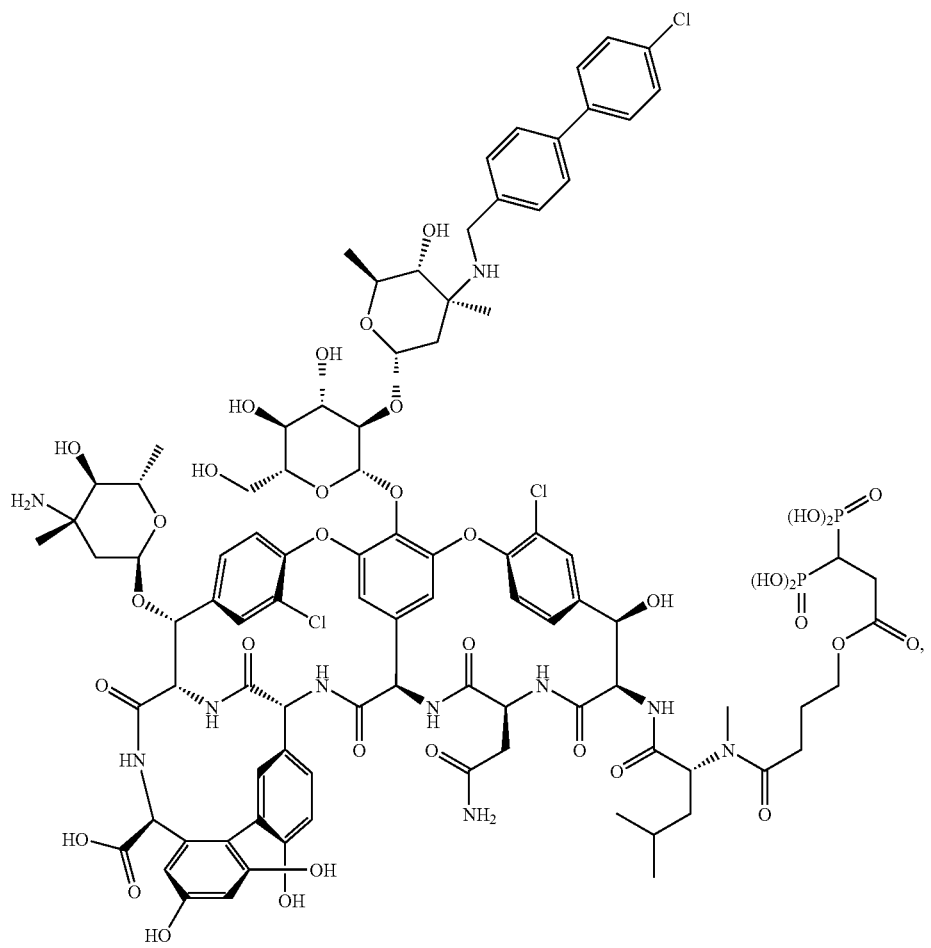

-continued
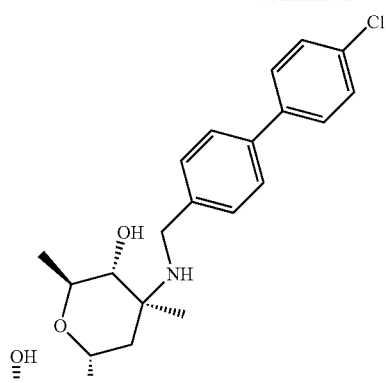
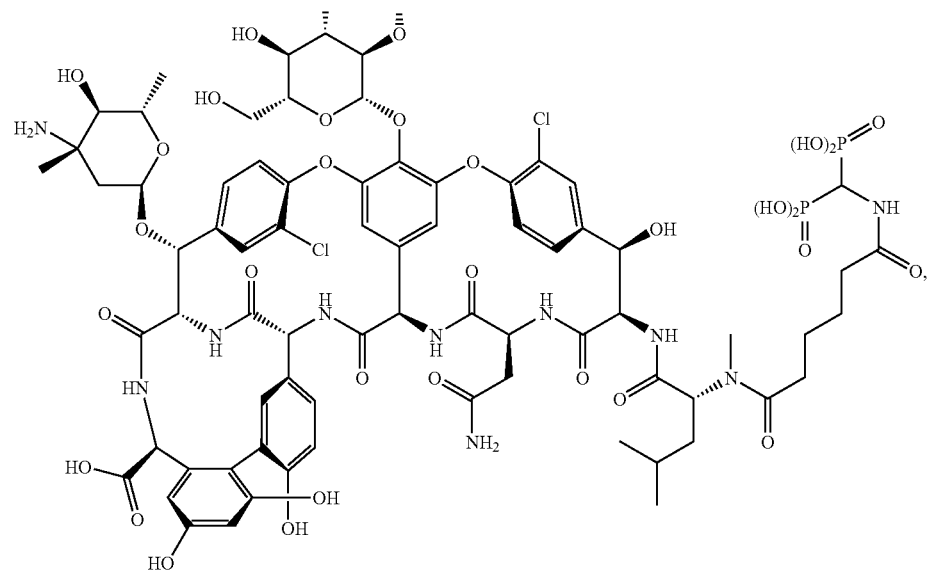
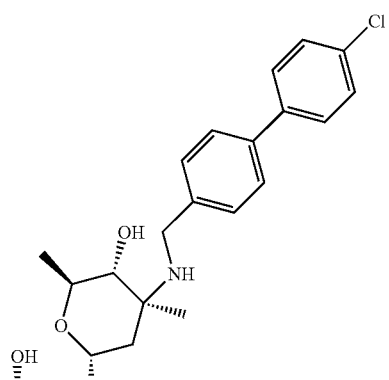

-continued

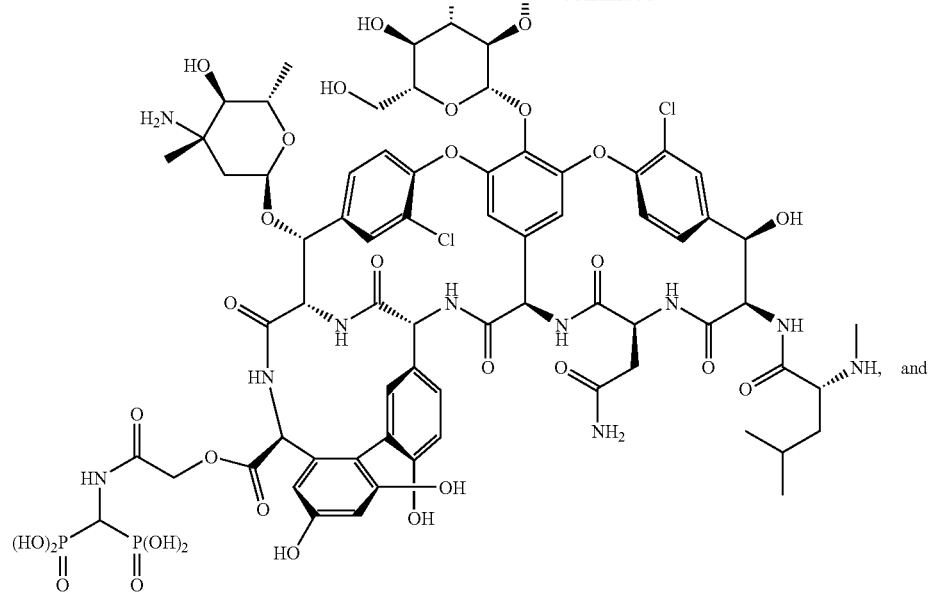

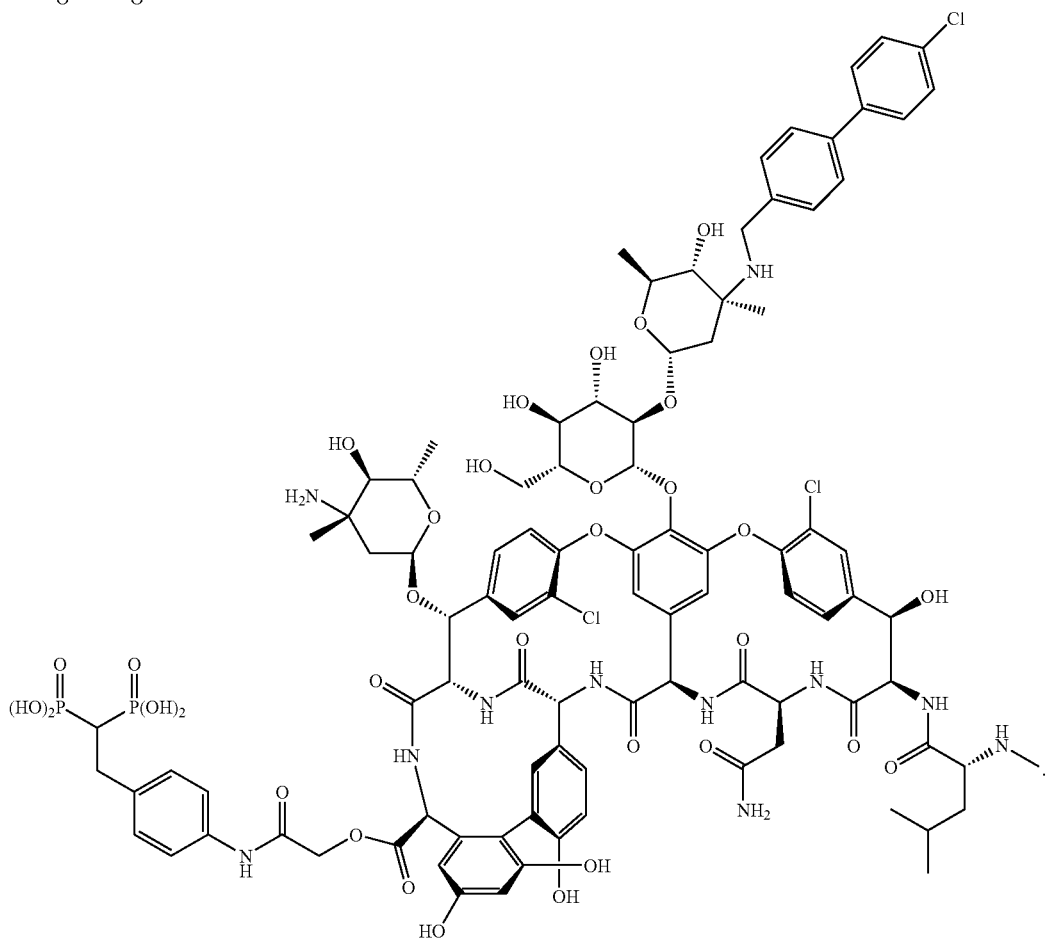

wherein R is $C_aH_b$ where a is an integer ≤20 and b is a non-null integer ≤2a+1

Further, the present invention covers the compounds of Formula I and of Formula II, as well as pharmaceutically acceptable salts, esters and prodrugs thereof. Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycolates, tartrates, methanesulfonates, propanesulfonates, naphthalene-1-sulfonates, naphthalene-2-sulfonates, and mandelates.

If the inventive compound is a base, the desired salt may be prepared by any suitable method known to the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such as p-toluenesulfonic acid or ethanesulfonic acid, or the like.

If the inventive compound is an acid, the desired salt may be prepared by any suitable method known to the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum, and lithium.

In the case of compounds, salts, or solvates that are solids, it is understood by those skilled in the art that the inventive compounds, salts, and solvates may exist in different crystal forms, all of which are intended to be within the scope of the present invention.

The inventive compounds may exist as single stereoisomers, racemates and/or mixtures of enantiomers and/or diastereomers. All such single stereoisomers, racemates and mixtures thereof are intended to be within the scope of the present invention. Preferably, the inventive compounds are used in optically pure form.

It is conceivable that the compounds of the Formula I and/or of Formula II be administered in the form of a prodrug which is broken down in the human or animal body to give a compound of the Formula I or of Formula II. Examples of prodrugs include in vivo hydrolysable esters of a compound of the Formula I and/or of Formula II.

An in vivo hydrolysable ester of a compound of the Formula I and/or of Formula II containing carboxy or hydroxy group is, for example, a pharmaceutically-acceptable ester which is hydrolyzed in the human or animal body to produce the parent acid or alcohol. Suitable pharmaceutically-acceptable esters for carboxy include (1-6C)alkoxymethyl esters for example methoxymethyl, (1-6C)alkanoyloxymethyl esters for example pivaloyloxymethyl, phthalidyl esters, (3-8C)cycloalkoxycarbonyloxy(1-6C)alkyl esters for example 1-cyclohexylcarbonyloxyethyl; 1,3-dioxolen-2-onylmethyl esters for example 5-methyl-1,3-dioxolen-2-onylmethyl; and (1-6C)alkoxycarbonyloxyethyl esters for example 1-methoxycarbonyloxyethyl and may be formed at any carboxy group in the compounds of this invention.

An in vivo hydrolysable ester of a compound of the Formula I and/or of Formula II containing a hydroxy group includes inorganic esters such as phosphate esters and alpha-acyloxyalkyl ethers and related compounds which as a result of in vivo hydrolysis of the ester break down to give the parent hydroxy group. Examples of alpha-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

D) Methods of Preparation

The inventive compounds, and their salts, solvates, crystal forms, active metabolites, and prodrugs, may be prepared by employing the techniques available in the art using starting materials that are readily available. Certain novel and exemplary methods of preparing the inventive compounds are described in the Exemplification section. Such methods are within the scope of this invention.

E) Antimicrobial Compositions and Methods of Treatment

A related aspect of the invention concerns the use of compounds of the invention as an active ingredient in a therapeutic or anti-bacterial composition for treatment or prevention purposes.

Pharmaceutical Compositions

The compounds of the present invention may be formulated as pharmaceutically acceptable compositions.

The present invention provides for pharmaceutical compositions comprising a compound of the present invention (e.g., those compounds of Formula (I) and (II)) in combination with a pharmaceutically acceptable carrier or excipient. Preferably, the compound of the present invention is a therapeutically effective amount of the compound. Such carriers include, but are not limited to saline, buffered saline, dextrose, water, glycerol, ethanol, and combinations thereof.

Acceptable methods of preparing suitable pharmaceutical forms of the pharmaceutical compositions according to the invention are known to those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for various routes of administration.

The compounds and compositions of the invention are conceived to have a broad spectrum of activity, including antibiotic resistant strains, against both Gram-positive (e.g. *Staphylococcus aureus, Staphylococcus epidermis, Streptococcus pyogenes, Enterococcus faecalis*) and Gram-negative bacteria (e.g. *E. coli, Chlamydia pneumoniae, Enterobacter* sp., *H. influenza, K. pneumoniae, Legionella pneumoniae, P. aeruginosa*).

Pharmaceutical Compositions and a Second Therapeutic Agent

A wide range of second therapeutic agents, such as antibiotics, can be used in combination with the compounds, compositions and methods of the present invention. Antibiotics used as second therapeutic agents may act by interfering with cell wall synthesis, plasma membrane integrity, nucleic acid synthesis, ribosomal function, folate synthesis, etc. A non-limiting list of useful antibiotics with which the compounds and compositions might be combined includes: Rifamycins, sulfonamides, beta-lactams, tetracyclines, chloramphenicol, aminoglycosides, macrolides, glycopeptides, streptogramins, quinolones, fluoroquinolones, oxazolidinones and lipopeptides. In particular, tetracycline, tetracycline derived antibacterial agents, glycylcycline, glycylcycline derived antibacterial agents, minocycline, minocycline derived antibacterial agents, oxazolidinone antibacterial agents, aminoglycoside antibacterial agents, quinolone antibacterial agents, vancomycin, vancomycin derived antibacterial agents, teicoplanin, teicoplanin derived antibacterial agents, eremomycin, eremomycin derived antibacterial agents, chloroeremomycin, chloroeremomycin derived antibacterial agents, daptomycin, daptomycin derived antibacterial agents, rifamycin and rifamycin derived antibacterial agents are preferred.

Methods for Inhibiting Bacterial Growth

According to a related aspect, the present invention concerns methods of inhibiting bacterial growth, and more particularly growth of Gram-positive bacteria. The method comprises contacting the bacteria for the purpose of such inhibition with an effective amount of a phosphonated glycopeptide or lipoglycopeptide compound or composition according to the invention (or a pharmaceutically acceptable prodrug, salt, active metabolite, or solvate thereof). For example, one can inhibit cell wall biosynthesis in a Gram-positive bacterium by contacting such a bacterium with a compound of the invention.

The contacting may be carried out in vitro (in biochemical and/or cellular assays), in vivo in a non-human animal, in vivo in mammals, including humans and/or ex vivo (e.g. for sterilization purposes).

The activity of the inventive compounds as inhibitors of cell-wall biosynthesis may be measured by any of the methods available to those skilled in the art, including in vivo and in vitro assays. Some examples of suitable assays have been described for measurement of binding to cell-wall fragments (Chu et al. Journal of Organic Chemistry (1992), 57:3524-3525. Cooper et al, Chemical Communications (1997), 1625-1626), binding to whole cell walls (Cegelski et al. Journal of Molecular Biology (2006), 357; 1253-1262), inhibition of enzymatic processes leading to cell wall components (Branstrom et al. FEMS Microbiology Letters (2000); 191:187-190. Leimkuhler et al. Journal of the American Chemical Society (2005); 127: 3250-3251) and inhibition of cell wall biosynthesis at the cellular level (Higgins et al., Antimicrobial Agents and Chemotherapy (2005); 49: 1127-1134).

A related aspect of the invention concerns the use of a compound of the invention as an active ingredient in a pharmaceutical, therapeutic or anti-bacterial composition for treatment purposes. As defined above, "treating" or "treatment" means at least the mitigation of a disease condition associated with a bacterial infection in a subject, including mammals such as a human, that is alleviated by a reduction of growth, replication, and/or propagation of any bacterium, such as Gram-positive organisms, and includes curing, healing, inhibiting, relieving from, improving and/or alleviating, in whole or in part, the disease condition.

The pharmaceutical compositions may be administered in any effective, convenient manner including, for instance, administration by topical, parenteral, oral, anal, intravaginal, intravenous, intraperitoneal, intramuscular, intraocular, subcutaneous, intranasal, intrabronchial, or intradermal routes among others.

In therapy or as a prophylactic, the compound(s) of the invention and/or pharmaceutically acceptable prodrugs, salts, active metabolites and solvates may be administered to an individual as an injectable composition, for example as a sterile aqueous dispersion, preferably isotonic. Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Alternative means for systemic administration include transmucosal and transdermal administration using penetrants such as bile salts or fusidic acids or other detergents. In addition, if a compound of the present invention can be formulated in an enteric or an encapsulated formulation, oral administration may also be possible. Administration of these compounds may also be topical and/or localized, in the form of salves, pastes, gels, and the like.

While the treatment can be administered in a systemic manner through the means described above, it may also be administered in a localized manner. For example, the treatment may be administered directly to a bone, such as through an injection into a bone. The treatment may also be administered in other localized manners, such as application to a wound through a topical composition or directly into a subcutaneous or other form of wound.

The active compound(s) and its pharmaceutically acceptable prodrugs, salts, metabolites and solvates may be also administered to an individual as part of a bone substitute or bone-repair compound such as bone cements or fillers (e.g. Skelite™, Millenium Biologics, Kingston, ON, Canada) and calcium or hydroxyapatite beads.

A dose of the pharmaceutical composition contains at least a pharmaceutically- or therapeutically-effective amount of the active compound (i.e., a compound of Formula (I), of Formula (II) and/or a pharmaceutically acceptable prodrug, salt, active metabolite, or solvate thereof), and is preferably made up of one or more pharmaceutical dosage units. The selected dose may be administered to a mammal, for example, a human patient, in need of treatment. A "therapeutically effective amount" is intended to mean that amount of a compound of Formula (I) and/or of Formula (II) (and/or a pharmaceutically acceptable prodrug, salt, active metabolite, or solvate thereof) that confers a therapeutic effect on the subject treated. The therapeutic effect may be objective (i.e. measurable by some test or marker (e.g. lower bacterial count)) or subjective (i.e. the subject gives an indication of or feels an effect).

The amount that will correspond to a "therapeutically effective amount" will vary depending upon factors such as the particular compound, the route of administration, excipient usage, the disease condition and the severity thereof, the identity of the mammal in need thereof, and the possibility of co-usage with other agents for treating a disease. Nevertheless the therapeutically effective amount can be readily determined by one of skill in the art. For administration to mammals, and particularly humans, it is expected that the daily dosage level of the active compound will be from 0.1 mg/kg to 200 mg/kg, typically around 1-5 mg/kg. The physician in any event will determine the actual dosage that will be most suitable for an individual and will vary with the age, weight and response of the particular individual. The above dosages are exemplary of the average case. There can, of course, be individual instances where higher or lower dosage ranges are merited, and such are within the scope of this invention.

The invention provides a method of treating a subject in need of treatment wherein a phosphonated glycopeptide or lipoglycopeptide antimicrobial molecule having high affinity to osseous tissues is administered to the subject. Preferably, the phosphonated group is coupled to the glycopeptide or lipoglycopeptide antimicrobial molecule through a cleavable linker. Preferably the subject is a mammal, such as a human. The method of treatment may also be applied in a veterinary aspect, to animals such as farm animals including horses, cattle, sheep, and goats, and pets such as dogs, cats and birds.

Although the invention is preferably directed to the prevention and/or treatment of bone-related infections, the invention encompasses therapeutic and prophylactic methods against other diseases caused by or related to bacterial infection, including but not limited to otitis, conjunctivitis, pneumonia, bacteremia, sinusitis, pleural emphysema and endocarditis, low grade infections in the vicinity of calcifications of atherosclerotic vessels, and meningitis. In such methods, an effective therapeutic or prophylactic amount of an antibacterial compound and/or composition as defined hereinbefore, is administered to a mammal (preferably a human) in an amount sufficient to provide a therapeutic effect and thereby prevent or treat the infection of the mammal. Exact amounts can be routinely determined by one skilled in the art and will vary depending on several factors, such as the particular bacterial strain involved and the particular antibacterial compound used.

Prophylaxis and Prevention

An additional use that is particularly contemplated for the compounds invention is for prophylaxis and prevention purposes. Indeed, many orthopedic surgeons consider that humans with prosthetic joints should be considered for antibiotic prophylaxis before a treatment that could produce a bacteremia. Deep infection is a serious complication sometimes leading to loss of the prosthetic joint and is accompanied by significant morbidity and mortality. The compounds and compositions of the invention may therefore be used as a replacement for prophylactic antibiotics in this situation. For instance, the compounds and/or compositions of the invention may be administered by injection to achieve a systemic and/or local effect against relevant bacteria shortly before an invasive medical treatment, such as surgery or insertion of an in-dwelling device (e.g. joint replacement (hip, knee, shoulder, etc.), bone grafting, fracture repair, dental operation or implant. Treatment may be continued after invasive medical treatment, such as post-operatively or during the in-body time of the device.

In addition, the compound and/or composition may also be administered before the invasive medical treatment to permit the accumulation of the compound into the bone tissues prior to the treatment.

In each instance, the compound(s) of the invention could be administered once, twice, thrice or more, from 1, 2, 3, 4, 5, 6, 7 days or more, to 10, 9, 8, 7, 6, 5, 4, 3, 2, or 1 hour or less before surgery for permitting an advisable systemic or local presence of the compounds, and/or accumulation in the bones, preferably in the areas potentially exposed to bacterial contamination during the surgical procedure. Even more preferably, the phosphonated compounds of the invention would be administered such that they can reach a local concentration of about 5, 10, 20, 30, 40, 50, 75, 100, 500 or even 1000 fold higher concentration than the concentration that would normally be achieved during the administration of the unmodified parent glycopeptide or lipoglycopeptide antimicrobial molecule, i.e. a non-phosphonated equivalent. The compound(s) may be administered after the invasive medical treatment for a period of time, such as 1, 2, 3, 4, 5 or 6 days, 1, 2, 3 or more weeks, or for the entire time in which the device is present in the body.

Therefore, the invention provides a method of inducing accumulation of an glycopeptide or lipoglycopeptide antimicrobial molecule in bones of a mammal wherein a phosphonated glycopeptide or lipoglycopeptide antimicrobial molecule having high affinity to osseous tissues is administered to a mammal. The phosphonated glycopeptide or lipoglycopeptide antimicrobial molecule binds osseous tissues and accumulates in bones of the mammal in amounts greater than amounts of a non-phosphonated equivalent of the glycopeptide or lipoglycopeptide antimicrobial molecule. Preferably, the phosphonated group is coupled to the glycopeptide or lipoglycopeptide antimicrobial molecule through a cleavable linker.

The invention further provides a method for prolonging the presence of an glycopeptide or lipoglycopeptide antimicrobial molecule in bones of a mammal wherein a phosphonated glycopeptide or lipoglycopeptide antimicrobial molecule having a high affinity to osseous tissues is administered to a mammal. The phosphonated group is coupled to the glycopeptide or lipoglycopeptide antimicrobial molecule through a cleavable linker. The phosphonated glycopeptide or lipoglycopeptide antimicrobial molecule binds osseous tissues and accumulates in bones of the mammal, and the linker is cleaved gradually within the bones thereby releasing the glycopeptide or lipoglycopeptide antimicrobial molecule and prolonging the presence of the glycopeptide or lipoglycopeptide antimicrobial molecule in the bones.

F) In-Dwelling Devices and Products Coated with the Phosphonated Glycopeptide or Lipoglycopeptide Antimicrobial Molecules of the Invention The invention further encompasses in-dwelling devices coated with the compounds of the invention. As used herein, the term "in-dwelling device" refers to surgical implants, orthopedic devices, prosthetic devices and catheters, i.e., devices that are introduced to the body of an individual and remain in position for an extended time. Such devices include, but are not limited to, artificial joints and implants, heart valves, pacemakers, vascular grafts, vascular catheters, cerebrospinal fluid shunts, urinary catheters, continuous ambulatory peritoneal dialysis (CAPD) catheters.

According to one embodiment, the in-dwelling device is bathed in or sprayed with a concentration of about 1 mg/ml to about 10 mg/ml of the compound and/or the composition of the invention, before its insertion in the body.

According to another embodiment, the in-dwelling device is made of, or pre-coated with, an osseous-like type of material (e.g. calcium phosphate, Ca-ion and hydroxyapatite (Yoshinari et al., Biomaterials (2001), 22(7): 709-715)). Such material is likely to advantageously improve binding of the compounds of the invention to the in-dwelling device, either during the coating of the device with the compounds of the invention and/or after their local or systemic administration. The in-dwelling devices may also be coated with an osseous material pre-loaded with or containing bound bone-targeting compound(s) according to the invention. For the above-mentioned embodiments, hydroxyapatite would be preferred as the osseous material. More details on coating methods, uses and advantages of hydroxyapatite-coated prostheses are found in the review by Dumbleton and Manly (The Journal of Bone & Joint Surgery (2004) 86A:2526-40) which is incorporated herein by reference.

G) Methods of Preparation

The inventive compounds, and their salts, solvates, crystal forms, active metabolites, and prodrugs, may be prepared by employing the techniques available in the art using starting materials that are readily available. Certain novel and exemplary methods of preparing the inventive compounds are described in the Exemplification section below. Such methods are within the scope of this invention.

EXAMPLES

The Examples set forth herein below provide exemplary syntheses of certain representative compounds of the invention. Also provided are exemplary methods for assaying the compounds of the invention for their activity as inhibitors of protein synthesis, assays for determining the minimum inhibitory concentration (MIC) of the compounds of the invention against microorganisms, and methods for testing in vivo activity and cytotoxicity.

Example 1

Synthesis of Vancomycin and Oritavancin Bisphosphonate Conjugates

A) General Experimental Procedures
A 1) Preparation of Bisphosphonate Building Blocks Following protocols described in Bioorg. Med. Chem. (1999), 7: 901-919, benzyl substituted bisphosphonate building blocks of the general structures III and V can be obtained by alkylation of the anion of I with 4-substituted benzyl bromide II or bromoacetate IV. Nitro compound IIIa can be converted to aniline IIIb by reduction of the nitro group under hydrogenation conditions, using a catalyst such as $PtO_2$. Esters like IIIc and Va can be converted to the corresponding acids IIId or Vb via ester cleavage. For example, ester IIIc where R'=t-Bu can be treated with TFA to afford the corresponding acid IIId. Under similar conditions, ester Va where X=Ot-Bu can be converted to acid Vb.

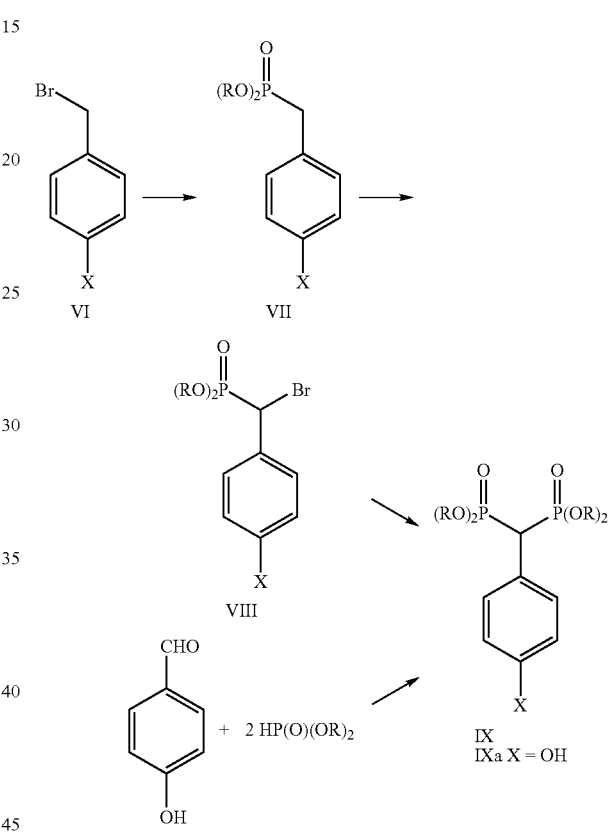

Aryl substituted methylene bisphosphonates of general formula IX can be obtained from the parent benzylic halides VI in a sequence of two Arbuzov reactions separated by a benzylic halogenation. The hydroxyl substituted parent molecule IXa can be obtained by the nucleophilic addition of the alkali metal salt of a dialkyl phosphite to 4-hydroxybenzaldehyde as described in Org. Biomol. Chem. (2004), 21:3162-3166.

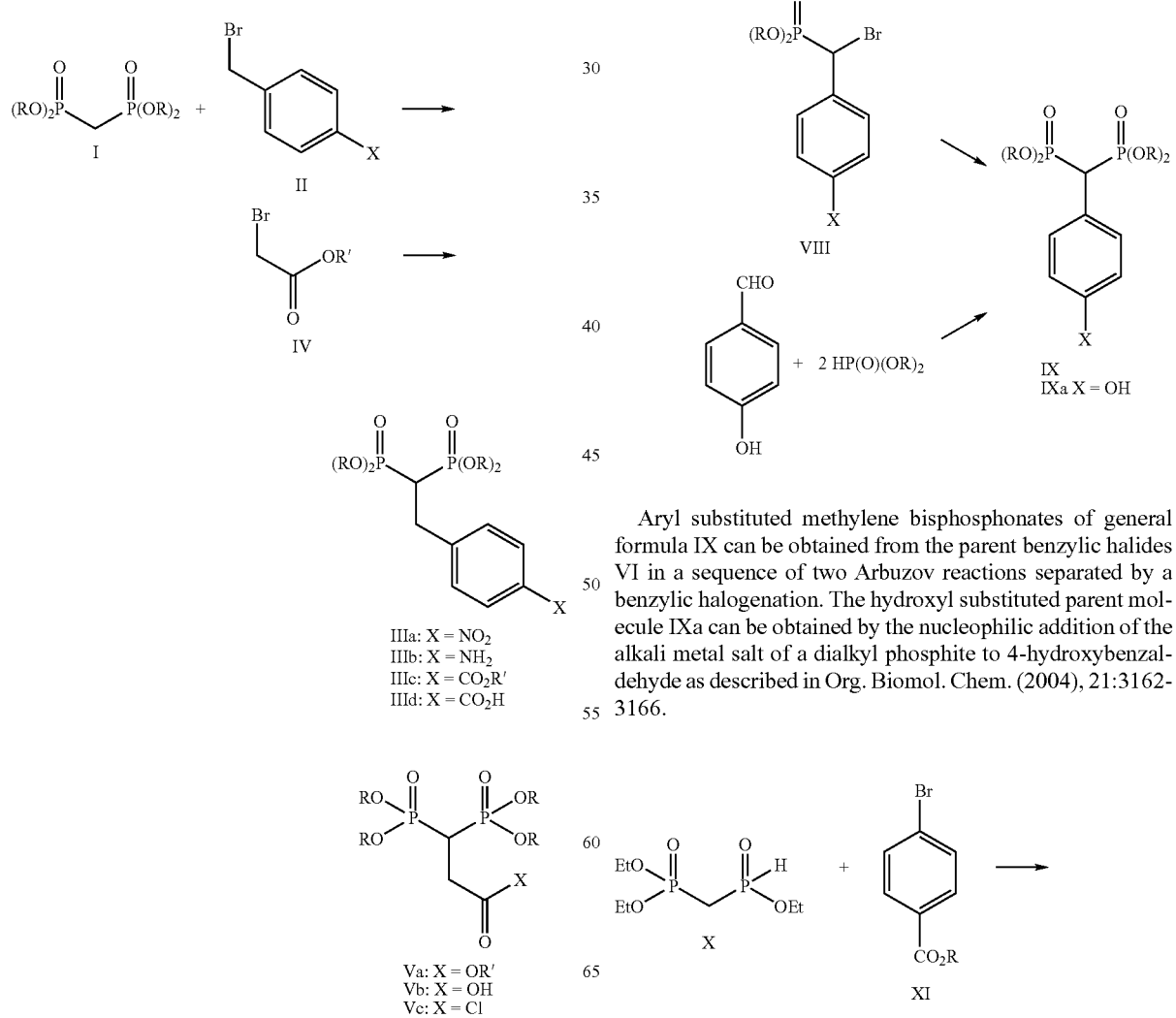

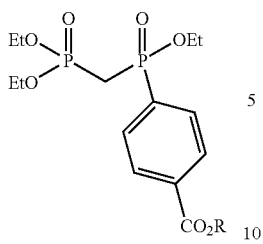

XIIa: R = t-Bu, Me
XIIb: R = H

Diethyl (ethoxyphosphinyl)methylphosphonate X can be prepared using the procedure described in Synth. Comm. (2002), 32: 2951-2957 and U.S. Pat. No. 5,952,478 (1999). It can be coupled with a 4-substituted bromobenzene (XI) to access acid XIIb, following cleavage of the ester intermediate XIIa.

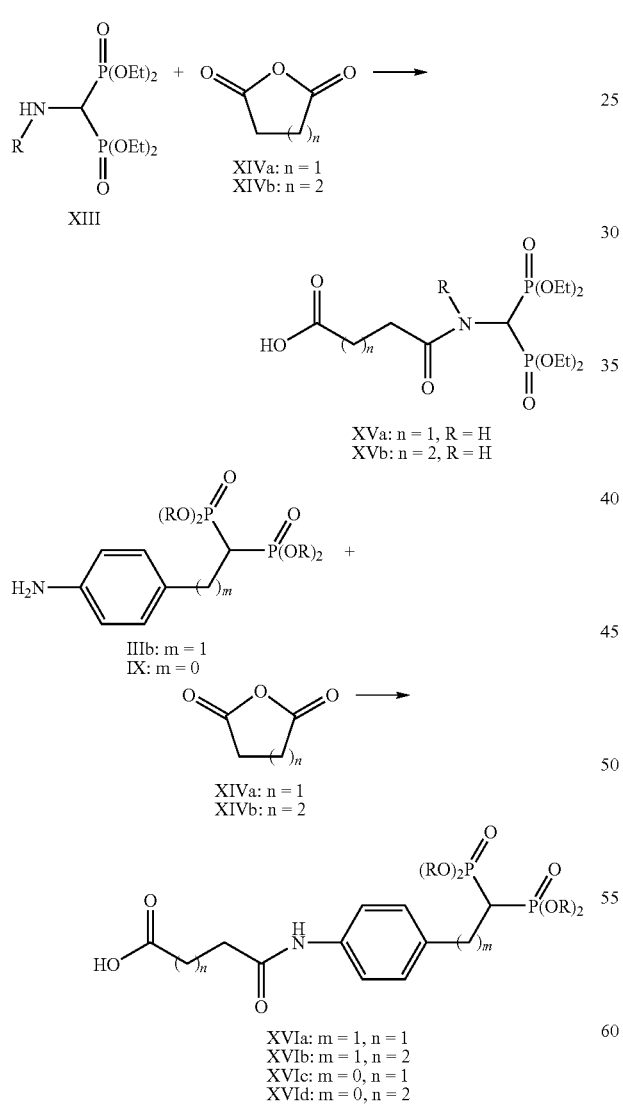

Amines of the general formula XIII can be prepared from dibenzylamine, diallylamine, or other N-benzyl and N-allyl secondary amines, diethyl phosphite and triethyl orthoformate following a protocol described in Synth. Comm. (1996), 26: 2037-2043. Acylation of XIII with succinic anhydride XIVa or glutaric anhydride XIVb can provide acids XVa and XVb respectively (J. Drug Targeting (1997), 5: 129-138). In a similar fashion, treatment of the previously described IIIb or IX with XIV(a-b) results in the succinamic and glutaramic acids XVI(a-d).

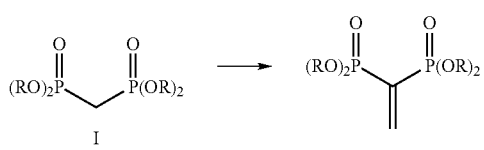

Olefin XVII can be prepared from I following a protocol described in J. Org. Chem. (1986), 51: 3488-3490.

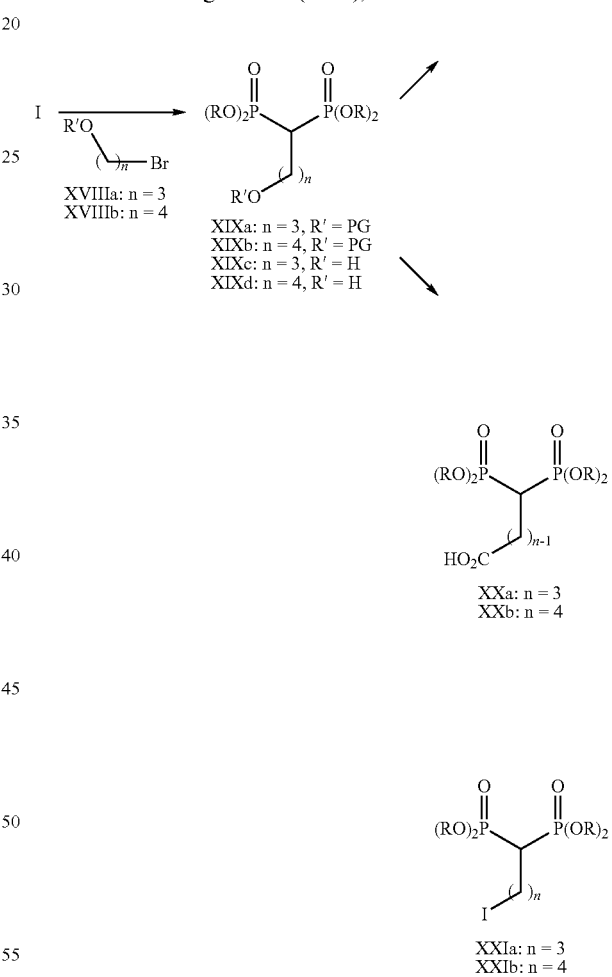

As described in Phosphorus, Sulfur and Silicon (1998), 132: 219-229, alcohols of general structure XIX(c-d) and iodides of general structure XXI can be prepared by alkylation of the anion of I by protected ω-hydroxy bromides of various chain length XVIII. After deprotection, alcohols can be converted to the corresponding iodides via treatment with in situ generated triphenylphosphine:iodine complex. These alcohols XIX(c-d) may additionally be converted to acids of general structure XX by conventional methods of oxidation, such as treatment with pyridinium dichromate.

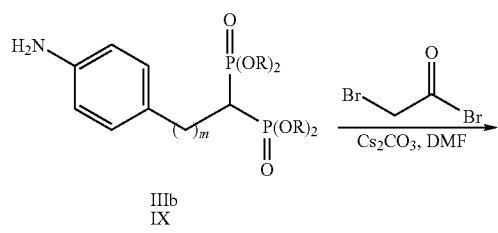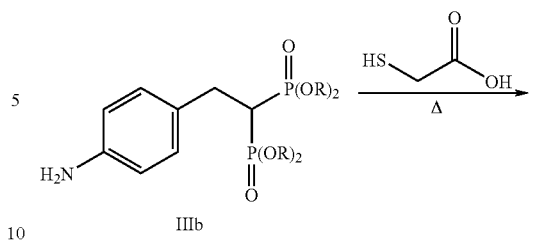

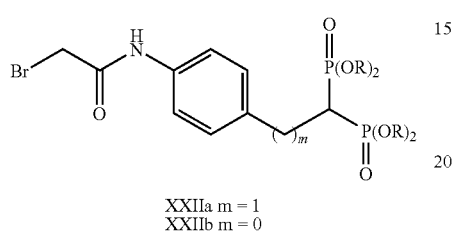

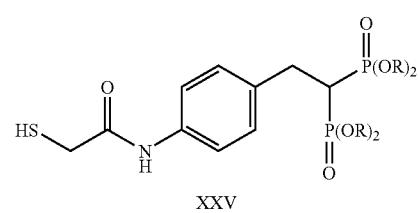

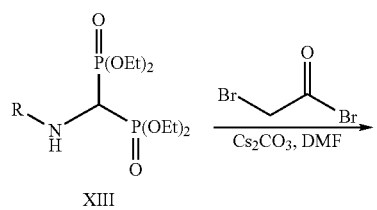

Bromoacetamides XXII(a-b) and XXIII from the parent amines IIIb, IX and XIII can be prepared according to a modification of the procedure described in J. Drug Targeting (1995), 3: 273-282.

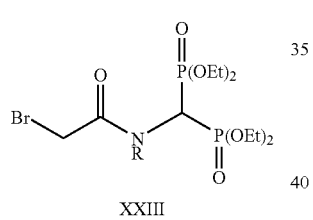

Thiols XXIV(a-b) can be prepared by alkylation of the anion of I with a protected 3-iodopropane-1-thiol following the protocol described in Bioorg. Med. Chem. (1999), 7: 901-919. Or they can be prepared from iodides XXI(a-b) and an appropriately chosen reagent able to supply the sulfhydryl group, including reagents such as thiourea followed by hydrolysis and thioacetic acid followed by hydrolysis or reduction.

Thioglycolamides XXV and XXVI can be made through the condensation of amine functionalized bisphosphonates such as IIIb and XIII with activated forms of thioglycolic acid, or with thioglycolic acid itself as described for other amines in J. Ind. Chem. Soc. (1997), 74: 679-682.

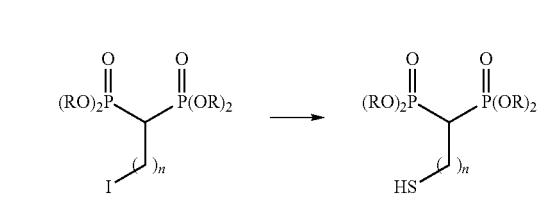

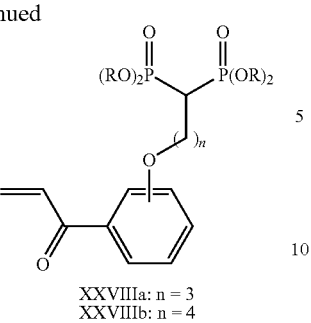

XXVIIIa: n = 3
XXVIIIb: n = 4

Vinyl ketones such as XXVIII(a-b) can be prepared through the condensation of the parent (hydroxyphenyl) vinyl ketone) (XVII with iodides XXI(a-b) in the presence of an appropriately chosen base.

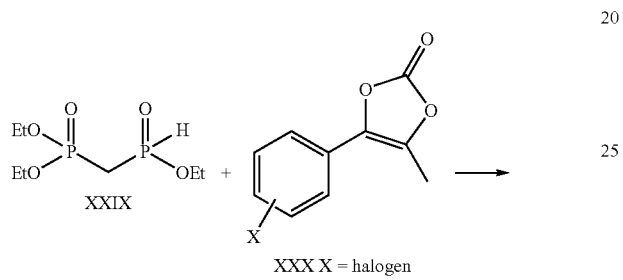

XXIX

XXX X = halogen

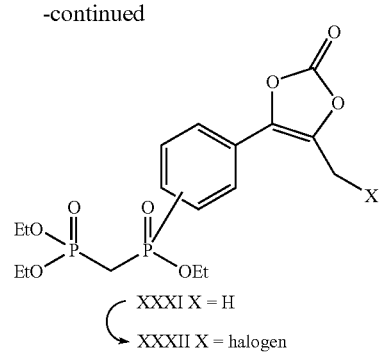

XXXI X = H
XXXII X = halogen

Diethyl (ethoxyphosphinyl)methylphosphonate XXIX can be prepared using the procedure described in Synth. Comm. (2002), 32: 2951-2957 and U.S. Pat. No. 5,952,478 (1999). It can be coupled with a halogenated 1,3-dioxolone XXX in the presence of a transition metal catalyst to furnish bisphosphonate XXXI. This can be followed by a radical halogenation reaction to provide bisphosphonate XXXII.

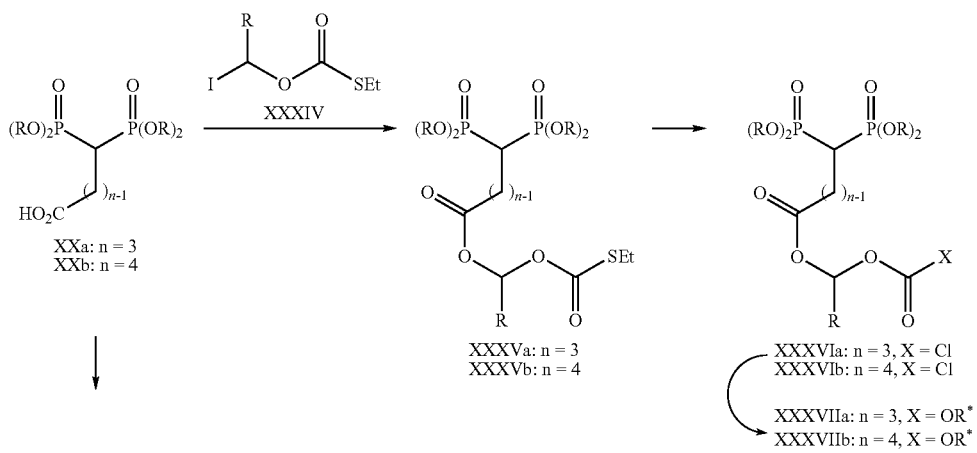

XXa: n = 3
XXb: n = 4

XXXVa: n = 3
XXXVb: n = 4

XXXVIa: n = 3, X = Cl
XXXVIb: n = 4, X = Cl

XXXVIIa: n = 3, X = OR*
XXXVIIb: n = 4, X = OR*

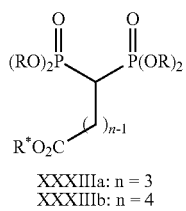

XXXIIIa: n = 3
XXXIIIb: n = 4

Acids XX(a-b) can be converted to activated esters XXXIII (a-b), where R* is p-nitrophenyl or N-succinimidyl, directly by treatment with a coupling agent and p-nitrophenol or N-hydroxysuccinimide or by conversion to the acid chlorides first. Iodoalkyl thiocarbamates XXXIV can be prepared according to Lund et al (Synthesis (1990): 1159-1166). They can be treated with acids XX(a-b) in the presence of a non nucleophilic base to provide acyloxymethyl thiocarbamates XXXV(a-b). These can be converted to the parent chloroformates XXXVI(a-b) by treatment with a chlorinating agent such as sulfuryl chloride, and subsequently to the activated carbonates XXXVII(a-b) where R*OH is p-nitrophenol or N-hydroxysuccinimide.

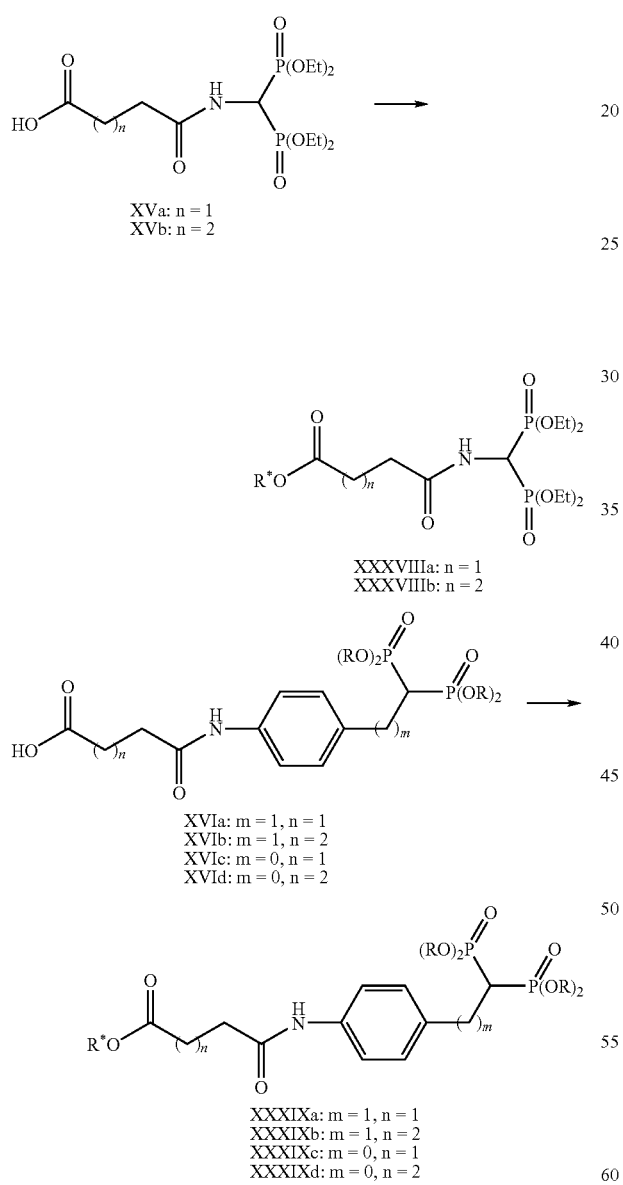

Similarly, acids XV(a-b) and XVI(a-d) can be converted to activated esters XXXVIII(a-b) and XXXIX(a-d) respectively, where R* is N-succinimidyl or p-nitrophenyl, by treatment with a coupling and either p-nitrophenol or N-hydroxysuccinimide.

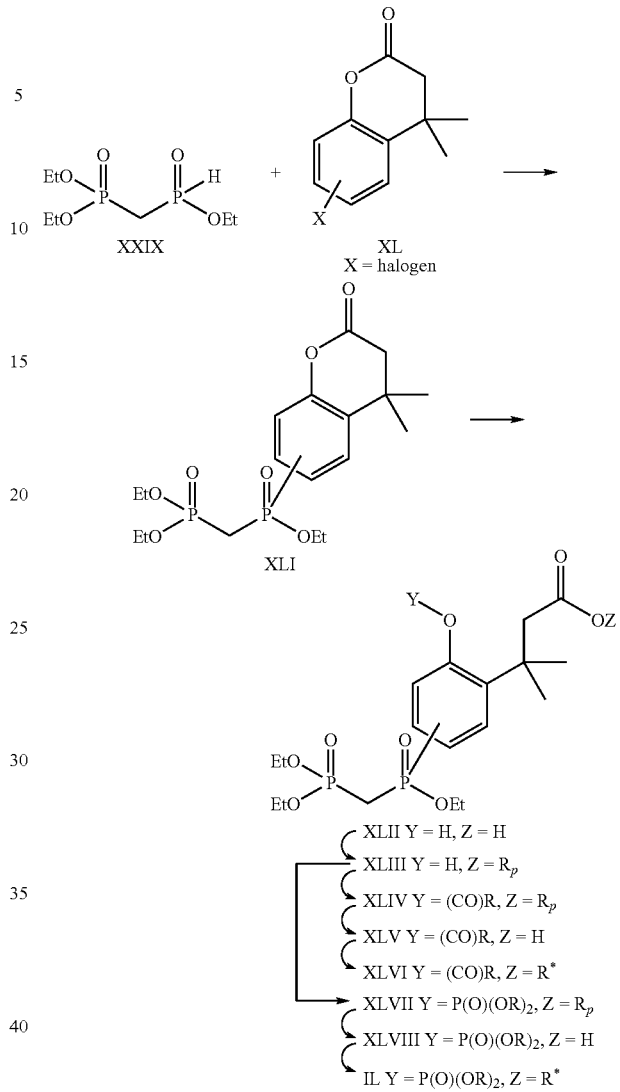

Diethyl (ethoxyphosphinyl)methylphosphonate XXIX can be coupled with a halogenated dihydrochromenenone XL in the presence of a transition metal catalyst to furnish bisphosphonate XLI. This compound can be hydrolyzed in the presence of a base to give the bisphosphonated dihydrocinnamic acid XLII. The carboxylic acid functionality in this compound can be protected as the ester (compound XLIII, where $R_p$ is a benzyl or an allyl group), the phenolic hydroxyl can be acylated (compound XLIV) or phosphorylated (compound XLVII) by treatment with an acid chloride or a phosphoryl chloride in the presence of a mild base, and the carboxylic acid can be deprotected under standard conditions to yield acids XLV and XLVIII. These acids can be further activated in the form of their p-nitrophenol or their N-hydroxysuccinimide esters (compounds XLVI and IL, R* is p-nitrophenyl or N-succinimidyl) by treatment with a coupling and either p-nitrophenol or N-hydroxysuccinimide.

The bisphosphonate building blocks described in this section are in the form of their phosphonic esters, R being Me, Et, i-Pr, allyl or Bn; or as the free bisphosphonic acids and/or free bisphosphonate salts.

A-2) Synthesis of Vancomycin and Oritavancin Bisphosphonate Conjugates

For the purposes of this discussion, the glycopeptides will be schematically represented, with only the relevant functional groups shown. Thus vancomycin will be represent as:

481
482
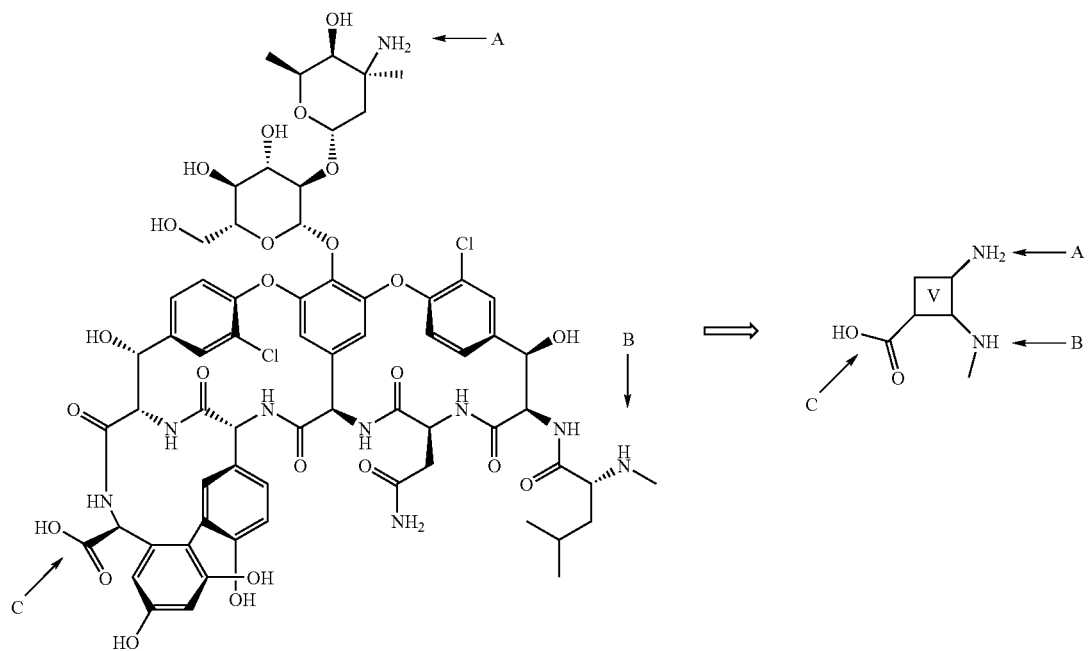
Whereby the letters correlate the functional groups on vancomycin and its schematic representation. Similarly, oritavancin will be represented as:
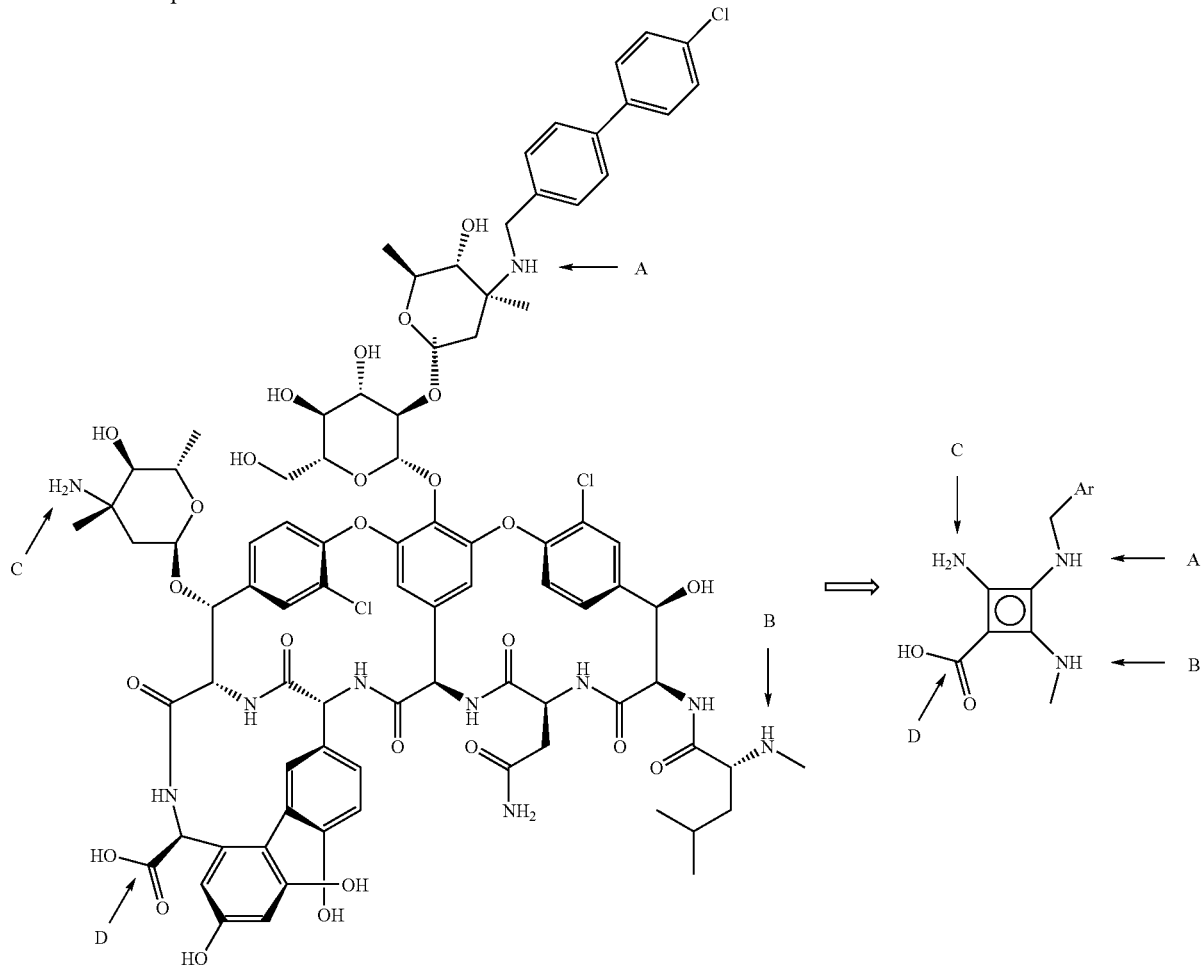

-continued
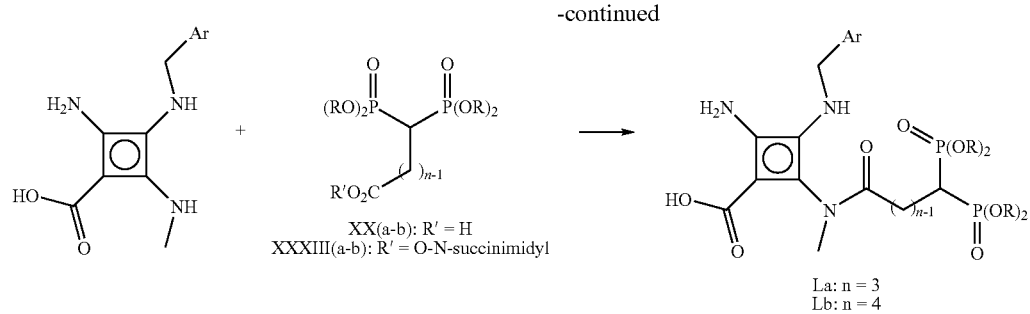
XX(a-b): R' = H
XXXIII(a-b): R' = O-N-succinimidyl
La: n = 3
Lb: n = 4
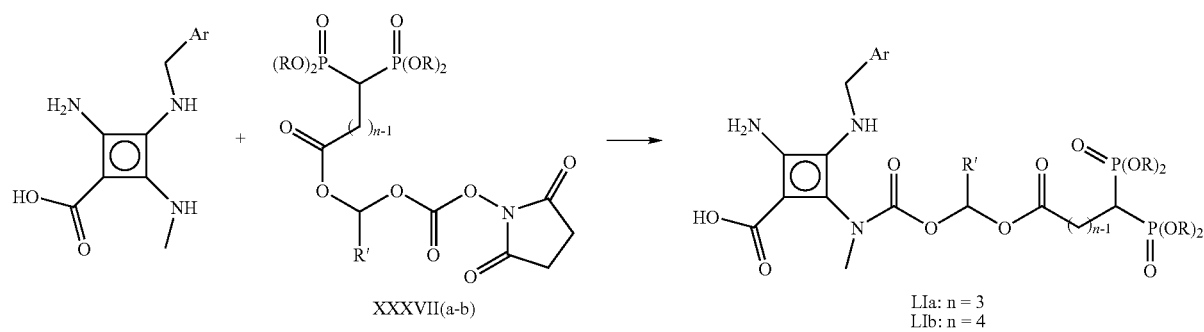
XXXVII(a-b)
LIa: n = 3
LIb: n = 4
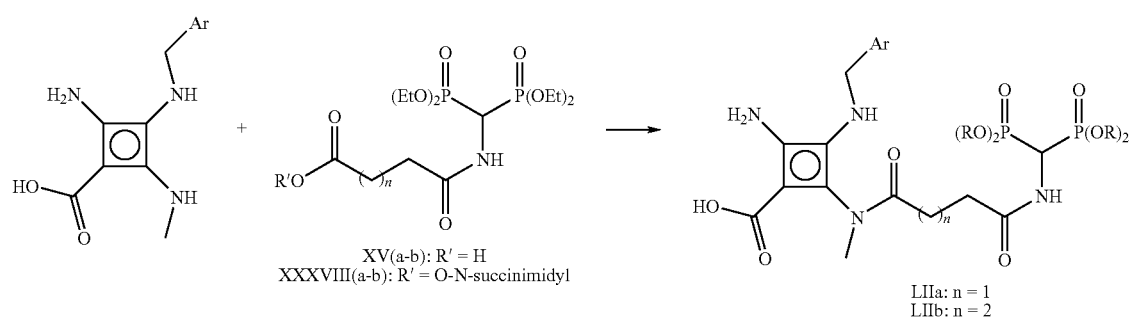
XV(a-b): R' = H
XXXVIII(a-b): R' = O-N-succinimidyl
LIIa: n = 1
LIIb: n = 2
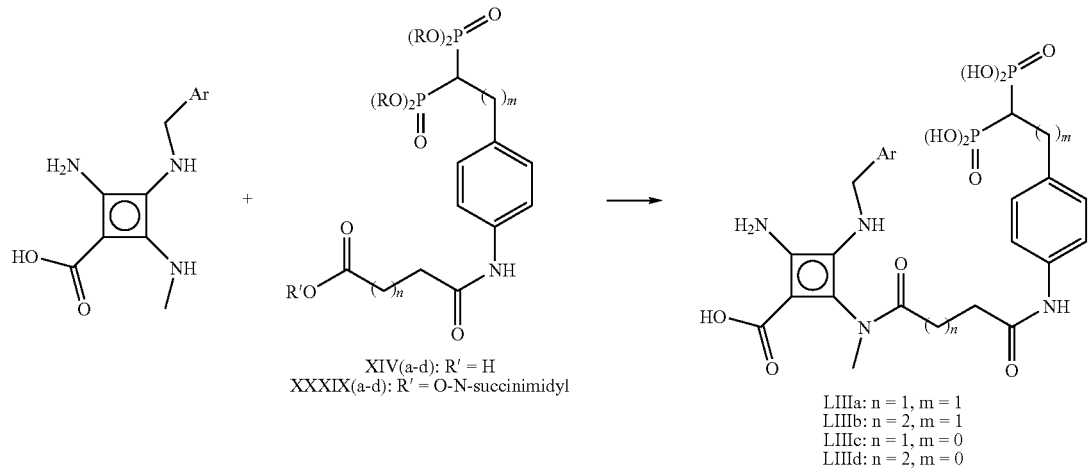
XIV(a-d): R' = H
XXXIX(a-d): R' = O-N-succinimidyl
LIIIa: n = 1, m = 1
LIIIb: n = 2, m = 1
LIIIc: n = 1, m = 0
LIIId: n = 2, m = 0

Oritavancin bisphosphonate conjugates involving amide linkages such as L(a-b), LI(a-b), LII(a-b) and LIII(a-d) can be prepared by the treatment of Oritavancin with bisphosphonated acids XX(a-b), XV(a-b) and XIV(a-d) in the presence of a suitably selected coupling agent, or by treatment with N-hydroxysuccinimide esters XXXIII(a-b), XXXVII(a-b), XXXVIII(a-b) and XXXIX(a-d) with or without the use of a non-nucleophilic base.

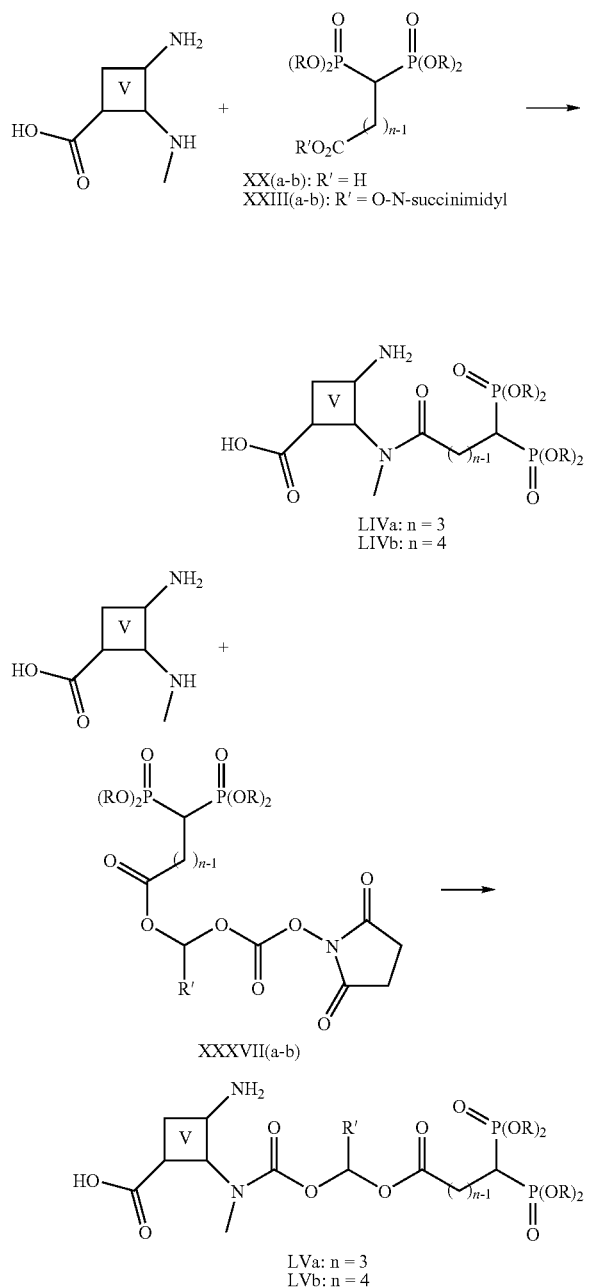
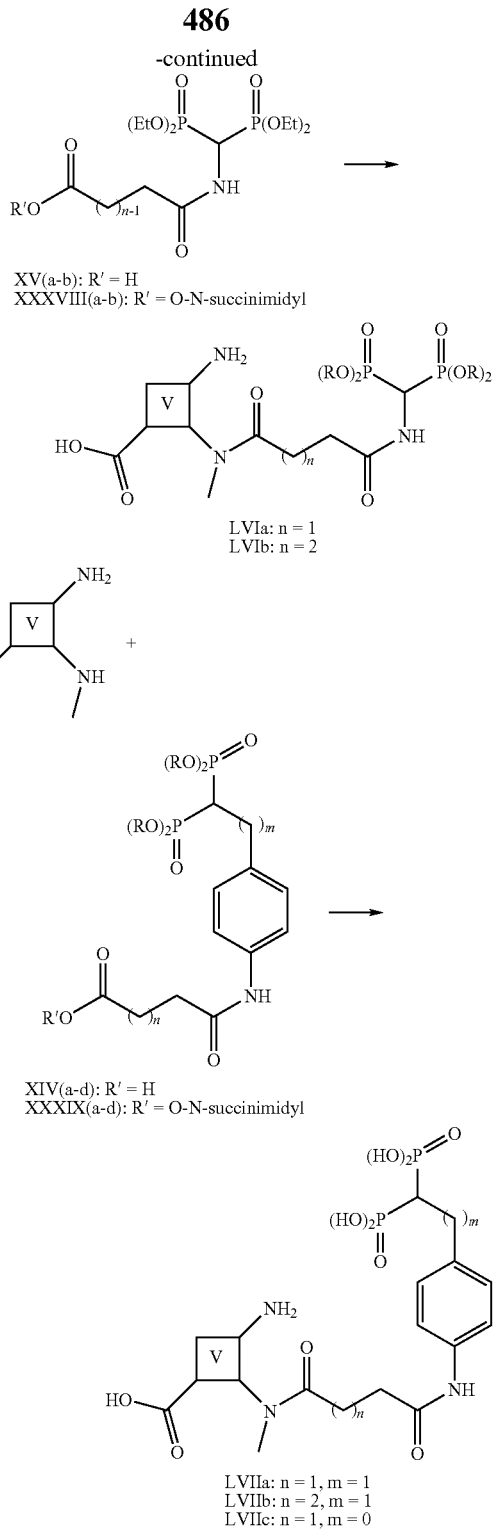

Similarly vancomycin bisphosphonate conjugates involving amide linkages, such as LIV(a-b), LV(a-b), LVI(a-b) and LVII(a-d) can be obtained by the treatment of vancomycin with the same bisphosphonated acids XX(a-b), XV(a-b) and XIV(a-d) in the presence of a suitably selected coupling agent, or the same N-hydroxysuccinimide esters XXXIII(a-b), XXXVII(a-b), XXXVIII(a-b) and XXXIX(a-d) with or without the use of a non-nucleophilic base.

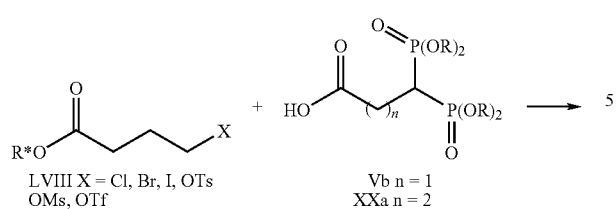
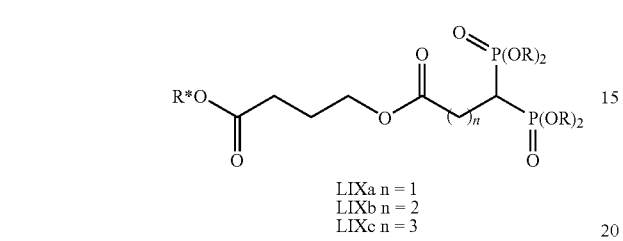
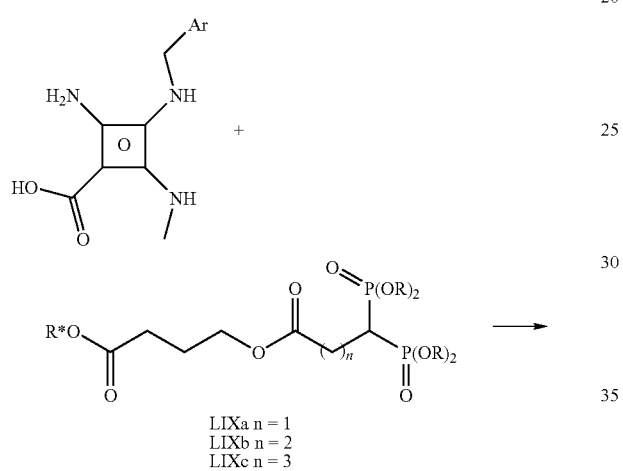
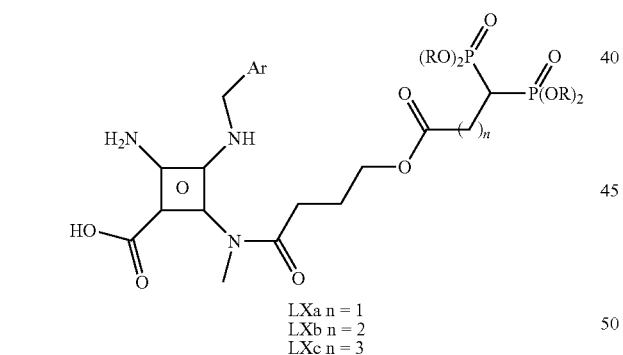
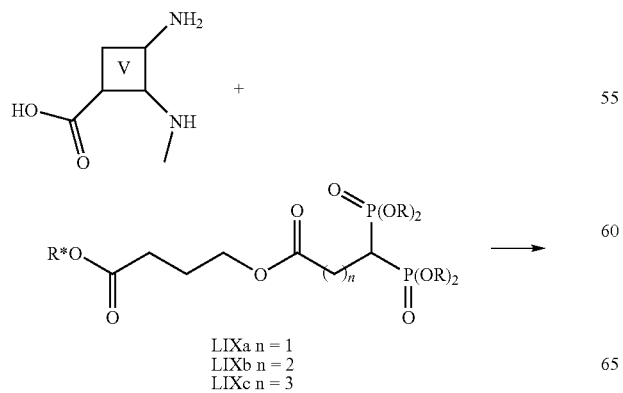

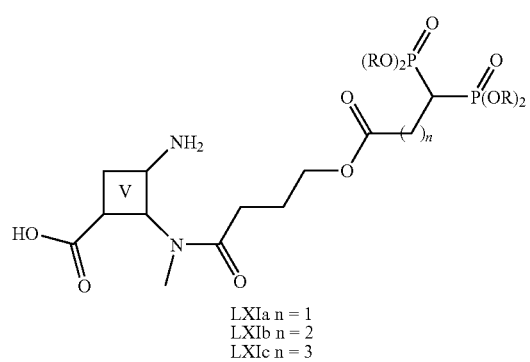

A spacer can also be introduced between the glycopeptide and the bisphosphonated moiety. Thus treatment of an activated ester of 4-substituted butyric acids, such as LVIII, with bisphosphonated acids Vb and XX(a-b) in the presence of a non-nucleophilic base results in activated esters LIX(a-c). These can react with oritavancin or vancomycin to give bisphosphonated glycopeptides LX(a-c) and LXI(a-c) with or without the use of a non-nucleophilic base.

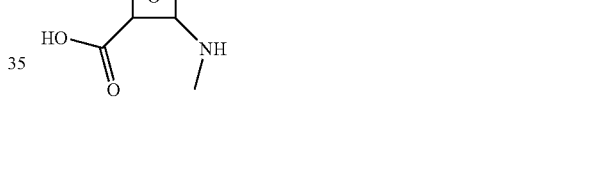
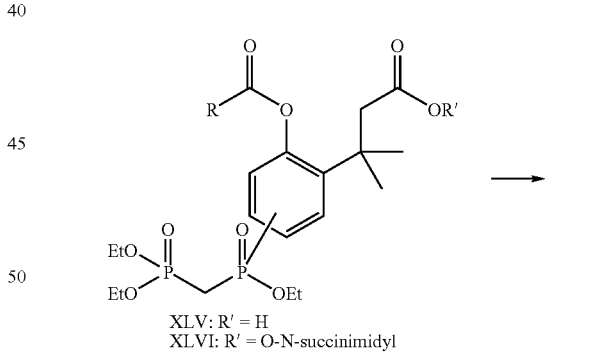
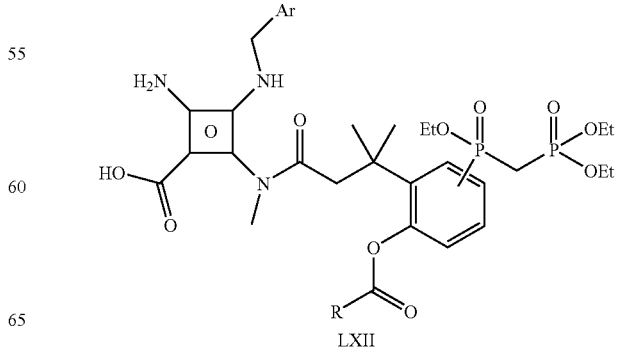

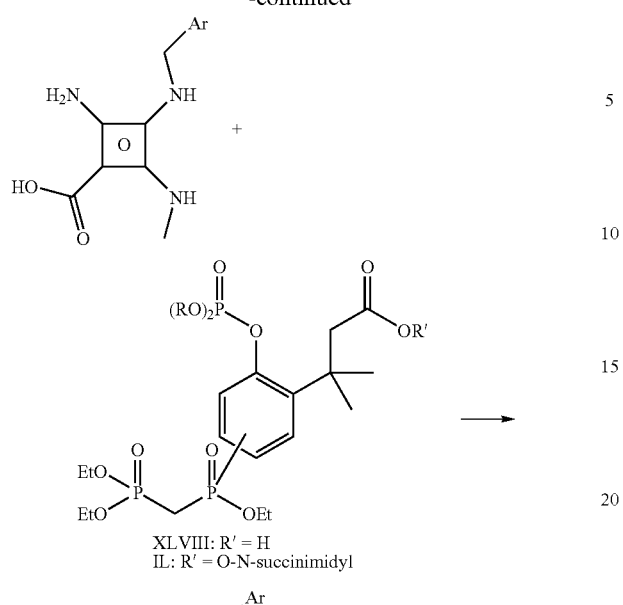

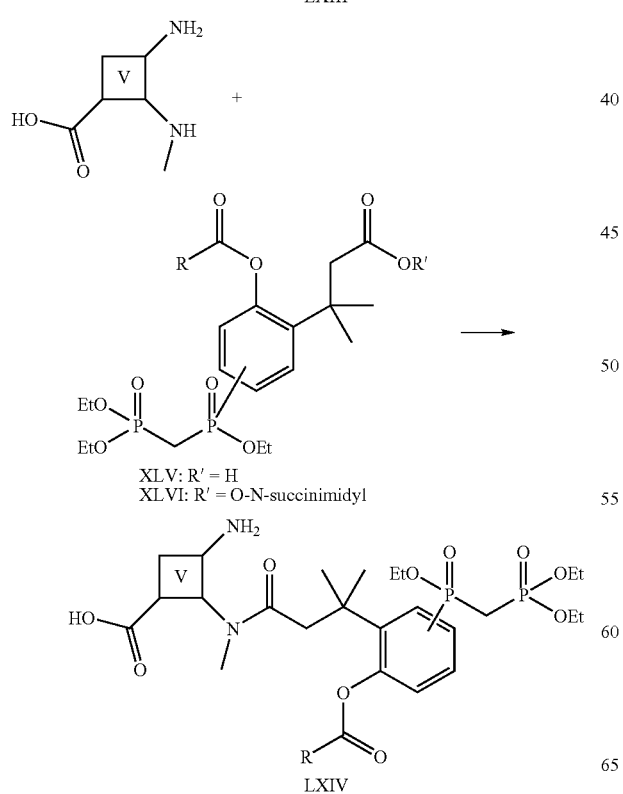

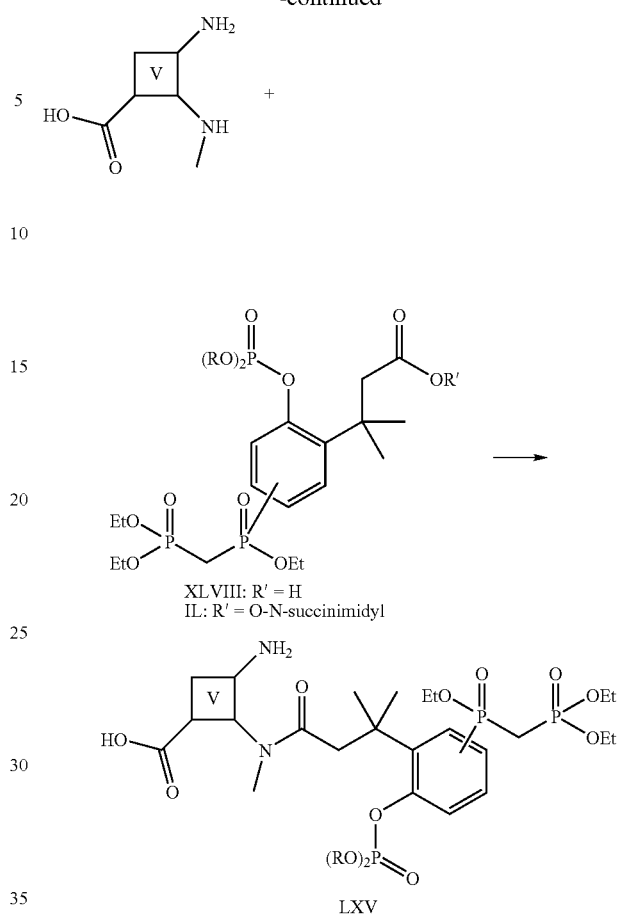

Treatments of oritavancin and vancomycin with either bis-phosphonated hydrocinnamic acids XLV and XLVIII in the presence of a coupling agent or with either of their activated ester XLVI and IL preferably in the presence of a non-nucleophilic base result in bisphosphonated glycopeptides LXII and LXIII respectively for oritavancin and LXIV and LXV respectively for vancomycin.

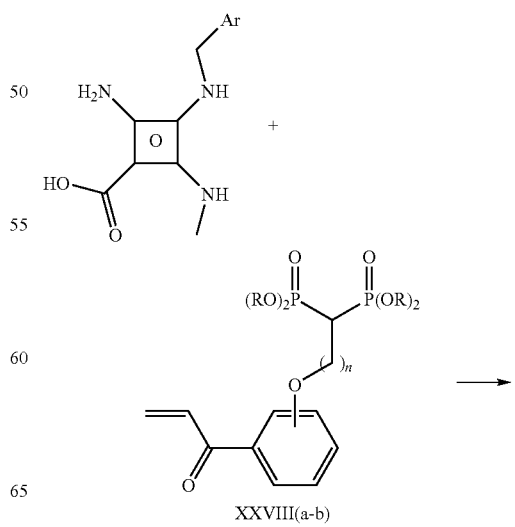

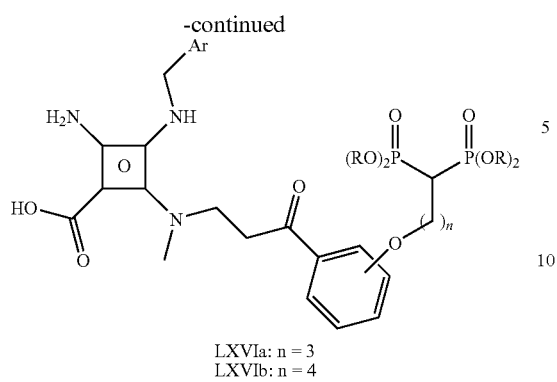

LXVIa: n = 3
LXVIb: n = 4

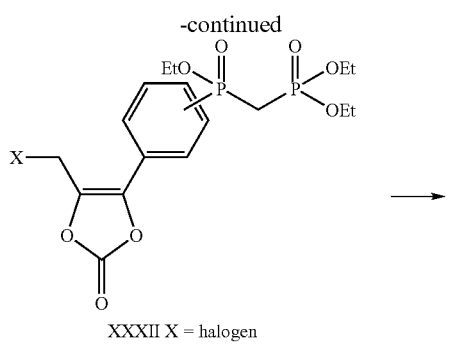

XXXII X = halogen

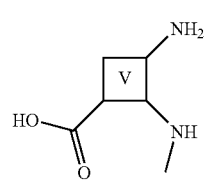

+

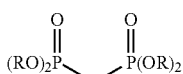

LXVIII

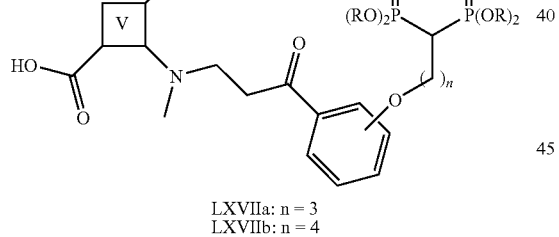

XXVIII(a-b)

LXVIIa: n = 3
LXVIIb: n = 4

Condenstation of oritavancin and vancomycin with bis-phosphonated enones XXVIII(a-b) preferably in the presence of a non-nucleophilic base results in glycopeptides LXVI(a-b) and LXVII(a-b) respectively conjugated to the bisphosphonate moiety through a β-amino ketone linker.

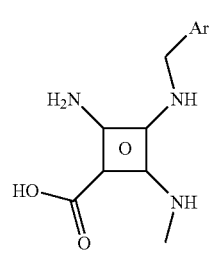

+

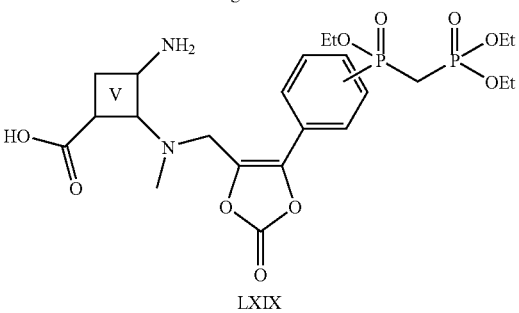

XXXII X = halogen

LXIX

Condenstation of oritavancin and vancomycin with bis-phosphonated halomethyl dioxolone XXXII in the presence of a non-nucleophilic base results in bisphosphonated glycopeptides LXVIII and LXIX respectively.

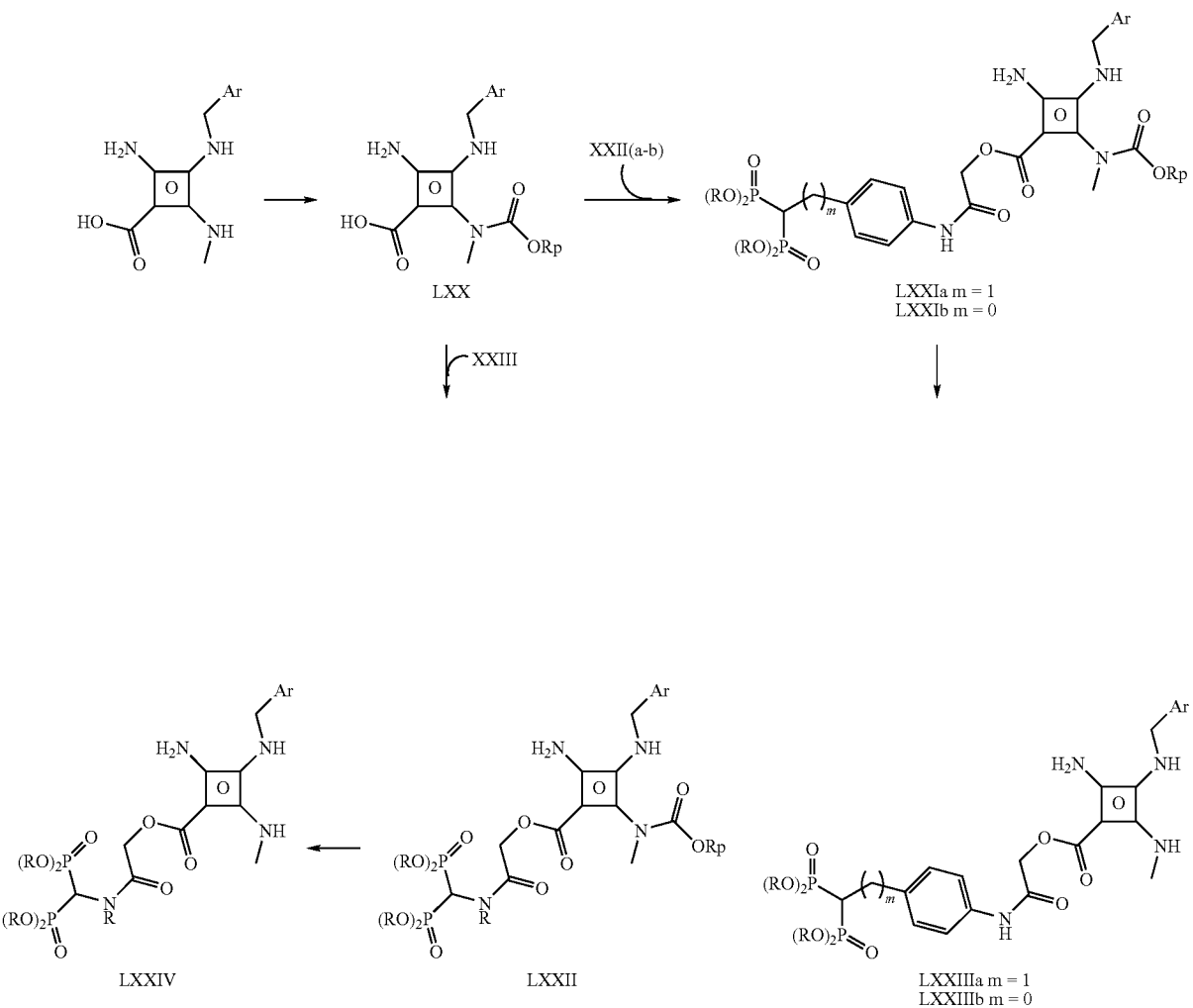

Oritavancin can be protected as the carbamate LXX (Rp is t-butyl, a fluorenylmethyl, a benzylic or an allylic group) by treatment with the corresponding chloroformate, pyrocarbonate or N-hydroxysuccinimide carbonate in the presence of a base. This carbamate can be condensated with bromoacetamides XXII(a-b) and XXIII to furnish glycolamides LXXI(a-b) and LXXII respectively. These bisphosphonated glycopeptides can then be deprotected under standard conditions to provide LXXIII(a-b) and LXXIV respectively.

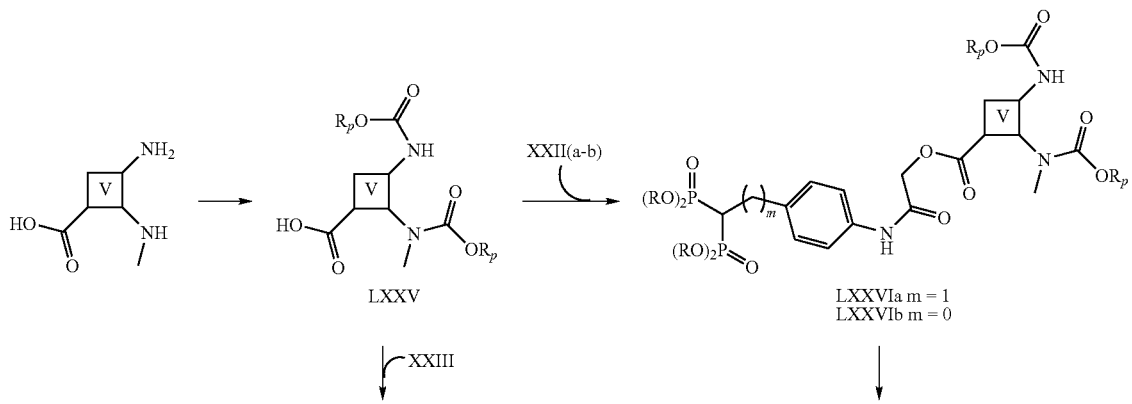

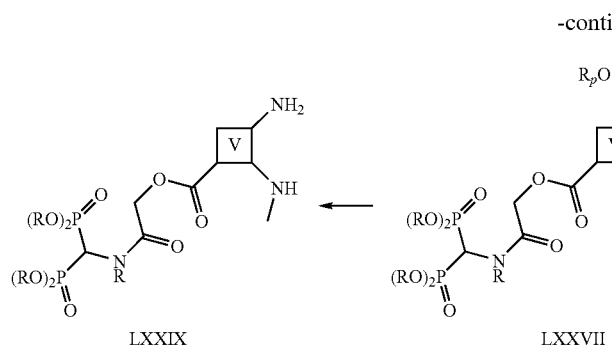

LXXIX

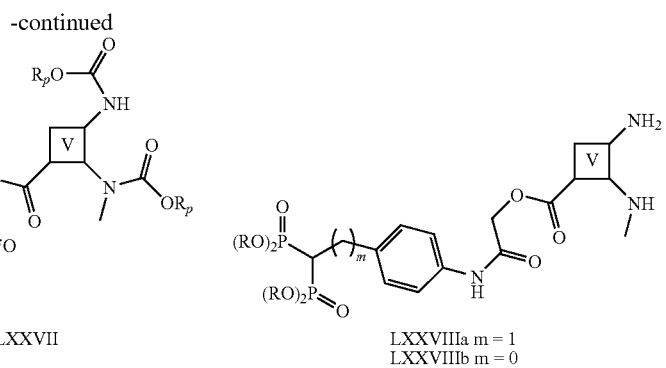

LXXVII

LXXVIIIa m = 1
LXXVIIIb m = 0

Vancomycin can be likewise protected as the biscarbamate LXXV (Rp is t-butyl, a fluorenylmethyl, a benzylic or an allylic group) by treatment with the corresponding chloroformate, pyrocarbonate or N-hydroxysuccinimide carbonate in the presence of a base. This carbamate can be similarly converted the bisphosphonated glycopeptides LXXVIII(a-b) and LXXIX after condensation with bromoacetamides XXII(a-b) and XXIII to give glycolamides LXXVI(a-b) and LXXVII respectively and their subsequent deprotection.

For all bisphosphonated glycopeptide conjugates, deprotection of the phosphonate esters to provide the corresponding phosphonic acids is undertaken according to the nature of R. If R=Me, Et or i-Pr, the ester is treated with TMSBr in a solvent such as $CH_2Cl_2$, with or without an amine or a heteroaromatic nitrogen containing base, and the resulting silylated intermediate is hydrolysed with water. When R=Allyl, the esters are hydrolyzed by treatment with a strong nucleophile in the presence of Pd(II) catalysts. When R=Bn, the esters are cleaved by hydrogenolysis using a catalyst such as Pd on carbon in a solvent such as ethanol.

The other protecting groups used can be put on and removed using the coventional methods described in the literature, for instance as reviewed in "*Protective Groups in Organic Synthesis*", Greene, T. W. and Wuts, P. M. G., Wiley-Interscience, New York, 1999.

B) Detailed Experimental Procedures

Scheme 1. Preparation of 3-[(tetraethyl bisphosphonomethyl)carbamoyl]propanoic acid (3a) and 4-[(tetraethyl bisphosphonomethyl)carbamoyl]butanoic acid (3b)

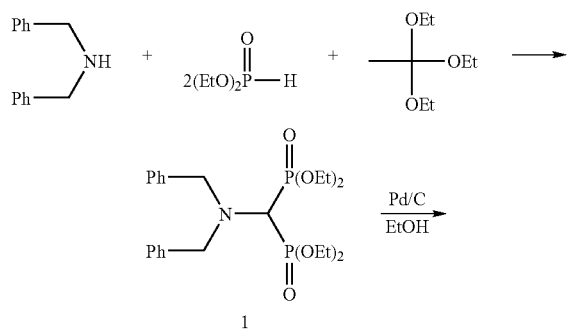

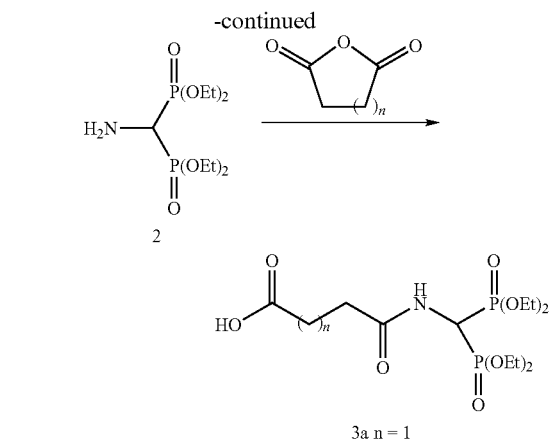

3a n = 1
3b n = 2

Tetraethyl N,N-Dibenzyl-1-aminomethylenebisphosphonate (1)

Compound 1 was prepared according to a modified protocol derived from *Synth. Comm.* 1996, 26, 2037-2043. Triethyl orthoformate (8.89 g, 60 mmol), diethyl phosphite (16.57 g, 120 mmol) and dibenzyl amine (11.80 g, 60 mmol) were combined in a 100 mL round bottom flask fitted with a distillation head. The reaction was heated to a temperature of 180-195° C. for 1 h under Ar. When EtOH evolution was complete, the reaction mixture was cooled to room temperature, diluted with $CHCl_3$ (300 mL), washed with aqueous NaOH (2M, 3×60 mL) and brine (2×75 mL), then dried over $MgSO_4$. After evaporation, a crude yield of 25.2 g (87%) was obtained. A 4.95 g portion of the crude oil was purified by chromatography (ethyl acetate:hexane:methanol 14:4:1) to yield pure 1 (2.36 g, 41%). $^1$H NMR (400 MHz, $CDCl_3$) δ 1.32 (dt, J=2.0, 7.0, 12H), 3.55 (t, J=25.0, 1H), 3.95-4.25 (m, 12H), 7.20-7.45 (m, 10H).

Tetraethyl 1-aminomethylenebisphosphonate(2)

Compound 1 (2.00 g, 4.14 mmol) was dissolved in EtOH (40 mL). To this solution was added palladium on carbon (10%, 1.5 g) and cyclohexene (2.5 mL, 24.7 mmol). The reaction mixture was refluxed under argon for 15 hours, filtered through celite and evaporated to give 2 as a slightly impure pale yellow oil (1.50 g, 119%), which was used directly in the next step without further purification. $^1$H NMR (400 MHz, $CDCl_3$) δ 1.35 (t, J=7.0, 12H), 3.58 (t, J=20.3, 1H), 3.65-3.90 (br s, 2H), 4.20-4.28 (m, 8H).

3-[(tetraethyl bisphosphonomethyl)carbamoyl]propanoic acid (3a)

Compound 3a was prepared as described in *J. Drug Targeting*, 1997, 5, 129-138. It was obtained as an oil which slowly solidified, in 57% crude yield from 2. The crude product could be purified by chromatography (10% AcOH/EtOAc) to give a white solid. $^1$H NMR (400 MHz, CDCl$_3$) δ 1.31 (t, J=7.0, 6H), 1.33 (t, J=7.1, 6H), 2.61-2.73 (m, 4H), 4.05-4.28 (m, 8H), 5.07 (td, J=21.6, J=9.8, 1H), 7.90 (d, J=9.4, 1H)

4-[(tetraethyl bisphosphonomethyl)carbamoyl]butanoic acid (3b)

Compound 3b was prepared as described in *J. Drug Targeting*, 1997, 5, 129-138. It was obtained as an orange oil, in 85% crude yield from 2. The crude product could be purified by chromatography (10% AcOH/EtOAc) to give a white solid. $^1$H NMR (400 MHz, CDCl$_3$) δ 1.30 (t, J=7.0, 6H), 1.34 (t, J=7.0, 6H), 1.92-2.02 (m, 2H), 2.38-2.44 (m, 2H), 2.54 (t, J=7.3, 1H), 4.04-4.28 (m, 8H), 5.16 (td, J=22.1, J=10.0, 1H), 8.45 (d, J=10.2, 1H).

Scheme 2. Preparation of vancomycin bisphosphonate conjugate 6

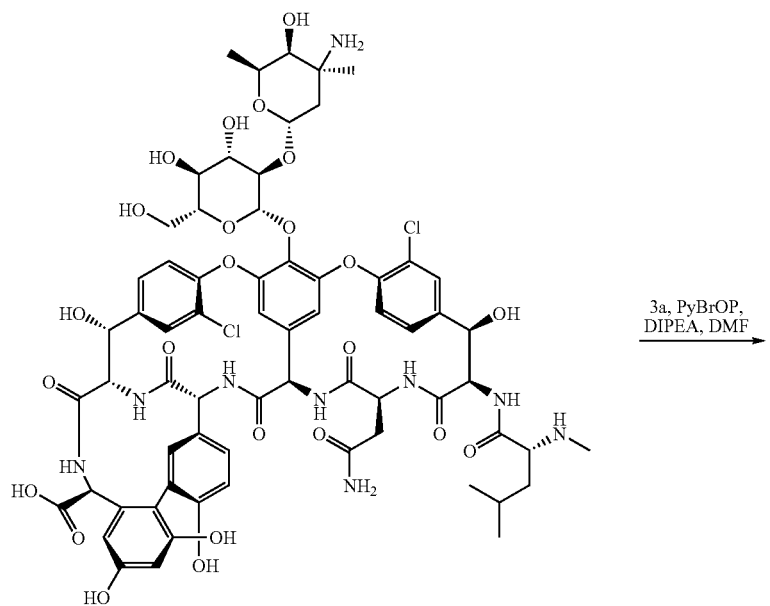

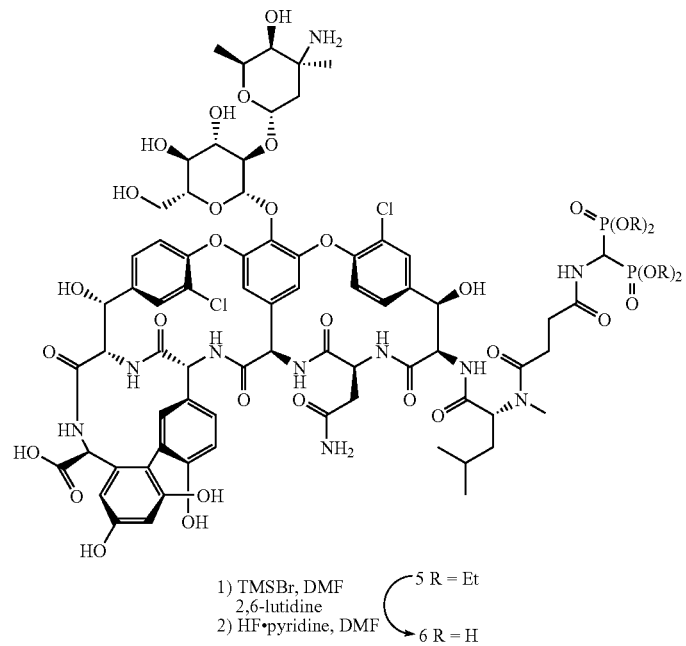

Vancomycin bisphosphonated conjugate 5. To a solution of 3a (47 mg. 1.16×10$^{-4}$ mol) and PyBroP (70 mg, 1.35×10 mol) in 1 mL of DMF was added DIPEA (30 µL, 1.73×10$^{-4}$ mol). The mixture was stirred for 15 min before it was added to a solution of Vanomycin hydrochloride (4, 100 mg, 6.73×10$^{-5}$ mol) and DIPEA (13 µL, 7.47×10$^{-5}$ mol) in 1.5 mL of DMF. The flask containing 3a was further rinsed with 1 mL of DMF and the rinse was added to the reaction mixture. After stirring under Argon at room temperature for an overnight, the mixture was concentrated in vacuo and the residue was subjected to C18 silica gel chromatography on a Biotage™ flash chromatography system using a gradient of 0-30% acetonitrile in 0.005% TFA in H$_2$O as the eluent to furnish 5 (45 mg, 2.45×10$^{-5}$ mol, 36% yield) as a white solid. ESI-MS: (M–H)$^-$ calculated for C$_{79}$H$_{100}$Cl$_2$N$_{10}$O$_{32}$P$_2$ 1833. found 1833.0.

Vancomycin Bisphosphonated Conjugate 6

Bromotrimethylsilane (243 µL, 1.84 mmol) was added drop-wise to a stirring solution of 5 (45 mg, 2.45×10$^{-5}$ mol) and 2,6-lutidine (430 µL, 3.70 mmol) in dry DMF (2.5 mL) which was cooled in an ice-bath. The resulting mixture was left to come to room temperature on its own and stir there for a total of 20 hr. The solvent was removed under reduced pressure to complete dryness. The residue was taken up in DMF (2.5 mL) and pyridine (200 µL, 2.48 mmoles) and HF.pyridine (70% HF, 32 µL, 1.23 mmoles) were added. The mixture was stirred for 2 h at room temperature before being concentrated in vacuo to dryness. The crude residue was purified by C18 silica gel chromatography on a Biotage™ flash chromatography system using a gradient of 0-30% acetonitrile in 0.005% TFA in H$_2$O as the eluent to furnish 6 as a white solid (11.3 mg, 6.56×10$^{-6}$ mol, 27% yield). ESI-MS: (M–H)$^-$ calculated for C$_{71}$H$_{84}$Cl$_2$N$_{10}$O$_{32}$P$_2$ 1721. found 1721.0.

Scheme 3. Preparation of oritavancin bisphosphonated conjugate 10

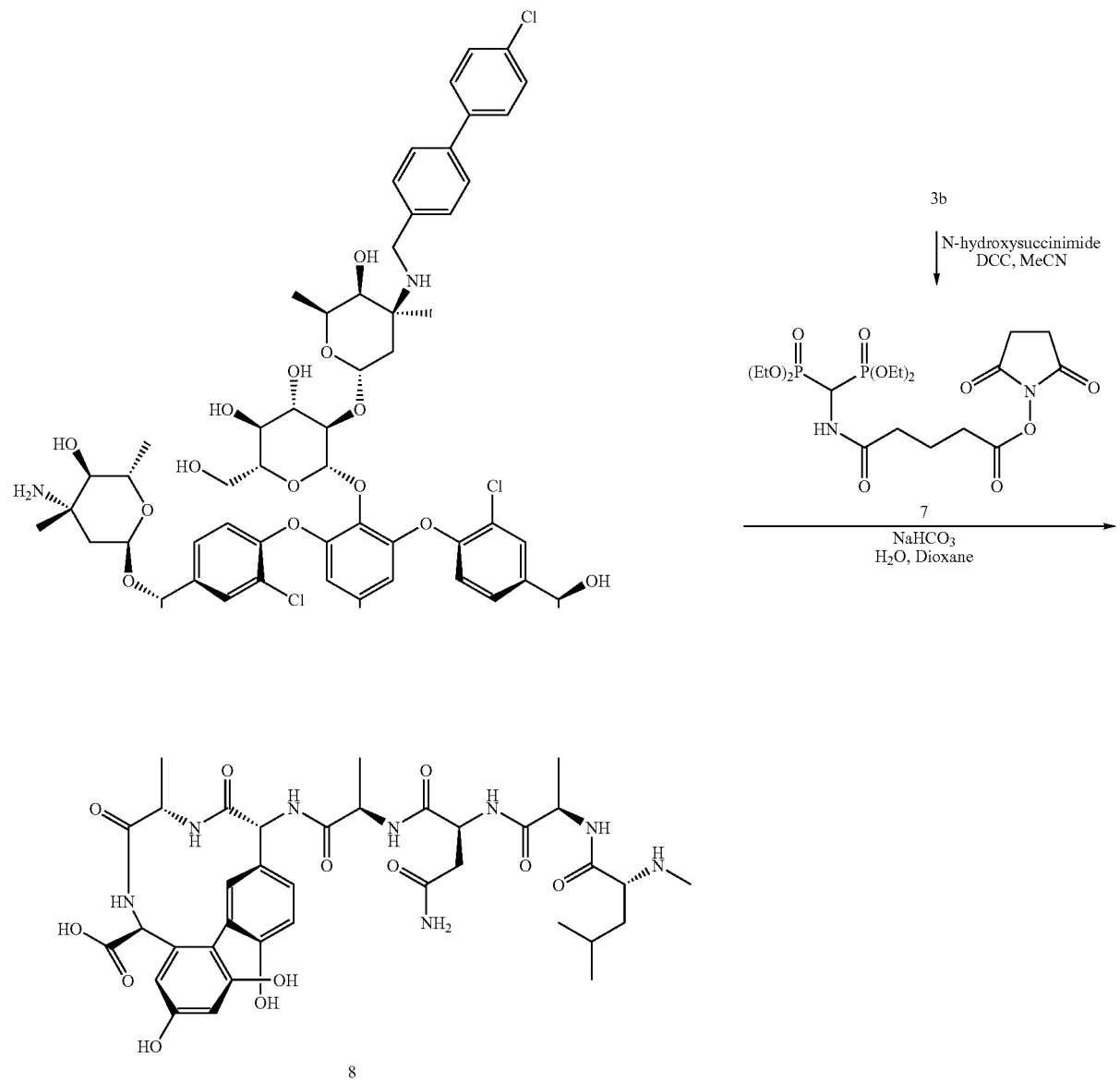

8

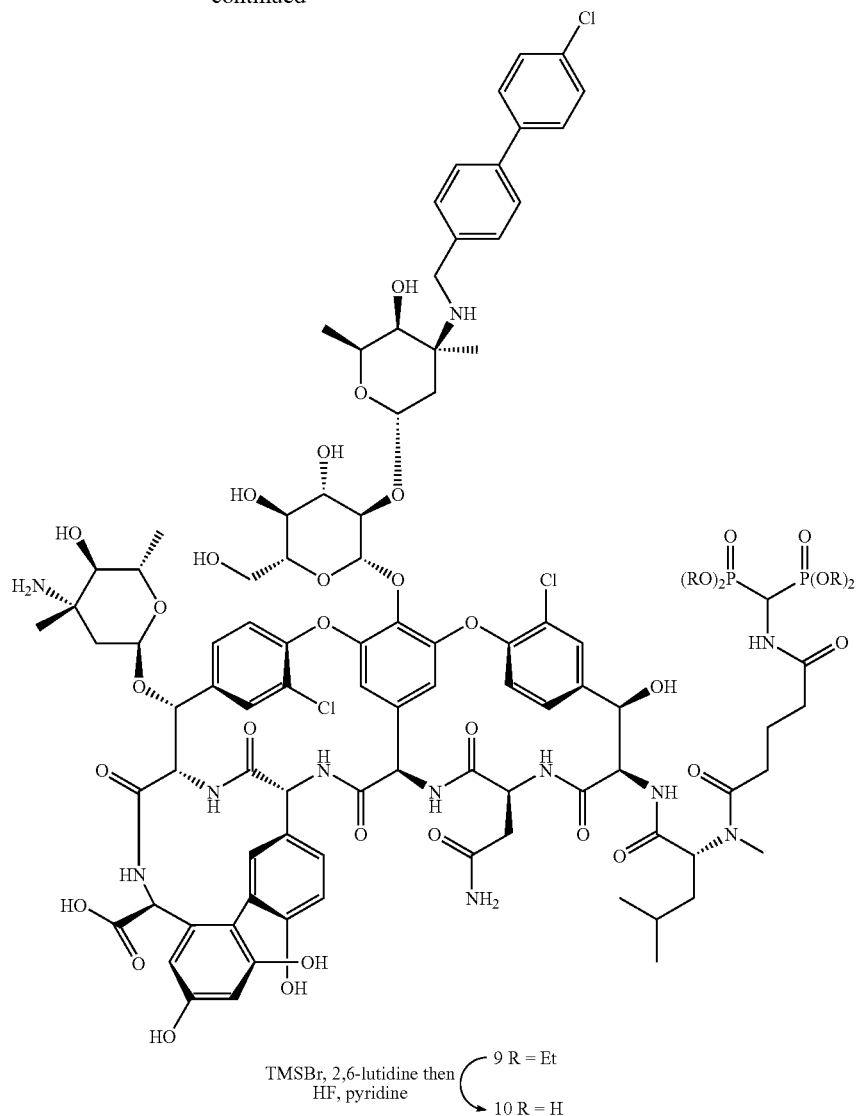

TMSBr, 2,6-lutidine then HF, pyridine
9 R = Et
10 R = H

N-succinimidyl 4-[(tetraethyl bisphosphonomethyl)carbamoyl]butanoate (7)

To a mixture of acid 3b (1.14 g, 2.73 mmoles) and N-hydroxysuccinimide (346 mg, 3.00 mmoles) in acetonitrile (14 mL) at 0° C. was added DCC (619 mg, 3.00 mmol). The mixture was stirred for 1 h at 0° C. and refrigerated overnight. The precipitate was removed by filtration and the filtrate was concentrated then purified by flash chromatography using a gradient of 0-5% MeOH in $CH_2Cl_2$ to provide compound 7 as a white solid (1.06 g, 76% yield). $^1$H NMR (400 MHz, $CDCl_3$) δ 1.33 (2×t, J=7.0 Hz, 12H), 2.12 (quint, J=7.0 Hz, 2H), 2.43 (t, J=6.9 Hz, 2H), 2.69 (t, J=7.0 Hz, 2H), 2.85 (s, 4H), 4.14-4.27 (m, 8H), 5.05 (dt, J=21.8, 10.1 Hz, 1H), 6.48 (d, J=9.9 Hz, 1H).

Oritavancin Bisphosphonate Conjugate 9

To a suspension of oritavancin bisphosphoric acid salt (8, 572 mg, 0.29 mmol) in dioxane/$H_2O$ (1:1, 10 mL) was added sodium bicarbonate (48 mg, 0.58 mmol) and the mixture was stirred until complete dissolution of oritavancin. Succinimidyl ester 7 (296 mg, 0.58 mmol) was added and the mixture was stirred at room temperature for 18 h, after which additional sodium bicarbonate (24 mg, 0.29 mmol) and succinimidyl ester 7 (70 mg, 0.15 mmol) were added. Stirring was continued for another 20 h and the reaction mixture was concentrated and lyophilized. Crude product was purified by C18 silica gel chromatography on a Biotage™ flash chromatography system using 15-100% MeOH in $Et_3N/H_3PO_4$ buffer (0.2% $Et_3N/H_2O+H_3PO_4$, pH=3). Pure fractions were comb concentrated and lyophilized and resulting product was desalted on a second Biotage™ C18 column using 15-80% MeCN in $H_2O$ (both containing 0.1% TFA). After concentration and lyophilization of the combined fractions, the di-TFA salt of the bisphosphonate conjugate 9 was obtained as a white solid (185 mg, 26%). ESI-MS: (M+H) calculated for $C_{100}H_{124}Cl_3N_{11}O_{34}P_2$ 2192. found 2192.2.

Oritavancin Bisphosphonated Conjugate 10

To a solution of the oritavancin bisphosphonate conjugate 9 (185 mg, 0.076 mmol) and 2,6-lutidine (621 μL, 5.35 mmol)

in DMF (4 mL) cooled at −78° C. was added TMSBr (454 μL, 3.44 mmol). The reaction mixture was stirred for 1 h at −78° C., then 23 h at room temperature. It was then concentrated to dryness under high vacuum, redissolved in DMF (4 mL) then treated with pyridine (495 μL, 6.11 mmol) and HF-pyridine (77 μL, 3.06 mmol). After stirring for 1 h at room temperature the mixture was concentrated to dryness under high vacuum. The crude product was purified by C18 silica gel chromatography on a Biotage™ flash chromatography system using 15-80% MeCN in H$_2$O (both containing 0.05% NH$_4$OH). Pure fractions were combined, concentrated and lyophilized to provide the tri-ammonium salt of oritavancin bisphosphonate conjugate 10 as a white solid (20 mg, 12%). LCMS: 99.3% (254 nm), 97.9% (220 nm), 99.2% (290 nm). ESI-MS: (M+H) calculated for C$_{92}$H$_{108}$Cl$_3$N$_{11}$O$_{34}$P$_2$ 2080. found 2080.5.

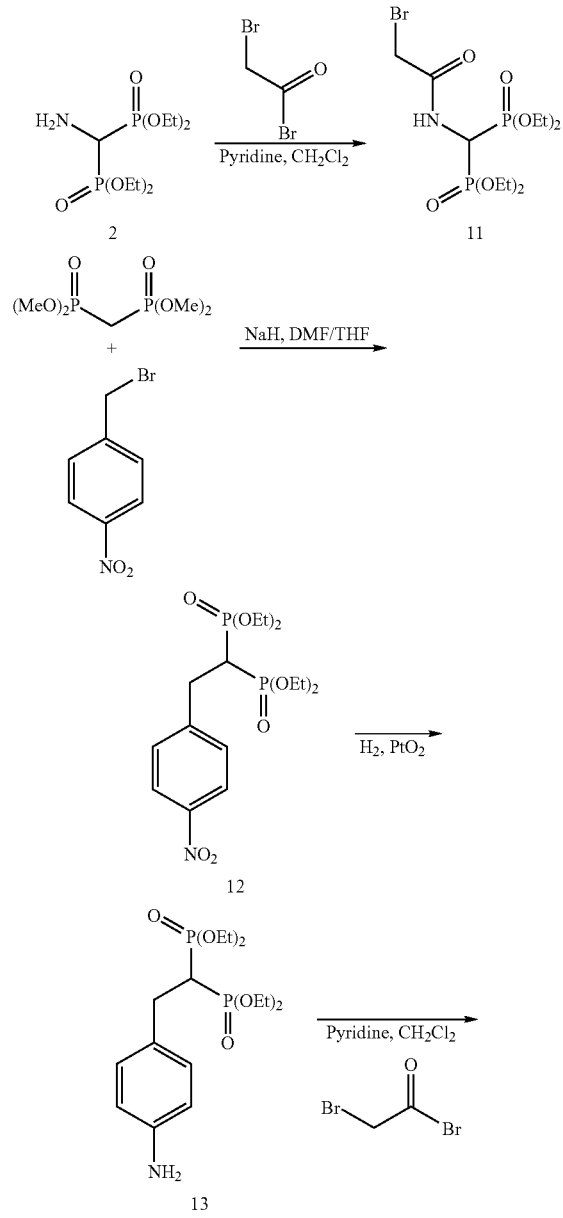

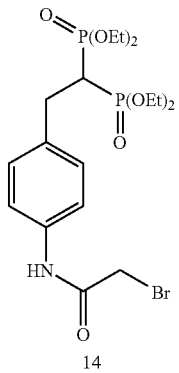

Tetraethyl 1-(N-2-bromoacetylamino)methylenebisphosphonate (11)

A solution of bromoacetyl bromide (0.35 mL, 4.0 mmol) in CH$_2$Cl$_2$ (1 mL) was added dropwise to a stirred, cooled (ice-bath) solution of 2 (1.1 g, 3.6 mmol) and pyridine (0.59 mL, 7.3 mmol) in CH$_2$Cl$_2$ (10 mL). After stirring at the same temperature for 4 hours, the reaction was quenched by the addition of water. The product was extracted with CH$_2$Cl$_2$ and the combined organics were washed with 10% aqueous HCl, brine, dried over sodium sulfate and concentrated at reduced pressure. The crude yellow oil was purified by silica gel column chromatography (0% to 3% MeOH in CH$_2$Cl$_2$) resulting in 11 as a colourless solid (0.58 g, 37%). $^1$H NMR (400 MHz, CDCl$_3$) δ 1.35 (t, J=7.2, 12H), 3.92 (s, 2H), 4.12-4.28 (m, 8H), 4.92 (dt, J=10.2, 21.7, 1H), 6.91 (bd, J=10.0, 1H).

Tetramethyl 1-(4-nitrobenzyl)methylenebisphosphonate (12)

Sodium hydride (1.02 g, 25.4 mmol) was added in portions to a stirring solution of tetramethyl methylenebisphosphonate in DMF (40 mL). After 30 min a solution of 4-nitrobenzylbromide (5.00 g, 23.1 mmol) in THF (5 mL) was added and the resulting mixture was stirred at room temperature for 4.5 hr. The reaction was quenched by the addition of saturated aqueous NH$_4$Cl (20 mL). After the addition of water (100 mL) the product was extracted with EtOAc and the combined organics were washed with brine, dried over MgSO$_4$, filtered and concentrated at reduced pressure. The crude product was purified by silica gel chromatography (0% to 10% MeOH in EtOAc) resulting in 12 as a colorless solid (2.55 g, 30%). $^1$H NMR (400 MHz, CDCl$_3$) δ 2.65 (tt, J=6.5, 23.8, 1H), 3.31 (dt, J=6.5, 16.5, 2H), 3.73 (d, J=7.0, 6H), 3.75 (d, J=7.0, 6H), 7.42 (d, J=8.9, 2H), 8.15 (d, J=8.9, 2H).

Tetramethyl 1-(4-aminobenzyl)methylenebisphosphonate (13)

A mixture of 12 (1.01 g, 2.75 mmol) and PtO$_2$ (0.035 g, 0.15 mmol) in EtOH (40 mL, 95%) was shaken in a PARR apparatus under 55 p.s.i of H$_2$ for 14 hr. The catalyst was removed by filtration through glass fiber filter paper and the solvent was removed under reduced pressure to give 13 as a pale yellow solid (0.959 g, 103%) that was used without purification. $^1$H NMR (400 MHz, CDCl$_3$) δ 2.62 (tt, J=6.3, 23.9, 1H), 3.12 (dt, J=6.3, 16.2, 2H), 3.70 (d, J=1.9, 6H), 3.73 (d, J=1.9, 6H), 6.61 (d, J=8.5, 2H), 7.04 (d, J=8.5, 2H).

Tetramethyl 1-(4-bromoacetamidobenzyl)methylenebisphosphonate (14)

A solution of 13 (0.959 g, 2.87 mmol) and pyridine (349 µL, 4.31 mmol) in CH$_2$Cl$_2$ was cooled in an ice-bath while stirring. A solution of bromoacetylbromide (250 µL, 2.87 mmol) in CH$_2$Cl$_2$ (5 mL) was added drop-wise and the resulting mixture was stirred for 4 h at that temperature. The reaction was quenched by the addition of water and the product was extracted with CH$_2$Cl$_2$. The combined organic layers were washed with brine, dried over sodium sulfate, filtered, and concentrated under reduced pressure. The crude yellow solid was purified by silica gel chromatography resulting in 14 as a colorless solid (0.897 g, 67%). $^1$H NMR (400 MHz, CDCl$_3$) δ 2.65 (tt, J=6.2, 24.4, 1H), 3.22 (dt, J=6.2, 17.4, 2H), 3.72 (d, J=3.7, 6H), 3.75 (d, J=3.7, 6H), 4.01 (s, 2H), 7.26 (d, J=8.6, 2H), 7.47 (d, J=8.6, 2H), 8.15 (bs, 1H): $^{31}$P (162 MHz, CDCl$_3$) δ 26.33 (s, 2P).

Scheme 5. Preparation of vancomycin bisphosphonate conjugate 18

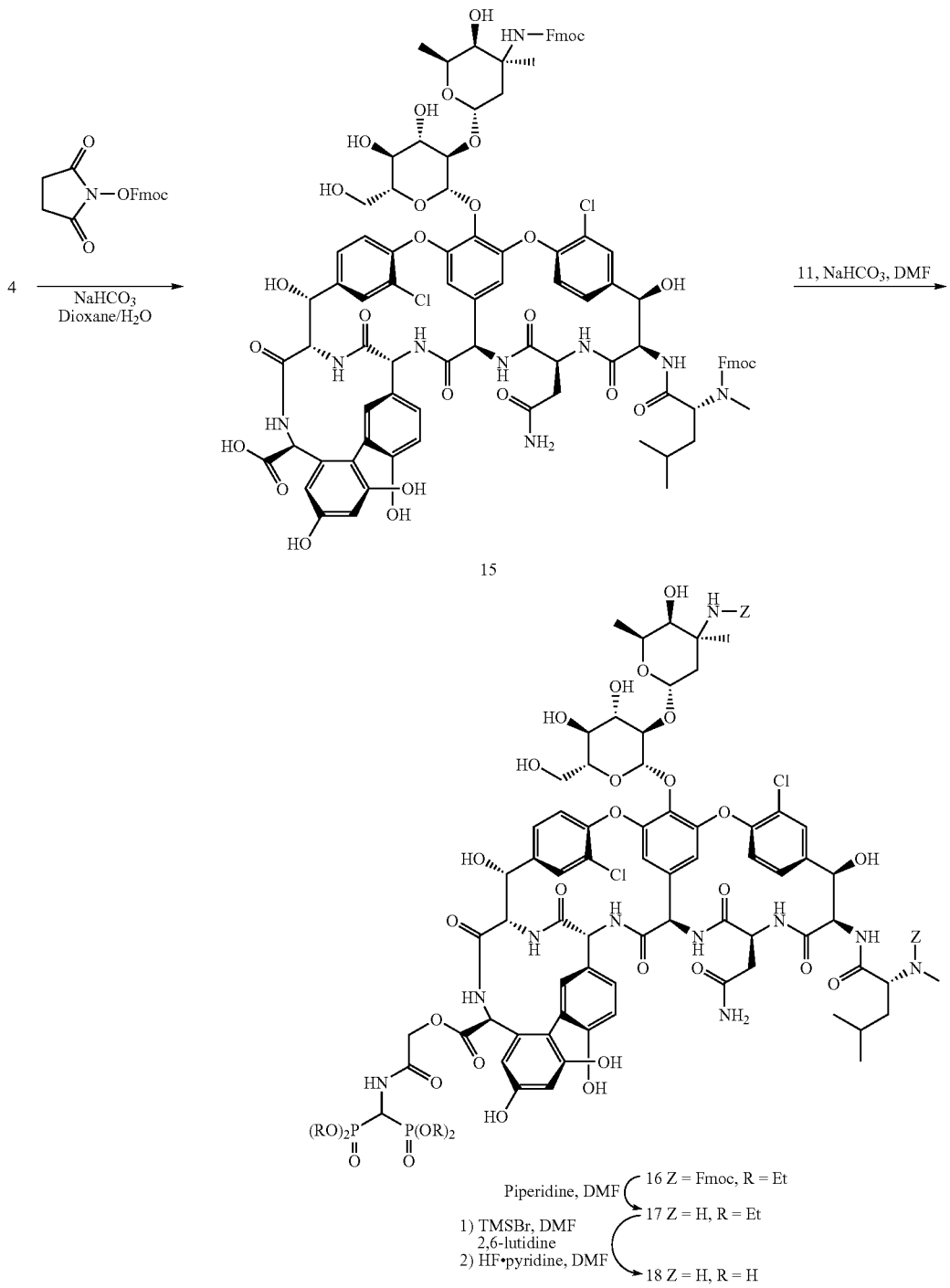

Fmoc Protected Vancomycin 15

To a suspension of vancomycin hydrochloride (4, 5 g, 3.36 mmol) in 200 mL of 1:1 Dioxane:H$_2$O was added NaHCO$_3$ (850 mg, 10.1 mmol) and the mixture was stirred to dissolution. To this solution was added 9-fluorenylmethyl N-succinimidyl carbonate (4.5 g, 13.3 mmoles) and the resulting mixture was stirred at room temperature for 24 h. Acetone (1 L) was added, and the precipitated product was filtered, rinsed with acetone and dried in vacuo to furnish 15 (6.8 g, 3.58 mmoles, quantitative yield) as a white solid which was used without further purification.

Vancomycin Bisphosphonate Conjugate 16

To a mixture of Fmoc protected vancomycin 15 (150 mg, $7.92 \times 10^{-5}$ mol) and sodium bicarbonate (20 mg, $2.38 \times 10^{-4}$ mol) in dry DMF (5 mL), cooled in an ice bath, was added bromoacetamide 11 (50 mg, $1.18 \times 10^{-4}$ mol). The mixture was left to come to room temperature and was stirred for a total of 5 days. The volatiles were removed in vacuo and the residue was subjected to C18 silica gel chromatography on a Biotage™ flash chromatography system using a gradient of 0-70% acetonitrile in 0.005% TFA in H$_2$O as the eluent to furnish 16 (100 mg, $4.47 \times 10^{-5}$ mol, 56% yield) as a white solid. ESI-MS: (M-H)$^-$ calculated for C$_{107}$H$_{119}$Cl$_2$N$_{10}$O$_{35}$P$_2$ 2236. found 2235.0.

Vancomycin Bisphosphonate Conjugate 17

To a solution of protected vancomycin derivative 16 (100 mg, $4.47 \times 10^{-5}$ mol) in dry DMF (2 mL) was added piperidine (170 μL, $1.18 \times 10^{-4}$ mol). The mixture was stirred at room temperature for 4 h and it was concentrated in vacuo. The residue was subjected to C18 silica gel chromatography on a Biotage™ flash chromatography system using a gradient of 0-30% methanol in 0.05% TFA in H$_2$O as the eluent to furnish 17 (66 mg, $3.68 \times 10^{-5}$ mol, 82% yield) as a white solid. ESI-MS: (M-H)$^-$ calculated for C$_{77}$H$_{98}$Cl$_2$N$_{10}$O$_{31}$P$_2$ 1791. found 1791.1.

Vancomycin Bisphosphonated Conjugate 18

Bromotrimethylsilane (243 μL, 1.84 mmol) was added drop-wise to a stirring solution of 17 (66 mg, $3.68 \times 10^{-5}$ mol) and 2,6-lutidine (430 μL, 3.70 mmol) in dry DMF (2.5 mL) which was cooled in an ice-bath. The resulting mixture was left to come to room temperature on its own and stir there for a total of 20 hr. The solvent was removed under reduced pressure to complete dryness. The residue was taken up in DMF (2.5 mL) and pyridine (300 μL, 3.72 mmoles) and HF.pyridine (70% HF, 48 μL, 1.85 mmoles) were added. The mixture was stirred for 2 h at room temperature before being concentrated in vacuo to complete dryness. The crude residue was purified by C18 silica gel chromatography on a Biotage™ flash chromatography system using a gradient of 0-30% acetonitrile in 0.005% TFA in H$_2$O as the eluent to furnish 18 as a white solid (27 mg, $1.61 \times 10^{-5}$ mol, 44% yield). ESI-MS: (M-H)$^-$ calculated for C$_{69}$H$_{82}$Cl$_2$N$_{10}$O$_{31}$P$_2$ 1679. found 1679.1

Scheme 6. Preparation of vancomycin bisphosphonate conjugate 21

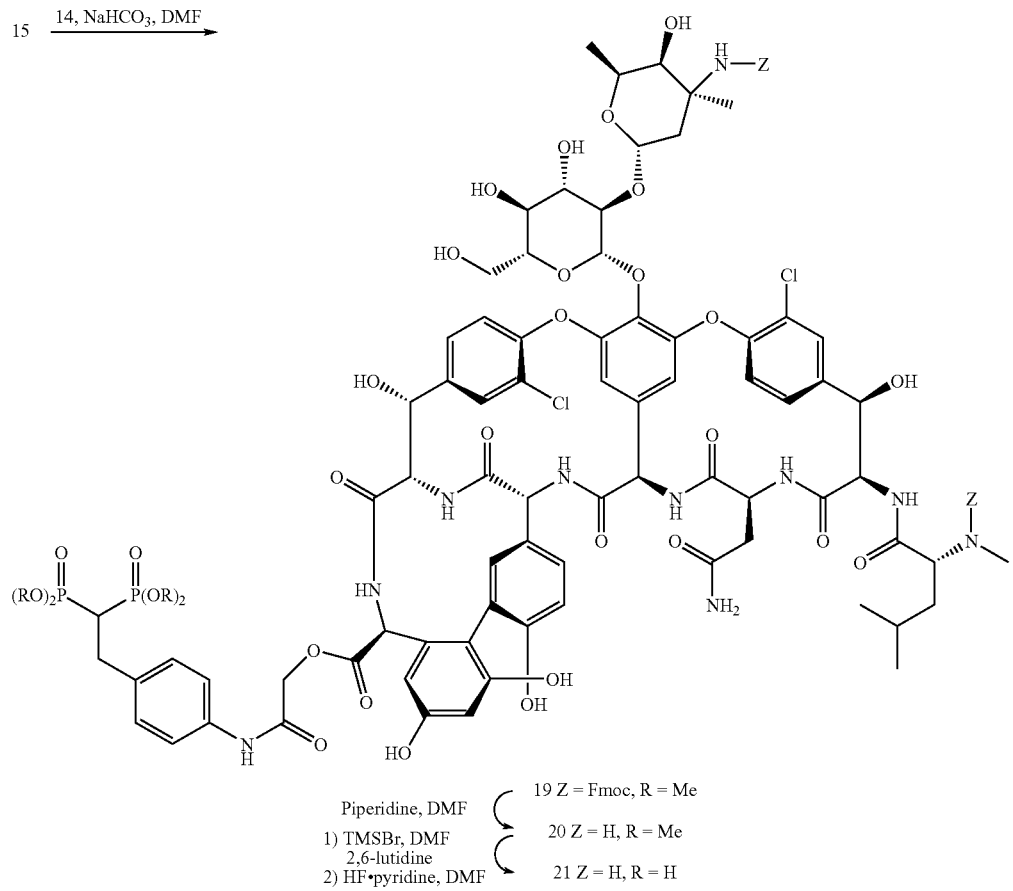

19 Z = Fmoc, R = Me
20 Z = H, R = Me
21 Z = H, R = H

Vancomycin Bisphosphonate Conjugate 19

To a mixture of Fmoc protected vancomycin 15 (1.5 g, $7.92 \times 10^{-4}$ mol) and sodium bicarbonate (200 mg, 2.38 mmol) in dry DMF (50 mL), cooled in an ice bath, was added bromoacetamide 14 (814 mg, 1.78 mmol). The mixture was left to come to room temperature and was stirred for a total of 5 days. The volatiles were removed in vacuo and the residue was subjected twice to C18 silica gel chromatography on a Biotage™ flash chromatography system using a gradient of 0-100% acetonitrile in 0.005% TFA in $H_2O$ as the eluent in the first one and a gradient of 0-60% acetonitrile in 0.005% TFA in $H_2O$ as the eluent in the second one to furnish 19 (1.1 g, $4.84 \times 10^{-4}$ mol, 61% yield) as a white solid. ESI-MS: (M–H)$^-$ calculated for $C_{110}H_{116}Cl_2N_{10}O_{35}P_2$ 2270. found 2269.9.

Vancomycin Bisphosphonate Conjugate 20

To a solution of protected vancomycin derivative 19 (1.1 g, $4.84 \times 10^4$ mol) in dry DMF (30 mL) was added piperidine (1.9 mL, 19.3 mmol). The mixture was stirred at room temperature for 4 h and it was concentrated in vacuo. The residue was subjected to C18 silica gel chromatography on a Biotage™ flash chromatography system using a gradient of 0-50% acetonitrile in 0.005% TFA in $H_2O$ as the eluent to furnish 20 (840 mg, $4.6 \times 10^4$ mol, 95% yield) as a white solid. ESI-MS: (M–H)$^-$ calculated for $C_{80}H_{96}Cl_2N_{10}O_{31}P_2$ 1825. found 1824.9.

Vancomycin Bisphosphonated Conjugate 21

Bromotrimethylsilane (3 mL, 1.84 mmol) was added dropwise to a stirring solution of 20 (840 mg, $4.60 \times 10^{-4}$ mol) and 2,6-lutidine (5.3 mL, 45.72 mmol) in dry DMF (30 mL) which was cooled in an ice-bath. The resulting mixture was left to come to room temperature on its own and stir there for a total of 20 hr. The solvent was removed under reduced pressure to complete dryness. The residue was taken up in DMF (30 mL) and pyridine (3.7 mL, 45.81 mmoles) and HF.pyridine (70% HF, 600 µL, 23.1 mmoles) were added. The mixture was stirred for 2 h at room temperature before being concentrated in vacuo to complete dryness. The crude residue was purified by C18 silica gel chromatography on a Biotage™ flash chromatography system using a gradient of 0-20% acetonitrile in 0.005% TFA in $H_2O$ as the eluent to furnish 21 as a white solid (340 mg, $1.92 \times 10^{-4}$ mol, 42% yield). ESI-MS: (M–H)$^-$ calculated for $C_{76}H_{88}Cl_2N_{10}O_{31}P_2$ 1769. found 1769.1.

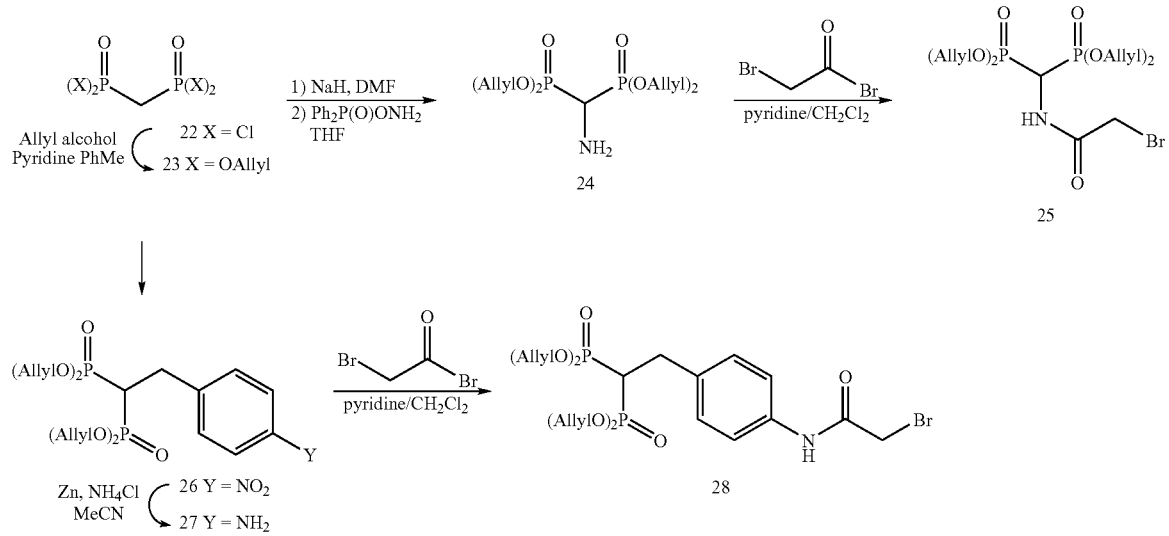

Scheme 7. Preparation of bisphosphonated bromoacetamides 25 and 28.

Tetraallyl Methylenebisphosphonate (23)

To a suspension of tetrachloromethylene bisphosphonate (22, 6.33 g, 25.3 mmol) in toluene (25 mL) at 0° C. was added a mixture of allyl alcohol (6.91 mL, 101 mmol) and pyridine (8.20 mL, 101 mmol) with a dropping funnel over 25 min. After the addition, the reaction mixture was warmed to room temperature and stirred for 20 h. The precipitate was removed by filtration and the solids were washed with toluene. The filtrate was concentrated and purified by flash chromatography on silica gel using 50% acetone/hexanes as eluent. Tetraallyl methylenebisphosphonate 23 was obtained as a clear yellowish oil (5.87 g, 17.5 mmol, 69%). $^1$H NMR (400 MHz, CDCl$_3$) δ 1.33 (t, J=21.1 Hz, 2H), 4.60-4.63 (m, 8H), 5.23-5.27 (m, 4H), 5.35-5.40 (m, 4H), 5.90-6.00 (m, 4H).

Tetraallyl 1-aminomethylenebisphosphonate (24)

To a solution of bisphosphonate 23 (2.0 g, 5.95 mmol) in DMF (6 mL) was added NaH (60% dispersion in mineral oil, 254 mg, 6.35 mmol) portionwise. The solution was stirred for 45 min at room temperature and added to a solution of O-(diphenylphophinyl)hydroxylamine (1.35 g, 5.77 mmol) in THF (40 mL), cooled in a dry ice/acetone bath. The resulting mixture was stirred for 10 min at the same temperature then 18 h at room temperature. CH$_2$Cl$_2$ (40 mL) was added, the solids were removed by filtration and washed with several portions of CH$_2$Cl$_2$. The combined filtrates were concentrated in vacuo and purified by flash chromatography on silica gel using a gradient of 0-5% MeOH/EtOAc to provide aminobisphosphonate 24 as a clear yellow oil (1.24 g, 3.53 mmol, 59%). $^1$H NMR (400 MHz, CDCl$_3$) δ 1.69 (bs, 2H), 3.52 (t, J=20.8 Hz, 1H), 4.64-4.67 (m, 8H), 5.24-5.27 (m, 4H), 5.36-5.42 (m, 4H), 5.92-6.02 (m, 4H).

Tetraallyl 1-bromoacetamidomethylenebisphosphonate (25)

To a solution of aminomethylenebisphosphonate 24 (1.24 g, 3.53 mmol) in CH$_2$Cl$_2$ (44 mL) at 0° C. was added pyridine (428 µL, 5.29 mmol) followed by bromoacetylbromide (307 µL, 3.53 mmol). The reaction mixture was stirred at 0° C. for 30 min and poured into a saturated aqueous NH$_4$Cl solution. The layers were separated and the aqueous layer was extracted with CH$_2$Cl$_2$ (2×). The combined organic layers were dried over MgSO$_4$, filtered and concentrated. The crude product was purified by flash chromatography on silica gel using EtOAc as eluant to provide bromide 25 as a clear colorless oil (1.24 g, 2.63 mmol, 74%). $^1$H NMR (400 MHz, CDCl$_3$) δ 3.91 (s, 2H), 4.61-4.67 (m, 8H), 5.04 (dt, J=21.7, 10.1 Hz, 1H), 5.24-5.28 (m, 4H), 5.35-5.40 (m, 4H), 5.88-5.99 (m, 4H), 7.07 (d, J=10.5 Hz, 1H).

Tetraallyl 1-(4-nitrobenzyl)methylenebisphosphonate (26)

To a solution of bisphosphonate 23 (8.02 g, 23.9 mmol) in DMF (24 mL) was added NaH (60% dispersion in mineral oil, 954 mg, 23.9 mmol) portionwise and the solution was stirred for 1.5 h at room temperature. A solution of p-nitrobenzyl bromide (7.75 g, 35.9 mmol) in THF (32 mL) was added and the mixture was stirred for 3 h at room temperature. It was then poured into a mixture of saturated aqueous NH$_4$Cl solution and water and extracted with CH$_2$Cl$_2$ (3×). The combined organic layers were washed with saturated brine once, dried over MgSO$_4$ and concentrated in vacuo. The crude product was purified by flash chromatography on silica gel using a gradient of 0-50% EtOAc in CH$_2$Cl$_2$ as eluant to provide nitrobenzyl bisphosphonate 26 as a clear yellow oil (4.42 g, 9.38 mmol, 39%). $^1$H NMR (400 MHz, CDCl$_3$) δ 2.73 (tt, J=23.8, 6.5 Hz, 1H), 3.37 (dt, J=16.4, 6.5 Hz, 2H), 4.51-4.61 (m, 8H), 5.21-5.25 (m, 4H), 5.29-5.35 (m, 4H), 5.83-5.93 (m, 4H), 7.44 (d, J=8.8 Hz, 2H), 8.14 (d, J=8.8 Hz, 2H).

Tetraallyl 1-(4-aminobenzyl)methylenebisphosphonate (27)

To a solution of nitroarene 26 (460 mg, 0.98 mmol) in MeOH (9 mL) was added saturated aqueous NH$_4$Cl solution (3 mL) and zinc powder (319 mg, 4.88 mmol). 15 drops of aqueous 1N HCl were added and the reaction was stirred at room temperature for 18 h. EtOAc and saturated NaHCO$_3$ aqueous solution were added and the mixture was filtered through celite. The filtrate was transferred into an extraction funnel and the layers were separated. The aqueous layer was extracted with EtOAc (2×). The combined organic layers were washed with saturated NaCl solution once, dried over MgSO$_4$, filtered and concentrated. The crude product was purified by flash chromatography on silica gel using a gradient of 0-5% MeOH in CH$_2$Cl$_2$ as eluant to provide aminobenzyl bisphosphonate 27 as a clear yellow oil (374 mg, 86%). $^1$H NMR (400 MHz, CDCl$_3$) δ 2.69 (tt, J=24.0, 6.1 Hz, 1H), 3.18 (dt, J=16.7, 6.2 Hz, 2H), 4.46-4.60 (m, 8H), 5.19-5.22 (m, 4H), 5.29-5.35 (m, 4H), 5.84-5.94 (m, 4H), 6.60 (d, J=8.6 Hz, 2H), 7.06 (d, J=8.4 Hz, 2H).

Tetraallyl 1-(4-bromoacetamidobenzyl)methylenebisphosphonate (28)

To a solution of aminobenzyl bisphosphonate 27 (180 mg, 0.41 mmol) in CH$_2$Cl$_2$ (5 mL) at 0° C. was added pyridine (49 µL, 0.61 mmol) followed by bromoacetylbromide (35 µL, 0.41 mmol). The reaction mixture was stirred at 0° C. for 30 min and at room temperature for another 2.5 h. The reaction mixture was diluted with CH$_2$Cl$_2$, washed with aqueous 1N HCl solution, saturated NaHCO$_3$ solution, and saturated NaCl solution, then dried over MgSO$_4$, filtered and concentrated. The crude product was purified by flash chromatography on silica gel using a gradient of 0-10% MeOH in CH$_2$Cl$_2$ as eluant to provide bromide 28 as a clear yellow oil (175 mg, $3.11\times10^{-4}$ mol, 76%). $^1$H NMR (400 MHz, CDCl$_3$) δ 2.72 (tt, J=23.9, 6.2 Hz, 1H), 3.26 (dt, J=16.3, 6.1 Hz, 2H), 4.02 (s, 2H), 4.48-4.62 (m, 8H), 5.20-5.24 (m, 4H), 5.29-5.35 (m, 4H), 5.83-5.94 (m, 4H), 7.25-7.28 (m, 2H), 7.42-7.46 (m, 2H), 8.11 (bs, 1H).

Scheme 8. Preparation of oritavancin bisphosphonate conjugate 31
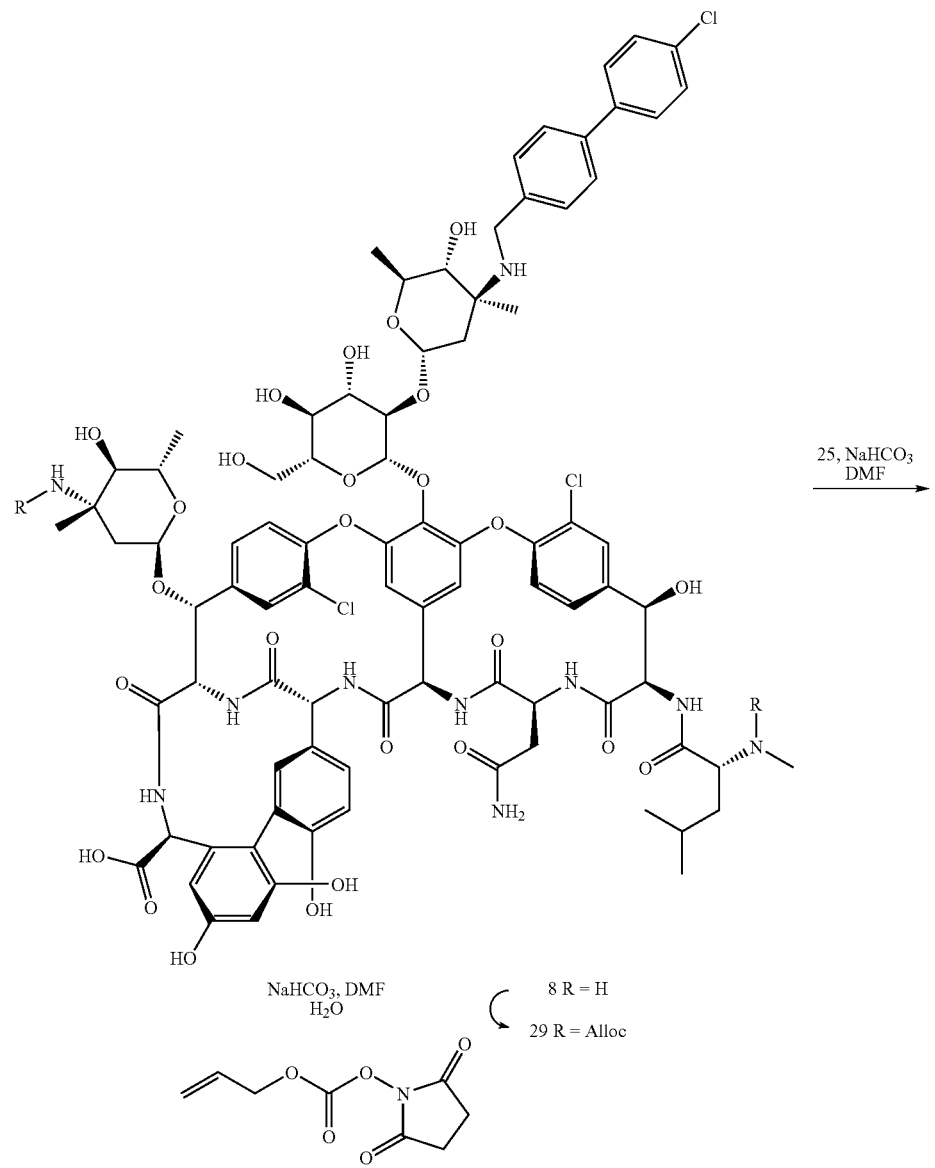

-continued

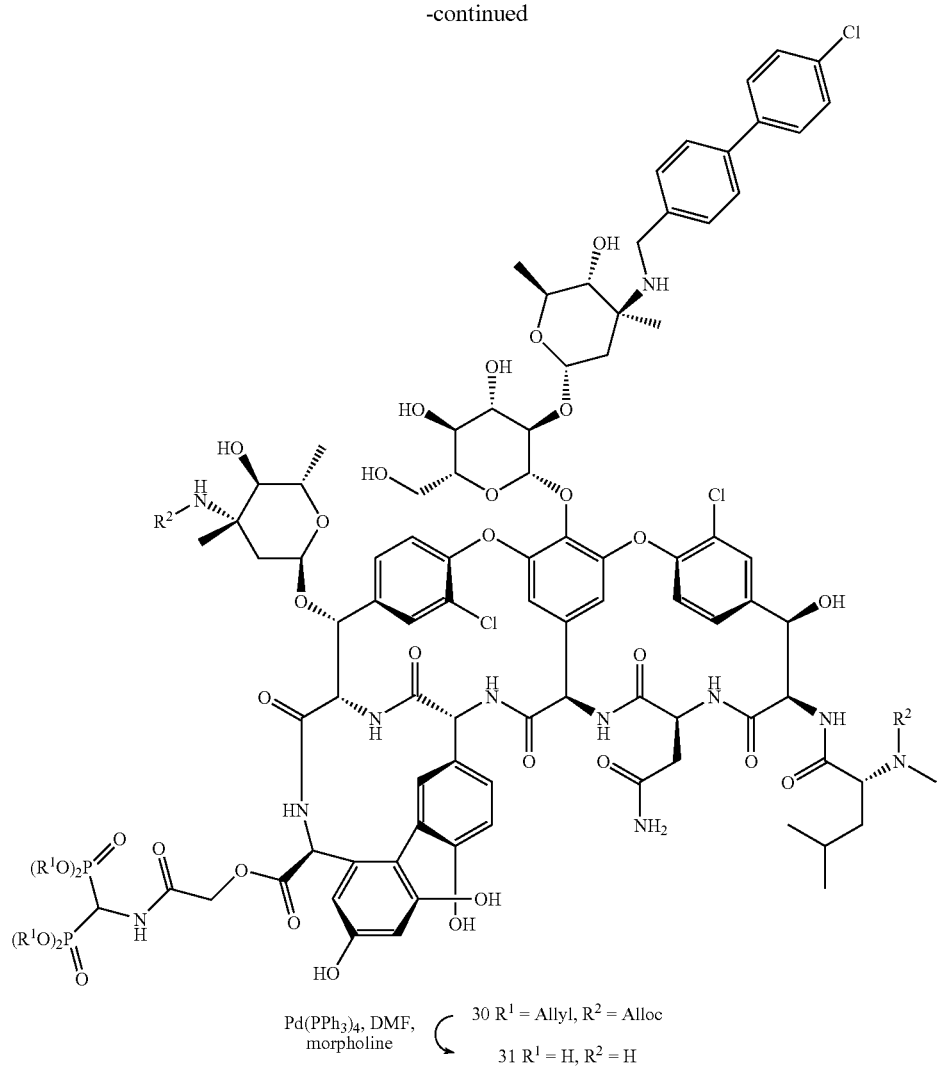

Pd(PPh₃)₄, DMF, morpholine

30 R¹ = Allyl, R² = Alloc
31 R¹ = H, R² = H

Di-N-Alloc oritavancin (29)

To oritavancin bisphosphoric acid salt (8, 2.0 g, 1.01 mmol) in DMF (80 mL) and H$_2$O (30 mL) was added sodium bicarbonate (676 mg, 8.04 mmol) and the mixture was stirred for 30 min. Allyl N-succinimidyl carbonate (641 mg, 3.22 mmol) was added and the mixture was stirred at room temperature for 48 h. A portion of nBuOH (ca. 10-15 mL) was added and the mixture was concentrated under vacuum to one quarter of its initial volume. H$_2$O was added and the pH was adjusted to 4.5 by adding aqueous 1N HCl. The precipitate was filtered and washed with H$_2$O and dried under vacuum to provide di-N-Alloc oritavancin 29 as a white solid (1.85 g, 8.9×10$^{-4}$ mol, 93%) which was used without further purification. ESI-MS: (M+H) calculated for $C_{94}H_{105}Cl_3N_{10}O_{30}$ 1961. found 1961.4.

Oritavancin Bisphosphonate Conjugate 30

To a solution of di-N-Alloc oritavancin 29 (527 mg, 0.25 mmol) in DMF (5 mL) was added sodium bicarbonate (43 mg, 0.51 mmol) and the mixture was stirred for 10 min after which bromide 25 (120 mg, 0.25 mmol) was added. After stirring for 72 h at room temperature, the reaction mixture was concentrated to dryness under vacuum. LCMS analysis of crude reaction mixture showed a mixture of starting material 29, desired product 30 and monodeallylated product in a 0.9:1:1.2 ratio. C18 silica gel chromatography on a Biotage™ flash chromatography system using 60-100% MeOH in Et$_3$N/ H$_3$PO$_4$ buffer (0.2% Et$_3$N/H$_2$O+H$_3$PO$_4$, pH=3) followed by a second column using 30-100% MeCN in H$_2$O (both containing 0.1% TFA) achieved partial separation of the constituents. Fractions containing product 30 and monodeallylated product were combined, concentrated and lyophilized to provide a mixture of product 30 and monodeallylated product (245 mg, 1:1 ratio) which was carried through the next step without further purification. ESI-MS: (M+H) calculated for $C_{109}H_{128}Cl_3N_{11}O_{37}P_2$ 2353. found 2353.2; calculated for $C_{106}H_{124}Cl_3N_{11}O_{37}P_2$ 2313. found 2313.4.

Oritavancin Bisphosphonate Conjugate 31

To a solution of the mixture of oritavancin bisphosphonate conjugate 30 and its monodeallylated analog (245 mg) in DMF (2 mL) was added morpholine (1.8 mL, 20.8 mmol) and Pd(PPh$_3$)$_4$ (24 mg, 0.02 mmol). The mixture was stirred for 4 h at room temperature and concentrated to dryness under vacuum. The crude material was purified by C18 silica gel chromatography on a Biotage™ flash chromatography system using 15-80% MeCN in $H_2O$ (both containing 0.05% $NH_4OH$) followed by a second column using 15-80% MeCN in $H_2O$ (both containing 0.1% TFA). Pure fractions were combined, concentrated and lyophilized to provide the tri-TFA salt of oritavancin bisphosphonate conjugate 31 as a white solid (58 mg, $2.45 \times 10^{-5}$ mol, 24%). ESI-MS: (M+H) calculated for $C_{89}H_{104}Cl_3N_{11}O_{33}P_2$ 2023. found 2023.8.

tography system using 15-100% MeOH in $Et_3N/H_3PO_4$ buffer (0.2% $Et_3N/H_2O+H_3PO_4$, pH=3). Pure fractions were combined, concentrated and lyophilized and desalted by a second column using 15-100% MeCN in $H_2O$ (both containing 0.1% TFA), providing oritavancin bisphosphonate conjugate 32 as a white solid (871 mg, 0.34 mmol, 67%). ESI-MS: (M+H) calculated for $C_{116}H_{134}Cl_3N_{11}O_{37}P_2$ 2443. found 2443.2.

Scheme 9. Preparation of oritavancin bisphosphonate conjugate 33.

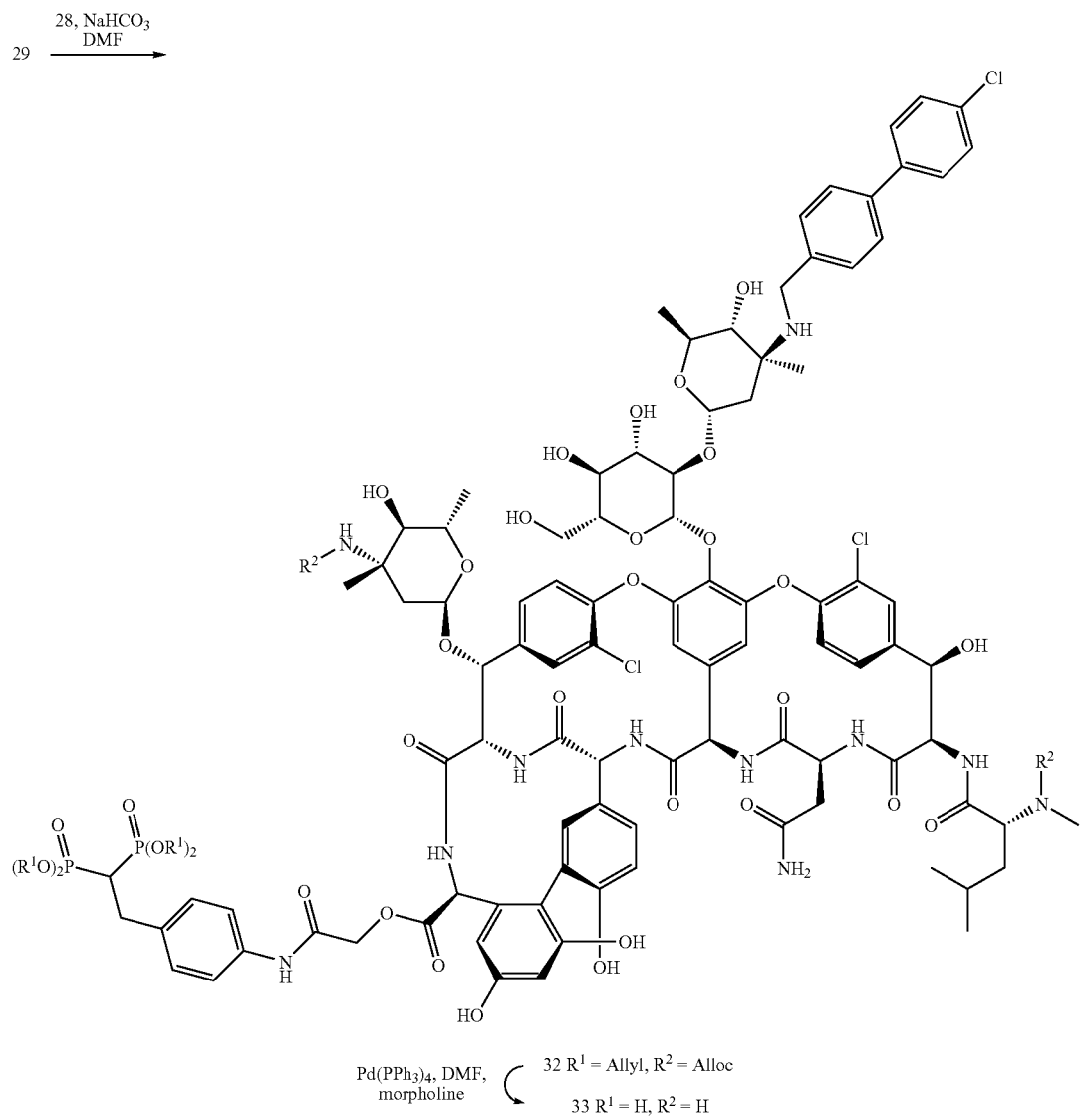

Oritavancin Bisphosphonate Conjugate 32

Oritavancin Bisphosphonate Conjugate 33

To a solution of di-N-Alloc oritavancin 29 (1 g, 0.51 mmol) in DMF (10 mL) was added sodium bicarbonate (86 mg, 1.02 mmol) and the mixture was stirred for 10 min after which bromide 28 (287 mg, 0.51 mmol) was added. After stirring for 48 h at room temperature, additional amounts of sodium bicarbonate (43 mg, 0.51 mmol) and bromide 28 (144 mg, 0.25 mmol) were added and stirring was continued for 48 h, after which the reaction mixture was concentrated to dryness under vacuum. The crude reaction mixture was purified by C18 silica gel chromatography on a Biotage™ flash chroma- To a solution oritavancin bisphosphonate conjugate 31 (871 mg, 0.34 mmol) in DMF (6 mL) was added morpholine (5.9 mL, 68.1 mmol) and $Pd(PPh_3)_4$ (79 mg, 0.068 mmol). The mixture was stirred for 4 h at room temperature and concentrated to dryness under vacuum. The crude material was purified by C18 silica gel chromatography on a Biotage™ flash chromatography system using 15-80% MeCN in $H_2O$ (both containing 0.05% $NH_4OH$), providing the triammonium salt of oritavancin bisphosphonate conjugate 33 as a white solid (472 mg, 0.21 mmol, 64%). ESI-MS: (M+H) calculated for $C_{96}H_{110}Cl_3N_{11}O_{33}P_2$ 2115. found 2115.2.

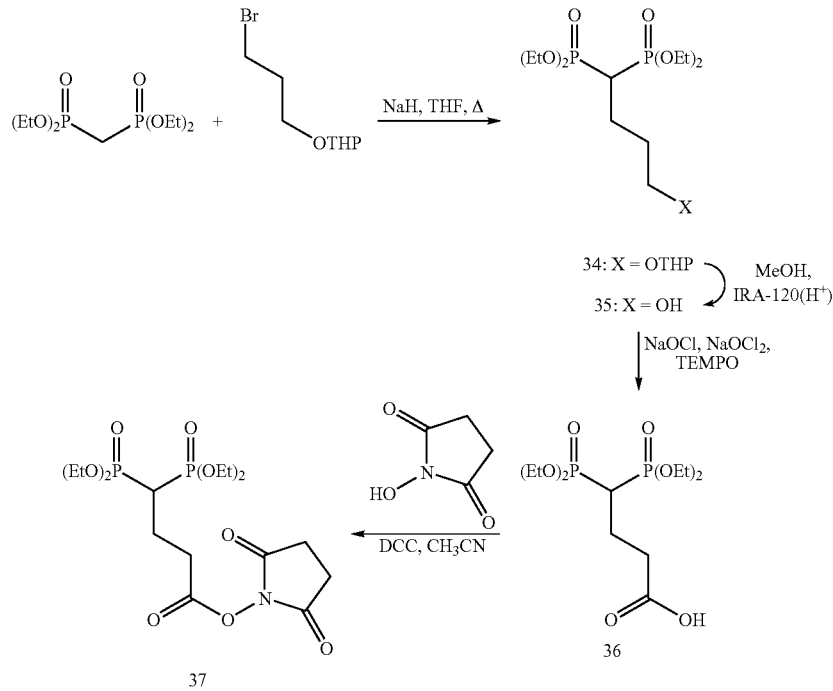

Scheme 10. Preparation of N-succinimidyl 4,4-bis(diethylphosphono)butyrate (37).

Tetraethyl 4-(2-Tetrahydro-2H-pyranyloxy)butylene-1,1-bisphosphonate (34)

To a suspension of NaH (60% suspension in mineral oil, 900 mg, 22.0 mmol) in dry THF (20 mL) was added dropwise tetraethyl methylenebisphosphonate (6.46 g, 22.4 mmol). The resulting clear solution was stirred 15 min at room temperature, after which 2-(3-bromopropoxy)tetrahydro-2H-pyran (5.05 g, 22.6 mmol) was added dropwise. The reaction mixture was heated to reflux for 6 h, diluted with $CH_2Cl_2$ (75 mL) and washed with brine (2×50 mL), dried ($MgSO_4$) and evaporated. It was used as such in the following step.

Tetraethyl 4-hydroxybutylene-1,1-bisphosphonate (35)

To a stirred solution of the crude product 34 (max. 22.4 mmol) in MeOH (40 mL) was added Amberlite IR-120 (0.6 g). The reaction mixture was heated to 50° C. for 4 h, filtered and concentrated in vacuo. The crude product was purified by flash chromatography on silica gel with gradient elution from 5-10% methanol/ethyl acetate to give pure 35 (2.67 g, 34% from tetraethyl methylenebisphosphonate). $^1$H NMR (400 MHz, $CDCl_3$) δ 1.34 (t, J=7.1 Hz, 12H), 1.81 (quint, J=6.5 Hz, 2H), 1.99-2.13 (m, 2H), 2.37 (tt, J=24.4, 5.6 Hz, 1H), 2.51 (t, J=5.9 Hz, 2H), 3.66 (q, J=5.9 Hz, 2H), 4.13-4.22 (m, 8H).

Tetraethyl 3-carboxypropylene-1,1-bisphosphonate (36)

To a solution of alcohol 35 (12.7 g, 36.7 mmol) in MeCN (200 mL) and phosphate buffer solution (200 mL, made from mixing equal volumes of 0.67M $Na_2HPO_4$ solution and 0.67M $NaH_2PO_4$ solution) at 35° C. was added a catalytic amount of TEMPO (430 mg, 2.75 mmol). The reaction flask, maintained at 35° C., was fitted with two addition funnels. One was filled with a solution of $NaClO_2$ (8.3 g, 91.7 mmol) in 75 mL $H_2O$. The other one was filled with a solution of household bleach (5.25%, 25 mL) in 250 mL $H_2O$. About ⅕ of the $NaClO_2$ solution was added, followed by about ⅕ of the bleach solution to initiate the reaction. The remainder of both solutions was added dropwise, simultaneously, with a rate adjusted so that both additions finished concurrently. The reaction mixture was stirred at 35° C. for 4 h, then at room temperature for 18 h. The reaction mixture was diluted with 300 mL $H_2O$ and the pH of the solution was adjusted to 8.0 by adding 1M NaOH. The resulting solution was cooled to 0° C. and a cold solution of $Na_2SO_3$ (6.1% wt, 185 mL) was added slowly. The mixture was stirred at 0° C. during 30 min, after which a portion of $Et_2O$ was added. After stirring vigorously, the mixture was poured into an extraction funnel and the $Et_2O$ layer was separated and discarded. The aqueous layer was acidified to pH 3.4 with conc. HCl and extracted (3×) with $CHCl_3$/i-PrOH mixture (4:1). The combined organic layers were dried over $MgSO_4$, filtered and concentrated to dryness, yielding 36 as a pale yellow oil (12.9 g, 98%), which could be used without further purification. $^1$H-NMR (400 MHz, $CDCl_3$) δ 1.34 (t, J=7.0 Hz, 12H), 2.18-2.28 (m, 2H), 2.60 (tt, J=23.9, 6.5 Hz, 1H), 2.69 (t, J=7.3 Hz, 2H), 4.14-4.23 (m, 8H).

N-succinimidyl 4,4-bis(diethylphosphono)butyrate (37)

To a solution of 36 (315 mg, 0.874 mmol) and N-hydroxysuccinimide (110 mg, 0.960 mmol) in acetonitrile (3 mL) cooled in an ice-bath was added DCC (198 mg, 0.960 mmol).

The resulting mixture was stirred at the same temperature for 1.5 hr and stored at 4° C. overnight. The precipitate was filtered off and the filtrate was concentrated to give 37 as a yellow liquid (360 mg, 93%) that was used without purification. $^1$H NMR (400 MHz, CDCl$_3$) δ 1.34 (t, J=7.0 Hz, 12H), 2.26-2.40 (m, 2H), 2.45 (tt, J=23.4, 6.1 Hz, 1H), 2.83 (bs, 4H), 3.01 (t, J=7.3, 2H), 4.15-4.24 (m, 8H). $^{31}$P NMR (162 MHz, CDCl$_3$) δ 23.44 (s, 2P), Scheme 11. Preparation of oritavancin bisphosphonate conjugate 39.

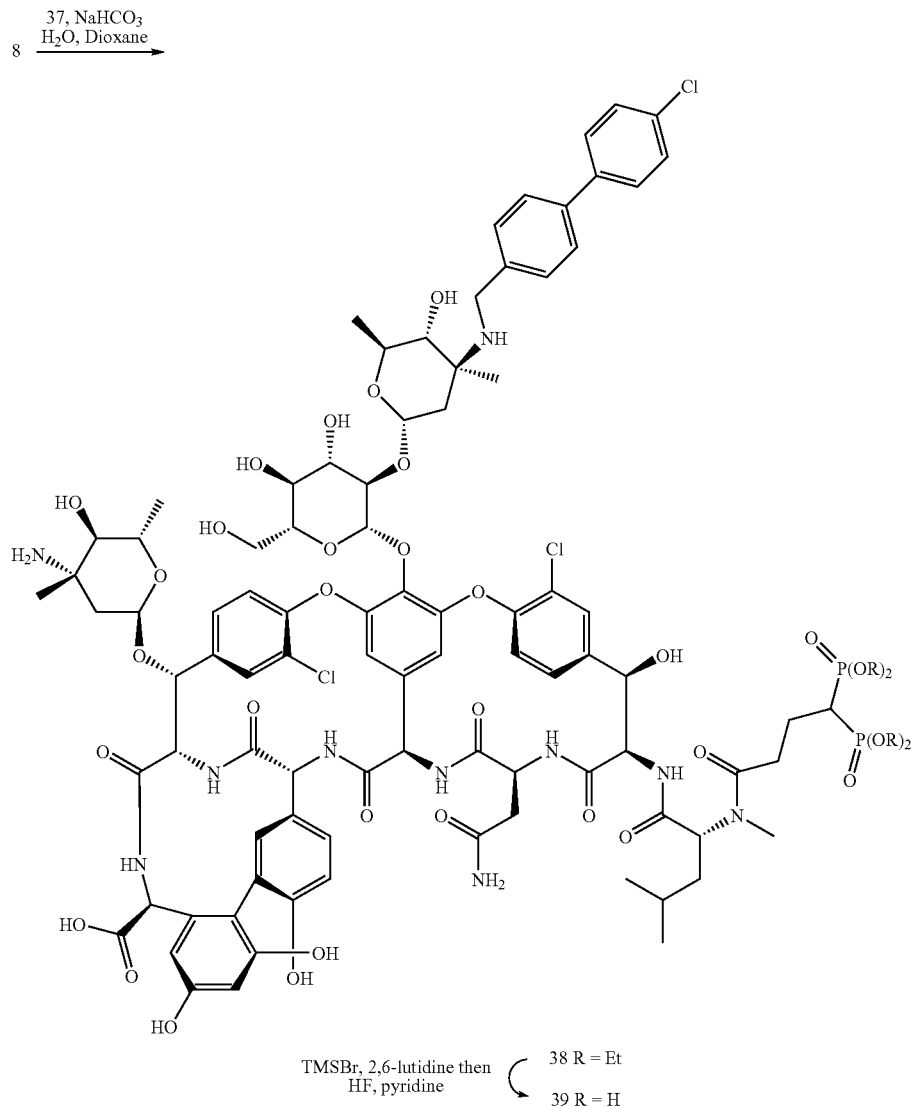

Oritavancin Bisphosphonate Conjugate 38

A suspension of oritavancin diphosphate salt (8, 1.38 g, 0.692 mmol) and NaHCO₃ (116 mg, 1.39 mmol) in dioxane/water (1:1, 20 mL) was stirred at room temperature for 15 min, at which time oritavancin had fully dissolved. 21 (412 mg, 0.901 mmol) was added to the flask and the resulting solution was stirred at room temperature for 16 hr. Et₂O/acetone (1:1, 20 mL) was added and the resulting precipitate was collected by filtration. The crude product was purified by C18 silica gel chromatography on a Biotage™ flash chromatography system using a gradient of 20-80% acetonitrile in 0.05% Formic acid in H₂O as the eluent to furnish the colourless solid 38 (370 mg, 22%) as the di-formate salt. ESI-MS (M+H) calculated for $C_{98}H_{121}Cl_3N_{10}O_{33}P_2$ 2136. found 2136

Oritavancin Bisphosphonate Conjugate 39

A solution of 38 (370 mg, 0.173 mmol) and 2,6-lutidine (1.41 mL, 12.1 mmol) in DMF (5 mL) was cooled to −70° C. (2-propanol/dry ice) followed by the drop-wise addition of TMSBr (915 µL, 6.93 mmol). The resulting slurry was stirred for 30 min at the same temperature then for 38 hr at room temperature. The solution was concentrated to dryness in vacuo without heating and the solid was resuspended in DMF (5 mL) followed by the addition of pyridine (1.40 mL, 17.3 mmol) and HF/pyridine (217 µL, 8.66 mmol). The resulting solution was stirred for 1 hr at room temperature then concentrated to dryness. The crude material was dissolved in water/CH₃CN (1:1, 3 mL), the pH was adjusted to 3 then the product was partially purified by C18 silica gel chromatography on a Biotage™ flash chromatography system using 15-80% acetonitrile in 0.05% TFA in H₂O as the eluent. The fractions containing the product were lyophilized and the semi-purified material was dissolved in water/CH₃CN (1:1, 3 mL), the pH was adjusted to 8 and further subjected to C18 silica gel chromatography on a Biotage™ flash chromatography system using 15-80% acetonitrile in 0.05% NH₄OH in H₂O resulting in the di-ammonium salt of 39 (53 mg, 15%) as a colourless solid: ESI-MS (M+H) calculated for $C_{90}H_{105}Cl_3N_{10}O_{33}F_2$ 2024. found 2024.7.

Scheme 12. Preparation of N-succinimidyl 3,3-bis(diethylphosphono)propanoate (42).

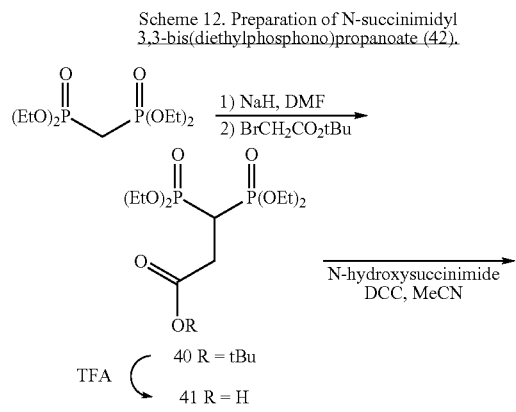

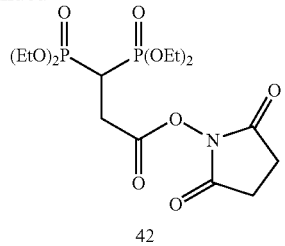

t-Butyl 3,3-bis(diethylphosphono)propanoate (40)

To a solution of tetraethyl methylenebisphosphonate (3.00 g, 10.4 mmol) in dry DMF (9 mL) was added NaH (60% suspension in mineral oil, 0.46 g, 11.5 mmol) portionwise. The resulting slurry was stirred for 30 min at room temperature, after which t-butyl bromoacetate (1.7 mL, 11.5 mmol) was quickly added neat. The reaction mixture was stirred for 1 h and quenched by adding 2 mL of a saturated solution of NH₄Cl. The reaction mixture was evaporated and purified by flash chromatography on silica gel eluting with 5% methanol/ethyl acetate to give pure 40 (2.1 g, 50%) as a clear colourless oil. ¹H NMR (400 MHz, CDCl₃) δ 1.33 (bt, J=7.0, 12H), 1.46 (s, 9H), 2H), 2.76 (dt, J=16.0, 6.1, 2H), 3.07 (tt, J=24.0, 6.1, 1H), 4.10-4.25 (m, 8H).

3,3-bis(diethylphosphono)propanoic acid (41)

Ester 40 (2.1 g, 5.2 mmol) was stirred in TFA (12 mL) for 2.5 min and concentrated under reduced pressure. Crude acid 41 was purified by flash chromatography (gradient elution 100% ethyl acetate-10% methanol/ethyl acetate). Acid 41 was obtained as a white solid (1.35 g, 75%). ¹H NMR (400 MHz, CDCl₃) δ 1.28-1.39 (m, 12H), 2.86 (dt, J=16.1, 6.3, 2H), 3.12 (tt, J=24.0, 6.3, 1H), 4.13-4.26 (m, 8H).

N-Succinimidyl 3,3-bis(diethylphosphono)propanoate (42)

To a solution of 41 (1.0 g, 2.89 mmol) and N-hydroxysuccinimide (366 mg, 3.18 mmol) in acetonitrile (14 mL) cooled in an ice-bath was added DCC (655 mg, 3.18 mmol). The resulting mixture was stirred at the same temperature for 1 h and stored at 4° C. overnight. The precipitate was filtered off and the filtrate was concentrated to give 42 as a white solid (1.29 g, quantitative) that was used without purification. ¹H NMR (400 MHz, CDCl₃) δ 1.32-1.37 (m, 12H), 2.84 (bs, 4H), 3.03 (tt, J=23.4, 6.0 Hz, 1H), 3.17 (dt, J=15.2, 6.0 Hz, 2H), 4.15-4.27 (m, 8H).

Scheme 13. Preparation of oritavancin bisphosphonate conjugate 44.

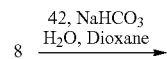

-continued

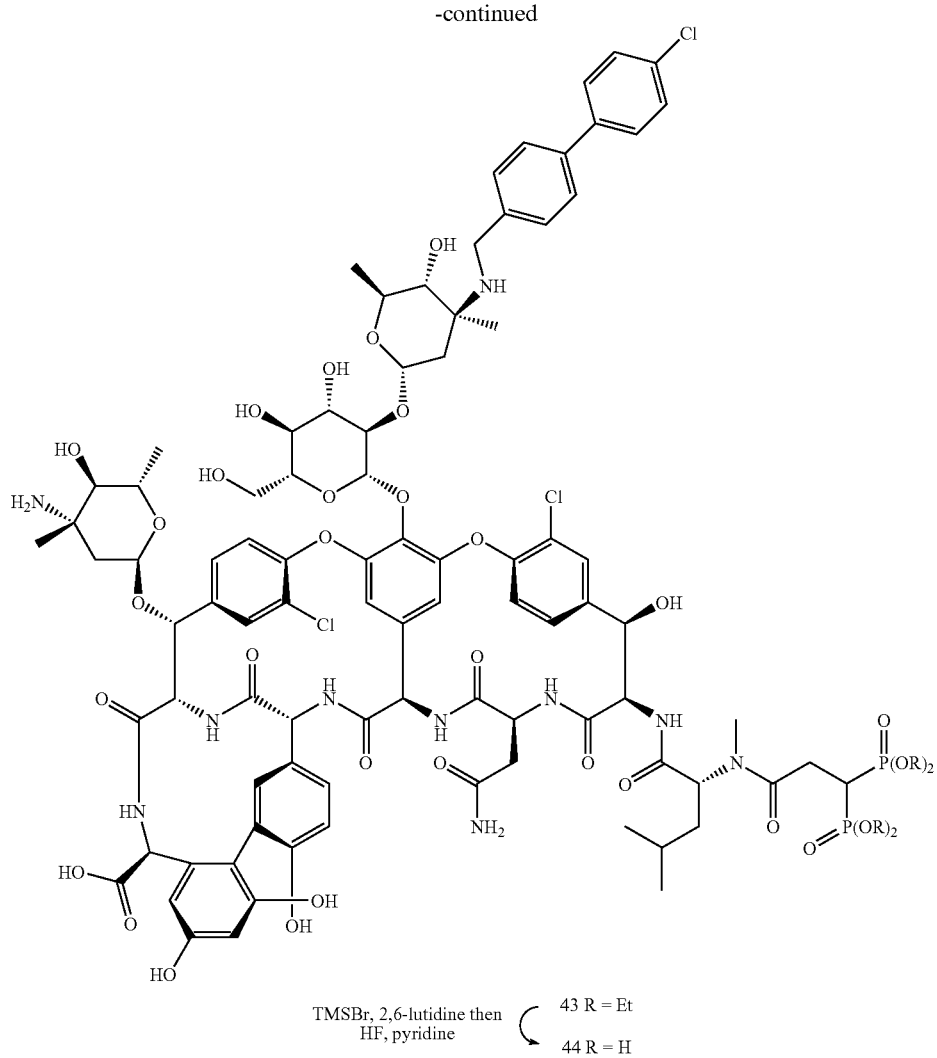

TMSBr, 2,6-lutidine then HF, pyridine

43 R = Et
44 R = H

Oritavancin Bisphosphonate Conjugate 43

To a suspension of oritavancin bisphosphoric acid salt (8, 1.0 g, 0.50 mmol) in dioxane/H$_2$O (1:1, 30 mL) was added sodium bicarbonate (84 mg, 1.01 mmol) and the mixture was stirred until complete dissolution of oritavancin. Succinimidyl ester 42 (446 mg, 1.01 mmol) was added and the mixture was stirred at room temperature for 24 h, after which additional sodium bicarbonate (42 mg, 0.50 mmol) and succinimidyl ester 42 (223 mg, 0.50 mmol) were added and the stirring was continued for 24 h. Additional sodium bicarbonate (42 mg, 0.50 mmol) and succinimidyl ester 42 (223 mg, 0.50 mmol) were added once more and the stirring was continued for 3 d. The reaction mixture was concentrated and lyophilized and the resulting crude product was purified by C18 silica gel chromatography on a Biotage™ flash chromatography system using 15-100% MeOH in Et$_3$N/H$_3$PO$_4$ buffer (0.2% Et$_3$N/H$_2$O+H$_3$PO$_4$, pH=3). Pure fractions were comb concentrated and lyophilized and desalted by a second column using 15-80% MeCN in H$_2$O (both containing 0.1% TFA), providing the di-TFA salt of oritavancin bisphosphonate conjugate 43 as a white solid (276 mg, 12%). ESI-MS: (M+H) calculated for C$_{97}$H$_{119}$Cl$_3$N$_{10}$O$_{33}$P$_2$ 2122. found 2122.2.

Oritavancin Bisphosphonate Conjugate 44

To a solution of the oritavancin bisphosphonate conjugate 43 (274 mg, 0.12 mmol) and 2,6-lutidine (975 µL, 8.4 mmol) in DMF (5 mL) cooled at −78° C. was added TMSBr (713 µL, 5.4 mmol). The reaction mixture was stirred for 15 min at −78° C., then 24 h at room temperature. It was then concentrated to dryness under high vacuum, redissolved in DMF (5 mL) then treated with pyridine (776 µL, 9.6 mmol) and HF-pyridine (120 µL, 4.8 mmol). After stirring for 1 h at room temperature the mixture was concentrated to dryness under high vacuum. The crude product was purified by C18 silica gel chromatography on a Biotage™ flash chromatography system using 15-80% MeCN in H$_2$O (both containing 0.1% TFA) followed by a second column using 15-80% MeCN in H$_2$O (both containing 0.05% NH$_4$OH). Pure fractions were combined, concentrated and lyophilized to provide the tri-ammonium salt of oritavancin bisphosphonate conjugate 44 as a white solid (34 mg, 14%). ESI-MS: (M+H) calculated for C$_{89}$H$_{103}$Cl$_3$N$_{10}$O$_{33}$P$_2$ 2009. found 2009.6.

Scheme 14. Preparation of N-succinimidyl 4-(3,3-bis(diethylphosphono)propanoyloxy) butyrate (48).

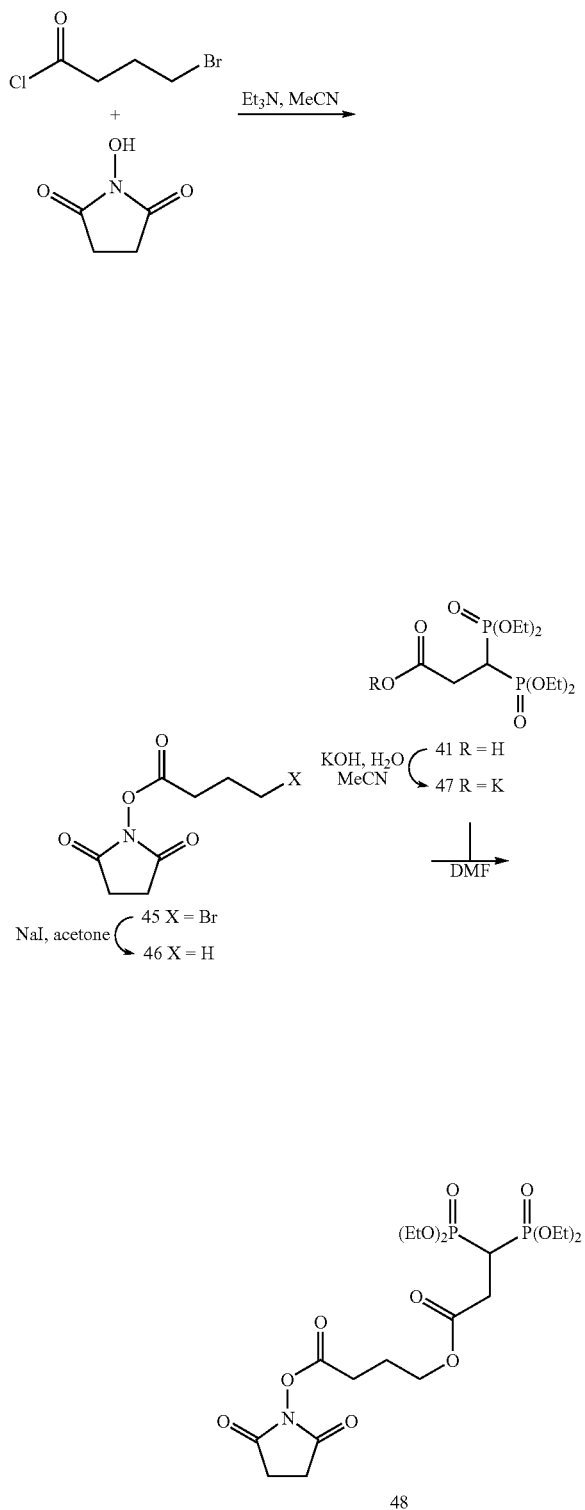

N-Succinimidyl 4-bromobutyrate (45)

A solution of 4-bromobutyryl chloride (1.0 mL, 8.69 mmol) in acetonitrile (10 mL) was added dropwise to a solution containing N-hydroxysuccinimide (1.0 g, 8.69 mmol) and triethylamine (1.2 mL, 8.69 mmol) in acetonitrile (10 mL) cooled in an ice bath. After stirring for 45 min at this temperature, the solids were removed by filtration and the filtrate was concentrated under vacuum. The crude product was then dissolved in EtOAc, washed with $H_2O$, half saturated $NaHCO_3$ solution, $H_2O$ and saturated NaCl solution, dried over $Na_2SO_4$, filtered and concentrated, yielding bromide 45 as a white solid (2.26 g, 99%) that was used without purification. $^1H$ NMR (400 MHz, $CDCl_3$) δ 2.30 (quint, J=6.5 Hz, 2H), 2.83 (t, J=6.4 Hz, 2H), 2.85 (bs, 4H), 3.52 (t, J=6.4 Hz, 2H).

N-Succinimidyl 4-iodobutyrate (46)

To bromide 45 (2.26 g, 8.56 mmol) in acetone (43 mL) was added sodium iodide (3.85 g, 25.7 mmol) and the mixture was stirred for 3 h at room temperature, then concentrated under vacuum. The crude product was then dissolved in EtOAc, washed with $H_2O$, 5% $Na_2S_2O_3$ solution, $H_2O$ and saturated NaCl solution, dried over $Na_2SO_4$, filtered and concentrated, yielding iodide 46 as a light yellow solid (2.55 g, 96%) that was used without purification. $^1H$ NMR (400 MHz, $CDCl_3$) δ 2.25 (quint, J=7.0 Hz, 2H), 2.77 (t, J=7.1 Hz, 2H), 2.85 (bs, 4H), 3.29 (t, J=6.7 Hz, 2H).

Potassium 3,3-bis(diethylphosphono)propanoate (47)

To a solution of acid 41 (516 mg, 1.49 mmol) in acetonitrile (5 mL) was added an aqueous 1M solution of KOH (1.64 ml, 1.64 mmol). After stirring for 20 min, the mixture was concentrated under vacuum and co-evaporated with $Et_2O$ and $CH_2Cl_2$ to provide potassium salt 47 as a white foam (550 mg, 96%). $^1H$ NMR (400 MHz, $CDCl_3$) δ 1.31 (t, J=7.1 Hz, 12H), 2.59 (dt, J=17.7, 5.8 Hz, 2H), 3.17 (tt, J=24.2, 6.1, 1H), 4.13 (2×quint, J=7.1 Hz, 8H).

N-Succinimidyl 4-(3,3-bis(diethylphosphono)propanoyloxy)butyrate (48)

A mixture of potassium salt 47 (160 mg, 0.42 mmol) and iodide 46 (129 mg, 0.42 mmol) in DMF (2 mL) was stirred for 3 h, concentrated under vacuum and purified by flash chromatography on silica gel using 5% $MeOH/CH_2Cl_2$ as eluent, providing 48 as a pale yellow oil (158 mg, 71%). $^1H$ NMR (400 MHz, $CDCl_3$) δ 1.33 (2×t, J=7.1 Hz, 12H), 2.11 (quint, J=6.8 Hz, 2H), 2.74 (t, J=7.5 Hz, 2H), 2.81-2.90 (m, 6H), 3.08 (tt, J=23.8, 6.4 Hz, 1H), 4.14-4.23 (m, 10H).

Scheme 15. Preparation of oritavancin bisphosphonate conjugate 50.

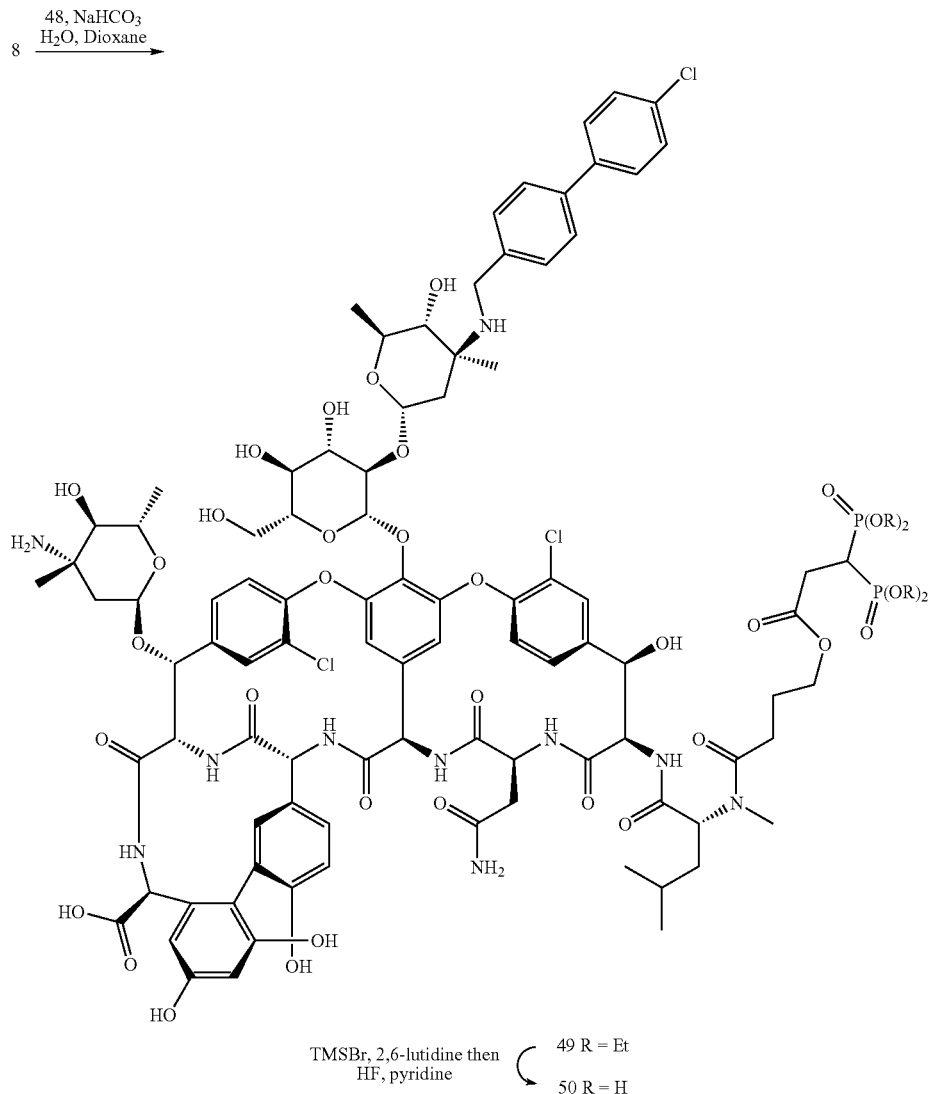

Oritavancin Bisphosphonate Conjugate 49

To a suspension of oritavancin bisphosphoric acid salt (8, 722 mg, 0.36 mmol) in dioxane/$H_2O$ (1:1, 24 mL) was added sodium bicarbonate (61 mg, 0.73 mmol) and the mixture was stirred until complete dissolution of oritavancin. Succinimidyl ester 48 (411 mg, 0.73 mmol) was added and the mixture was stirred at room temperature for 48 h, after which the reaction mixture was concentrated and lyophilized and the resulting crude product was purified by C18 silica gel chromatography on a Biotage™ flash chromatography system using 15-100% MeOH in $Et_3N/H_3PO_4$ buffer (0.2% $Et_3N$/ $H_2O+H_3PO_4$, pH=3). Pure fractions were combined, concentrated, lyophilized and desalted by a second column using 30-100% MeCN in $H_2O$ (both containing 0.1% TFA), providing the di-TFA salt of oritavancin bisphosphonate conjugate 49 as a white solid (451 mg, 51%). ESI-MS: (M+H) calculated for $C_{101}H_{125}Cl_3N_{10}O_{35}P_2$ 2207. found 2207.4.

Oritavancin Bisphosphonate Conjugate 50

To a solution of the oritavancin bisphosphonate conjugate 49 (450 mg, 0.18 mmol) and 2,6-lutidine (1.5 mL, 12.9 mmol) in DMF (10 mL) cooled in a dry ice/acetone bath was added TMSBr (1.1 mL, 8.31 mmol). The reaction mixture was stirred for 15 min at the same temperature, then 24 h at room temperature. It was then concentrated to dryness under high vacuum, redissolved in DMF (10 mL) then treated with pyridine (1.16 mL, 14.4 mmol) and HF-pyridine (180 µL, 7.20 mmol). After stirring for 1 h at room temperature, the mixture was concentrated to dryness under high vacuum. The crude product was purified by C18 silica gel chromatography on a Biotage™ flash chromatography system using 15-80% MeCN in $H_2O$ (both containing 0.05% $NH_4OH$). Pure fractions were combined, concentrated and lyophilized to provide the tri-ammonium salt of oritavancin bisphosphonate conjugate 50 as a white solid (203 mg, 53%). ESI-MS: (M+H) calculated for $C_{93}H_{109}Cl_3N_{10}O_{35}P_2$ 2096. found 2096.2.

Scheme 16. preparation of (5,5-bis(diethylphosphono)pentanoyloxymethyl) N-succinimidyl carbonate (32).

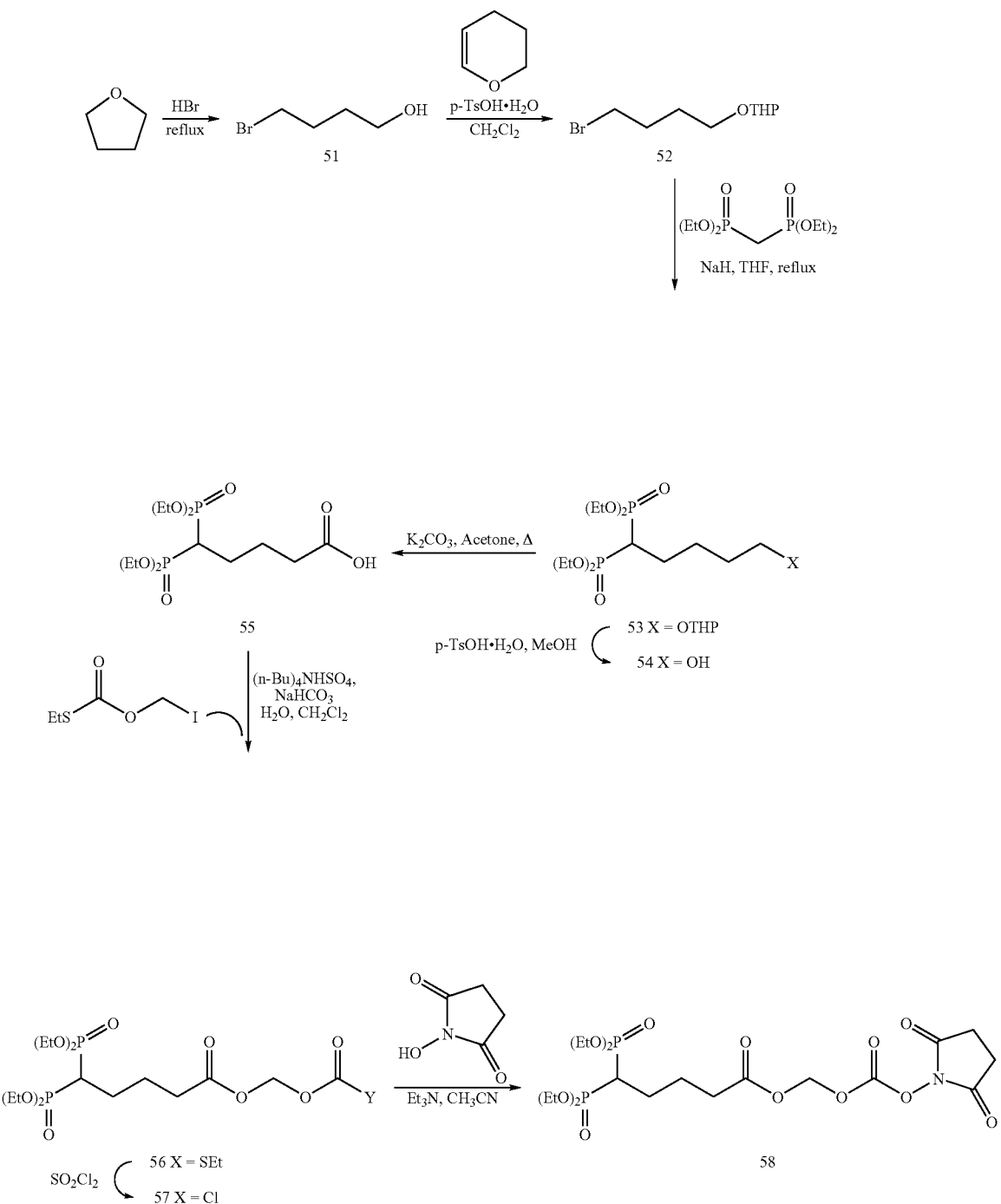

4-Bromo-1-butanol (51)

To 67.5 mL (832.2 mmol) of refluxing tetrahydrofuran was added 31 mL (274 mmol) of 48% hydrobromic acid dropwise and the yellow solution was allowed to reflux for another 2 h. After cooled to room temperature, the reaction was carefully neutralized with saturated sodium bicarbonate aqueous solution. The resultant mixture was extracted with diethyl ether (3×) and dried over anhydrous sodium sulfate. Removal of the solvent afforded the product 51 as a yellow oil (10.7 g, 26%).

$^1$H NMR (400 MHz, CDCl$_3$): δ 1.69-1.76 (m, 2H), 2.01-1.94 (m, 2H), 3.46 (t, J=6.6 Hz, 2H), 3.70 (t, J=6.4 Hz, 2H).

2-(4-Bromobutoxy)-tetrahydro-2H-pyran (52)

3,4-Dihydro-2H-pyran (8.5 mL, 90.96 mmol) was added dropwise to the dichloromethane (20 mL) solution of 51 (10.7 g, 69.93 mmol) and p-toluenesulfonic acid monohydrate (26.5 mg, 0.1372 mmol). The mixture was stirred at room temperature over night. After removing the solvent, the residue was purified by flash chromatography on silica gel with 5:1 hexanes/ethyl acetate as the eluent to yield product 52 as a colorless oil (15.3 g, 92%). $^1$H NMR (400 MHz, CDCl$_3$): δ 1.48-1.62 (m, 4H), 1.68-1.85 (m, 4H), 1.94-2.02 (m, 2H), 3.40-3.53 (m, 4H), 3.74-3.88 (m, 2H), 4.57-4.59 (m, 1H).

Tetraethyl 5-(2-Tetrahydro-2H-pyranyloxy)pentylene-1,1-bisphosphonate (53)

To the suspension of sodium hydride (60% in oil, 840.5 mg, 21.0 mmol) in 40 mL of THF was carefully added tetraethyl methylenebisphosphonate (6.16 g, 21.0 mmol) and the resultant pale yellow clear solution was stirred at room temperature for 45 min. Then the bromide 52 (4.97 g, 21.0 mmol) was introduced plus 5 mL of THF rinse. The reaction was brought to reflux overnight and allowed to cool to room temperature before being quenched with saturated ammonium chloride aqueous solution. Another small amount of water was required to dissolve the solid. The mixture was extracted with ethyl acetate (3×), dried over anhydrous sodium sulfate and concentrated in vacuo. Flash chromatography on silica gel with 20:1 (v/v) dichloromethane/methanol as the eluent afforded 7.3 g of impure product 53 as a slightly yellow oil. The material was used directly in the next step without further purification. Selected $^1$H NMR (400 MHz, CDCl$_3$): δ 2.28 (tt, J=6.1, 24.3 Hz, 1H), 3.37-3.51 (m, 2H), 3.71-3.89 (m, 2H), 4.56-4.58 (m, 1H).

Tetraethyl 5-hydroxypentylene-1,1-bisphosphonate (54)

The crude compound 53 was dissolved in 20 mL of methanol and 74.6 mg (0.386 mmol) of p-toluenesulfonic acid monohydrate was added. After overnight stirring at room temperature, the mixture was concentrated and subjected to flash chromatography with gradient elution from 15:1 ethyl acetate/methanol to 8:1 then 6:1 to afford 54 as a colorless oil (3.1 g, 41% over two steps). $^1$H NMR (400 MHz, CDCl$_3$): δ 1.24-1.36 (m, 12H), 1.55-1.72 (m, 4H), 1.89-2.03 (m, 2H), 2.16 (bs, 1H), 2.29 (tt, J=6.1, 24.3 Hz, 1H), 3.66 (bs, 2H), 4.11-4.22 (m, 8H).

Tetraethyl 5-carboxypentylene-1,1-bisphosphonate (55)

To a mixture of alcohol 54 (475 mg, 1.32 mmol), TEMPO (15 mg, 0.095 mmol), MeCN (6 mL) and sodium phosphate buffer (6 mL, 0.67 M, pH=6.7) heated to 35° C. were added dropwise a sodium chlorite solution (300 mg in 2 mL of water) and dilute bleach (0.75 mL of solution of 1 mL of commercial bleach in 19 mL of water) simultaneously from separate syringes. The mixture turned from yellow to red. After 5 h, reaction was complete by TLC and $^1$H NMR and was cooled to room temperature. Water (30 mL) was added and the pH was adjusted to about 9 with the addition of 3 mL of 1N NaOH. The reaction was quenched by pouring into a cold Na$_2$SO$_3$ solution (500 mg in 10 mL of water) and maintained below 20° C. After 30 min stirring at the same temperature, 30 mL of diethyl ether was used to extract the mixture and the organic phase was discarded. The pH of the aqueous phase was readjusted to between 3-4 by adding 5 mL of 1N HCl and the mixture was extracted with dichloromethane (3×). The combined extracts were dried over sodium sulfate and concentrated to afford the acid 55 quantitatively, which could be used in the following steps without further purification. $^1$H NMR (400 MHz, CDCl$_3$): δ 1.34 (t, J=7.0, 12H), 1.86-2.06 (m, 4H), 2.33 (tt, J=24.2, 5.9, 1H), 2.36 (t, J=7.3, 2H), 4.14-4.22 (8H).

S-Ethyl O-(5,5-bis(diethylphosphono)pentanoyloxy)methyl carbonothioate (56)

Acid 55 (606 mg, 1.619 mmol), tetrabutylammonium hydrogensulfate (552 mg, 1.626 mmol) and sodium bicarbonate (274.2 mg, 3.264 mmol) were added to the mixture of 4 mL of water and 4 mL of dichloromethane. After the evolution of gas stopped, 310.8 mg (1.263 mmol) of S-ethyl O-iodomethyl carbonothioate (synthesized according to Folkmann, M.; Lund, F. J. *Synthesis*, 1990, 1159-1166) in 1 mL of dichloromethane was added and the mixture was stirred for 2 h. The organic phase was separated, washed with water (1×) and dried over sodium sulfate. After filtration and concentration, the residue was stirred in ether for 10 min. The solid was removed and the filtrate was concentrated and subjected to flash chromatography on silica gel with elution in 20:1 (v/v) dichloromethane/methanol to afford compound 56 (519.2 mg, 83%) as a colorless oil. $^1$HNMR (400 MHz, CDCl$_3$): δ 1.33 (t, J=7.3, 3H), 1.35 (t, J=7.7, 12H), 1.86-2.04 (m, 4H), 2.28 (tt, J=23.8, 6.2, 1H), 2.40 (t, J=7.3, 2H), 2.90 (q, J=7.3, 2H), 4.14-4.22 (m, 8H), 5.80 (s, 2H).

(Carbonochloridoyloxy)methyl 5,5-bis(diethylphosphono)pentanoate (57)

Compound 56 neat (519.2 mg, 1.054 mmol) was cooled in an ice/water bath and sulfuryl chloride (128 μL, 1.58 mmol) was carefully added. The reaction mixture was allowed to warm to room temperature and was stirred overnight. After removal of the excess sulfuryl chloride in vacuo, the crude acid chloride 57 was used directly in the next step without further purification. $^1$HNMR (400 MHz, CDCl$_3$): δ 1.35 (t, J=7.0, 12H), 1.86-2.06 (m, 4H), 2.28 (tt, J=23.8, 6.2, 1H), 2.45 (t, J=7.0, 2H), 4.14-4.24 (m, 8H), 5.82 (s, 2H). $^{31}$P NMR (162 MHz, CDCl$_3$) δ 24.34 (s, 2P)

(5,5-bis(diethylphosphono)pentanoyloxymethyl) N-succinimidyl carbonate (58)

A solution of N-hydroxysuccinimide (281 mg, 2.44 mmol) and triethylamine (340 μl, 2.44 mmol) in acetonitrile (10 mL) was cooled in an ice-bath. A solution of 57 (1.14 g, 2.44 mmol) in acetonitrile (2 mL) was added drop-wise over 5 min. After stirring a further 15 min at the same temperature the solution was filtered and the filtrate was concentrated under reduced pressure. The residue was resuspended in EtOAc and washed with water, 5% aqueous Na$_2$S$_2$O$_3$, water and brine then dried over Na$_2$SO$_4$ and concentrated to give 58 (925 mg, 70%) as a yellow liquid that was used without purification. $^1$H NMR (400 MHz, CDCl$_3$): δ 1.34 (t, J=7.1, 12H), 1.87-2.00 (m, 4H), 2.29 (tt, J=24.1, 5.4, 1H), 2.45 (t, J=7.0, 2H), 2.85 (s, 4H), 4.14-4.24 (m, 8H), 5.86 (s, 2H). $^{31}$P NMR (162 MHz, CDCl$_3$) δ 24.42 (s, 2P).

Scheme 17. Preparation of oritavancin bisphosphonate conjugate 60.

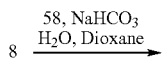

8 58, NaHCO$_3$
H$_2$O, Dioxane

-continued

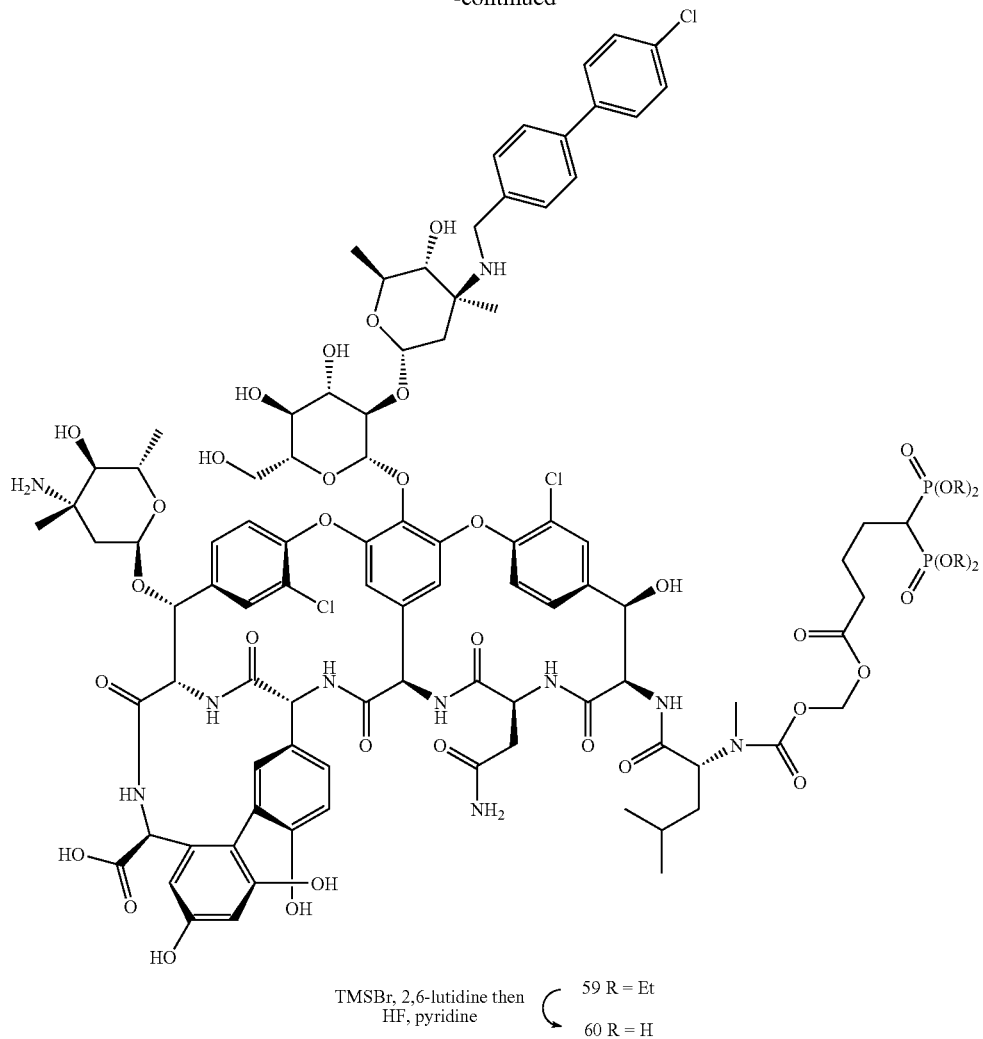

TMSBr, 2,6-lutidine then HF, pyridine

59 R = Et
60 R = H

Oritavancin Bisphosphonate Conjugate 59

A suspension of oritavancin diphosphate (8, 1.00 g, 0.503 mmol) and NaHCO$_3$ (84 mg, 1.0 mmol) in dioxane/H$_2$O (1/1, 10 mL) was stirred at room temperature for 15 min. The homogenous solution was then cooled in an ice-bath and a solution of 58 (341 mg, 0.604 mmol) in acetonitrile (1 mL) was added and the resulting solution was stirred at 0° C. for 4 hr. Acetone/ether/acetonitrile (1/1/2, 20 mL) were added and the precipitate was collected by filtration. The crude product was purified by C18 silica gel chromatography on a Biotage™ flash chromatography system using 20-80% acetonitrile in 0.05% TFA in H$_2$O to furnish the colourless solid 59 (360 mg, 32%) as the di-TFA salt. ESI-MS (M+H) calculated for C$_{101}$H$_{125}$Cl$_3$N$_{10}$O$_{36}$P$_2$ 2223. found 2223.6.

Oritavancin Bisphosphonate Conjugate 60

A solution of 59 (360 mg, 0.162 mmol) and 2,6-lutidine (1.32 mL, 11.3 mmol) in DMF (5 mL) was cooled to –70° C. (2-propanol/dry ice) followed by the drop-wise addition of TMSBr (1.07 mL, 8.10 mmol). The resulting slurry was stirred for 30 min at the same temperature then for 40 hr at room temperature. The solution was concentrated to dryness without heating and the solid was resuspended in DMF (5 mL) followed by the addition of pyridine (1.31 mL, 16.2 mmol) and HF/pyridine (203 μL, 8.10 mmol). The resulting solution was stirred for 1 hr at room temperature then concentrated to dryness. The crude material was purified by C18 silica gel chromatography on a Biotage™ flash chromatography system (15% to 80% acetonitrile in 0.05% TFA in H$_2$O) resulting in the di-TFA salt of 60 (160 mg, 44%) as a colourless solid: ESI MS (M–H) calculated for C$_{93}$H$_{109}$Cl$_3$N$_{10}$O$_{36}$P$_2$ 2110. found 2110.7 (M–H): $^{31}$P NMR (162 MHz, CDCl$_3$) δ 21.61 (s, 2P).

Scheme 18. preparation of (4,4-bis(diethylphosphono) butanoyloxymethyl) N-succinimidyl carbonate (63).

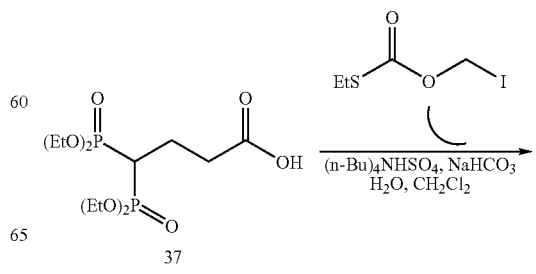

37

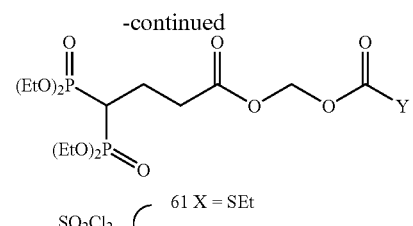

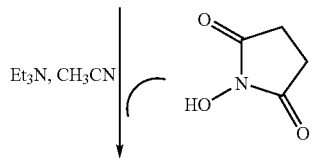

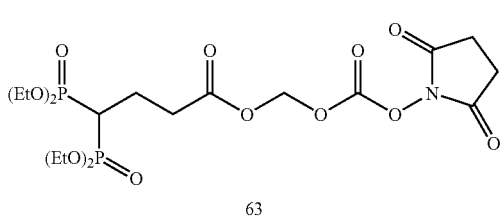

S-Ethyl O-(4,4-bis(diethylphosphono)butanoyloxy)methyl carbonothioate (61)

A mixture of 37 (2.00 g, 5.55 mmol), tetrabutylammonium hydrogensulfate (1.88 g, 5.55 mmol) and sodium bicarbonate (933 mg, 11.1 mmol) in H$_2$O/dicholoromethane (1/1, 60 mL) was stirred at room temperature for 1.5 hr. A solution of S-ethyl O-iodomethyl carbonothionate (1.23 g, 5.00 mmol, Synthesis, 1990, 1159-1166) in dichloromethane (10 mL) was added in 1 mL portions over 1 hr and the resulting mixture was stirred for a further 2 hr. The mixture was diluted with dichloromethane (20 mL) and the organic phase was separated, washed with water and brine then dried over sodium sulfate, filtered and concentrated. The residue was resuspended in ether, stirred for 1 hr, filtered and concentrated to give 61 (2.03 g, 76%) as a yellow liquid that was used without purification. $^1$H NMR (400 MHz, CDCl$_3$): δ 1.31 (t, J=7.5, 3H), 1.32 (t, J=7.3, 12H), 2.15-2.29 (m, 2H), 2.47 (tt, J=23.9, 6.7, 1H), 2.73 (t, J=7.5, 2H), 2.87 (q, J=7.3, 2H), 4.12-4.21 (m, 8H), 5.78 (s, 2H): $^{31}$P NMR (162 MHz, CDCl$_3$) δ 23.95 (s, 2P).

(Carbonochloridoyloxy)methyl 4,4-bis(diethylphosphono)butanoate (62)

Sulfuryl chloride (687 µL, 8.49 mmol) was added dropwise to 61 (2.03 g, 4.24 mmol). The neat reaction was stirred at room temperature for 2.5 hr. The excess sulfuryl chloride was removed under reduced pressure resulting in chloroformate 62 (1.87 g, 97%) that was used without purification. $^1$H NMR (400 MHz, CDCl$_3$): δ 1.35 (t, J=7.1, 12H), 2.17-2.36 (m, 2H), 2.53 (tt, J=23.8, 6.5, 1H), 2.80 (t, J=7.5, 2H), 4.15-4.24 (m, 8H), 5.82 (s, 2H). $^{31}$P NMR (162 MHz, CDCl$_3$) δ 23.72 (s, 2P).

(4,4-bis(diethylphosphono)butanoyloxymethyl) N-succinimidyl carbonate (63)

A solution of N-hydroxysuccinimide (89 mg, 0.77 mmol) and triethylamine (108 µL, 0.770 mmol) were dissolved in acetonitrile (2 mL) was cooled in an ice-bath followed by the addition of 62 (350 mg, 0.770 mmol) in acetonitrile (1 mL) over 10 min. The resulting solution was stirred for a further 15 min at the same temperature then the solution was filtered and the filtrate was concentrated under reduced pressure. The residue was resuspended in EtOAc and washed with 5% aqueous Na$_2$S$_2$O$_3$, 5% aqueous NaHCO$_3$, water and brine then filtered and dried over Na$_2$SO$_4$ and concentrated to give 63 (410 mg, 100%) as a yellow liquid that was used without purification. $^1$H NMR (400 MHz, CDCl$_3$): δ 1.34 (t, J=7.2, 12H), 2.18-2.32 (m, 2H), 2.50 (tt, J=24.2, 7.6, 1H), 2.80 (t, J=7.8, 2H), 2.85 (s, 4H), 4.15-4.23 (m, 8H), 5.87 (s, 2H). $^{31}$P NMR (162 MHz, CDCl$_3$) δ 23.76 (s, 2P).

Scheme 19. Preparation of oritavancin bisphosphonate conjugate 65.

8  63, NaHCO$_3$
   H$_2$O, Dioxane
   →

-continued

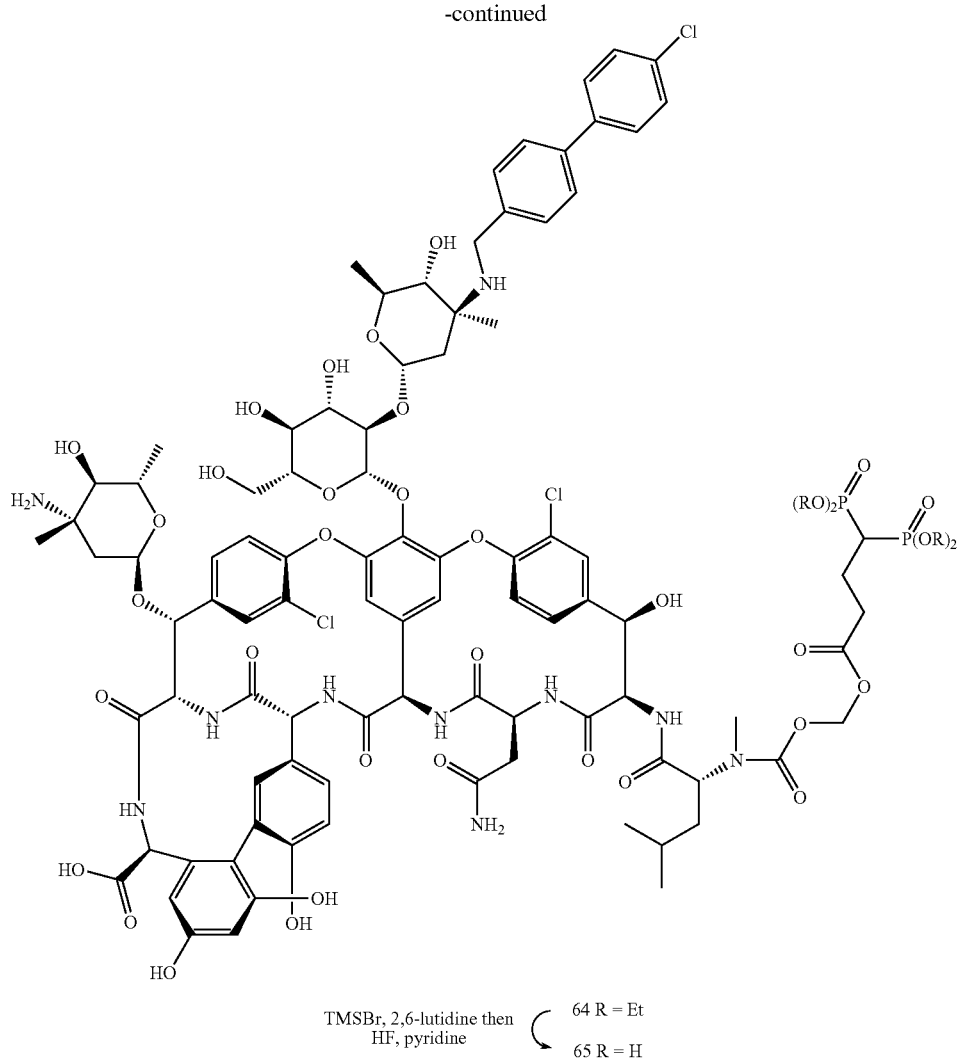

TMSBr, 2,6-lutidine then HF, pyridine

64 R = Et
65 R = H

Oritavancin Bisphosphonate Conjugate 64

A suspension of oritavancin diphosphate (8, 537 mg, 0.270 mmol) and NaHCO$_3$ (68 mg, 0.81 mmol) in dioxane/H$_2$O (1/1, 8 mL) was stirred at room temperature for 15 min. The homogenous solution was then cooled in an ice-bath and a solution of 63 (287 mg, 0.540 mmol) in acetonitrile (1 mL) was added drop-wise and the resulting solution was stirred at 0° C. for 4 hr. Acetone/ether/acetonitrile (1/1/2, 20 mL) were added and the precipitate was collected by filtration. The crude product was purified by C18 silica gel chromatography on a Biotage™ flash chromatography system (15% to 80% acetonitrile in 0.05% TFA in H$_2$O) resulting in the colourless solid 64 (287 mg, 44%) as the di-TFA salt. ESI MS: (M+H) calculated for $C_{100}H_{123}Cl_3N_{10}O_{36}P_2$ 2209. found 2209.4.

Oritavancin Bisphosphonate Conjugate 65

A solution of 64 (280 mg, 0.115 mmol) and 2,6-lutidine (800 μL, 6.89 mmol) in DMF (5 mL) was cooled to −70° C. (2-propanol/dry ice) followed by the drop-wise addition of TMSBr (683 μL, 5.17 mmol). The resulting slurry was stirred for 30 min at the same temperature then for 28 hr at room temperature. The solution was concentrated to dryness without heating and the solid was resuspended in DMF (5 mL) followed by the addition of pyridine (1.31 mL, 16.2 mmol) and HF/pyridine (203 μL, 8.10 mmol). The resulting solution was stirred for 1 hr at room temperature then concentrated to dryness. The crude material was purified by C18 silica gel chromatography on a Biotage™ flash chromatography system (15% to 80% acetonitrile in 0.05% TFA in H$_2$O) resulting in the di-TFA salt of 65 (90 mg, 54%) as a colourless solid: ESI MS: (M+H) calculated for $C_{92}H_{107}Cl_3N_{10}O_{36}P_2$ 2098. found 2098.3.

Example 2

Determination of In Vitro Antibacterial Activity

In Vitro Antibacterial Activity

Susceptibility of *S. aureus* strain ATCC13709 to the commercial antibiotics and synthesized compounds was determined by following the guidelines set by the Clinical and Laboratory Standards Institute (formerly the National Committee for Clinical Laboratory Standards) (M26-A). Compounds were diluted two-fold serially in either DMSO (Vancomycin 4, Oritavancin 8, compounds 10, 31, 33, 39, 44, 50, 60, 65), DMF (compounds 18 and 21) or in PBS (compound 6) and transferred to cation-adjusted Mueller Hinton broth (CAMHB; Becton Dickinson). 50 µL of compounds diluted in CAMHB was mixed with 100 µL of bacteria diluted in CAMHB in 96-well microtiter plates. The final number of micro-organisms in the assay was 5×10$^5$ c.f.u. per mL and the final concentration of DMSO or DMF in the assay, if present, was 1.25%. Assays were set up in duplicate and incubated at 37° C. for 18 h. The concentration of compound that inhibited visible growth was reported as the minimum inhibitory concentration (MIC).

Susceptibility testing experiments were also carried out in the presence of serum. These experiments were carried out similar to the susceptibility testing with the following modifications. 75 µL of compounds diluted in CAMHB was mixed with 75 µL of bacteria diluted in 100% serum from any given source (commercial pooled mouse serum (MS) and human serum (HS), Equitech-Bio Inc.). The final concentration of animal serum in the assay was 50% and the concentrations of all other components were identical to those described for susceptibility testing. The data is summarized in Table 1.

TABLE 1

Antibacterial susceptibility of bacteria to selected compounds
(Minimum inhibitory concentrations in µg/mL)

| | S. aureus ATCC 13709 | | | |
|---|---|---|---|---|
| Compound | CAMHB$^a$ | CAMHB + 50% Mouse Serum | CAMHB + 50% Human Serum | CAMHB + 50% Rat Serum |
| Vancomycin (4) | 1 | 2 | 1 | 2 |
| 6 | 64 | 32 | 16 | 128 |
| 18 | 16 | 16 | 8 | 32 |
| 21 | 16 | 16 | 16 | 32 |
| Oritavancin (8) | 0.5 | 2 | 1 | 0.25 |
| 10 | >32 | >32 | >32 | >32 |
| 31 | 16 | 2 | 32 | 2 |
| 33 | >32 | 8 | >32 | 8 |
| 39 | >32 | >32 | >32 | >32 |
| 44 | 32 | 4 | 32 | 4 |
| 50 | 32 | 32 | >32 | >32 |
| 60 | 32 | 32 | >32 | 32 |
| 65 | 8 | 0.5 | 4 | 1 |

$^a$Cation adjusted Mueller-Hinton broth.

It can be broadly deduced that the bisphosphonated prodrugs 6, 10, 18, 21, 31, 33, 39, 44, 50, 60 and 65 possess antibacterial activities which are at least 16 to 32 fold weaker than the parent drugs (vancomycin for 6, 18, and 21 and oritavancin for 10, 31, 33, 39, 44, 50, 60 and 65). This suggests the introduction of a bisphosphonated moiety to be detrimental to the antibacterial nature of the molecules.

The presence of serum greatly impacted the MIC values associated with bisphosphonate conjugated drugs 31, 33, 44 and 65 in the absence of bone mineral. If the antibacterial activity seen results from the parent glycopeptide released from the prodrugs during the course of the assay, this suggests a possible participation from serum components, perhaps hydrolytic enzymes, in the cleavage of the prodrugs. In essence, the release of the drug does appear to be less in aqueous buffer than in serum for compounds 31, 33, 44 and 65. The differences between compounds 18 and 21—prodrugs of vancomycin—and 31 and 33—prodrugs of oritavancin bearing the same linkers—is particularly stricking and suggests that simple changes in glycopeptide structure greatly impact the ability of the prodrug to regenerate the parent drug.

These assay suggest that it is favourable for the bisphosphonated glycopeptides to be prodrugs, given that cleavage to the parent compound would result in raised antibacterial activity.

Example 3

Binding of Compounds to Bone Powder In Vitro and Subsequent Regeneration of the Parent Drug Bone Powder Binding The ability of the molecules from Example 1 to bind to bone powder was established using a microbiological assay for detection. An individual compound was dissolved in PBS+2% DMSO and added at a concentration of 1 mg/ml in a slurry of bone meal powder (Now Foods, Bloomingdale, Ill., USA) in PBS at 10 mg/ml. The suspension of drug/prodrug in bone meal powder was incubated at 37° C. for 1 h to allow for binding, and centrifuged at 13 000 rpm for 2 min, before recovering the supernatant. The bone meal powder pellet was then washed three times with 1 ml of PBS+2% DMSO. The supernatant was assessed for drug content by microbioassays as follows: For vancomycin, isolated colonies of the indicator strain Bacillus subtilis 1A754 were resuspended in 0.85% saline to $OD_{600}$=0.2 and spread on Cation-adjusted Miller Hinton agar (CAMHA) plates. Known volumes of the supernatants were applied to discs and dried. The discs were then placed on the seeded CAMHA plates. The plates were incubated at 37° C. for 18 h after which the diameters of the zone of inhibition generated by the discs were measured. For oritavancin concentrations were determined with Mueller-Hinton agar containing 5% lysed horse blood and a clinical isolate of Streptococcus pneumoniae (ATCC 700902). Oritavancin standards and samples were placed in wells created in the agar and allowed to diffuse into the agar for 24 h. The indicator strain (prepared in saline to an $OD_{600}$ of 0.2) was applied to the agar and plates were incubated at 37° C. in an atmosphere of 5% $CO_2$ for 24 h, after which diameters of the zones of inhibition were measured.

The amount of prodrug was deduced from standard curves of known amounts of the parent drug (vancomycin 4 or oritavancin 8) that were used as reference for each experiment. The results are displayed in Table 2.

The results confirm that the bisphosphonated prodrugs are very efficiently removed from solution by osseous matter. They also undeniably lend credence to the use of bisphosphonates as mediators for bone delivery, by comparing prodrugs 18, 21, 39, 60 and 65 (>95% bound) to parent drug (binding not detected). It is reasonable to believe that a portion of the unbound material detected not to be bisphosphonated prodrug but contaminating or regenerated parent drug. Nevertheless, it is also probable that the extent of binding to the osseous matter is reflective of the kinetics of bone absorption/adsorption. There was no zone of inhibition seen for compound 6 in the bioassay, and as such the level of binding could not be determined.

Regeneration of Drug from Bone Powder-Bound Prodrug

The ability of the prodrug to release the active entity at the site of infection is paramount for use in vivo. This can be partially predetermined by measuring the release of the drug from prodrug bound to osseous matter in vitro.

Amounts of parent drug "regenerated" from the phosphonated prodrug were measured as follows. Washed bone powder-bound prodrugs from the above experiment were resuspended in 400 µL PBS+2% DMSO or in 400 µL 50% (v/v in PBS+2% DMSO) human or rat serum. The suspension was incubated overnight at 37° C., centrifuged at 13,000 rpm for 2 min and the supernatant was recovered. The amount of regenerated parent drug in the supernatant was determined by measurements using the microbiological assays that were previously described for the prodrugs themselves. The amount of released drug from prodrug was deduced from standard curves of known amounts of parent drug that were used as reference for each experiment. The amount of regenerated drug assessed by this bioassay was corroborated by MIC determination. The percentage of drug regenerated in PBS or serum after the overnight incubation (Table 2) was deduced from the difference between the amount of bound prodrug and the amount of regenerated drug (not shown).

TABLE 2

Bone binding and Conversion of bisphosphonated glycopeptide prodrugs to parent drugs after binding to bone (expressed as % prodrug converted after 24 h incubation)

| Compound | Parent | % Bone binding | Medium | % Conversion |
|---|---|---|---|---|
| Vancomycin | — | 0 | PBS | — |
| | | | 50% human serum | — |
| | | | 50% rat serum | — |
| 6 | Vancomycin | ?? | PBS | ?? |
| | | | 50% human serum | ?? |
| | | | 50% rat serum | ?? |
| 18 | Vancomycin | 96.5 | PBS | 2.09 |
| | | | 50% human serum | 2.34 |
| | | | 50% rat serum | 2.58 |
| 21 | Vancomycin | 96.7 | PBS | 3.5 |
| | | | 50% human serum | 3.5 |
| | | | 50% rat serum | 4.1 |
| Oritavancin | — | 0 | PBS | — |
| | | | 50% human serum | — |
| | | | 50% rat serum | — |
| 39 | Oritavancin | 99.8 | PBS | 0.01 |
| | | | 50% human serum | n.d. |
| | | | 50% rat serum | 0.9 |
| 60 | Oritavancin | 99.9 | PBS | <LOD |
| | | | 50% human serum | n.d. |
| | | | 50% rat serum | 0.05 |
| 65 | Oritavancin | 96.9 | PBS | 0.2 |
| | | | 50% human serum | n.d. |
| | | | 50% rat serum | 26.4 |

—: not applicable.
??: cannot be measured using current technique.
n.d.: not determined.
<LOD: below the limit of detection The data presented in Table 2 provides evidence as to the importance of the selection of an appropriate bisphosphonate linker on the ability of the prodrugs to release the parent active entity. Several trends are revealed by this data. First, with compounds 18 and 21, both containing glycolamide linkers known to be effective in previous reports (Nielsen et al., Journal of Pharmaceutical Sciences (1988); 77(4):285-98.), there is a fair amount of drug released from the bone matter after 24 h. On the other hand, no zones of inhibition were observed for bisphosphonated Vancomycin 6, which therefore either does not bind bone powder, and unlikely event given the very high binding of the other compounds, or, more probably, fails to regenerate. For the Oritavancin prodrugs, the first trend observed is the very large difference between the rates of cleavage in PBS and those in serum. It is possible that the linkers may be very sensitive to the presence of select serum components, but it is also possible that the recovery of Oritavancin in PBS be low when released, as in the experiment, and better when spiked, as in the controls. This uncertainty requires the analysis to focus only on values in serum. Surprisingly, the simple amide linker in prodrug 39 is still fairly labile, more so than prodrug 60 which has a bisphosphonated version of the known acyloxymethyl carbamate linker (Alexander et al, Journal of Medicinal Chemistry (1988); 31: 318-322). Yet, the loss of a single carbon atom in the chain of the linker results in a marked acceleration in the rate of cleavage (see 65 versus 60). As in the case of 39, it appears that proximity of the bisphosphonate group to the site of cleavage results in accelerated hydrolysis, suggesting this moiety to be involved in the mechanism of cleavage.

These bone binding and regeneration experiments demonstrate both the affinity of the prodrugs for osseous matter and the ability of some of these molecules to release their parent molecule over time. This augurs well for these molecules to be effective means of delivering glycopeptide and lipoglycopeptides to the site of infection in the treatment of osteomyelitis.

It is understood that the examples and embodiments described herein are for illustrative purposes only and that various modifications or changes in light thereof will be suggested to persons skilled in the art and are to be included within the spirit and purview of this application and scope of the appended claims.

All documents, publications, patents, books, manuals, articles, papers, abstracts, posters and other materials referenced herein are expressly incorporated herein by reference in their entireties.

What is claimed is:

1. A compound represented by Formula (I):

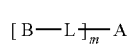

or a pharmaceutically acceptable salt, ester or prodrug thereof, wherein:

A is a glycopeptide or lipoglycopeptide antimicrobial molecule having a structure represented by the following Formula ($A_1$):

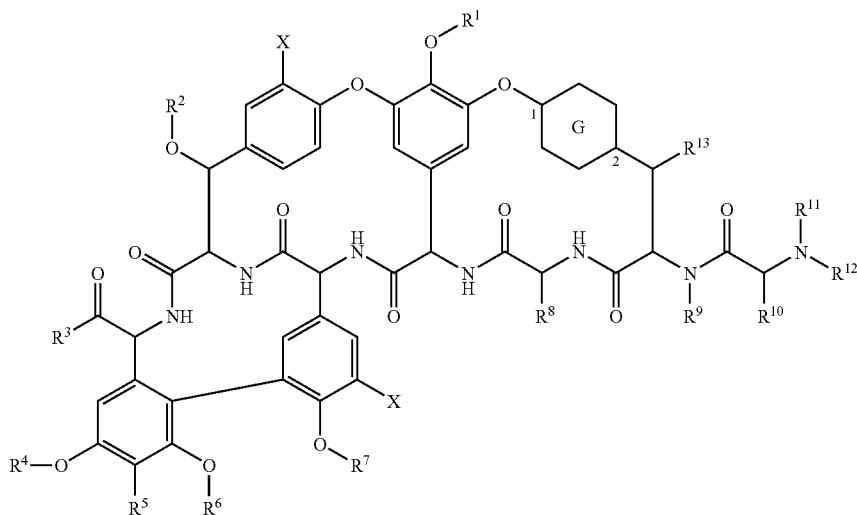

(A₁)

or a pharmaceutically acceptable salt, ester or prodrug thereof, wherein:

$R^1$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$R^a$—Y—$R^b$—$(Z)_x$; or $R^1$ is a saccharide group optionally substituted with —$R^a$—Y—$R^b$—$(Z)_x$, —$R^f$, —C(O)$R_f$, or —C(O)—$R^a$—Y—$R^b$—$(Z)_x$;

$R^2$ is hydrogen or a saccharide group optionally substituted with $R^a$—Y—$R^b$—$(Z)_x$, —$R^f$, —C(O)$R^f$, or —C(O)—$R^a$—Y—$R^b$—$(Z)_x$;

$R^3$ is —$OR^c$, —$NR^cR^c$, —O—$R^a$—Y—$R^b$—$(Z)_x$, —$NR^c$—$R^a$—Y—$R^b$—$(Z)_x$, —$NR^cR^e$, or —O—$R^e$;

$R^4$ is selected from the group consisting of hydrogen, alkyl, substituted alkyl, alkenyl, substituted alkenyl, alkynyl, substituted alkynyl, —$R^a$—Y—$R^b$—$(Z)_x$, —C(O)$R^d$ and a saccharide group optionally substituted with —$R^a$—Y—$R^b$—$(Z)_x$, —$R^f$, or —C(O)—$R^a$—Y—$R^b$—$(Z)_x$, or $R^4$ and $R^5$ can be joined, together with the atoms to which they are attached, to form a heterocyclic ring optionally substituted with —$NR^c$—$R^a$—Y—$R^b$—$(Z)_x$;

$R^5$ is selected from the group consisting of hydrogen, halo, —CH($R^c$)—$NR^cR^c$, —CH($R^c$)—$NR^cR^e$, —CH($R^c$)—$NR^c$—$R^a$—Y—$R^b$—$(Z)_x$, —CH($R^c$)—$R^x$, and —CH($R^c$)—$NR^c$—$R^aC(O)$—$R^x$;

$R^6$ is selected from the group consisting of hydrogen, alkyl, substituted alkyl, alkenyl, substituted alkenyl, alkynyl, substituted alkynyl, —$R^a$—Y—$R^b$—$(Z)_x$, —C(O)$R^d$ and a saccharide group optionally substituted with —$R^a$—Y—$R^b$—$(Z)_x$, —$R^f$, —C(O)$R^f$, or —C(O)—$R^a$—Y—$R^b$—$(Z)_x$, or $R^5$ and $R^6$ can be joined, together with the atoms to which they are attached, to form a heterocyclic ring optionally substituted with —$NR^c$—$R^a$—Y—$R^b$—$(Z)_x$;

$R^7$ is selected from the group consisting of hydrogen, alkyl, substituted alkyl, alkenyl, substituted alkenyl, alkynyl, substituted alkynyl, —$R^a$—Y—$R^b$—$(Z)_x$, and —C(O)$R^d$;

$R^8$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$R^a$—Y—$R^b$—$(Z)_x$;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^{10}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or $R^8$ and $R^{10}$ are joined to form —$Ar^1$—O—$Ar^2$—, where $Ar^1$ and $Ar^2$ are independently arylene or heteroarylene;

$R^{11}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic, or $R^{10}$ and $R^{11}$ are joined, together with the carbon and nitrogen atoms to which they are attached, to form a heterocyclic ring;

$R^{12}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —C(O)$R^d$, —C(NH)$R^d$, —C(O)$NR^cR^c$, —C(O)$OR^d$, —C(NH)$NR^cR^c$, —$R^a$—Y—$R^b$—$(Z)_x$, and —C(O)—$R^b$—Y—$R^b$—$(Z)_x$, or $R^{11}$ and $R^{12}$ are joined, together with the nitrogen atom to which they are attached, to form a heterocyclic ring;

$R^{13}$ is hydrogen or —$OR^{14}$;

$R^{14}$ is hydrogen, —C(O)$R^d$ or a saccharide group;

$R^a$ is each independently selected from the group consisting of alkylene, substituted alkylene, alkenylene, substituted alkenylene, alkynylene and substituted alkynylene;

$R^b$ is each independently selected from the group consisting of a covalent bond, alkylene, substituted alkylene, alkenylene, substituted alkenylene, alkynylene and substituted alkynylene;

$R^c$ is each independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

$R^d$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^e$ is each a saccharide group;

$R^f$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, and heterocyclic;

$R^x$ is an N-linked amino saccharide or an N-linked heterocycle;

X is each independently selected from the group consisting of hydrogen, fluoro, chloro, bromo and iodo;

Y is each independently selected from the group consisting of, —CH$_2$—, —O—, —S—, —S—S—, —N$R^c$—, —S(O)—, —SO$_2$—, —N$R^c$C(O)—, —OSO$_2$—, —OC(O)—, —N($R^c$)SO$_2$—, —C(O)N$R^c$—, —C(O)O—, —SO$_2$N$R^c$—, —SO$_2$O—, —P(O)(O$R^c$)O—, —P(O)(O$R^c$)N$R^c$—, —OP(O)(O$R^c$)O—, —OP(O)(O$R^c$)N$R^c$—, —OC(O)O—, —N$R^c$C(O)O—, —N$R^c$C(O)N$R^c$—, —OC(O)N$R^c$—, —C(O)—, and —N($R^c$)SO$_2$N$R^c$—;

Z is each independently selected from the group consisting of hydrogen, aryl, cycloalkyl, cycloalkenyl, heteroaryl, heterocyclic; and a saccharide;

x is 1 or 2; and

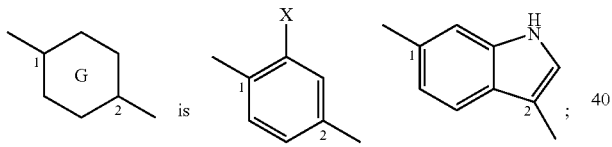

B is a bisphosphonate is selected from the group consisting of:

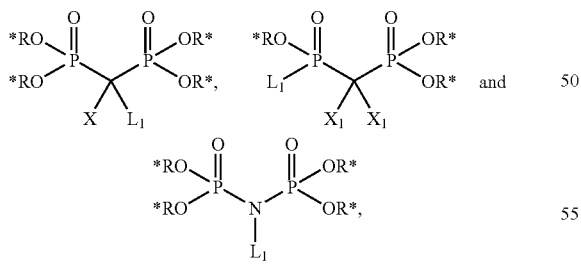

wherein:

each R* is independently selected from the group consisting of H, lower alkyl, cycloalkyl, aryl and heteroaryl, with the proviso that at least two R* are H;

X is H, OH, NH$_2$, or a halo group;

$X_1$ are both H, or each is independently selected from the group consisting of H, OH, NH$_2$, and a halo group; and $L_1$ is the point of attachment to $R^b$;

L is a hydrolysable linker for covalently coupling B to A; and m is 1, 2, 3, 4, 5, 6 or 7, wherein B-L- is represented by the following formula (BL$_1$):

$$A_a\text{-Z} \qquad (BL_1)$$

wherein:

$A_a$ indicates the point of attachment to the glycopeptide or lipoglycopeptide antimicrobial molecule A; and Z is selected from the group consisting of

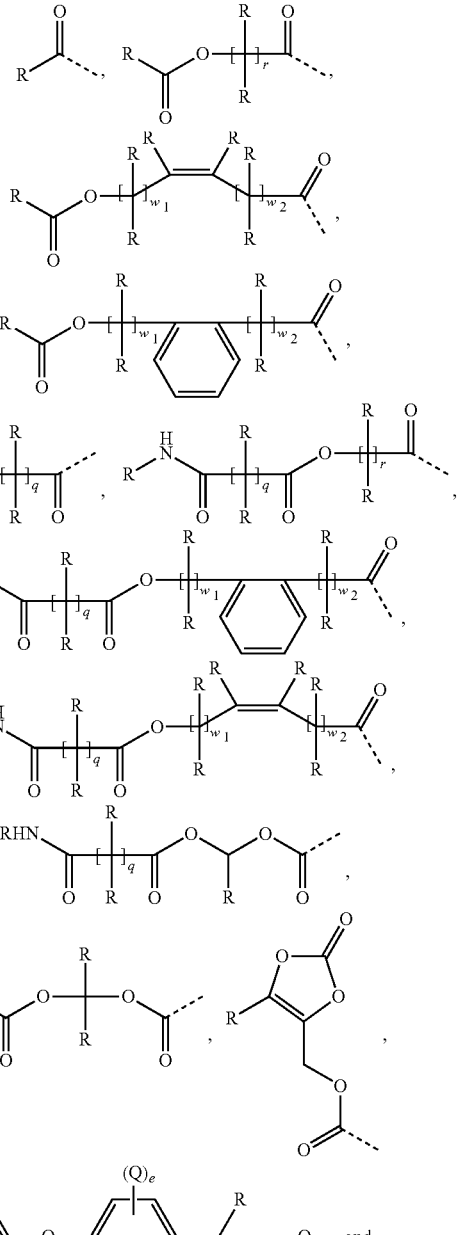

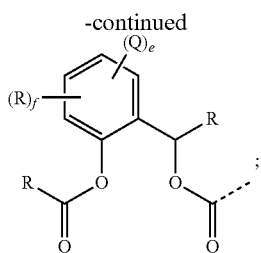

-continued each R is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, amino, substituted amino, hydroxyl, alkoxy, substituted alkoxy, aryloxy, substituted aryloxy, and —$R^a$—Y—$R^b$—Y—$R^b$—B;

each $R^a$ is independently selected from the group consisting of a covalent bond, alkylene, substituted alkylene, alkenylene, substituted alkenylene, alkynylene, substituted alkynylene, arylene, substituted arylene, —(CO)-alkylene-, substituted —(CO)-alkylene-, —(CO)-alkenylene-, substituted —(CO)-alkenylene-, —(CO)-alkynylene-, substituted —(CO)-alkynylene-, —(CO)-arylene- and substituted —(CO)-arylene-;

each $R^b$ is independently selected from the group consisting of a covalent bond, alkylene, substituted alkylene, alkenylene, substituted alkenylene, alkynylene, substituted alkynylene, arylene and substituted arylene;

each Y is independently selected from the group consisting of a covalent bond, —$CH_2$—, —O—, —S—S—, —$NR^c$—, —S(O)—, —$SO_2$—, —$NR^cC(O)$—, —$OSO_2$—, —OC(O)—, —N($R^c$)$SO_2$—, —C(O)$NR^c$—, —C(O)O—, —$SO_2NR^c$—, —$SO_2O$—, —P(O)(O$R^c$)O—, —P(O)(O$R^c$)$NR^c$—, —OP(O)(O$R^c$)O—, —OP(O)(O$R^c$)$NR^c$—, —OC(O)O—, —$NR^cC(O)O$—, —$NR^cC(O)NR^c$—, —OC(O)$NR^c$—, —C(O)—, and —N($R^c$)$SO_2NR^c$—;

each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$—;

each $R^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

B is a phosphonated group;

each Q is independently selected from the group consisting of nitro, chloro, bromo, iodo and fluoro;

q is 2 or 3;

r is 1, 2, 3, 4 or 5;

$w_1$ and $w_2$ are each integers ≥0 such that their sum ($w_1+w_2$) is 1, 2 or 3; and e and f are integers ≥0 such that e+f=4;

with the proviso that at least one R in Formula ($BL_1$) is —$R^a$—Y—$R^b$—Y—$R^b$—B.

2. The compound of claim 1, wherein at least one of said B-L- is coupled to a hydroxyl functionality on said glycopeptide or lipoglycopeptide antibiotic A, and wherein each of said B-L- coupled to a hydroxyl functionality is independently selected from the group consisting of:

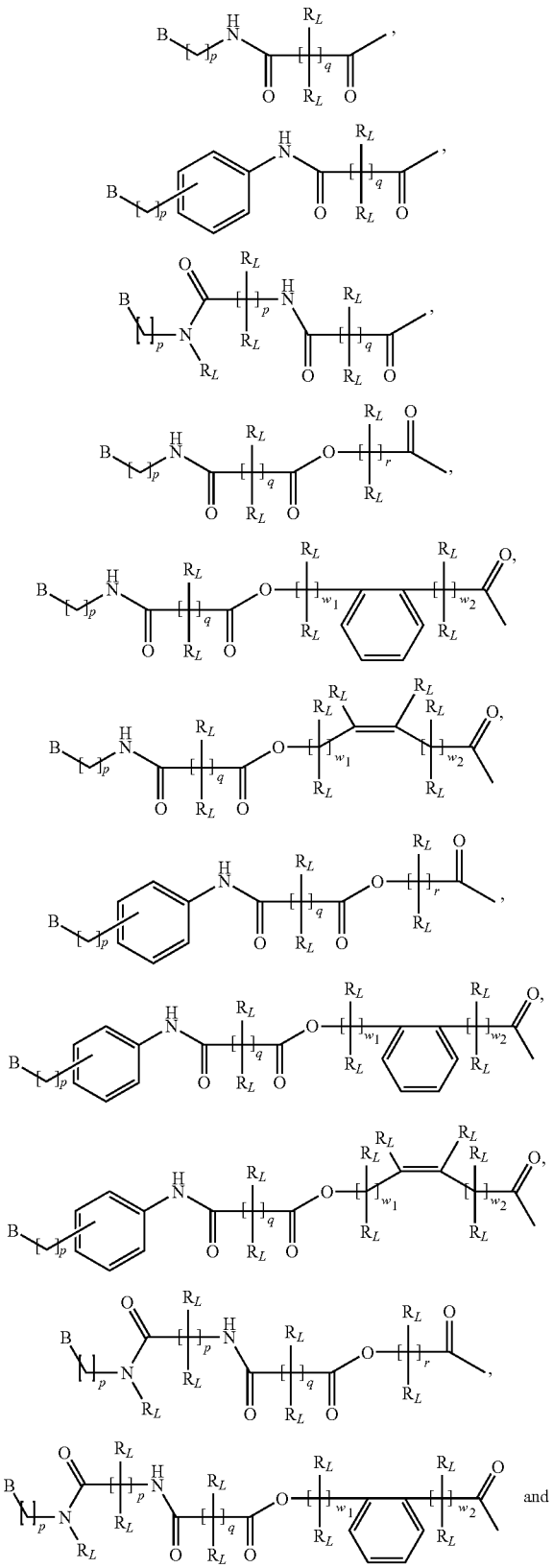

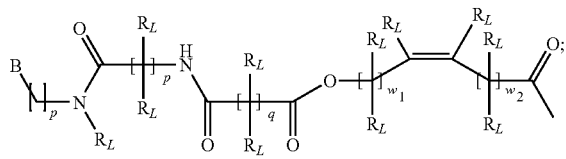

wherein:
B represents said phosphonated group;
each p is independently 0 or an integer ≤10;
each $R_L$ is independently selected from the group consisting of H, ethyl and methyl;
q is 2 or 3;
n is an integer ≤10;
r is 1, 2, 3, 4 or 5; and
$w_1$ and $w_2$ are each integers ≥0 such that their sum ($w_1+w_2$) is 1, 2 or 3.

3. The compound of claim 1, wherein at least one of said B-L- is coupled to a nitrogen atom on said glycopeptide or lipoglycopeptide antibiotic A, and wherein each of said B-L- coupled to a nitrogen atom is independently selected from the group consisting of:

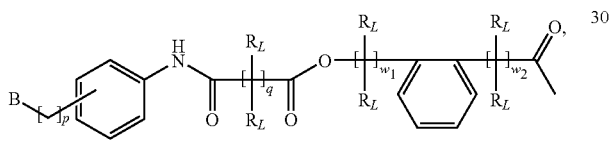

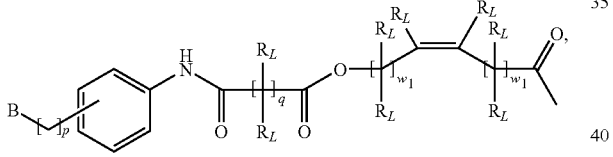

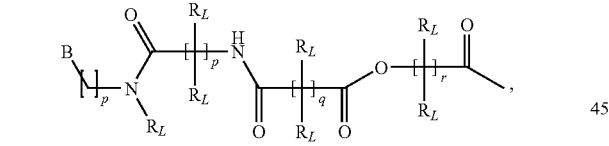

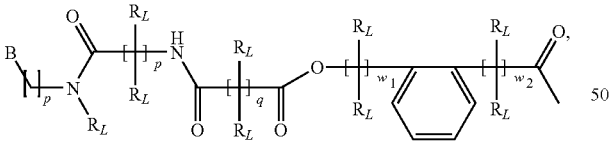

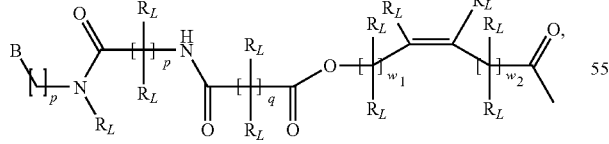

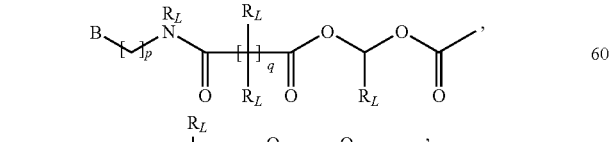

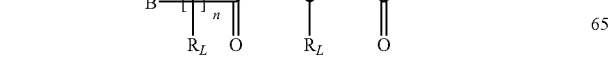

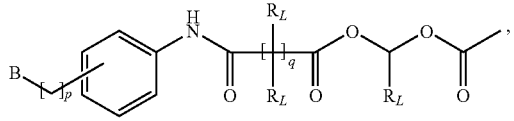

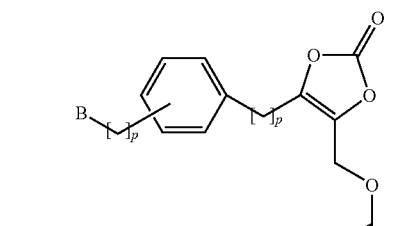

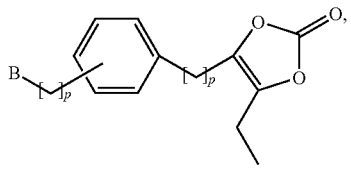

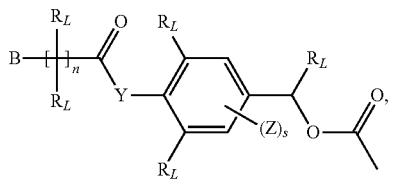

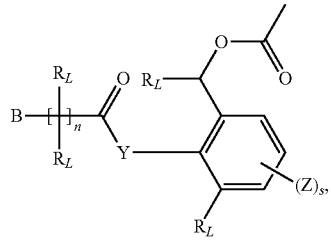

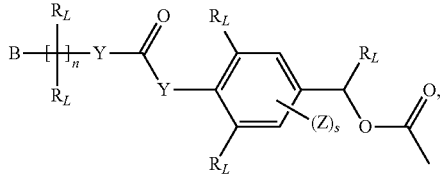

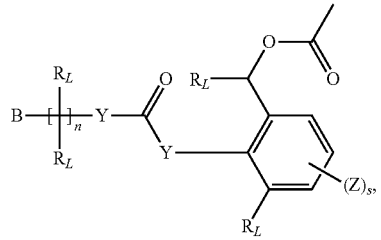

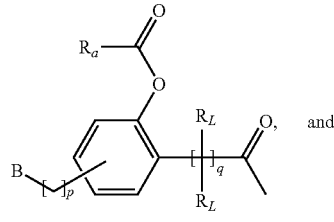

and

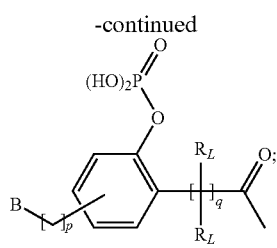

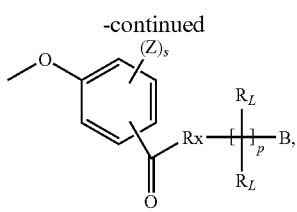

wherein:

B represents said phosphonated group;

n is an integer ≤10;

each p is independently 0 or an integer ≤10;

each $R_L$ is independently selected from the group consisting of H, ethyl and methyl;

q is 2 or 3;

r is 1, 2, 3, 4 or 5;

$w_1$ and $w_2$ are each integers ≥0 such that their sum ($w_1$+$w_2$) is 1, 2 or 3;

X is —$CH_2$—, —$CONR_L$—, —CO—O—$CH_2$—, or —CO—O—;

each Y is —O—;

each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro, wherein s is 1, 2, 3 or 4; and $R_a$ is $C_xH_y$ where x is an integer of 0 to 20 and y is an integer of 1 to 2x+1.

4. The compound of claim 1, wherein at least one of said B-L- is coupled to the carbonyl of a carboxylate group on said glycopeptide or lipoglycopeptide antibiotic A, and wherein each of said B-L- coupled to the carbonyl of a carboxylate group is:

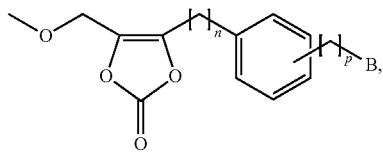

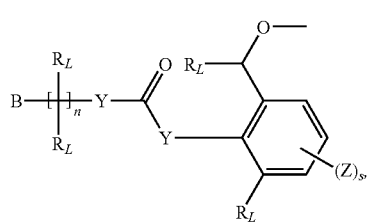

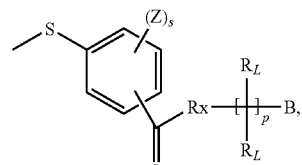

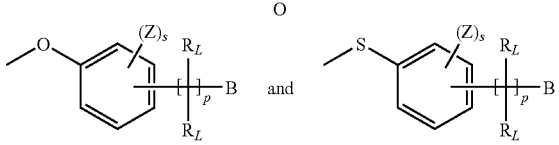

wherein:

n is an integer ≤10;

p is 0 or an integer ≤10; and

B represents the phosphonated group.

5. The compound of claim 1, wherein A is oritavancin or a derivative thereof.

6. The compound of claim 1, wherein A is selected from the group consisting of vancomycin or a derivative thereof, teicoplanin or a derivative thereof, dalbavancin or a derivative thereof, telavancin or a derivative thereof, compound A35512 A, compound A35512 C, compound A35512 E, compound A35512 F, compound A35512 G, compound A35512 H, compound A40926 A, compound A40926 B, compound A40926 PB, parvodicin B2, parvodicin C1, parvodicin C3, compound A41030, compound A42867, compound A477, compound A47934, compound A51568A, N-demethylvancomycin, compound A80407, compound A83850, compound A84575, compound AB65, compound AM374, actaplanin, compound A4696, actinoidin, ardacin, aricidin, compound AAD216, avoparcin, compound LL-AV290, azureomycin, balhimycin, balhimycin V, chloroorienticin, compound A82846B, compound LY264826, chloroeremomycin, chloropeptin, chloropolysporin, complestatin, decaplanin, dechlorobalhimycin, dechlorobalhimycin V, chlorobalhimycin, chlorobromobalhimycin, fluorobalhimycin, deglucobalhimycin, N-demethylbalhimycin, N-demethylvancomycin, devancosamine-vancomycin, eremomycin, galacardin, helvecardin, izupeptin, kibdelin, kistamicin, mannopeptin, methylbalhimycin, compound MM47761, compound MM47766, compound MM47767, compound MM49721, compound MM49727, compound MM55256, compound MM55260, compound MM55266, compound MM55268, compound MM55270, compound MM55272, compound MM56597, compound MM56598, nogabecin F, compound OA7653, orienticin, dechloroeremomycin, compound PA42867, compound PA45052, chloroorienticin, parvodicin, rhamnosyl-balhimycin, ristocetin, ristomycin, spontin, symnonicin, teichomycin, Targocid, ureido-balhimycin and [ψ[$CH_2NH$]$Tpg^4$]Vancomycin.

7. A compound selected from the group consisting of:
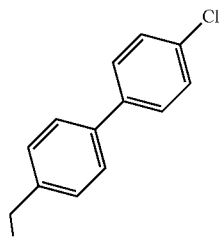
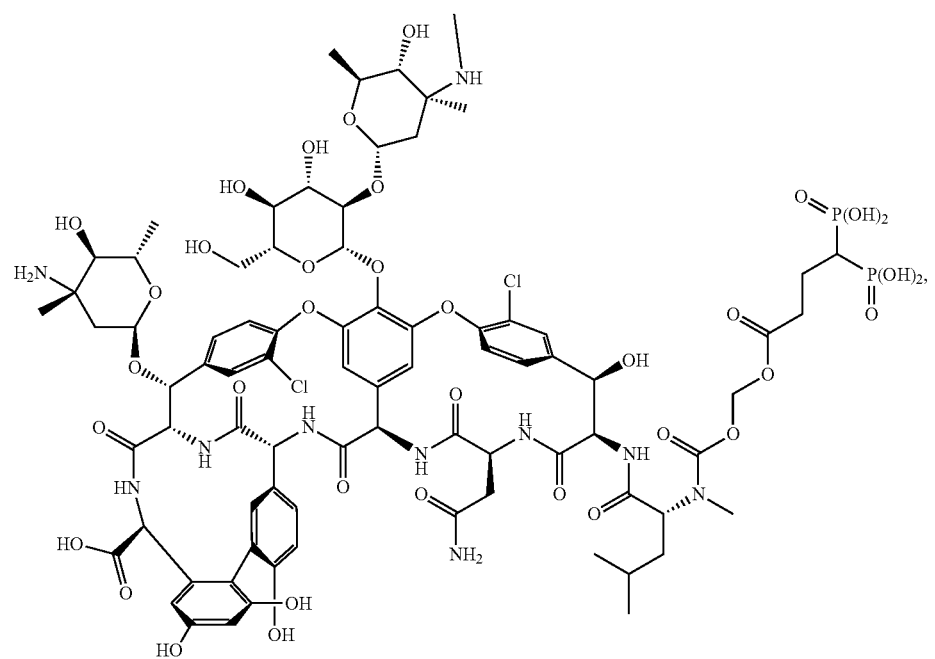
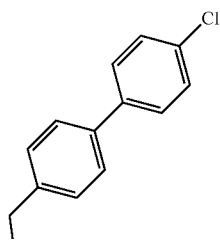

-continued
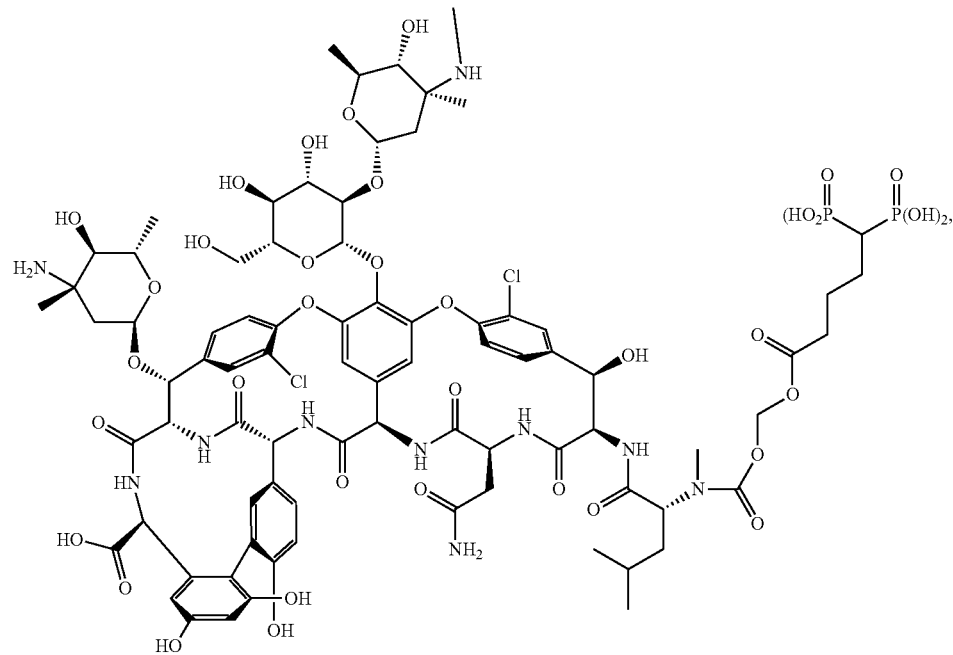
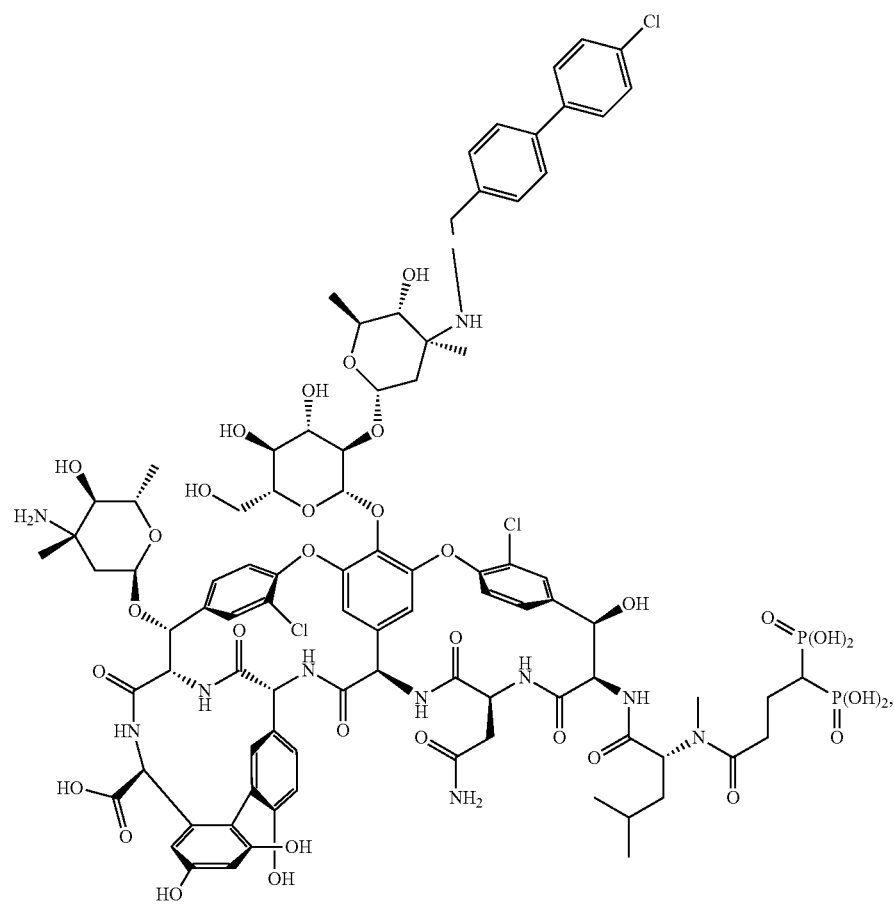

-continued
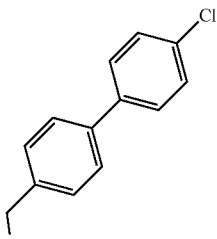
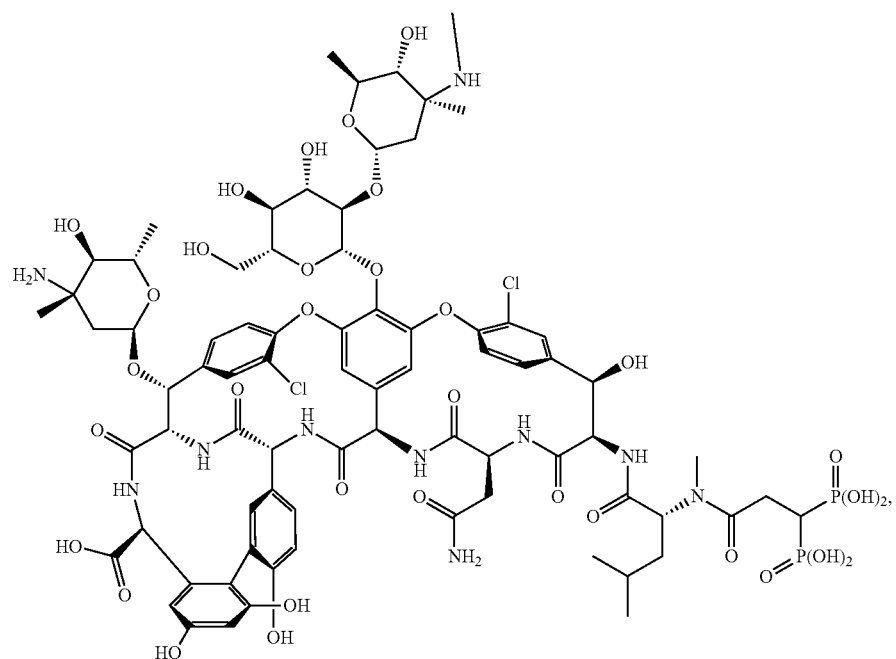
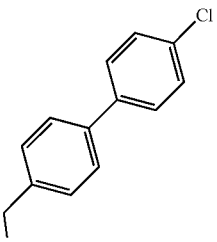

561
-continued
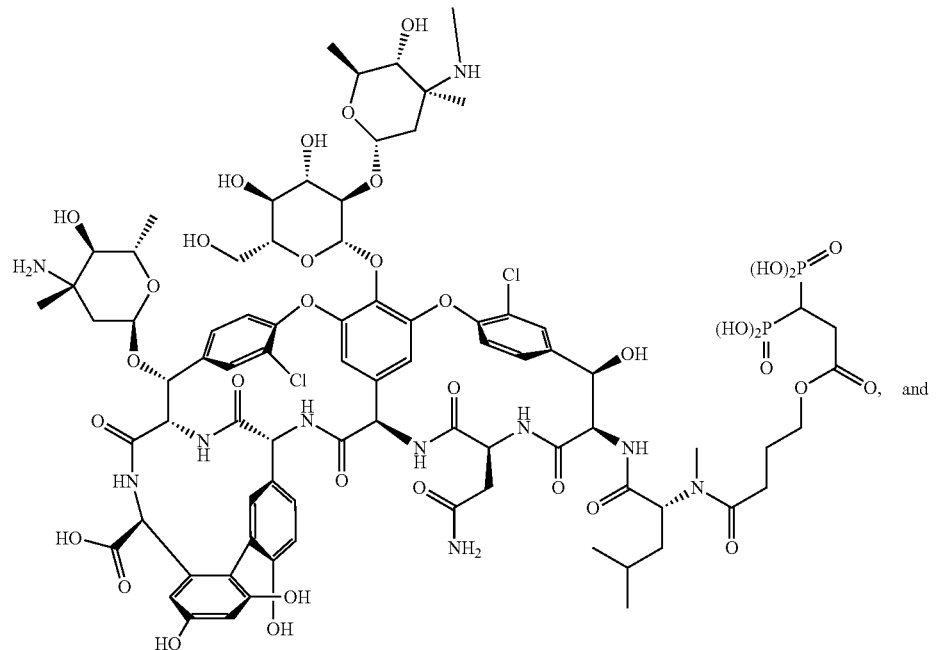
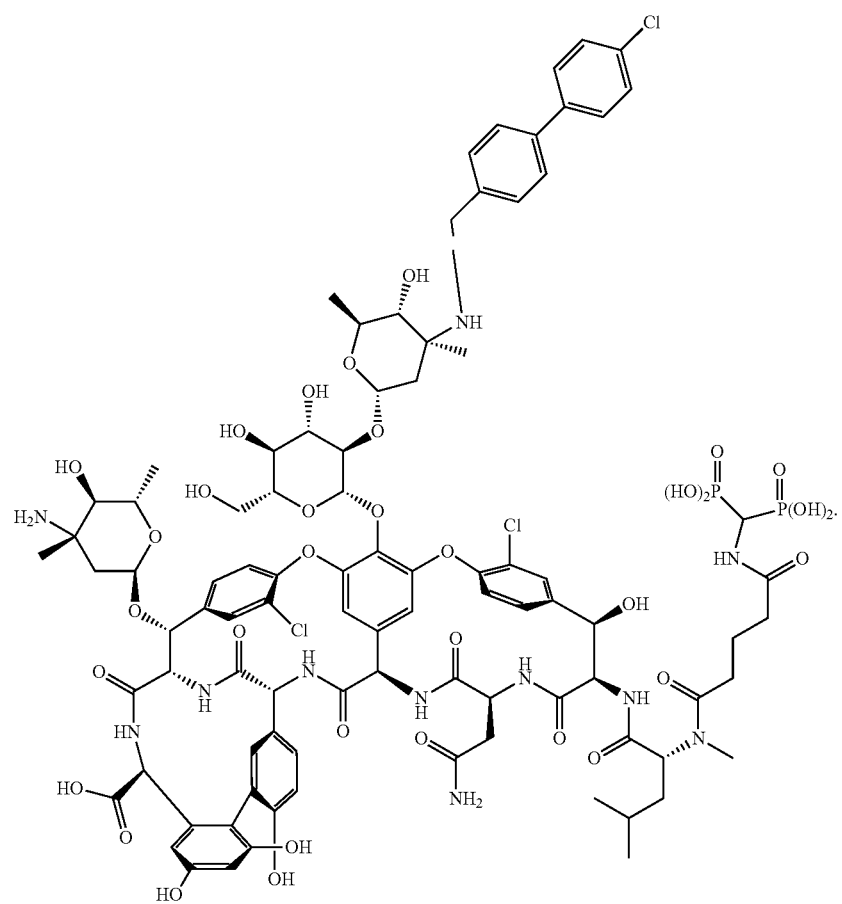
, and

8. A compound represented by the following Formula (II):

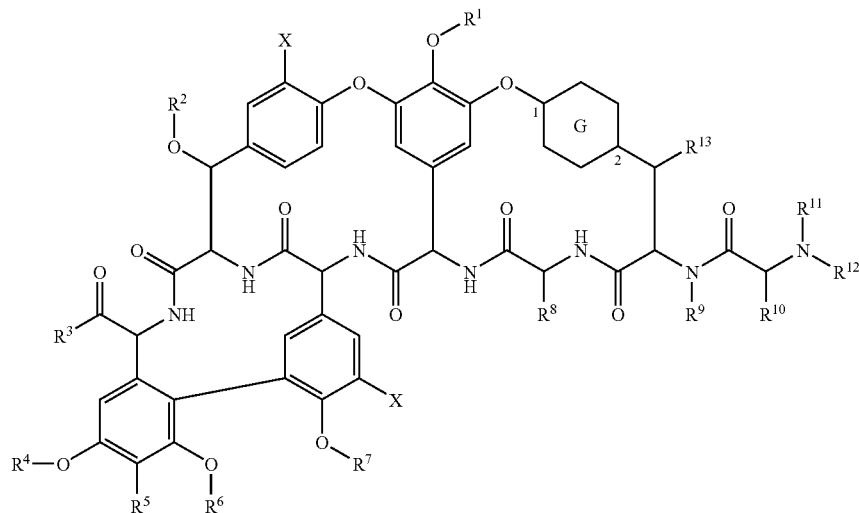

(II)

or a pharmaceutically acceptable salt, ester or prodrug thereof, wherein:

$R^1$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, and —$R^a$—Y—$R^b$—$(Z)_x$; or $R^1$ is a saccharide group optionally substituted with —$R^a$—Y—$R^b$—$(Z)_x$, —$R^f$, —C(O)$R^f$, or —C(O)—$R^a$—Y—$R^b$—$(Z)_x$;

$R^2$ is hydrogen or a saccharide group optionally substituted with —$R^a$—Y—$R^b$—$(Z)_x$, —$R^f$, —C(O)$R^f$, or —C(O)—$R^a$—Y—$R^b$—$(Z)_x$;

$R^3$ is selected from the group consisting of —OR$^c$, —NR$^c$R$^c$, —O—$R^a$—Y—$R^b$—$(Z)_x$, —NR$^c$—$R^a$—Y—$R^b$—$(Z)_x$, —NR$^c$R$^e$, —O—R$^e$, —NL$^8$R$^c$, and —NL$^9$R$^e$;

$R^4$ is selected from the group consisting of hydrogen, alkyl, substituted alkyl, alkenyl, substituted alkenyl, alkynyl, substituted alkynyl, —$R^a$—Y—$R^b$—$(Z)_x$, —C(O)$R^d$ and a saccharide group optionally substituted with —$R^a$—Y—$R^b$—$(Z)_x$, —$R^f$, or —C(O)—$R^a$—Y—$R^b$—$(Z)_x$, or $R^4$ and $R^5$ can be joined, together with the atoms to which they are attached, to form a heterocyclic ring optionally substituted with —NR$^c$—$R^a$—Y—$R^b$—$(Z)_x$ or —NL$^{13}$-$R^a$—Y—$R^b$—$(Z)_x$;

$R^5$ is selected from the group consisting of hydrogen, halo, —CH(R$^c$)—NR$^c$R$^c$, —CH(R$^c$)—NR$^c$R$^e$, —CH(R$^c$)—NR$^c$—$R^a$—Y—$R^b$—$(Z)_x$, —CH(R$^c$)—R$^x$, —CH(R$^c$)—NR$^c$—$R^a$—C(O)—R$^x$; —CH(R$^c$)—NL$^{14}$R$^c$, —CH(R$^c$)—NL$^{15}$R$^e$, —CH(R$^c$)—NL$^{16}$-$R^a$—Y—$R^b$—$(Z)_x$, and —CH(R$^c$)—NL$^{17}$-$R^a$—C(O)—R$^x$;

$R^6$ is selected from the group consisting of hydrogen, alkyl, substituted alkyl, alkenyl, substituted alkenyl, alkynyl, substituted alkynyl, —$R^a$—Y—$R^b$—$(Z)_x$, —C(O)$R^d$ and a saccharide group optionally substituted with —$R^a$—Y—$R^b$—$(Z)_x$, —$R^f$, —C(O)$R^f$, or —C(O)—$R^a$—Y—$R^b$—$(Z)_x$;

or $R^5$ and $R^6$ can be joined, together with the atoms to which they are attached, to form a heterocyclic ring optionally substituted with —NR$^c$—$R^a$—Y—$R^b$—$(Z)_x$ or —NL$^{23}$-$R^a$—Y—$R^b$—$(Z)_x$;

$R^7$ is selected from the group consisting of hydrogen, alkyl, substituted alkyl, alkenyl, substituted alkenyl, alkynyl, substituted alkynyl, —$R^a$—Y—$R^b$—$(Z)_x$, and —C(O)$R^d$;

$R^8$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$R^a$—Y—$R^b$—$(X)_x$;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic; and -L$^{26}$;

$R^{10}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or $R^8$ and $R^{10}$ are joined to form —Ar$^1$—O—Ar$^2$—, where Ar$^1$ and Ar$^2$ are independently arylene or heteroarylene;

$R^{11}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, and -L$^{28}$; or $R^{10}$ and $R^{11}$ are joined, together with the carbon and nitrogen atoms to which they are attached, to form a heterocyclic ring which may optionally be substituted with —NL$^{31}$R$^c$;

$R^{12}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, -L$^{32}$, —C(O)$R^d$, —C(NH)$R^d$, —C(O)NR$^c$R$^c$, —C(O)OR$^d$, —C(NH)

NR$^c$R$^c$, —R$^a$—Y—R$^b$—(Z)$_x$, and —C(O)—R$^b$—Y—R$^b$—(Z)$_x$, —C(O)NL$^{34}$R$^c$, and —C(NH)NL$^{36}$R$^c$; or R$^{11}$ and R$^{12}$ are joined, together with the nitrogen atom to which they are attached, to form a heterocyclic ring which may optionally be substituted with —NL$^{41}$R$^c$;

R$^{13}$ is hydrogen or —OR$^{14}$;

R$^{14}$ is selected from the group consisting of hydrogen, —C(O)R$^d$ and a saccharide group optionally substituted with —R$^a$—Y—R$^b$—(Z)$_x$, —R$^f$, —C(O)R$^f$, or —C(O)—R$^a$—Y—R$^b$—(Z)$_x$;

R$^a$ is each independently selected from the group consisting of alkylene, substituted alkylene, alkenylene, substituted alkenylene, alkynylene and substituted alkynylene;

R$^b$ is each independently selected from the group consisting of a covalent bond, alkylene, substituted alkylene, alkenylene, substituted alkenylene, alkynylene and substituted alkynylene;

R$^c$ is each independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^d$;

R$^d$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

R$^e$ is each a saccharide group optionally substituted with —R$^a$—Y—R$^b$—(Z)$_x$, —R$^f$, —C(O)R$^f$, or —C(O)—R$^a$—Y—R$^b$—(Z)$_x$;

R$^f$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, and heterocyclic;

R$^x$ is an N-linked amino saccharide or an N-linked heterocycle, either of which may be optionally substituted with —R$^a$—Y—R$^b$—(Z)$_x$, —R$^f$, —C(O)R$_f$ or —C(O)—R$^a$—Y—R$^b$—(Z)$_x$;

X is each independently selected from the group consisting of hydrogen, fluoro, chloro, bromo and iodo;

Y is each independently selected from the group consisting of —CH$_2$—, —O—, —S—, —S—S—, —NR$^c$—, —S(O)—, —SO$_2$—, —NR$^c$C(O)—, —OSO$_2$—, —OC(O)—, —N(R$^c$)SO$_2$—, —C(O)NR$^c$—, —C(O)O—, —SO$_2$NR$^c$—, —SO$_2$O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^c$C(O)O—, —NR$^c$C(O)NR$^c$—, —OC(O)NR$^c$—, —C(O)—, —N(R$^c$)SO$_2$NR$^c$—, —NL$^{50}$-, —NL$^{51}$C(O)—, —OSO$_2$—, —OC(O)—, —N(L$^{52}$)SO$_2$—, —C(O)NL$^{53}$-, —SO$_2$NL$^{54}$-, —P(O)(OR$^c$)NL$^{57}$-, —OP(O)(OR$^c$)NL$^{60}$-, —NL$^{61}$C(O)O—, —NL$^{62}$C(O)NR$^c$—, —NR$^c$C(O)NL$^{63}$-, —OC(O)NL$^{64}$-, —N(L$^{65}$)SO$_2$NR$^c$— and —N(R$^c$)SO$_2$NL$^{66}$-;

Z is each independently selected from the group consisting of hydrogen, aryl, cycloalkyl, cycloalkenyl, heteroaryl, heterocyclic, a saccharide, and -L$^{68}$;

x is 1 or 2; and

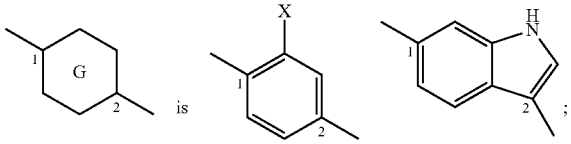 is each L$^8$, L$^9$, L$^{13}$, L$^{14}$, L$^{15}$, L$^{16}$, L$^{17}$, L$^{23}$, L$^{26}$, L$^{28}$, L$^{31}$, L$^{32}$, L$^{34}$, L$^{36}$, L$^{41}$, L$^{50}$, L$^{51}$, L$^{52}$, L$^{53}$, L$^{54}$, L$^{57}$, L$^{60}$, L$^{61}$, L$^{62}$, L$^{63}$, L$^{64}$, L$^{65}$, L$^{66}$ and L$^{68}$ is a hydrolysable linker independently selected from the group consisting of

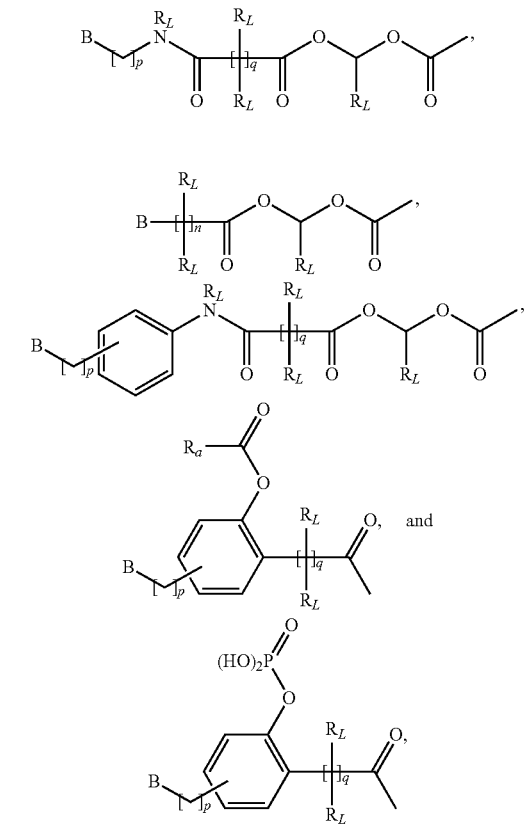

wherein:
B represents a phosphonated group selected from the group consisting of:

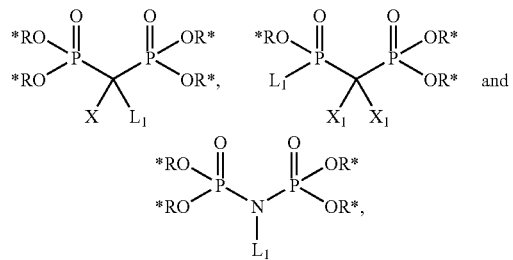

wherein:
each R* is independently selected from the group consisting of H, lower alkyl, cycloalkyl, aryl and heteroaryl, with the proviso that at least two R* are H;
X is H, OH, NIL, or a halo group;
$X_1$ are both H, or each is independently selected from the group consisting of H, OH, $NH_2$, and a halo group; and
$L_1$ is the point of attachment to the linker;
n is an integer ≤10;
each p is independently 0 or an integer ≤10;
each $R_L$ is independently selected from the group consisting of H, ethyl and methyl;
q is 2 or 3; and
$R_a$ is $C_xH_y$ where x is an integer of 0 to 20 and y is an integer of 1 to 2x+1;
with the proviso that at least one of $L^8$, $L^9$, $L^{13}$, $L^{14}$, $L^{15}$, $L^{16}$, $L^{17}$, $L^{23}$, $L^{26}$, $L^{28}$, $L^{31}$, $L^{32}$, $L^{34}$, $L^{36}$, $L^{41}$, $L^{50}$, $L^{51}$, $L^{52}$, $L^{53}$, $L^{54}$, $L^{57}$, $L^{60}$, $L^{61}$, $L^{62}$, $L^{63}$, $L^{64}$, $L^{65}$, $L^{66}$, and $L^{68}$ is present.

9. A pharmaceutical composition comprising a compound of any one of claims 1, and 8, and a pharmaceutically acceptable carrier or excipient.

10. A method for treating a bacterial infection in a subject, comprising administering to a subject in need of treatment a pharmaceutically effective amount of a pharmaceutical composition of claim 9.

11. A method for preventing a bacterial infection in a subject, comprising administering to a subject in need of prevention a pharmaceutically effective amount of a pharmaceutical composition of claim 9.

12. The method of claim 10 wherein said subject is a human.

13. The method of claim 11 wherein said subject is a human.

14. The method of claim 10, further comprising administering a second antibiotic concurrent with administration of said pharmaceutical composition, wherein said second antibiotic is selected from the group consisting of tetracycline, a tetracycline derived antibacterial agent, glycylcycline, a glycylcycline derived antibacterial agent, minocycline, a minocycline derived antibacterial agent, an oxazolidinone antibacterial agent, an aminoglycoside antibacterial agent, a quinolone antibacterial agent, vancomycin, a vancomycin derived antibacterial agent, a teicoplanin, a teicoplanin derived antibacterial agent, eremomycin, an eremomycin derived antibacterial agent, chloroeremomycin, a chloroeremomycin derived antibacterial agent, daptomycin, a daptomycin derived antibacterial agent, Rifamycin, a Rifamycin derived antibacterial agent, Rifampin, a Rifampin derived antibacterial agent, Rifalazil, a Rifalazil derived antibacterial agent, Rifabutin, a Rifabutin derived antibacterial agent, Rifapentin, a Rifapentin derived antibacterial agent, Rifaximin and a Rifaximin derived antibacterial agent.

15. The method of claim 11, further comprising administering a second antibiotic concurrent with administration of said pharmaceutical composition wherein said second antibiotic is selected from the group consisting of tetracycline, a tetracycline derived antibacterial agent, glycylcycline, a glycylcycline derived antibacterial agent, minocycline, a minocycline derived antibacterial agent, an oxazolidinone antibacterial agent, an aminoglycoside antibacterial agent, a quinolone antibacterial agent, vancomycin, a vancomycin derived antibacterial agent, a teicoplanin, a teicoplanin derived antibacterial agent, eremomycin, an eremomycin derived antibacterial agent, chloroeremomycin, a chloroeremomycin derived antibacterial agent, daptomycin, a daptomycin derived antibacterial agent, Rifamycin, a Rifamycin derived antibacterial agent, Rifampin, a Rifampin derived antibacterial agent, Rifalazil, a Rifalazil derived antibacterial agent, Rifabutin, a Rifabutin derived antibacterial agent, Rifapentin, a Rifapentin derived antibacterial agent, Rifaximin and a Rifaximin derived antibacterial agent.

16. A method of accumulating of a glycopeptide or lipoglycopeptide antimicrobial molecule in a bone of a mammal, comprising administering a pharmaceutical composition of claim 9 to a mammal, whereby said compound binds osseous tissue and accumulates in a bone of said mammal.

17. A method for prolonging the presence of a glycopeptide or lipoglycopeptide antimicrobial molecule in a bone of a mammal, comprising administering a pharmaceutical composition of claim 9 to a mammal, whereby the compound of said pharmaceutical composition binds osseous tissue and accumulates in a bone of said mammal, and whereby cleavage of said linker of said compound is gradual within the bone, thereby prolonging the presence of the glycopeptide or lipoglycopeptide antimicrobial molecule in said bone.

* * * * *